US00RE50490E

(19) United States
(12) Reissued Patent
Li et al.

(10) Patent Number: US RE50,490 E
(45) Date of Reissued Patent: *Jul. 15, 2025

(54) SUBSTITUTED QUINAZOLINE COMPOUNDS AND METHODS OF USE THEREOF

(71) Applicant: Araxes Pharma LLC, San Diego, CA (US)

(72) Inventors: Liansheng Li, San Diego, CA (US); Jun Feng, San Diego, CA (US); Yun Oliver Long, San Diego, CA (US); Yuan Liu, San Diego, CA (US); Tao Wu, Carlsbad, CA (US); Pingda Ren, San Diego, CA (US); Yi Liu, San Diego, CA (US)

(73) Assignee: Araxes Pharma LLC, San Diego, CA (US)

( * ) Notice: This patent is subject to a terminal disclaimer.

(21) Appl. No.: 17/985,017

(22) Filed: Nov. 10, 2022

Related U.S. Patent Documents

Reissue of:
(64) Patent No.: 10,829,458
Issued: Nov. 10, 2020
Appl. No.: 16/281,905
Filed: Feb. 21, 2019

U.S. Applications:
(63) Continuation of application No. 15/093,951, filed on Apr. 8, 2016, now Pat. No. 10,246,424.
(Continued)

(51) Int. Cl.
*C07D 239/74* (2006.01)
*C07D 239/94* (2006.01)
(Continued)

(52) U.S. Cl.
CPC ..... *C07D 239/74* (2013.01); *C07D 239/94* (2013.01); *C07D 239/95* (2013.01);
(Continued)

(58) Field of Classification Search
CPC .. C07D 239/74; C07D 239/94; C07D 239/95; C07D 401/04; C07D 401/12;
(Continued)

(56) References Cited

U.S. PATENT DOCUMENTS 3,702,849 A 11/1972 Cronin et al.
3,752,660 A 8/1973 Little
(Continued)

FOREIGN PATENT DOCUMENTS

CN 1267291 A 9/2000
CN 104 418 860 B 9/2016
(Continued)

OTHER PUBLICATIONS

Adibekian et al., "Optimization and characterization of a triazole urea dual inhibitor for lysophospholipase 1 (LYPLA1) and lysophospholipase 2 (LYPLA2)," *Probe Reports from the NIH Molecular Libraries Program*, 2011, 42 pages.
(Continued)

*Primary Examiner* — Alan D Diamond
(74) *Attorney, Agent, or Firm* — Seed IP Law Group LLP

(57) ABSTRACT

Compounds having activity as inhibitors of G12C mutant KRAS protein are provided. The compounds have one of the following structures (I), (II) or (III):

(I)

(II)

or (III)

or a pharmaceutically acceptable salt, stereoisomer or prodrug thereof, wherein $R^1$, $R^{2a}$, $R^{2b}$, $R^{2c}$, $R^{3a}$, $R^{3b}$, $R^{4a}$, $R^{4b}$, $R^{5a}$, $R^{5b}$, $R^6$, A, B, $G^1$, $G^2$, $L^1$, $L^2$, $m^1$, $m^2$, n, x, y, X and E are as defined herein. Methods associated with preparation and use of such compounds, pharmaceutical compositions comprising such compounds and methods to modulate the activity of G12C mutant KRAS protein for treatment of disorders, such as cancer, are also provided.

29 Claims, 3 Drawing Sheets

Related U.S. Application Data

(60) Provisional application No. 62/265,320, filed on Dec. 9, 2015, provisional application No. 62/265,316, filed on Dec. 9, 2015, provisional application No. 62/255,891, filed on Nov. 16, 2015, provisional application No. 62/145,818, filed on Apr. 10, 2015, provisional application No. 62/145,705, filed on Apr. 10, 2015.

(51) Int. Cl.

| | |
|---|---|
| ***C07D 239/95*** | (2006.01) |
| ***C07D 401/04*** | (2006.01) |
| ***C07D 401/12*** | (2006.01) |
| ***C07D 401/14*** | (2006.01) |
| ***C07D 403/04*** | (2006.01) |
| ***C07D 403/12*** | (2006.01) |
| ***C07D 403/14*** | (2006.01) |
| ***C07D 405/12*** | (2006.01) |
| ***C07D 405/14*** | (2006.01) |
| ***C07D 409/12*** | (2006.01) |
| ***C07D 413/12*** | (2006.01) |
| ***C07D 417/04*** | (2006.01) |
| ***C07D 471/08*** | (2006.01) |
| ***C07D 487/10*** | (2006.01) |
| ***C07D 491/10*** | (2006.01) |
| ***C07F 9/6558*** | (2006.01) |

(52) U.S. Cl.

CPC ..... *C07D 401/04* (2013.01); *C07D 401/12* (2013.01); *C07D 401/14* (2013.01); *C07D 403/04* (2013.01); *C07D 403/12* (2013.01); *C07D 403/14* (2013.01); *C07D 405/12* (2013.01); *C07D 405/14* (2013.01); *C07D 409/12* (2013.01); *C07D 413/12* (2013.01); *C07D 417/04* (2013.01); *C07D 471/08* (2013.01); *C07D 487/10* (2013.01); *C07D 491/10* (2013.01); *C07F 9/65583* (2013.01)

(58) Field of Classification Search

CPC .. C07D 401/14; C07D 403/04; C07D 403/12; C07D 403/14; C07D 405/12; C07D 405/14; C07D 409/12; C07D 413/12; C07D 417/04; C07D 471/08; C07D 487/10; C07D 491/10; C07F 9/65583; A61P 35/00; A61P 35/04; A61K 31/4725

See application file for complete search history.

(56) References Cited

U.S. PATENT DOCUMENTS

| | | | |
|---|---|---|---|
| 4,439,606 | A | 3/1984 | Du et al. |
| 4,649,219 | A | 3/1987 | Itoh et al. |
| 4,656,181 | A | 4/1987 | Sunkel et al. |
| 4,861,760 | A | 8/1989 | Mazuel et al. |
| 4,911,920 | A | 3/1990 | Jani et al. |
| 5,010,175 | A | 4/1991 | Rutter et al. |
| 5,033,252 | A | 7/1991 | Carter |
| 5,052,558 | A | 10/1991 | Carter |
| 5,212,162 | A | 5/1993 | Missel et al. |
| 5,288,514 | A | 2/1994 | Ellman |
| 5,323,907 | A | 6/1994 | Kalvelage |
| 5,403,841 | A | 4/1995 | Lang et al. |
| 5,538,848 | A | 7/1996 | Livak et al. |
| 5,539,083 | A | 7/1996 | Cook et al. |
| 5,593,853 | A | 1/1997 | Chen et al. |
| 5,605,798 | A | 2/1997 | Koster |
| 5,670,505 | A | 9/1997 | Matsuo et al. |
| 5,731,352 | A | 3/1998 | Lesieur et al. |
| 5,777,324 | A | 7/1998 | Hillenkamp |
| 5,858,659 | A | 1/1999 | Sapolsky et al. |
| 5,861,510 | A | 1/1999 | Piscopio et al. |
| 5,863,949 | A | 1/1999 | Robinson et al. |
| 5,919,626 | A | 7/1999 | Shi et al. |
| 5,925,525 | A | 7/1999 | Fodor et al. |
| 5,952,174 | A | 9/1999 | Nikiforov et al. |
| 6,002,008 | A | 12/1999 | Wissner et al. |
| 6,017,696 | A | 1/2000 | Heller |
| 6,043,031 | A | 3/2000 | Koster et al. |
| 6,045,996 | A | 4/2000 | Cronin et al. |
| 6,051,380 | A | 4/2000 | Sosnowski et al. |
| 6,068,818 | A | 5/2000 | Ackley et al. |
| 6,214,872 | B1 | 4/2001 | Robinson |
| 6,251,639 | B1 | 6/2001 | Kurn |
| 6,511,993 | B1 | 1/2003 | Dack et al. |
| 6,903,118 | B1 | 6/2005 | Biedermann et al. |
| 7,074,801 | B1 | 7/2006 | Yoshida et al. |
| 7,595,397 | B2 | 9/2009 | Zindell et al. |
| 7,879,863 | B2 | 2/2011 | Tokumasu et al. |
| 8,399,454 | B2 | 3/2013 | Bian et al. |
| 8,426,401 | B2 | 4/2013 | Bian et al. |
| 8,466,288 | B2 | 6/2013 | Aronov et al. |
| 8,604,017 | B2 | 12/2013 | Bian et al. |
| 8,697,684 | B2 | 4/2014 | Bian et al. |
| 8,741,887 | B2 | 6/2014 | Bian et al. |
| 8,759,333 | B2 | 6/2014 | Connolly et al. |
| 9,227,978 | B2 | 1/2016 | Ren et al. |
| 9,273,057 | B2 | 3/2016 | Purandare et al. |
| 9,376,559 | B2 | 6/2016 | Holtcamp et al. |
| 9,745,319 | B2 | 8/2017 | Ren et al. |
| 9,810,690 | B2 | 11/2017 | Patricelli et al. |
| 9,840,516 | B2 | 12/2017 | Li et al. |
| 9,862,701 | B2 | 1/2018 | Li et al. |
| 9,926,267 | B2 | 3/2018 | Ren et al. |
| 9,988,357 | B2 | 6/2018 | Mani et al. |
| 10,111,874 | B2 | 10/2018 | Janes et al. |
| 10,144,724 | B2 | 12/2018 | Li et al. |
| 10,246,424 | B2 * | 4/2019 | Li ..... C07D 403/12 |
| 10,273,207 | B2 | 4/2019 | Ren et al. |
| 10,280,172 | B2 | 5/2019 | Li et al. |
| 10,351,550 | B2 | 7/2019 | Li et al. |
| 10,370,386 | B2 | 8/2019 | Li et al. |
| 10,377,743 | B2 | 8/2019 | Li et al. |
| 10,414,757 | B2 | 9/2019 | Li et al. ..... A61P 43/00 |
| 10,428,064 | B2 | 10/2019 | Li et al. |
| 10,556,906 | B2 | 2/2020 | Kuramoto et al. |
| 10,646,488 | B2 | 5/2020 | Liu et al. |
| 10,647,703 | B2 | 5/2020 | Li et al. |
| 10,745,385 | B2 * | 8/2020 | Li ..... C07D 403/14 |
| 11,377,441 | B2 * | 7/2022 | Li ..... C07D 403/04 |
| 2002/0169300 | A1 | 11/2002 | Waterman et al. |
| 2003/0022344 | A1 | 1/2003 | Williams et al. |
| 2003/0166620 | A1 | 9/2003 | Lee et al. |
| 2003/0171400 | A1 | 9/2003 | Pikul et al. |
| 2004/0106634 | A1 | 6/2004 | Satoh et al. |
| 2005/0012070 | A1 | 1/2005 | Inoue et al. |
| 2005/0119266 | A1 | 6/2005 | Shi et al. |
| 2005/0227997 | A1 | 10/2005 | Noe et al. |
| 2007/0249648 | A1 | 10/2007 | Bladh et al. |
| 2008/0004285 | A1 | 1/2008 | De Jonghje et al. |
| 2008/0004348 | A1 | 1/2008 | Yous et al. |
| 2008/0039450 | A1 | 2/2008 | Jensen et al. |
| 2008/0070892 | A1 | 3/2008 | Harris et al. |
| 2009/0036430 | A1 | 2/2009 | De Jonghje et al. |
| 2009/0054402 | A1 | 2/2009 | Wang et al. |
| 2009/0124636 | A1 | 5/2009 | Barber et al. |
| 2009/0298075 | A1 | 12/2009 | Travers et al. |
| 2010/0331300 | A1 | 12/2010 | Bian et al. |
| 2011/0046370 | A1 | 2/2011 | Sim et al. |
| 2011/0217309 | A1 | 9/2011 | Buck et al. |
| 2011/0230476 | A1 | 9/2011 | Niu et al. |
| 2011/0269244 | A1 | 11/2011 | Petter et al. |
| 2011/0311447 | A1 | 12/2011 | Tu et al. |
| 2011/0319290 | A1 | 12/2011 | Raymond et al. |
| 2012/0083476 | A1 | 4/2012 | Breitenbucher et al. |
| 2013/0012489 | A1 | 1/2013 | Mederski |
| 2013/0029964 | A1 | 1/2013 | Aoki et al. |
| 2013/0274252 | A1 | 10/2013 | Pandey et al. |
| 2013/0302407 | A1 | 11/2013 | Rao et al. |
| 2014/0315886 | A1 | 10/2014 | Suzuki et al. |
| 2015/0087628 | A1 | 3/2015 | Ostrem et al. |

(56) References Cited

U.S. PATENT DOCUMENTS

| | | | |
|---|---|---|---|
| 2015/0374678 | A1 | 12/2015 | Chamberlain et al. |
| 2016/0166571 | A1 | 6/2016 | Janes et al. |
| 2016/0368930 | A1 | 12/2016 | Ostrem et al. |
| 2017/0022184 | A1 | 1/2017 | Li et al. |
| 2017/0131278 | A1 | 5/2017 | Patricelli et al. |
| 2017/0197945 | A1 | 7/2017 | Li et al. |
| 2017/0247376 | A1 | 8/2017 | Li et al. |
| 2018/0015087 | A1 | 1/2018 | Liu et al. |
| 2018/0086753 | A1 | 3/2018 | Li et al. |
| 2018/0118757 | A1 | 5/2018 | Li et al. |
| 2018/0127396 | A1 | 5/2018 | Li et al. |
| 2018/0141927 | A1 | 5/2018 | Li et al. |
| 2018/0194748 | A1 | 7/2018 | Li et al. |
| 2018/0246102 | A1 | 8/2018 | Patricelli et al. |
| 2018/0273515 | A1 | 9/2018 | Li et al. |
| 2018/0273523 | A1 | 9/2018 | Li et al. |
| 2018/0282307 | A1 | 10/2018 | Li et al. |
| 2018/0282308 | A1 | 10/2018 | Li et al. |
| 2018/0319775 | A1 | 11/2018 | Li et al. |
| 2019/0055211 | A1 | 2/2019 | Li et al. |
| 2019/0062313 | A1 | 2/2019 | Li et al. |
| 2019/0062314 | A1 | 2/2019 | Li et al. |
| 2019/0092767 | A1 | 3/2019 | Li et al. |
| 2019/0262342 | A1 | 8/2019 | Janes et al. |
| 2019/0343838 | A1 | 11/2019 | Allen et al. |
| 2019/0345158 | A1 | 11/2019 | Li et al. |
| 2019/0367489 | A1 | 12/2019 | Li et al. |
| 2019/0375743 | A1 | 12/2019 | Hudson et al. |
| 2019/0382377 | A1 | 12/2019 | Li et al. |
| 2019/0389796 | A1 | 12/2019 | Ren et al. |
| 2019/0389851 | A1 | 12/2019 | Li et al. |
| 2020/0010454 | A1 | 1/2020 | Li et al. |
| 2020/0062761 | A1 | 2/2020 | Li et al. |
| 2020/0102321 | A1 | 4/2020 | Li et al. |
| 2020/0115363 | A1 | 4/2020 | Li et al. |

FOREIGN PATENT DOCUMENTS

| | | | |
|---|---|---|---|
| EP | 0 094 498 | A2 | 11/1983 |
| EP | 0 606 046 | A1 | 7/1994 |
| EP | 0 780 386 | A1 | 6/1997 |
| EP | 0 818 442 | A2 | 1/1998 |
| EP | 0 931 788 | A2 | 7/1999 |
| EP | 1 004 578 | A1 | 5/2000 |
| EP | 0 655 442 | B1 | 5/2001 |
| EP | 1 348 434 | A1 | 10/2003 |
| EP | 1 736 465 | A1 | 12/2006 |
| EP | 2 133 334 | A1 | 12/2009 |
| EP | 2 270 002 | A1 | 1/2011 |
| EP | 2 889 291 | A1 | 7/2015 |
| GB | 939516 | A | 10/1963 |
| GB | 9912961.1 | | 6/1999 |
| JP | 58-203966 | A | 11/1983 |
| JP | 59-163372 | A | 9/1984 |
| JP | 2002-508356 | A | 3/2002 |
| JP | 2003-535860 | A | 12/2003 |
| JP | 2005-502623 | A | 1/2005 |
| JP | 2005-179557 | A | 7/2005 |
| JP | 2007-16011 | A | 1/2007 |
| JP | 2008-524154 | A | 7/2008 |
| JP | 2013-516422 | A | 5/2013 |
| JP | 2013-107855 | A | 6/2013 |
| JP | 2013-522249 | A | 6/2013 |
| WO | 86/01207 | A1 | 2/1986 |
| WO | 90/05719 | A1 | 5/1990 |
| WO | 91/19735 | A1 | 12/1991 |
| WO | 92/00091 | A1 | 1/1992 |
| WO | 93/20242 | A1 | 10/1993 |
| WO | 96/05309 | A2 | 2/1996 |
| WO | 96/13262 | A1 | 5/1996 |
| WO | 96/27583 | A1 | 9/1996 |
| WO | 96/33172 | A1 | 10/1996 |
| WO | 97/00271 | A1 | 1/1997 |
| WO | 97/30992 | A1 | 8/1997 |
| WO | 98/03516 | A1 | 1/1998 |
| WO | 98/07697 | A1 | 2/1998 |
| WO | 98/30566 | A1 | 8/1998 |
| WO | 98/33496 | A1 | 8/1998 |
| WO | 98/33768 | A1 | 8/1998 |
| WO | 98/34915 | A1 | 8/1998 |
| WO | 98/35951 | A2 | 8/1998 |
| WO | 98/43960 | A1 | 10/1998 |
| WO | 98/34918 | A1 | 12/1998 |
| WO | 98/57948 | A1 | 12/1998 |
| WO | 99/29667 | A1 | 2/1999 |
| WO | 99/52910 | A1 | 6/1999 |
| WO | 99/32454 | A1 | 7/1999 |
| WO | 99/07675 | A1 | 10/1999 |
| WO | 99/52889 | A1 | 10/1999 |
| WO | 99/67641 | A1 | 12/1999 |
| WO | 00/39587 | A1 | 7/2000 |
| WO | 00/74681 | A1 | 12/2000 |
| WO | 02/04420 | A1 | 1/2002 |
| WO | 02/080928 | A1 | 10/2002 |
| WO | 02/088107 | A1 | 11/2002 |
| WO | 03/004480 | A2 | 1/2003 |
| WO | 2004/033427 | A1 | 4/2004 |
| WO | 2004/074283 | A1 | 9/2004 |
| WO | 2004/080976 | A1 | 9/2004 |
| WO | 2005/070891 | A2 | 8/2005 |
| WO | 2005/082892 | A2 | 9/2005 |
| WO | 2006/066948 | A1 | 6/2006 |
| WO | 2006/097261 | A1 | 9/2006 |
| WO | 2006/135993 | A1 | 12/2006 |
| WO | 2007/047146 | A2 | 4/2007 |
| WO | 2007/095588 | A1 | 8/2007 |
| WO | 2007/113226 | A1 | 10/2007 |
| WO | 2007/144394 | A2 | 12/2007 |
| WO | 2008/009078 | A2 | 1/2008 |
| WO | 2008/028691 | A1 | 3/2008 |
| WO | 2008/112440 | A1 | 9/2008 |
| WO | 2010/027746 | A2 | 3/2010 |
| WO | 2010/087399 | A1 | 8/2010 |
| WO | 2010/121918 | A1 | 10/2010 |
| WO | 2011/002816 | A1 | 1/2011 |
| WO | 2011/016559 | A1 | 2/2011 |
| WO | 2011/031896 | A2 | 3/2011 |
| WO | 2011/082285 | A1 | 7/2011 |
| WO | 2011/093524 | A1 | 8/2011 |
| WO | 2011/148922 | A1 | 12/2011 |
| WO | 2011/153553 | A2 | 12/2011 |
| WO | 2012/016082 | A1 | 2/2012 |
| WO | 2012/041872 | A1 | 4/2012 |
| WO | 2012/054716 | A1 | 4/2012 |
| WO | 2012/061557 | A2 | 5/2012 |
| WO | 2012/174489 | A2 | 12/2012 |
| WO | 2013/064068 | A1 | 5/2013 |
| WO | 2013/096151 | A1 | 6/2013 |
| WO | 2013/096455 | A1 | 6/2013 |
| WO | 2013/106641 | A1 | 7/2013 |
| WO | 2013/140148 | A1 | 9/2013 |
| WO | 2013/155077 | A1 | 10/2013 |
| WO | 2013/155223 | A1 | 10/2013 |
| WO | 2013/184757 | A1 | 12/2013 |
| WO | 2014/011900 | A2 | 1/2014 |
| WO | 2014/071109 | A1 | 5/2014 |
| WO | 2014/143659 | A1 | 9/2014 |
| WO | 2014/152588 | A1 | 9/2014 |
| WO | 2014/159837 | A1 | 10/2014 |
| WO | 2014/201435 | A1 | 12/2014 |
| WO | 2015/003166 | A1 | 1/2015 |
| WO | 2015/017502 | A1 | 2/2015 |
| WO | 2015/054572 | A1 | 4/2015 |
| WO | 2015/108992 | A1 | 7/2015 |
| WO | 2015/132799 | A2 | 9/2015 |
| WO | 2015/143148 | A1 | 9/2015 |
| WO | 2015/144001 | A1 | 10/2015 |
| WO | 2015/184349 | A2 | 12/2015 |
| WO | 2016/044772 | A1 | 3/2016 |
| WO | 2016/049524 | A1 | 3/2016 |
| WO | 2016/049565 | A1 | 3/2016 |
| WO | 2016/049568 | A1 | 3/2016 |
| WO | 2016/118951 | A2 | 7/2016 |
| WO | 2016/164675 | A1 | 10/2016 |

(56) References Cited

FOREIGN PATENT DOCUMENTS

| | | | |
|---|---|---|---|
| WO | 2016/168540 | A1 | 10/2016 |
| WO | 2017/015562 | A1 | 1/2017 |
| WO | 2017/058902 | A1 | 4/2017 |
| WO | 2017/058915 | A1 | 4/2017 |
| WO | 2017/068412 | A1 | 4/2017 |
| WO | 2017/070256 | A2 | 4/2017 |
| WO | 2017/172979 | A1 | 10/2017 |
| WO | 2018/140512 | A1 | 8/2018 |
| WO | 2020/028706 | A1 | 2/2020 |
| WO | 2020/086739 | A1 | 4/2020 |

OTHER PUBLICATIONS

Al-Muhammed et al., "In-vivo studies on dexamethasone sodium phosphate liposomes," *J. Microencapsulation* 13(3):293-306, 1996.
American Chemical Society, STN Database: Nov. 16, 1984, RN5530-21-2.
Appel et al., "Supramolecular Cross-Linked Networks via Host-Guest Complexation with Cucurbit[8]uril," *J. Am. Chem. Soc.* 132(40):14251-14260, Jul. 2010.
Arkin et al., "Binding of small molecules to an adaptive protein-protein interface," *PNAS* 100(4):1603-1608, Feb. 2003.
Bachovchin et al., "Identification of selective inhibitors of uncharacterized enzymes by high-throughput screening with fluorescent activity-based probes," *Nat. Biotechnol* 27(7)"387-394, 2009.
Banker et al. (eds.), *Modern Pharmaceutics*, New York, Marcel Dekker, Inc., 1996, pp. 451 and 596. (3 pages).
Barbe et al., "Highly Chemoselective Metal-Free Reduction of Tertiary Amides," *J. Am. Chem. Soc.* 130:18-19, 2008.
Begue et al., "Ions α-Cetocarbenium. Influence De La Structure Sur L'Evolution Des Ions α-Cetocyclohexylcarbenium," *Tetrahedron* 31(20):2505-2511, 1975. (English Abstract Only).
Berge et al., "Pharmaceutical Salts," *Journal of Pharmaceutical Sciences* 66(1):1-19, 1977.
Bundgard, "Design of Prodrugs," pp. 7-9, 21 24, 1985.
Chemcats Chemical Abstract, Accession No. 1301347730, Sep. 9, 2015, 2 pages.
Chemocare, "Taxol," retrieved from http://www.chemocare.com/chemotherapy/drug-info/Taxol.aspx on Feb. 22, 2017, 3 pages.
Cho et al., "An Unnatural Biopolymer," *Science* 261:1303-1305, Sep. 1993.
Chonn et al., "Recent advances in liposomal drug-delivery systems," *Current Opinion in Biotechnology* 6:698-708, 1995.
Choong et al., "Identification of Potent and Selective Small-Molecule Inhibitors of Caspase-3 through the Use of Extended Tethering and Structure-Based Drug Design," *J. Med. Chem.* 45:5005-5022, 2002.
Cox et al., "Durging the undruggable RAS: Mission Possible?," *Nat. Rev. Drug Discov.* 13(11):828-851, 2014.
DeWitt et al., ""Diversomers": An approach to nonpeptide, nonoligomeric chemical diversity," *Proc. Natl. Acad. Sci.* 90:6909-6913, Aug. 1993.
Duncan et al., "N-Dialkylaminoalkybiphenylamines as Antimalarial and Atischistosomal Agents," *Journal of Medicinal Chemistry* 12:25-29, Jan. 1969.
Erlanson et al., "Site-directed ligand discovery," *Proc. Natl Acad. Sci. U.S.A.* 97(17):9367-9372, Aug. 2000.
Forbes et al., "Cosmic 2005," *British Journal of Cancer* 94:318-322, 2006.
Furka et al., "General method for rapid synthesis of multicomponent peptide mixtures," *Int. J. Peptide Protein Res.* 37:487-493, 1991.
Gorfe et al., "Mapping the Nucleotide and Isoform-Dependent Structural and Dynamical Features of Ras Proteins," *Structure* 16:885-896, Jun. 2008.
Haggam et al., "Facile synthesis of some condensed 1,3-thiazines and thiazoles under conventional conditions: antitumor activity," *Research on Chemical Intermediates* 43(11):6299-6315, 2017.
Hagihara et al., "Vinylogous Polypeptides: An Alternative Peptide Backbone," *J. Am. Chem. Soc.* 114(16):6568-6570, 1992.
Hall et al., "The Effect of $Mg^{2+}$ on Guanine Nucleotide Exchange Rate of $p21^{N\text{-}ras}$," *The Journal of Biological Chemistry* 261(24):10963-10965, 1986.
Hall et al., "The structural basis for the transition from Ras-GTP to Ras-GDP," *PNAS* 99(19):12138-12142, Sep. 2002.
Hansen et al., "The reactivity-driven biochemical mechanism of covalent $KRAS^{G12C}$ inhibitors," *Nature Structural & Molecular Biology* 25:454-462, 2018. (14 pages).
Hardy et al., "Discovery of an allosteric site in the caspases," *PNAS* 101(34):12461-12466, Aug. 2004.
Hattori et al., "Neutralizing monoclonal antibody against ras oncogene product p21 which impairs guanine nucleotide exchange," *Mol. Cell. Biol.* 7(5):1999-2002, May 1987.
Higuchi et al., "Pro-drugs as Novel Delivery Systems," ACS Symposium Series 14.
Ito et al., "Regional Polysterism in the GTP-Bound Form of the Human c-Ha-Ras Protein," *Biochemistry* 36(30):9109-1919, Jul. 1997.
Janes et al., "Targeting KRAS Mutant Cancers with a Covalent C12C-Specific Inhibitor," *Cell* 172:578-589, 2018.
Janes et al., "Combination Therapies for Treatment of Cancer," U.S. Appl. No. 14/858,766, filed Sep. 18, 2015, 421 pages.
Johnson et al., "The Chemistry of β-Bromopropionyl Isocyanate. I. Synthesis of 1-Aryldihydrouracils," *The Journal of Organic Chemistry* 24(9):1391-1392, Sep. 1959.
Jones et al., "Increased frequency of the k-ras G12C mutation in MYH polyposis colorectal adenomas," *British Journal of Cancer* 90:1591-1593, 2004.
Jordan, "Tamoxifen: A most unlikely pioneering medicine," *Nature Reviews* 2:205-213, Mar. 2003.
Kelly et al., "Synthesis of Isomeric 3-Piperidinyl and 3-Pyrrolidinyl Benzo[5,6]cyclohepta[1,2-b]pyridines: Sulfonamido Derivatives as Inhibitors of Ras Prenylation," *Bioorganic & Medicinal Chemistry* 6(6):673-686, Jun. 1998.
Knochel et al., "Functionalization of heterocyclic compounds using polyfunctional magnesium and zinc reagents," Beilstein Journal of Organic Chemistry 7:1261-1277, 2011.
Kraulis et al., "Solution Structure and Dynamics of Ras p21-GDP Determined by Heteronuclear Three- amd Four-Dimensional NMR Spectroscopy," *Biochemistry* 33:3515-3531, 1994.
Kumar et al., "Synthesis of 3-Sulfonylamino Quinolines form 1-(2-Aminophenyl) Propargyl Alcohols through a Ag(I)-Catalyzed Hydroamination, (2+3) Cycloaddition, and an Unusual Strain-Driven Ring Expansion," *Organic Letters* 17(9):2226-2229, Apr. 2015.
Kuroyanagi et al., "Structure-Activity Relationships of 1,3-Benzoxazole-4-carbonitriles as Novel Antifungal Agents with Potent in Vivo Efficacy," *Chem. Pharm. Bull.* 59(3):341-352, 2011.
Le Picard et al., "Design and Synthesis of Naphthalenic Derivatives as Potential Inhibitors of Hydroxyindole-O-methyltransferase," *Pharm. Pharmacol. Commun.* 5:183-188, 1999.
Lee et al., "The mutation spectrum revealed by paired genome sequences from a lung cancer patient," *Nature* 465:473-477, May 2010.
Lenzen et al., "[10] Analysis of Intrinsic and CDC25-Stimulated Guanine Nucleotide Exchange of $p21^{ras}$-Nucleotide Complexes by Fluorescence Measurements," *Methods in Enzymology* 255:95-109, 1995.
Li et al., "Inhibitors of KRAS G12C," filed Oct. 10, 2014, U.S. Appl. No. 14/511,425, 353 pages.
Li et al., "Methods and Compositions for Inhibition of RAS," U.S. Appl. No. 15/508,387, filed Mar. 2, 2017, 145 pages.
Li et al., "Substituted Quinazoline Compounds and Methods of Use Thereof," U.S. Appl. No. 15/217,304, filed Jul. 22, 2016, 131 pages.
Liang et al., "Parallel Synthesis and Screening of a Solid Phase Carbohydrate Library," *Science* 274:1520-1522, Nov. 1996.
Liu et al., "*Polygonatum cyrtonema* lectin induces murine fibrosarcoma L929 cell apoptosis and autophagy via blocking Ras-Raf and PI3K-Akt signaling pathways," *Biochimie* 92:1934-1938, 2010.
Loboda et al., "A gene expression signature of RAS pathway dependence predicts response to PI3K and RAS pathway inhibitors and expands the population of RAS pathway activated tumors," *BMC Medical Genomics* 3(26):1-11, 2010.

(56) References Cited

OTHER PUBLICATIONS

Lone et al., "A substrate-free activity-based protein profiling screen for the discovery of selective PREPL inhibitors," *J. Am Chem Soc.* 133(30):11665-11674, Aug. 2011, 20 pages.
Long, "Taxol: An important compound with an impressive structure," Organic and General Chemistry at Flathead Valley Community College, Sep. 10, 2011, retrieved from https://longscience.com/2011/09/10/taxol-an-organic-compound-you-should-know-about/ on Feb. 22, 2017, 4 pages.
Malani et al., "Synthesis, characteiization and in vitro screening on bacterial, fungal and malarial strain of piprazinyl cyano biphenyl based compounds," *Bioorganic Chemistry* 51:16-23, 2013.
Margarit et al., "Structural Evidence for Feedback Activation by Ras●GTP of the Ras-Specific Nucleotide Exchange Factor SOS," *Cell* 112:685-695, Mar. 2003.
Mattos et al., "Multiple Binding Modes," in Kubinyi (ed.), *3D QSAR in Drug Design—Theory Methods and Applications*, vol. 2-3, Springer, Boston, Massachusetts, USA, 1998, pp. 243-244. (6 pages).
Maurer et al., "Small-molecule ligands bind to a distinct pocket in Ras and inhibit SOS-mediated nucleotide exchange activity," *PNAS* 109(14):5299-5304, Apr. 2012.
McGregor et al., "Expanding the Scope of Electrophiles Capable of Targeting K-Ras Oncogenes," *Biochemistry* 56:3178-3183, 2017.
McMahon, "VEGF Receptor Signaling in Tumor Angiogenesis," *The Oncologist* 5(suppl. 1):3-10, 2000.
Milburn et al., "Molecular switch for signal transduction: structural differences between active and inactive forms of protooncogenic ras proteins," *Science* 247(4945):939-945, Feb. 1990.
Minto et al., "Pharmacokinetics and Pharmacodynamics of Nandrolone Esters in Oil Vehicle: Effects of Ester, Injection Site and Injection Volume," *The Journal of Pharmacology and Experimental Therapeutics* 281(1):93-102, 1997.
Noe et al., "Selective Inhibition of Aggrecanase in Osteoarthritis Treatment," U.S. Appl. No. 60/148,464, filed Aug. 12, 1999, 92 pages.
Ohnmacht, Jr. et al., "Antimalarials. 5. α-Dibutylaminomethyl- and α-(2-Piperidyl)-3-quinolinemethanols," *Journal of Medicinal Chemistry* 14(1):17-24, 197.
Ostrem et al., "K-Ras(G12C) inhibitors allosterically control GTP affinity and effector interactions," *Nature* 503(7477):548-551, 2013. (14 pages).
Pacold et al., "Crystal structure and functional analysis of Ras binding to its effector phosphoinositide 3-kinase gamma," *Cell* 103(6):931-943, Dec. 2000.
Palmioli et al., "First experimental identification of Ras-inhibitor binding interface using a water-soluble Ras ligand," *Bioorganic and Medicinal Chemistry* 19:4217-4222, 2009.
Palmioli et al., "Selective cytotoxicity of a bicyclic Ras inhibitor in cancer cells expressing K-Ras$^{G13D}$," *Biochemical and Biophysical Research Communications* 386(4):593-597, Sep. 2009.
Pardin et al., "Synthesis and evaluation of peptidic irreversible inhibitors of tissue transglutaminase," *Bioorg Med Chem* 15(24):8379-8385, 2006.
Pathan et al., "Lead identification for the K-Ras protein: Viitual screening and combinatonal fragment-based approaches," *OncoTargets and Therapy* 9:2575-2584, 2016.
Patricelli et al., "Selective Inhibition of Oncogenic KRAS Output with Small Molecules Targeting the Inactive State," *Cancer Discovery* 6(3)316-329, 2016.
Pautsch et al., "Crystal structure of the C3bot-RaIA complex reveals a novel type of action of a bacterial exoenzyme," *The EMBO Journal* 24:3670-3680, 2005.
Pedeboscq et al., "Synthesis and evaluation of apoptosis induction of thienopyrimidine compounds on KRAS and BRAF mutated colorectal cancer cell lines," *Bioorganic & Medicinal Chemistry* 20:6724-6731, 2012.
Peri et al., "Arabinose-derived bicyclic amino acids: synthesis, conformational analysis and construction of an $\alpha_{v\beta3}$-selective RGD peptide," *J. Am. Chem. Soc., Perkins Trans* 1(5):638-644, Feb. 2002.
Peri et al., "Sugar-Derived Ras Inhibitors: Group Epitope Mapping by NMR Spectroscopy and Biological Evaluation," *Eur. J. Org. Chem.* 2006(16):3707-3720, Aug. 2006.
Peri et al., "Synthesis of bicyclic sugar azido acids and their incorporation in cyclic peptides," *Chem. Commun.* 23:2303-2304, Jan. 2000.
Pinedo et al., "Aggressive combination therapy to cure patients with metastatic cancer," *The Lancet Oncology* 1:72-73, Oct. 2000.
Pinedo et al., "Translational Research: The Role of VEGF in Tumor Angiogenesis," *The Oncologist* 5(suppl. 1):1-2, 2000.
Pingda Ren et al., "Covalent Inhibitors of KRAS G12C," U.S. Appl. No. 14/933,734, filed Nov. 5, 2015, 355 pages.
Polinsky, "High-Speed Chemistry Libraries: Assessment of Drug-Likeness," in Wermuth (ed.), *The Practice of Medicinal Chemistry*, 2nd Ed., Academic Press, Cambridge, Massachusetts, USA, 2003, pp. 147-157.
PubChem CID 10375614, Create Date: Oct. 25, 2006, date accessed Aug. 8, 2017.
PubChem Compound, "AKOS024742141," Nov. 27, 2010, retrieved from http://pubchem.ncbi.nih.gov/compound/49702158#x304 on Nov. 20, 2015, 12 pages.
PubChem Compound, "(2S,6R)-hexahydrofuro[3,2-b]furan-2,6-diyl dicarbonochloridate:Compound Summary CID 53396983," Oct. 30, 2011, retrieved from http://pubchem.ncbi.nlm.nih.gov/compound/53396983, 6 pages.
PubChem Compound, "(4-hydroxypiperidin-1-yl)-pyridin-4-ylmethanone: AC1LGBNJ," retrieved on Feb. 17, 2014, from http://pubchem.ncbi.nlm.nih.gov/summary/summary.cgi?cid=76837, Jul. 8, 2005, 5 pages.
PubChem Compound, "Compound Summary for CID 21765509: Molecular Formula C18H21N5O8," Dec. 5, 2007, retrieved from http://pubchem.ncbi.nlm.nih.gov/compound/21765509, 4 pages.
PubChem Compound, "Compound Summary for CID 21765511: Molecular Formula C18H21N5O8," Dec. 5, 2007, retrieved from http://pubchem.ncbi.nlm.nih.gov/compound/21765511, 4 pages.
PubChem Compound, "Compound Summary for CID 60018735: Molecular Formula C30H30O13," Aug. 20, 2012, retrieved from http://pubchem.ncbi.nlm.nih.gov/compound/60018735#section=Top, 1 page.
PubChem Compound, "Compound Summary for CID 72623693: AGN-PC-0D83J7," Jan. 9, 2014, retrieved from http://pubchem.ncbi.nlm.nih.gov/compound/72623693, 6 pages.
PubChem Compound, "Compound Summary for CID 9897840: Molecular Formula C50H46O20," Oct. 25, 2006, retrieved from http://pubchem.ncbi.nlm.nih.gov/compound/9897840, 6 pages.
PubChem Compound, "NJUUFNUHACGHNX-UHFFFAOYSA-N," Sep. 5, 2014, retrieved from https://pubchem.ncbi.nlm.nih.gov/compound/77081212, CID 77081212, 6 pages.
PubChem Compound, "Schembl6674271," Dec. 1, 2012, retrieved from http://pubchem.ncbi.nim.nih.gov/compound/69861127#x304, CID 69861127, 12 pages.
PubChem Compound, "Schembl6797439," Dec. 1, 2012, retrieved from http://pubchem.ncbi.nim.nih.gov/compound/69898605#x304, CID 69898605, 12 pages.
PubChem Substance Record for SID 22405303, Mar. 5, 2007, CID 2579941 (MLS000416491), retreived from https://pubchem.ncbi.nlm.nih.gov/substance/22405303, on May 15, 2017, 7 pages.
PubChem Substance Record for SID 44253980, Dec. 5, 2007, CID 966800 (1-Benzoylpyrrolidine), retrieved from https://pubchem.ncbi.nlm.nih.gov/substance/44253980#section=Top on May 11, 2017, 5 pages.
Ren et al., "Irreversible Covalent Inhibitors of the GTPASE K-RAS G12C," U.S. Appl. No. 14/777,334, filed Sep. 15, 2015, 87 pages.
Rensland et al., "Substrate and Product Structural Requirements for Binding of Nucleotides to H-ras p21: The Mechanism of Discrimination between Guanosine and Adenosine Nucleotides," *Biochemistry* 34(2):593-599, 1995.

(56) References Cited

OTHER PUBLICATIONS

Sasaki et al., "Selective Formation of Stable Triplexes Including a TA or a CG Interrupting Site with New Bicyclic Nucleoside Analogues (WNA)," *J. Am. Chem. Soc.* 126(2):516-528, Jan. 2004.
Schubbert et al., "Biochemical and Functional Characterization of Germ Line KRAS Mutations," *Molecular and Cellular Biology* 27(22):7765-7770, Nov. 2007.
Shima et al., "Discovery of small molecule Ras inhibitors that display antitumor activity by interfering with Ras, GTP-effector interaction," *Enzymes* 34(pt. b):1-23, 2013.
Singh et al., "A Gene Expression Signature Associated with "K-Ras Addiction" Reveals Regulators of EMT and Tumor Cell Survival," *Cancer Cell* 15:489-500, Jun. 2009.
Spiegel et al., "Small-molecule modulation of Ras signaling," *Nature Chemical Biology* 10:613-622, Aug. 2014.
Stefanachi et al., "1-, 3-, and 8-substituted-9-deazaxanthines as potent and selective antagonists at the human A2B adenosine receptor," *Bioorg Med Chem* 16(6):2852-2869, 2008.
STN Registry No. 1066881-73-9, "[1,4'-Bipiperidine]-4-carboxamide, 1'-(1-cyclohexen-1-ylcarbonyl)-N-(3-pyridinylmethyl)-," Oct. 27, 2008, 1 page.
STN Registry No. 1066896-20-5, "Methanone, [3-[4-(1,3-benzodioxol-5-ylmethyl)-1-piperazinyl)-1-piperidinyl]-1-cyclopenten-1-yl-," Oct. 27, 2008, 1 page.
STN Registry No. 1066915-72-7, "[3-[4-(1,3-benzodioxol-5-ylmethyl)-1-piperazinyl[-1-piperidinyl]-1-cyclohexen-1-yl-," Oct. 27, 2008, 1 page.
STN Registry No. 1069510-87-7, "[1,4'-Bipiperidine]-4-carboxadmide, 1'-(1-cyclohexen-1-ylcarbonyl]-N-(2-pyridinylmethyl)-," Nov. 2, 2008, 1 page.
STN Registry No. 1069530-02-4, "[1,4'-Bipiperidine]-4-carboxamide, 1'-(1-cyclopenten-1-ylcarbonyl]-N-(2-pyridinylmethyl)-," Nov. 2, 2008, 1 page.
STN Registry No. 1069736-48-6, "[1,4'-Bipiperidine]-4-carboxamide, 1'-(1-cyclopenten-1-ylcarbonyl]-N-(3-pyridinylmethyl)-," Nov. 2, 2008, 1 page.
STN Registry No. 1069909-93-8, "[1,4'-Bipiperidine]-4-carboxamide, 1'-(1-cyclopenten-1-ylcarbonyl]-N-(2-phenylethyl)-," Nov. 2, 2008, 1 page.
STN Registry No. 1212098-43-5, "Methanone, 1-cyclohexen-l-yl [(3R,4R)-3-hydroxy-4-[4-(2-phenylethyl)-1-piperazinyl]-1-piperidinyl]-, rel-," Mar. 21, 2010, 1 page.
STN Registry No. 1309145-12-7, "Methanone, 1-cyclopenten-l-yl [(3R,4R)-3-hydroxy-4-[4-(2-phenylethyl)-1-piperazinyl]-1-piperidinyl]-, rel-," Jun. 13, 2011, 1 page.
Streuff et al., "First asymmetric aminohydroxylation of acrylamides," *Tetrahedron: Asymmetry* 16(21):3492-3496, Oct. 2005.
Sun et al., "Discovery of small molecules that bind to K-Ras and inhibit Sos-mediated activation," *Angew Chem Int Ed Engl.* 51(25):6140-6143, 2012.
Sunaga et al., "Knockdown of Oncogenic KRAS in Non-Small Cell Lung Cancers Suppresses Tumor Growth and Sensitizes Tumor Cells to Targeted Therapy," *Molecular Cancer Therapeutics* 10(2):336-346, Feb. 2011.
Sundberg et al., "The O-Styrylnitrene Route to 2-Substituted Indoles. Pyrolysis of O-Azidostyrenes," *Journal of Organic Chemistry* 37(5):719-724, 1972.
Sydor et al., "Transient Kinetic Studies on the Interaction of Ras and the Ras-Binding Domain of c-Raf-1 Reveal Rapid Equilibration of the Complex," Biochemistry 37:14292-14299, 1998.
Taveras et al., "Ras Oncoprotein Inhibitors: The Discovery of Potent, Ras Nucleotide Exchange Inhibitors and the Structural Determination of a Drug-Protein Complex," *Bioorganic and Medicinal Chemistry* 5(1):125-133, 1997.
Terfloth et al., "Electronic Screening: Lead Finding from Database Mining," in Wennuth (ed.), *The Practice of Medicinal Chemistry*, 2nd Ed, Academic Press, Cambridge, Massachusetts, USA, 2003, pp. 131-145.
Tsubaki et al., "Reduction of metastasis, cell invasion, and adhesion in mouse osteosarcoma by YM529/ONO-5920-induced blockade of the Ras/MEK/ERK and Ras/PI3K/Akt pathway," *Toxicology and Applied Pharmacology* 259(3):402-410, Jan. 2012.
Tulshian et al., "Synthesis and Phosphodiesterase Activity of Carboxylic Acid Mimetics of Cyclic Guanosine 3',5'-Monophosphate," *J. Med. Chem.* 36(9):1210-1220, Jan. 1993.
Vetter et al., "The Guanine Nucleotide-Binding Switch in Three Dimensions," *Science* 294(5545):1299-1304, Nov. 2001.
Vippagunta et al., "Crystalline solids," *Advanced Drug Delivery Reviews* 48:3-26, 2001.
Wolff, (ed.), *Burger's Medicinal Chemistry and Drug Discovery*, Fifth Edition, vol. 1: *Principles and Practice*, San Diego, California, John Wiley & Sons, 1994, pp. 975-977.
Wu et al., "Stereoselective synthesis of dioxabicycles from 1-C-allyl-2-O-benzyl-glycosides—an intramolecular cyclization between 2-O-benzyl oxygen and the allyl double bond," *Can. J. Chem.* 84(1):597-602, Jan. 2006.
Xu et al., "Design, Synthesis, and Biological Evaluation of 2-Oxo-3,4-dihydropyrimido[4,5-d]pyrimidinyl Derivatives as New Irreversible Epidermal Growth Factor Receptor Inhibitors with Improved Pharmacokinetic Properties," *Journal of Medicinal Chemistry* 56:8803-8813, 2013.
Yan et al., "Discovery and characterization of small molecules that target the GRPase Ral," *Nature* 515:443-447, Nov. 2014, 15 pages.
Yang et al., "Fragment-Based Discovery of Nonpeptidic BACE-1 Inhibitors Using Tethering," *Biochemistry* 48:4488-4496, 2009.
Young et al., "Oncogenic and Wild-type Ras Play Divergent Roles in the Regulation of Mitogen-Activated Protein Kinase Signaling," *Cancer Discovery* 3(1):112-123, Jan. 2013.
Zenkl et al., "Sugar-Responsive Fluorescent Nanospheres," *Macromol. Biosci.* 8:146-152, 2008.
PubChem Compound "(Z)-1-(4-(5-(5-(Trifluoromethyl)-1,2,4-oxadiazol-3-yl)pyridin-2-yl)piperazin-1-yl)but-2-en-1-one" CID: 49702158, Create: Nov. 27, 2010, 4 pages.
Canon et al., "The Clinical KRAS (G12C) Inhibitor AMG 510 Drives Anti-Tumor Immunity," *Nature* 575:217-223, 2019 (26 Pages).
Horig et al., "From bench to clinic and back: perspective on the 1st IQPC translational research conference," *Journal of Translational Medicine* 2(44):1-8, 2004.
Keith et al., "Heteroarylureas with spirocyclic diamine cores as inhibitors of fatty acid amide hydrolase," *Bioogranic & Medicinal Chemistry Letters* 24:737-741, 2014.
Liu et al., "Targeting the untargetable KRAS in cancer therapy," *Acta Pharmaceutica Sinica B* 9(5):871-879, 2019.
Mirguet et al., "From ApoA1 upregulation to BET family bromodomain inhibition: Discovery of I-BET151," *Bioorganic & Medicinal Chemistry Letters* 22:2963-2967, 2012.
Reilly et al., "Examination of Diazaspiro Cores as Piperazine Bioisosteres in the Olaparib Framework Shows Reduced DNA Damage and Cytotoxicity," *J. Med. Chem.* 61:5367-5379, 2018.
Schafer et al., "Failure is an option: learning from unsuccessful proof-of-concept trials," *Drug Discovery Today* 13(21/22):913-916, 2008.
Silverman, "Prodrugs and Drug Delivery Systems," *The Organic Chemistry of Drug Design and Drug Action*, p. 352-399, 1992.
STN Registry Nos. 1179043-51-6; 1156698-93-9; 1156156-36-3; 1070748-55-8; 1; 1070685-77-6; 1070667-53-6; 1070315-89-7; 1069961-90-5; 1069566-58-0; 1065560-16-8; 1065554-88-2; 1061025-62-4; 1060435-61-1; 958948-04-4; 958839-16-2, 6 pages.
Zheng et al., "The use of spirocyclic scaffolds in drug discovery," *Bioorganic & Medicinal Chemistry Letters* 24:3673-3682, 2014.

* cited by examiner

| Oncogene | Tumor Type | Cumulative Mutation Frequency (All Tumors) |
|---|---|---|
| Bcr–Abl | 90% CML | <1% |
| EGFR | 10% NSCLC | <5% |
| ALK | 5% NSCLC | <1% |
| B–Raf | 66% Melanoma | <5% |
| Flt3 | 25% AML | <1% |
| PI3kα | 25% Breast; 25% Endometrial; 15% CRC | 15–20% |
| K–Ras | >80% Pancreatic; >40% colon >20% lung | ~20% |

*FIG. 3*

SUBSTITUTED QUINAZOLINE COMPOUNDS AND METHODS OF USE THEREOF

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

BACKGROUND

Technical Field

The present invention is generally directed to novel compounds and methods for their preparation and use as therapeutic or prophylactic agents, for example for treatment of cancer.

Description of the Related Art

RAS represents a group of closely related monomeric globular proteins of 189 amino acids (21 kDa molecular mass) which are associated with the plasma membrane and which bind either GDP or GTP. RAS acts as a molecular switch. When RAS contains bound GDP, it is in the resting or off position and is "inactive". In response to exposure of the cell to certain growth promoting stimuli, RAS is induced to exchange its bound GDP for a GTP. With GTP bound, RAS is "switched on" and is able to interact with and activate other proteins (its "downstream targets"). The RAS protein itself has a very low intrinsic ability to hydrolyze GTP back to GDP, thus turning itself into the off state. Switching RAS off requires extrinsic proteins termed GTPase-activating proteins (GAPs) that interact with RAS and greatly accelerate the conversion of GTP to GDP. Any mutation in RAS which affects its ability to interact with GAP or to convert GTP back to GDP will result in a prolonged activation of the protein and consequently a prolonged signal to the cell telling it to continue to grow and divide. Because these signals result in cell growth and division, overactive RAS signaling may ultimately lead to cancer.

Structurally, RAS proteins contain a G domain which is responsible for the enzymatic activity of RAS—the guanine nucleotide binding and the hydrolysis (GTPase reaction). It also contains a C-terminal extension, known as the CAAX box, which may be post-translationally modified and is responsible for targeting the protein to the membrane. The G domain is approximately 21-25 kDa in size and it contains a phosphate binding loop (P-loop). The P-loop represents the pocket where the nucleotides are bound in the protein, and this is the rigid part of the domain with conserved amino acid residues which are essential for nucleotide binding and hydrolysis (Glycine 12, Threonine 26 and Lysine 16). The G domain also contains the so called Switch I (residues 30-40) and Switch II (residues 60-76) regions, both of which are the dynamic parts of the protein which are often represented as the "spring-loaded" mechanism because of their ability to switch between the resting and loaded state. The key interaction is the hydrogen bonds formed by Threonine-35 and glycine-60 with the γ-phosphate of GTP which maintain Switch 1 and Switch 2 regions respectively in their active conformation. After hydrolysis of GTP and release of phosphate, these two relax into the inactive GDP conformation.

The most notable members of the RAS subfamily are HRAS, KRAS and NRAS, mainly for being implicated in many types of cancer. However, there are many other members including DIRAS1; DIRAS2; DIRAS3; ERAS; GEM; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS and RRAS2.

Mutations in any one of the three main isoforms of RAS (HRAS, NRAS, or KRAS) genes are among the most common events in human tumorigenesis. About 30% of all human tumors are found to carry some mutation in RAS genes. Remarkably, KRAS mutations are detected in 25-30% of tumors. By comparison, the rates of oncogenic mutation occurring in the NRAS and HRAS family members are much lower (8% and 3% respectively). The most common KRAS mutations are found at residue G12 and G13 in the P-loop and at residue Q61.

G12C is a frequent mutation of KRAS gene (glycine-12 to cysteine). This mutation had been found in about 13% of cancer occurrences, about 43% of lung cancer occurrences, and in almost 100% of MYH-associates polyposis (familial colon cancer syndrome). However targeting this gene with small molecules is a challenge.

Accordingly, while progress has been made in this field, there remains a need in the art for improved compounds and methods for treatment of cancer, for example by inhibition of KRAS, HRAS or NRAS. The present invention fulfills this need and provides further related advantages.

BRIEF SUMMARY

In brief, the present invention provides compounds, including stereoisomers, pharmaceutically acceptable salts, tautomers and prodrugs thereof, which are capable of modulating G12C mutant KRAS, HRAS and/or NRAS proteins. In some instances, the compounds act as electrophiles which are capable of forming a covalent bond with the cysteine residue at position 12 of a KRAS, HRAS or NRAS G12C mutant protein. Methods for use of such compounds for treatment of various diseases or conditions, such as cancer, are also provided.

In one embodiment, compounds having the following structure (I) are provided:

(I)

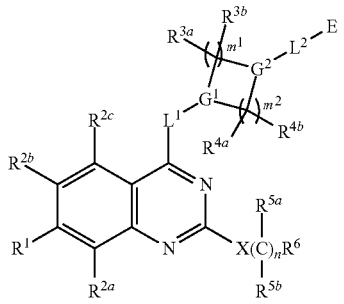

or a pharmaceutically acceptable salt, stereoisomer or prodrug thereof, wherein $R^1$, $R^{2a}$, $R^{2b}$, $R^{2c}$, $R^{3a}$, $R^{3b}$, $R^{4a}$, $R^{4b}$, $R^{5a}$, $R^{5b}$, $R^6$, $G^1$, $G^2$, $L^1$, $L^2$, $m^1$, $m^2$, n, X and E are as defined herein. Pharmaceutical compositions comprising one or more compounds of structure (I) and a pharmaceutically acceptable carrier are also provided in various other embodiments.

In a different embodiment is provided a compound having the following structure (II):

(II)

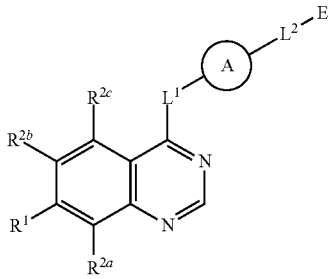

or a pharmaceutically acceptable salt, stereoisomer or prodrug thereof, wherein $R^1$, $R^{2a}$, $R^{2b}$, $R^{2c}$, A, $L^1$, $L^2$ and E are as defined herein. Pharmaceutical compositions comprising one or more compounds of structure (II) and a pharmaceutically acceptable carrier are also provided in various other embodiments.

In other different embodiments, a compound of structure (III) is provided:

(III)

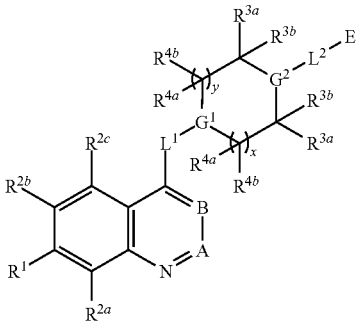

or a pharmaceutically acceptable salt, stereoisomer or prodrug thereof, wherein $R^1$, $R^{2a}$, $R^{2b}$, $R^{2c}$, $R^{3a}$, $R^{3b}$, $R^{4a}$, $R^{4b}$, A, B, $G^1$, $G^2$, $L^1$, $L^2$, x, y and E are as defined herein. Pharmaceutical compositions comprising one or more compounds of structure (II) and a pharmaceutically acceptable carrier are also provided in various other embodiments.

In other embodiments, the present invention provides a method for treatment of cancer, the method comprising administering an effective amount of a pharmaceutical composition comprising any one or more of the compounds of structure (I), (II) or (III) to a subject in need thereof.

Other provided methods include a method for regulating activity of a KRAS, HRAS or NRAS G12C mutant protein, the method comprising reacting the KRAS, HRAS or NRAS G12C mutant protein with any one of the compounds of structure (I), (II) or (III). In other embodiments, a method for inhibiting proliferation of a cell population, the method comprising contacting the cell population with any one of the compounds of structure (I) is also provided.

In other embodiments, the invention is directed to a method for treating a disorder mediated by a KRAS, HRAS or NRAS G12C mutation in a subject in need thereof, the method comprising:

determining if the subject has a KRAS, HRAS or NRAS G12C mutation; and if the subject is determined to have the KRAS, HRAS or NRAS G12C mutation, then administering to the subject a therapeutically effective amount of a pharmaceutical composition comprising any one or more compounds of structure (I), (II) or (III).

In still more embodiments, the invention is directed to a method for preparing a labeled KRAS, HRAS or NRAS G12C mutant protein, the method comprising reacting the KRAS, HRAS or NRAS G12C mutant with a compound of structure (I), (II) or (III), to result in the labeled KRAS, HRAS or NRAS G12C protein.

These and other aspects of the invention will be apparent upon reference to the following detailed description.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve figure legibility.

Further, the particular shapes of the elements as drawn are not intended to convey any information regarding the actual shape of the particular elements, and have been solely selected for ease of recognition in the figures.

FIG. 3 shows some common oncogenes, their respective tumor type and cumulative mutation frequencies (all tumors).

DETAILED DESCRIPTION

Figure 1:
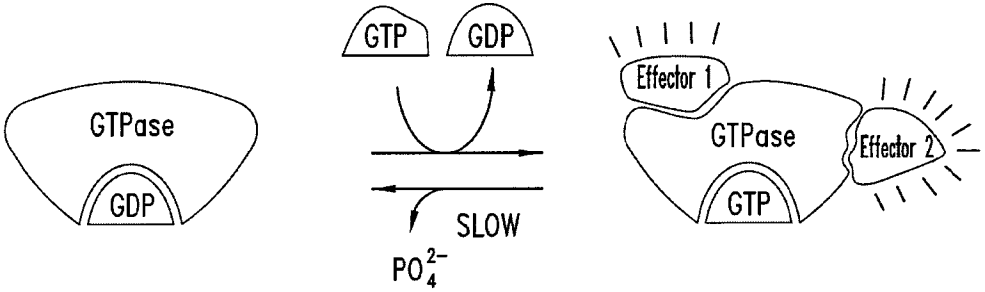
FIG. 1 illustrates the enzymatic activity of RAS.
Figure 2:
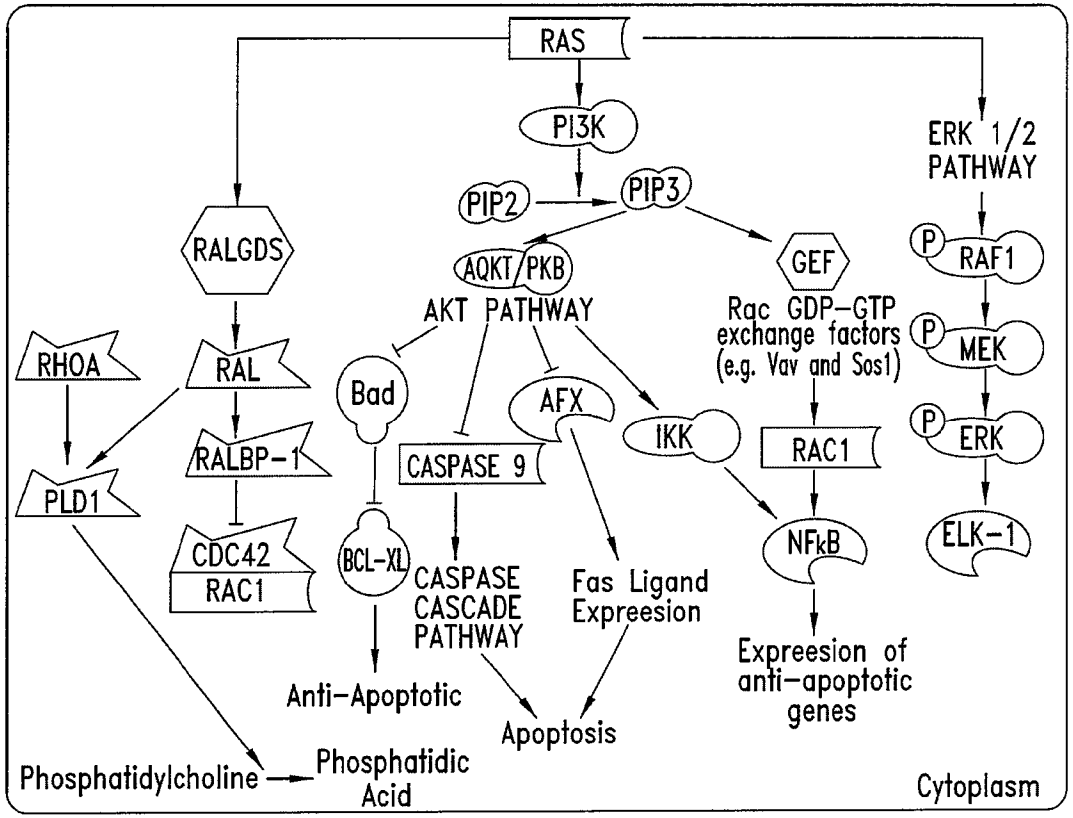
FIG. 2 depicts a signal transduction pathway for RAS.

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless defined otherwise, all technical and scientific terms used herein have the same meaning as is commonly understood by one of skill in the art to which this invention belongs. As used in the specification and claims, the singular form "a", "an" and "the" include plural references unless the context clearly dictates otherwise.

"Amidinyl" refers to a radical of the form —(C═$NR_a$)$NR_bR_c$, wherein $R_a$, $R_b$ and $R_c$ are each independently H or $C_1$-$C_6$ alkyl.

"Amino" refers to the —$NH_2$ radical.

"Aminylsulfone" refers to the —$S(O)_2NH_2$ radical.

"Carboxy" or "carboxyl" refers to the —$CO_2H$ radical.

"Cyano" refers to the —CN radical.

"Guanidinyl" refers to a radical of the form —$NR_d(C{=}NR_a)NR_bR_c$, wherein $R_a$, $R_b$, $R_c$, and $R_d$ are each independently H or $C_1$-$C_6$ alkyl.

"Hydroxy" or "hydroxyl" refers to the —OH radical.

"Imino" refers to the =NH substituent.

"Nitro" refers to the —$NO_2$ radical.

"Oxo" refers to the =O substituent.

"Thioxo" refers to the =S substituent.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Alkyl includes alkenyls (one or more carbon-carbon double bonds) and alkynyls (one or more carbon-carbon triple bonds such as ethynyl and the like). "Amidinylalkyl" refers to an alkyl group comprising at least one amidinyl substituent. "Guanidinylalkyl" refers to an alkyl group comprising at least one guanidinyl substituent. Unless stated otherwise specifically in the specification, an alkyl, amidinylalkyl and/or guanidinylalkyl group is optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain is optionally substituted.

"Alkylcycloalkyl" refers to a radical of the formula —$R_bR_d$ where $R_b$ is cycloalkyl as defined herein and $R_d$ is an alkyl radical as defined above. Unless stated otherwise specifically in the specification, a alkylcycloalkyl group is optionally substituted.

"Alkoxy" refers to a radical of the formula —$OR_a$ where $R_a$ is an alkyl radical as defined above containing one to twelve carbon atoms. "Amidinylalkyloxy" refers to an alkoxy group comprising at least one amidinyl substituent on the alkyl group. "Guanidinylalkyloxy" refers to an alkoxy group comprising at least one guanidinyl substituent on the alkyl group. "Alkylcarbonylaminylalkyloxy" refers to an alkoxy group comprising at least one alkylcarbonylaminyl substituent on the alkyl group. "Heterocyclylalkyloxy" refers to an alkoxy group comprising at least one heterocyclyl substituent on the alkyl group. "Heteroarylalkyloxy" refers to an alkoxy group comprising at least one heteroaryl substituent on the alkyl group. "Aminylalkyloxy" refers to an alkoxy group comprising at least one substituent of the form —$NR_aR_b$, where $R_a$ and $R_b$ are each independently H or $C_1$-$C_6$ alkyl, on the alkyl group. Unless stated otherwise specifically in the specification, an alkoxy, amidinylalkyloxy, guanidinylalkyloxy, alkylcarbonylaminyl, heterocyclylalkyloxy, heteroarlyalkyloxy and/or aminylalkyloxy group is optionally substituted.

"Alkoxyalkyl" refers to a radical of the formula —$R_bOR_a$ where $R_a$ is an alkyl radical as defined above containing one to twelve carbon atoms and $R_b$ is an alkylene radical as defined above containing one to twelve carbon atoms. Unless stated otherwise specifically in the specification, an alkoxyalkyl group is optionally substituted.

"Alkoxycarbonyl" refers to a radical of the formula —$C(=O)OR_a$ where $R_a$ is an alkyl radical as defined above containing one to twelve carbon atoms. Unless stated otherwise specifically in the specification, an alkoxycarbonyl group is optionally substituted.

"Aryloxy" refers to a radical of the formula —$OR_a$ where $R_a$ is an aryl radical as defined herein. Unless stated otherwise specifically in the specification, an aryloxy group is optionally substituted.

"Alkylaminyl" refers to a radical of the formula —$NHR_a$ or —$NR_aR_a$ where each $R_a$ is, independently, an alkyl radical as defined above containing one to twelve carbon atoms. A "haloalkylaminyl" group is an alkylaminyl group comprising at least one halo substituent on the alkyl group. A "hydroxylalkylaminyl" group is an alkylaminyl group comprising at least one hydroxyl substituent on the alkyl group. An "amidinylalkylaminyl" group is an alkylaminyl group comprising at least one amidinyl substituent on the alkyl group. A "guanidinylalkylaminyl" group is an alkylaminyl group comprising at least one guanidinyl substituent on the alkyl group. Unless stated otherwise specifically in the specification, an alkylaminyl, haloalkylaminyl, hydroxylalkylaminyl, amidinylalkylaminyl and/or guanidinylalkylaminyl group is optionally substituted.

"Aminylalkyl" refers to an alkyl group comprising at least one aminyl substituent (—$NR_aR_b$ wherein $R_a$ and $R_b$ are each independently H or $C_1$-$C_6$ alkyl). The aminyl substituent can be on a tertiary, secondary or primary carbon. In some embodiments of aminylalkyl, both $R_a$ and $R_b$ are H. Unless stated otherwise specifically in the specification, an aminylalkyl group is optionally substituted.

"Aminylalkylaminyl" refers to a radical of the formula —$NR_aR_b$ wherein $R_a$ is H or $C_1$-$C_6$ alkyl and $R_b$ is aminylalkyl. Unless stated otherwise specifically in the specification, an aminylalkylaminyl group is optionally substituted.

"Aminylalkoxy" refers to a radical of the formula —$OR_aNH_2$ wherein $R_a$ is alkylene. Unless stated otherwise specifically in the specification, an aminylalkoxy group is optionally substituted.

"Alkylaminylalkoxy" refers to a radical of the formula —$OR_aNR_bR_c$ wherein $R_a$ is alkylene and $R_b$ and $R_c$ are each independently H or $C_1$-$C_6$ alkyl, provided one of $R_b$ or $R_c$ is $C_1$-$C_6$ alkyl. Unless stated otherwise specifically in the specification, an alkylaminylalkoxy group is optionally substituted.

"Alkylcarbonylaminyl" refers to a radical of the formula —$NH(C{=}O)R_a$ where $R_a$ is an alkyl radical as defined above containing one to twelve carbon atoms. Unless stated otherwise specifically in the specification, an alkylcarbonylaminyl group is optionally substituted. An alkenylcarbonylaminyl is an alkylcarbonylaminyl containing at least one carbon-carbon double bond. An alkenylcarbonylaminyl group is optionally substituted.

"Alkylcarbonylaminylalkoxy" refers to a radical of the formula —$OR_bNH(C{=}O)R_a$ where $R_a$ is an alkyl radical as defined above containing one to twelve carbon atoms and $R_b$ is alkylene. Unless stated otherwise specifically in the specification, an alkylcarbonylaminylalkoxy group is optionally substituted.

"Alkylaminylalkyl" refers to an alkyl group comprising at least one alkylaminyl substituent. The alkylaminyl substituent can be on a tertiary, secondary or primary carbon. Unless stated otherwise specifically in the specification, an alkylaminylalkyl group is optionally substituted.

"Aminylcarbonyl" refers to a radical of the formula —C(=O)$R_aR_b$ where $R_a$ and $R_b$ are each independently H or alkyl. Unless stated otherwise specifically in the specification, an aminylcarbonyl group is optionally substituted.

"Alkylaminylcarbonyl" refers to a radical of the formula —C(=O)$NR_aR_b$, where $R_a$ and $R_b$ are each independently H or alkyl, provided at least one of $R_a$ or $R_b$ is alkyl. Unless stated otherwise specifically in the specification, an alkylaminylcarbonyl group is optionally substituted.

"Aminylcarbonylalkyl" refers to a radical of the formula —$R_c$C(=O)$NR_aR_b$, where $R_a$ and $R_b$ are each independently H or alkyl and R, is alkylene. Unless stated otherwise specifically in the specification, an aminylcarbonylalkyl group is optionally substituted.

"Aminylcarbonycycloalkylalkyl" refers to a radical of the formula —$R_c$C(=O)$NR_aR_b$, where $R_a$ and $R_b$ are each independently H or alkyl and $R_c$ is cycloalkyl. Unless stated otherwise specifically in the specification, an aminylcarbonylcycloalkyl group is optionally substituted.

"Aryl" refers to a carbocyclic ring system radical comprising hydrogen, 6 to 18 carbon atoms and at least one aromatic ring. For purposes of this invention, the aryl radical is a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. Unless stated otherwise specifically in the specification, an aralkyl group is optionally substituted.

"Arylalkyloxy" refers to a radical of the formula —$OR_b$—$R_c$ where $R_b$ is an alkylene chain as defined above and $R_c$ is one or more aryl radicals as defined above, for example, benzyl, diphenylmethyl and the like. Unless stated otherwise specifically in the specification, an arylalkyloxy group is optionally substituted.

"Arylalkylaminyl" refers to a radical of the formula —N($R_a$)$R_b$—$R_c$ where $R_a$ is H or $C_1$-$C_6$ alkyl, $R_b$ is an alkylene chain as defined above and $R_c$ is one or more aryl radicals as defined above, for example, benzyl, diphenylmethyl and the like. Unless stated otherwise specifically in the specification, an arylalkylaminyl group is optionally substituted.

"Carboxyalkyl" refers to a radical of the formula —$R_b$—$R_c$ where $R_b$ is an alkylene chain as defined above and $R_c$ is a carboxyl group as defined above. Unless stated otherwise specifically in the specification, carboxyalkyl group is optionally substituted.

"Cyanoalkyl" refers to a radical of the formula —$R_b$—$R_c$ where $R_b$ is an alkylene chain as defined above and $R_c$ is a cyano group as defined above. Unless stated otherwise specifically in the specification, a cyanoalkyl group is optionally substituted.

"Carbocyclic" or "carbocycle" refers to a ring system, wherein each of the ring atoms are carbon.

"Cycloalkyl" refers to a stable non-aromatic monocyclic or polycyclic carbocyclic radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethylbicyclo[2.2.1]heptanyl, and the like. A "cycloalkenyl" is a cycloalkyl comprising one or more carbon-carbon double bonds within the ring. Unless otherwise stated specifically in the specification, a cycloalkyl (or cycloalkenyl) group is optionally substituted.

"Cyanocycloalkyl" refers to a radical of the formula —$R_b$—$R_c$ where $R_b$ is cycloalkyl and $R_c$ is a cyano group as defined above. Unless stated otherwise specifically in the specification, a cyanocycloalkyl group is optionally substituted.

"Cycloalkylaminylcarbonyl" refers to a radical of the formula —C(=O)$NR_aR_b$, where $R_a$ and $R_b$ are each independently H or cycloalkyl, provided at least one of $R_a$ or $R_b$ is cycloalkyl. Unless stated otherwise specifically in the specification, n cycloalkylaminylcarbonyl group is optionally substituted.

"Cycloalkylalkyl" refers to a radical of the formula —$R_bR_d$ where $R_b$ is an alkylene chain as defined above and $R_d$ is a cycloalkyl radical as defined above. Unless stated otherwise specifically in the specification, a cycloalkylalkyl group is optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring is replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group is optionally substituted.

"Haloalkoxy" refers to a radical of the formula —$OR_a$ where $R_a$ is a haloalkyl radical as defined herein containing one to twelve carbon atoms. Unless stated otherwise specifically in the specification, a haloalkoxy group is optionally substituted.

"Heterocyclyl" or "heterocyclic ring" refers to a stable 3- to 18-membered non-aromatic ring radical having one to twelve ring carbon atoms (e.g., two to twelve) and from one to six ring heteroatoms selected from the group consisting of nitrogen, oxygen and sulfur. Unless stated otherwise specifically in the specification, the heterocyclyl radical is a monocyclic, bicyclic, tricyclic or tetracyclic ring system, which may include fused, spirocyclic ("spiro-heterocyclyl") and/or bridged ring systems; and the nitrogen, carbon or sulfur atoms in the heterocyclyl radical is optionally oxidized; the nitrogen atom is optionally quaternized; and the heterocyclyl radical is partially or fully saturated.

Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification. "Heterocyclyloxy" refers to a heterocyclyl group bound to the remainder of the molecule via an oxygen bond (—O—). "Heterocyclylaminyl" refers to a heterocyclyl group bound to the remainder of the molecule via a nitrogen bond (—$NR_a$—, where $R_a$ is H or $C_1$-$C_6$ alkyl). Unless stated otherwise specifically in the specification, a heterocyclyl, heterocyclyloxy and/or heterocyclylaminyl group is optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group is optionally substituted.

"Heterocyclylalkyl" refers to a radical of the formula —$R_bR_e$ where $R_b$ is an alkylene chain as defined above and $R_e$ is a heterocyclyl radical as defined above, and if the heterocyclyl is a nitrogen-containing heterocyclyl, the heterocyclyl is optionally attached to the alkyl radical at the nitrogen atom. Unless stated otherwise specifically in the specification, a heterocyclylalkyl group is optionally substituted.

"Heterocyclylalkyloxy" refers to a radical of the formula —$OR_bR_e$ where $R_b$ is an alkylene chain as defined above and $R_e$ is a heterocyclyl radical as defined above, and if the heterocyclyl is a nitrogen-containing heterocyclyl, the heterocyclyl is optionally attached to the alkyl radical at the nitrogen atom. Unless stated otherwise specifically in the specification, a heterocyclylalkyloxy group is optionally substituted.

"Heterocyclylalkylaminyl" refers to a radical of the formula —$N(R_c)R_bR_e$ where $R_b$ is an alkylene chain as defined above and $R_e$ is a heterocyclyl radical as defined above, and if the heterocyclyl is a nitrogen-containing heterocyclyl, the heterocyclyl is optionally attached to the alkyl radical at the nitrogen atom, $R_c$ is H or $C_1$-$C_6$ alkyl. Unless stated otherwise specifically in the specification, a heterocyclylalkyloxy group is optionally substituted.

"Heteroaryl" refers to a 5- to 14-membered ring system radical comprising hydrogen atoms, one to thirteen ring carbon atoms, one to six ring heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). "Heteroaryloxy" refers to a heteroaryl group bound to the remainder of the molecule via an oxygen bond (—O—). "Heteroarylaminyl" refers to a heteroaryl group bound to the remainder of the molecule via a nitrogen bond (—$NR_a$—, where $R_a$ is H or $C_1$-$C_6$ alkyl). Unless stated otherwise specifically in the specification, a heteroaryl, heteroaryloxy and/or heteroarylaminyl group is optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group is optionally substituted.

"Heteroarylalkyl" refers to a radical of the formula —$R_bR_f$ where $R_b$ is an alkylene chain as defined above and $R_f$ is a heteroaryl radical as defined above. Unless stated otherwise specifically in the specification, a heteroarylalkyl group is optionally substituted.

"Heteroarylalkyloxy" refers to a radical of the formula —$OR_bR_f$ where $R_b$ is an alkylene chain as defined above and $R_f$ is a heteroaryl radical as defined above, and if the heteroaryl is a nitrogen-containing heterocyclyl, the heterocyclyl is optionally attached to the alkyl radical at the nitrogen atom. Unless stated otherwise specifically in the specification, a heteroarylalkyloxy group is optionally substituted.

"Heteroarylalkylaminyl" refers to a radical of the formula —$NR_cR_bR_f$ where $R_b$ is an alkylene chain as defined above and $R_f$ is a heteroaryl radical as defined above, and if the heteroaryl is a nitrogen-containing heterocyclyl, the heterocyclyl is optionally attached to the alkyl radical at the nitrogen atom, and $R_c$ is H or $C_1$-$C_6$ alkyl. Unless stated otherwise specifically in the specification, a heteroarylalkyloxy group is optionally substituted. "Hydroxylalkyl" refers to an alkyl group comprising at least one hydroxyl substituent. The —OH substituent may be on a primary, secondary or tertiary carbon. Unless stated otherwise specifically in the specification, a hydroxylalkyl group is optionally substituted. "Hydroxylalkylaminyl" is an alkylaminyl groups comprising at least one —OH substituent, which is on a primary, secondary or tertiary carbon. Unless stated otherwise specifically in the specification, a hydroxylalkylaminyl group is optionally substituted.

"Phosphate" refers to the —$OP(=O)(R_a)R_b$ group, where $R_a$ is OH, $O^-$ or $OR_c$ and $R_b$ is OH, $O^-$, $OR_c$, or a further phosphate group (e.g., to form a di- or triphosphate), wherein $R_c$ is a counter ion (e.g., Na+ and the like).

"Phosphoalkoxy" refers to an alkoxy group, as defined herein, which is substituted with at least least one phosphate group, as defined herein. Unless stated otherwise specifically in the specification, an phosphoalkoxy group is optionally substituted.

"Thioalkyl" refers to a radical of the formula —$SR_a$ where $R_a$ is an alkyl radical as defined above containing one to twelve carbon atoms. Unless stated otherwise specifically in the specification, a thioalkyl group is optionally substituted.

The term "substituted" used herein means any of the above groups (e.g., alkyl, alkylene, alkylcycloalkyl, alkoxy, amidinylalkyloxy, guanidinylalkyloxy, alkylcarbonylaminylalkyloxy, heterocyclylalkyloxy, heteroarylalkyloxy, aminylalkyloxy, alkoxyalkyl, alkoxycarbonyl, haloalkylaminyl, hydroxylalkylaminyl, amidinylalkylaminyl, guanidinylalkylaminyl, aminylalkyl, aminylalkylaminyl, aminylalkoxy, alkylaminylalkoxy aryloxy, alkylaminyl, alkylcarbonylaminyl, alkylaminylalkyl, aminylcarbonyl, alkylaminylcarbonyl, alkylcarbonylaminylalkoxy, aminylcarbonylalkyl, aminylcarbonycycloalkylalkyl, thioalkyl, aryl, aralkyl, arylalkyloxy, arylalkylaminyl, carboxyalkyl, cyanoalkyl, cycloalkyl, cycloalkyloxy, cycloalkylaminyl, cyanocycloalkyl, cycloalkylaminylcarbonyl, cycloalkylalkyl, haloalkyl, haloalkoxy, heterocyclyl, heterocyclyloxy, heterocyclylaminyl, N-heterocyclyl, heterocyclylalkyl, heterocyclylalkyloxy, heterocyclylalkylaminyl, heteroaryl, N-heteroaryl, heteroarylalkyl, heteroarylalkyloxy, heteroarylalkylaminyl, hydroxylalkylaminyl, phosphoalkoxy and/or hydroxylalkyl) wherein at least one hydrogen atom (e.g., 1, 2, 3 or all hydrogen atoms) is replaced by a bond to a non-hydrogen atom such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $—NR_gR_h$, $—NR_gC(=O)R_h$, $—NR_gC(=O)NR_gR_h$, $—NR_gC(=O)OR_h$, $—NR_gSO_2R_h$, $—OC(=O)NR_gR_h$, $—OR_g$, $—SR_g$, $—SOR_g$, $—SO_2R_g$, $—OSO_2R_g$, $—SO_2OR_g$, $=NSO_2R_g$, and $—SO_2NR_gR_h$. "Substituted also means any of the above groups in which one or more hydrogen atoms are replaced with $—C(=O)R_g$, $—C(=O)OR_g$, $—C(=O)NR_gR_h$, $—CH_2SO_2R_g$, $—CH_2SO_2NR_gR_h$. In the foregoing, $R_g$ and $R_h$ are the same or different and independently hydrogen, alkyl, alkoxy, alkylaminyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an aminyl, cyano, hydroxyl, imino, nitro, oxo, thioxo, halo, alkyl, alkoxy, alkylaminyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Electrophile" or "electrophilic moiety" is any moiety capable of reacting with a nucleophile (e.g., a moiety having a lone pair of electrons, a negative charge, a partial negative charge and/or an excess of electrons, for example a —SH group). Electrophiles typically are electron poor or comprise atoms which are electron poor. In certain embodiments an electrophile contains a positive charge or partial positive charge, has a resonance structure which contains a positive charge or partial positive charge or is a moiety in which delocalization or polarization of electrons results in one or more atom which contains a positive charge or partial positive charge. In some embodiments, the electrophiles comprise conjugated double bonds, for example an α,β-unsaturated carbonyl or α,β-unsaturated thiocarbonyl compound.

The term "effective amount" or "therapeutically effective amount" refers to that amount of a compound described herein that is sufficient to effect the intended application including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refer to an approach for obtaining beneficial or desired results with respect to a disease, disorder or medical condition including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

"Pharmaceutically acceptable salt" includes both acid and base addition salts.

All compounds of the invention (i.e., compounds of structure (I), (II) or (III)) which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The terms "antagonist" and "inhibitor" are used interchangeably, and they refer to a compound having the ability to inhibit a biological function of a target protein, whether by inhibiting the activity or expression of the protein, such as KRAS, HRAS or NRAS G12C. Accordingly, the terms "antagonist" and "inhibitors" are defined in the context of the biological role of the target protein. While preferred antagonists herein specifically interact with (e.g. bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g. bind to) the target, compounds that initiate or enhance a biological activity of the target polypeptide by interacting with other members of the signal transduction pathway of which the target polypeptide is a member are also specifically included within this definition.

As used herein, "agent" or "biologically active agent" refers to a biological, pharmaceutical, or chemical compound or other moiety. Non-limiting examples include a simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "selective inhibition" or "selectively inhibit" refers to a biologically active agent refers to the agent's ability to preferentially reduce the target signaling activity as compared to off-target signaling activity, via direct or indirect interaction with the target.

"Subject" refers to an animal, such as a mammal, for example a human. The methods described herein can be useful in both human therapeutics and veterinary applications. In some embodiments, the subject is a mammal, and in some embodiments, the subject is human.

"Mammal" includes humans and both domestic animals such as laboratory animals and household pets (e.g., cats, dogs, swine, cattle, sheep, goats, horses, rabbits), and non-domestic animals such as wildlife and the like.

"Radiation therapy" means exposing a subject, using routine methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium-153-EDTMP, or high-energy radiation, including without limitation x-rays, gamma rays, and neutrons.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

"Prodrug" is meant to indicate a compound that may be converted under physiological conditions or by solvolysis to a biologically active compound described herein (e.g., compound of structure (I), (II) or (III)). Thus, the term "prodrug" refers to a precursor of a biologically active compound that is pharmaceutically acceptable. In some aspects, a prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

In some embodiments, prodrugs include compounds of structure (I), (II) or (III) having a phosphate, phosphoalkoxy, ester or boronic ester substituent. Without being bound by theory, it is believed that such substituents are converted to a hydroxyl group under physiological conditions. Accordingly, embodiments include any of the compounds disclosed herein, wherein a hydroxyl group has been replaced with a phosphate, phosphoalkoxy, ester or boronic ester group, for example a phosphate or phosphoalkoxy group. For example, in some embodiments a hydroxyl group on the $R^1$ moiety is replaced with a phosphate, phosphoalkoxy, ester or boronic ester group, for example a phosphate or alkoxy phosphate group. Exemplary prodrugs of certain embodiments thus include compounds having one of the following $R^1$ moieties:

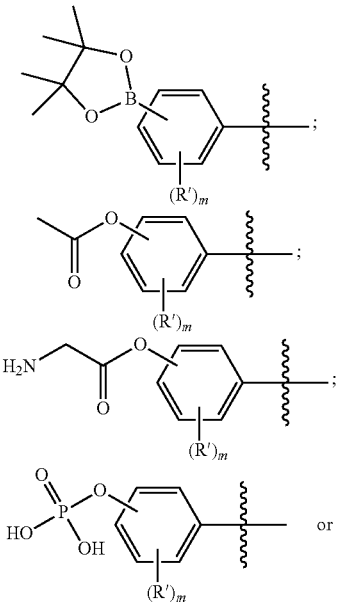

-continued

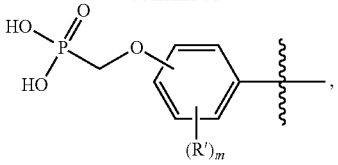

wherein each R' is independently H or an optional substituent, and n is 1, 2, 3 or 4.

The term "in vivo" refers to an event that takes place in a subject's body.

Embodiments of the invention disclosed herein are also meant to encompass all pharmaceutically acceptable compounds of structure (I), (II) or (III) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, C, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to pharmacologically important site of action. Certain isotopically-labeled compounds of structure (I), (II) or (III), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence are preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of structure (I), (II) or (III) can generally be prepared by conventional techniques known to those skilled in the art or by processes analogous to those described in the Preparations and Examples as set out below using an appropriate isotopically-labeled reagent in place of the non-labeled reagent previously employed.

Certain embodiments are also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, embodiments include compounds produced by a process comprising administering a compound of this invention to a mammal for a period of time sufficient to yield a metabolic product thereof. Such products are typically identified by administering a radiolabeled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

Often crystallizations produce a solvate of the compound of the invention. As used herein, the term "solvate" refers to an aggregate that comprises one or more molecules of a compound of the invention with one or more molecules of solvent. In some embodiments, the solvent is water, in which case the solvate is a hydrate. Alternatively, in other embodiments, the solvent is an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. In some aspects, the compound of the invention is a true solvate, while in other cases, the compound of the invention merely retains adventitious water or is a mixture of water plus some adventitious solvent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The compounds of the invention (i.e., compounds of structure (I), (II) or (III)), or their pharmaceutically acceptable salts may contain one or more asymmetric centers and may thus give rise to enantiomers, diastereomers, and other stereoisomeric forms that are defined, in terms of absolute stereochemistry, as (R)- or (S)- or, as (D)- or (L)- for amino acids. Embodiments thus include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

Embodiments of the present invention include all manner of rotamers and conformationally restricted states of a compound of the invention. Atropisomers, which are stereoisomers arising because of hindered rotation about a single bond, where energy differences due to steric strain or other contributors create a barrier to rotation that is high enough to allow for isolation of individual conformers, are also included. As an example, certain compounds of the invention may exist as mixtures of atropisomers or purified or enriched for the presence of one atropisomer. Non-limiting examples of compounds which exist as atropisomers include the following compounds:

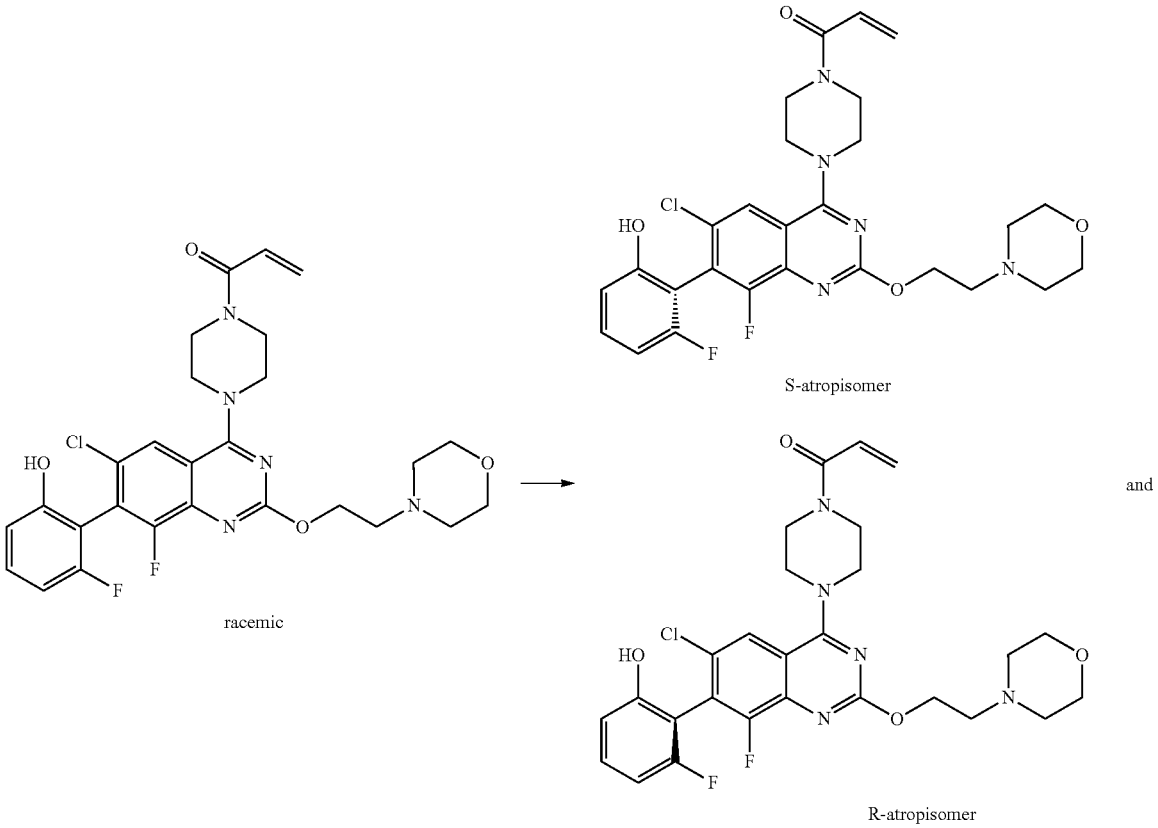

-continued

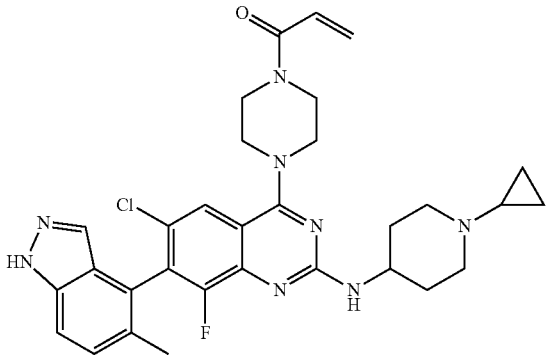

racemic

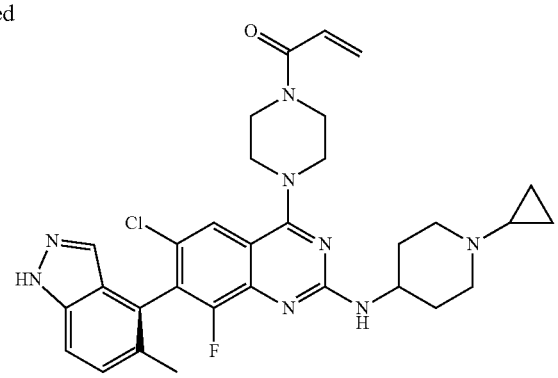

S-atropisomer

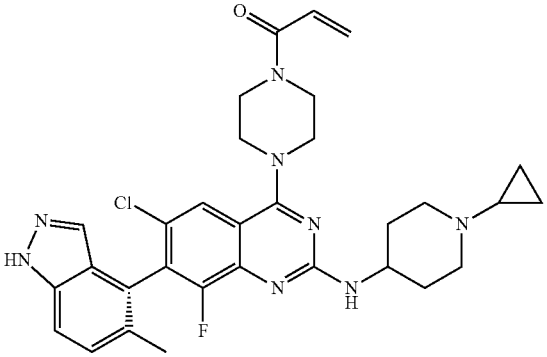

R-atropisomer

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. Embodiments thus include tautomers of the disclosed compounds.

The chemical naming protocol and structure diagrams used herein are a modified form of the I.U.P.A.C. nomenclature system, using the ACD/Name Version 9.07 software program and/or ChemDraw Ultra Version 11.0.1 software naming program (CambridgeSoft). For complex chemical names employed herein, a substituent group is typically named before the group to which it attaches. For example, cyclopropylethyl comprises an ethyl backbone with a cyclopropyl substituent. Except as described below, all bonds are identified in the chemical structure diagrams herein, except for all bonds on some carbon atoms, which are assumed to be bonded to sufficient hydrogen atoms to complete the valency.

Compounds

In an aspect, the invention provides compounds which are capable of selectively binding to and/or modulating a G12C mutant KRAS, HRAS or NRAS protein.

The compounds may modulate the G12C mutant KRAS, HRAS or NRAS protein by reaction with an amino acid. While not wishing to be bound by theory, the present applicants believe that, in some embodiments, the compounds of the invention selectively react with the G12C mutant KRAS, HRAS or NRAS proteins by forming a covalent bond with the cysteine at the 12 position of a G12C mutant KRAS, HRAS or NRAS protein. By binding to the Cysteine 12, the compounds of the invention may lock the switch II of the G12C mutant KRAS, HRAS or NRAS into an inactive stage. This inactive stage may be distinct from those observed for GTP and GDP bound KRAS, HRAS or NRAS. Some compounds of the invention may also be able to perturb the switch I conformation. Some compounds of the invention may favor the binding of the bound KRAS, HRAS or NRAS to GDP rather than GTP and therefore sequester the KRAS, HRAS or NRAS into an inactive KRAS, HRAS or NRAS GDP state. Because effector binding to KRAS, HRAS or NRAS is highly sensitive to the conformation of switch I and II, the irreversible binding of these compounds may disrupt KRAS, HRAS or NRAS downstream signaling.

Compounds of Structure (I)

In one embodiment of the present invention, compounds having activity as modulators of a G12C mutant KRAS, HRAS or NRAS protein are provided, the compounds have the following structure (I):

(I)

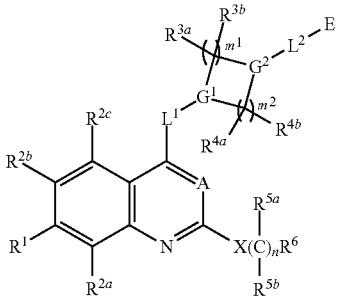

or a pharmaceutically acceptable salt, stereoisomer or prodrug thereof, wherein:

A is N or CR';

$G^1$ and $G^2$ are each independently N or CH;

$L^1$ is a bond or $NR^7$;

R' is H, cyano, alkyl, cycloalkyl, amino, aminylalkyl, alkoxy, alkoxyalkyl, alkoxycarbonyl, aminylalkoxy, alkylaminylalkoxy, alkylaminyl, alkylaminylalkyl, aminylalkylaminyl, carboxyalkyl, alkylcarbonylaminyl, aminylcarbonyl, alkylaminylcarbonyl or aminylcarbonylalkyl;

$L^2$ is a bond or alkylene;

$R^1$ is aryl or heteroaryl;

$R^{2a}$, $R^{2b}$ and $R^{2c}$ are each independently H, amino, cyano, halo, hydroxyl, $C_1$-$C_6$ alkyl, $C_1$-$C_6$ alkylaminyl, $C_1$-$C_6$ haloalkyl, $C_1$-$C_6$ alkoxy, $C_1$-$C_6$ haloalkoxy; $C_3$-$C_8$ cycloalkyl, heterocyclylalkyl, $C_1$-$C_6$ alkynyl, $C_1$-$C_6$ alkenyl, aminylalkyl, alkylaminylalkyl, cyanoalkyl, carboxyalkyl, aminylcarbonylalkyl, aminylcarbonyl, heteroaryl or aryl;

$R^{3a}$ and $R^{3b}$ are, at each occurrence, independently H, —OH, —$NH_2$, —$CO_2H$, halo, cyano, $C_1$-$C_6$ alkyl, $C_1$-$C_6$ haloalkyl, $C_1$-$C_6$ haloalkoxy, $C_3$-$C_8$ cycloalkyl, heterocyclylalkyl, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl; or $R^{3a}$ and $R^{3b}$ join to form oxo, a carbocyclic or heterocyclic ring; or $R^{3a}$ is H, —OH, —$NH_2$, —$CO_2H$, halo, cyano, $C_1$-$C_6$ alkyl, $C_1$-$C_6$ haloalkyl, $C_1$-$C_6$ haloalkoxy, $C_3$-$C_8$ cycloalkyl, heterocyclylalkyl, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl, and $R^{3b}$ joins with $R^{4b}$ to form a carbocyclic or heterocyclic ring;

$R^{4a}$ and $R^{4b}$ are, at each occurrence, independently H, —OH, —$NH_2$, —$CO_2H$, halo, cyano, $C_1$-$C_6$ alkyl, $C_1$-$C_6$ haloalkyl, $C_1$-$C_6$ haloalkoxy, $C_3$-$C_8$ cycloalkyl, heterocyclylalkyl, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl; or $R^{4a}$ and $R^{4b}$ join to form oxo, a carbocyclic or heterocyclic ring; or $R^{4a}$ is H, —OH, —$NH_2$, —$CO_2H$, halo, cyano, $C_1$-$C_6$ alkyl, $C_1$-$C_6$ haloalkyl, $C_1$-$C_6$ haloalkoxy, $C_3$-$C_8$ cycloalkyl, heterocyclylalkyl, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl, and $R^{4b}$ joins with $R^{3b}$ to form a carbocyclic or heterocyclic ring;

$R^{5a}$ and $R^{5b}$ are, at each occurrence, independently H, hydroxyl, halo or $C_1$-$C_6$ alkyl, or $R^{5a}$ and $R^{5b}$ join to form oxo;

$R^6$ is amino, cyano, substituted alkyl, haloalkyl, hydroxylalkly, alkoxyalkyl, aminylalkyl, alkylaminylalkyl; or substituted or unsubstituted: $C_1$-$C_6$ alkylphosphoryl, $C_1$-$C_6$ alkylphosphorylaminyl, cycloalkyl, heterocyclyl, aryl or heteroaryl when $R^1$ is substituted or unsubstituted aryl or substituted or unsubstituted heteroarylaryl; or $R^6$ is methyl when $R^1$ is substituted aryl or substituted or unsubstituted heteroarylaryl;

$R^7$ is, at each occurrence, independently H, $C_1$-$C_6$ alkyl, $C_3$-$C_8$ cycloalkyl or heterocyclyl;

$m^1$ and $m^2$ are each independently 1, 2 or 3;

n is an integer from 0 to 6;

X is a bond, —O—, —$NR^7$— or —S—; and

E is an electrophilic moiety capable of forming a covalent bond with the cysteine residue at position 12 of a KRAS, HRAS or NRAS G12C mutant protein.

In some embodiments, each occurrence of alkyl, alkylene, aryl, heteroaryl, alkynyl, hydroxylalkly, alkoxyalkyl, aminylalkyl, alkylaminylalkyl, cyanoalkyl, carboxyalkyl, aminylcarbonylalkyl, alkylphosphoryl, alkylphosphorylaminyl, aminylcarbonyl, alkylaminyl, haloalkyl, alkoxy, haloalkoxy; cycloalkyl, heterocyclylalkyl, heteroarylalkyloxy, heteroarylalkylaminyl and carbocyclic and heterocyclic rings is optionally substituted with one or more substituents unless otherwise specified.

In some embodiments of structure (I):

A is N, CH or C—CN;

$G^1$ and $G^2$ are each independently N or CH;

$L^1$ is a bond or $NR^7$;

$L^2$ is a bond or alkylene;

$R^1$ is aryl or heteroaryl;

$R^{2a}$, $R^{2b}$ and $R^{2c}$ are each independently H, amino, cyano, halo, hydroxyl, $C_1$-$C_6$ alkyl, $C_1$-$C_6$ alkyl amino, $C_1$-$C_6$ haloalkyl (e.g., $CF_3$), $C_1$-$C_6$ alkoxy, $C_1$-$C_6$ haloalkoxy; $C_3$-$C_8$ cycloalkyl, heterocycylalkyl, heteroaryl or aryl;

$R^{3a}$ and $R^{3b}$ are, at each occurrence, independently H, —OH, —$NH_2$, —$CO_2H$, halo, cyano, $C_1$-$C_6$ alkyl, $C_1$-$C_6$ haloalkyl, $C_1$-$C_6$ haloalkoxy, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl; or $R^{3a}$ and $R^{3b}$ join to form oxo, a carbocyclic or heterocyclic ring; or $R^{3a}$ is H, —OH, —$NH_2$, —$CO_2H$, halo, cyano, $C_1$-$C_6$ alkyl, $C_1$-$C_6$ haloalkyl, $C_1$-$C_6$ haloalkoxy, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl, and $R^{3b}$ joins with $R^{4b}$ to form a carbocyclic or heterocyclic ring;

$R^{4a}$ and $R^{4b}$ are, at each occurrence, independently H, —OH, —$NH_2$, —$CO_2H$, halo, cyano, $C_1$-$C_6$ alkyl, $C_1$-$C_6$ haloalkyl, $C_1$-$C_6$ haloalkoxy, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl; or $R^{4a}$ and $R^{4b}$ join to form oxo, a carbocyclic or heterocyclic ring; or $R^{4a}$ is H, —OH, —$NH_2$, —$CO_2H$, halo, cyano, $C_1$-$C_6$ alkyl, $C_1$-$C_6$ haloalkyl, $C_1$-$C_6$ haloalkoxy, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl, and $R^{4b}$ joins with $R^{3b}$ to form a carbocyclic or heterocyclic ring;

$R^{5a}$ and $R^{5b}$ are, at each occurrence, independently H, hydroxyl, halo or $C_1$-$C_6$ alkyl, or $R^{5a}$ and $R^{5b}$ join to form oxo;

$R^6$ is amino, cyano, substituted $C_1$-$C_6$ alkyl, haloalkyl, hydroxylalkly, alkoxyalkyl, aminylalkyl, alkylaminylalkyl; or substituted or unsubstituted: $C_1$-$C_6$ alkylphosphoryl, $C_1$-$C_6$ alkylphosphorylaminyl, cycloalkyl, heterocyclyl, aryl or heteroaryl when $R^1$ is substituted or unsubstituted aryl or substituted or unsubstituted heteroarylaryl; or $R^6$ is methyl when $R^1$ is substituted aryl or substituted or unsubstituted heteroarylaryl;

$R^7$ is, at each occurrence, independently H, $C_1$-$C_6$ alkyl, $C_3$-$C_8$ cycloalkyl or heterocyclyl;

$m^1$ and $m^2$ are each independently 1, 2 or 3;

n is an integer from 0 to 6;

X is a bond, —O—, —$NR^7$— or —S—; and

E is an electrophilic moiety capable of forming a covalent bond with the cysteine residue at position 12 of a KRAS, HRAS or NRAS G12C mutant protein.

In other embodiments of the compound of structure (I):

A is N;

$G^1$ and $G^2$ are each independently N or CH;

$L^1$ is a bond or $NR^7$;

$L^2$ is a bond or alkylene;

$R^1$ is aryl or heteroaryl;

$R^{2a}$, $R^{2b}$ and $R^{2c}$ are each independently H, amino, halo, hydroxyl, $C_1$-$C_6$ alkyl, $C_1$-$C_6$ alkyl amino, $C_1$-$C_6$ haloalkyl (e.g., $CF_3$), $C_1$-$C_6$ alkoxy, $C_3$-$C_8$ cycloalkyl, heteroaryl or aryl;

$R^{3a}$ and $R^{3b}$ are, at each occurrence, independently H, —OH, —$NH_2$, —$CO_2H$, halo, cyano, $C_1$-$C_6$ alkyl, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl; or $R^{3a}$ and $R^{3b}$ join to form a carbocyclic or heterocyclic ring; or $R^{3a}$ is H, —OH, —$NH_2$, —$CO_2H$, halo, cyano, $C_1$-$C_6$ alkyl, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl, and $R^{3b}$ joins with $R^{4b}$ to form a carbocyclic or heterocyclic ring;

$R^{4a}$ and $R^{4b}$ are, at each occurrence, independently H, —OH, —$NH_2$, —$CO_2H$, halo, cyano, $C_1$-$C_6$ alkyl, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl; or $R^{4a}$ and $R^{4b}$ join to form a carbocyclic or heterocyclic ring; or $R^{4a}$ is H, —OH, —$NH_2$, —$CO_2H$, halo, cyano, $C_1$-$C_6$ alkyl, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl, and $R^{4b}$ joins with $R^{3b}$ to form a carbocyclic or heterocyclic ring;

$R^{5a}$ and $R^{5b}$ are, at each occurrence, independently H, hydroxyl, halo or $C_1$-$C_6$ alkyl, or $R^{5a}$ and $R^{5b}$ join to form oxo;

$R^6$ is amino, cyano, substituted $C_1$-$C_6$ alkyl, cycloalkyl, heterocyclyl, aryl or heteroaryl when $R^1$ is substituted or unsubstituted aryl or substituted or unsubstituted heteroarylaryl; or $R^6$ is methyl when $R^1$ is substituted aryl or substituted or unsubstituted heteroarylaryl;

$R^7$ is, at each occurrence, independently H, $C_1$-$C_6$ alkyl, $C_3$-$C_8$ cycloalkyl or heterocycloalkyl;

$m^1$ and $m^2$ are each independently 1, 2 or 3;

n is an integer from 0 to 6;

X is a bond, —O—, —$NR^7$— or —S—; and

E is an electrophilic moiety capable of forming a covalent bond with the cysteine residue at position 12 of a KRAS, HRAS or NRAS G12C mutant protein.

In some embodiments, $R^6$ is amino, cyano, substituted $C_1$-$C_6$ alkyl, cycloalkyl, heterocyclyl, aryl or heteroaryl when $R^1$ is substituted or unsubstituted aryl or substituted or unsubstituted heteroarylaryl; or $R^6$ is methyl when $R^1$ is substituted aryl or substituted or unsubstituted heteroarylaryl.

In some different embodiments, A is N. In other embodiments, A is C—CN. In other embodiments, A is CH.

The structure of E is not particularly limited provided it is capable of forming a covalent bond with a nucleophile, such as the cysteine residue at position 12 of a KRAS, HRAS or NRAS G12C mutant protein. Accordingly, moieties which are capable of reaction with (e.g., by covalent bond formation) a nucleophile are preferred. In certain embodiments, E is capable of reacting in a conjugate addition manner (e.g., 1.4-conjugate addition) with an appropriately reactive nucleophile. In some embodiments, E comprises conjugated pi bonds such that delocalization of electrons results in at least one atom (e.g., a carbon atom) having a positive charge, partial positive charge or a polarized bond. In other embodiments, E comprises one or more bonds wherein the electronegativity of the two atoms forming the bonds is sufficiently different such that a partial positive charge (e.g., by polarization of the bond) resides on one of the atoms, for example on a carbon atom. E moieties comprising carbon-halogen bonds, carbon-oxygen bonds or carbon bonds to various leaving groups known in the art are examples of such E moieties.

In certain embodiments of the foregoing, E has the following structure:

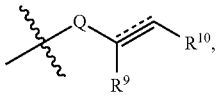

wherein:

≡ represents a double or triple bond;

Q is —C(=O)—, —C(=$NR^{8'}$)—, —$NR^8$C(=O)—, —S(=O)$_2$— or —$NR^8$S(=O)$_2$—;

$R^8$ is H, $C_1$-$C_6$ alkyl, hydroxylalkyl, aminoalkyl, alkoxyalkyl, aminylalkyl, alkylaminylalkyl, cyanoalkyl, carboxyalkyl, aminylcarbonylalkyl, $C_3$-$C_8$ cycloalkyl or heterocycloalkyl;

$R^{8'}$ is H, —OH, —CN or $C_1$-$C_6$ alkyl; and when ≡ is a double bond then $R^9$ and $R^{10}$ are each independently H, halo, cyano, carboxyl, $C_1$-$C_6$ alkyl, alkoxycarbonyl, aminylalkyl, alkylaminylalkyl, aryl, heterocyclyl, heterocyclylalkyl, heteroaryl or hydroxylalkyl, or $R^9$ and $R^{10}$ join to form a carbocyclic, heterocyclic or heteroaryl ring;

when ≡ is a triple bond; then $R^9$ is absent and $R^{10}$ is H, $C_1$-$C_6$alkyl, aminylalkyl, alkylaminylalkyl or hydroxylalkyl.

In certain embodiments when ≡ is a double bond then $R^9$ and $R^{10}$ are each independently H, cyano, $C_1$-$C_6$alkyl, aminylalkyl, alkylaminylalkyl, or hydroxylalkyl or $R^9$ and $R^{10}$ join to form a carbocyclic or heterocyclic ring.

In some of the foregoing embodiments, Q is —C(=O)—, —$NR^8$C(=O)—, —S(=O)$_2$— or —$NR^8$S(=O)$_2$—.

In some other of the foregoing embodiments, Q is —C(=$NR^{8'}$)—, wherein $R^8$ is H, —OH, —CN or $C_1$-$C_6$alkyl. For example, in some embodiments $R^8$ is H. In other embodiments, $R^8$ is —CN. In other embodiments, $R^8$ is —OH.

Accordingly, in some embodiments, the compound has the following structure (I'a):

(I'a)

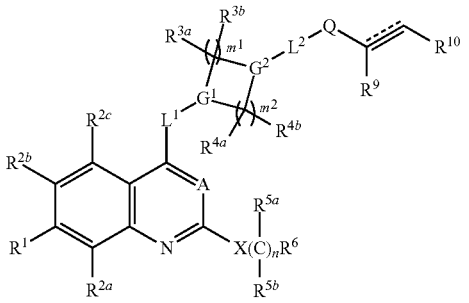

wherein:

≡ represents a double or triple bond;

Q is —C(=O)—, —C(=NR$^{8'}$)—, —NR$^8$C(=O)—, —S(=O)$_2$— or —NR S(=O)$_2$—;

R$^{8'}$ is H, C$_1$-C$_6$ alkyl, hydroxylalkyl, aminoalkyl, alkoxyalkyl, aminylalkyl, alkylaminylalkyl, cyanoalkyl, carboxyalkyl, aminylcarbonylalkyl, C$_3$-C$_8$ cycloalkyl or heterocycloalkyl;

R$^{8'}$ is H, —OH, —CN or C$_1$-C$_6$ alkyl;

when ≡ is a double bond then R$^9$ and R$^{10}$ are each independently H, halo, cyano, carboxyl, C$_1$-C$_6$ alkyl, alkoxycarbonyl, aminylalkyl, alkylaminylalkyl, aryl, heterocyclyl, heterocyclylalkyl, heteroaryl or hydroxylalkyl, or R$^9$ and R$^{10}$ join to form a carbocyclic, heterocyclic or heteroaryl ring; and when ≡ is a triple bond then R$^9$ is absent and R$^{10}$ is H, C$_1$-C$_6$ alkyl, aminylalkyl, alkylaminylalkyl or hydroxylalkyl.

In other embodiments, the compound has one of the following structures (I'b), (I'c), (I'd) or (I'e):

(I'b)

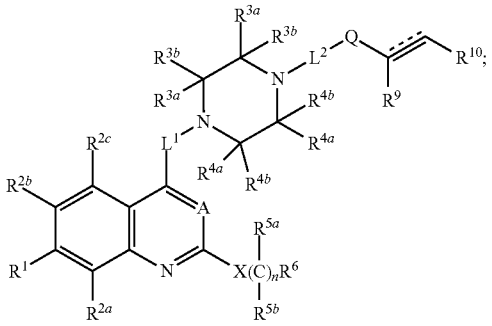

(I'c)

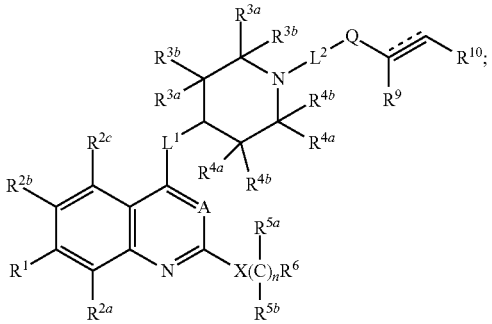

(I'd)

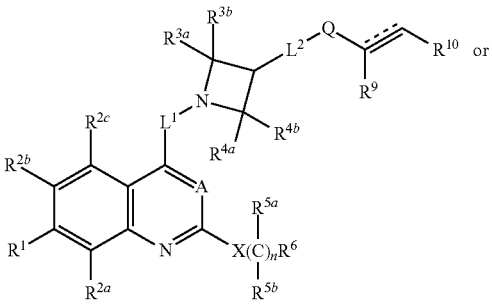

-continued (I'e)

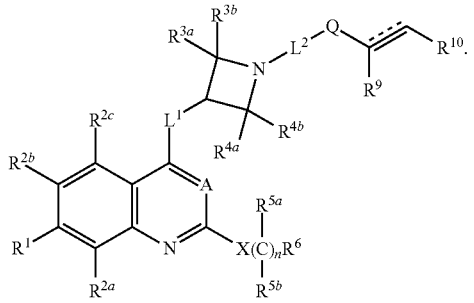

In any of the foregoing embodiments of the compounds of structure (I), (I'a), (I'b), (I'c), (I'd) or (I'e), A is N. In some other of the foregoing embodiments of the compounds of structure (I), (I'a), (I'b), (I'c), (I'd) or (I'e), A is C—CN.

Without wishing to be bound by theory, Applicants believe correct selection of the R$^1$ substituent may play a part in the compounds' inhibitory activity (e.g., against KRAS, HRAS or NRAS G12C). In some embodiments, R$^1$ is aryl or heterocyclyl (e.g., heteroaryl or aliphatic heterocyclyl), each of which is optionally substituted with one or more substituents. In some embodiments, R$^1$ is capable of reversible interaction with KRAS, HRAS or NRAS G12C mutant protein. In some embodiments R$^1$ has high affinity towards KRAS, HRAS or NRAS and is highly specific towards G12C KRAS, HRAS or NRAS. In some embodiments R$^1$ is capable of hydrophobic interaction with KRAS, HRAS or NRAS G12C. In some embodiments R$^1$ is able to form hydrogen bonds with various residues of G12C KRAS, HRAS or NRAS protein.

In any of the foregoing embodiments, R$^1$ is aryl. For example in some embodiments R$^1$ is phenyl, and in other embodiments R$^1$ is naphthyl. R$^1$ is substituted or unsubstituted. In some specific embodiments, R$^1$ is substituted with one or more substituents. In some embodiments, R$^1$ is substituted with halo, amino, hydroxyl, C$_1$-C$_6$ alkyl, cyano, C$_1$-C$_6$ haloalkyl, C$_1$-C$_6$ alkoxy, alkylaminyl, cycloalkyl, heterocyclylalkyl, aryl, heteroaryl, boronic acid, —OC(=O)R, phosphate, phosphoalkoxy or C$_1$-C$_6$ alkylcarbonyloxy, or combinations thereof, wherein R is C$_1$-C$_6$ alkyl. For example, in some embodiments R$^1$ is substituted with halo, hydroxyl, C$_1$-C$_6$ alkyl, C$_1$-C$_6$ haloalkyl, C$_1$-C$_6$ alkoxy or C$_1$-C$_6$ alkylcarbonyloxy, or combinations thereof. In different embodiments, R$^1$ is substituted with fluoro, chloro, hydroxyl, methyl, isopropyl, cyclopropyl, trifluoromethyl or methoxy, or combinations thereof. In some even more embodiments, R$^1$ is substituted with fluoro, hydroxyl, methyl, isopropyl, trifluoromethyl or methoxy, or combinations thereof.

In some embodiments, R$^1$ has one of the following structures:

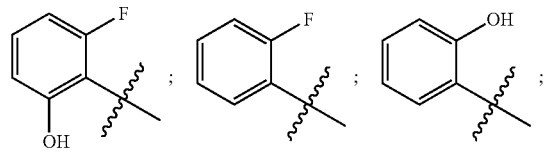

-continued
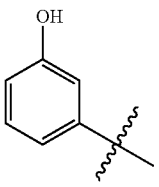
;
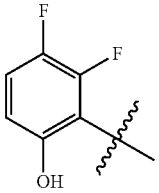
;
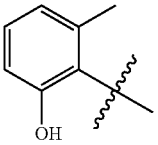
;
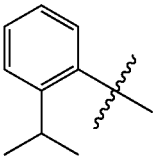
;
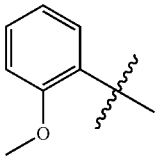
;
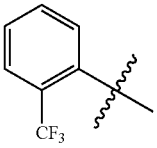
;
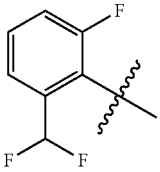
;
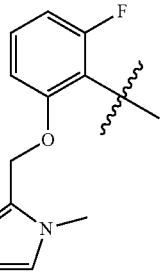
;
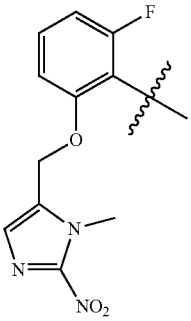
;
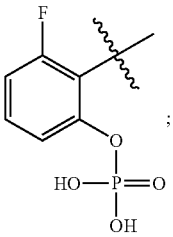
;
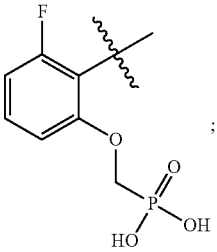
;
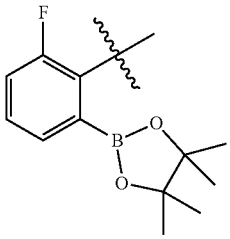
;
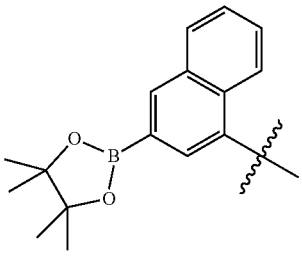
;
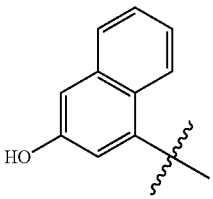
;
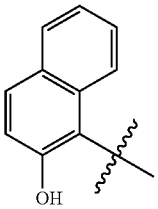
;
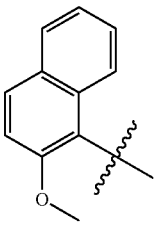
;
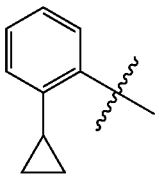
or
-continued
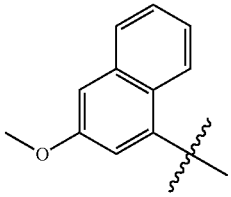
.
In some more specific embodiments, $R^1$ has one of the following structures:
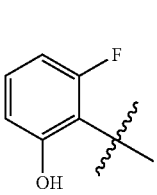
;
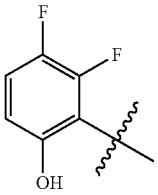
;
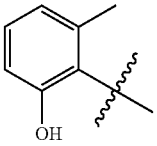
;
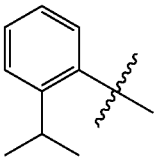
;
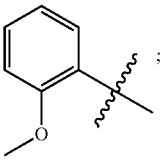
;
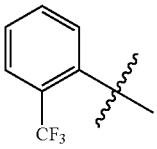
;
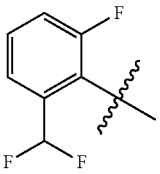
;
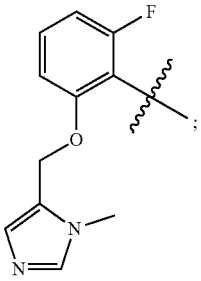
;
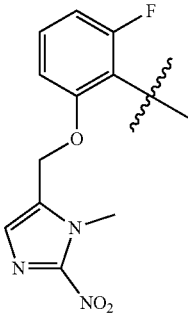
;
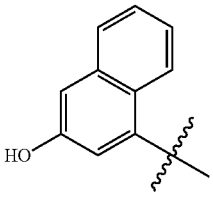
or
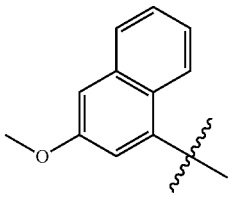
.
In some specific embodiments, $R^1$ has one of the following structures:

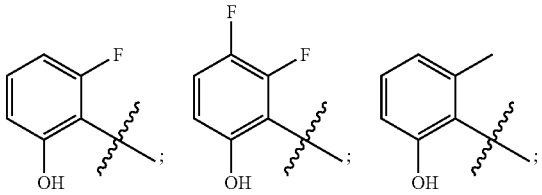

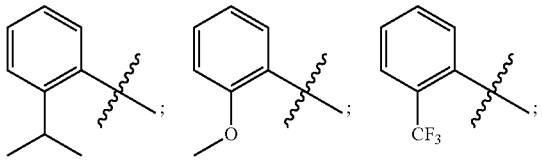

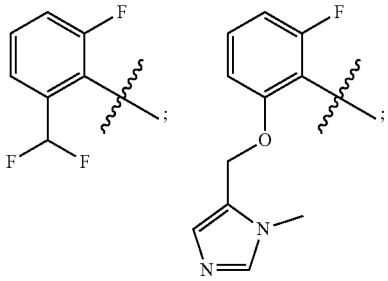

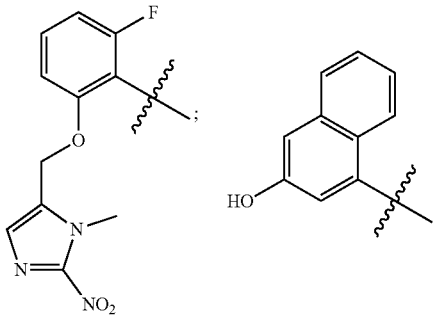

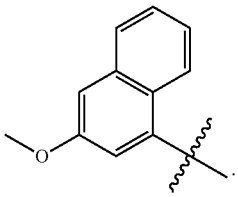

In still different embodiments, $R^1$ has one of the following structures:

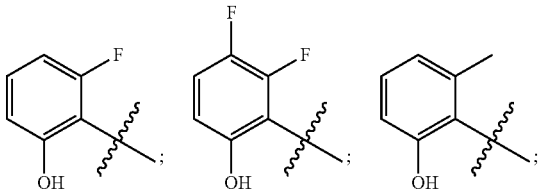

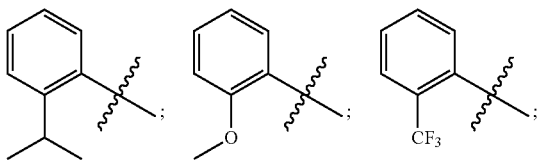

-continued

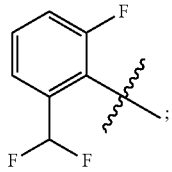

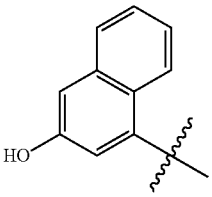

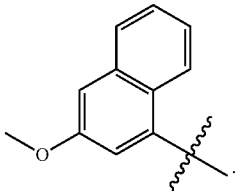

In some different embodiments of the foregoing compounds, $R^1$ is heteroaryl, for example a heteroaryl comprising nitrogen. In other embodiments, $R^1$ is indazolyl, indolyl, benzoimidazole, benzotriazole or quinolinyl, for example indazolyl or quinolinyl. In more embodiments, $R^1$ is heteroaryl which is substituted with one or more substituents. For example, in certain embodiments, $R^1$ is substituted with hydroxyl, halo or $C_1$-$C_6$ alkyl, or combinations thereof, for example hydroxyl or $C_1$-$C_6$ alkyl.

In some more specific embodiments, $R^1$ has one of the following structures:

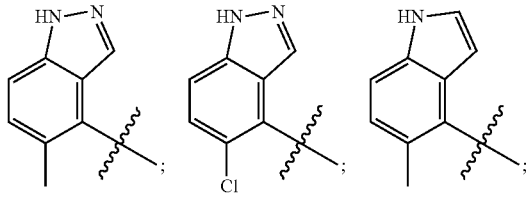

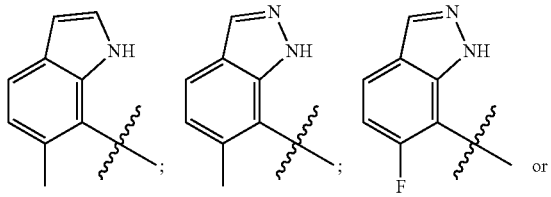

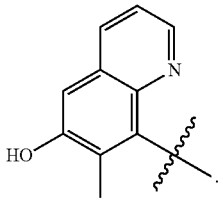

for example one of the following structures:

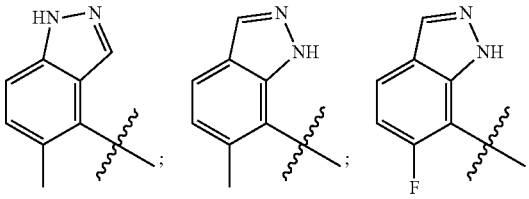

-continued

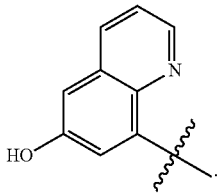

In some embodiments, $R^{2a}$ and $R^{2b}$ are each independently halo, haloalkyl, alkyl, or alkoxy. In some of the foregoing embodiments $R^{2c}$ is H. In other of any of the foregoing embodiments, $R^{2a}$ and $R^{2b}$ are each halo. In some embodiments, $R^{2a}$ is fluoro, chloro or methoxy. For example, in some embodiments $R^{2a}$ is fluoro, and in other embodiments, $R^{2b}$ is chloro. In different embodiments, $R^{2b}$ is chloro, fluoro or $CF_3$.

In some more specific embodiments, the compounds have the following structure (I'f):

(I'f)

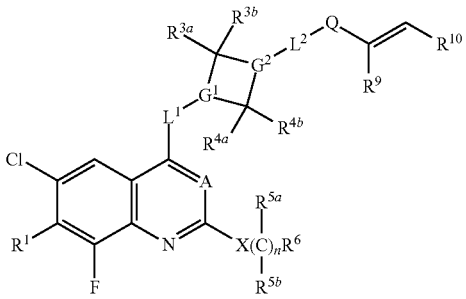

For example, in even further different embodiments, the compounds have one of the following structures (I'g) or (I'h):

(I'g)

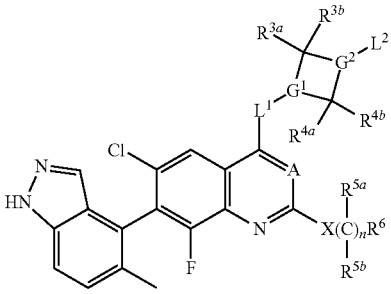

or

-continued (I'h)

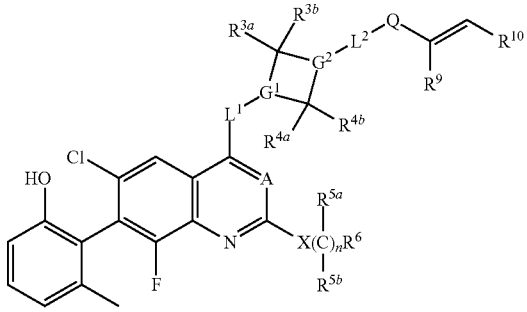

In any of the foregoing embodiments of the compounds of structure (I'f), (I'g) or (I'h), A is N. In some other of the foregoing embodiments of the compounds of structure (I'f), (I'g) or (I'h), A is C—CN.

In some other embodiments of the foregoing, n is 0, X is a bond and $R^6$ is heterocyclyl. In some of these embodiments, $R^6$ is azetidinyl, pyrrolidinyl, piperidinyl or morpholinyl. In other embodiments, $R^6$ is substituted, for example in some embodiments $R^6$ is substituted with $C_1$-$C_6$ alkyl, $C_1$-$C_6$ alkylaminyl, heterocyclyl or spiro-heterocyclyl, or combinations thereof. In some embodiments, $R^6$ has one of the following structures:

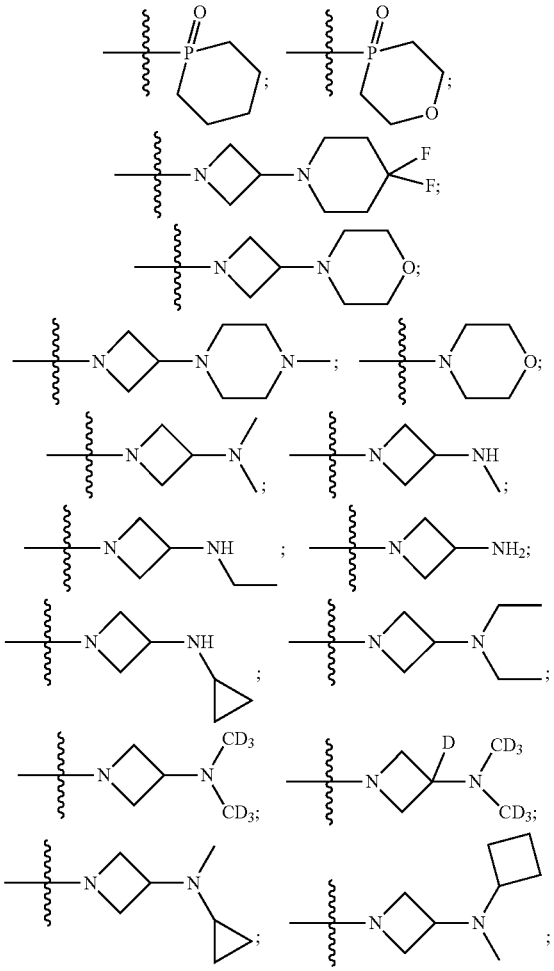

-continued
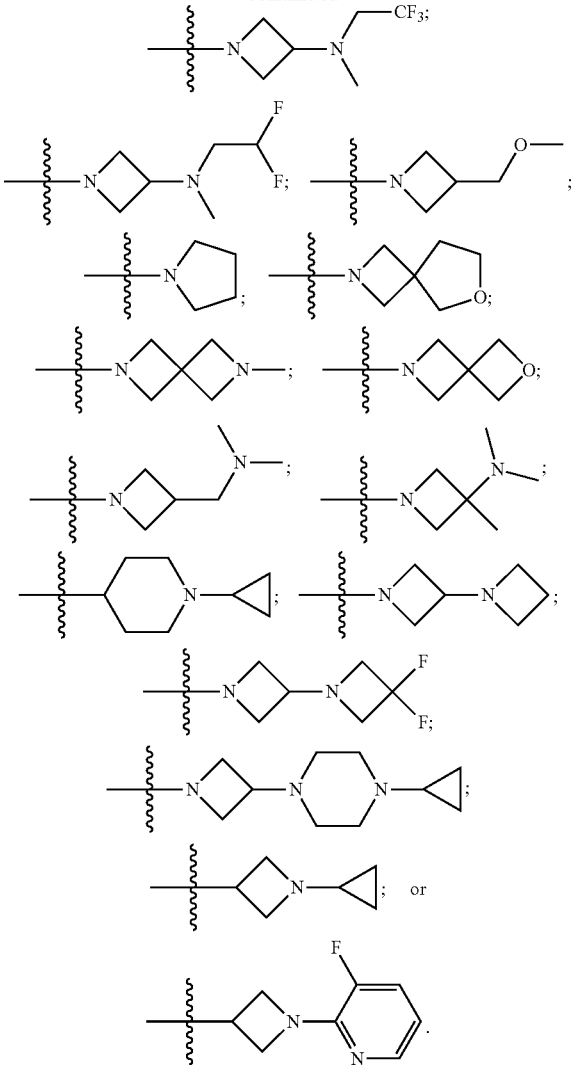
In some other different embodiments, $R^6$ has one of the following structures:
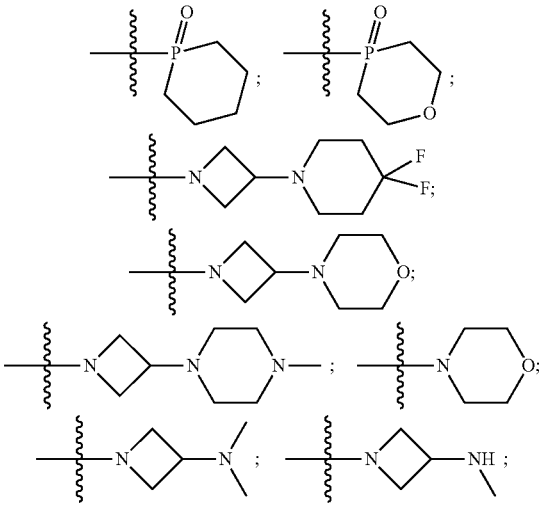
-continued
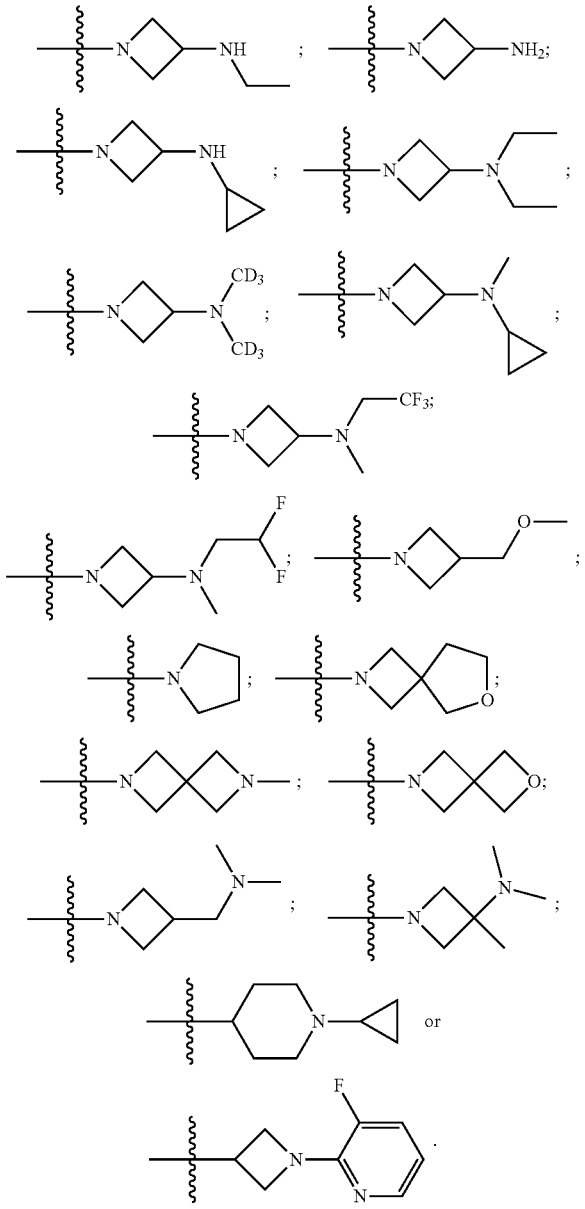
In some specific embodiments, $R^6$ has one of the following structures:
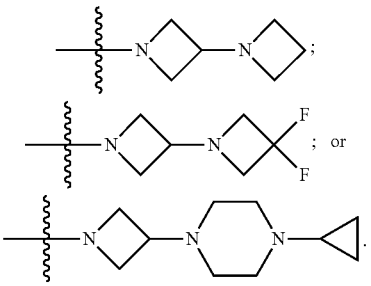
In some specific embodiments, $R^6$ has one of the following structure:

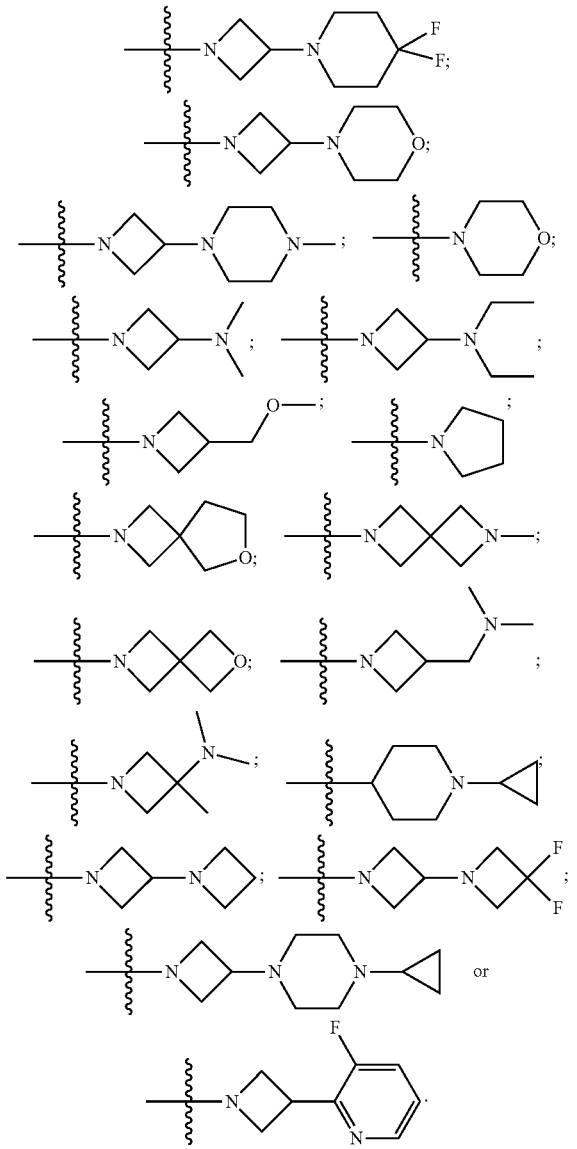

In some other different embodiments of the foregoing, n is an integer from 1 to 6, X is —O— and $R^6$ is heterocyclyl or heteroaryl, provided that $R^6$ is not morpholinyl, piperazinyl, pyrrolidinyl or imidazolyl when $R^1$ is indazolyl. In some of these embodiments, $R^6$ is azetidinyl, pyrrolidinyl, pyrrolidinonyl, piperidinyl, piperazinyl, pyridinyl, pyrimidinyl, pyridazinyl, oxazolyl, morpholinyl, morpholinonyl, thiomorpholinyl, or an oxidized analogue thereof, dioxolanyl, or tetrahydropyranyl. In some further these embodiments, $R^6$ is azetidinyl, pyrrolidinyl, pyrrolidinonyl, piperidinyl, piperazinyl, pyridinyl, pyrimidinyl, pyridazinyl, oxazolyl, morpholinyl, morpholinonyl, thiomorpholinyl, or an oxidized analogue thereof, or tetrahydropyranyl. In some other embodiments, $R^6$ is substituted, for example substituted with oxo, cyano, halo, $C_1$-$C_6$ alkyl, $C_3$-$C_8$ cycloalkyl, $C_1$-$C_6$ alkoxy, $C_1$-$C_6$ haloalkyl, heteroaryl, or combinations thereof. In some other embodiments, $R^6$ is substituted, for example substituted with oxo, cyano, halo, $C_1$-$C_6$ alkyl, $C_1$-$C_6$ alkoxy, $C_1$-$C_6$ haloalkyl, or combinations thereof. In some different embodiments, n is 1. In some other embodiments, n is 2. In some more different embodiments, n is 3. In other different embodiments, $R^6$ has one of the following structures:

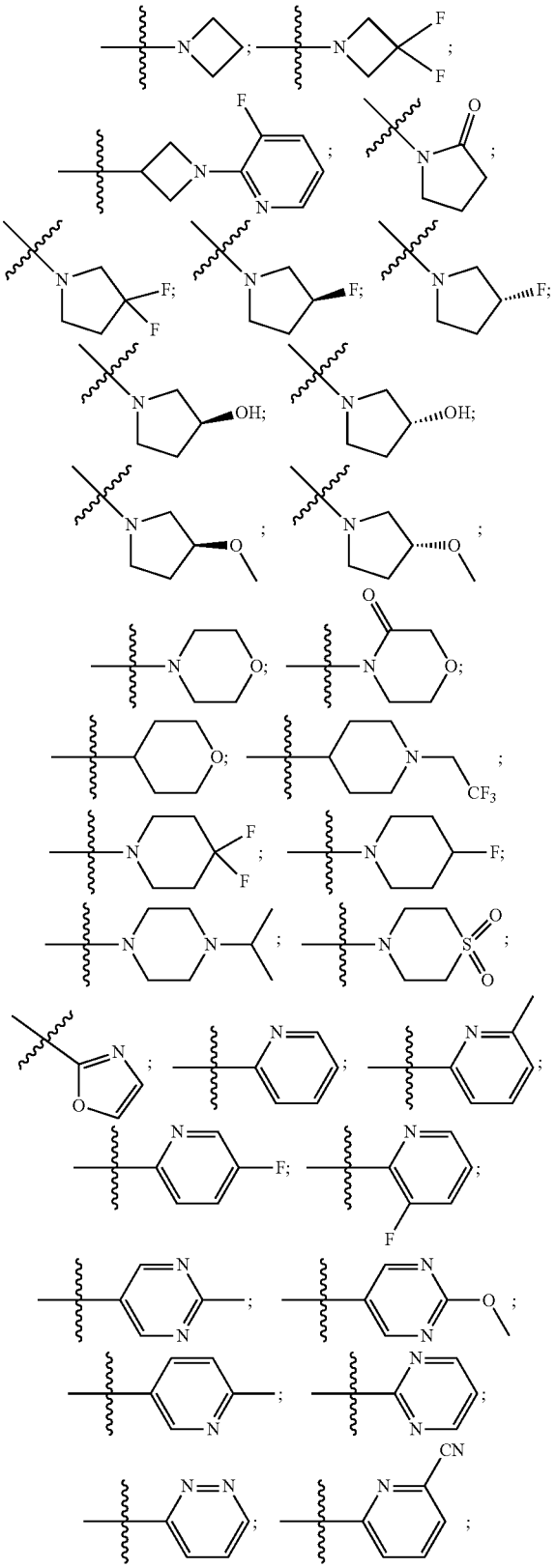

-continued

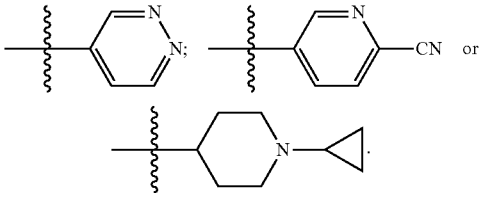

In some specific embodiments, $R^6$ has one of the following structures:

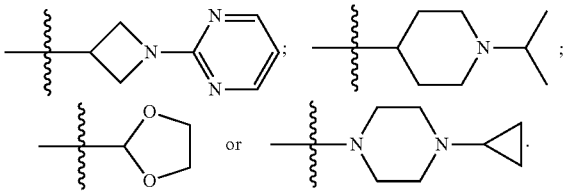

In some specific embodiments, $R^6$ has one of the following structures:

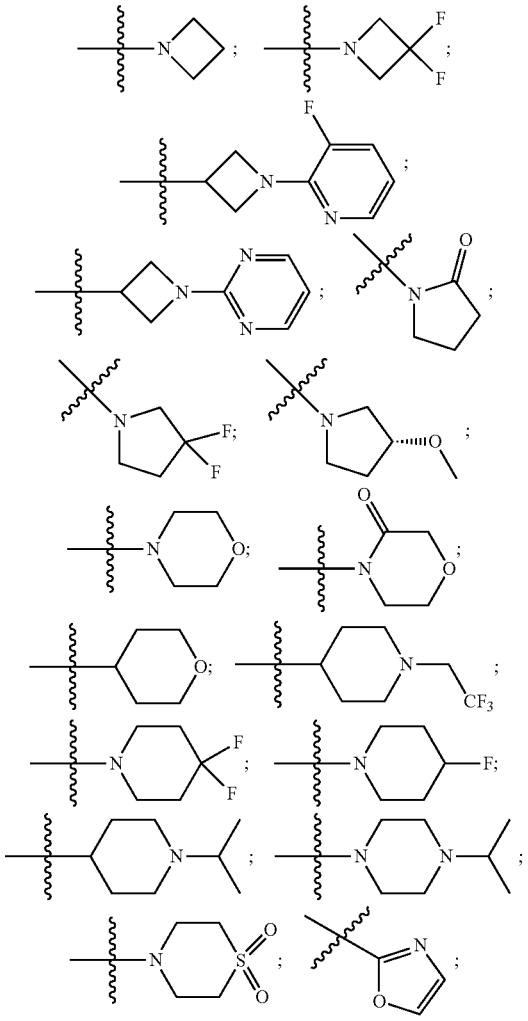

-continued

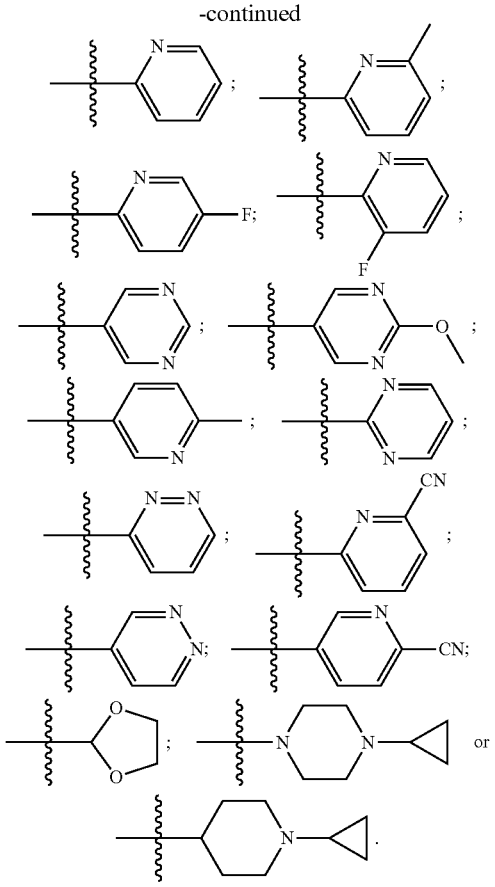

In still more embodiments of the foregoing, n is an integer from 1 to 6, X is —$NR^7$— and $R^6$ is heterocyclyl or heteroaryl, provided that $R^6$ is not N-methylimidazolyl when $R^1$ is indazolyl. In some of these embodiments, $R^6$ is piperidinyl, pyridinyl, imidazolyl, pyrrolidinyl, pyrimidyl, or azetidinyl. In some other embodiments, $R^6$ is piperidinyl, pyridinyl, imidazolyl, pyrrolidinyl, or azetidinyl. In other embodiments, $R^6$ is substituted, for example in some embodiments $R^6$ is substituted with halo, hydroxyl, $C_1$-$C_6$ alkyl $C_3$-$C_8$ cycloalkyl, or combinations thereof. In some different embodiments, n is 1. In some other embodiments, n is 2. In some more different embodiments, n is 3. In various embodiments, $R^7$ is H or methyl. In other more specific embodiments, $R^6$ has one of the following structures:

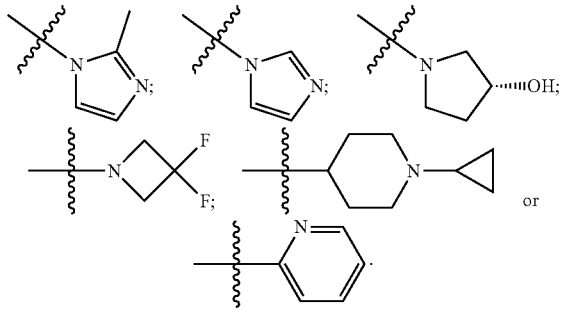

In other specific embodiments, $R^6$ has one of the following structures:

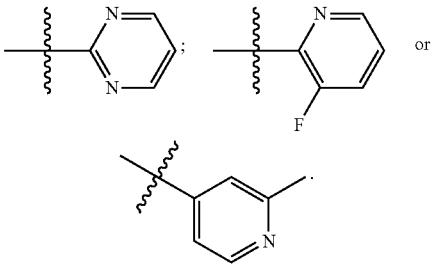

In other specific embodiments, $R^6$ has one of the following structures:

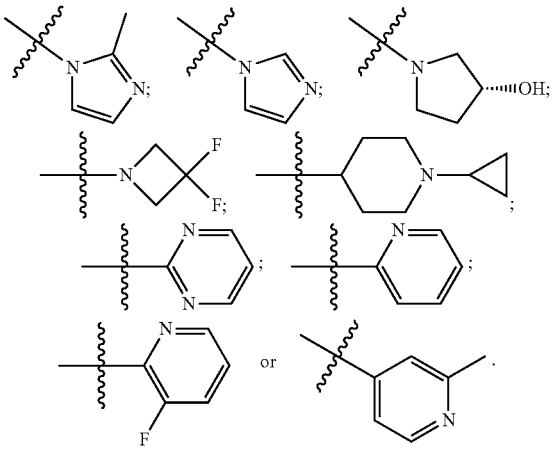

In still other embodiments, n is 0, X is —O— and $R^6$ is cycloalkyl, heterocyclyl or heteroaryl, provided that $R^6$ is not tetrahydropyranyl or tetrahydrofuranyl when $R^{2a}$ is H and provided that $R^6$ is not N-methylpyrazolyl when $R^1$ is indazolyl. In some of these embodiments, $R^6$ is cyclohexyl, oxetanyl, tetrahydropyranyl, pyrrolyl, pyrazolyl, azetidinyl, or piperidinyl. In other embodiments, $R^6$ is cyclohexyl, oxetanyl, tetrahydropyranyl, pyrrolyl, pyrazolyl, or piperidinyl. In certain other embodiments, $R^6$ is substituted, for example substituted with hydroxyl, $C_1$-$C_6$ alkyl, $C_3$-$C_8$ cycloalkyl, $C_1$-$C_6$ haloalkyl, $C_3$-$C_7$ cycloalkyl, $C_1$-$C_6$ alkylcarbonyl, heterocyclyl, or combinations thereof. In other embodiments, $R^6$ is substituted with hydroxyl, $C_1$-$C_6$ alkyl, $C_3$-$C_8$ cycloalkyl, $C_1$-$C_6$ haloalkyl, $C_3$-$C_7$ cycloalkyl, $C_1$-$C_6$ alkylcarbonyl, heterocyclyl, or combinations thereof. In some other more specific embodiments, $R^6$ has one of the following structures:

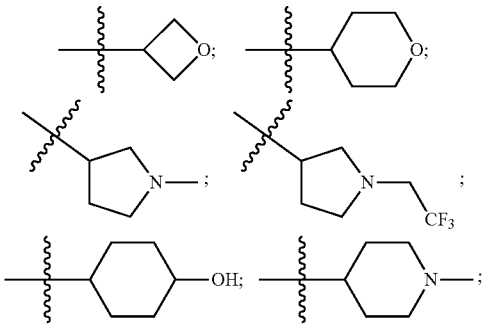

-continued

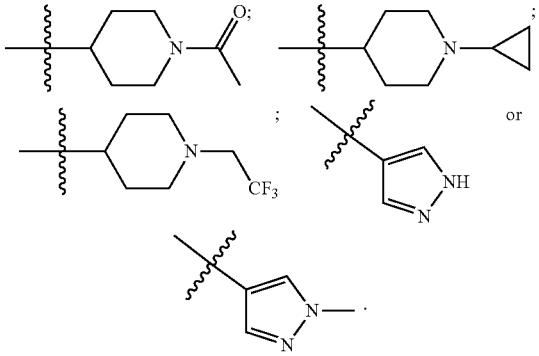

In other specific embodiments, $R^6$ has one of the following structures:

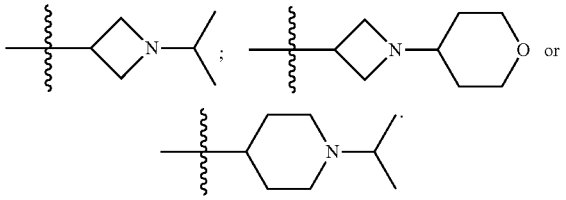

In other specific embodiments, $R^6$ has one of the following structures:

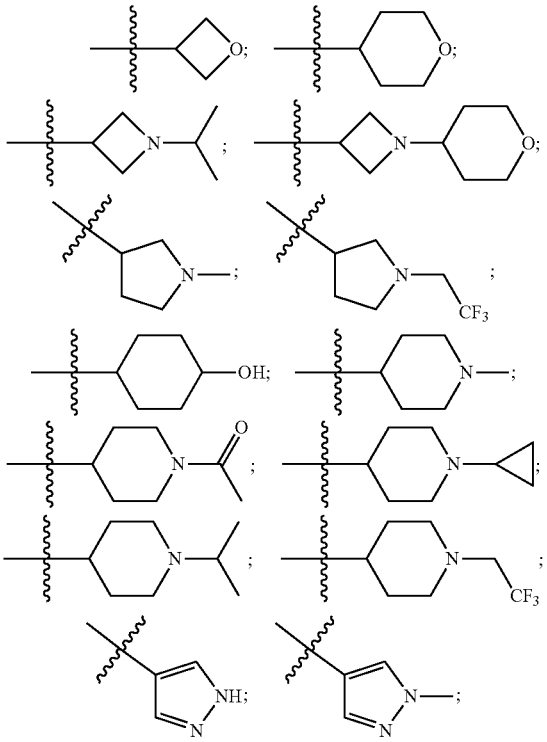

In still other embodiments, n is 0, X is —$NR^7$— and $R^6$ is a 3, 4, 6, 7 or 8-membered heterocyclyl (e.g., 3, 4, 6, or 7-membered) or 3, 4, 6 or 7-membered heteroaryl, provided that $R^6$ is not tetrahydropyranyl or N-methylpiperidinyl when $R^1$ is indazolyl; or n is 0, X is —$NR^7$— and $R^6$ is a 5-membered, oxygen-containing heterocyclyl and $R^1$ is aryl. For example, in some embodiments $R^6$ is piperidinyl, tetrahydrofuranyl, tetrahydrothiopyranyl, or an oxidized analogue thereof, azabicyclo[3.2.1]octanyl, or tetrahydropyranyl. In some other embodiments $R^6$ is piperidinyl, tetrahydrofuranyl, tetrahydrothiopyranyl, or an oxidized analogue thereof, or tetrahydropyranyl. In some further embodiments of the foregoing, $R^6$ is substituted, for example substituted with hydroxyl, $C_1$-$C_6$ alkyl, $C_1$-$C_6$ haloalkyl, $C_3$-$C_8$ cycloalkyl, cycloalkylalky, heterocyclyl, $C_1$-$C_6$ alkylcarbonyl, heteroaryl, or combinations thereof. In other embodiments, $R^6$ is substituted with hydroxyl, $C_1$-$C_6$ alkyl, $C_1$-$C_6$ haloalkyl, $C_3$-$C_7$ cycloalkyl, cycloalkylalky, heterocyclyl, $C_1$-$C_6$ alkylcarbonyl, or combinations thereof. In even more embodiments, $R^6$ has one of the following structures:

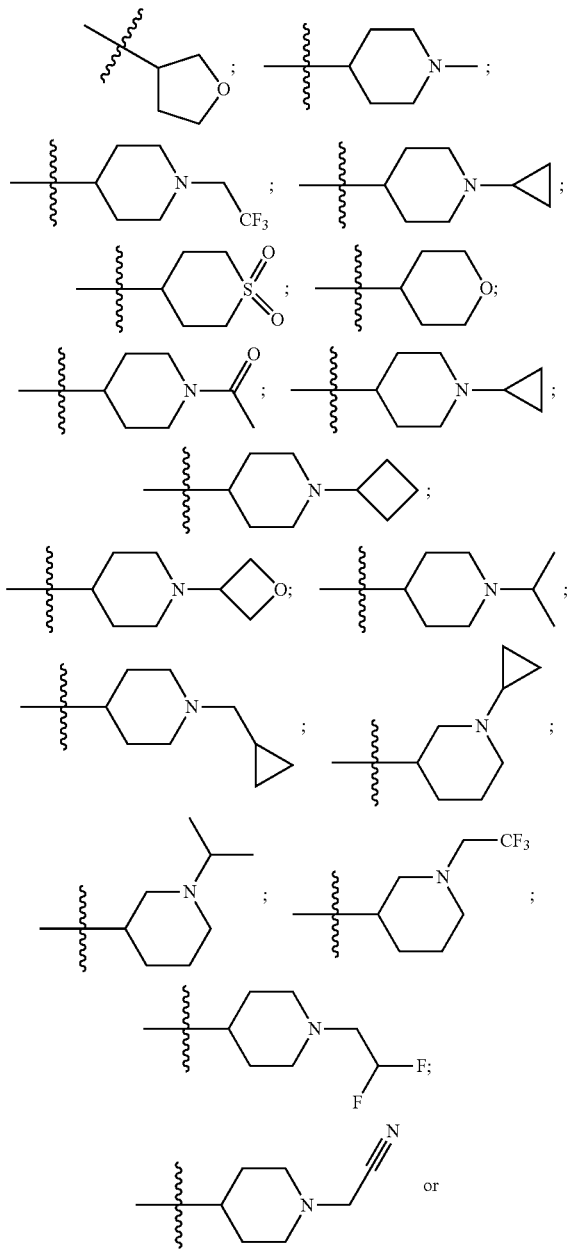

-continued

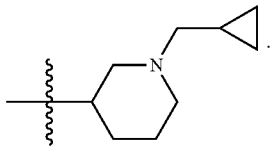

In some specific embodiments, $R^6$ has one of the following structures:

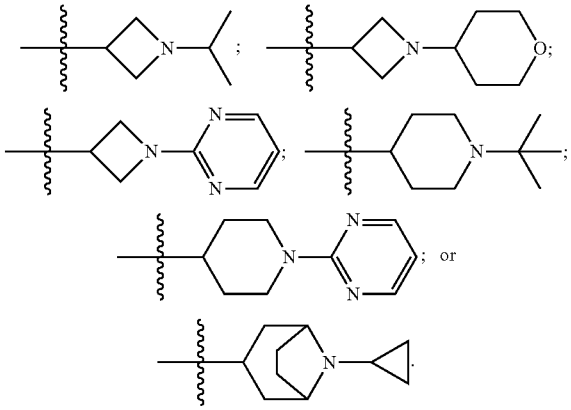

In some specific embodiments, $R^6$ has one of the following structures:

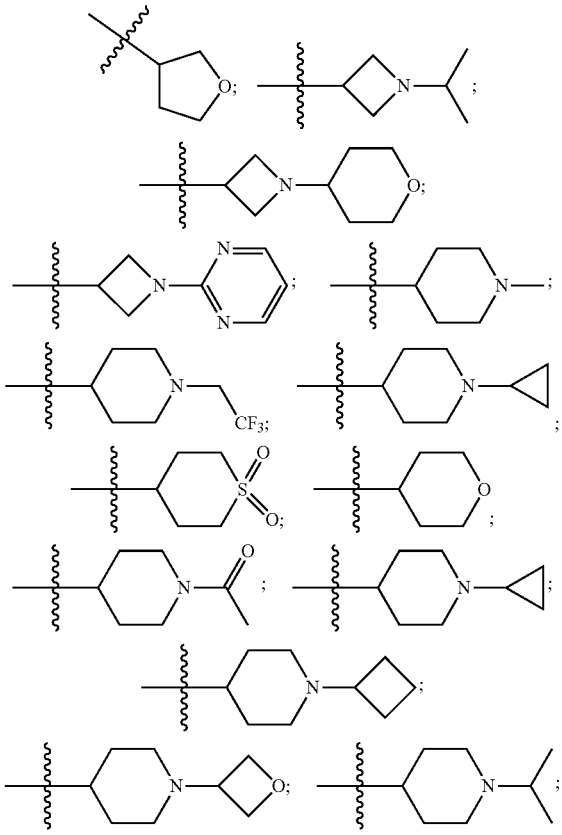

-continued

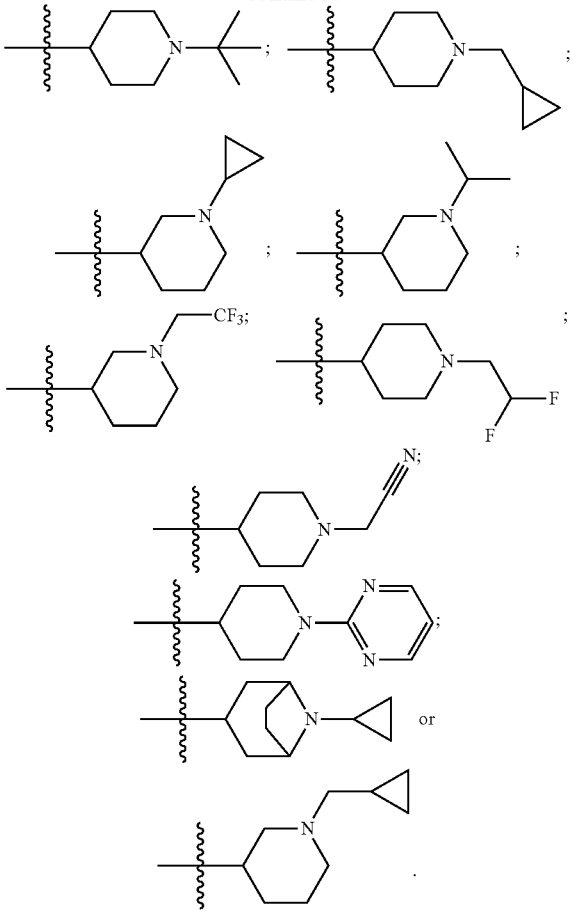

In still other embodiments, $R^6$ is substituted alkyl, for example $C_1$-$C_6$ alkyl. In some of these embodiments $R^6$ is substituted with one substituent selected from the group consisting of alkylaminylcarbonyl, $C_2$-$C_6$ dialkylaminyl, halo, $C_1$-$C_6$ monoalkylaminyl, heteroarylamino, heteroarylalkyloxy and alkylsulfonyl, for example, alkylaminylcarbonyl, $C_2$-$C_6$ dialkylaminyl, halo, $C_1$-$C_6$ monoalkylaminyl, heteroarylamino, and alkylsulfonyl, and wherein $R^6$ optionally comprises one or more additional substituent. In further embodiments, $R^6$ has one of the following structures:

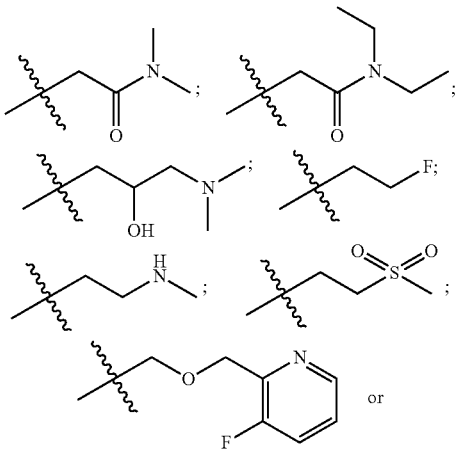

-continued

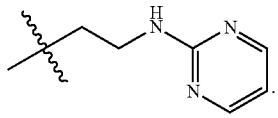

For example, one of the following structures:

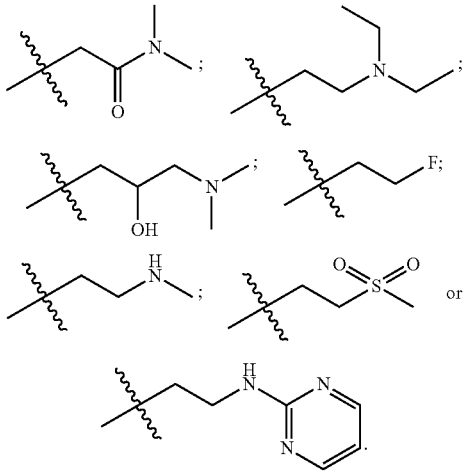

In some embodiments, $R^6$ has one of the following structures:

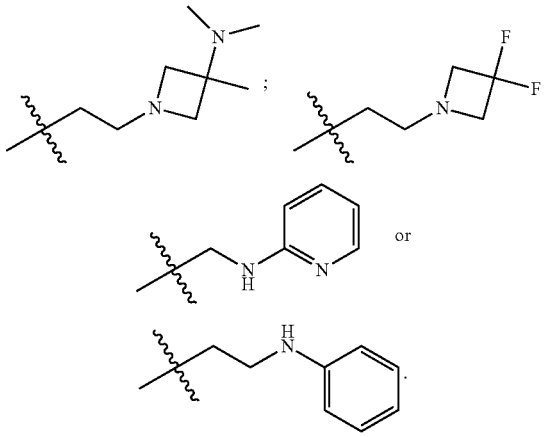

In some embodiments, $R^6$ has one of the following structures:

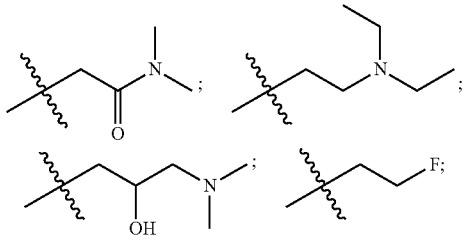

-continued

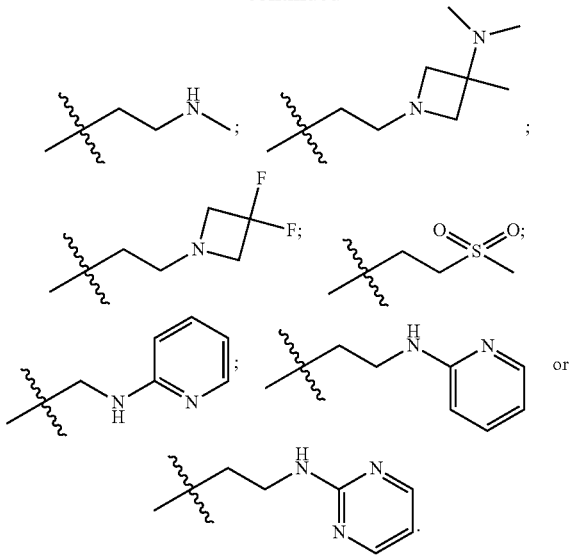

In yet more embodiments, $R^6$ is alkyl, for example $C_1$-$C_6$ alkyl, substituted with at least one hydroxyl and X is —O—.

In other embodiments, $R^6$ is alkyl, for example $C_1$-$C_6$ alkyl, substituted with at least one hydroxyl and $R^1$ is heteroaryl. In other embodiments, $R^6$ is alkyl, for example $C_1$-$C_6$ alkyl, substituted with at least one hydroxyl and $R^1$ is aryl or heteroaryl.

In still different embodiments, $R^6$ is substituted $C_2$-$C_6$ alkyl, X is a bond and n is 0. In some of these embodiments, $R^6$ is substituted with dialkylaminyl.

In some embodiments, $R^6$ is cyano. In other embodiments, $R^6$ is amino. In other embodiments, $R^6$ is $C_1$-$C_6$ alkylphosphoryl, such as —P(=O)$(CH_3)_2$. In other embodiments, $R^6$ is $C_1$-$C_6$ alkylphosphoryaminyl, such as —NHP(=O)$(CH_3)_2$. In still other embodiments, $R^6$ is perhalomethyl, such as —$CF_3$.

In still more embodiments, X is a bond, n is an integer from 1 to 3 and $R^6$ is heteroarylalkyloxy or heteroarylalkylaminyl. For example, in some of these embodiments n is 1. In other embodiments, $R^6$ is pyridinylalkyloxy, pyridinylalkylaminyl, pyrimidinylalkyloxy or pyrimidinylalkylaminyl. In other more specific embodiments

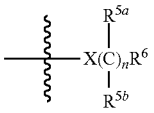

has one of the following structures:

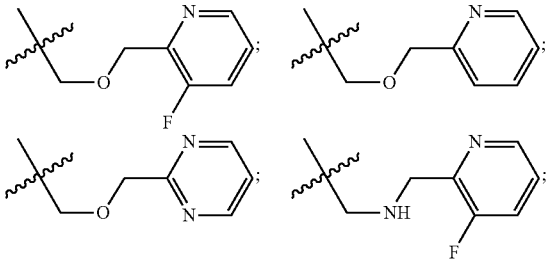

-continued

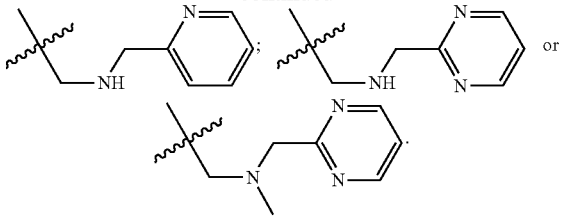

In still other embodiments, X is $NR^7$ and n is 1, wherein $R^{5a}$ and $R^{5b}$ join to form oxo. In further of these embodiments, $R^6$ is heteroaryl, for example pyridinyl. In more specific embodiments, —X$(CR^{5a}R^{5b})_nR^6$ has the following structure:

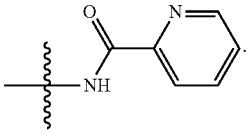

In some embodiments of the foregoing, X is a bond. In other embodiments, X is —O—. In different embodiments, X is —$NR^7$—. In some other different embodiments, X is —S—. In other different embodiments, X is a bond, n is 1 and $R^{5a}$ and $R^{5b}$ join to form oxo.

In yet more of any of the foregoing embodiments, E has the following structure:

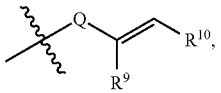

wherein:

Q is —C(=O)—, —C(=$NR^{8'}$)—, —$NR^8$C(=O)—, —S(=O)$_2$— or —NR S(=O)$_2$—;

$R^8$ is H, $C_1$-$C_6$alkyl or hydroxylalkyl;

$R^{8'}$ is H, —OH, —CN or $C_1$-$C_6$alkyl; and $R^9$ and $R^{10}$ are each independently H, halo, cyano, carboxyl, $C_1$-$C_6$ alkyl, alkoxycarbonyl, aminylalkyl, alkylaminylalkyl, aryl, heterocyclyl, heterocyclylalkyl, heteroaryl or hydroxylalkyl, or $R^9$ and $R^{10}$ join to form a carbocyclic, heterocyclic or heteroaryl ring.

In still other of any of the foregoing embodiments, E has the following structure:

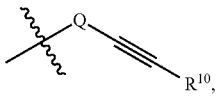

wherein:

Q is —C(=O)—, —$NR^8$C(=O)—, —S(=O)$_2$— or —$NR^8$S(=O)$_2$—;

$R^8$ is H, $C_1$-$C_6$alkyl or hydroxylalkyl; and $R^{10}$ is H, $C_1$-$C_6$alkyl, aminylalkyl, alkylaminylalkyl or hydroxylalkyl.

The Q moiety is typically selected to optimize the reactivity (i.e., electrophilicity) of E. In some of the foregoing embodiments Q is —C(=O)—, —$NR^8$C(=O)—, —S(=O)$_2$— or —$NR^8$S(=O)$_2$—. In certain of the foregoing embodiments, Q is —C(=O)—. In other embodiments, Q is —S(=O)$_2$—. In still more embodiments, Q is —NR$^8$C(=O)—. In still more different embodiments, Q is —NR$^8$S(=O)$_2$—.

In some other of the foregoing embodiments, Q is —C(=NR$^{8'}$)—, wherein R$^{8'}$ is H, —OH, —CN or C$_1$-C$_6$alkyl. For example, in some embodiments R$^{8'}$ is H. In other embodiments, R$^{8'}$ is —CN. In other embodiments, R$^{8'}$ is —OH.

In some of the foregoing embodiments, R$^8$ is H. In other of these embodiments, R$^8$ is hydroxylalkyl, for example in some embodiments the hydroxylalkyl is 2-hydroxylalkyl.

In some of any one of the foregoing embodiments, at least one of R$^9$ or R$^{10}$ is H. For example, in some embodiments each of R$^9$ and R$^{10}$ are H.

In other of the foregoing embodiments, R$^{10}$ is alkylaminylalkyl. In some of these embodiments, R$^{10}$ has the following structure:

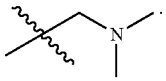

In other embodiments, R$^{10}$ is hydroxylalkyl, such as 2-hydroxylalkyl.

In some other different embodiments of the foregoing embodiments, R$^9$ and R$^{10}$ join to form a carbocyclic ring. For example, in some of these embodiments the carbocyclic ring is a cyclopentene, cyclohexene or phenyl ring. In other embodiments, the carbocyclic ring is a cyclopentene or cyclohexene ring. In other embodiments, the carbocyclic ring is a phenyl ring, for example a phenyl ring having the following structure:

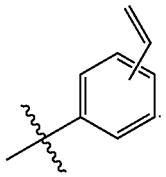

In some of any of the foregoing embodiments E is an electrophile capable of bonding with a KRAS, HRAS or NRAS protein comprising G12C mutation. In some embodiments, the electrophile E is capable of forming an irreversible covalent bond with a G12C mutant KRAS, HRAS or NRAS protein. In some cases, the electrophile E may bind with the cysteine residue at the position 12 of a G12C mutant KRAS, HRAS or NRAS protein. In various embodiments of any of the foregoing, E has one of the following structures:

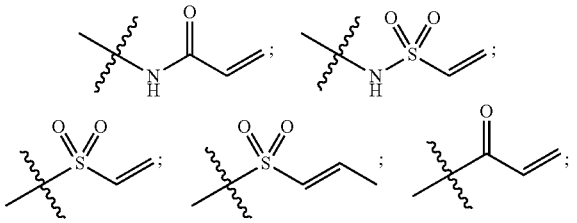

-continued

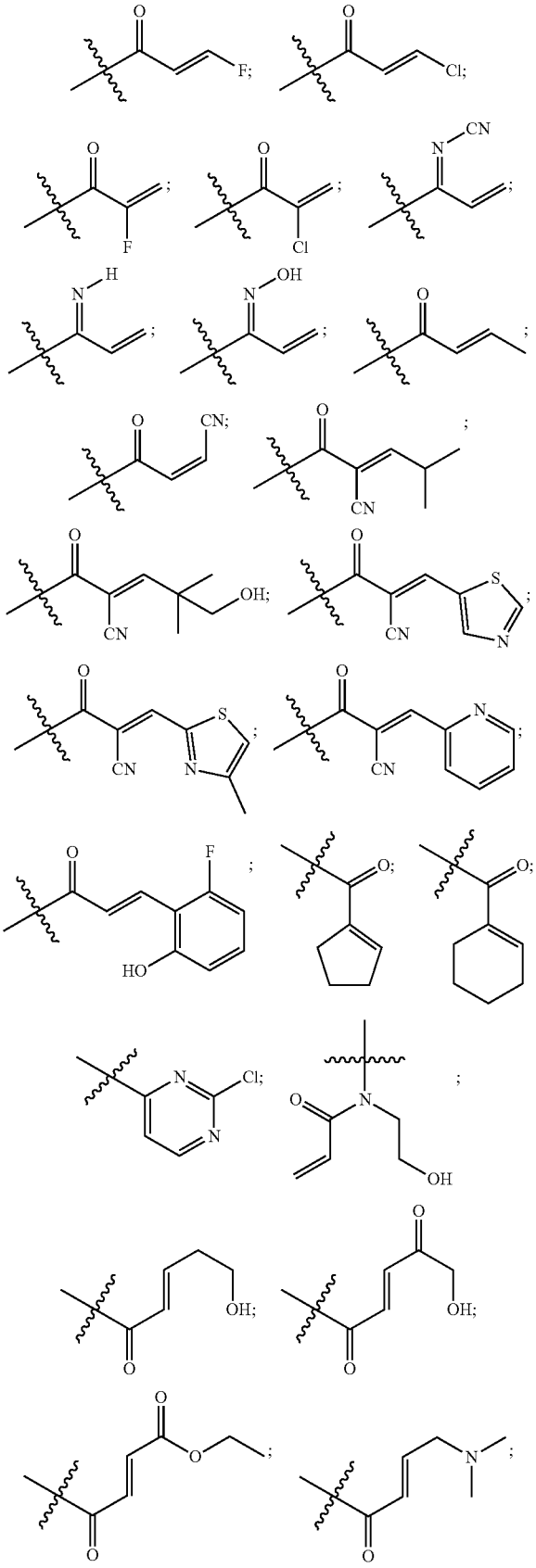

-continued
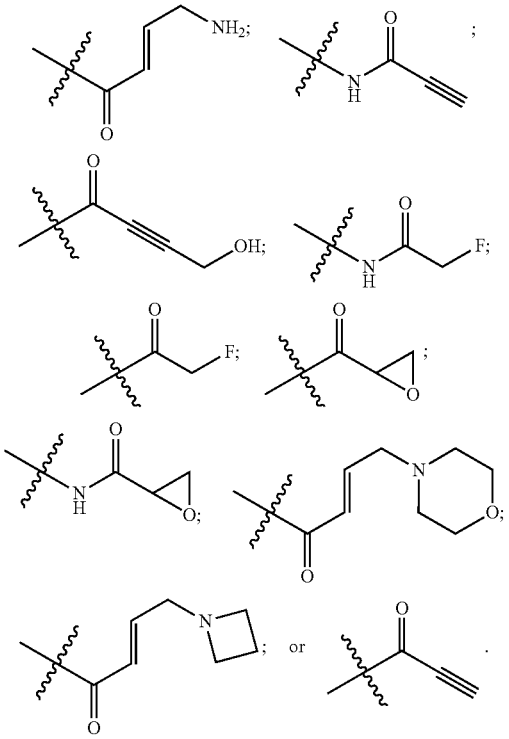
In some embodiments, E has one of the following structures:
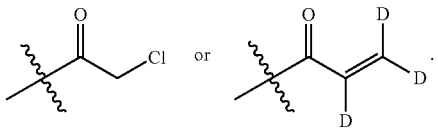
In other embodiments of any of the foregoing, E has one of the following structures:
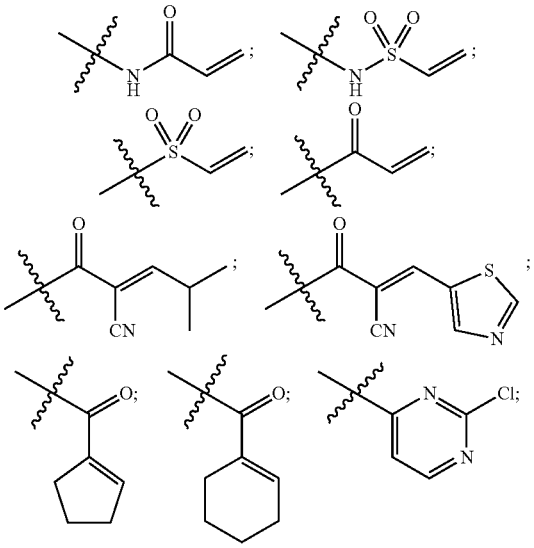
-continued
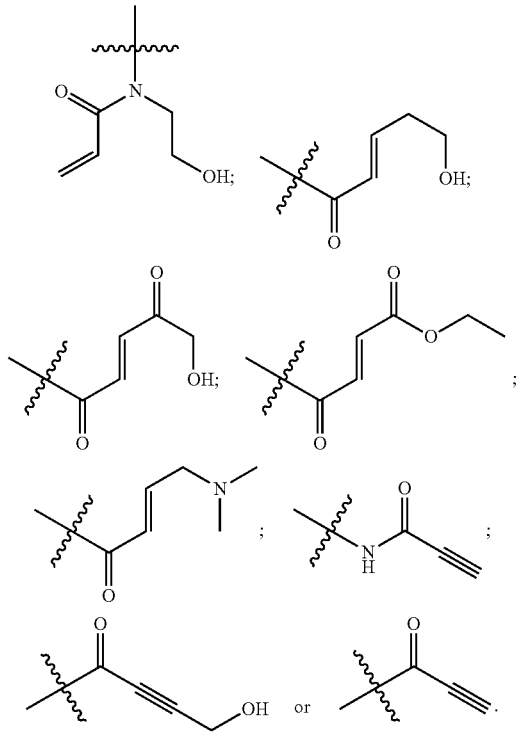
In different embodiments, E has one of the following structures:
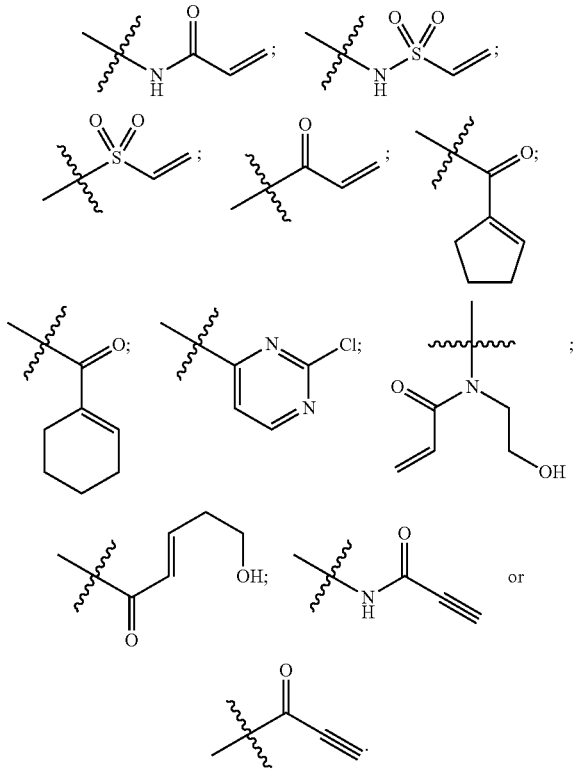

In some cases E has one of the following structures:

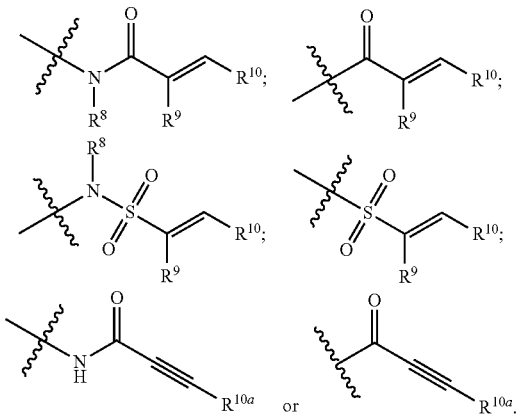

wherein:

$R^8$ is H or $C_1$-$C_6$alkyl;

$R^9$ is H, cyano or $C_1$-$C_6$alkyl, or $R^9$ joins with $R^{10}$ to form a carbocycle;

$R^{10}$ is H or $C_1$-$C_6$alkyl or $R^{10}$ joins with $R^9$ to form a carbocycle and $R^{10a}$ is H or $C_1$-$C_6$alkyl.

In some embodiments E is

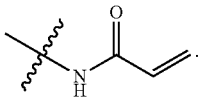

In some embodiments E is

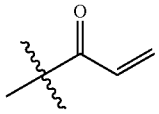

In some embodiments E is

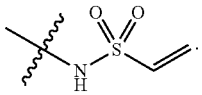

In some of any of the foregoing embodiments, $L^1$ is a bond. In other embodiments, $L^1$ is $NR^7$. For example, in some of these embodiments, $R^7$ is $C_1$-$C_6$alkyl. In other embodiments, $L^1$ is NH.

$L^2$ can be selected to provide proper spacing and/or orientation for the E group to form a bond with the KRAS, HRAS or NRAS protein. In some of the foregoing embodiments, $L^2$ is a bond. In other of the foregoing embodiments, $L^2$ is alkylene. In some embodiments, the alkylene is substituted. In other embodiments the alkylene is unsubstituted. For example, in some embodiments $L^2$ is $CH_2$ or $CH_2CH_2$.

In certain embodiments, $R^{3a}$ and $R^{3b}$ are, at each occurrence, independently H, —OH, —$NH_2$, —$CO_2H$, halo, cyano, hydroxylalkly, aminylalkyl, cyanoalkyl, carboxyalkyl or aminylcarbonyl, and $R^{4a}$ and $R^{4b}$ are, at each occurrence, independently H, —OH, —$NH_2$, —$CO_2H$, halo, cyano, hydroxylalkly, aminylalkyl, cyanoalkyl, carboxyalkyl or aminylcarbonyl.

In other of the foregoing embodiments, $R^{3a}$ and $R^{4a}$ are, at each occurrence, independently H, —OH, hydroxylalkly, cyano, or aminylcarbonyl and $R^{3b}$ and $R^{4b}$ are H.

In certain other embodiments, $R^{3a}$ and $R^{4a}$ are H and $R^{3b}$ and $R^{4b}$ are, at each occurrence, independently H, —OH, —$NH_2$, —$CO_2H$, halo, cyano, hydroxylalkly, aminylalkyl, cyanoalkyl, carboxyalkyl or aminylcarbonyl.

In any of the foregoing embodiments, at least one of $R^{3a}$, $R^{3b}$, $R^{4a}$ or $R^{4b}$ is H. In some embodiments, each of $R^{3a}$, $R^{3b}$, $R^{4a}$ and $R^{4b}$ are H.

In some embodiments, $R^{3a}$ is —OH, —$NH_2$, —$CO_2H$, halo, cyano, hydroxylalkly, aminylalkyl, cyanoalkyl, carboxyalkyl or aminylcarbonyl, and $R^{3b}$, $R^{4a}$ and $R^{4b}$ are H.

In other of the foregoing embodiments, $R^{3a}$ and $R^{4a}$ are, at each occurrence, independently H or $C_1$-$C_6$ alkyl. In some embodiments, at least one of $R^{3a}$, $R^{4a}$, $R^{3b}$ and $R^{4b}$ is independently $C_1$-$C_6$ alkyl, such as methyl. In some embodiments, one occurrence of $R^{3a}$ is $C_1$-$C_6$ alkyl, such as methyl, and the remaining $R^{3a}$ and each $R^{4a}$ is H. In some other embodiments, two occurrences of $R^{3a}$ are $C_1$-$C_6$ alkyl, such as methyl, and the remaining $R^{3a}$ and each $R^{4a}$ is H. In some other embodiments, one occurrence of $R^{3a}$ and one occurrence of $R^{4a}$ is independently $C_1$-$C_6$ alkyl, such as methyl, and the remaining $R^{3a}$ and $R^{4a}$ are each H.

In other embodiments, $R^{4a}$ is —OH, —$NH_2$, —$CO_2H$, halo, cyano, hydroxylalkly, aminylalkyl, cyanoalkyl, carboxyalkyl or aminylcarbonyl, and $R^{3a}$, $R^{3b}$ and $R^{4b}$ are H.

In other embodiments, $R^{3a}$ is H, —OH, —$NH_2$, —$CO_2H$, halo, cyano, hydroxylalkly, aminylalkyl, cyanoalkyl, carboxyalkyl or aminylcarbonyl, and $R^{3b}$ joins with $R^{4b}$ to form a carbocyclic or heterocyclic ring;

In still more embodiments, $R^{4a}$ is H, —OH, —$NH_2$, —$CO_2H$, halo, cyano, hydroxylalkly, aminylalkyl, cyanoalkyl, carboxyalkyl or aminylcarbonyl, and $R^{4b}$ joins with $R^{3b}$ to form a carbocyclic or heterocyclic ring.

In other embodiments, $R^{3a}$ and $R^{3b}$ join to form a carbocyclic or heterocyclic ring. In other embodiments, $R^{4a}$ and $R^{4b}$ join to form a carbocyclic or heterocyclic ring.

In still other embodiments, $R^{3a}$ or $R^{4a}$ is aminylcarbonyl. For example, in certain embodiments, the aminylcarbonyl is

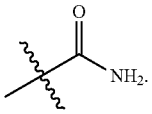

In other embodiments, $R^{3a}$ or $R^{4a}$ is cyano. In other embodiments, $R^{3a}$ or $R^{4a}$ is —OH. In other embodiments, $R^{3a}$ or $R^{4a}$ is hydroxylalkyl, for example hydroxylmethyl.

In some embodiments of any of the foregoing compounds (e.g., the compounds of structures (I), (I'a), (I'b), (I'c), (I'd) or (I'e)), $R^1$ is aryl or heteroaryl and $R^{2a}$, $R^{2b}$ and $R^{2c}$ are independently selected from H and halo, for example in some further embodiments $R^1$ is aryl or heteroaryl and $R^{2a}$ and $R^{2b}$ are independently selected from halo, such as chloro and fluoro, and $R^{2c}$ is H. In some embodiments, $R^1$ is aryl or heteroaryl, $R^{2a}$ is chloro, $R^{2b}$ is fluoro and $R^{2c}$ is H. In other embodiments $R^1$ is aryl or heteroaryl, one of $R^{2a}$ or $R^{2b}$ is halo, such as chloro or fluoro, and the other one of $R^{2a}$ or $R^{2b}$ is H.

In some embodiments of any of the compounds described herein, $C_1$-$C_6$ haloalkyl is $CF_3$ (e.g., when one or more of $R^{2a}$, $R^{2b}$ or $R^{2c}$ is $C_1$-$C_6$ haloalkyl).

In some embodiments $m^1$ is 1. In other embodiments $m^1$ is 2. In still more embodiments, $m^1$ is 3. In different embodiments, $m^2$ is 1. In some other embodiments, $m^2$ is 2. In yet still more embodiments, $m^2$ is 3.

In some other particular embodiments of any of the foregoing compounds, $m^1$ is 1, and $m^2$ is 1. In other embodiments, $m^1$ is 1 and, $m^2$ is 2. In still other embodiments $m^1$ is 2, and $m^2$ is 2. In more embodiments, $m^1$ is 1, and $m^2$ is 3.

In any of the foregoing embodiments, $G^1$ and $G^2$ are each independently selected from N and CH. In some embodiments, at least one of $G^1$ or $G^2$ is N. In some embodiments, each of $G^1$ and $G^2$ are N. In some embodiments, each of $G^1$ and $G^2$ are N and $m^1$ and $m^2$ are each 2. In some other embodiments, at least one of $G^1$ or $G^2$ is CH. In other embodiments, each of $G^1$ and $G^2$ are CH.

For example, in other embodiments the compounds have one of the following structures (I'i) or (I'j):

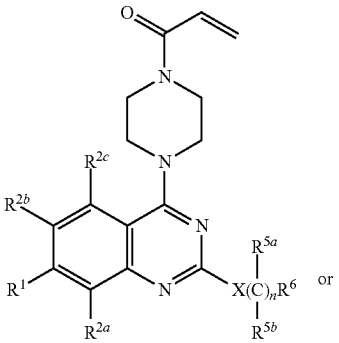

or

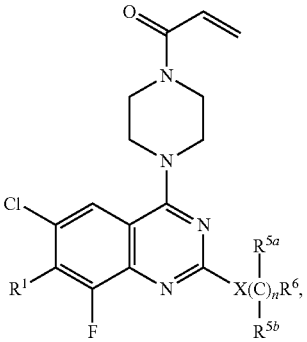

wherein $R^1$, $R^{2a}$, $R^{2b}$, $R^{2c}$, $R^{5a}$, $R^{5b}$, $R^6$, X and n are as defined according to any of the foregoing embodiments. In some more specific embodiments of compounds (I'i) or (I'j), $R^1$ has one of the following structures:

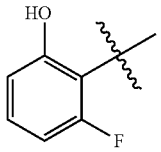

or

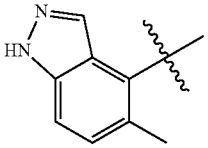

In any of the foregoing embodiments, A is N. In other of the foregoing embodiments, A is C—CN. In other of the foregoing embodiments, A is CH.

Some embodiments of the compounds include more than one stereoisomer. Other embodiments are directed to a single stereoisomer. In some embodiments the compounds are racemic (e.g., mixture of atropisomers), while in other embodiments the compounds are substantially a single isomer, for example a substantially purified atropisomer.

In various different embodiments, the compound has one of the structures set forth in Table 1 below. The compounds in Table 1 were each prepared and analyzed by mass spectrometry and/or $^1$H NMR. Experimental mass spectrometry data is included in Table 1. Exemplary synthetic procedures are described in more detail below and in the Examples. General methods by which the compounds may be prepared are provided below and indicated in Table 1.

TABLE 1

Representative Compounds of Structure (I)

| No. | Structure | Name | Method | $[M + H]^+$ |
|---|---|---|---|---|
| I-1 | 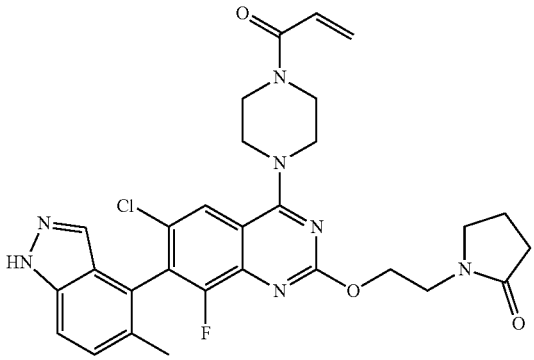 | 1-(2-(4-(4-acryloylpiperazin-1-yl)-6-chloro-8-fluoro-7-(5-methyl-1H-indazol-4-yl)quinazolin-2-yloxy)ethyl) pyrrolidin-2-one | A | 578.1 |

TABLE 1-continued

| Representative Compounds of Structure (I) | | | | |
|---|---|---|---|---|
| No. | Structure | Name | Method | $[M + H]^+$ |
| I-2 | 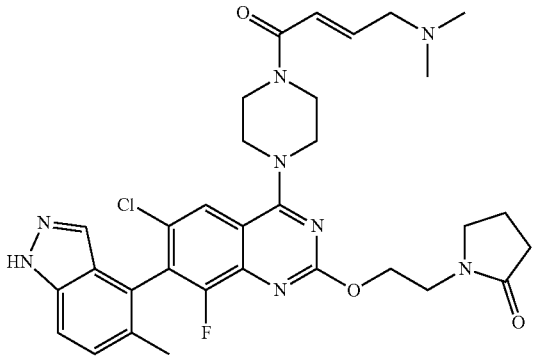 | (E)-1-(2-(6-chloro-4-(4-(4-(dimethylamino) but-2-enoyl) piperazin-1-yl)-8-fluoro-7-(5-methyl-1H-indazol-4-yl)quinazolin-2-yloxy)ethyl) pyrrolidin-2-one | A | 635.3 |
| I-3 | 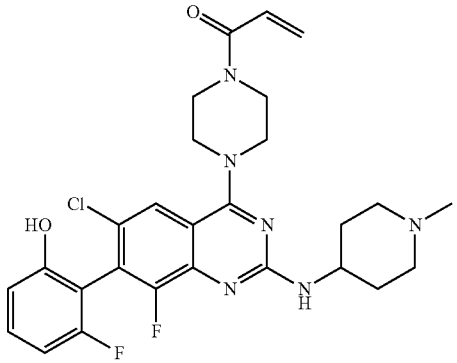 | 1-(4-(6-chloro-8-fluoro-7-(2-fluoro-6-hydroxyphenyl)-2-(1-methylpiperidin-4-ylamino) quinazolin-4-yl) piperazin-1-yl) prop-2-en-1-one | B | 543.2 |
| I-4 | 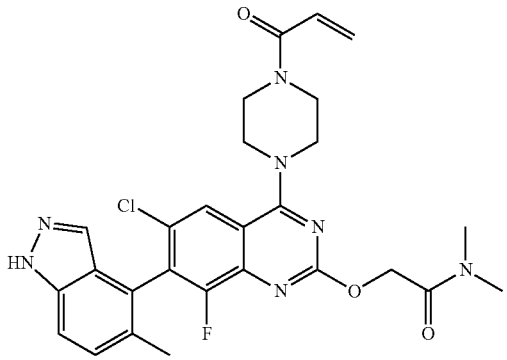 | 2-(4-(4-acryloylpiperazin-1-yl)-6-chloro-8-fluoro-7-(5-methyl-1H-indazol-4-yl)quinazolin-2-yloxy)-N,N-dimethyl-acetamide | A | 552.2 |
| I-5 | 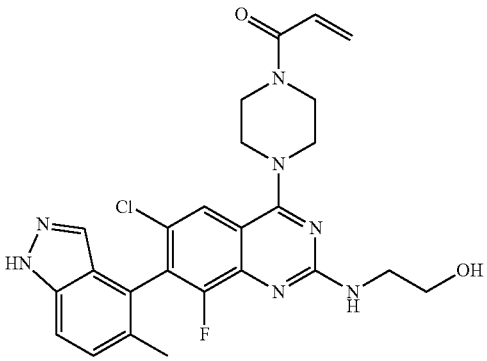 | 1-(4-(6-chloro-8-fluoro-2-(2-hydroxyethyl-amino)-7-(5-methyl-1H-indazol-4-yl)quinazolin-4-yl)piperazin-1-yl)prop-2-en-1-one | B | 510.3 |

TABLE 1-continued

| Representative Compounds of Structure (I) | | | | |
|---|---|---|---|---|
| No. | Structure | Name | Method | $[M + H]^+$ |
| I-6 | 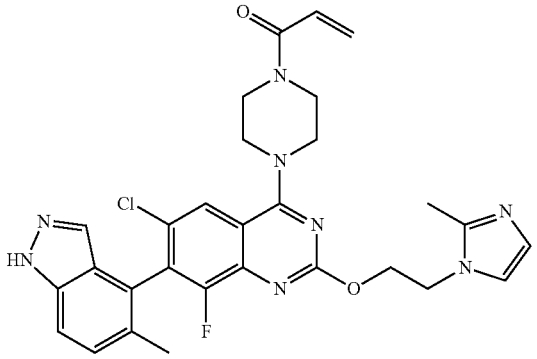 | 1-(4-(6-chloro-8-fluoro-2-(2-(2-methyl-1H-imidazol-1-yl)ethoxy)-7-(5-methyl-1H-indazol-4-yl)quinazolin-4-yl)piperazin-1-yl)prop-2-en-1-one | D | 575.2 |
| I-7 | 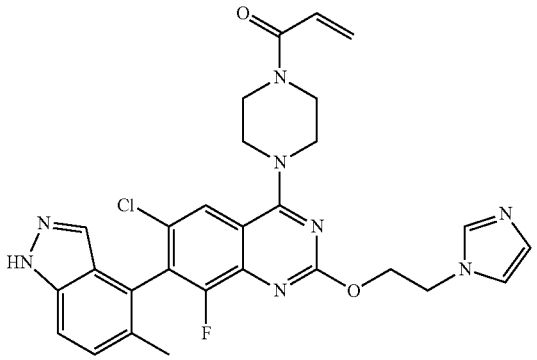 | 1-(4-(2-(2-(1H-imidazol-1-yl)ethoxy)-6-chloro-8-fluoro-7-(5-methyl-1H-indazol-4-yl)quinazolin-4-yl)piperazin-1-yl)prop-2-en-1-one | D | 561.2 |
| I-8 | 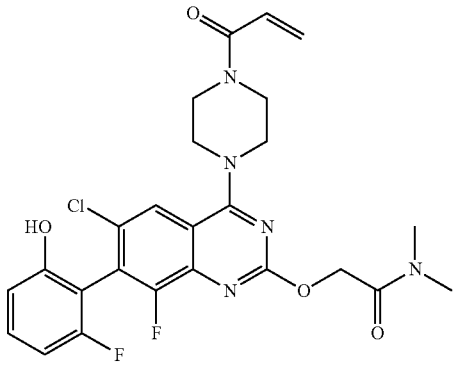 | 2-(4-(4-acryloyl-piperazin-1-yl)-6-chloro-8-fluoro-7-(2-fluoro-6-hydroxyphenyl)quinazolin-2-yloxy)-N,N-dimethyl-acetamide | A | 532.1 |
| I-9 | 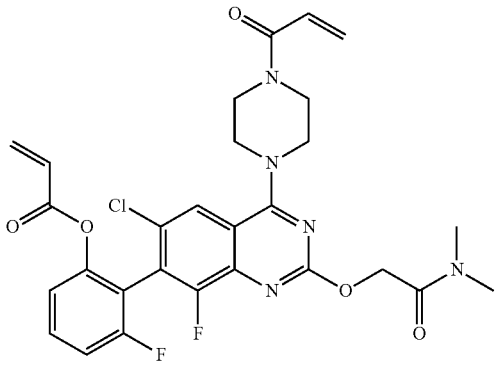 | 2-(4-(4-acryloyl-piperazin-1-yl)-6-chloro-2-(2-(dimethylamino)-2-oxoethoxy)-8-fluoroquinazolin-7-yl)-3-fluorophenyl acrylate | A | 586.1 |

TABLE 1-continued

| Representative Compounds of Structure (I) | | | | |
|---|---|---|---|---|
| No. | Structure | Name | Method | $[M + H]^+$ |
| I-10 | 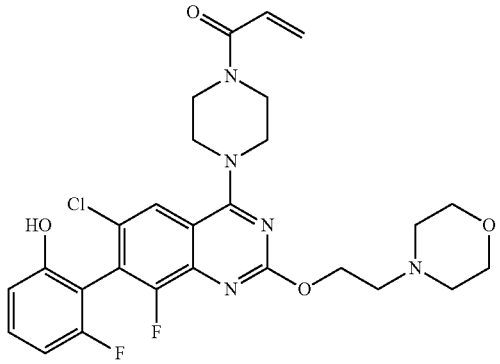 | 1-(4-(6-chloro-8-fluoro-7-(2-fluoro-6-hydroxyphenyl)-2-(2-morpholino-ethoxy) quinazolin-4-yl)piperazin-1-yl)prop-2-en-1-one | A | 560.2 |
| I-11 | 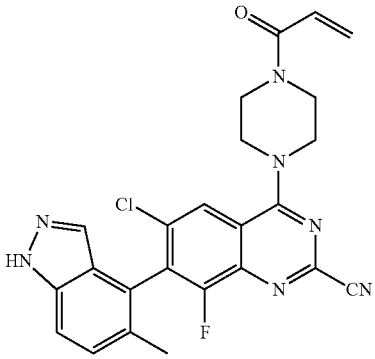 | 4-(4-acryloyl-piperazin-1-yl)-6-chloro-8-fluoro-7-(5-methyl-1H-indazol-4-yl)quinazoline-2-carbonitrile | G | 476.2 |
| I-12 | 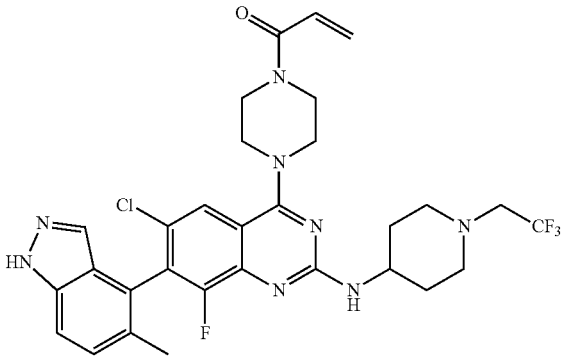 | 1-(4-(6-chloro-8-fluoro-7-(5-methyl-1H-indazol-4-yl)-2-(1-(2,2,2-trifluoroethyl) piperidin-4-ylamino) quinazolin-4-yl)piperazin-1-yl)prop-2-en-1-one | B | 631.3 |
| I-13 | 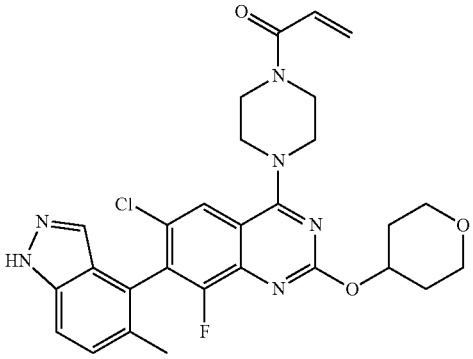 | 1-(4-(6-chloro-8-fluoro-7-(5-methyl-1H-indazol-4-yl)-2-(tetrahydro-2H-pyran-4-yloxy)quinazolin-4-yl)piperazin-1-yl)prop-2-en-1-one | A | 551.3 |

TABLE 1-continued

Representative Compounds of Structure (I)

| No. | Structure | Name | Method | $[M + H]^+$ |
|---|---|---|---|---|
| I-14 | 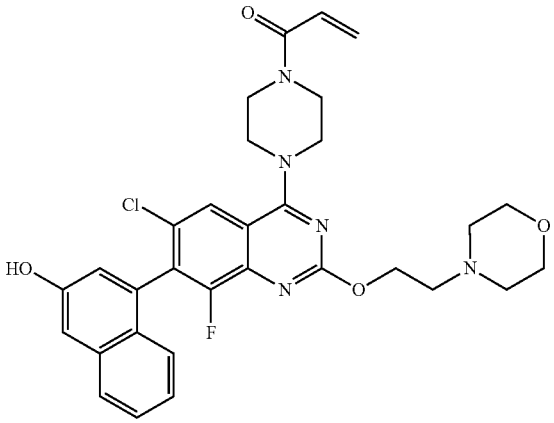 | 1-(4-(6-chloro-8-fluoro-7-(3-hydroxy-naphthalen-1-yl)-2-(2-morpholino-ethoxy) quinazolin-4-yl)piperazin-1-yl)prop-2-en-1-one | A | 592.3 |
| I-15 | 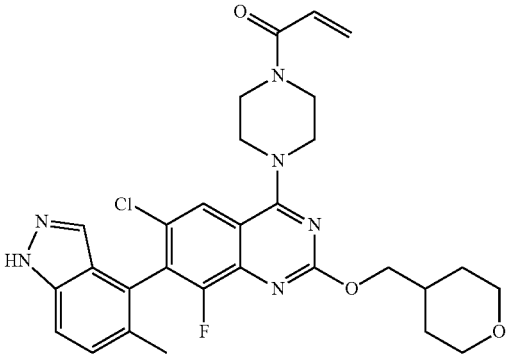 | 1-(4-(6-chloro-8-fluoro-7-(5-methyl-1H-indazol-4-yl)-2-((tetrahydro-2H-pyran-4-yl) methoxy) quinazolin-4-yl) piperazin-1-yl)prop-2-en-1-one | A | 565.4 |
| I-16 | 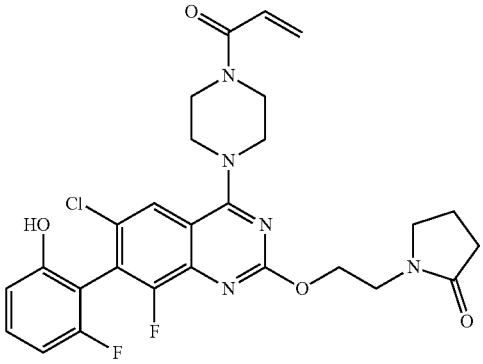 | 1-(2-(4-(4-acryloyl-piperazin-1-yl)-6-chloro-8-fluoro-7-(2-fluoro-6-hydroxyphenyl) quinazolin-2-yloxy)ethyl) pyrrolidin-2-one | A | 558.2 |
| I-17 | 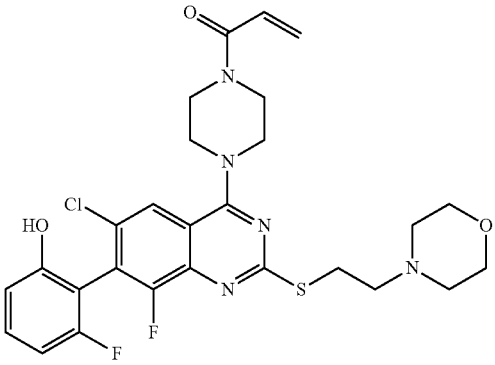 | 1-(4-(6-chloro-8-fluoro-7-(2-fluoro-6-hydroxyphenyl)-2-(2-morpholino-ethylthio) quinazolin-4-yl)piperazin-1-yl)prop-2-en-1-one | A | 576.2 |

TABLE 1-continued

| Representative Compounds of Structure (I) | | | | |
|---|---|---|---|---|
| No. | Structure | Name | Method | $[M + H]^+$ |
| I-18 | 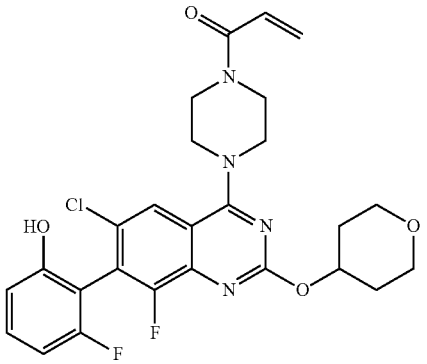 | 1-(4-(6-chloro-8-fluoro-7-(2-fluoro-6-hydroxyphenyl)-2-(tetrahydro-2H-pyran-4-yloxy) quinazolin-4-yl)piperazin-1-yl)prop-2-en-1-one | A | 531.3 |
| I-19 | 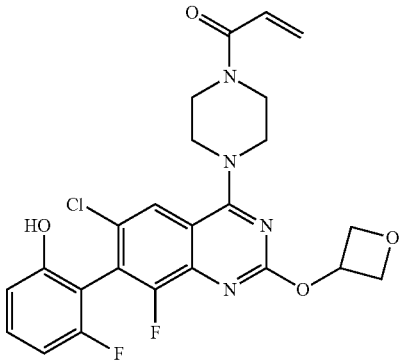 | 1-(4-(6-chloro-8-fluoro-7-(2-fluoro-6-hydroxyphenyl)-2-(oxetan-3-yloxy) quinazolin-4-yl)piperazin-1-yl)prop-2-en-1-one | A | 503.2 |
| I-20 | 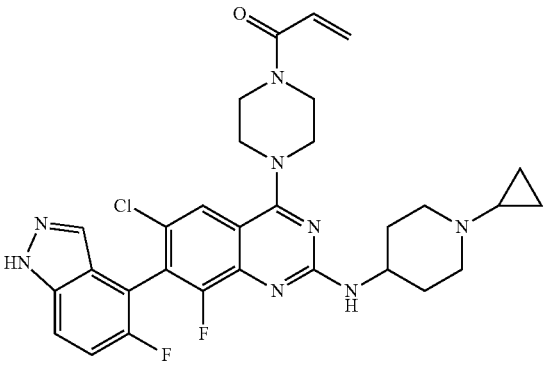 | 1-(4-(6-chloro-2-(1-cyclopropyl-piperidin-4-ylamino)-8-fluoro-7-(5-methyl-1H-indazol-4-yl)quinazolin-4-yl)piperazin-1-yl)prop-2-en-1-one | B | 589.3 |
| I-21 | 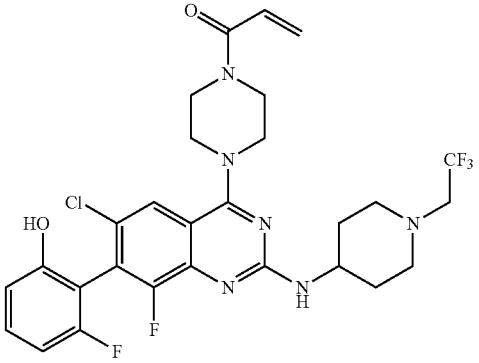 | 1-(4-(6-chloro-8-fluoro-7-(2-fluoro-6-hydroxyphenyl)-2-(1-(2,2,2-trifluoroethyl) piperidin-4-ylamino) quinazolin-4-yl) piperazin-1-yl)prop-2-en-1-one | B | 611.3 |

TABLE 1-continued

Representative Compounds of Structure (I)

| No. | Structure | Name | Method | $[M + H]^+$ |
|---|---|---|---|---|
| I-22 | 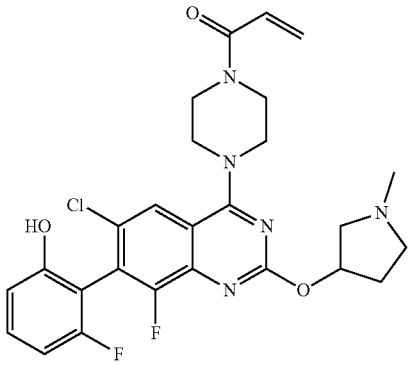 | 1-(4-(6-chloro-8-fluoro-7-(2-fluoro-6-hydroxyphenyl)-2-(1-methyl-pyrrolidin-3-yloxy) quinazolin-4-yl)piperazin-1-yl)prop-2-en-1-one | A | 530.2 |
| I-23 | 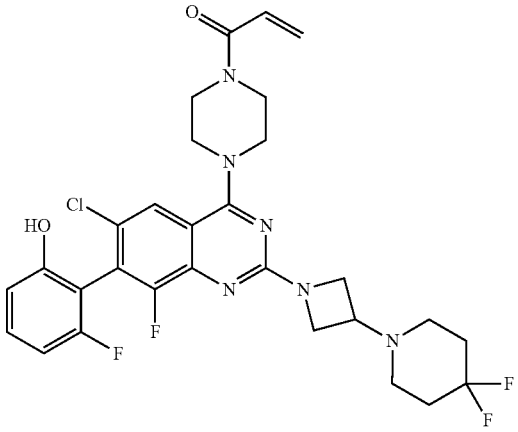 | 1-(4-(6-chloro-2-(3-(4,4-difluoro-piperidin-1-yl) azetidin-1-yl)-8-fluoro-7-(2-fluoro-6-hydroxyphenyl) quinazolin-4-yl) piperazin-1-yl) prop-2-en-1-one | B | 605.2 |
| I-24 | 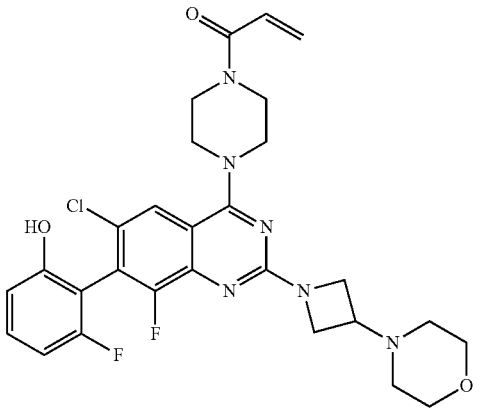 | 1-(4-(6-chloro-8-fluoro-7-(2-fluoro-6-hydroxyphenyl)-2-(3-morpholino-azetidin-1-yl) quinazolin-4-yl)piperazin-1-yl)prop-2-en-1-one | B | 571.3 |
| I-25 | 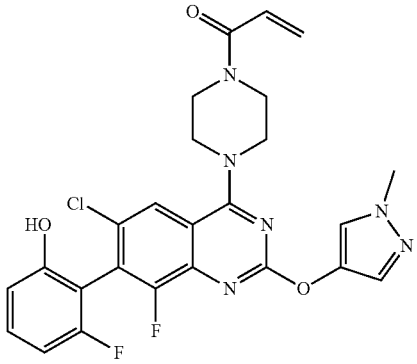 | 1-(4-(6-chloro-8-fluoro-7-(2-fluoro-6-hydroxyphenyl)-2-(1-methyl-1H-pyrazol-4-yloxy) quinazolin-4-yl)piperazin-1-yl)prop-2-en-1-one | A | 527.2 |

TABLE 1-continued

| Representative Compounds of Structure (I) | | | | |
|---|---|---|---|---|
| No. | Structure | Name | Method | $[M + H]^+$ |
| I-26 | 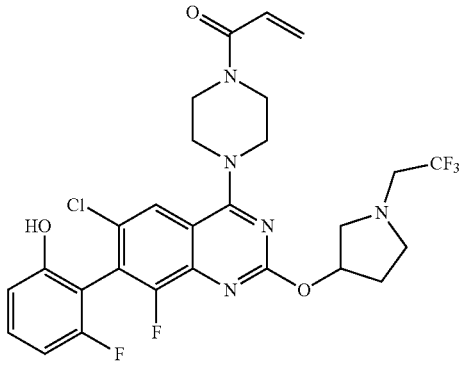 | 1-(4-(6-chloro-8-fluoro-7-(2-fluoro-6-hydroxyphenyl)-2-(1-(2,2,2-trifluoroethyl) pyrrolidin-3-yloxy) quinazolin-4-yl)piperazin-1-yl)prop-2-en-1-one | A | 598.3 |
| I-27 | 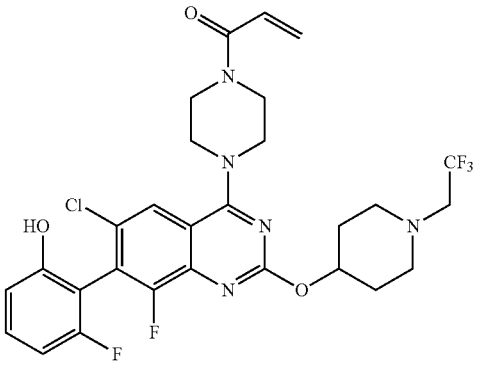 | 1-(4-(6-chloro-8-fluoro-7-(2-fluoro-6-hydroxyphenyl)-2-(1-(2,2,2-trifluoroethyl) piperidin-4-yloxy) quinazolin-4-yl)piperazin-1-yl)prop-2-en-1-one | A | 612.4 |
| I-28 | 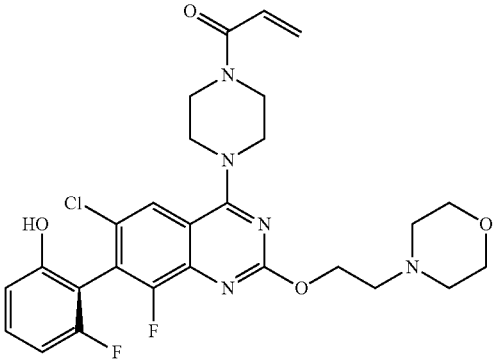 | (R)-1-(4-(6-chloro-8-fluoro-7-(2-fluoro-6-hydroxyphenyl)-2-(2-morpholino-ethoxy) quinazolin-4-yl)piperazin-1-yl)prop-2-en-1-one | A | 560.2 |
| I-29 | 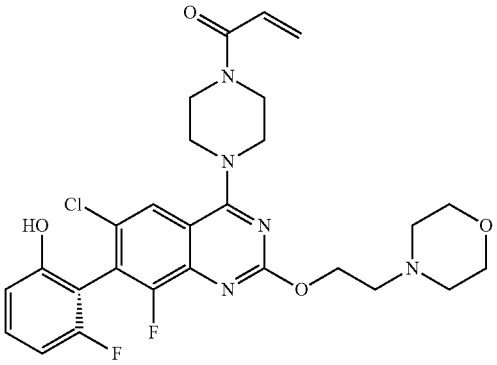 | (S)-1-(4-(6-chloro-8-fluoro-7-(2-fluoro-6-hydroxyphenyl)-2-(2-morpholino-ethoxy) quinazolin-4-yl)piperazin-1-yl)prop-2-en-1-one | A | 560.2 |

TABLE 1-continued

| Representative Compounds of Structure (I) | | | | |
|---|---|---|---|---|
| No. | Structure | Name | Method | $[M + H]^+$ |
| I-30 | 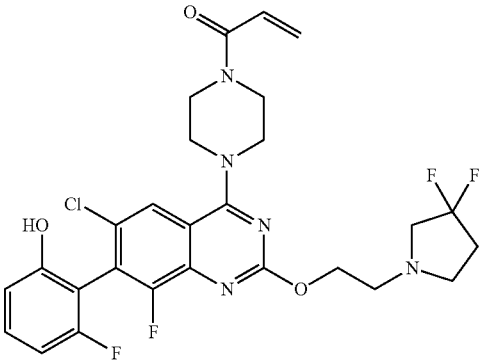 | 1-(4-(6-chloro-2-(2-(3,3-difluoro-pyrrolidin-1-yl)ethoxy)-8-fluoro-7-(2-fluoro-6-hydroxyphenyl) quinazolin-4-yl) piperazin-1-yl) prop-2-en-1-one | A | 580.3 |
| I-31 | 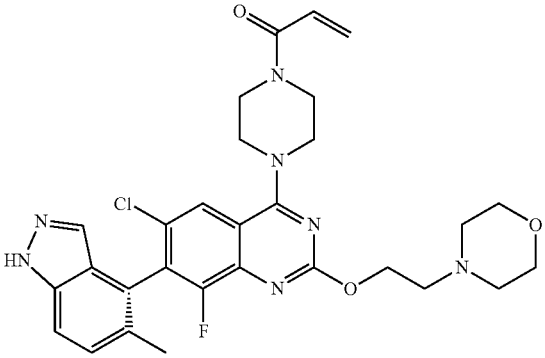 | (R)-1-(4-(6-chloro-8-fluoro-7-(5-methyl-1H-indazol-4-yl)-2-(2-morpholino-ethoxy) quinazolin-4-yl)piperazin-1-yl)prop-2-en-1-one | A | 580.3 |
| I-32 | 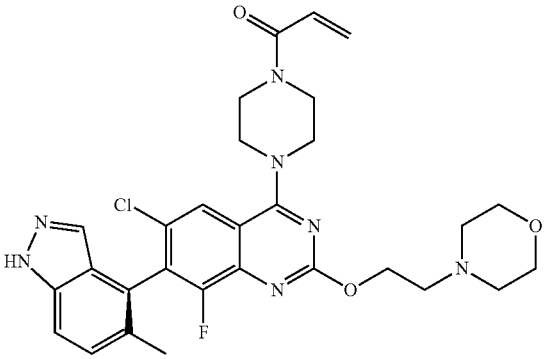 | (S)-1-(4-(6-chloro-8-fluoro-7-(5-methyl-1H-indazol-4-yl)-2-(2-morpholino-ethoxy) quinazolin-4-yl)piperazin-1-yl)prop-2-en-1-one | A | 580.3 |
| I-33 | 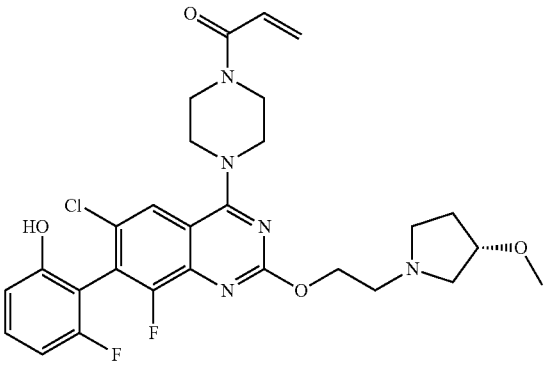 | 1-(4-(6-chloro-8-fluoro-7-(2-fluoro-6-hydroxyphenyl)-2-(2-((S)-3-methoxy-pyrrolidin-1-yl) ethoxy) quinazolin-4-yl) piperazin-1-yl)prop-2-en-1-one | A | 574.2 |

TABLE 1-continued

| Representative Compounds of Structure (I) | | | | |
|---|---|---|---|---|
| No. | Structure | Name | Method | $[M + H]^+$ |
| I-34 | 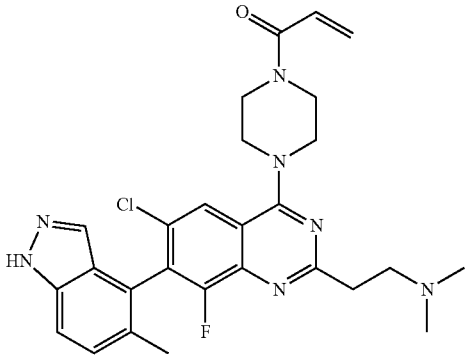 | 1-(4-(6-chloro-2-(2-(dimethyl-amino)ethyl)-8-fluoro-7-(5-methyl-1H-indazol-4-yl) quinazolin-4-yl)piperazin-1-yl)prop-2-en-1-one | E | 523.3 |
| I-35 | 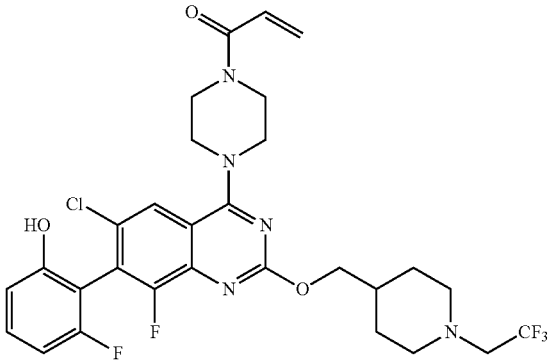 | 1-(4-(6-chloro-8-fluoro-7-(2-fluoro-6-hydroxyphenyl)-2-((1-(2,2,2-trifluoroethyl) piperidin-4-yl) methoxy) quinazolin-4-yl)piperazin-1-yl)prop-2-en-1-one | A | 626.3 |
| I-36 | 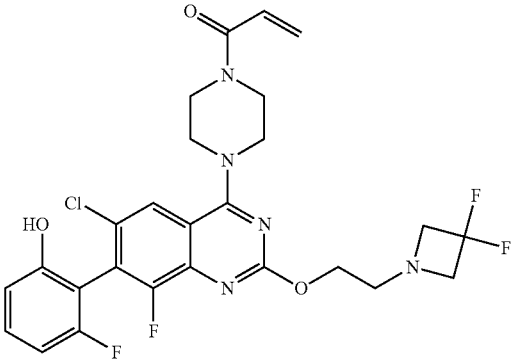 | 1-(4-(6-chloro-2-(2-(3,3-difluoroazetidin-1-yl)ethoxy)-8-fluoro-7-(2-fluoro-6-hydroxyphenyl) quinazolin-4-yl) piperazin-1-yl) prop-2-en-1-one | A | 566.3 |
| I-37 | 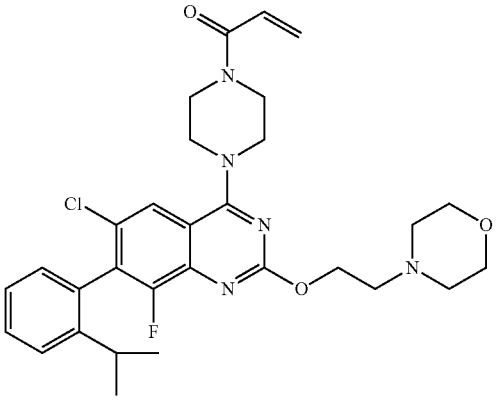 | 1-(4-(6-chloro-8-fluoro-7-(2-isopropylphenyl)-2-(2-morpholino-ethoxy) quinazolin-4-yl)piperazin-1-yl)prop-2-en-1-one | A | 568.3 |

TABLE 1-continued

Representative Compounds of Structure (I)

| No. | Structure | Name | Method | $[M + H]^+$ |
|---|---|---|---|---|
| I-38 | 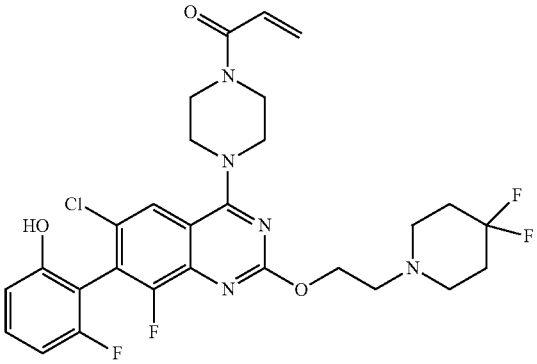 | 1-(4-(6-chloro-2-(2-(4,4-difluoro-piperidin-1-yl) ethoxy)-8-fluoro-7-(2-fluoro-6-hydroxyphenyl) quinazolin-4-yl) piperazin-1-yl) prop-2-en-1-one | A | 594.2 |
| I-39 | 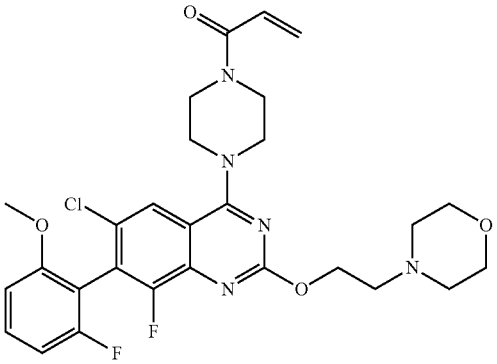 | 1-(4-(6-chloro-8-fluoro-7-(2-fluoro-6-methoxyphenyl)-2-(2-morpholino-ethoxy) quinazolin-4-yl)piperazin-1-yl)prop-2-en-1-one | A | 574.3 |
| I-40 | 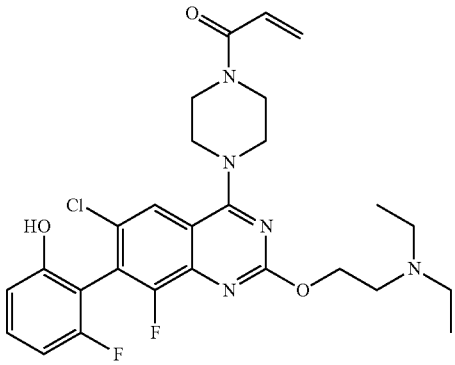 | 1-(4-(6-chloro-2-(2-(diethyl-amino)ethoxy)-8-fluoro-7-(2-fluoro-6-hydroxyphenyl) quinazolin-4-yl) piperazin-1-yl) prop-2-en-1-one | A | 546.3 |
| I-41 | 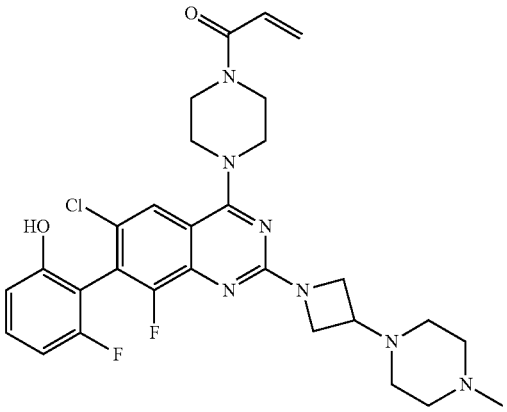 | 1-(4-(6-chloro-8-fluoro-7-(2-fluoro-6-hydroxyphenyl)-2-(3-(4-methyl-piperazin-1-yl)azetidin-1-yl)quinazolin-4-yl)piperazin-1-yl)prop-2-en-1-one | A | 584.3 |

TABLE 1-continued

Representative Compounds of Structure (I)

| No. | Structure | Name | Method | $[M + H]^+$ |
|---|---|---|---|---|
| I-42 | 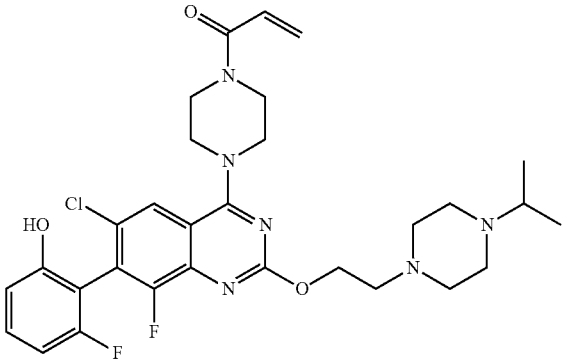 | 1-(4-(6-chloro-8-fluoro-7-(2-fluoro-6-hydroxyphenyl)-2-(2-(4-isopropyl-piperazin-1-yl) ethoxy) quinazolin-4-yl)piperazin-1-yl)prop-2-en-1-one | A | 601.3 |
| I-43 | 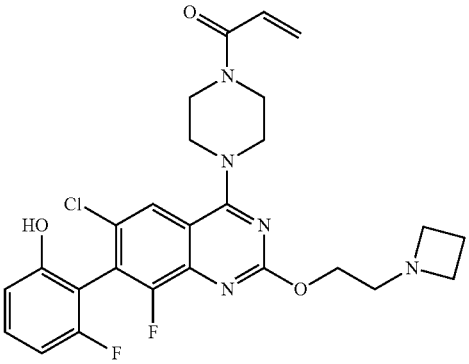 | 1-(4-(2-(2-(azetidin-1-yl) ethoxy)-6-chloro-8-fluoro-7-(2-fluoro-6-hydroxyphenyl) quinazolin-4-yl) piperazin-1-yl) prop-2-en-1-one | A | 530.3 |
| I-44 | 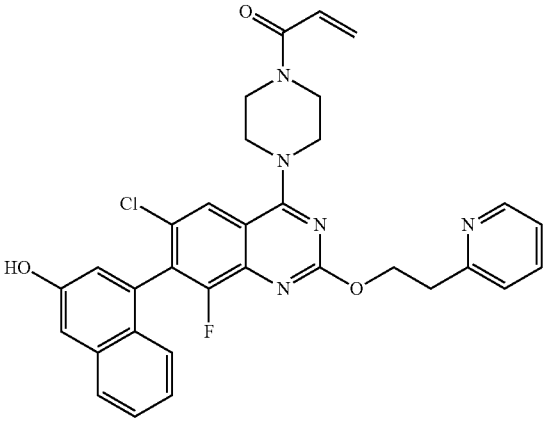 | 1-(4-(6-chloro-8-fluoro-7-(3-hydroxy-naphthalen-1-yl)-2-(2-(pyridin-2-yl)ethoxy) quinazolin-4-yl) piperazin-1-yl) prop-2-en-1-one | C | 585.2 |
| I-45 | 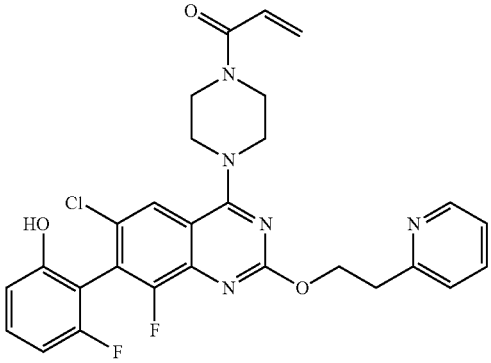 | 1-(4-(6-chloro-8-fluoro-7-(2-fluoro-6-hydroxyphenyl)-2-(2-(pyridin-2-yl)ethoxy) quinazolin-4-yl)piperazin-1-yl)prop-2-en-1-one | C | 553.2 |

TABLE 1-continued

Representative Compounds of Structure (I)

| No. | Structure | Name | Method | $[M + H]^+$ |
|---|---|---|---|---|
| I-46 | 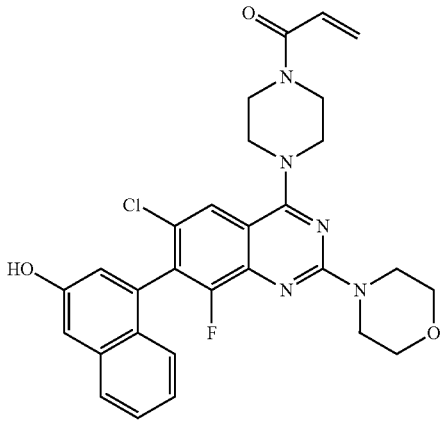 | 1-(4-(6-chloro-8-fluoro-7-(3-hydroxy-naphthalen-1-yl)-2-morpholino-quinazolin-4-yl)piperazin-1-yl)prop-2-en-1-one | B | 548.2 |
| I-47 | 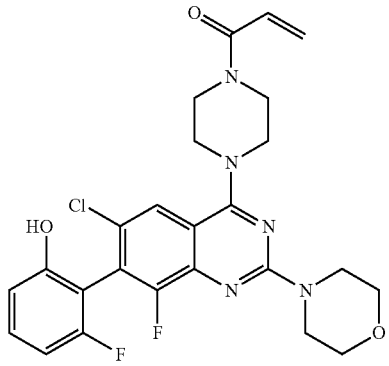 | 1-(4-(6-chloro-8-fluoro-7-(2-fluoro-6-hydroxyphenyl)-2-morpholino-quinazolin-4-yl)piperazin-1-yl)prop-2-en-1-one | B | 516.1 |
| I-48 | 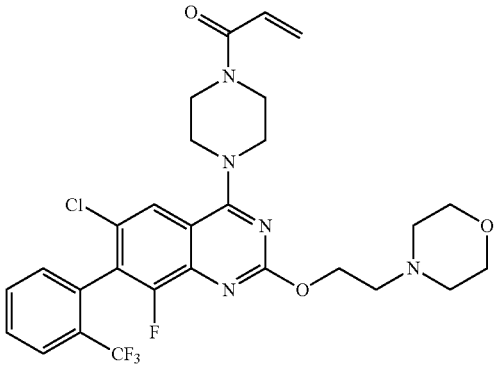 | 1-(4-(6-chloro-8-fluoro-2-(2-morpholino-ethoxy)-7-(2-(trifluoromethyl) phenyl) quinazolin-4-yl)piperazin-1-yl)prop-2-en-1-one | A | 594.3 |
| I-49 | 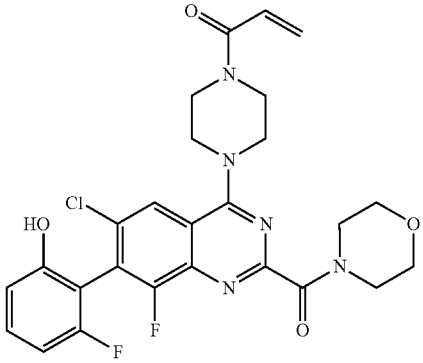 | 1-(4-(6-chloro-8-fluoro-7-(2-fluoro-6-hydroxyphenyl)-2-(morpholine-4-carbonyl) quinazolin-4-yl) piperazin-1-yl) prop-2-en-1-one | F | 544.3 |

TABLE 1-continued

| Representative Compounds of Structure (I) | | | | |
|---|---|---|---|---|
| No. | Structure | Name | Method | $[M + H]^+$ |
| I-50 | 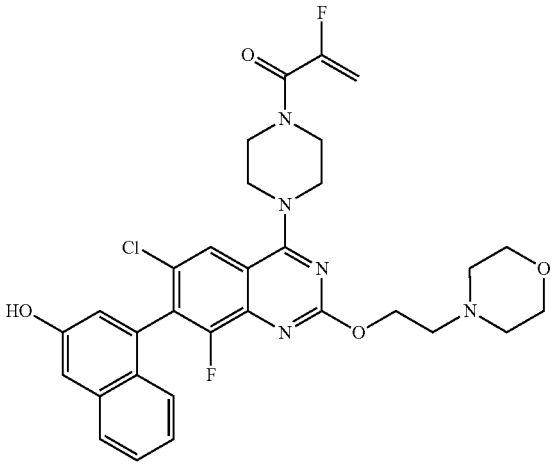 | 1-(4-(6-chloro-8-fluoro-7-(3-hydroxy-naphthalen-1-yl)-2-(2-morpholino-ethoxy) quinazolin-4-yl)piperazin-1-yl)-2-fluoroprop-2-en-1-one | A | 610.3 |
| I-51 | 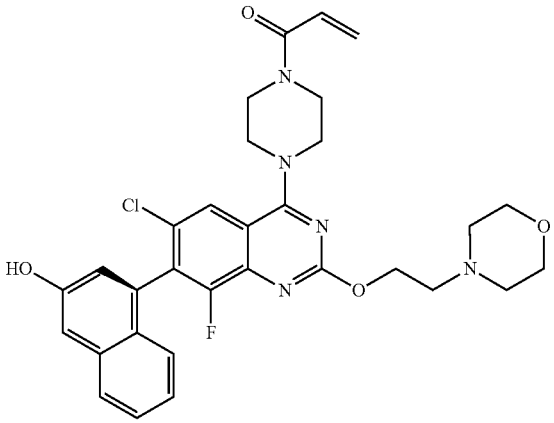 | (S)-1-(4-(6-chloro-8-fluoro-7-(3-hydroxy-naphthalen-1-yl)-2-(2-morpholino-ethoxy) quinazolin-4-yl)piperazin-1-yl)prop-2-en-1-one | A | 592.3 |
| I-52 | 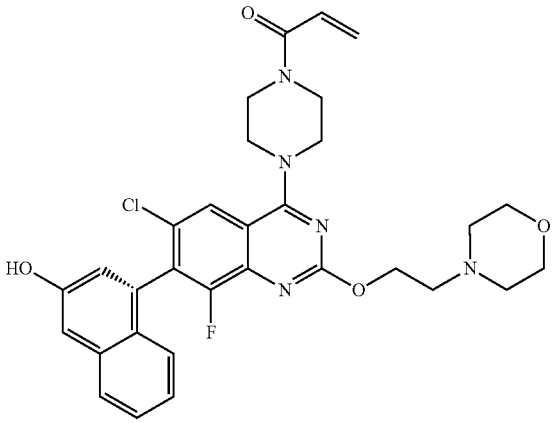 | (R)-1-(4-(6-chloro-8-fluoro-7-(3-hydroxy-naphthalen-1-yl)-2-(2-morpholino-ethoxy) quinazolin-4-yl)piperazin-1-yl)prop-2-en-1-one | A | 592.3 |

TABLE 1-continued

Representative Compounds of Structure (I)

| No. | Structure | Name | Method | $[M + H]^+$ |
|---|---|---|---|---|
| I-53 | 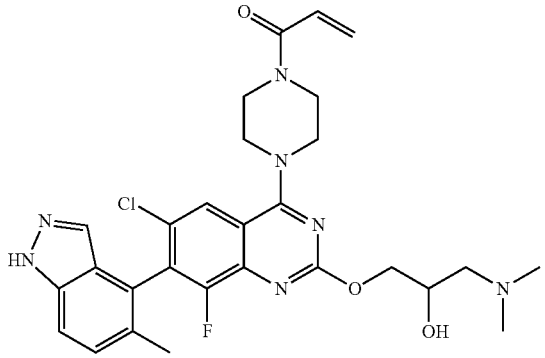 | 1-(4-(6-chloro-2-(3-(dimethylamino)-2-hydroxypropoxy)-8-fluoro-7-(5-methyl-1H-indazol-4-yl)quinazolin-4-yl)piperazin-1-yl)prop-2-en-1-one | C | 569.2 |
| I-54 | 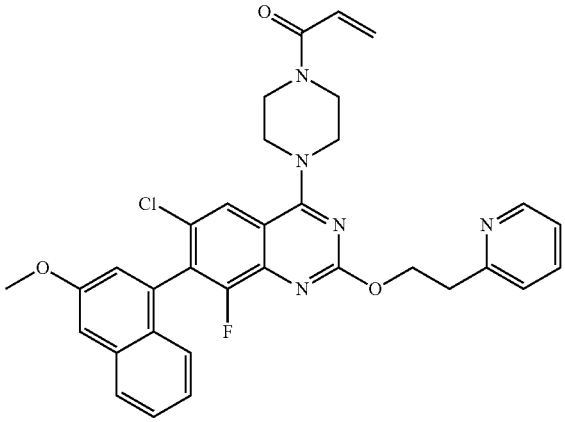 | 1-(4-(6-chloro-8-fluoro-7-(3-methoxynaphthalen-1-yl)-2-(2-(pyridin-2-yl)ethoxy)quinazolin-4-yl)piperazin-1-yl)prop-2-en-1-one | C | 599.2 |
| I-55 | 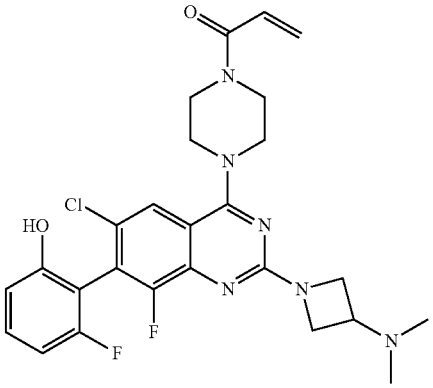 | 1-(4-(6-chloro-2-(3-(dimethylamino)azetidin-1-yl)-8-fluoro-7-(2-fluoro-6-hydroxyphenyl)quinazolin-4-yl)piperazin-1-yl)prop-2-en-1-one | B | 529.2 |
| I-56 | 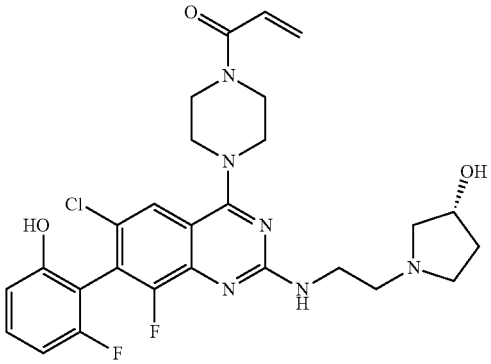 | 1-(4-(6-chloro-8-fluoro-7-(2-fluoro-6-hydroxyphenyl)-2-(2-((R)-3-hydroxypyrrolidin-1-yl)ethylamino)quinazolin-4-yl)piperazin-1-yl)prop-2-en-1-one | B | 560.2 |

TABLE 1-continued

Representative Compounds of Structure (I)

| No. | Structure | Name | Method | $[M + H]^+$ |
|---|---|---|---|---|
| I-57 | 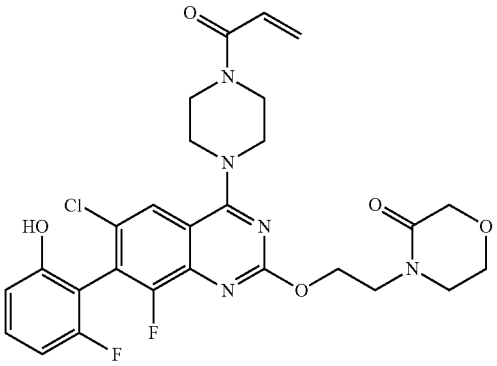 | 4-(2-(4-(4-acryloyl-piperazin-1-yl)-6-chloro-8-fluoro-7-(3-hydroxy-naphthalen-1-yl)quinazolin-2-yloxy)ethyl) morpholin-3-one | C | 605.3* |
| I-58 | 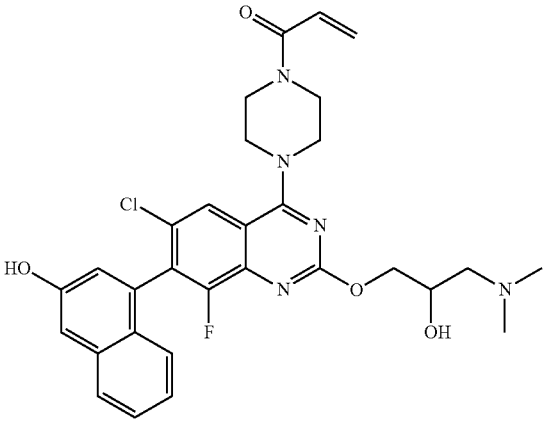 | 1-(4-(6-chloro-2-(3-(dimethyl-amino)-2-hydroxy-propoxy)-8-fluoro-7-(3-hydroxy-naphthalen-1-yl)quinazolin-4-yl)piperazin-1-yl)prop-2-en-1-one | C | 581.2 |
| I-59 | 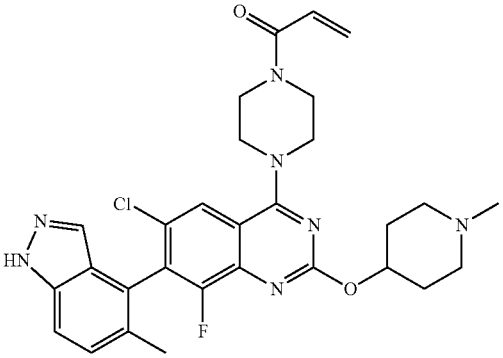 | 1-(4-(6-chloro-8-fluoro-7-(5-methyl-1H-indazol-4-yl)-2-(1-methyl-piperidin-4-yloxy) quinazolin-4-yl)piperazin-1-yl)prop-2-en-1-one | A | 564.3 |
| I-60 | 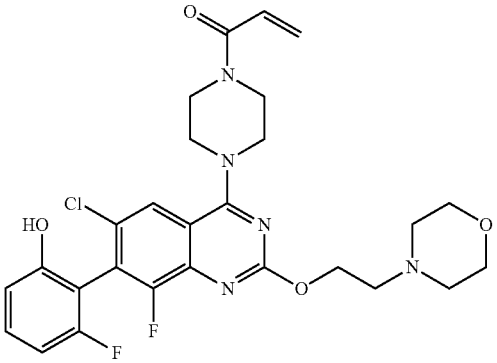 | 1-(4-(6-chloro-8-fluoro-7-(2-fluoro-6-hydroxyphenyl)-2-(2-morpholino-ethoxy) quinazolin-4-yl)piperazin-1-yl)-2-fluoroprop-2-en-1-one | A | 578.4 |

TABLE 1-continued

Representative Compounds of Structure (I)

| No. | Structure | Name | Method | $[M + H]^+$ |
|---|---|---|---|---|
| I-61 | 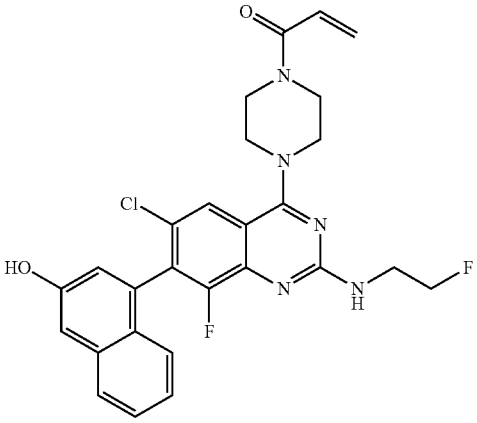 | 1-(4-(6-chloro-8-fluoro-2-(2-fluoroethyl-amino)-7-(3-hydroxy-naphthalen-1-yl)quinazolin-4-yl)piperazin-1-yl)prop-2-en-1-one | B | 524.3 |
| I-62 | 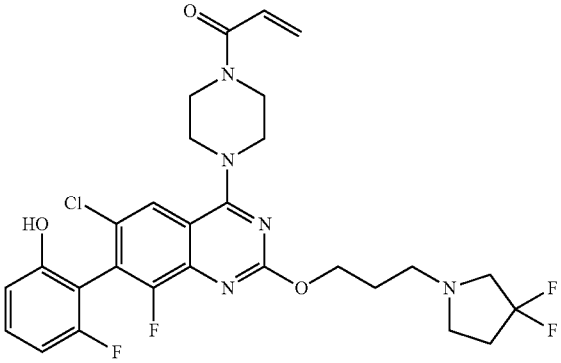 | 1-(4-(6-chloro-2-(3-(3,3-difluoro-pyrrolidin-1-yl) propoxy)-8-fluoro-7-(2-fluoro-6-hydroxyphenyl) quinazolin-4-yl) piperazin-1-yl) prop-2-en-1-one | A | 594.3 |
| I-63 | 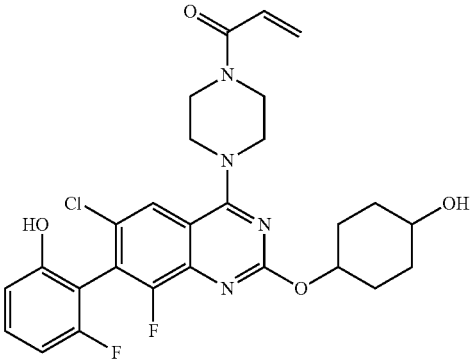 | 1-(4-(6-chloro-8-fluoro-7-(2-fluoro-6-hydroxyphenyl)-2-(4-hydroxy-cyclohexyloxy) quinazolin-4-yl)piperazin-1-yl)prop-2-en-1-one | A | 545.2 |
| I-64 | 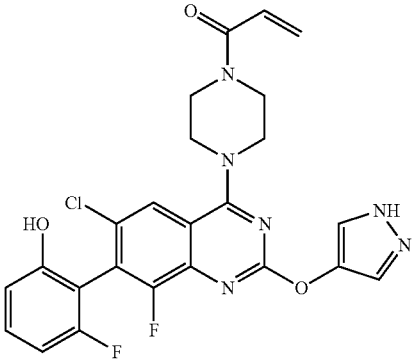 | 1-(4-(2-(1H-pyrazol-4-yloxy)-6-chloro-8-fluoro-7-(2-fluoro-6-hydroxyphenyl) quinazolin-4-yl) piperazin-1-yl) prop-2-en-1-one | A | 513.2 |

TABLE 1-continued

Representative Compounds of Structure (I)

| No. | Structure | Name | Method | $[M + H]^+$ |
|---|---|---|---|---|
| I-65 | 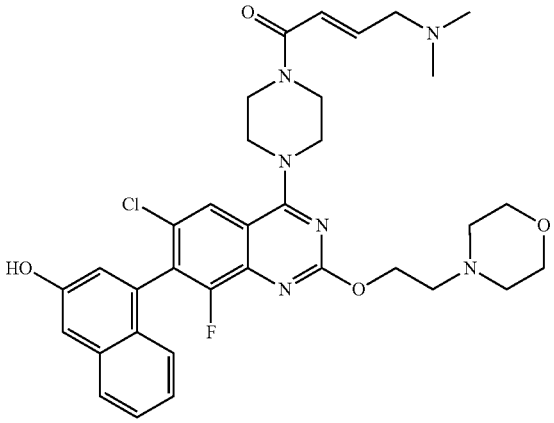 | (E)-1-(4-(6-chloro-8-fluoro-7-(3-hydroxy-naphthalen-1-yl)-2-(2-morpholino-ethoxy) quinazolin-4-yl)piperazin-1-yl)-4-(dimethyl-amino)but-2-en-1-one | A | 649.4 |
| I-66 | 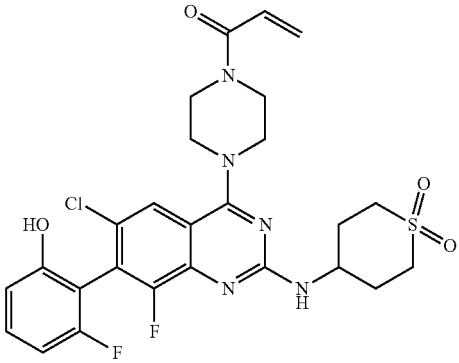 | 1-(4-(6-chloro-8-fluoro-7-(2-fluoro-6-hydroxyphenyl)-2-(tetrahydro-2H-dioxothio-pyran-4-ylamino) quinazolin-4-yl) piperazin-1-yl) prop-2-en-1-one | B | 578.2 |
| I-67 | 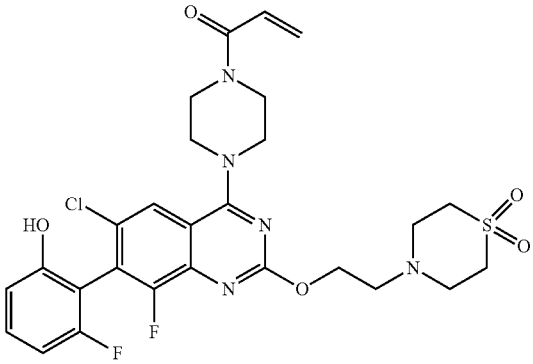 | 1-(4-(6-chloro-8-fluoro-7-(2-fluoro-6-hydroxyphenyl)-2-(2-dioxothio-morpholino-ethoxy) quinazolin-4-yl)piperazin-1-yl)prop-2-en-1-one | A | 608.3 |
| I-68 | 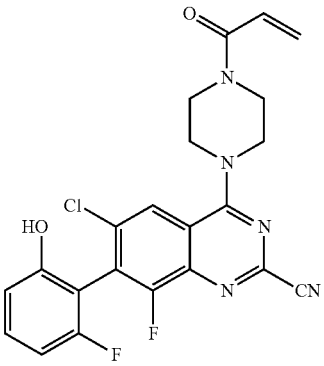 | 4-(4-acryloyl-piperazin-1-yl)-6-chloro-8-fluoro-7-(2-fluoro-6-hydroxyphenyl) quinazoline-2-carbonitrile | G | 456.2 |

TABLE 1-continued

Representative Compounds of Structure (I)

| No. | Structure | Name | Method | $[M + H]^+$ |
|---|---|---|---|---|
| I-69 | 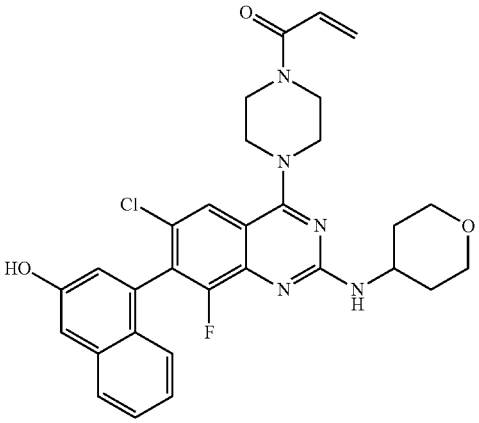 | 1-(4-(6-chloro-8-fluoro-7-(3-hydroxy-naphthalen-1-yl)-2-(tetrahydro-2H-pyran-4-ylamino) quinazolin-4-yl)piperazin-1-yl)prop-2-en-1-one | B | 562.3 |
| I-70 | 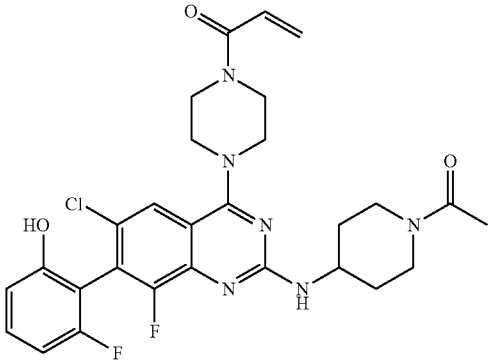 | 1-(4-(2-(1-acetyl-piperidin-4-ylamino)-6-chloro-8-fluoro-7-(2-fluoro-6-hydroxyphenyl) quinazolin-4-yl) piperazin-1-yl) prop-2-en-1-one | B | 571.3 |
| I-71 | 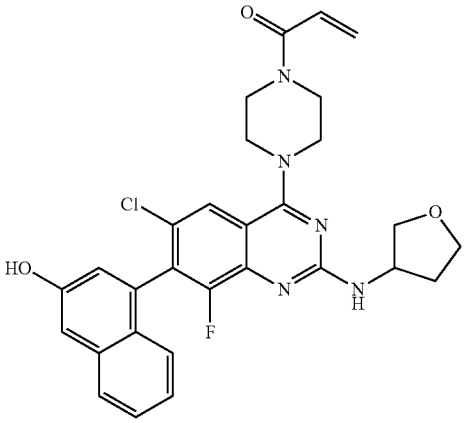 | 1-(4-(6-chloro-8-fluoro-7-(3-hydroxy-naphthalen-1-yl)-2-(tetrahydro-furan-3-ylamino) quinazolin-4-yl)piperazin-1-yl)prop-2-en-1-one | B | 548.3 |
| I-72 | 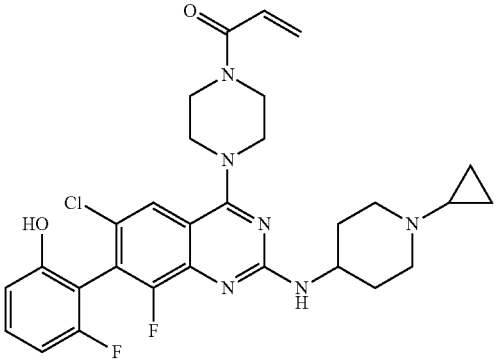 | 1-(4-(6-chloro-2-(1-cyclopropyl-piperidin-4-ylamino)-8-fluoro-7-(2-fluoro-6-hydroxyphenyl) quinazolin-4-yl) piperazin-1-yl) prop-2-en-1-one | B | 569.3 |

TABLE 1-continued

| Representative Compounds of Structure (I) | | | | |
|---|---|---|---|---|
| No. | Structure | Name | Method | $[M + H]^+$ |
| I-73 | 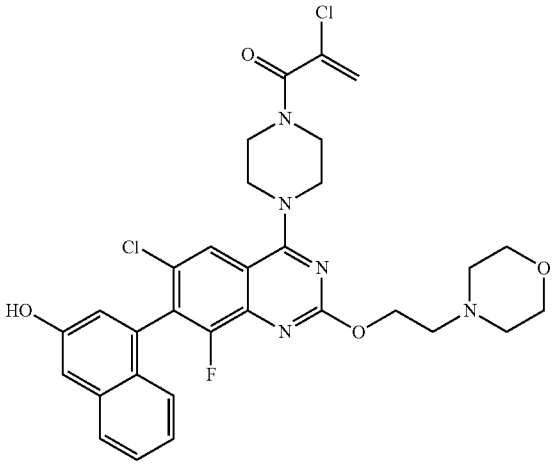 | 2-chloro-1-(4-(6-chloro-8-fluoro-7-(3-hydroxy-naphthalen-1-yl)-2-(2-morpholino-ethoxy) quinazolin-4-yl)piperazin-1-yl)prop-2-en-1-one | A | 626.2 |
| I-74 | 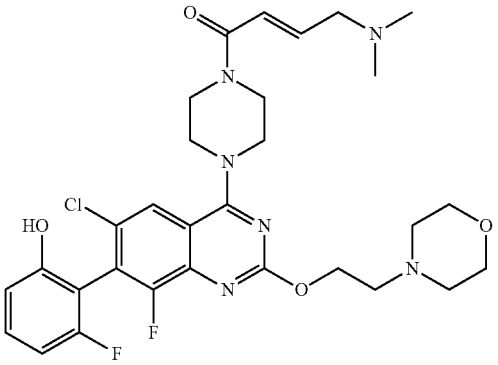 | (E)-1-(4-(6-chloro-8-fluoro-7-(2-fluoro-6-hydroxyphenyl)-2-(2-morpholino-ethoxy) quinazolin-4-yl)piperazin-1-yl)-4-(dimethyl-amino)but-2-en-1-one | A | 617.3 |
| I-75 | 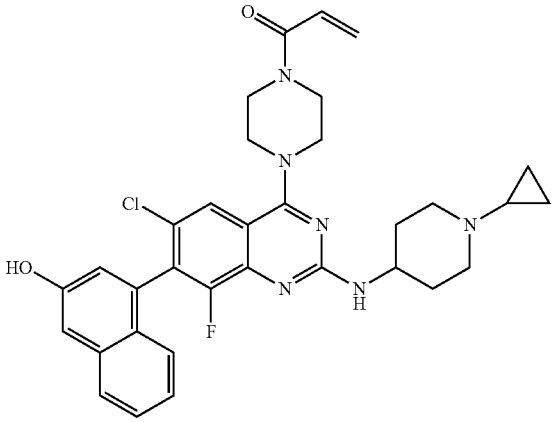 | 1-(4-(6-chloro-2-(1-cyclo-propylpiperidin-4-ylamino)-8-fluoro-7-(3-hydroxy-naphthalen-1-yl)quinazolin-4-yl)piperazin-1-yl)prop-2-en-1-one | B | 601.3 |

TABLE 1-continued

Representative Compounds of Structure (I)

| No. | Structure | Name | Method | $[M + H]^+$ |
|---|---|---|---|---|
| I-76 | 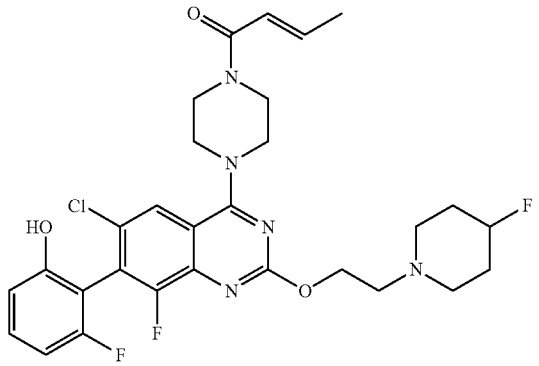 | 1-(4-(6-chloro-8-fluoro-7-(2-fluoro-6-hydroxyphenyl)-2-(2-(4-fluoro-piperidin-1-yl) ethoxy) quinazolin-4-yl)piperazin-1-yl)prop-2-en-1-one | A | 576.3 |
| I-77 | 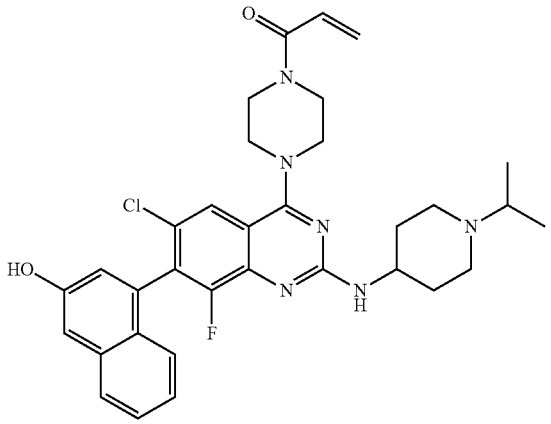 | 1-(4-(6-chloro-8-fluoro-7-(3-hydroxy-naphthalen-1-yl)-2-(1-isopropyl-piperidin-4-ylamino) quinazolin-4-yl)piperazin-1-yl)prop-2-en-1-one | B | 603.4 |
| I-78 | 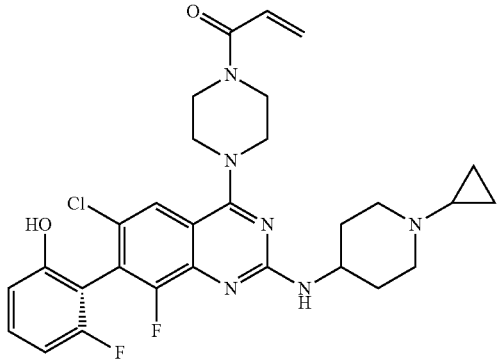 | (S)-1-(4-(6-chloro-2-(1-cyclopropyl-piperidin-4-ylamino)-8-fluoro-7-(2-fluoro-6-hydroxyphenyl) quinazolin-4-yl)piperazin-1-yl)prop-2-en-1-one | B | 569.3 |
| I-79 | 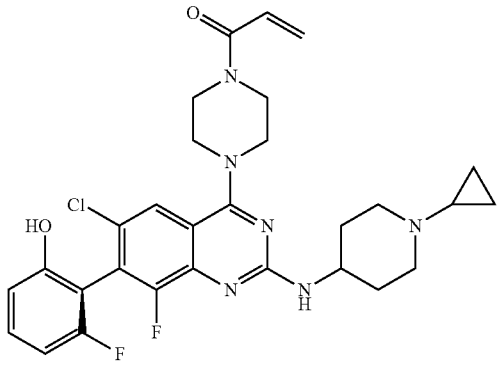 | (R)-1-(4-(6-chloro-2-(1-cyclopropyl-piperidin-4-ylamino)-8-fluoro-7-(2-fluoro-6-hydroxyphenyl) quinazolin-4-yl) piperazin-1-yl) prop-2-en-1-one | B | 569.3 |

TABLE 1-continued

Representative Compounds of Structure (I)

| No. | Structure | Name | Method | $[M + H]^+$ |
|---|---|---|---|---|
| I-80 | 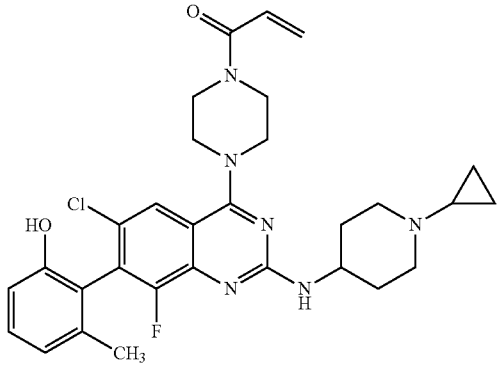 | 1-(4-(6-chloro-2-(1-cyclopropyl-piperidin-4-ylamino)-8-fluoro-7-(2-hydroxy-6-methylphenyl) quinazolin-4-yl) piperazin-1-yl) prop-2-en-1-one | B | 565.3 |
| I-81 | 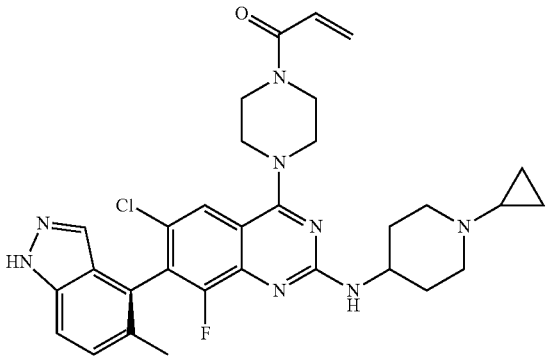 | (S)-1-(4-(6-chloro-2-(1-cyclopropyl-piperidin-4-ylamino)-8-fluoro-7-(5-methyl-1H-indazol-4-yl) quinazolin-4-yl)piperazin-1-yl)prop-2-en-1-one | B | 589.4 |
| I-82 | 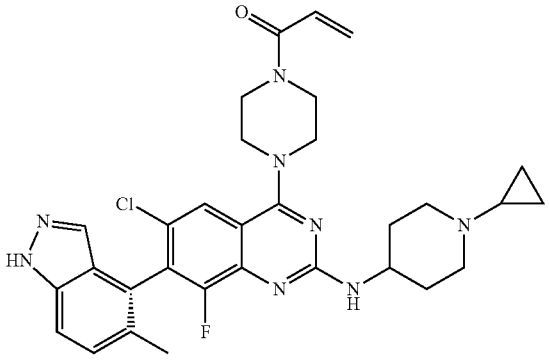 | (R)-1-(4-(6-chloro-2-(1-cyclopropyl-piperidin-4-ylamino)-8-fluoro-7-(5-methyl-1H-indazol-4-yl)quinazolin-4-yl)piperazin-1-yl)prop-2-en-1-one | B | 589.3 |
| I-83 | 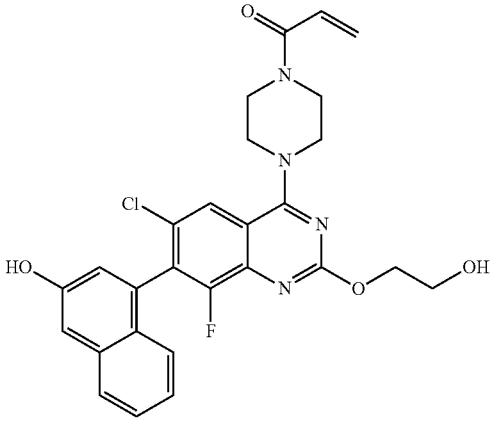 | 1-(4-(6-chloro-8-fluoro-2-(2-hydroxyethoxy)-7-(3-hydroxy-naphthalen-1-yl) quinazolin-4-yl)piperazin-1-yl)prop-2-en-1-one | A | 523.7 |

TABLE 1-continued

| Representative Compounds of Structure (I) | | | | |
|---|---|---|---|---|
| No. | Structure | Name | Method | $[M + H]^+$ |
| I-84 | 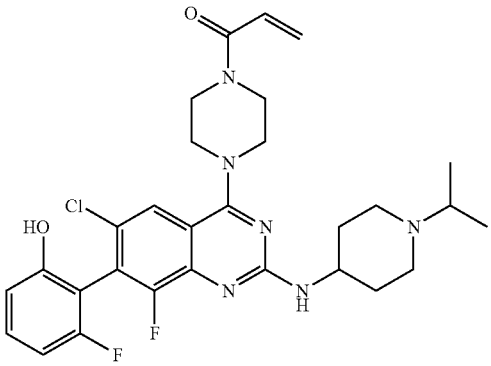 | 1-(4-(6-chloro-8-fluoro-7-(2-fluoro-6-hydroxyphenyl)-2-(1-isopropyl-piperidin-4-ylamino) quinazolin-4-yl)piperazin-1-yl)prop-2-en-1-one | B | 571.4 |
| I-85 | 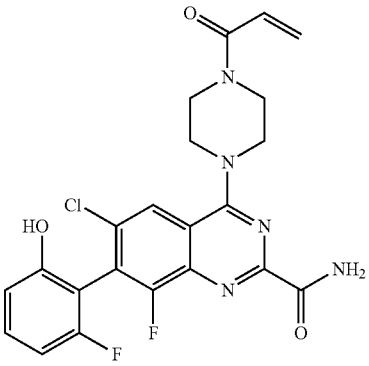 | 4-(4-acryloyl-piperazin-1-yl)-6-chloro-8-fluoro-7-(2-fluoro-6-hydroxyphenyl) quinazoline-2-carboxamide | G | 474.3 |
| I-86 | 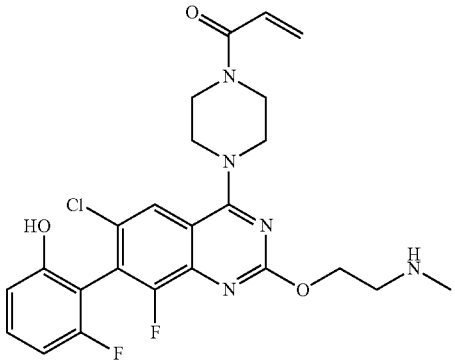 | 1-(4-(6-chloro-8-fluoro-7-(2-fluoro-6-hydroxyphenyl)-2-(2-(methyl-amino)ethoxy) quinazolin-4-yl)piperazin-1-yl)prop-2-en-1-one | A | 504.2 |
| I-87 | 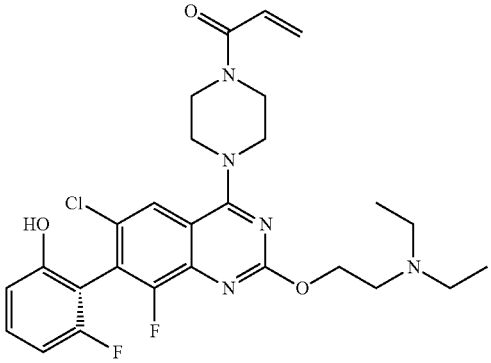 | (S)-1-(4-(6-chloro-2-(2-(diethylamino) ethoxy)-8-fluoro-7-(2-fluoro-6-hydroxyphenyl) quinazolin-4-yl) piperazin-1-yl) prop-2-en-1-one | A | 546.4 |

TABLE 1-continued

Representative Compounds of Structure (I)

| No. | Structure | Name | Method | $[M + H]^+$ |
|---|---|---|---|---|
| I-88 | 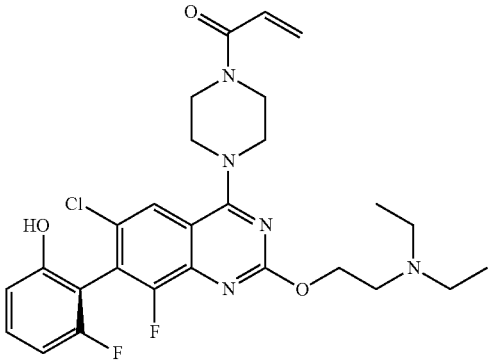 | (R)-1-(4-(6-chloro-2-(2-(diethylamino) ethoxy)-8-fluoro-7-(2-fluoro-6-hydroxyphenyl) quinazolin-4-yl) piperazin-1-yl) prop-2-en-1-one | A | 546.4 |
| I-89 | 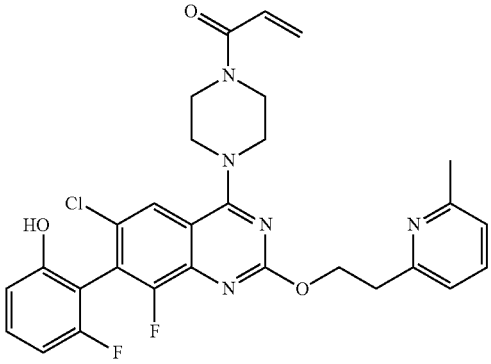 | 1-(4-(6-chloro-8-fluoro-7-(2-fluoro-6-hydroxyphenyl)-2-(2-(6-methyl-pyridin-2-yl) ethoxy) quinazolin-4-yl)piperazin-1-yl)prop-2-en-1-one | A | 566.3 |
| I-90 | 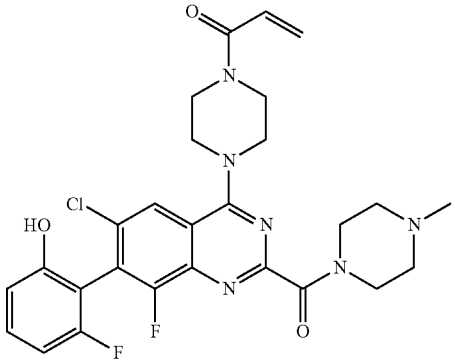 | 1-(4-(6-chloro-8-fluoro-7-(2-fluoro-6-hydroxyphenyl)-2-(4-methyl-piperazine-1-carbonyl) quinazolin-4-yl)piperazin-1-yl)prop-2-en-1-one | F | 557.3 |
| I-91 | 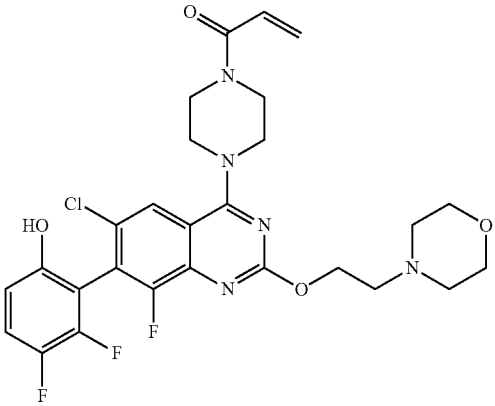 | 1-(4-(6-chloro-7-(2,3-difluoro-6-hydroxyphenyl)-8-fluoro-2-(2-morpholino-ethoxy) quinazolin-4-yl)piperazin-1-yl)prop-2-en-1-one | A | 578.1 |

TABLE 1-continued

Representative Compounds of Structure (I)

| No. | Structure | Name | Method | $[M + H]^+$ |
|---|---|---|---|---|
| I-92 | 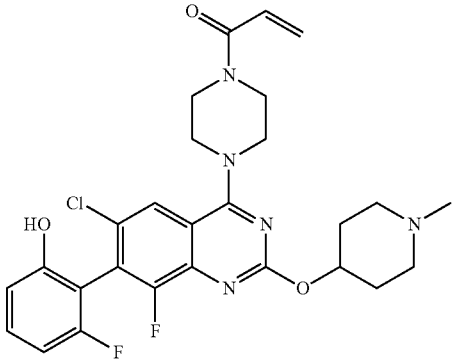 | 1-(4-(6-chloro-8-fluoro-7-(2-fluoro-6-hydroxyphenyl)-2-(1-methyl-piperidin-4-yloxy) quinazolin-4-yl)piperazin-1-yl)prop-2-en-1-one | C | 544.2 |
| I-93 | 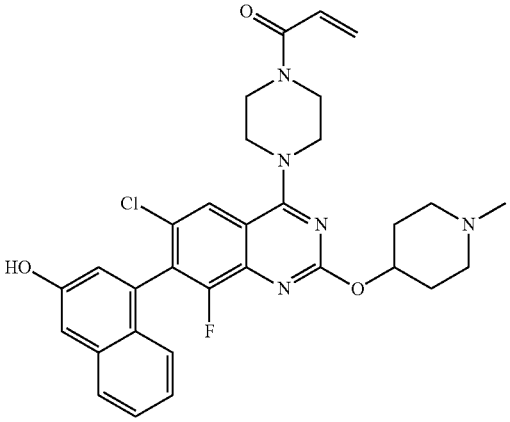 | 1-(4-(6-chloro-8-fluoro-7-(3-hydroxy-naphthalen-1-yl)-2-(1-methyl-piperidin-4-yloxy) quinazolin-4-yl)piperazin-1-yl)prop-2-en-1-one | C | 576.2 |
| I-94 | 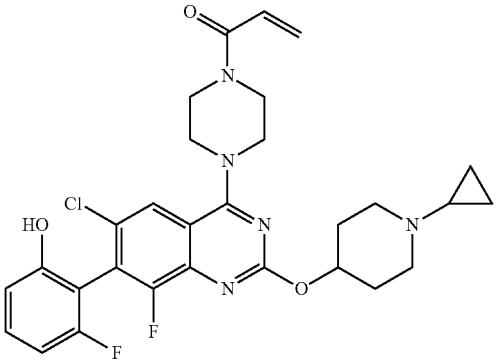 | 1-(4-(6-chloro-2-(1-cyclopropyl-piperidin-4-yloxy)-8-fluoro-7-(2-fluoro-6-hydroxyphenyl) quinazolin-4-yl)piperazin-1-yl)prop-2-en-1-one | C | 570.2 |
| I-95 | 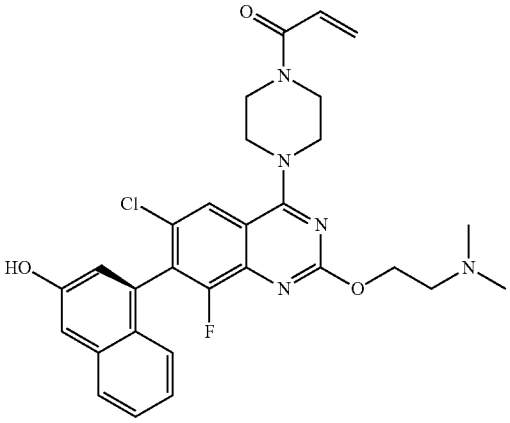 | (S)-1-(4-(6-chloro-2-(2-(dimethylamino) ethoxy)-8-fluoro-7-(3-hydroxy-naphthalen-1-yl)quinazolin-4-yl)piperazin-1-yl)prop-2-en-1-one | A | 550.3 |

TABLE 1-continued

Representative Compounds of Structure (I)

| No. | Structure | Name | Method | $[M + H]^+$ |
|---|---|---|---|---|
| I-96 | 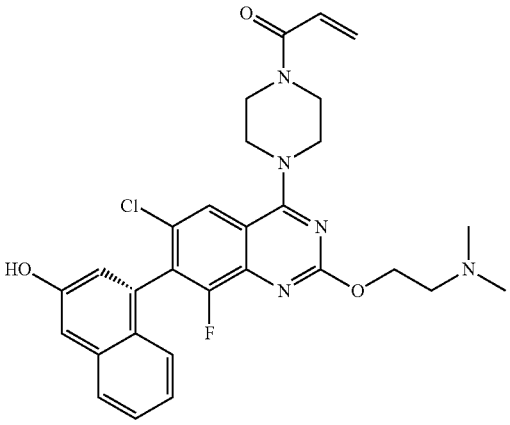 | (R)-1-(4-(6-chloro-2-(2-(dimethylamino) ethoxy)-8-fluoro-7-(3-hydroxy-naphthalen-1-yl) quinazolin-4-yl)piperazin-1-yl)prop-2-en-1-one | A | 550.3 |
| I-97 | 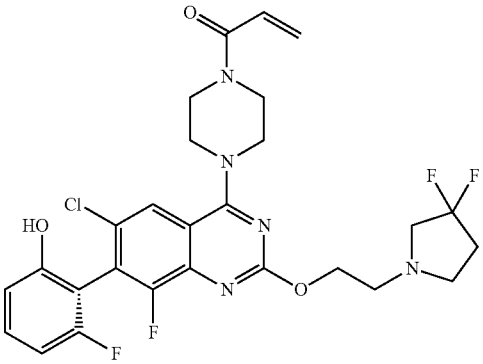 | (S)-1-(4-(6-chloro-2-(2-(3,3-difluoro-pyrrolidin-1-yl)ethoxy)-8-fluoro-7-(2-fluoro-6-hydroxyphenyl) quinazolin-4-yl)piperazin-1-yl)prop-2-en-1-one | A | 580.3 |
| I-98 | 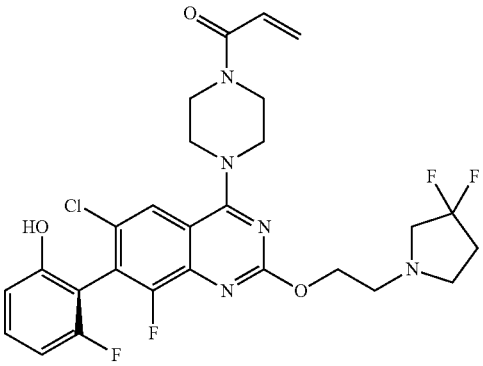 | (R)-1-(4-(6-chloro-2-(2-(3,3-difluoro-pyrrolidin-1-yl)ethoxy)-8-fluoro-7-(2-fluoro-6-hydroxyphenyl) quinazolin-4-yl) piperazin-1-yl) prop-2-en-1-one | A | 580.3 |
| I-99 | 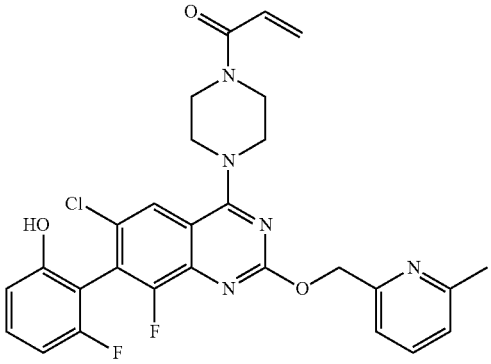 | 1-(4-(6-chloro-8-fluoro-7-(2-fluoro-6-hydroxyphenyl)-2-((6-methyl-pyridin-2-yl) methoxy) quinazolin-4-yl) piperazin-1-yl)prop-2-en-1-one | A | 552.3 |

TABLE 1-continued

| Representative Compounds of Structure (I) | | | | |
|---|---|---|---|---|
| No. | Structure | Name | Method | $[M + H]^+$ |
| I-100 | 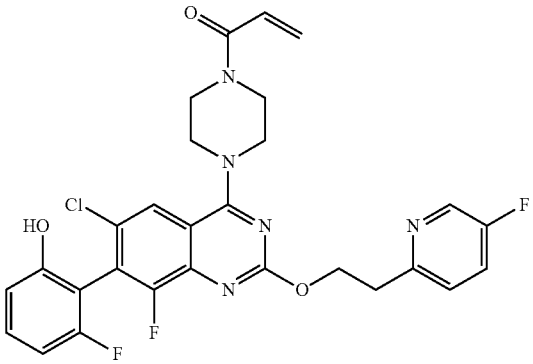 | 1-(4-(6-chloro-8-fluoro-7-(2-fluoro-6-hydroxyphenyl)-2-(2-(5-fluoro-pyridin-2-yl) ethoxy) quinazolin-4-yl) piperazin-1-yl) prop-2-en-1-one | A | 570.3 |
| I-101 | 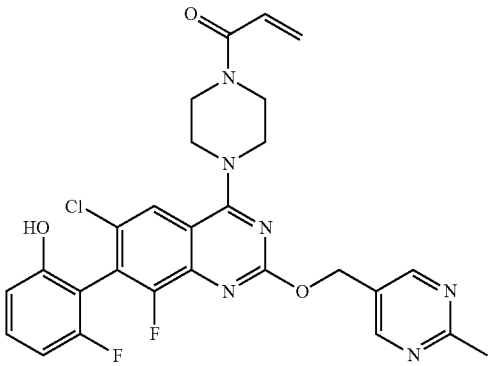 | 1-(4-(6-chloro-8-fluoro-7-(2-fluoro-6-hydroxyphenyl)-2-((2-methyl-pyrimidin-5-yl)methoxy) quinazolin-4-yl) piperazin-1-yl) prop-2-en-1-one | A | 553.4 |
| I-102 | 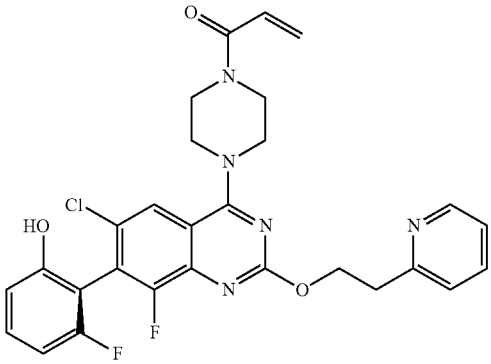 | (R)-1-(4-(6-chloro-8-fluoro-7-(2-fluoro-6-hydroxyphenyl)-2-(2-(pyridin-2-yl)ethoxy) quinazolin-4-yl) piperazin-1-yl) prop-2-en-1-one | A | 552.3 |
| I-103 | 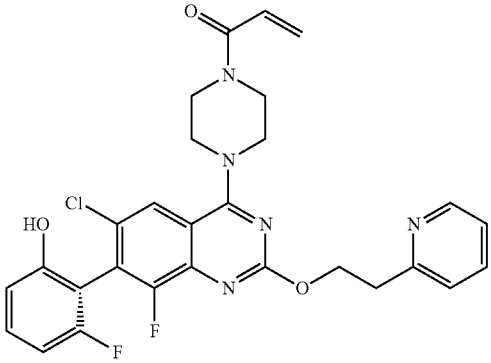 | (S)-1-(4-(6-chloro-8-fluoro-7-(2-fluoro-6-hydroxyphenyl)-2-(2-(pyridin-2-yl)ethoxy) quinazolin-4-yl) piperazin-1-yl) prop-2-en-1-one | A | 552.3 |

TABLE 1-continued

Representative Compounds of Structure (I)

| No. | Structure | Name | Method | $[M + H]^+$ |
|---|---|---|---|---|
| I-104 | 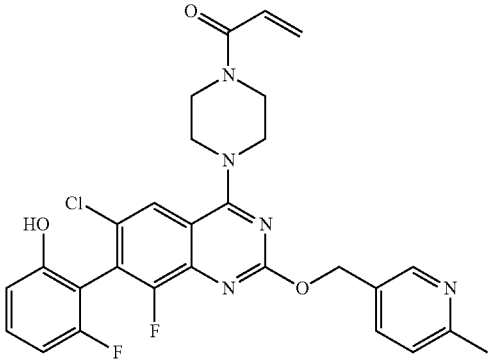 | 1-(4-(6-chloro-8-fluoro-7-(2-fluoro-6-hydroxyphenyl)-2-((6-methyl-pyridin-3-yl) methoxy) quinazolin-4-yl) piperazin-1-yl) prop-2-en-1-one | A | 552.4 |
| I-105 | 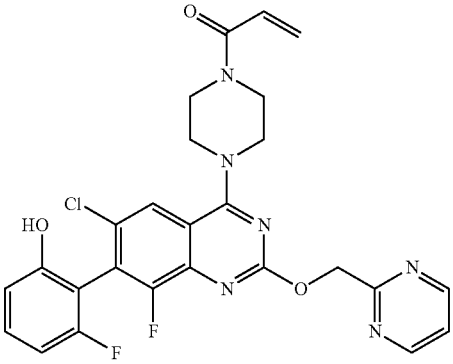 | 1-(4-(6-chloro-8-fluoro-7-(2-fluoro-6-hydroxyphenyl)-2-(pyrimidin-2-ylmethoxy) quinazolin-4-yl) piperazin-1-yl) prop-2-en-1-one | A | 539.3 |
| I-106 | 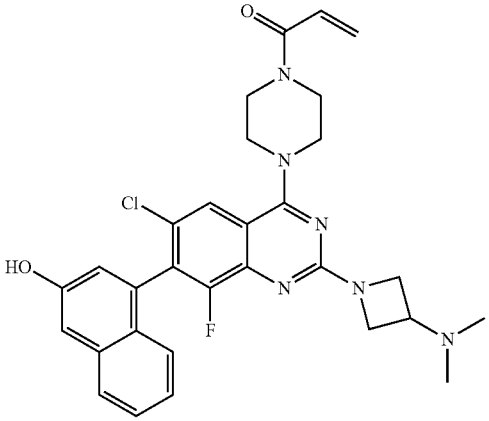 | 1-(4-(6-chloro-2-(3-(dimethyl-amino)azetidin-1-yl)-8-fluoro-7-(3-hydroxy-naphthalen-1-yl) quinazolin-4-yl) piperazin-1-yl) prop-2-en-1-one | B | 561.3 |
| I-107 | 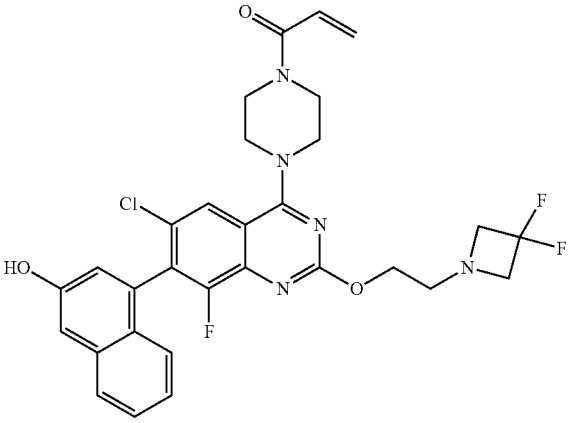 | 1-(4-(6-chloro-2-(2-(3,3-difluoro-azetidin-1-yl) ethoxy)-8-fluoro-7-(3-hydroxy-naphthalen-1-yl) quinazolin-4-yl) piperazin-1-yl) prop-2-en-1-one | A | 598.4 |

TABLE 1-continued

Representative Compounds of Structure (I)

| No. | Structure | Name | Method | $[M + H]^+$ |
|---|---|---|---|---|
| I-108 | 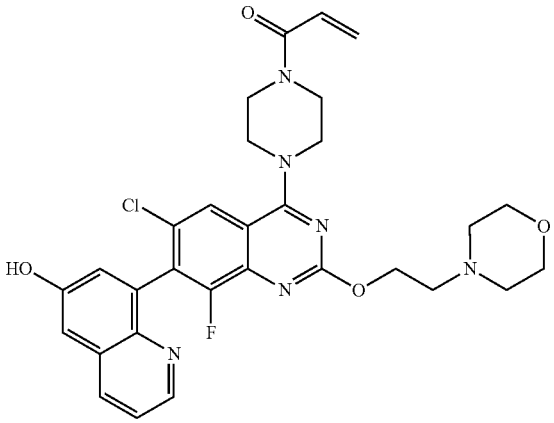 | 1-(4-(6-chloro-8-fluoro-7-(6-hydroxy-quinolin-8-yl)-2-(2-morpholino-ethoxy) quinazolin-4-yl) piperazin-1-yl) prop-2-en-1-one | A | 593.4 |
| I-109 | 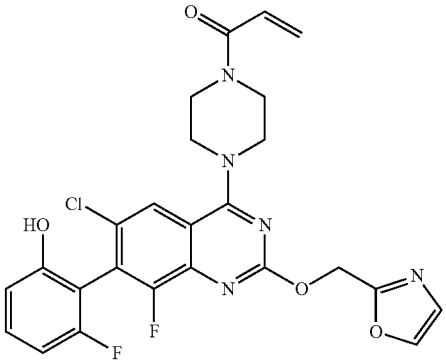 | 1-(4-(6-chloro-8-fluoro-7-(2-fluoro-6-hydroxyphenyl)-2-(oxazol-2-ylmethoxy) quinazolin-4-yl) piperazin-1-yl) prop-2-en-1-one | A | 528.2 |
| I-1I-10 | 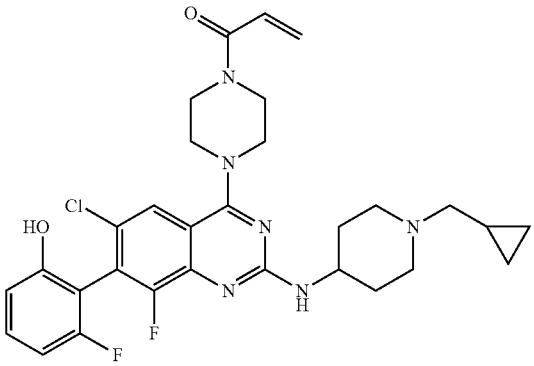 | 1-(4-(6-chloro-2-(1-(cyclopropyl-methyl)piperidin-4-ylamino)-8-fluoro-7-(2-fluoro-6-hydroxyphenyl) quinazolin-4-yl) piperazin-1-yl) prop-2-en-1-one | B | 583.3 |
| I-111 | 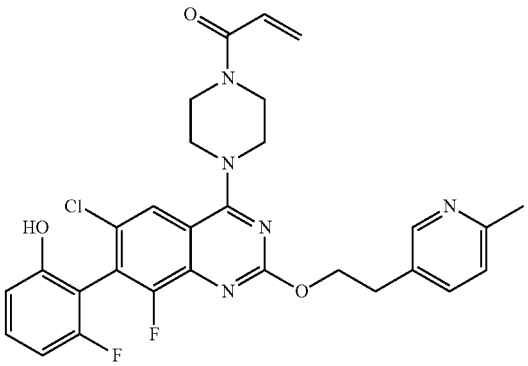 | 1-(4-(6-chloro-8-fluoro-7-(2-fluoro-6-hydroxyphenyl)-2-(2-(6-methyl-pyridin-3-yl) ethoxy) quinazolin-4-yl) piperazin-1-yl) prop-2-en-1-one | A | 566.3 |

TABLE 1-continued

| Representative Compounds of Structure (I) | | | | |
|---|---|---|---|---|
| No. | Structure | Name | Method | $[M + H]^+$ |
| I-112 | 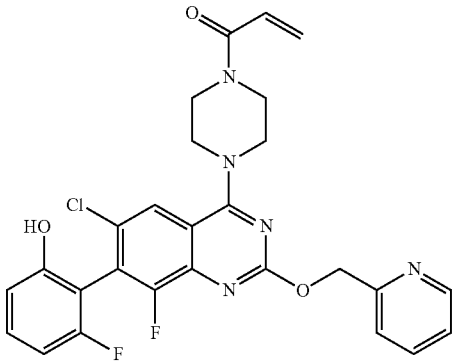 | 1-(4-(6-chloro-8-fluoro-7-(2-fluoro-6-hydroxyphenyl)-2-(pyridin-2-ylmethoxy) quinazolin-4-yl) piperazin-1-yl) prop-2-en-1-one | A | 538.3 |
| I-113 | 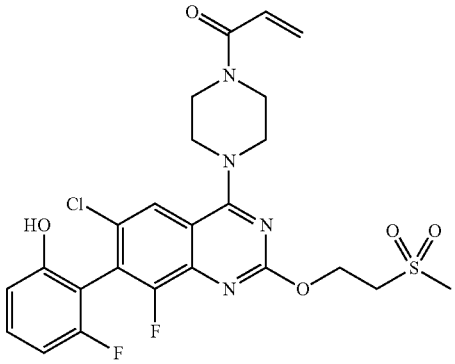 | 1-(4-(6-chloro-8-fluoro-7-(2-fluoro-6-hydroxyphenyl)-2-(2-(methyl-sulfonyl) ethoxy) quinazolin-4-yl) piperazin-1-yl) prop-2-en-1-one | A | 552.2 |
| I-114 | 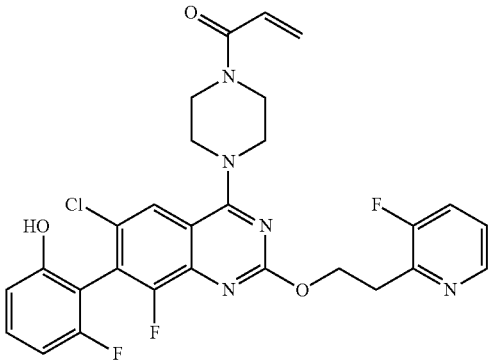 | 1-(4-(6-chloro-8-fluoro-7-(2-fluoro-6-hydroxyphenyl)-2-(2-(3-fluoro-pyridin-2-yl) ethoxy) quinazolin-4-yl) piperazin-1-yl) prop-2-en-1-one | A | 570.3 |
| I-115 | 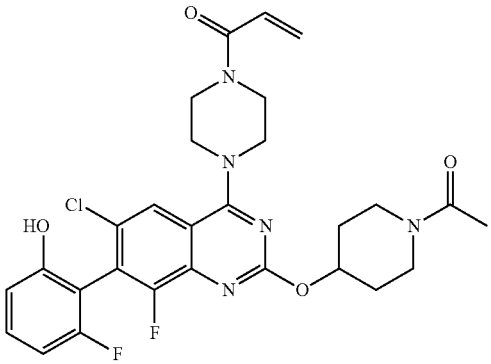 | 1-(4-(2-(1-acetylpiperidin-4-yloxy)-6-chloro-8-fluoro-7-(2-fluoro-6-hydroxyphenyl) quinazolin-4-yl) piperazin-1-yl) prop-2-en-1-one | A | 572.2 |

TABLE 1-continued

Representative Compounds of Structure (I)

| No. | Structure | Name | Method | $[M + H]^+$ |
|---|---|---|---|---|
| I-116 | 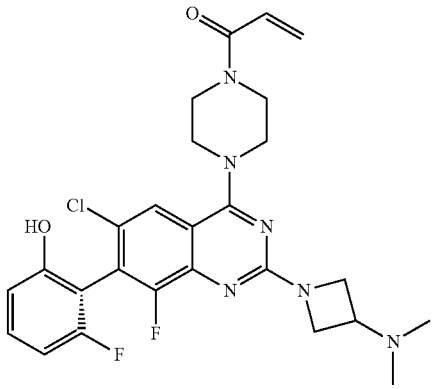 | (S)-1-(4-(6-chloro-2-(3-(dimethylamino) azetidin-1-yl)-8-fluoro-7-(2-fluoro-6-hydroxyphenyl) quinazolin-4-yl) piperazin-1-yl) prop-2-en-1-one | B | 529.2 |
| I-117 | 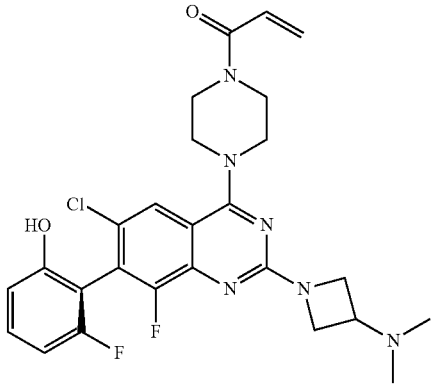 | (R)-1-(4-(6-chloro-2-(3-(dimethylamino) azetidin-1-yl)-8-fluoro-7-(2-fluoro-6-hydroxyphenyl) quinazolin-4-yl) piperazin-1-yl) prop-2-en-1-one | B | 529.2 |
| I-118 | 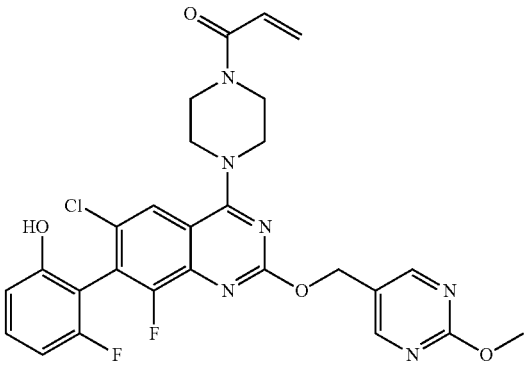 | 1-(4-(6-chloro-8-fluoro-7-(2-fluoro-6-hydroxyphenyl)-2-((2-methoxy-pyrimidin-5-yl) methoxy) quinazolin-4-yl) piperazin-1-yl) prop-2-en-1-one | A | 569.2 |
| I-119 | 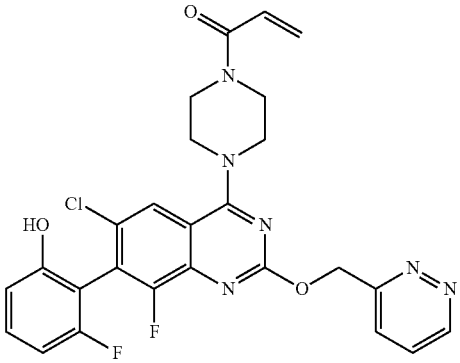 | 1-(4-(6-chloro-8-fluoro-7-(2-fluoro-6-hydroxyphenyl)-2-(pyridazin-3-ylmethoxy) quinazolin-4-yl) piperazin-1-yl) prop-2-en-1-one | A | 539.2 |

TABLE 1-continued

| Representative Compounds of Structure (I) | | | | |
|---|---|---|---|---|
| No. | Structure | Name | Method | $[M + H]^+$ |
| I-120 | 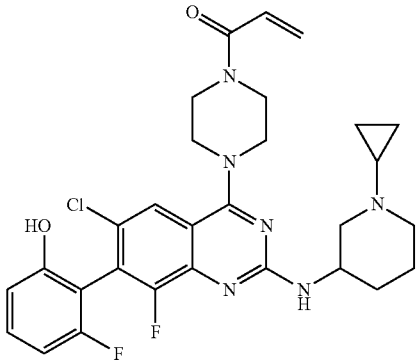 | 1-(4-(6-chloro-2-(1-cyclopropyl-piperidin-3-ylamino)-8-fluoro-7-(2-fluoro-6-hydroxyphenyl) quinazolin-4-yl) piperazin-1-yl) prop-2-en-1-one | B | 569.3 |
| I-121 | 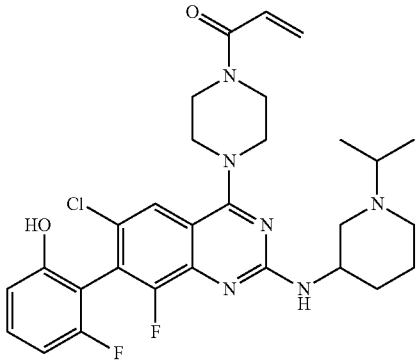 | 1-(4-(6-chloro-8-fluoro-7-(2-fluoro-6-hydroxyphenyl)-2-(1-isopropyl-piperidin-3-ylamino) quinazolin-4-yl) piperazin-1-yl) prop-2-en-1-one | B | 571.3 |
| I-122 | 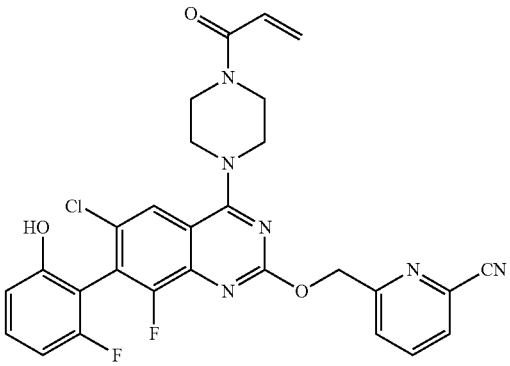 | 6-((4-(4-acryloyl-piperazin-1-yl)-6-chloro-8-fluoro-7-(2-fluoro-6-hydroxyphenyl) quinazolin-2-yloxy)methyl) picolinonitrile | A | 563.2 |
| I-123 | 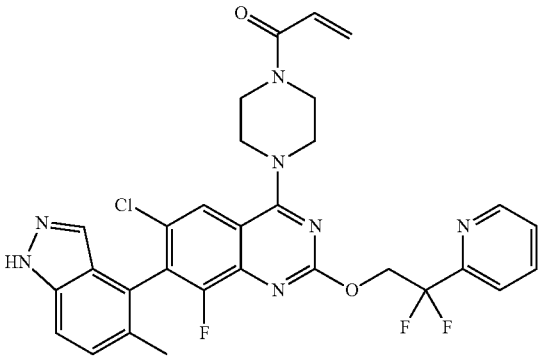 | 1-(4-(6-chloro-2-(2,2-difluoro-2-(pyridin-2-yl) ethoxy)-8-fluoro-7-(5-methyl-1H-indazol-4-yl) quinazolin-4-yl) piperazin-1-yl) prop-2-en-1-one | C | 609.2 |

TABLE 1-continued

| Representative Compounds of Structure (I) | | | | |
|---|---|---|---|---|
| No. | Structure | Name | Method | $[M + H]^+$ |
| I-124 | 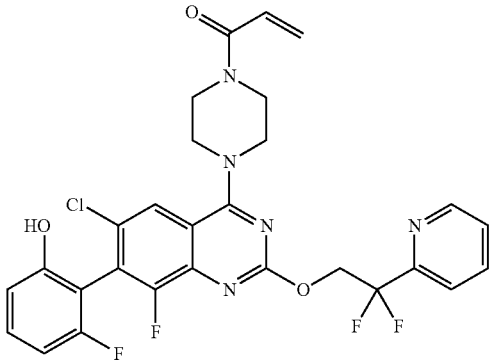 | 1-(4-(6-chloro-2-(2,2-difluoro-2-(pyridin-2-yl)ethoxy)-8-fluoro-7-(2-fluoro-6-hydroxyphenyl)quinazolin-4-yl)piperazin-1-yl)prop-2-en-1-one | C | 589.2 |
| I-125 | 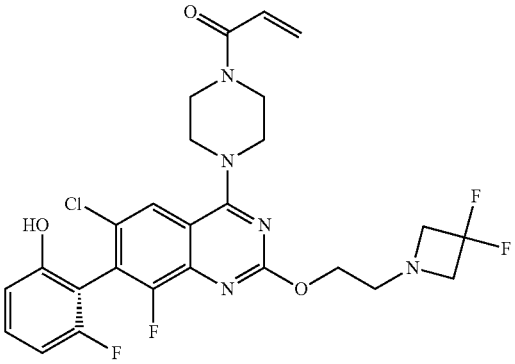 | (S)-1-(4-(6-chloro-2-(2-(3,3-difluoroazetidin-1-yl)ethoxy)-8-fluoro-7-(2-fluoro-6-hydroxyphenyl)quinazolin-4-yl)piperazin-1-yl)prop-2-en-1-one | A | 566.6 |
| I-126 | 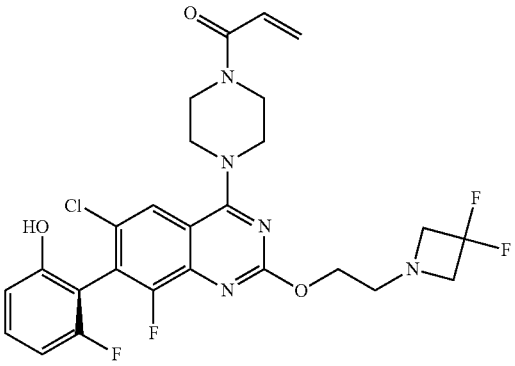 | (R)-1-(4-(6-chloro-2-(2-(3,3-difluoroazetidin-1-yl)ethoxy)-8-fluoro-7-(2-fluoro-6-hydroxyphenyl)quinazolin-4-yl)piperazin-1-yl)prop-2-en-1-one | A | 566.6 |
| I-127 | 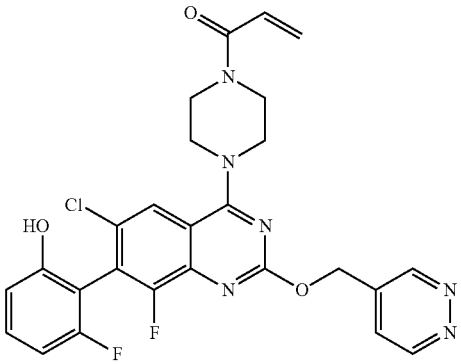 | 1-(4-(6-chloro-8-fluoro-7-(2-fluoro-6-hydroxyphenyl)-2-(pyridazin-4-ylmethoxy)quinazolin-4-yl)piperazin-1-yl)prop-2-en-1-one | A | 539.6 |

TABLE 1-continued

Representative Compounds of Structure (I)

| No. | Structure | Name | Method | $[M + H]^+$ |
|---|---|---|---|---|
| I-128 | 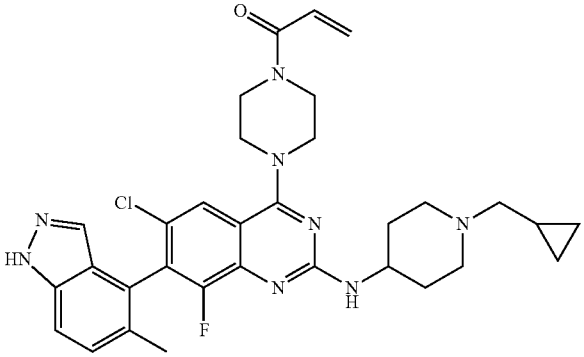 | 1-(4-(6-chloro-2-(1-(cyclopropylmethyl) piperidin-4-ylamino)-8-fluoro-7-(5-methyl-1H-indazol-4-yl) quinazolin-4-yl) piperazin-1-yl) prop-2-en-1-one | B | 603.4 |
| I-129 | 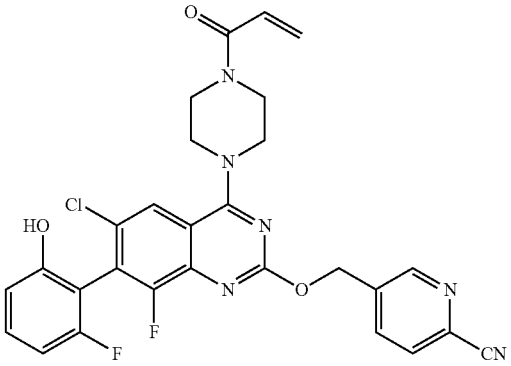 | 5-((4-(4-acryloyl-piperazin-1-yl)-6-chloro-8-fluoro-7-(2-fluoro-6-hydroxyphenyl) quinazolin-2-yloxy)methyl) picolinonitrile | A | 563.3 |
| I-130 | 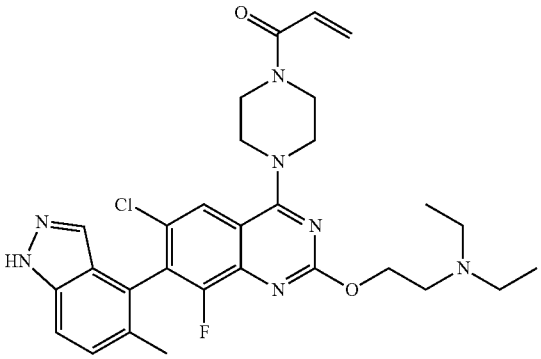 | 1-(4-(6-chloro-2-(2-(diethyl-amino)ethoxy)-8-fluoro-7-(5-methyl-1H-indazol-4-yl) quinazolin-4-yl) piperazin-1-yl) prop-2-en-1-one | A | 566.20 |
| I-131 | 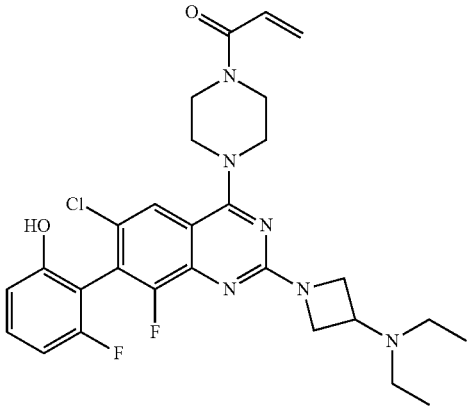 | 1-(4-(6-chloro-2-(3-(diethyl-amino)azetidin-1-yl)-8-fluoro-7-(2-fluoro-6-hydroxyphenyl) quinazolin-4-yl) piperazin-1-yl) prop-2-en-1-one | B | 557.4 |

TABLE 1-continued

| Representative Compounds of Structure (I) | | | | |
|---|---|---|---|---|
| No. | Structure | Name | Method | $[M + H]^+$ |
| I-132 | 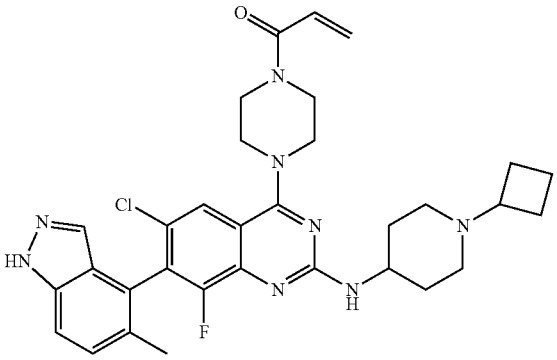 | 1-(4-(6-chloro-2-(1-cyclobutyl-piperidin-4-ylamino)-8-fluoro-7-(5-methyl-1H-indazol-4-yl) quinazolin-4-yl) piperazin-1-yl) prop-2-en-1-one | B | 603.4 |
| I-133 | 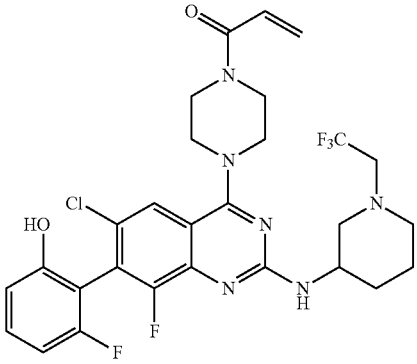 | 1-(4-(6-chloro-8-fluoro-7-(2-fluoro-6-hydroxyphenyl)-2-(1-(2,2,2-trifluoroethyl) piperidin-3-ylamino) quinazolin-4-yl) piperazin-1-yl) prop-2-en-1-one | B | 611.8 |
| I-134 | 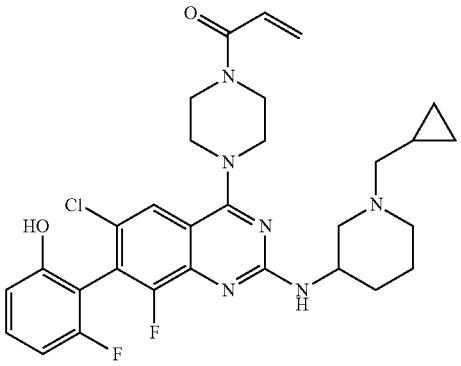 | 1-(4-(6-chloro-2-(1-(cyclopropyl-methyl)piperidin-3-ylamino)-8-fluoro-7-(2-fluoro-6-hydroxyphenyl) quinazolin-4-yl) piperazin-1-yl) prop-2-en-1-one | B | 583.4 |
| I-135 | 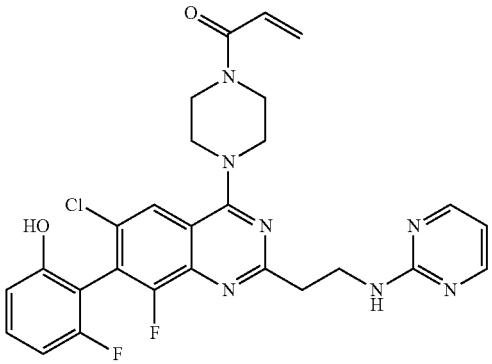 | 1-(4-(6-chloro-8-fluoro-7-(2-fluoro-6-hydroxyphenyl)-2-(2-(pyrimidin-2-ylamino)ethyl) quinazolin-4-yl) piperazin-1-yl) prop-2-en-1-one | H | 552.7 |

TABLE 1-continued

| Representative Compounds of Structure (I) | | | | |
|---|---|---|---|---|
| No. | Structure | Name | Method | $[M + H]^+$ |
| I-136 | 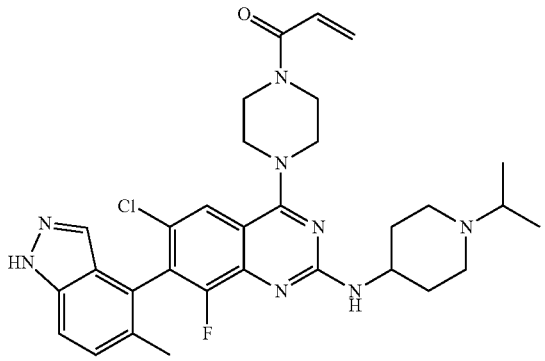 | 1-(4-(6-chloro-8-fluoro-2-(1-isopropyl-piperidin-4-ylamino)-7-(5-methyl-1H-indazol-4-yl) quinazolin-4-yl) piperazin-1-yl) prop-2-en-1-one | B | 591.4 |
| I-137 | 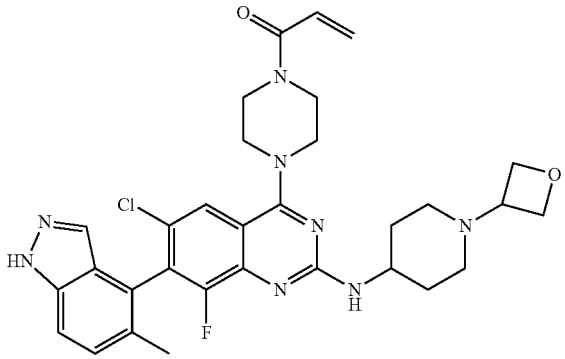 | 1-(4-(6-chloro-8-fluoro-7-(5-methyl-1H-indazol-4-yl)-2-(1-(oxetan-3-yl)piperidin-4-ylamino) quinazolin-4-yl) piperazin-1-yl) prop-2-en-1-one | B | 605.4 |
| I-138 | 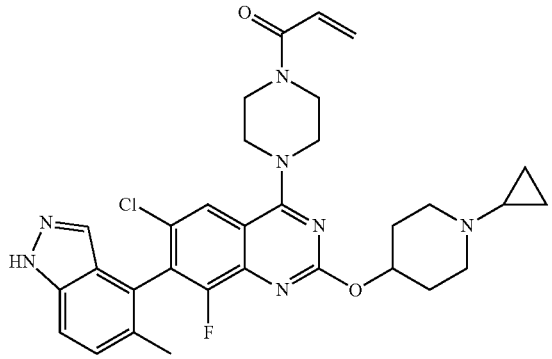 | 1-(4-(6-chloro-2-(1-cyclopropyl-piperidin-4-ylamino)-8-fluoro-7-(5-methyl-1H-indazol-4-yl) quinazolin-4-yl) piperazin-1-yl) prop-2-en-1-one | C | 590.2 |
| I-139 | 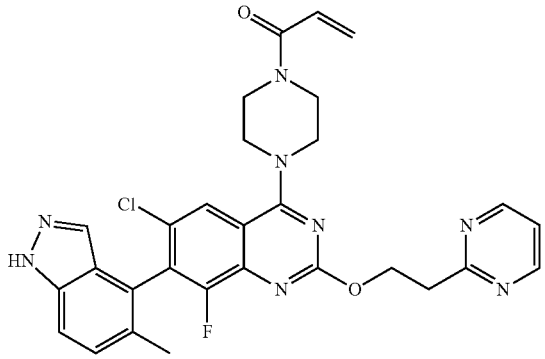 | 1-(4-(6-chloro-8-fluoro-7-(5-methyl-1H-indazol-4-yl)-2-(2-(pyrimidin-2-yl)ethoxy) quinazolin-4-yl) piperazin-1-yl) prop-2-en-1-one | C | 574.2 |

TABLE 1-continued

| Representative Compounds of Structure (I) | | | | |
|---|---|---|---|---|
| No. | Structure | Name | Method | $[M + H]^+$ |
| I-140 | 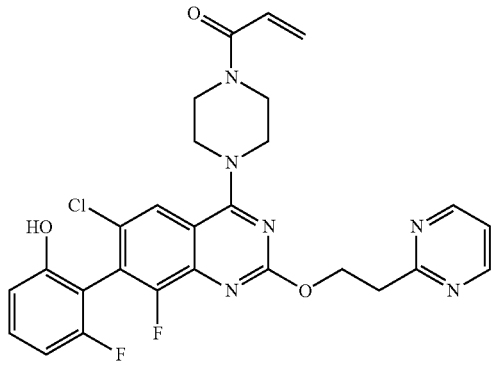 | 1-(4-(6-chloro-8-fluoro-7-(2-fluoro-6-hydroxyphenyl)-2-(2-(pyrimidin-2-yl)ethoxy) quinazolin-4-yl) piperazin-1-yl) prop-2-en-1-one | C | 554.1 |
| I-141 | 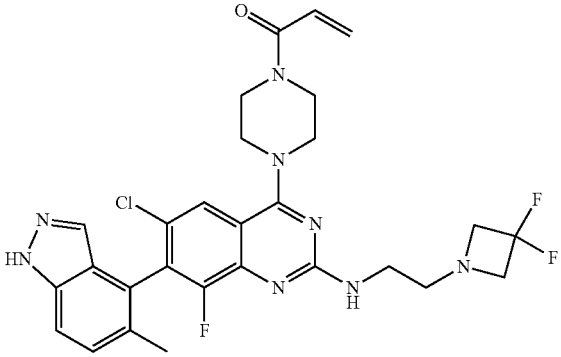 | 1-(4-(6-chloro-2-(2-(3,3-difluoro-azetidin-1-yl) ethylamino)-8-fluoro-7-(5-methyl-1H-indazol-4-yl) quinazolin-4-yl) piperazin-1-yl) prop-2-en-1-one | D | 585.2 |
| I-142 | 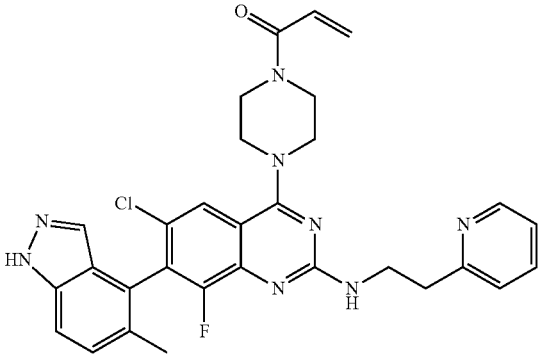 | 1-(4-(6-chloro-8-fluoro-7-(5-methyl-1H-indazol-4-yl)-2-(2-(pyridin-2-yl) ethylamino) quinazolin-4-yl) piperazin-1-yl) prop-2-en-1-one | D | 571.2 |
| I-143 | 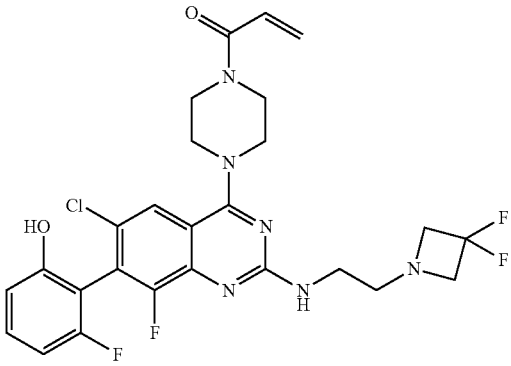 | 1-(4-(6-chloro-2-(2-(3,3-difluoro-azetidin-1-yl) ethylamino)-8-fluoro-7-(2-fluoro-6-hydroxyphenyl) quinazolin-4-yl) piperazin-1-yl) prop-2-en-1-one | D | 565.2 |

TABLE 1-continued

| Representative Compounds of Structure (I) | | | | |
|---|---|---|---|---|
| No. | Structure | Name | Method | $[M + H]^+$ |
| I-144 | 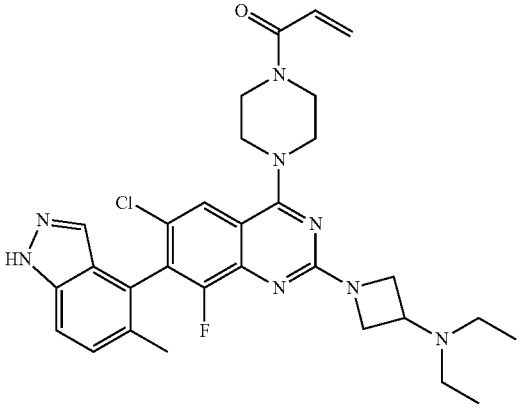 | 1-(4-(6-chloro-2-(3-(diethylamino) azetidin-1-yl)-8-fluoro-7-(5-methyl-1H-indazol-4-yl) quinazolin-4-yl) piperazin-1-yl) prop-2-en-1-one | D | 577.2 |
| I-145 | 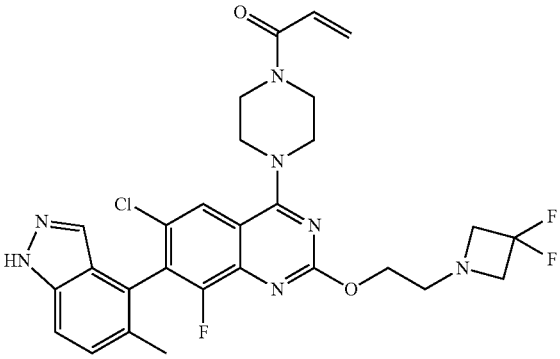 | 1-(4-(6-chloro-2-(2-(3,3-difluoro-azetidin-1-yl) ethoxy)-8-fluoro-7-(5-methyl-1H-indazol-4-yl) quinazolin-4-yl) piperazin-1-yl) prop-2-en-1-one | C | 586.2 |
| I-146 | 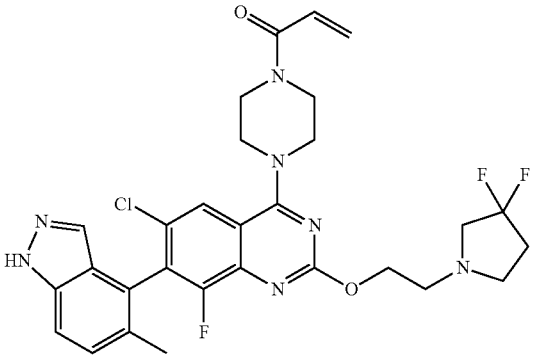 | 1-(4-(6-chloro-2-(2-(3,3-difluoro-pyrrolidin-1-yl) ethoxy)-8-fluoro-7-(5-methyl-1H-indazol-4-yl) quinazolin-4-yl) piperazin-1-yl) prop-2-en-1-one | C | 600.2 |
| I-147 | 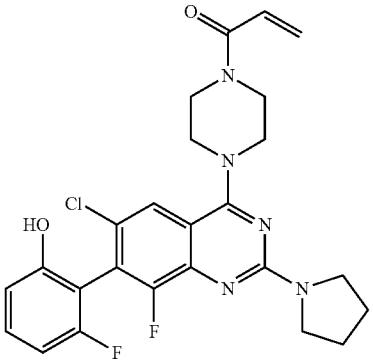 | 1-(4-(6-chloro-8-fluoro-7-(2-fluoro-6-hydroxyphenyl)-2-(pyrrolidin-1-yl)quinazolin-4-yl)piperazin-1-yl)prop-2-en-1-one | B | 500.1 |

TABLE 1-continued

Representative Compounds of Structure (I)

| No. | Structure | Name | Method | $[M + H]^+$ |
|---|---|---|---|---|
| I-148 | 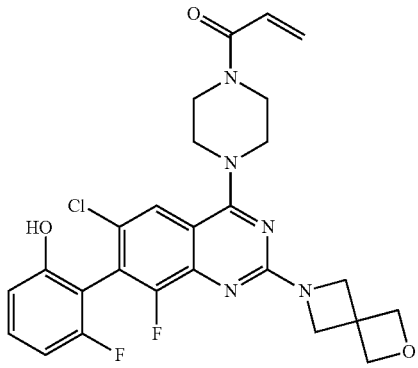 | 1-(4-(6-chloro-8-fluoro-7-(2-fluoro-6-hydroxyphenyl)-2-(2-oxa-6-azaspiro[3.3]heptan-6-yl)quinazolin-4-yl)piperazin-1-yl)prop-2-en-1-one | B | 528.2 |
| I-149 | 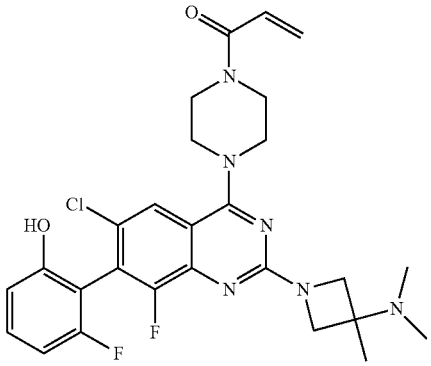 | 1-(4-(6-chloro-2-(3-(dimethylamino)-3-methylazetidin-1-yl)-8-fluoro-7-(2-fluoro-6-hydroxyphenyl)quinazolin-4-yl)piperazin-1-yl)prop-2-en-1-one | B | 543.2 |
| I-150 | 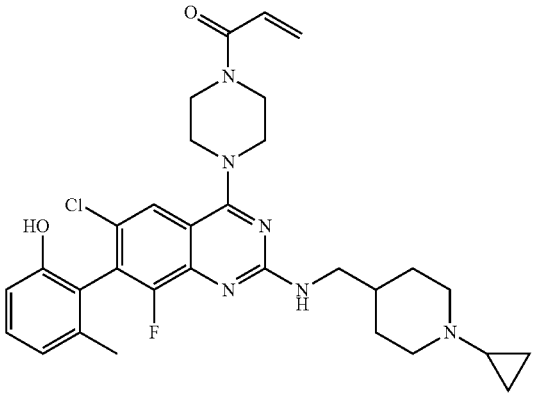 | 1-(4-(6-chloro-2-((1-cyclopropylpiperidin-4-yl)methylamino)-8-fluoro-7-(2-fluoro-6-hydroxyphenyl)quinazolin-4-yl)piperazin-1-yl)prop-2-en-1-one | B | 583.4 |
| I-151 | 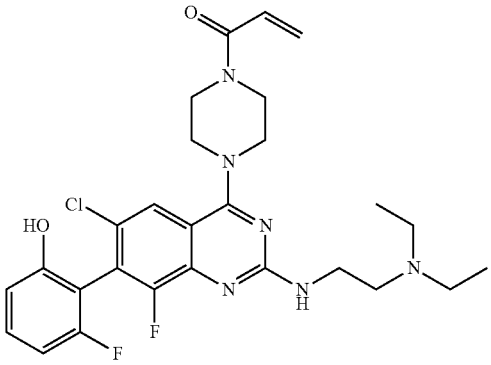 | l-(4-(6-chloro-2-(2-(diethylamino)ethylamino)-8-fluoro-7-(2-fluoro-6-hydroxyphenyl)quinazolin-4-yl)piperazin-1-yl)prop-2-en-1-one | B | 545.4 |

TABLE 1-continued

| Representative Compounds of Structure (I) | | | | |
|---|---|---|---|---|
| No. | Structure | Name | Method | $[M + H]^+$ |
| I-152 | 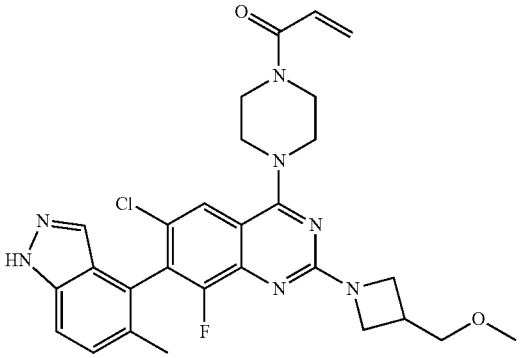 | 1-(4-(6-chloro-8-fluoro-2-(3-(methoxy-methyl) azetidin-1-yl)-7-(5-methyl-1H-indazol-4-yl) quinazolin-4-yl) piperazin-1-yl) prop-2-en-1-one | D | 551.2 |
| I-153 | 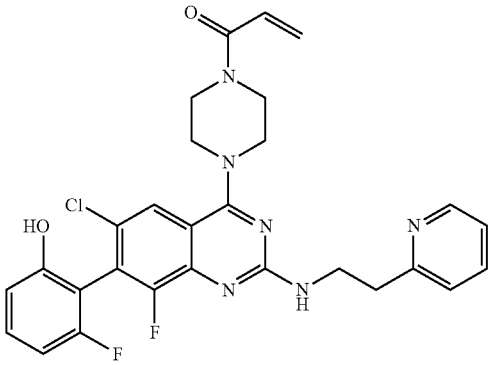 | 1-(4-(6-chloro-8-fluoro-7-(2-fluoro-6-hydroxyphenyl)-2-(2-(pyridin-2-yl)ethylamino) quinazolin-4-yl) piperazin-1-yl) prop-2-en-1-one | D | 551.2 |
| I-154 | 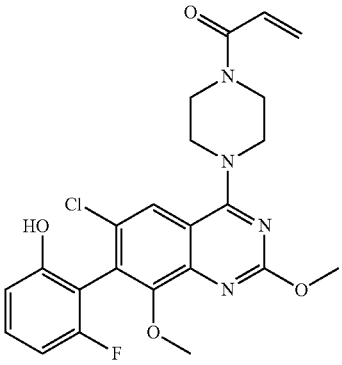 | 1-(4-(6-chloro-7-(2-fluoro-6-hydroxyphenyl)-2,8-dimethoxy-quinazolin-4-yl) piperazin-1-yl) prop-2-en-1-one | I | 473.2 |
| I-155 | 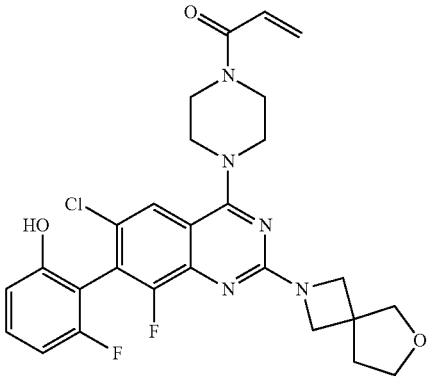 | 1-(4-(6-chloro-8-fluoro-7-(2-fluoro-6-hydroxyphenyl)-2-(6-oxa-2-azaspiro[3,4] octan-2-yl) quinazolin-4-yl) piperazin-1-yl) prop-2-en-1-one | B | 542.2 |

TABLE 1-continued

Representative Compounds of Structure (I)

| No. | Structure | Name | Method | $[M + H]^+$ |
|---|---|---|---|---|
| I-156 | 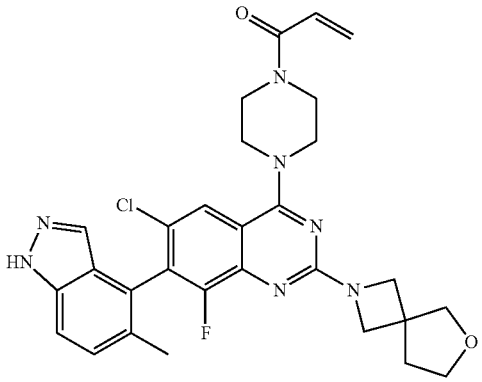 | 1-(4-(6-chloro-8-fluoro-7-(5-methyl-1H-indazol-4-yl)-2-(6-oxa-2-azaspiro[3,4]octan-2-yl)quinazolin-4-yl)piperazin-1-yl)prop-2-en-1-one | B | 562.2 |
| I-157 | 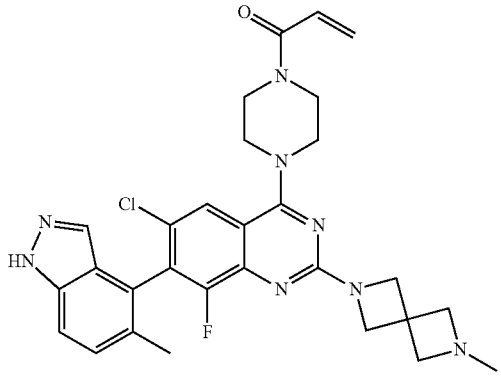 | 1-(4-(6-chloro-8-fluoro-7-(5-methyl-1H-indazol-4-yl)-2-(6-methyl-2,6-diazaspiro[3.3]heptan-2-yl)quinazolin-4-yl)piperazin-1-yl)prop-2-en-1-one | B | 561.2 |
| I-158 | 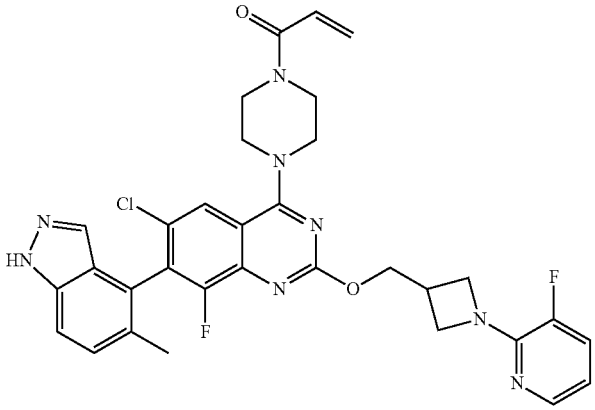 | 1-(4-(6-chloro-8-fluoro-2-((1-(3-fluoropyridin-2-yl)azetidin-3-yl)methoxy)-7-(5-methyl-1H-indazol-4-yl)quinazolin-4-yl)piperazin-1-yl)prop-2-en-1-one | C | 632.2 |
| I-159 | 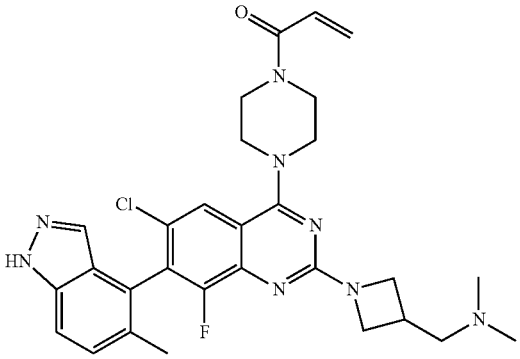 | 1-(4-(6-chloro-2-(3-((dimethylamino)methyl)azetidin-1-yl)-8-fluoro-7-(5-methyl-1H-indazol-4-yl)quinazolin-4-yl)piperazin-1-yl)prop-2-en-1-one | D | 564.3 |

TABLE 1-continued

Representative Compounds of Structure (I)

| No. | Structure | Name | Method | $[M + H]^+$ |
|---|---|---|---|---|
| I-160 | 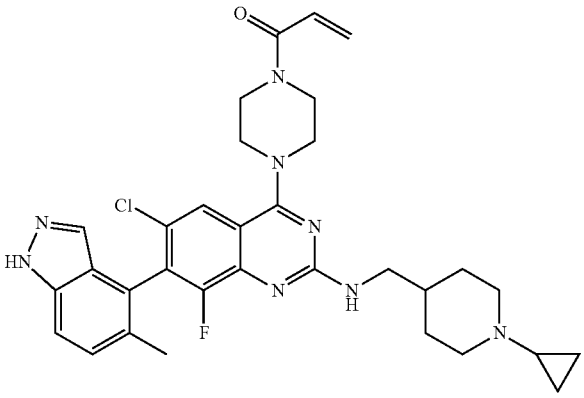 | 1-(4-(6-chloro-2-((1-cyclopropyl-piperidin-4-yl)methylamino)-8-fluoro-7-(5-methyl-1H-indazol-4-yl)quinazolin-4-yl)piperazin-l-yl)prop-2-en-1-one | B | 603.3 |
| I-161 | 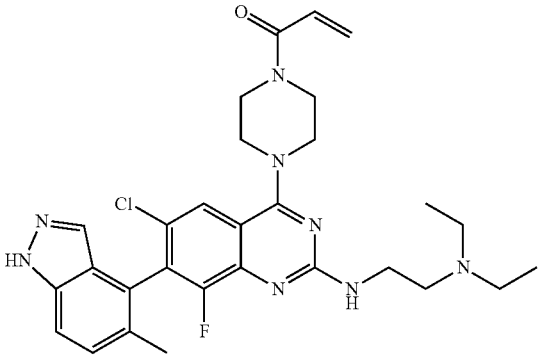 | 1-(4-(6-chloro-2-(2-(diethylamino)ethylamino)-8-fluoro-7-(5-methyl-1H-indazol-4-yl)quinazolin-4-yl)piperazin-1-yl)prop-2-en-1-one | B | 585.3 |
| I-162 | 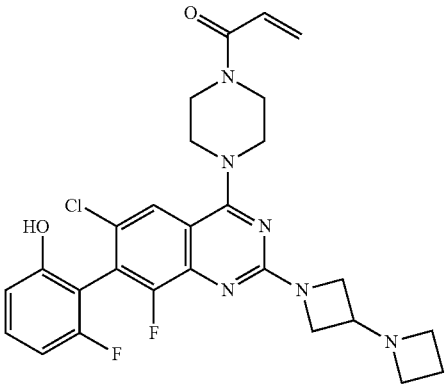 | 1-(4-(2-([1,3'-biazetidin]-1'-yl)-6-chloro-8-fluoro-7-(2-fluoro-6-hydroxyphenyl)quinazolin-4-yl)piperazin-1-yl)prop-2-en-1-one | J | 541.30 |
| I-163 | 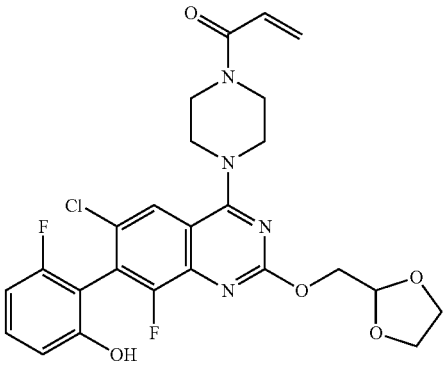 | 1-(4-(2-((1,3-dioxolan-2-yl)methoxy)-6-chloro-8-fluoro-7-(2-fluoro-6-hydroxyphenyl)quinazolin-4-yl)piperazin-1-yl)prop-2-en-1-one | A | 533.10 |

TABLE 1-continued

| Representative Compounds of Structure (I) | | | | |
|---|---|---|---|---|
| No. | Structure | Name | Method | $[M + H]^+$ |
| I-164 | 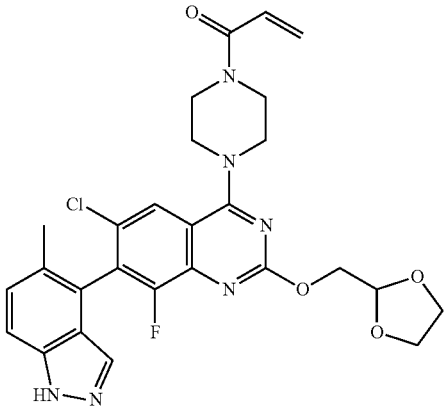 | 1-(4-(2-((1,3-dioxolan-2-yl)methoxy)-6-chloro-8-fluoro-7-(5-methyl-1H-indazol-4-yl) quinazolin-4-yl) piperazin-1-yl) prop-2-en-1-one | A | 553.15 |
| I-165 | 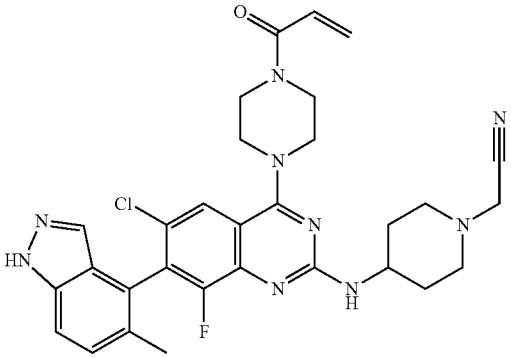 | 2-(4-((4-(4-acryloyl-piperazin-1-yl)-6-chloro-8-fluoro-7-(5-methyl-1H-indazol-4-yl) quinazolin-2-yl) amino) piperidin-1-yl) acetonitrile | B | 588.35 |
| I-166 | 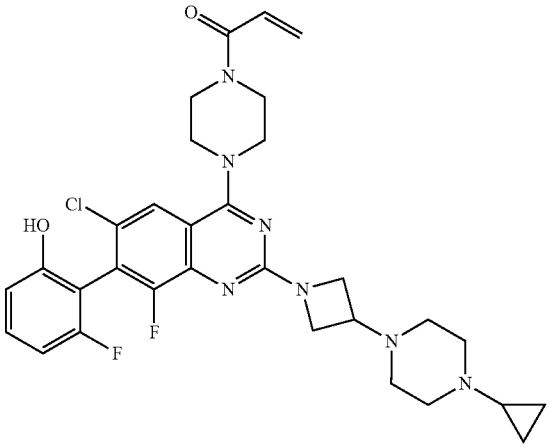 | 1-(4-(6-chloro-2-(3-(4-cyclopropyl-piperazin-1-yl) azetidin-1-yl)-8-fluoro-7-(2-fluoro-6-hydroxyphenyl) quinazolin-4-yl) piperazin-1-yl) prop-2-en-1-one | J | 610.35 |

TABLE 1-continued

| Representative Compounds of Structure (I) | | | | |
|---|---|---|---|---|
| No. | Structure | Name | Method | $[M + H]^+$ |
| I-167 | 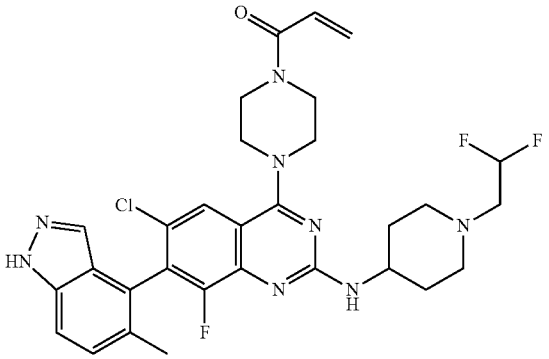 | 1-(4-(6-chloro-2-((1-(2,2-difluoroethyl) piperidin-4-yl) amino)-8-fluoro-7-(5-methyl-1H-indazol-4-yl) quinazolin-4-yl) piperazin-1-yl) prop-2-en-1-one | B | 613.35 |
| I-168 | 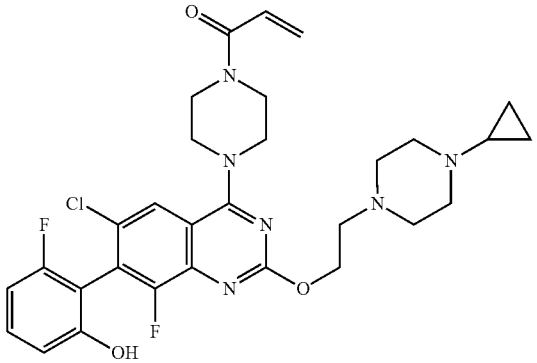 | 1-(4-(6-chloro-2-(2-(4-cyclopropyl-piperazin-1-yl) ethoxy)-8-fluoro-7-(2-fluoro-6-hydroxyphenyl) quinazolin-4-yl) piperazin-1-yl) prop-2-en-1-one | K | 599.30 |
| I-169 | 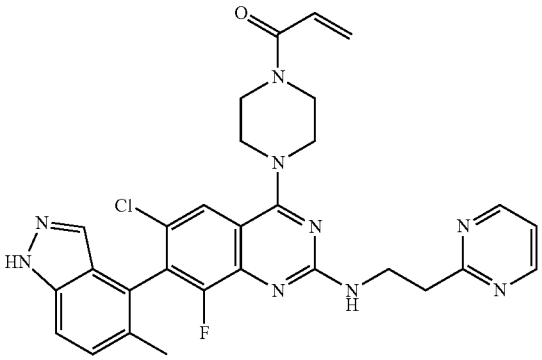 | 1-(4-(6-chloro-8-fluoro-7-(5-methyl-1H-indazol-4-yl)-2-((2-(pyrimidin-2-yl)ethyl) amino) quinazolin-4-yl) piperazin-1-yl) prop-2-en-1-one | D | 572.2 |
| I-170 | 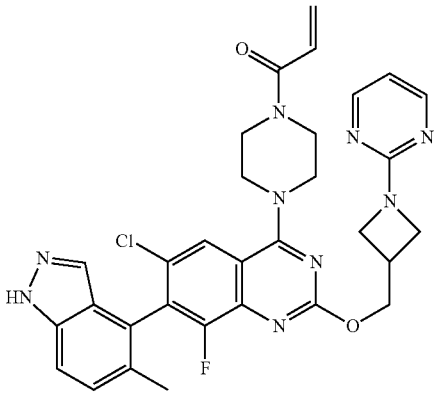 | 1-(4-(6-chloro-8-fluoro-7-(5-methyl-1H-indazol-4-yl)-2-((1-(pyrimidin-2-yl)azetidin-3-yl)methoxy) quinazolin-4-yl) piperazin-1-yl) prop-2-en-1-one | C | 614.2 |

TABLE 1-continued

| Representative Compounds of Structure (I) | | | | |
|---|---|---|---|---|
| No. | Structure | Name | Method | $[M + H]^+$ |
| I-171 | 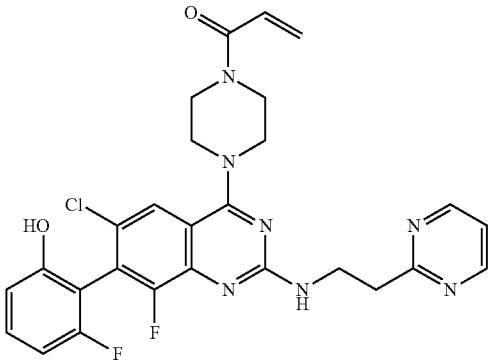 | 1-(4-(6-chloro-8-fluoro-7-(2-fluoro-6-hydroxyphenyl)-2-((2-(pyrimidin-2-yl)ethyl)amino) quinazolin-4-yl) piperazin-1-yl) prop-2-en-1-one | B | 552.1 |
| I-172 | 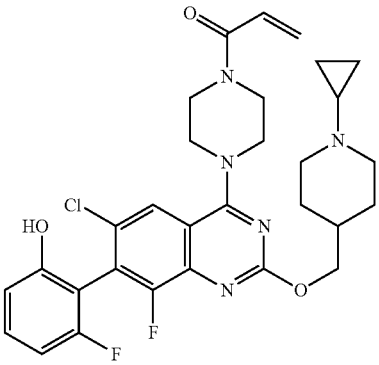 | 1-(4-(6-chloro-2-((1-cyclopropyl-piperidin-4-yl) methoxy)-8-fluoro-7-(2-fluoro-6-hydroxyphenyl) quinazolin-4-yl) piperazin-1-yl) prop-2-en-1-one | K | 584.25 |
| I-173 | 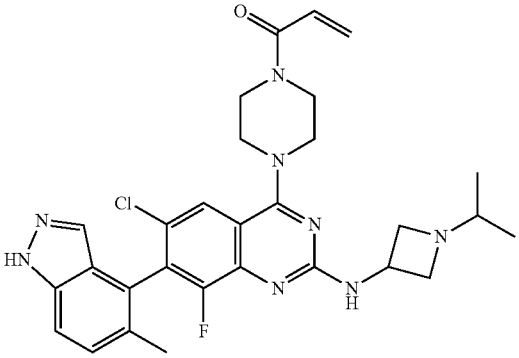 | 1-(4-(6-chloro-8-fluoro-2-((1-isopropyl-azetidin-3-yl) amino)-7-(5-methyl-1H-indazol-4-yl) quinazolin-4-yl) piperazin-1-yl) prop-2-en-1-one | B | 563.35 |
| I-174 | 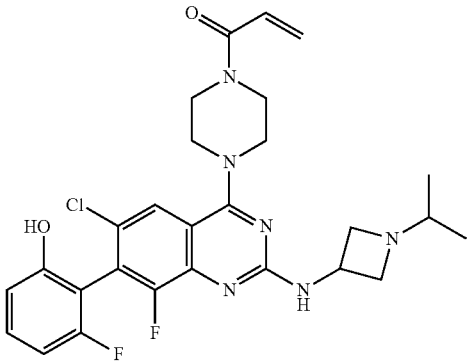 | 1-(4-(6-chloro-8-fluoro-7-(2-fluoro-6-hydroxyphenyl)-2-((1-isopropyl-azetidin-3-yl) amino) quinazolin-4-yl) piperazin-1-yl) prop-2-en-1-one | J | 543.30 |

TABLE 1-continued

Representative Compounds of Structure (I)

| No. | Structure | Name | Method | $[M + H]^+$ |
|---|---|---|---|---|
| I-175 | 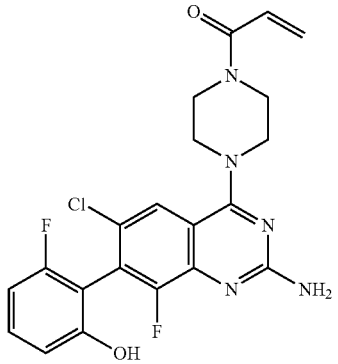 | 1-(4-(2-amino-6-chloro-8-fluoro-7-(2-fluoro-6-hydroxyphenyl) quinazolin-4-yl) piperazin-1-yl) prop-2-en-1-one | J | 446.10 |
| I-176 | 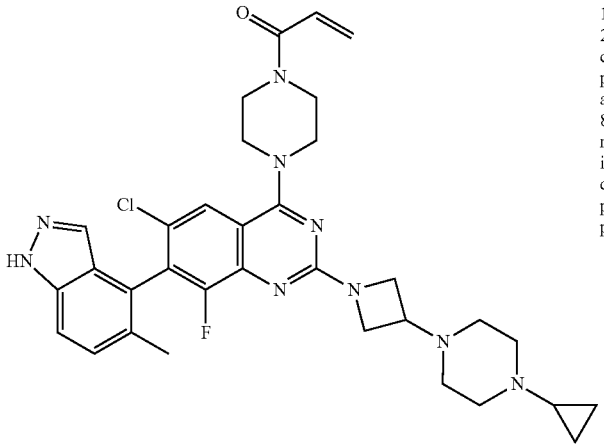 | 1-(4-(6-chloro-2-(3-(4-cyclopropyl-piperazin-1-yl) azetidin-1-yl)-8-fluoro-7-(5-methyl-1H-indazol-4-yl) quinazolin-4-yl) piperazin-1-yl) prop-2-en-1-one | B | 630.35 |
| I-177 | 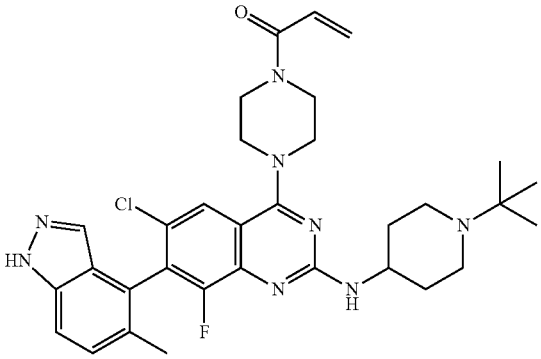 | 1-(4-(2-((1-(tert-butyl) piperidin-4-yl) amino)-6-chloro-8-fluoro-7-(5-methyl-1H-indazol-4-yl) quinazolin-4-yl) piperazin-1-yl) prop-2-en-1-one | B | 605.35 |
| I-178 | 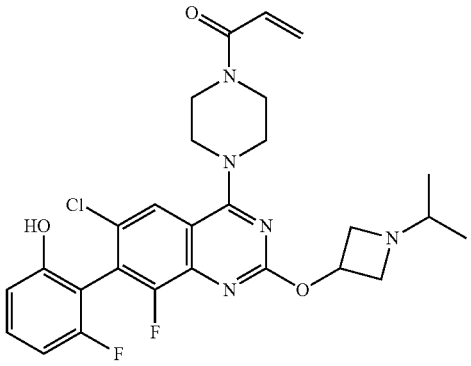 | 1-(4-(6-chloro-8-fluoro-7-(2-fluoro-6-hydroxyphenyl)-2-((1-isopropyl-azetidin-3-yl) oxy)quinazolin-4-yl)piperazin-1-yl)prop-2-en-1-one | K | 544.25 |

TABLE 1-continued

Representative Compounds of Structure (I)

| No. | Structure | Name | Method | $[M + H]^+$ |
|---|---|---|---|---|
| I-179 | 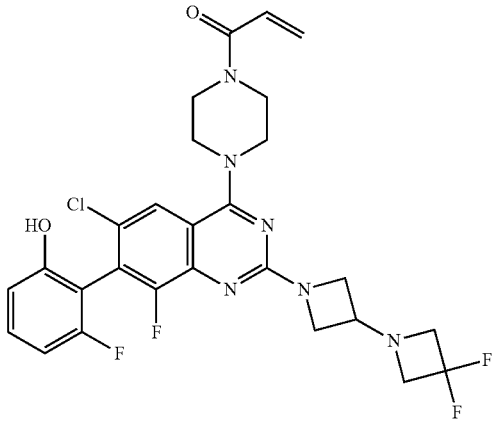 | 1-(4-(6-chloro-2-(3,3-difluoro-[1,3'-biazetidin]-1'-yl)-8-fluoro-7-(2-fluoro-6-hydroxyphenyl) quinazolin-4-yl) piperazin-1-yl) prop-2-en-1-one | J | 577.20 |
| I-180 | 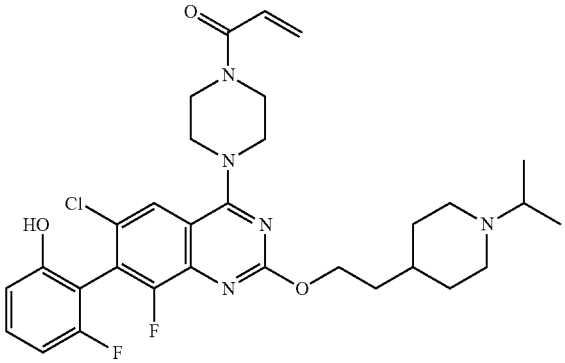 | 1-(4-(6-chloro-8-fluoro-7-(2-fluoro-6-hydroxyphenyl)-2-(2-(1-isopropyl-piperidin-4-yl) ethoxy) quinazolin-4-yl) piperazin-1-yl) prop-2-en-1-one | K | 600.35 |
| I-181 | 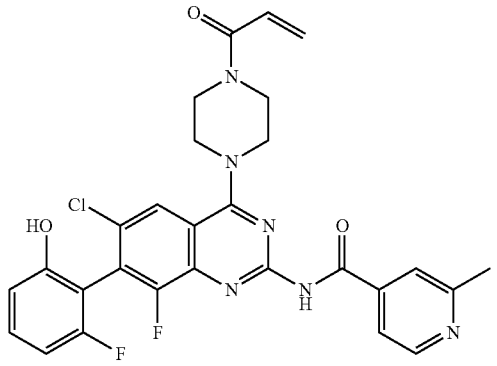 | N-(4-(4-acryloyl-piperazin-1-yl)-6-chloro-8-fluoro-7-(2-fluoro-6-hydroxyphenyl) quinazolin-2-yl)-2-methyliso-nicotinamide | ??? | 565.10 |
| I-182 | 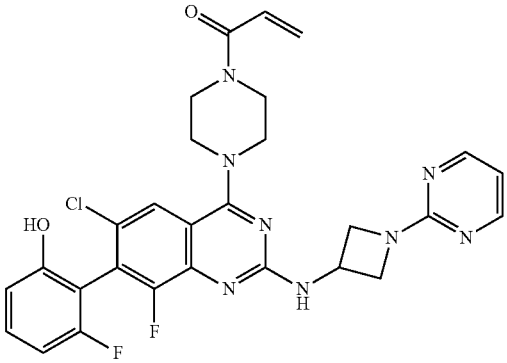 | 1-(4-(6-chloro-8-fluoro-7-(2-fluoro-6-hydroxyphenyl)-2-((1-(pyrimidin-2-yl)azetidin-3-yl)amino) quinazolin-4-yl) piperazin-1-yl) prop-2-en-1-one | B | 579.1 |

TABLE 1-continued

Representative Compounds of Structure (I)

| No. | Structure | Name | Method | $[M + H]^+$ |
|---|---|---|---|---|
| I-183 | 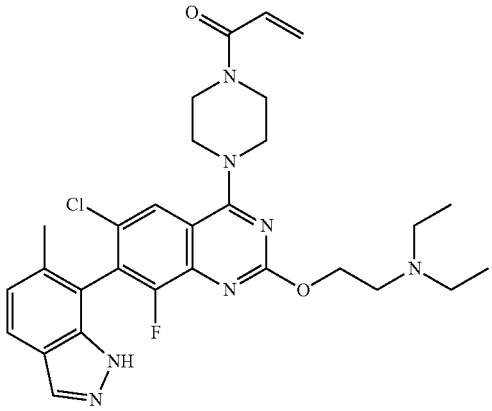 | 1-(4-(6-chloro-2-(2-(diethyl-amino)ethoxy)-8-fluoro-7-(6-methyl-1H-indazol-7-yl) quinazolin-4-yl) piperazin-1-yl) prop-2-en-1-one | A | 566.30 |
| I-184 | 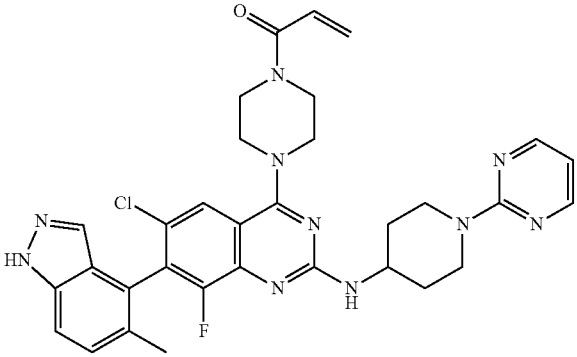 | 1-(4-(6-chloro-8-fluoro-7-(5-methyl-1H-indazol-4-yl)-2-((1-(pyrimidin-2-yl)piperidin-4-yl)amino) quinazolin-4-yl) piperazin-1-yl) prop-2-en-1-one | D | 627.2 |
| I-185 | 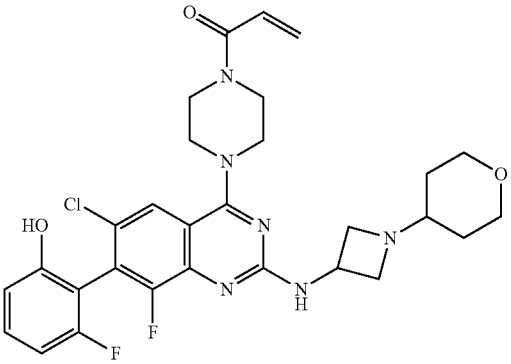 | 1-(4-(6-chloro-8-fluoro-7-(2-fluoro-6-hydroxyphenyl)-2-((1-(tetrahydro-2H-pyran-4-yl) azetidin-3-yl) amino) quinazolin-4-yl) piperazin-1-yl) prop-2-en-1-one | A | 585.25 |
| I-186 | 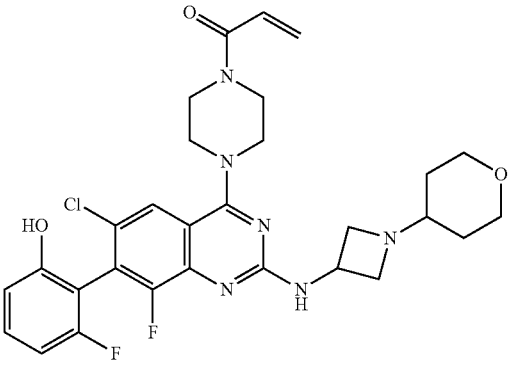 | 1-(4-(6-chloro-8-fluoro-7-(2-fluoro-6-hydroxyphenyl)-2-((1-(tetrahydro-2H-pyran-4-yl) azetidin-3-yl)oxy) quinazolin-4-yl) piperazin-1-yl) prop-2-en-1-one | K | 586.25 |

TABLE 1-continued

Representative Compounds of Structure (I)

| No. | Structure | Name | Method | $[M + H]^+$ |
|---|---|---|---|---|
| I-187 | 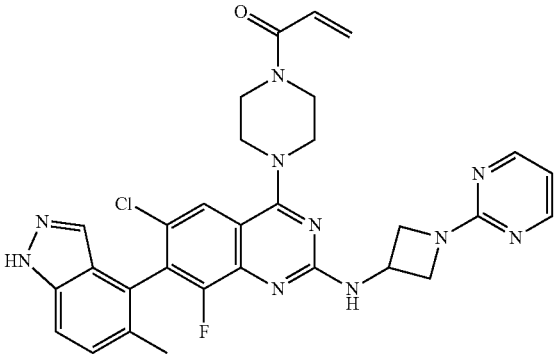 | 1-(4-(6-chloro-8-fluoro-7-(5-methyl-1H-indazol-4-yl)-2-((1-(pyrimidin-2-yl)azetidin-3-yl)amino) quinazolin-4-yl) piperazin-1-yl) prop-2-en-1-one | D | 599.2 |
| I-188 | 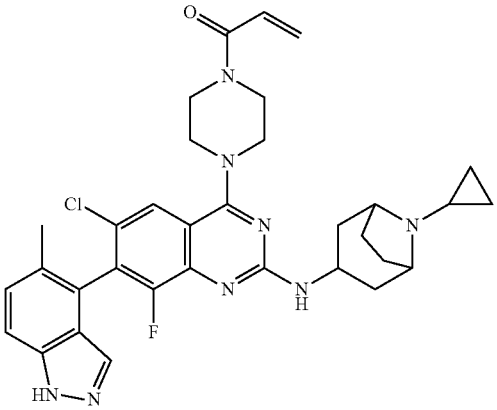 | 1-(4-(6-chloro-2-((8-cyclopropyl-8-azabicyclo[3.2.1] octan-3-yl) amino)-8-fluoro-7-(5-methyl-1H-indazol-4-yl) quinazolin-4-yl) piperazin-1-yl) prop-2-en-1-one | B | 615.35 |
| I-189 | 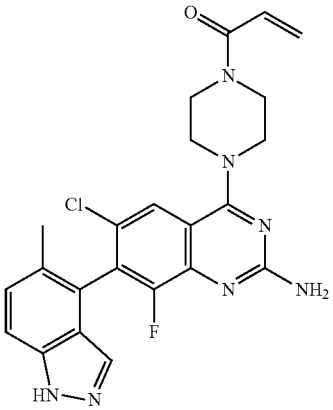 | 1-(4-(2-amino-6-chloro-8-fluoro-7-(5-methyl-1H-indazol-4-yl) quinazolin-4-yl) piperazin-1-yl) prop-2-en-1-one | B | 466.15 |
| I-190 | 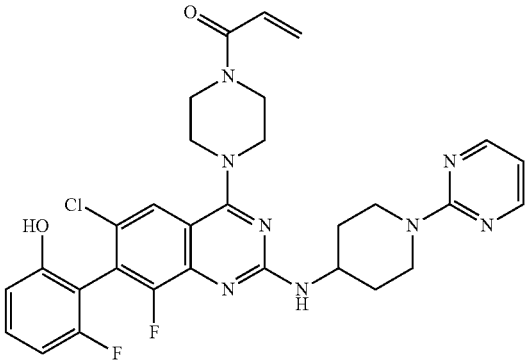 | 1-(4-(6-chloro-8-fluoro-7-(2-fluoro-6-hydroxyphenyl)-2-((1-(pyrimidin-2-yl)piperidin-4-yl)amino) quinazolin-4-yl) piperazin-1-yl) prop-2-en-1-one | B | 607.2 |

TABLE 1-continued

Representative Compounds of Structure (I)

| No. | Structure | Name | Method | $[M + H]^+$ |
|---|---|---|---|---|
| I-191 | 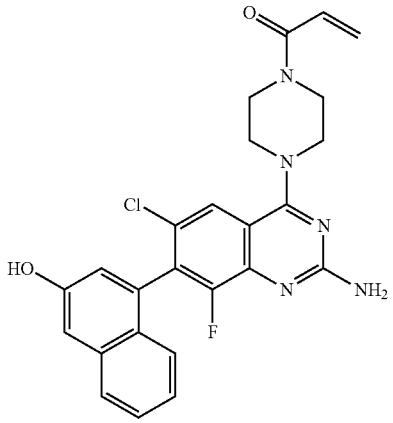 | 1-(4-(2-amino-6-chloro-8-fluoro-7-(3-hydroxy-naphthalen-1-yl) quinazolin-4-yl) piperazin-1-yl) prop-2-en-1-one | B | 478.25 |
| I-192 | 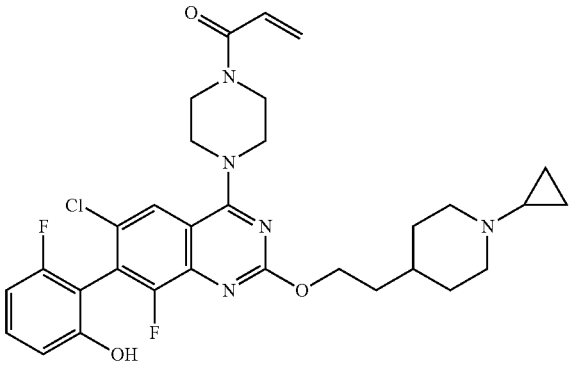 | 1-(4-(6-chloro-2-(2-(1-cyclopropyl-piperidin-4-yl) ethoxy)-8-fluoro-7-(2-fluoro-6-hydroxyphenyl) quinazolin-4-yl) piperazin-1-yl) prop-2-en-1-one | K | 598.30 |
| I-193 | 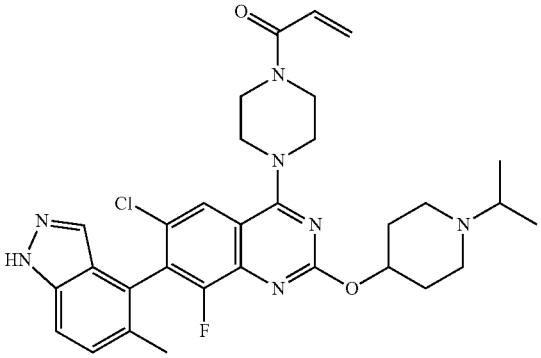 | 1-(4-(6-chloro-8-fluoro-2-((1-isopropyl-piperidin-4-yl) oxy)-7-(5-methyl-1H-indazol-4-yl) quinazolin-4-yl) piperazin-1-yl) prop-2-en-1-one | A | 592.2 |
| I-194 | 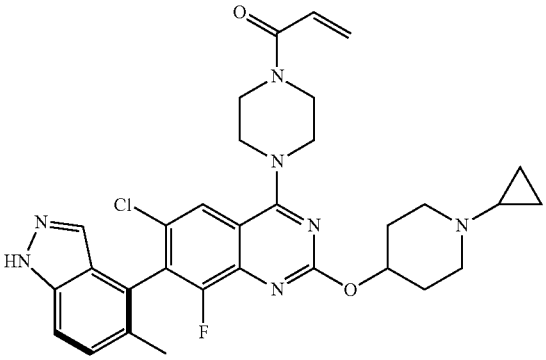 | (S)-1-(4-(6-chloro-2-((1-cyclopropyl-piperidin-4-yl) oxy)-8-fluoro-7-(6-methyl-1H-indazol-7-yl) quinazolin-4-yl) piperazin-1-yl) prop-2-en-1-one | A | 590.40 |

TABLE 1-continued

| Representative Compounds of Structure (I) | | | | |
|---|---|---|---|---|
| No. | Structure | Name | Method | $[M + H]^+$ |
| I-195 | 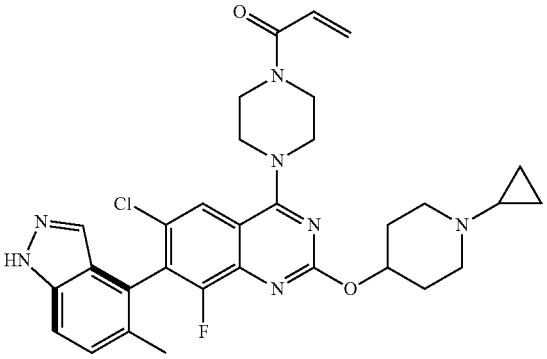 | 1-(4-(6-chloro-2-((1-cyclopropyl-piperidin-4-yl) oxy)-8-fluoro-7-(6-methyl-1H-indazol-7-yl) quinazolin-4-yl) piperazin-1-yl) prop-2-en-1-one | A | 590.40 |
| I-196 | 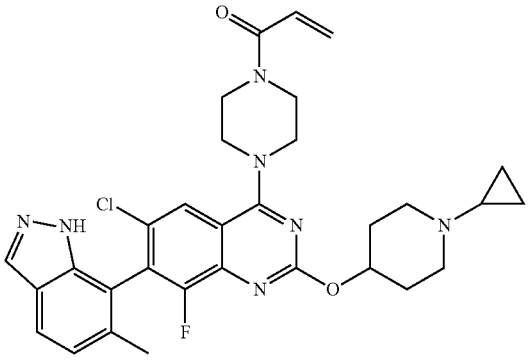 | 1-(4-(6-chloro-2-((1-cyclo-propylpiperidin-4-yl)amino)-8-fluoro-7-(6-methyl-1H-indazol-7-yl) quinazolin-4-yl) piperazin-1-yl) prop-2-en-1-one | B | 589.45 |
| I-197 | 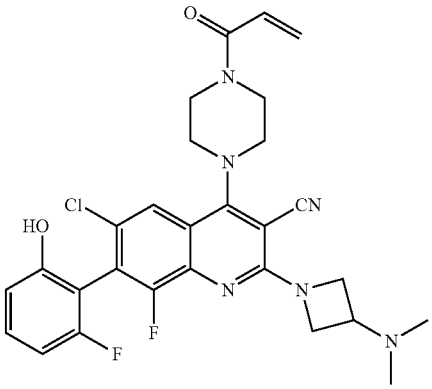 | 4-(4-acryloyl-piperazin-1-yl)-6-chloro-2-(3-(dimethyl-amino) azetidin-1-yl)-8-fluoro-7-(2-fluoro-6-hydroxyphenyl) quinoline-3-carbonitrile | P | 553.35 |
| I-198 | 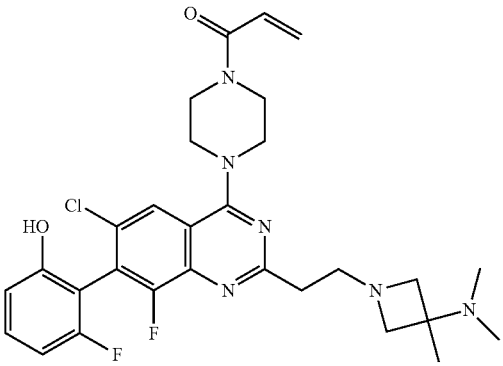 | 1-(4-(6-chloro-2-(2-(3-(dimethyl-amino)-3-methyl-azetidin-1-yl) ethyl)-8-fluoro-7-(2-fluoro-6-hydroxyphenyl) quinazolin-4-yl) piperazin-1-yl) prop-2-en-1-one | E | 571.2 |

TABLE 1-continued

Representative Compounds of Structure (I)

| No. | Structure | Name | Method | $[M + H]^+$ |
|---|---|---|---|---|
| I-199 | 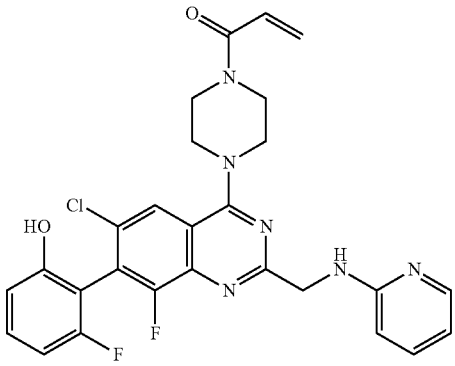 | 1-(4-(6-chloro-8-fluoro-7-(2-fluoro-6-hydroxyphenyl)-2-((pyridin-2-ylamino)methyl) quinazolin-4-yl) piperazin-1-yl) prop-2-en-1-one | L | 537.30 |
| I-200 | 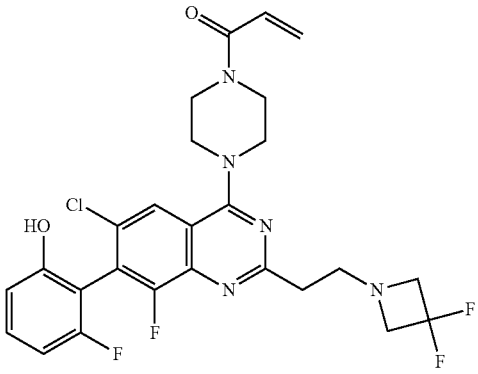 | 1-(4-(6-chloro-2-(2-(3,3-difluoro-azetidin-1-yl) ethyl)-8-fluoro-7-(2-fluoro-6-hydroxyphenyl) quinazolin-4-yl) piperazin-1-yl) prop-2-en-1-one | E | 550.15 |
| I-201 | 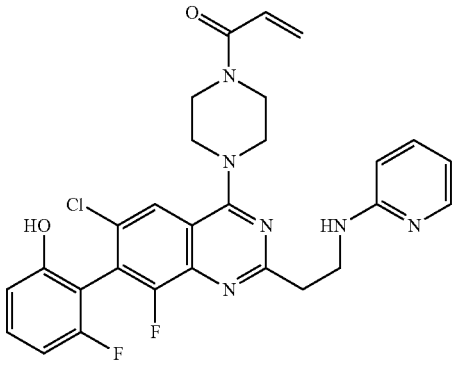 | 1-(4-(6-chloro-8-fluoro-7-(2-fluoro-6-hydroxyphenyl)-2-(2-(pyridin-2-ylamino)ethyl) quinazolin-4-yl) piperazin-1-yl) prop-2-en-1-one | H | 551.25 |
| I-202 | 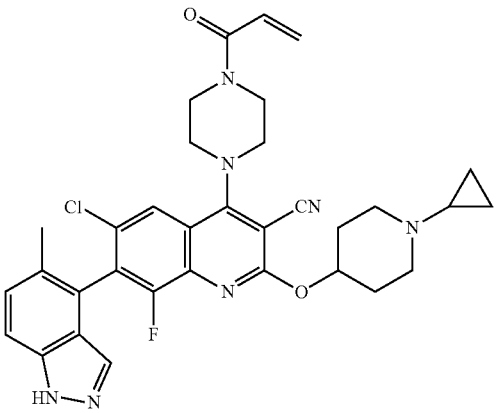 | 4-(4-acryloyl-piperazin-1-yl)-6-chloro-2-((1-cyclopropyl-piperidin-4-yl)amino)-8-fluoro-7-(5-methyl-1H-indazol-4-yl) quinoline-3-carbonitrile | P | 613.4 |

TABLE 1-continued

Representative Compounds of Structure (I)

| No. | Structure | Name | Method | $[M + H]^+$ |
|---|---|---|---|---|
| I-203 | 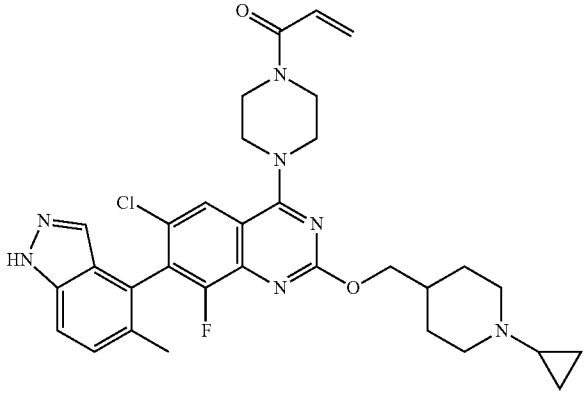 | 1-(4-(6-chloro-2-((1-cyclopropyl-piperidin-4-yl) methoxy)-8-fluoro-7-(5-methyl-1H-indazol-4-yl) quinazolin-4-yl) piperazin-1-yl) prop-2-en-1-one | A | 604.45 |
| I-204 | 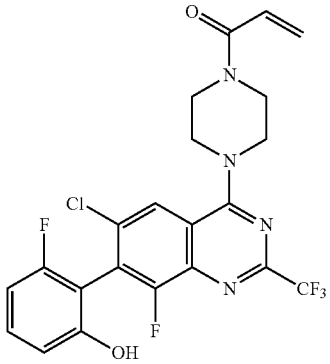 | 1-(4-(6-chloro-8-fluoro-7-(2-fluoro-6-hydroxyphenyl)-2-(trifluoro-methyl) quinazolin-4-yl) piperazin-1-yl) prop-2-en-1-one | M | 499.25 |
| I-205 | 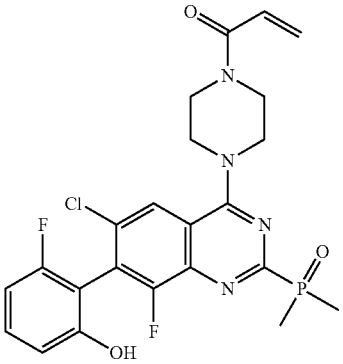 | 1-(4-(6-chloro-2-(dimethyl-phosphoryl)-8-fluoro-7-(2-fluoro-6-hydroxyphenyl) quinazolin-4-yl) piperazin-1-yl) prop-2-en-1-one | N | 507.15 |
| I-206 | 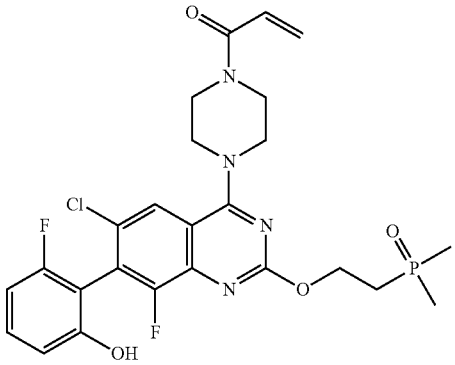 | 1-(4-(6-chloro-2-(2-(dimethyl-phosphoryl) ethoxy)-8-fluoro-7-(2-fluoro-6-hydroxyphenyl) quinazolin-4-yl) piperazin-1-yl) prop-2-en-1-one | K | 551.15 |

TABLE 1-continued

Representative Compounds of Structure (I)

| No. | Structure | Name | Method | $[M + H]^+$ |
|---|---|---|---|---|
| I-207 | 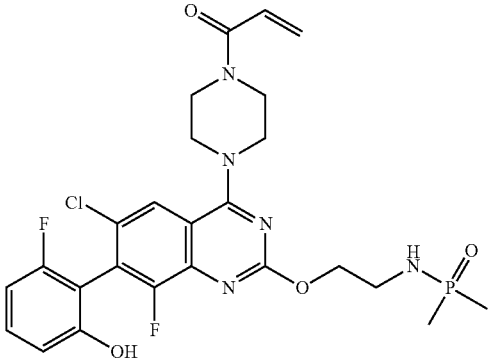 | N-(2-(4-(4-acryloyl-piperazin-1-yl)-6-chloro-8-fluoro-7-(2-fluoro-6-hydroxyphenyl) quinazolin-2-yloxy)ethyl)-P,P-dimethyl-phosphinic amide | K | 566.3 |
| I-208 | 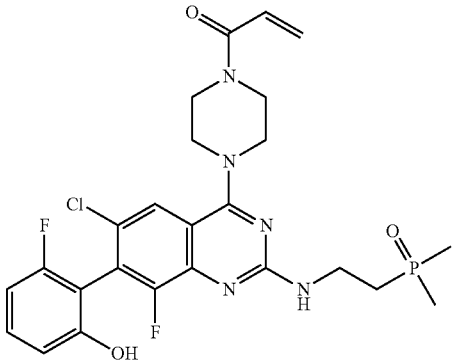 | 1-(4-(6-chloro-2-(2-(dimethyl-phosphoryl) ethylamino)-8-fluoro-7-(2-fluoro-6-hydroxyphenyl) quinazolin-4-yl) piperazin-1-yl) prop-2-en-1-one | J | 550.25 |
| I-209 | 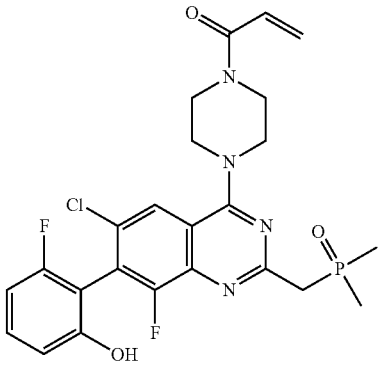 | 1-(4-(6-chloro-2-((dimethyl-phosphoryl) methyl)-8-fluoro-7-(2-fluoro-6-hydroxyphenyl) quinazolin-4-yl) piperazin-1-yl) prop-2-en-1-one | O | 521.20 |
| I-210 | 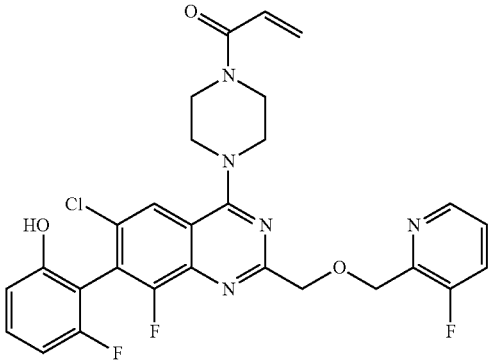 | 1-(4-(6-chloro-8-fluoro-7-(2-fluoro-6-hydroxyphenyl)-2-(((3-fluoro-pyridin-2-yl) methoxy) methyl) quinazolin-4-yl) piperazin-1-yl) prop-2-en-1-one | Q | 569.6 |

*$[M - H]^-$

In various different embodiments of any of the embodiments of the compounds of structure (I), the compounds illustrated in Table 2 are excluded from the invention.

TABLE 2

Compounds Excluded From Certain Embodiments

| No. | Structure | Name |
|---|---|---|
| 2-1 | 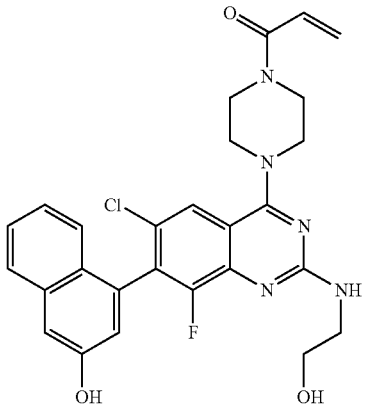 | 1-(4-(6-chloro-8-fluoro-2-(2-hydroxyethylamino)-7-(3-hydroxynaphthalen-1-yl)quinazolin-4-yl)piperazin-1-yl)prop-2-en-1-one |
| 2-2 | 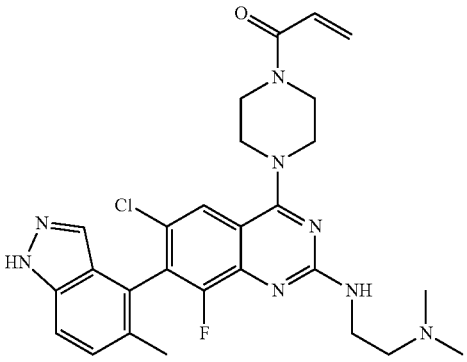 | 1-(4-(6-chloro-2-(2-(dimethylamino)ethyl-amino)-8-fluoro-7-(5-methyl-1H-indazol-4-yl)quinazolin-4-yl)piperazin-1-yl)prop-2-en-1-one |
| 2-3 | 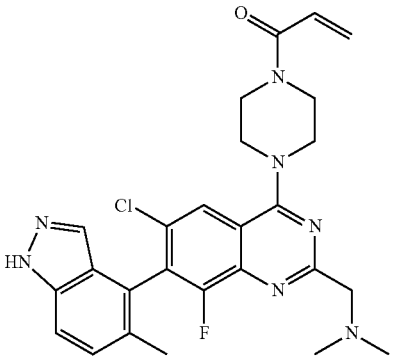 | 1-(4-(6-chloro-2-((dimethylamino)methyl)-8-fluoro-7-(5-methyl-1H-indazol-4-yl)quinazolin-4-yl)piperazin-1-yl)prop-2-en-1-one |

TABLE 2-continued

| Compounds Excluded From Certain Embodiments | | |
|---|---|---|
| No. | Structure | Name |
| 2-4 | 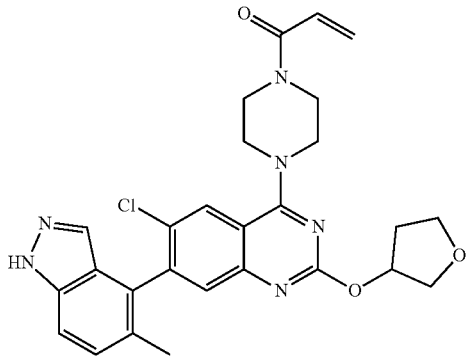 | 1-(4-(6-chloro-7-(5-methyl-1H-indazol-4-yl)-2-(tetrahydrofuran-3-yloxy)quinazolin-4-yl)piperazin-1-yl)prop-2-en-1-one |
| 2-5 | 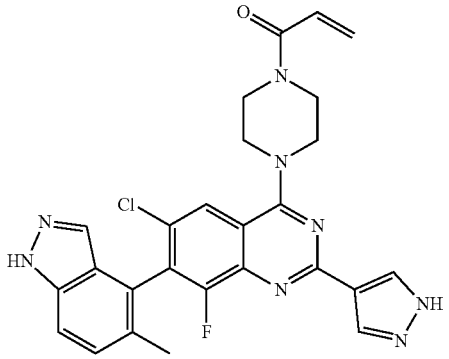 | 1-(4-(6-chloro-8-fluoro-7-(5-methyl-1H-indazol-4-yl)-2-(1H-pyrazol-4-yl)quinazolin-4-yl)piperazin-1-yl)prop-2-en-1-one |
| 2-6 | 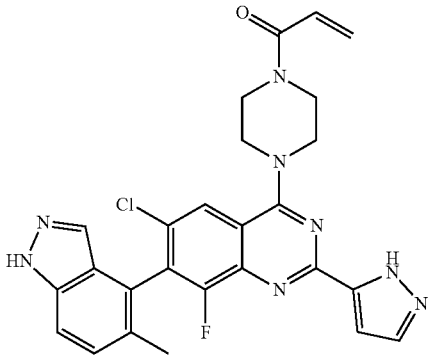 | 1-(4-(6-chloro-8-fluoro-7-(5-methyl-1H-indazol-4-yl)-2-(1H-pyrazol-5-yl)quinazolin-4-yl)piperazin-1-yl)prop-2-en-1-one |
| 2-7 | 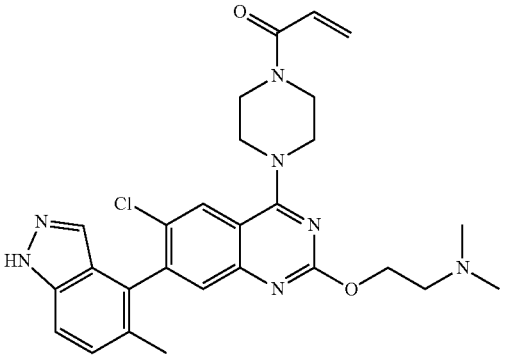 | 1-(4-(6-chloro-2-(2-(dimethylamino)ethoxy)-7-(5-methyl-1H-indazol-4-yl)quinazolin-4-yl)piperazin-1-yl)prop-2-en-1-one |

TABLE 2-continued

| Compounds Excluded From Certain Embodiments | | |
|---|---|---|
| No. | Structure | Name |
| 2-8 | 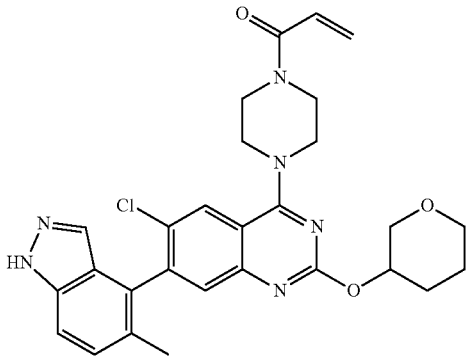 | 1-(4-(6-chloro-7-(5-methyl-1H-indazol-4-yl)-2-(tetrahydro-2H-pyran-3-yloxy)quinazolin-4-yl)piperazin-1-yl)prop-2-en-1-one |
| 2-9 | 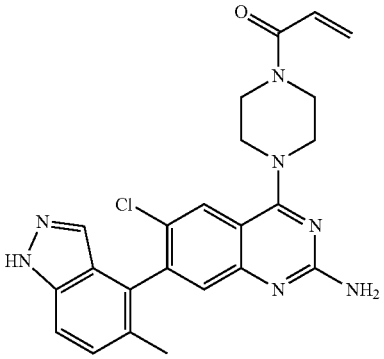 | 1-(4-(2-amino-6-chloro-7-(5-methyl-1H-indazol-4-yl)quinazolin-4-yl)piperazin-1-yl)prop-2-en-1-one |
| 2-10 | 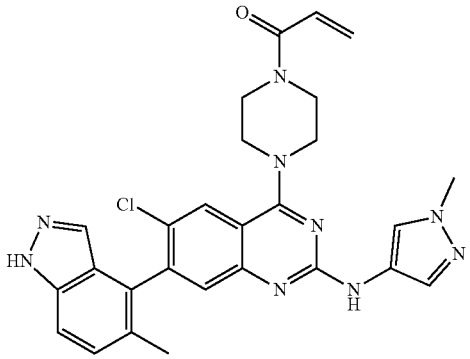 | 1-(4-(6-chloro-8-fluoro-7-(5-methyl-1H-indazol-4-yl)-2-(1-methyl-1H-pyrazol-4-ylamino)quinazolin-4-yl)piperazin-1-yl)prop-2-en-1-one |
| 2-11 | 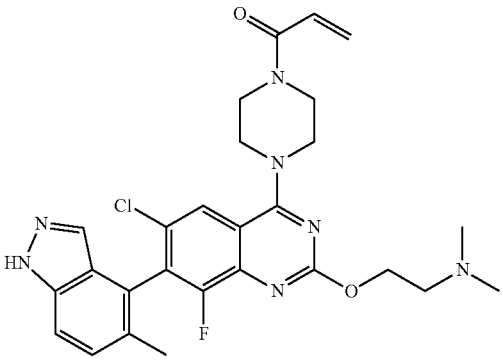 | 1-(4-(6-chloro-2-(2-(dimethylamino)ethoxy)-8-fluoro-7-(5-methyl-1H-indazol-4-yl)quinazolin-4-yl)piperazin-1-yl)prop-2-en-1-one |

TABLE 2-continued

| Compounds Excluded From Certain Embodiments | | |
|---|---|---|
| No. | Structure | Name |
| 2-12 | 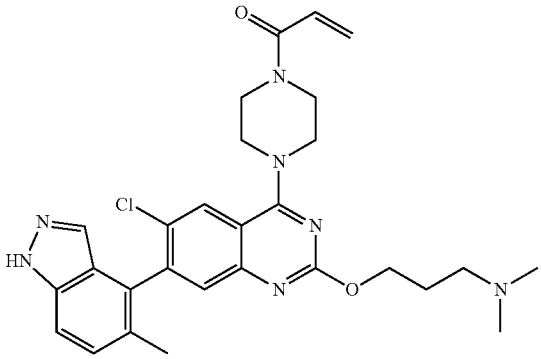 | 1-(4-(6-chloro-2-(3-(dimethylamino)propoxy)-7-(5-methyl-1H-indazol-4-yl)quinazolin-4-yl)piperazin-1-yl)prop-2-en-1-one |
| 2-13 | 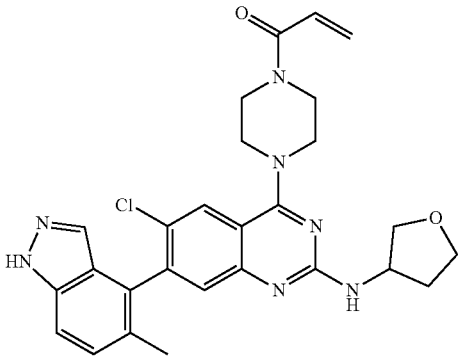 | 1-(4-(6-chloro-7-(5-methyl-1H-indazol-4-yl)-2-(tetrahydrofuran-3-ylamino)quinazolin-4-yl)piperazin-1-yl)prop-2-en-1-one |
| 2-14 | 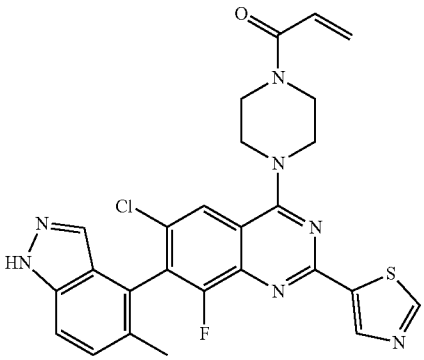 | 1-(4-(6-chloro-8-fluoro-7-(5-methyl-1H-indazol-4-yl)-2-(thiazol-5-yl)quinazolin-4-yl)piperazin-1-yl)prop-2-en-1-one |
| 2-15 | 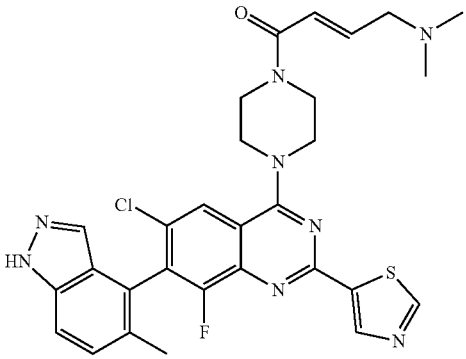 | (E)-1-(4-(6-chloro-8-fluoro-7-(5-methyl-1H-indazol-4-yl)-2-(thiazol-5-yl)quinazolin-4-yl)piperazin-1-yl)-4-(dimethylamino)but-2-en-1-one |

TABLE 2-continued

| Compounds Excluded From Certain Embodiments | | |
|---|---|---|
| No. | Structure | Name |
| 2-16 | 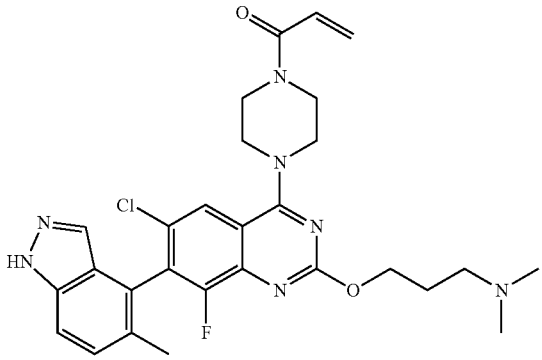 | 1-(4-(6-chloro-2-(3-(dimethylamino)propoxy)-8-fluoro-7-(5-methyl-1H-indazol-4-yl)quinazolin-4-yl)piperazin-1-yl)prop-2-en-1-one |
| 2-17 | 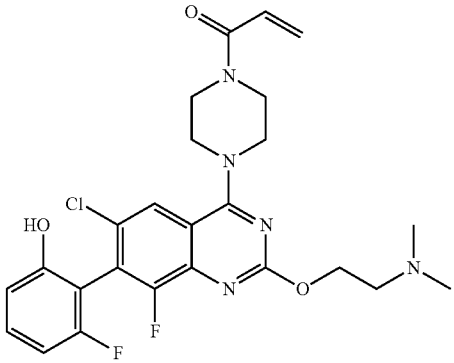 | 1-(4-(6-chloro-2-(2-(dimethylamino)ethoxy)-8-fluoro-7-(2-fluoro-6-hydroxyphenyl)quinazolin-4-yl)piperazin-1-yl)prop-2-en-1-one |
| 2-18 | 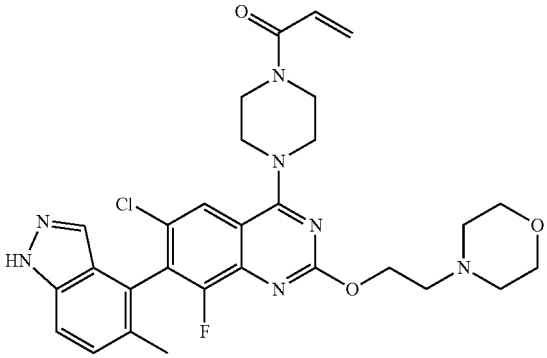 | 1-(4-(6-chloro-8-fluoro-7-(5-methyl-1H-indazol-4-yl)-2-(2-morpholino-ethoxy)quinazolin-4-yl)piperazin-1-yl)prop-2-en-1-one |
| 2-19 | 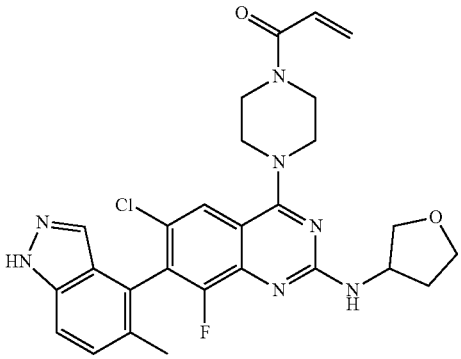 | 1-(4-(6-chloro-8-fluoro-7-(5-methyl-1H-indazol-4-yl)-2-(tetrahydrofuran-3-ylamino)quinazolin-4-yl)piperazin-1-yl)prop-2-en-1-one |

TABLE 2-continued

| Compounds Excluded From Certain Embodiments | | |
|---|---|---|
| No. | Structure | Name |
| 2-20 | 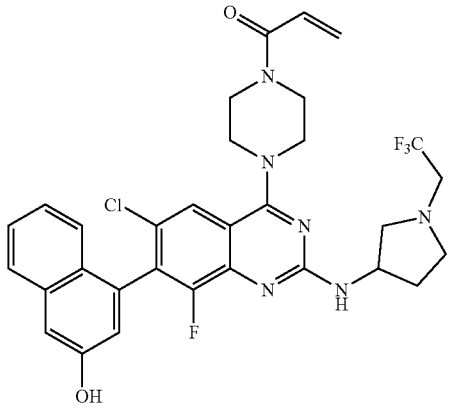 | 1-(4-(6-chloro-8-fluoro-7-(3-hydroxynaphthalen-1-yl)-2-(1-(2,2,2-trifluoroethyl)pyrrolidin-3-ylamino)quinazolin-4-yl)piperazin-1-yl)prop-2-en-1-one |
| 2-21 | 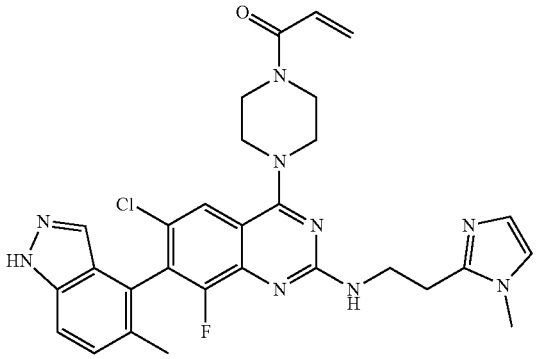 | 1-(4-(6-chloro-8-fluoro-2-(2-(1-methyl-1H-imidazol-2-yl)ethylamino)-7-(5-methyl-1H-indazol-4-yl)quinazolin-4-yl)piperazin-1-yl)prop-2-en-1-one |
| 2-22 | 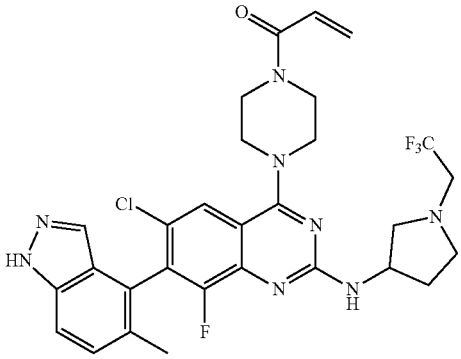 | 1-(4-(6-chloro-8-fluoro-7-(5-methyl-1H-indazol-4-yl)-2-(1-(2,2,2-trifluoroethyl)pyrrolidin-3-ylamino)quinazolin-4-yl)piperazin-1-yl)prop-2-en-1-one |
| 2-23 | 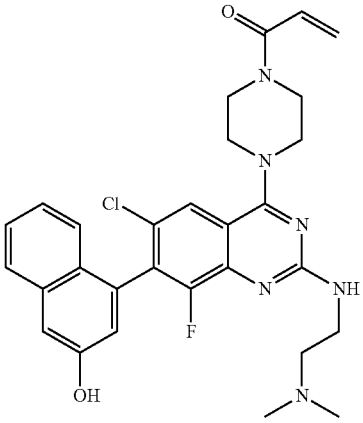 | 1-(4-(6-chloro-2-(2-(dimethylamino)ethylamino)-8-fluoro-7-(3-hydroxynaphthalen-1-yl)quinazolin-4-yl)piperazin-1-yl)prop-2-en-1-one |

TABLE 2-continued

| Compounds Excluded From Certain Embodiments | | |
|---|---|---|
| No. | Structure | Name |
| 2-24 | 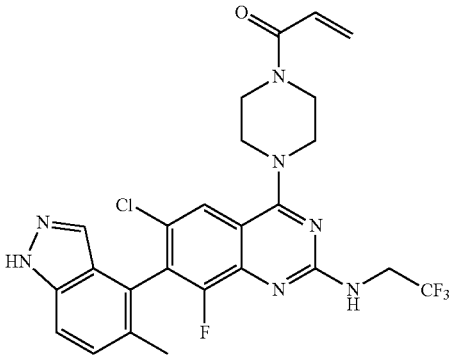 | 1-(4-(6-chloro-8-fluoro-7-(5-methyl-1H-indazol-4-yl)-2-(2,2,2-trifluoro-ethylamino)quinazolin-4-yl)piperazin-1-yl)prop-2-en-1-one |
| 2-25 | 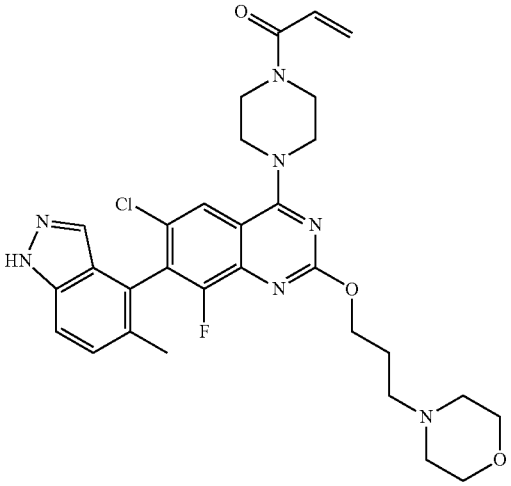 | 1-(4-(6-chloro-8-fluoro-7-(5-methyl-1H-indazol-4-yl)-2-(3-morpholino-propoxy)quinazolin-4-yl)piperazin-1-yl)prop-2-en-1-one |
| 2-26 | 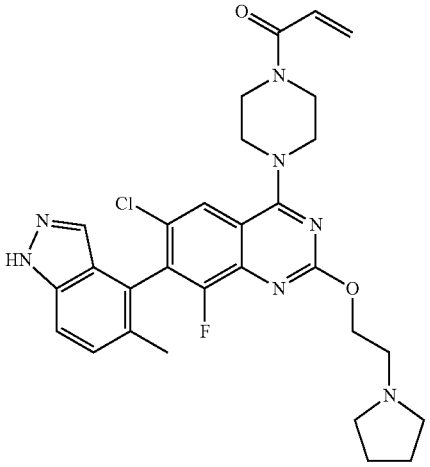 | 1-(4-(6-chloro-8-fluoro-7-(5-methyl-1H-indazol-4-yl)-2-(2-(pyrrolidin-1-yl)ethoxy)quinazolin-4-yl)piperazin-1-yl)prop-2-en-1-one |

TABLE 2-continued

| Compounds Excluded From Certain Embodiments | | |
|---|---|---|
| No. | Structure | Name |
| 2-27 | 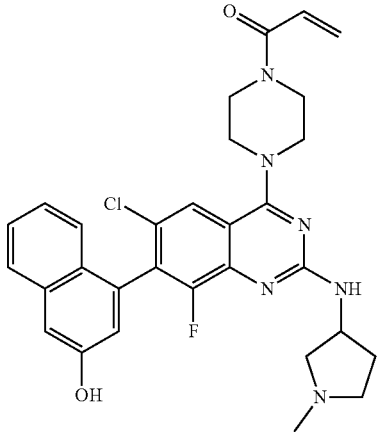 | 1-(4-(6-chloro-8-fluoro-7-(3-hydroxynaphthalen-1-yl)-2-(1-methylpyrrolidin-3-ylamino)quinazolin-4-yl)piperazin-1-yl)prop-2-en-1-one |
| 2-28 | 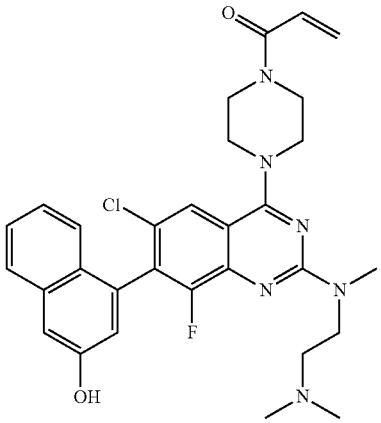 | 1-(4-(6-chloro-2-((2-(dimethylamino)ethyl)(methyl)amino)-8-fluoro-7-(3-hydroxynaphthalen-1-yl)quinazolin-4-yl)piperazin-1-yl)prop-2-en-1-one |
| 2-29 | 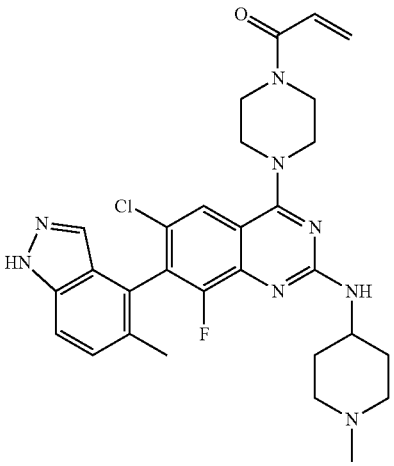 | l-(4-(6-chloro-8-fluoro-7-(5-methyl-1H-indazol-4-yl)-2-(1-methylpiperidin-4-ylamino)quinazolin-4-yl)piperazin-1-yl)prop-2-en-1-one |

TABLE 2-continued

| Compounds Excluded From Certain Embodiments | | |
|---|---|---|
| No. | Structure | Name |
| 2-30 | 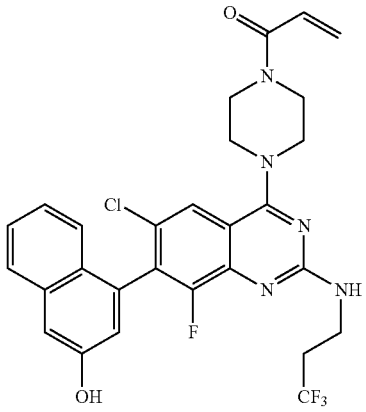 | 1-(4-(6-chloro-8-fluoro-7-(3-hydroxynaphthalen-1-yl)-2-(3,3,3-trifluoro-propylamino)quinazolin-4-yl)piperazin-1-yl)prop-2-en-1-one |
| 2-31 | 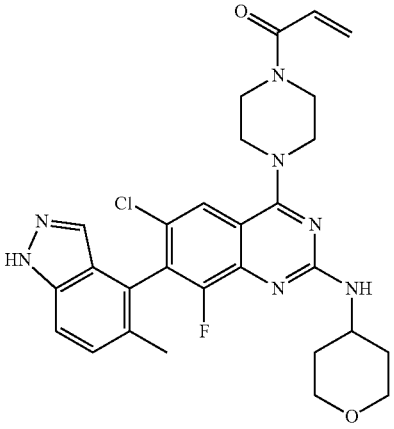 | 1-(4-(6-chloro-8-fluoro-7-(5-methyl-1H-indazol-4-yl)-2-(tetrahydro-2H-pyran-4-ylamino)quinazolin-4-yl)piperazin-1-yl)prop-2-en-1-one |
| 2-32 | 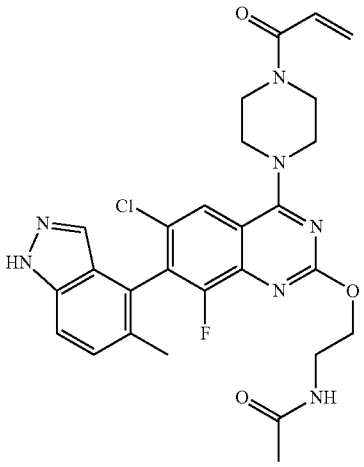 | N-(2-(4-(4-acryloylpiperazin-1-yl)-6-chloro-8-fluoro-7-(5-methyl-1H-indazol-4-yl)quinazolin-2-yloxy)ethyl)acetamide |

TABLE 2-continued

| Compounds Excluded From Certain Embodiments | | |
|---|---|---|
| No. | Structure | Name |
| 2-33 | 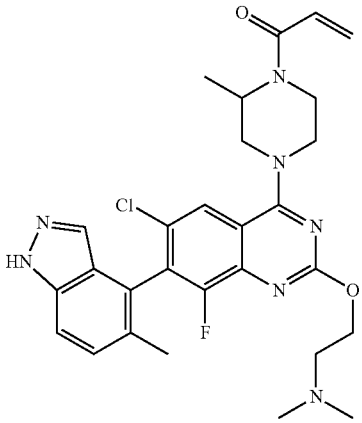 | 1-(4-(6-chloro-2-(2-(dimethylamino)ethoxy)-8-fluoro-7-(5-methyl-1H-indazol-4-yl)quinazolin-4-yl)-2-methylpiperazin-1-yl)prop-2-en-1-one |
| 2-34 | 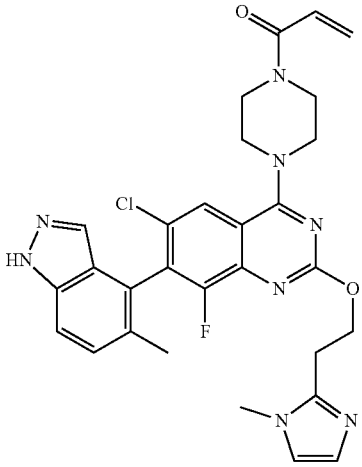 | 1-(4-(6-chloro-8-fluoro-2-(2-(1-methyl-1H-imidazol-2-yl)ethoxy)-7-(5-methyl-1H-indazol-4-yl)quinazolin-4-yl)piperazin-1-yl)prop-2-en-1-one |
| 2-35 | 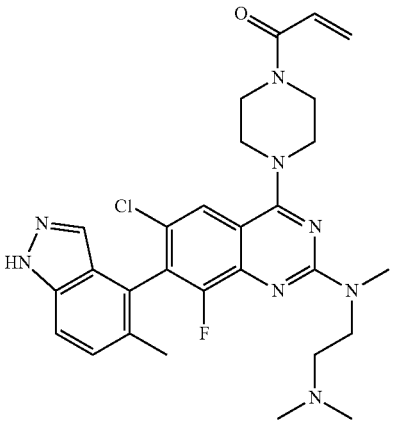 | 1-(4-(6-chloro-2-((2-(dimethylamino)ethyl)(methyl)amino)-8-fluoro-7-(5-methyl-1H-indazol-4-yl)quinazolin-4-yl)piperazin-1-yl)prop-2-en-1-one |

TABLE 2-continued

| Compounds Excluded From Certain Embodiments | | |
|---|---|---|
| No. | Structure | Name |
| 2-36 | 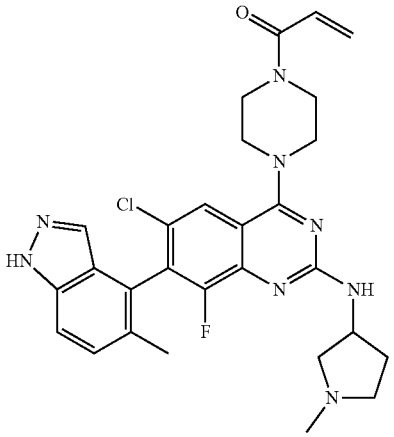 | 1-(4-(6-chloro-8-fluoro-7-(5-methyl-1H-indazol-4-yl)-2-(1-methylpyrrolidin-3-ylamino)quinazolin-4-yl)piperazin-1-yl)prop-2-en-1-one |
| 2-37 | 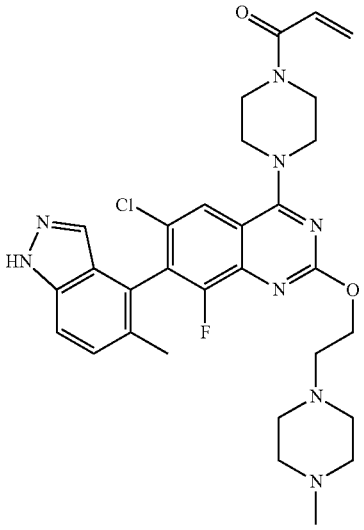 | 1-(4-(6-chloro-8-fluoro-7-(5-methyl-1H-indazol-4-yl)-2-(2-(4-methylpiperazin-1-yl)ethoxy)quinazolin-4-yl)piperazin-1-yl)prop-2-en-1-one |
| 2-38 | 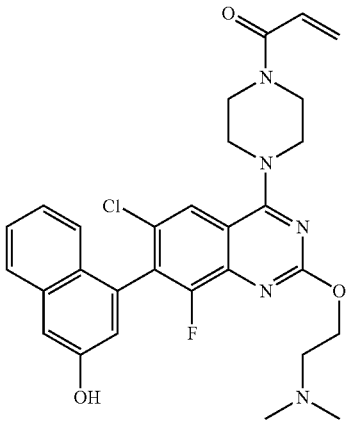 | 1-(4-(6-chloro-2-(2-(dimethylamino)ethoxy)-8-fluoro-7-(3-hydroxynaphthalen-1-yl)quinazolin-4-yl)piperazin-1-yl)prop-2-en-1-one |

TABLE 2-continued
| Compounds Excluded From Certain Embodiments | | |
|---|---|---|
| No. | Structure | Name |
| 2-39 | 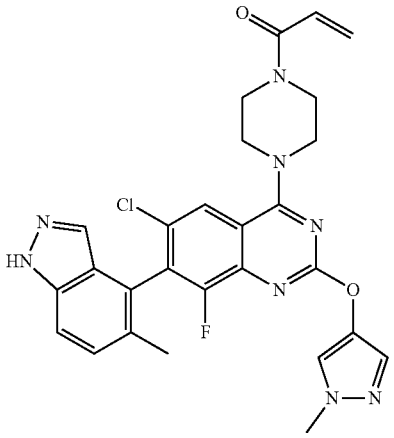 | 1-(4-(6-chloro-8-fluoro-7-(5-methyl-1H-indazol-4-yl)-2-(1-methyl-1H-pyrazol-4-yloxy)quinazolin-4-yl)piperazin-1-yl)prop-2-en-1-one |
| 2-40 | 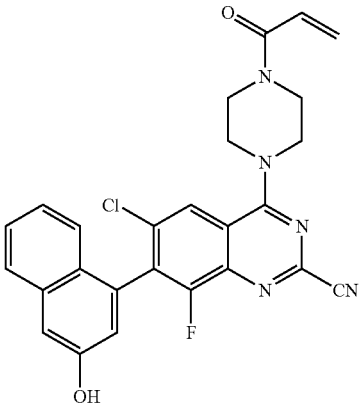 | 4-(4-acryloylpiperazin-1-yl)-6-chloro-8-fluoro-7-(3-hydroxynaphthalen-1-yl)quinazoline-2-carbonitrile |
| 2-41 | 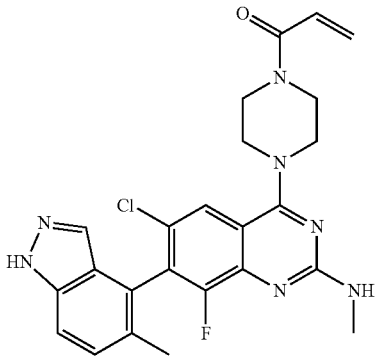 | 1-(4-(6-chloro-8-fluoro-7-(5-methyl-1H-indazol-4-yl)-2-(methylamino)quinazolin-4-yl)piperazin-1-yl)prop-2-en-1-one |

The following General Reaction Schemes illustrate exemplary methods of making compounds of compounds of structure (I):

(I)

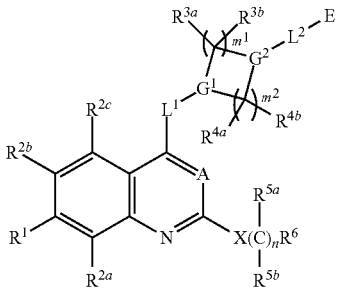

or a pharmaceutically acceptable salt, stereoisomer or prodrug thereof, wherein $R^1$, $R^{2a}$, $R^{2b}$, $R^{2c}$, $R^{3a}$, $R^{3b}$, $R^{4a}$, $R^{4b}$, $R^{5a}$, $R^{5b}$, $R^6$, A, $G^1$, $G^2$, $L^1$, $L^2$, $m^1$, $m^2$, n, X and E are as defined herein. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

General Reaction Scheme 1

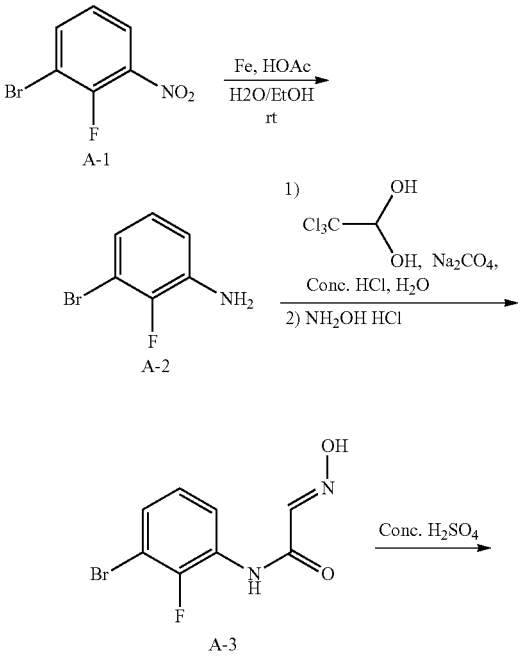

-continued

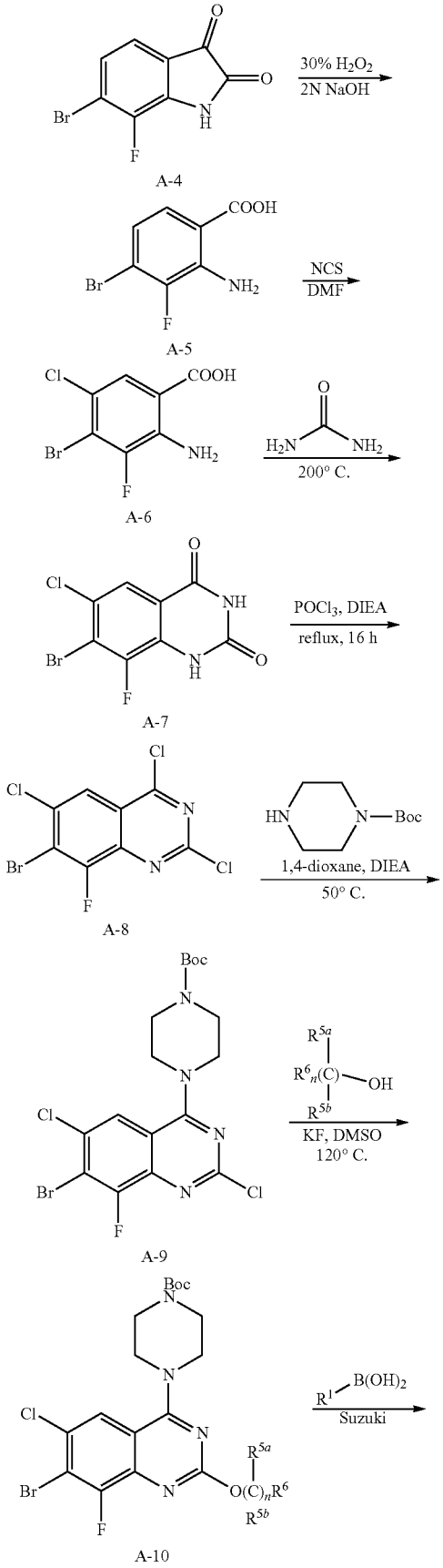

-continued

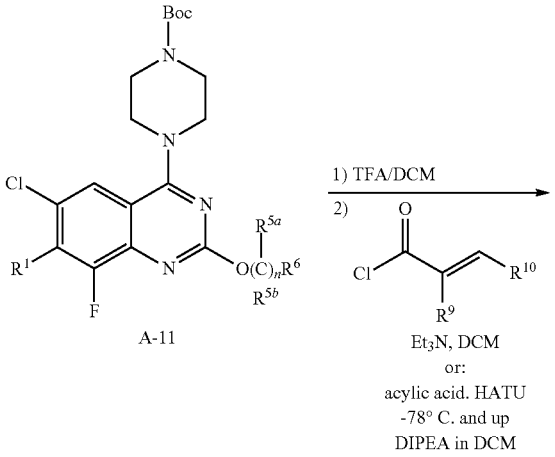

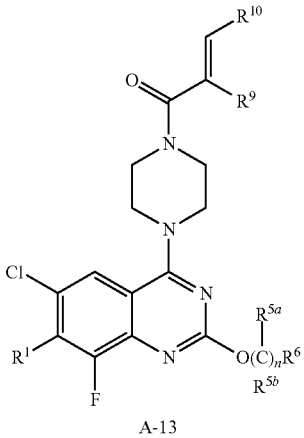

Embodiments of the compound of structure (I) (e.g., compound A-13) can be prepared according to General Reaction Scheme 1 ("Method A"), wherein $R^1$, $R^{5a}$, $R^{5b}$, $R^6$, $R^9$, $R^{10}$ and n are as defined herein. Referring to General Reaction Scheme 1, compounds of structure A-1 are purchased from commercial sources and reduced under appropriate conditions to form aniline A-2. A-2 is then treated with 2,2,2-trichloroethane-1,1-diol and sodium sulfate to yield A-3, which is subsequently cyclized by treatment with concentrated sulfuric acid. Ring-opening oxidation of A-4 then yields A-5, which can be optionally chlorinated to yield A-6 when a chloro substituent in the $R^{2b}$ position is desired. Reaction of A-6 with urea yield A-7, which is then chlorinated to yield quinazoline A-8. A-8 is then reacted with mono-boc protected piperazine to yield A-9. Reaction of A-9 with an appropriately-substituted alcohol provides A-10. The desired $R^1$ substituent may then be added by way of Suzuki coupling to yield A-11. Removal of the boc protecting group, followed by reaction with an appropriately substituted acryloyl chloride yields the desired compound A-13.

General Reaction Scheme 2

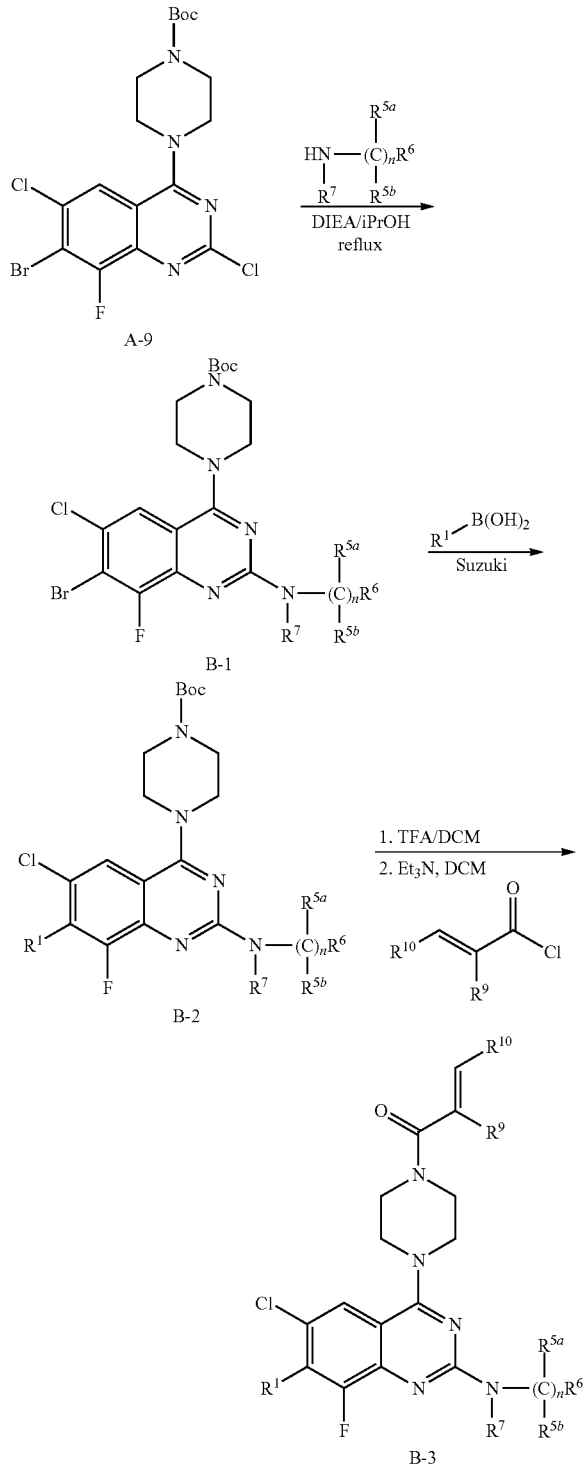

Alternatively, embodiments of the compound of structure (I) (e.g., compound B-3) can be prepared according to General Reaction Scheme 2 ("Method B"), wherein $R^1$, $R^{5a}$, $R^{5b}$, $R^6$, $R^7$, $R^9$, $R^{10}$ and n are as defined herein. Compound A-9 is prepared according to the procedures of General Reaction Scheme 2. Reaction of A-9 with an appropriately substituted amine yields B-1. Suzuki coupling of B-1 with an appropriately substituted boronic acid yields B2. B-3 is then prepared in a manner analogous to the procedures of General Scheme 1.

General Reaction Scheme 3

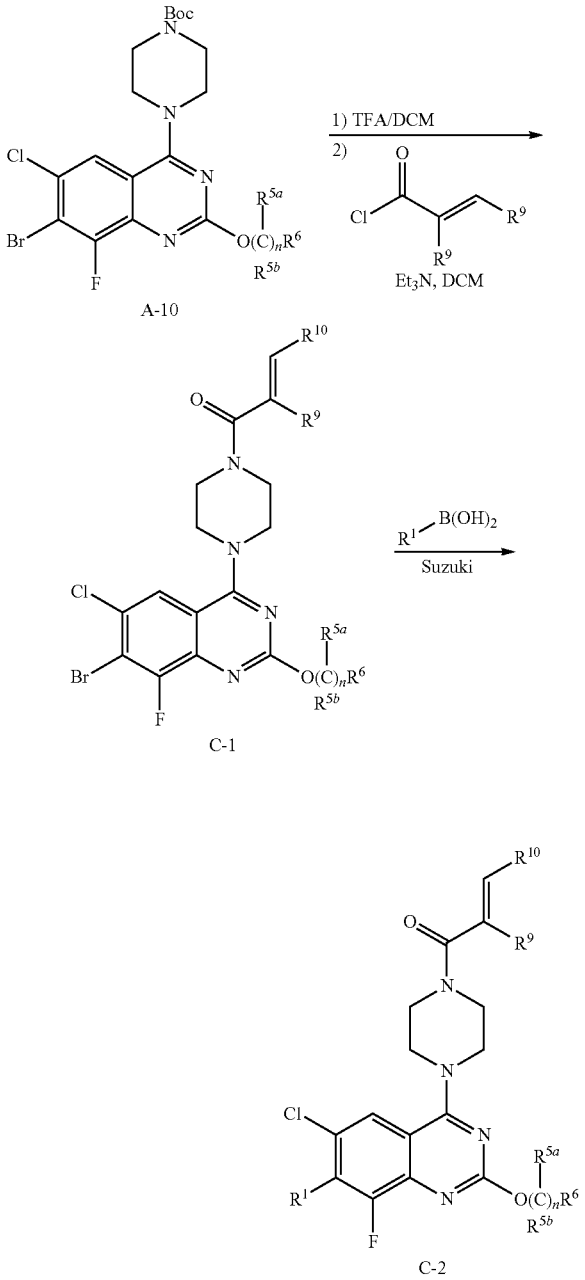

Other embodiments of the compound of structure (I) (e.g., compound C-2) can be prepared according to General Reaction Scheme 3 ("Method C"), wherein $R^1$, $R^{5a}R^{5b}$, $R^6$, $R^9$, $R^{10}$ and n are as defined herein. Method C is analogous to Method A, except the order of some synthetic steps are reversed. Specifically, A-10 is prepared according to General reaction Scheme 1. The boc protecting group is then removed and the free amine is reacted with an appropriated acryloyl chloride to yield C-1. Finally, Suzuki coupling with an appropriate boronic acid yields the desired C-2.

General Reaction Scheme 4

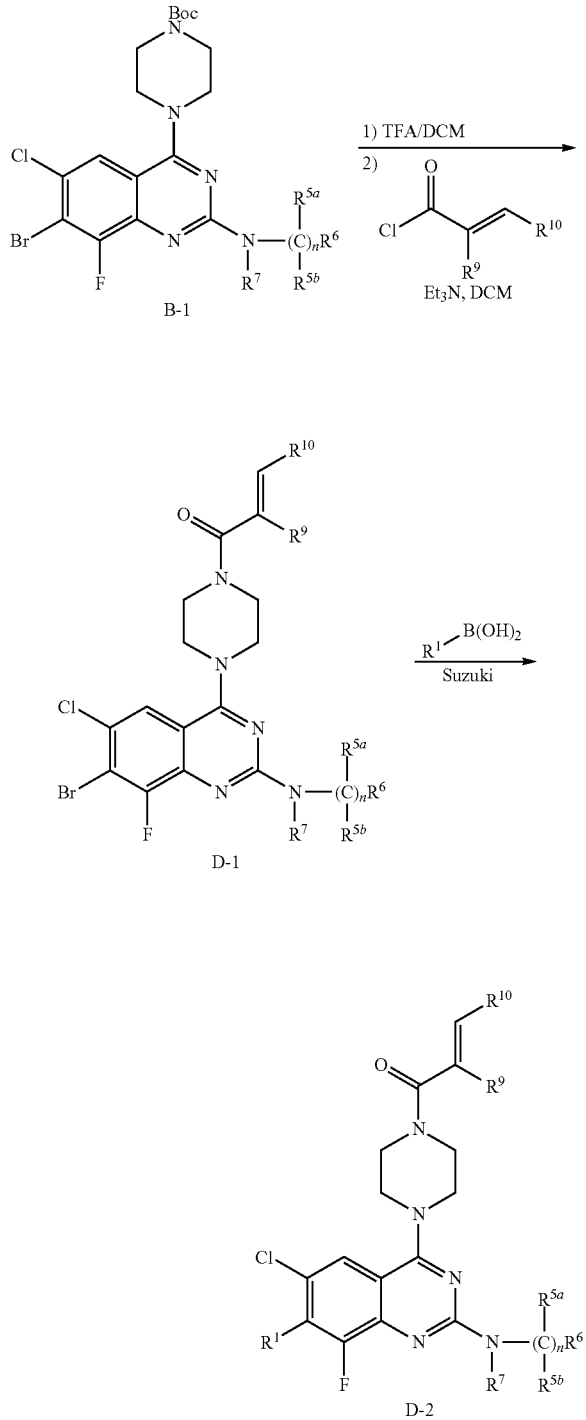

Other embodiments of the compound of structure (I) (e.g., compound D-2) can be prepared according to General Reaction Scheme 4 ("Method D"), wherein $R^1$, $R^{5a}R^{5b}$, $R^6$, $R^7$, $R^9$, $R^{10}$ and n are as defined herein. General Reaction Scheme 4 provides an alternate route to compounds, such as D-2. Compound B-1, which is prepared according to General Reaction Scheme 2, is first deprotected, and then reacted with an appropriate acryloyl chloride. Suzuki chemistry then provides the desired compound D-2.

General Reaction Scheme 5

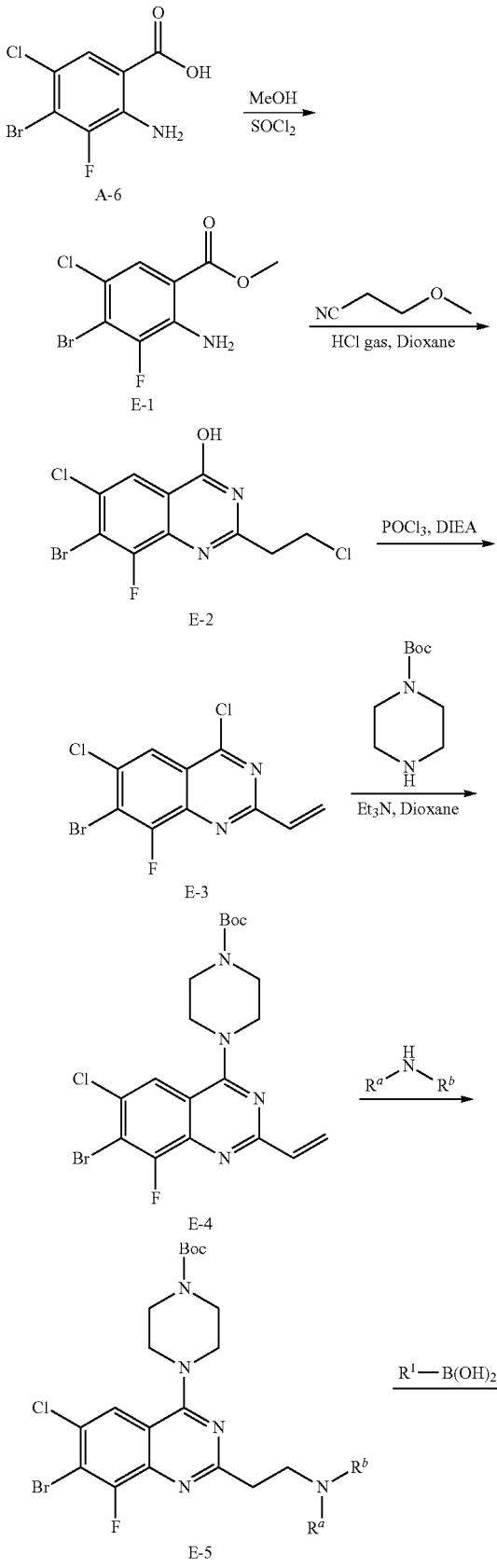

-continued

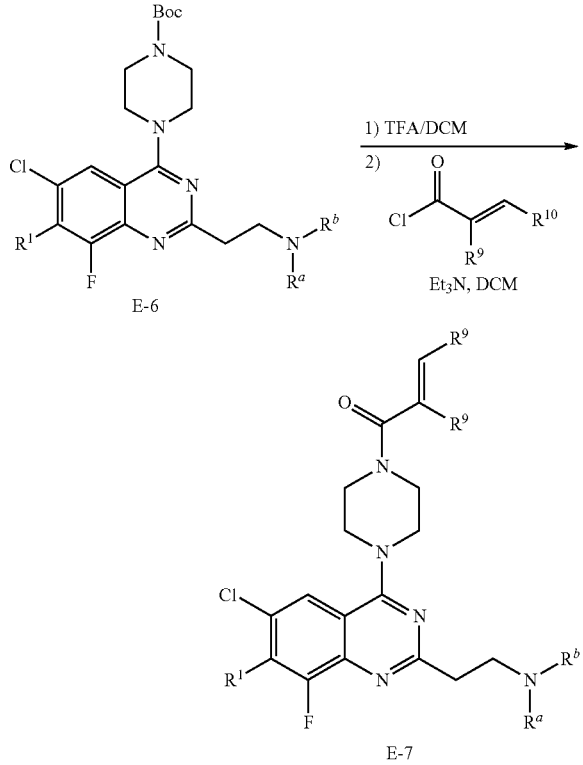

Other embodiments of the compound of structure (I) (e.g., compound E-7) can be prepared according to General Reaction Scheme 5 ("Method E"), wherein $R^1$, $R^9$ and $R^{10}$ are as defined herein, and $R^a$ and $R^b$ are each independently $C_1$-$C_6$ alkyl. As shown in General Reaction Scheme 5, compound A-6 from General reaction Scheme 1 is esterified to form E-1, which is then cyclized to form quinazoline E-2. Treatment of E-2 with phosphorous trichloride yields E-3, which is then reacted with mono-boc piperazine to form E-4. Reaction of E-4 with an appropriately substituted amine, followed by Suzuki reaction to install the desired $R^1$ substituent, yields E-6. Compound E-7 is then prepared according to methods described above.

General Reaction Scheme 6

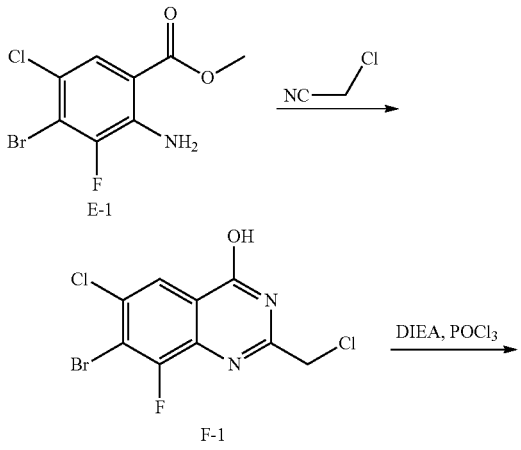

-continued

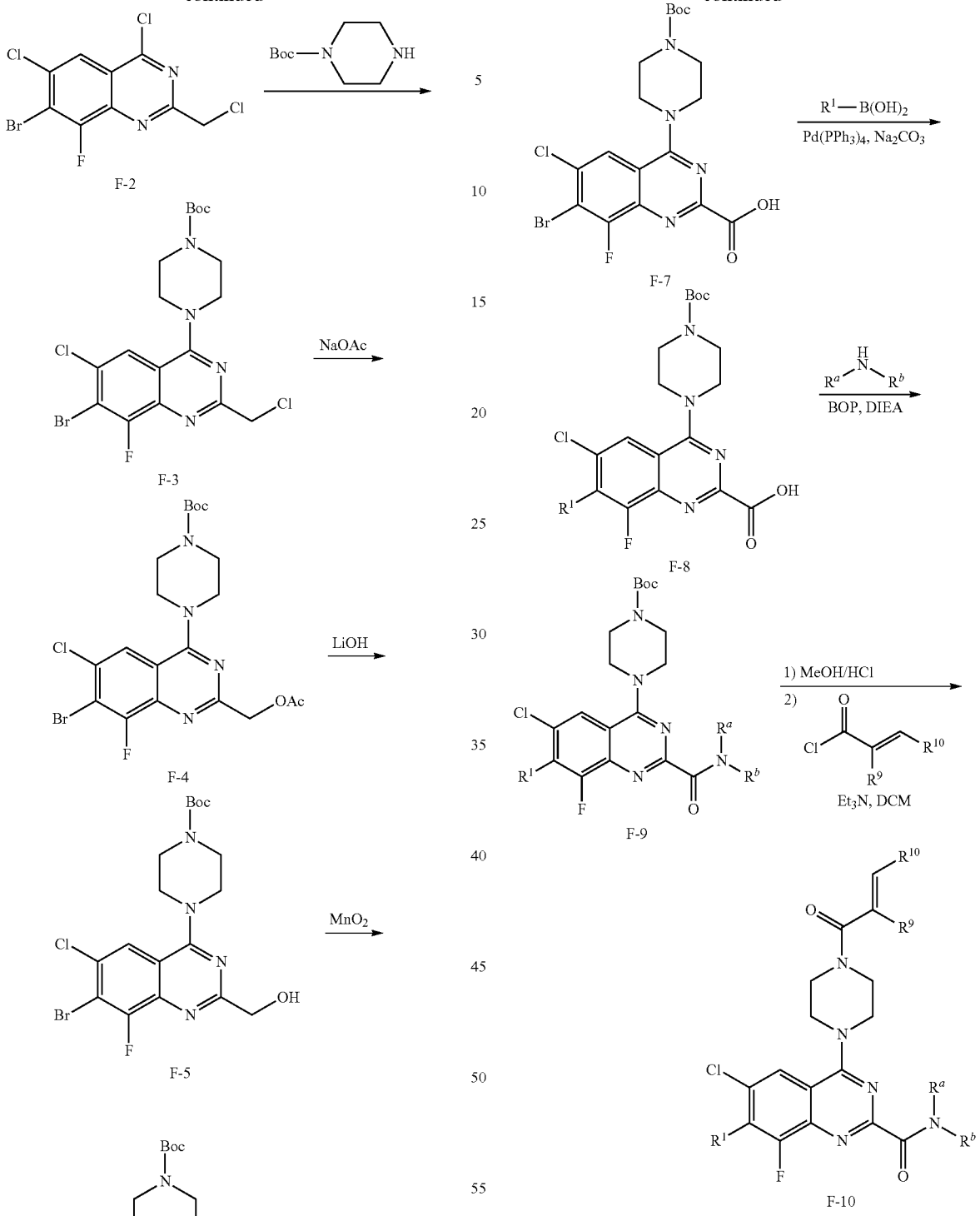

Other embodiments of the compound of structure (I) (e.g., compound F-10) can be prepared according to General Reaction Scheme 6 ("Method F"), wherein $R^1$, $R^9$ and $R^{10}$ are as defined herein, and $R^a$ and $R^b$ join to form heterocyclyl. Compound E-1 is first cyclized to form quinazoline F-1, which is subsequently chlorinated to provide F-2. Reaction of F-2 with mono-boc piperazine yields F-3. F-3 is then converted to alcohol F-5 via a two-step process by way of intermediate acetate F-4. Oxidation of F-5 to aldehyde F-6, followed by further oxidation with sodium perchlorate yields F-7. Suzuki reaction then provides the desired $R^1$ substituted compound F-8. F-10 is produced from F-8 in a manner analogous to that described with respect to General Reaction Scheme 5 above.

General Reaction Scheme 7

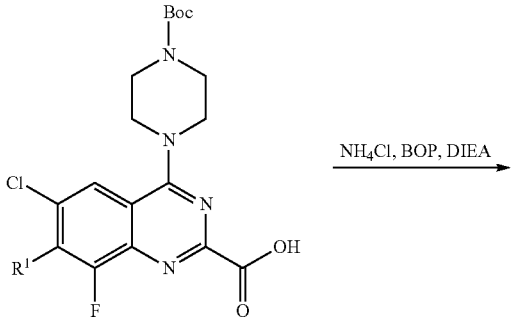

F-8

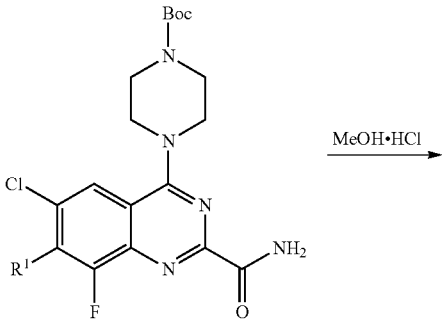

G-1

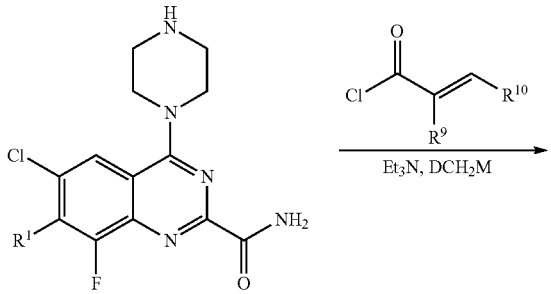

G-2

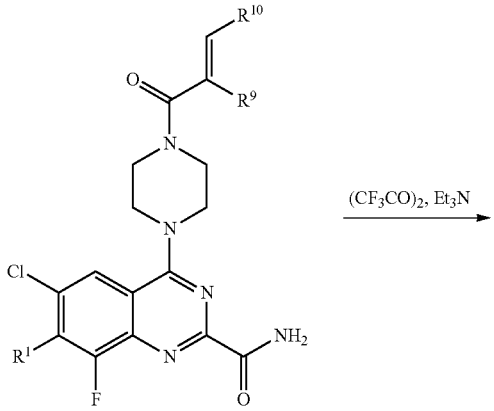

G-3

-continued

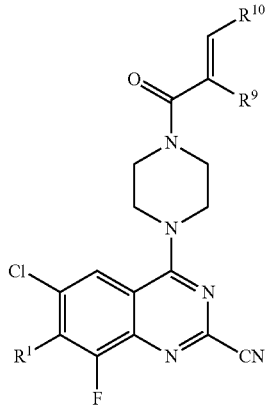

G-4

Other embodiments of the compound of structure (I) (e.g., compound G-3 or G-4) can be prepared according to General Reaction Scheme 7 ("Method G"), wherein $R^1$, $R^9$ and $R^{10}$ are as defined herein. As shown in General Reaction Scheme 7, carboxylic acid F-8, prepared according to General Reaction Scheme 6, is converted to amide G-1. G-1 is converted to G-3 following the general procedures outlined above. If desired, compound G-3 is converted to nitrile G-4 by reaction with trifluoroacetic acid anhydride.

General Reaction Scheme 8

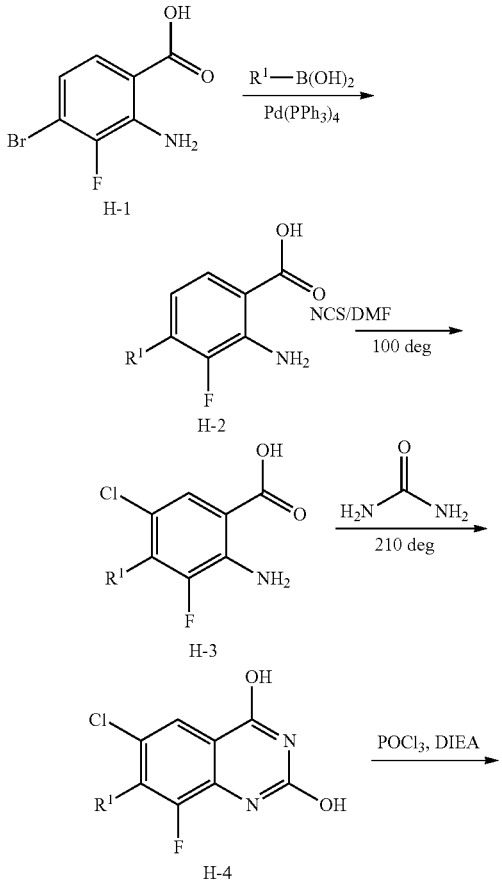

H-1

H-2

H-3

H-4

-continued

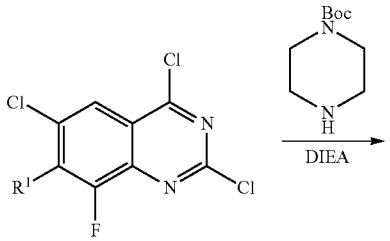

H-5

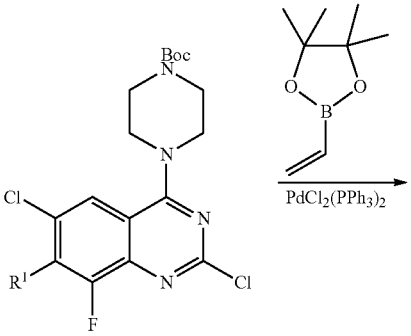

H-6

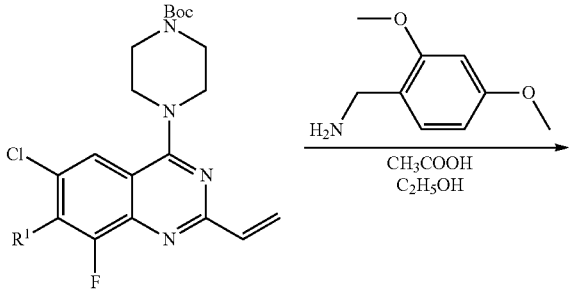

H-7

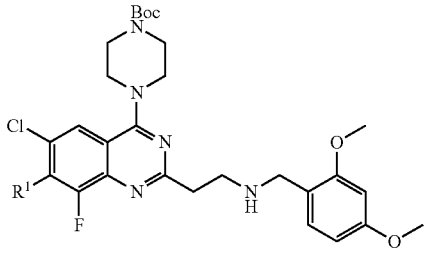

H-8

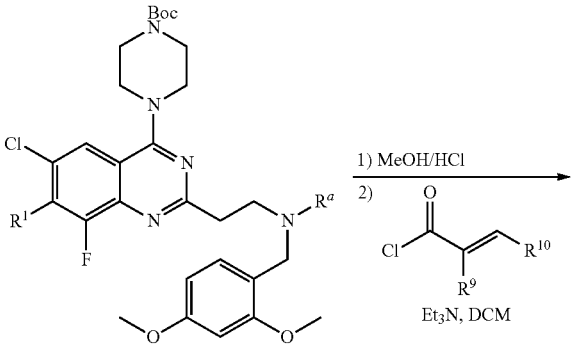

H-9

-continued

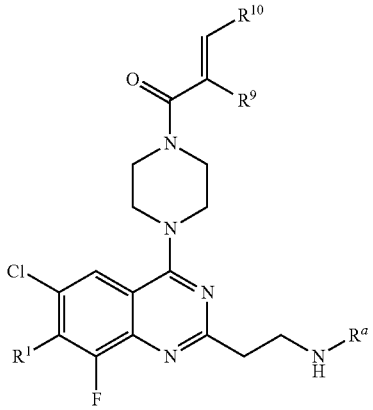

H-10

Other embodiments of the compound of structure (I) (e.g., compound H-10) can be prepared according to General Reaction Scheme 8 ("Method H"), wherein $R^1$, $R^9$ and $R^{10}$ are as defined herein above and $R^a$ is heteroaryl. Referring to General Reaction Scheme 8, H-1 is purchased from commercial sources or prepared according to known procedures. Suzuki coupling provides the desired $R^1$ substituent in compound H-2, which can then be chlorinated to H-3 followed by cyclization to quinazoline H-4. Chlorination of H-4 followed by reaction with mono-boc piperazine provides H-6. H-6 is alkylated to provide H-7 which then undergoes amination to yield H-8. Reaction of H-8 with an appropriately activated $R_a$ moiety, provides H-9. Removal of the N-protecting groups and acylation of the free piperazine nitrogen provides the desired compound H-10.

General Reaction Scheme 9

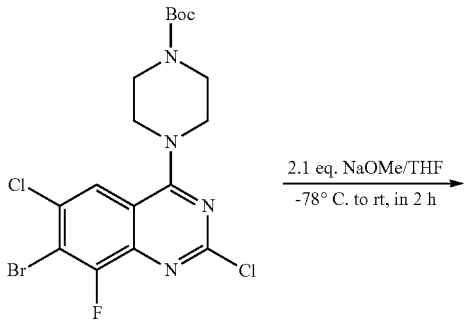

A-9

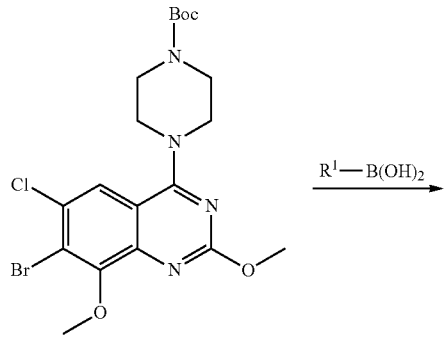

I-1

-continued

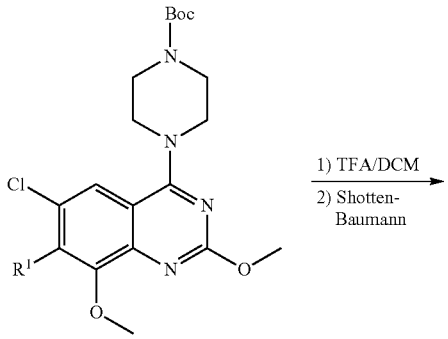

I-2

-continued

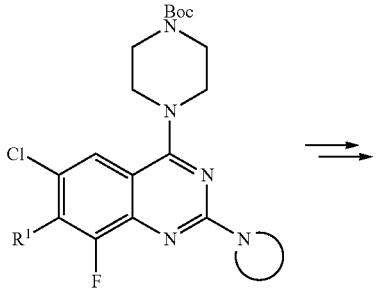

J-2

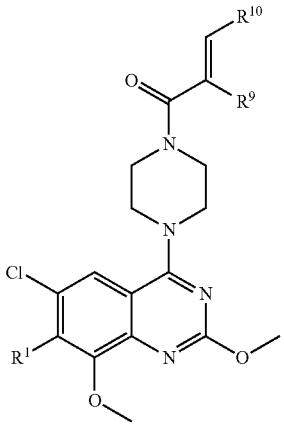

I-3

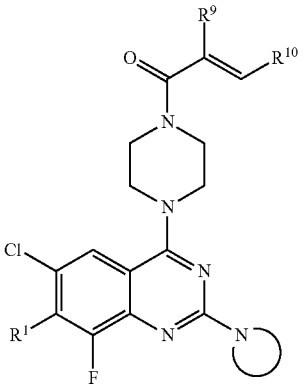

J-3

Other embodiments of the compound of structure (I) (e.g., compound I-3) can be prepared according to General Reaction Scheme 9 ("Method I"), wherein $R^1$, $R^9$ and $R^{10}$ are as defined herein above. Referring to General Reaction Scheme 9, compound A-9 is treated with sodium methoxide to provide I-1, which is converted to I-2 under Suzuki conditions. Removal of the Boc protecting group, followed by Shotten-Baumann reaction provides I-3.

Other embodiments of the compound of structure (I) (e.g., compound J-3) can be prepared according to General Reaction Scheme 10 ("Method J"), wherein $R^1$, $R^9$ and $R^{10}$ are as defined herein above. Referring to General Reaction Scheme 10, compound H-6 is prepared according to the above procedures and reacted with an appropriate nitrogen-containing heterocycle or heteroaryl (represented by J-1) to obtain J-2. J-2 is then treated in a manner analogous to the above procedures to obtain J-3.

General Reaction Scheme 10

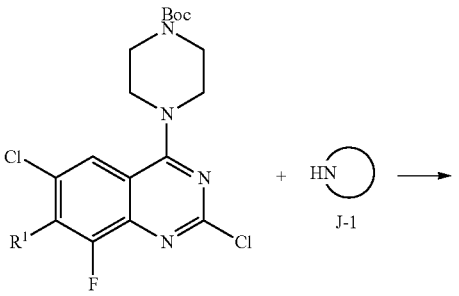

H-6

General Reaction Scheme 11

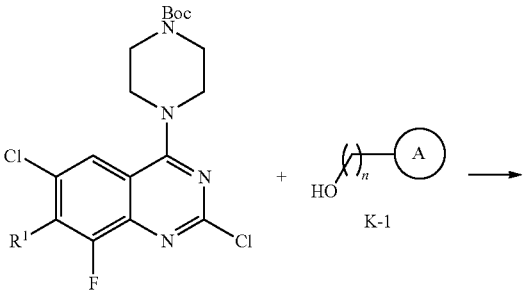

H-6

-continued

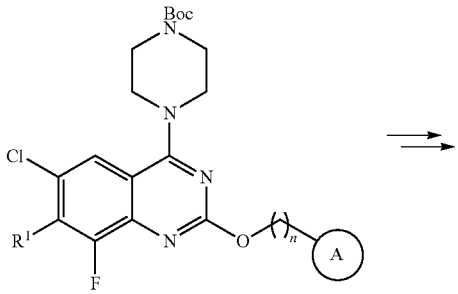

K-2

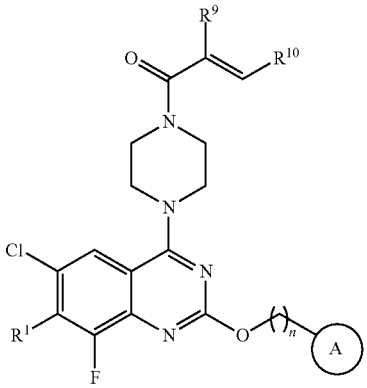

K-3

Other embodiments of the compound of structure (I) (e.g., compound K-3) can be prepared according to General Reaction Scheme 11 ("Method K"), wherein $R^1$, $R^9$, $R^{10}$ and n are as defined herein above. Referring to General Reaction Scheme 11, compound H-6 is prepared according to the above procedures and reacted with an appropriate hydroxyl or alkylhydroxyl-substituted cycloalkyl, aryl, heterocycle or heteroarly (represented by K-1, where A is a cycloalkyl, arly, heterocycl or heteroaryl) to obtain K-2. K-2 is then treated in a manner analogous to the above procedures to obtain K-3.

General Reaction Scheme 12

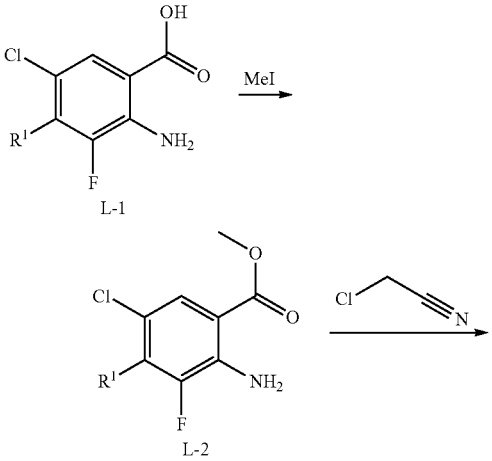

L-1

L-2

-continued

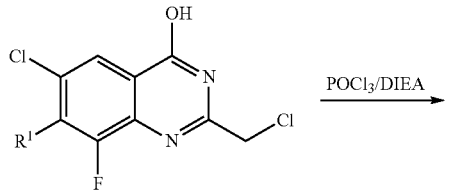

L-3

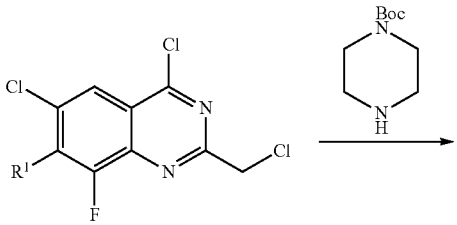

L-4

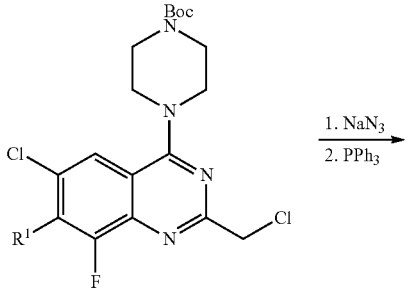

L-5

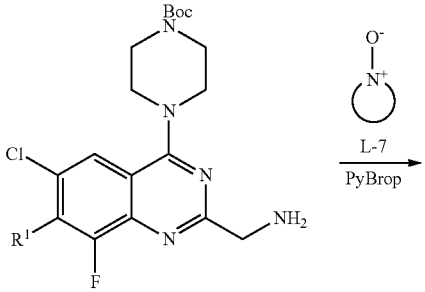

L-6

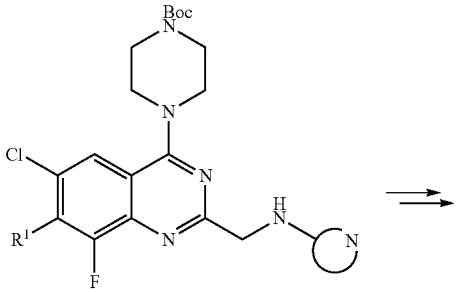

L-8

-continued

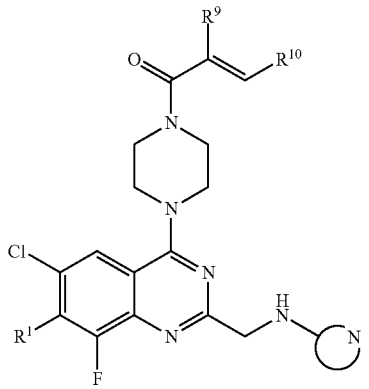

L-9

Other embodiments of the compound of structure (I) (e.g., compound L-9) can be prepared according to General Reaction Scheme 12 ("Method L"), wherein $R^1$, $R^9$ and $R^{10}$ are as defined herein above. Referring to General Reaction Scheme 12, compound L-1 is prepared according to procedures analogous to those above (e.g., Suzuki reaction) or prepared according to methods known in the art. L-1 is methylated, for example with methyl iodoide, to form L-2. Ring closure of L-2 yields L-3, which can then be chlorinated with an appropriate reagent, such as $POCl_3$. Reaction of L-4 with boc-protected piperazine yields L-5. Conversion of L-5 to the corresponding azide, followed by azide reduction yields L-6. Reaction of L-6 with an appropriate heteroaryl or heterocyclic N-oxide (represented by L-7) yields L-8, which is then treated in a manner analogous to the above procedures to obtain L-9.

General Reaction Scheme 13

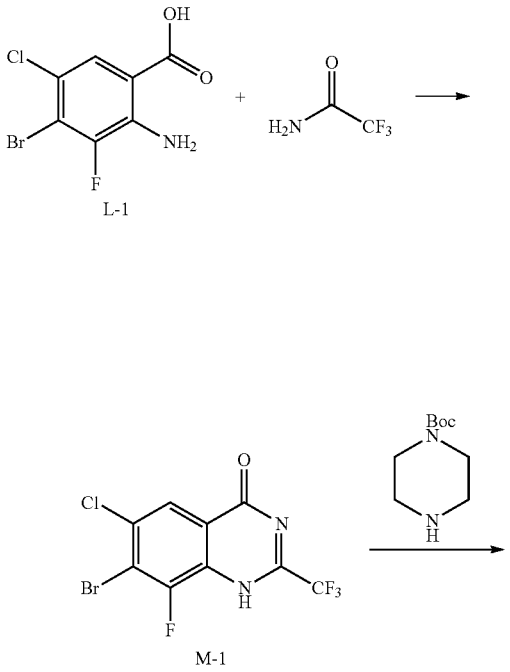

-continued

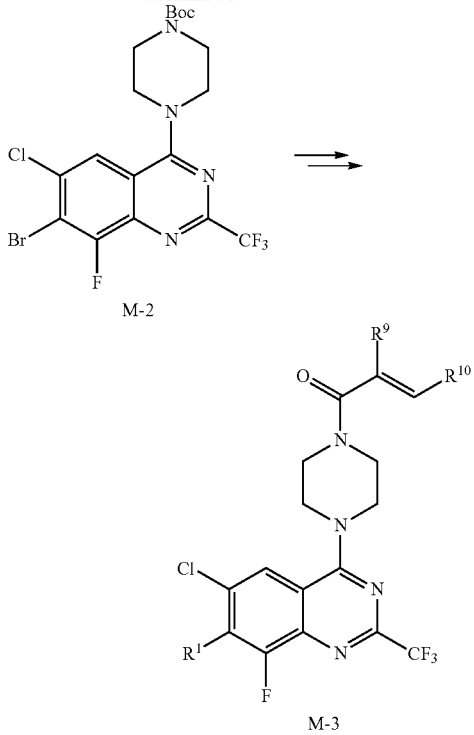

M-2

M-3

Other embodiments of the compound of structure (I) (e.g., compound M-3) can be prepared according to General Reaction Scheme 13 ("Method M"), wherein $R^1$, $R^9$ and $R^{10}$ are as defined herein above. Referring to General Reaction Scheme 13, compound L-1 is reacted with trifluoracetamide to form M-1. M-1 is reacted with Boc-protected piperazine to yield M-2, which is then treated in a manner analogous to the procedures of General reaction Scheme 1 to obtain M-3.

General Reaction Scheme 14

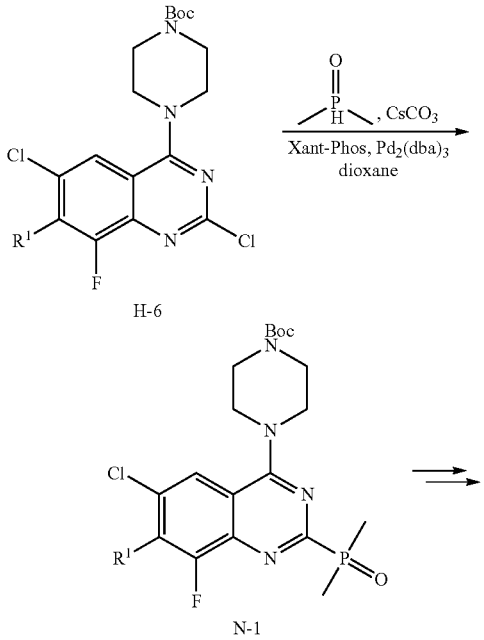

H-6

N-1

-continued

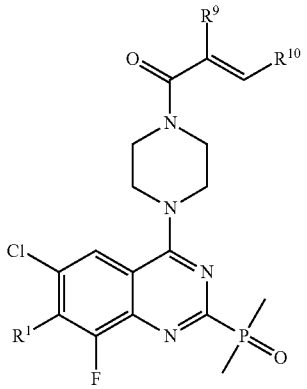

N-2

Other embodiments of the compound of structure (I) (e.g., compound N-2) can be prepared according to General Reaction Scheme 14 ("Method N"), wherein $R^1$, $R^9$ and $R^{10}$ are as defined herein above. Referring to General Reaction Scheme 14, compound H-6 is prepared as described above and phosphorylated under appropriate conditions to yield N-1, which is then treated in a manner analogous to the above procedures to obtain N-2.

-continued

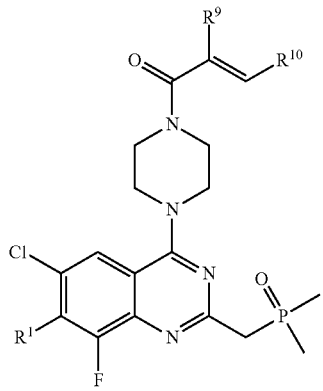

O-2

Other embodiments of the compound of structure (I) (e.g., compound O-2) can be prepared according to General Reaction Scheme 15 ("Method O"), wherein $R^1$, $R^9$ and $R^{10}$ are as defined herein above. Referring to General Reaction Scheme 15, compound L-5 is prepared as described above and phosphorylated under appropriate conditions to yield O-1, which is then treated in a manner analogous to the above procedures to obtain O-2.

General Reaction Scheme 15

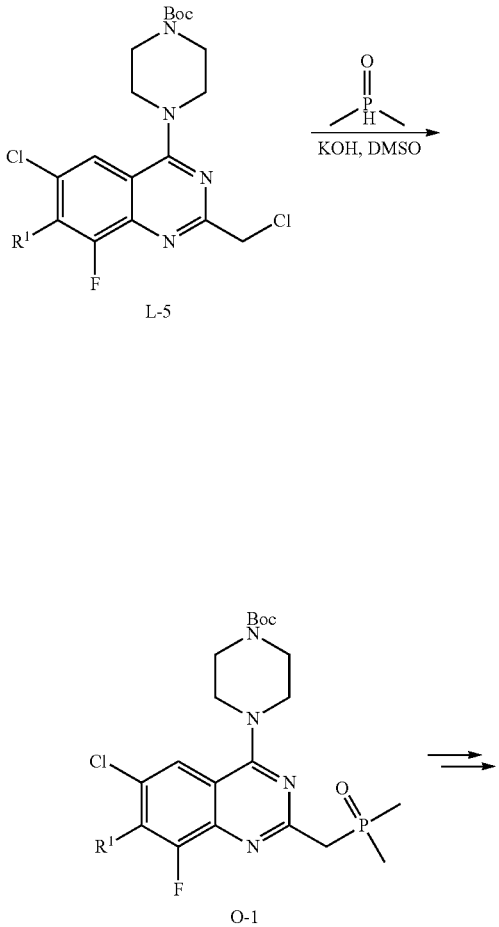

L-5

O-1

General Reaction Scheme 16

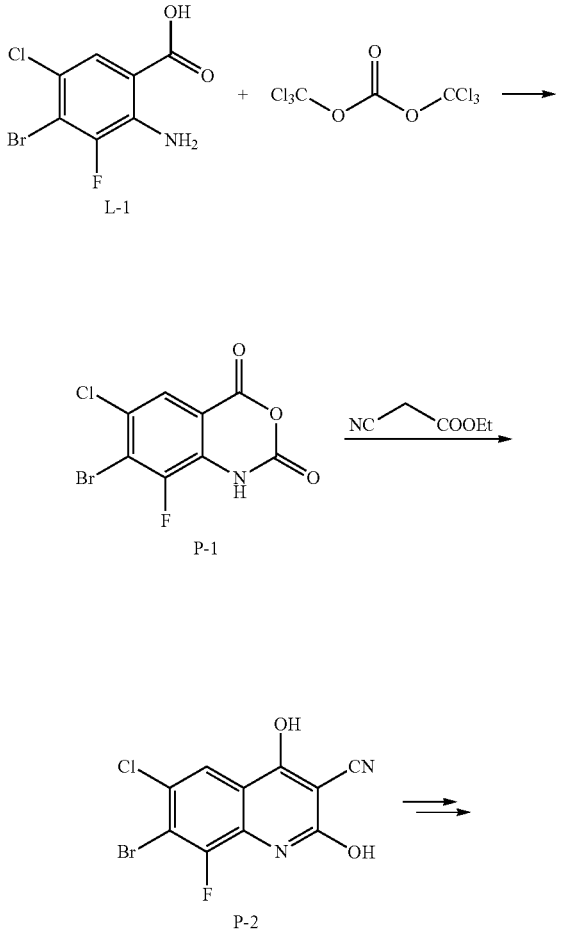

L-1

P-1

P-2

-continued

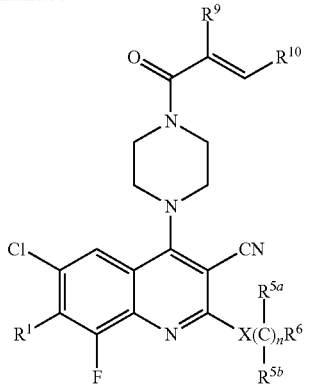

P-3

Other embodiments of the compound of structure (I) (e.g., compound P-3) can be prepared according to General Reaction Scheme 16 ("Method P"), wherein $R^1$, $R^{5a}$, $R^{5b}$, $R^6$, $R^9$, $R^{10}$ and n are as defined herein above. Referring to General Reaction Scheme 16, compound L-1 is prepared as described above and treated with bis(trichloromethyl) carbonate to form 1H-benzo[d][1,3]oxazine-2,4-dione P-1. P-1 may then be treated with ethyl cyanoacetate to form P-2. P-2 is then converted to various embodiments of structure (I) according to the general procedures described herein.

General Reaction Scheme 17

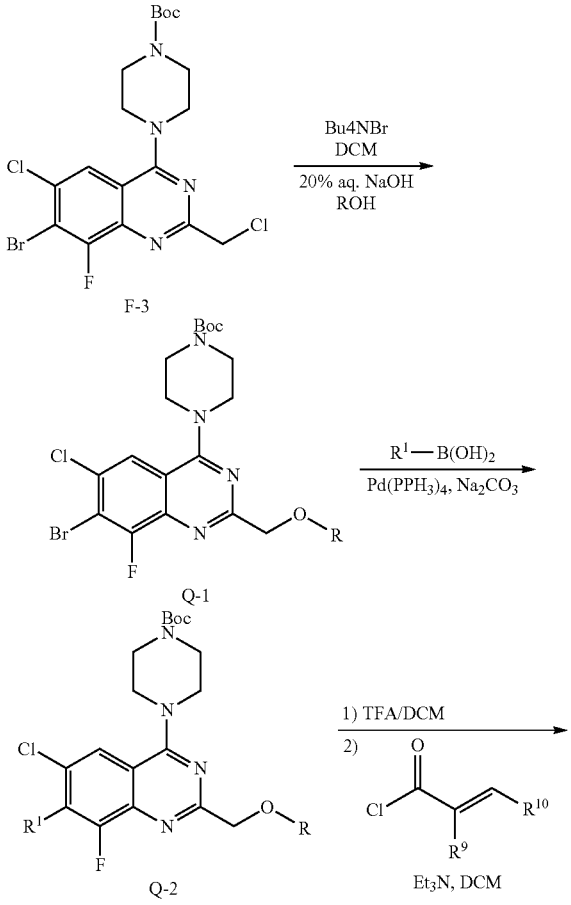

-continued

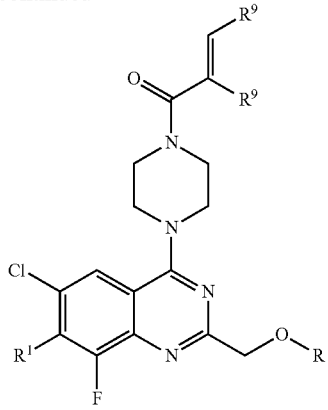

Q-3

Other embodiments of the compound of structure (I) (e.g., compound Q-3) can be prepared according to General Reaction Scheme 17 ("Method Q"), wherein $R^1$, $R^9$ and $R^{10}$ are as defined herein above and R is a substituted or unsubstituted alkyl. Referring to General Reaction Scheme 17, compound F-3 is treated with alcohol ROH to provide Q-1, which is converted to Q-2 under Suzuki conditions. Desired compound Q-3 is then prepared according to the general methods described above.

Compounds of Structure (II)

In another embodiment, the compounds have the following structure (II):

(II)

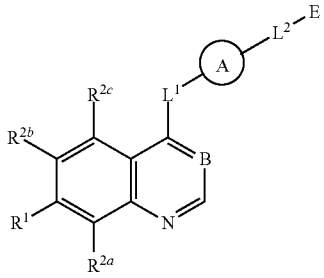

or a pharmaceutically acceptable salt, stereoisomer or prodrug thereof, wherein:

A is a monocyclic or bicyclic moiety;

B is N or CR';

$L^1$ is a bond or $NR^5$;

$L^2$ is a bond or alkylene;

R' is H, cyano, alkyl, cycloalkyl, amino, aminylalkyl, alkoxy, alkoxyalkyl, alkoxycarbonyl, aminylalkoxy, alkylaminylalkoxy, alkylaminyl, alkylaminylalkyl, aminylalkylaminyl, carboxyalkyl, alkylcarbonylaminyl, aminylcarbonyl, alkylaminylcarbonyl or aminylcarbonylalkyl;

$R^1$ is aryl or heteroaryl;

$R^{2a}$, $R^{2b}$ and $R^{2c}$ are each independently H, amino, halo, hydroxyl, cyano, $C_1$-$C_6$ alkyl, $C_1$-$C_6$ alkyl amino, $C_1$-$C_6$ haloalkyl (e.g., $CF_3$), $C_1$-$C_6$ alkoxy, $C_1$-$C_6$ haloalkoxy, $C_3$-$C_8$ cycloalkyl, heterocycyclylalkyl, $C_1$-$C_6$ alkynyl, $C_1$-$C_6$ alkenyl, aminylalkyl, alkylaminylalkyl, cyanoalkyl, carboxyalkyl, aminylcarbonylalkyl, aminylcarbonyl; heteroaryl or aryl;

$R^5$ is, at each occurrence, independently H, $C_1$-$C_6$ alkyl, $C_3$-$C_8$ cycloalkyl or heterocyclylalkyl; and E is an electrophilic moiety capable of forming a covalent bond with the cysteine residue at position 12 of a KRAS, HRAS or NRAS G12C mutant protein.

In some embodiments of structure (II), $R^{2a}$, $R^{2b}$ and $R^{2c}$ are each independently H, amino, halo, hydroxyl, cyano, $C_1$-$C_6$ alkyl, $C_1$-$C_6$ alkyl amino, $C_1$-$C_6$ haloalkyl (e.g., $CF_3$), $C_1$-$C_6$ alkoxy, $C_1$-$C_6$ haloalkoxy, $C_3$-$C_8$ cycloalkyl, heterocycyclylalkyl, heteroaryl or aryl. In some other embodiments of structure (II), B is N or C—CN. In some embodiments of structure (II), $R^{2a}$, $R^{2b}$ and $R^{2c}$ are each independently H, amino, halo, hydroxyl, cyano, $C_1$-$C_6$ alkyl, $C_1$-$C_6$ alkyl amino, $C_1$-$C_6$ haloalkyl (e.g., $CF_3$), $C_1$-$C_6$ alkoxy, $C_1$-$C_6$ haloalkoxy, $C_3$-$C_8$ cycloalkyl, heterocycyclylalkyl, heteroaryl or aryl, and B is N or C—CN.

In some other embodiments, the compound has one of the following structures (II'), (II") or (II'"):

(II')

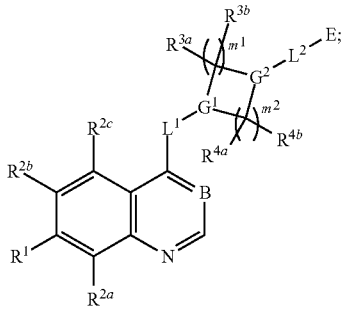

(II")

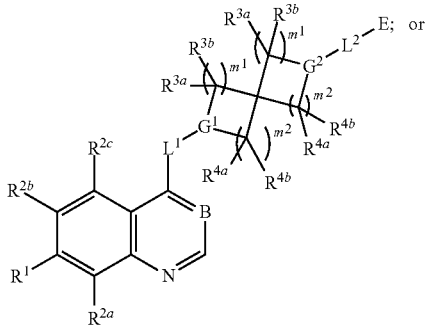

(III'")

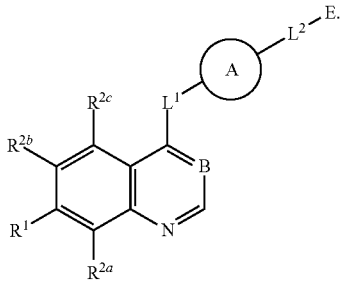

or a pharmaceutically acceptable salt, stereoisomer or prodrug thereof, wherein:

A' is a monocyclic aryl or heteroaryl;

B is N or CR';

$G^1$ and $G^2$ are each independently N or CH;

$L^1$ is a bond or $NR^5$;

$L^2$ is a bond or alkylene;

R' is H, cyano, alkyl, cycloalkyl, amino, aminylalkyl, alkoxy, alkoxyalkyl, alkoxycarbonyl, aminylalkoxy, alkylaminylalkoxy, alkylaminyl, alkylaminylalkyl, aminylalkylaminyl, carboxyalkyl, alkylcarbonylaminyl, aminylcarbonyl, alkylaminylcarbonyl or aminylcarbonylalkyl;

$R^1$ is aryl or heteroaryl;

$R^{2a}$, $R^{2b}$ and $R^{2c}$ are each independently H, amino, halo, hydroxyl, cyano, $C_1$-$C_6$ alkyl, $C_1$-$C_6$ alkylaminyl, $C_1$-$C_6$ haloalkyl (e.g., $CF_3$), $C_1$-$C_6$ alkoxy, $C_1$-$C_6$ haloalkoxy, $C_3$-$C_8$ cycloalkyl, heterocyclylalkyl, heteroaryl or aryl;

$R^{3a}$ and $R^{3b}$ are, at each occurrence, independently H, —OH, —$NH_2$, —$CO_2H$, halo, cyano, $C_1$-$C_6$ alkyl, $C_1$-$C_6$ haloalkyl, $C_1$-$C_6$ haloalkoxy, $C_3$-$C_8$ cycloalkyl, heterocyclylalkyl; $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl; or $R^{3a}$ and $R^{3b}$ join to form oxo, a carbocyclic or heterocyclic ring; or $R^{3a}$ is H, —OH, —$NH_2$, —$CO_2H$, halo, cyano, $C_1$-$C_6$ alkyl, $C_1$-$C_6$ haloalkyl, $C_1$-$C_6$ haloalkoxy, $C_3$-$C_8$ cycloalkyl, heterocyclylalkyl, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl, and $R^{3b}$ joins with $R^{4b}$ to form a carbocyclic or heterocyclic ring;

$R^{4a}$ and $R^{4b}$ are, at each occurrence, independently H, —OH, —$NH_2$, —$CO_2H$, halo, cyano, $C_1$-$C_6$ alkyl, $C_1$-$C_6$ haloalkyl, $C_1$-$C_6$ haloalkoxy, $C_3$-$C_8$ cycloalkyl, heterocyclylalkyl; $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl; or $R^{4a}$ and $R^{4b}$ join to form oxo, a carbocyclic or heterocyclic ring; or $R^{4a}$ is H, —OH, —$NH_2$, —$CO_2H$, halo, cyano, $C_1$-$C_6$ alkyl, $C_1$-$C_6$ haloalkyl, $C_1$-$C_6$ haloalkoxy, $C_3$-$C_8$ cycloalkyl, heterocyclylalkyl, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl, and $R^{4b}$ joins with $R^{3b}$ to form a carbocyclic or heterocyclic ring;

$R^5$ is, at each occurrence, independently H, $C_1$-$C_6$ alkyl, $C_3$-$C_8$ cycloalkyl or heterocycloalkyl;

$m^1$ and $m^2$ are, at each occurrence, independently 1, 2 or 3; and

E is an electrophilic moiety capable of forming a covalent bond with the cysteine residue at position 12 of a KRAS, HRAS or NRAS G12C mutant protein.

In some embodiments of structures (II'), (II") or (II'"):

B is N or C—CN; and $R^{3a}$ and $R^{3b}$ are, at each occurrence, independently H, —OH, —$NH_2$, —$CO_2H$, halo, cyano, $C_1$-$C_6$ alkyl, $C_1$-$C_6$ haloalkyl, $C_1$-$C_6$ haloalkoxy, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl; or $R^{3a}$ and $R^{3b}$ join to form oxo, a carbocyclic or heterocyclic ring; or $R^{3a}$ is H, —OH, —$NH_2$, —$CO_2H$, halo, cyano, $C_1$-$C_6$ alkyl, $C_1$-$C_6$ haloalkyl, $C_1$-$C_6$ haloalkoxy, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl, and $R^{3b}$ joins with $R^{4b}$ to form a carbocyclic or heterocyclic ring; and $R^{4a}$ and $R^{4b}$ are, at each occurrence, independently H, —OH, —$NH_2$, —$CO_2H$, halo, cyano, $C_1$-$C_6$ alkyl, $C_1$-$C_6$ haloalkyl, $C_1$-$C_6$ haloalkoxy, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl; or $R^{4a}$ and $R^{4b}$ join to form oxo, a carbocyclic or heterocyclic ring; or $R^{4a}$ is H, —OH, —$NH_2$, —$CO_2H$, halo, cyano, $C_1$-$C_6$ alkyl, $C_1$-$C_6$ haloalkyl, $C_1$-$C_6$ haloalkoxy, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl, and $R^{4b}$ joins with $R^{3b}$ to form a carbocyclic or heterocyclic ring.

In some embodiments, the compound has structure (II'). In other embodiments of (II'):

$G^1$ and $G^2$ are each independently N or CH;

$L^1$ is a bond or $NR^5$;

$L^2$ is a bond or alkylene;

$R^1$ is aryl or heteroaryl;

$R^{2a}$, $R^{2b}$ and $R^{2c}$ are each independently H, amino, halo, hydroxyl, cyano, $C_1$-$C_6$ alkyl, $C_1$-$C_6$ alkyl amino, $C_1$-$C_6$ haloalkyl (e.g., $CF_3$), $C_1$-$C_6$ alkoxy, $C_3$-$C_8$ cycloalkyl, heteroaryl or aryl;

$R^{3a}$ and $R^{3b}$ are, at each occurrence, independently H, —OH, —$NH_2$, —$CO_2H$, halo, cyano, $C_1$-$C_6$ alkyl, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl; or $R^{3a}$ and $R^{3b}$ join to form a carbocyclic or heterocyclic ring; or $R^{3a}$ is H, —OH, —$NH_2$, —$CO_2H$, halo, cyano, $C_1$-$C_6$ alkyl, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl, and $R^{3b}$ joins with $R^{4b}$ to form a carbocyclic or heterocyclic ring;

$R^{4a}$ and $R^{4b}$ are, at each occurrence, independently H, —OH, —$NH_2$, —$CO_2H$, halo, cyano, $C_1$-$C_6$ alkyl, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl; or $R^{4a}$ and $R^{4b}$ join to form a carbocyclic or heterocyclic ring; or $R^{4a}$ is H, —OH, —$NH_2$, —$CO_2H$, halo, cyano, $C_1$-$C_6$ alkyl, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl, and $R^{4b}$ joins with $R^{3b}$ to form a carbocyclic or heterocyclic ring;

$R^5$ is, at each occurrence, independently H, $C_1$-$C_6$ alkyl, $C_3$-$C_8$ cycloalkyl or heterocycloalkyl;

$m^1$ and $m^2$ are each independently 1, 2 or 3; and

E is an electrophilic moiety capable of forming a covalent bond with the cysteine residue at position 12 of a KRAS, HRAS or NRAS G12C mutant protein.

In some different embodiments, A is N. In other embodiments, A is C—CN.

The structure of E is not particularly limited provided it is capable of forming a covalent bond with a nucleophile, such as the cysteine residue at position 12 of a KRAS, HRAS or NRAS G12C mutant protein. Accordingly, moieties which are capable of reaction with (e.g., by covalent bond formation) a nucleophile are preferred. In certain embodiments, E is capable of reacting in a conjugate addition manner (e.g., 1.4-conjugate addition) with an appropriately reactive nucleophile. In some embodiments, E comprises conjugated pi bonds such that delocalization of electrons results in at least one atom (e.g., a carbon atom) having a positive charge, partial positive charge or a polarized bond. In other embodiments, E comprises one or more bonds wherein the electronegativity of the two atoms forming the bonds is sufficiently different such that a partial positive charge (e.g., by polarization of the bond) resides on one of the atoms, for example on a carbon atom. E moieties comprising carbon-halogen bonds, carbon-oxygen bonds or carbon bonds to various leaving groups known in the art are examples of such E moieties.

In certain embodiments of the foregoing, E has the following structure:

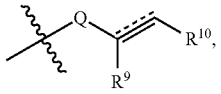

wherein:

≡ represents a double or triple bond;

Q is —C(═O)—, —C(═$NR^{8'}$)—, —$NR^8$C(═O)—, —S(═O)$_2$— or —NR S(═O)$_2$—;

$R^8$ is H, $C_1$-$C_6$ alkyl, hydroxylalkyl, aminoalkyl, alkoxyalkyl, aminylalkyl, alkylaminylalkyl, cyanoalkyl, carboxyalkyl, aminylcarbonylalkyl, $C_3$-$C_8$ cycloalkyl or heterocycloalkyl;

$R^8$ is H, —OH, —CN or $C_1$-$C_6$ alkyl; and when ≡ is a double bond then $R^9$ and $R^{10}$ are each independently H, halo, cyano, carboxyl, $C_1$-$C_6$ alkyl, alkoxycarbonyl, aminylalkyl, alkylaminylalkyl, aryl, heterocyclyl, heterocyclylalkyl, heteroaryl or hydroxylalkyl, or $R^9$ and $R^{10}$ join to form a carbocyclic, heterocyclic or heteroaryl ring;

when ≡ is a triple bond; then $R^9$ is absent and $R^{10}$ is H, $C_1$-$C_6$alkyl, aminylalkyl, alkylaminylalkyl or hydroxylalkyl.

In certain embodiments when ≡ is a double bond then $R^9$ and $R^{10}$ are each independently H, cyano, $C_1$-$C_6$alkyl, aminylalkyl, alkylaminylalkyl, or hydroxylalkyl or $R^9$ and $R^{10}$ join to form a carbocyclic or heterocyclic ring.

In some of the foregoing embodiments, Q is —C(═O)—, —$NR^8$C(═O)—, —S(═O)$_2$— or —$NR^8$S(═O)$_2$—.

In some other of the foregoing embodiments, Q is —C(═$NR^{8'}$)—, wherein $R^{8'}$ is H, —OH, —CN or $C_1$-$C_6$alkyl. For example, in some embodiments $R^8$ is H. In other embodiments, $R^{8'}$ is —CN. In other embodiments, $R^{8'}$ is —OH.

Accordingly, in some embodiments, the compound has one of the following structures (II'a), (II"a) or (II'"a):

(II'a)

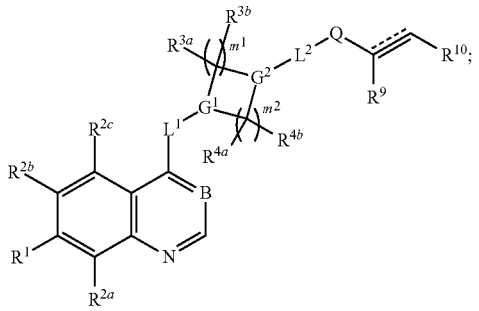

(II"a)

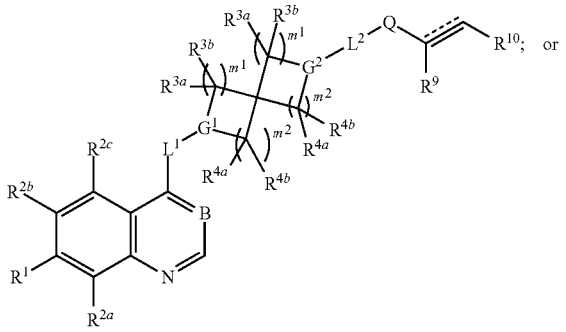

-continued (II'''a)

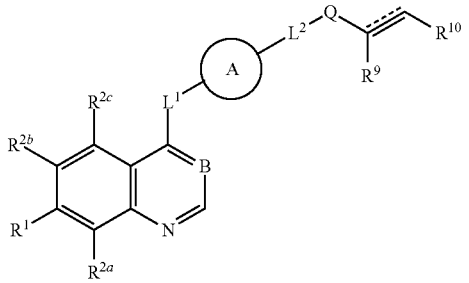

wherein:

≡ represents a double or triple bond;

Q is —C(═O)—, —C(═NR$^{8'}$)—, —NR$^8$C(═O)—, —S(═O)$_2$— or —NR$^8$S(═O)$_2$—;

R$^8$ is H, C$_1$-C$_6$ alkyl, hydroxylalkyl, aminoalkyl, alkoxyalkyl, aminylalkyl, alkylaminylalkyl, cyanoalkyl, carboxyalkyl, aminylcarbonylalkyl, C$_3$-C$_8$ cycloalkyl or heterocycloalkyl;

R$^{8'}$ is H, —OH, —CN or C$_1$-C$_6$ alkyl;

when ≡ is a double bond then R$^9$ and R$^{10}$ are each independently H, halo, cyano, carboxyl, C$_1$-C$_6$ alkyl, alkoxycarbonyl, aminylalkyl, alkylaminylalkyl, aryl, heterocyclyl, heterocyclylalkyl, heteroaryl or hydroxylalkyl, or R$^9$ and R$^{10}$ join to form a carbocyclic, heterocyclic or heteroaryl ring; and when ≡ is a triple bond then R$^9$ is absent and R$^{10}$ is H, C$_1$-C$_6$ alkyl, aminylalkyl, alkylaminylalkyl or hydroxylalkyl.

In some embodiments, the compound has structure (II'a).

In other embodiments, the compound has one of the following structures (II'b), (II'c), (II'd), (II'e), (II'f), (II'g), (II''b), (II''c), (II'''b), (II'''c) or (II'''d):

(II'b)

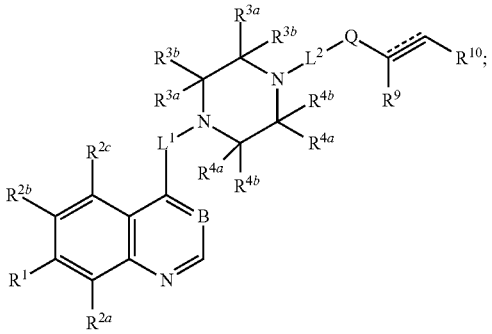

(II'c)

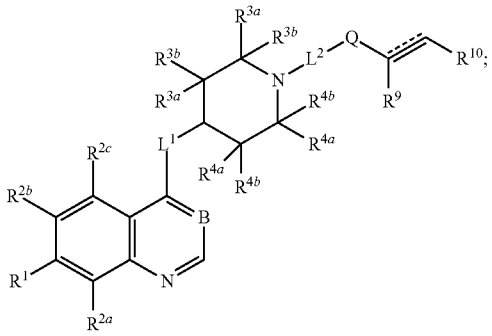

-continued (II'd)

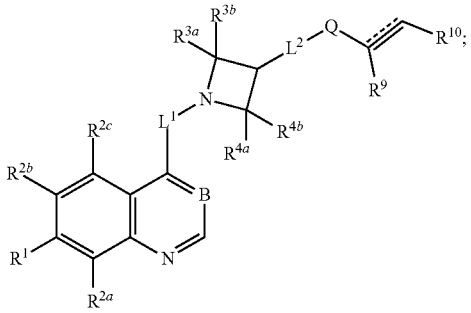

(II'e)

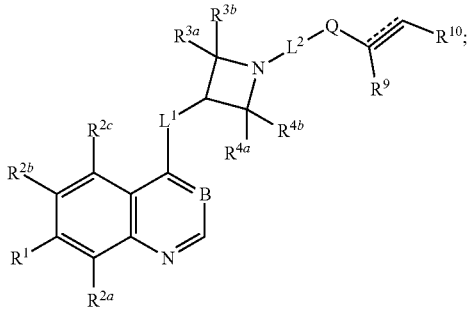

(II'f)

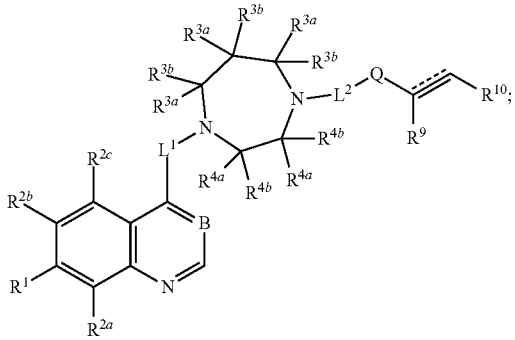

(II'g)

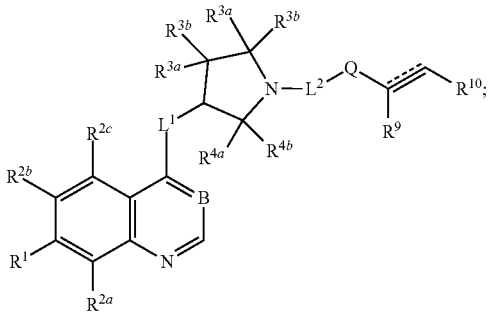

-continued (III″b)

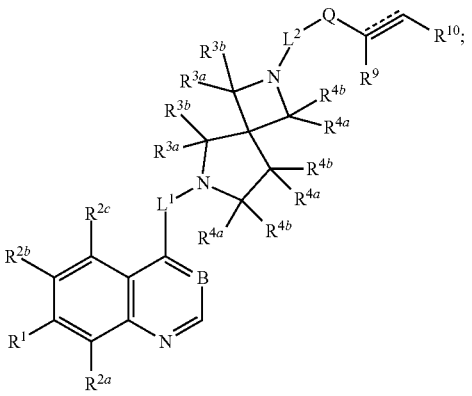

(II″c)

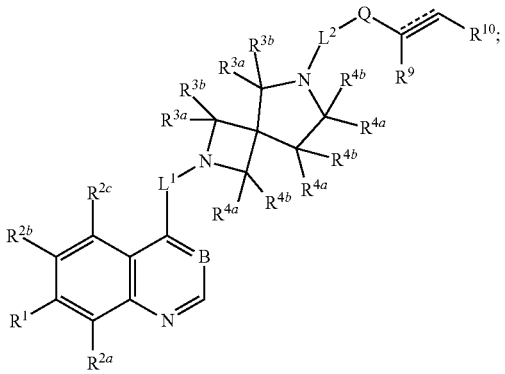

(II‴b)

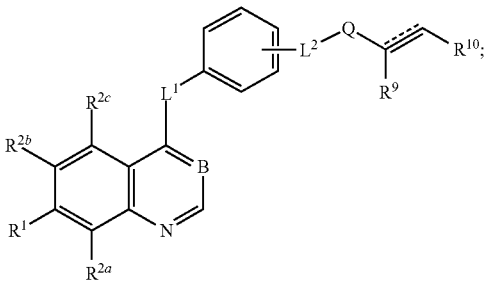

(II‴c)

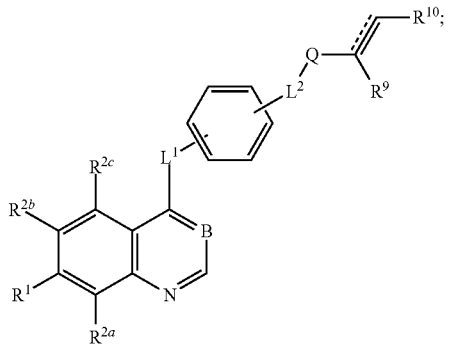

-continued (II‴d)

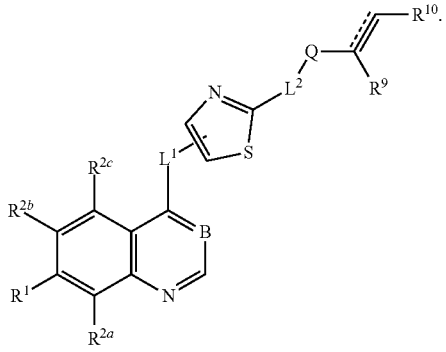

In some embodiments, the compound has one of structures (II'b), (II'c), (II'd) or (II'e).

In any of the foregoing embodiments of the compounds of structure (II), (II'), (II"), (II'"), (II'a), (II"a), (II'"a), (II'b), (II'c), (II'd), (II'e), (II'f), (II'g), (II"b), (II"c), (II'"b), (II'"c) or (II'"d) A is N. In some other of the foregoing embodiments of the compounds of structure (II), (II'), (II"), (II'"), (II'a), (II"a), (II'"a), (II'b), (II'c), (II'd), (II'e), (II'f), (II'g), (II"b), (II"c), (II'"b), (II'"c) or (II'"d), A is C—CN.

Without wishing to be bound by theory, Applicants believe correct selection of the $R^1$ substituent may play a part in the compounds' inhibitory activity (e.g., against KRAS, HRAS or NRAS G12C). In some embodiments, $R^1$ is aryl or heterocyclyl (e.g., heteroaryl or aliphatic heterocyclyl), each of which is optionally substituted with one or more substituents. In some embodiments, $R^1$ is capable of reversible interaction with KRAS, HRAS or NRAS G12C mutant protein. In some embodiments $R^1$ has high affinity towards KRAS, HRAS or NRAS and is highly specific towards G12C KRAS, HRAS or NRAS. In some embodiments $R^1$ is capable of hydrophobic interaction with KRAS, HRAS or NRAS G12C. In some embodiments $R^1$ is able to form hydrogen bonds with various residues of G12C KRAS, HRAS or NRAS protein.

In any of the foregoing embodiments, $R^1$ is aryl. For example in some embodiments $R^1$ is phenyl, and in other embodiments $R^1$ is naphthyl. $R^1$ is substituted or unsubstituted. In some specific embodiments, $R^1$ is substituted with one or more substituents. In some embodiments, $R^1$ is substituted with halo, amino, hydroxyl, $C_1$-$C_6$ alkyl, cyano, $C_1$-$C_6$ haloalkyl, $C_1$-$C_6$ alkoxy, alkylaminyl, cycloalkyl, heterocyclylalkyl, aryl, heteroaryl, boronic acid, —OC(═O)R, phosphate, phosphoalkoxy or $C_1$-$C_6$ alkylcarbonyloxy, or combinations thereof, wherein R is $C_1$-$C_6$ alkyl. For example, in some embodiments $R^1$ is substituted with halo, cyano, amino, hydroxyl, $C_1$-$C_6$ alkyl, $C_1$-$C_6$ haloalkyl, $C_1$-$C_6$ alkoxy, heteroarylalkyloxy or $C_1$-$C_6$ alkylcarbonyloxy, or combinations thereof. In some other embodiments $R^1$ is substituted with halo, hydroxyl, $C_1$-$C_6$ alkyl, $C_1$-$C_6$ haloalkyl, $C_1$-$C_6$ alkoxy or $C_1$-$C_6$ alkylcarbonyloxy, or combinations thereof. In some even more embodiments, $R^1$ is substituted with fluoro or hydroxyl, or combinations thereof.

In some more specific embodiments, $R^1$ has one of the following structures:

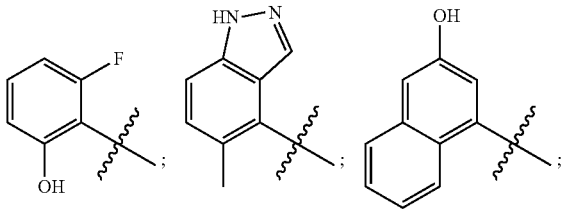
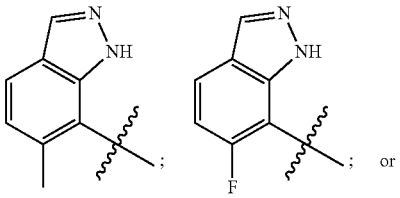
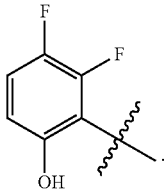
In some more specific embodiments, $R^1$ has one of the following structures:
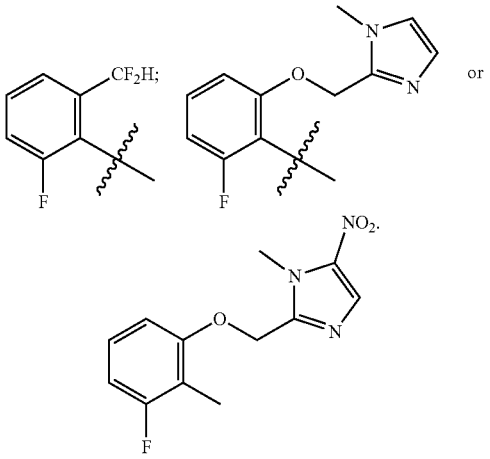
In some more specific embodiments, $R^1$ has one of the following structures:
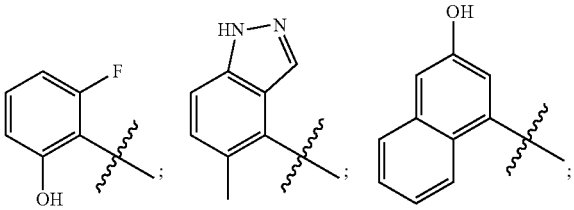
-continued
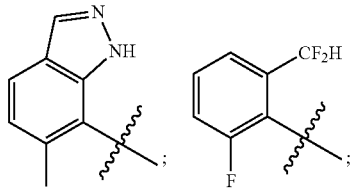
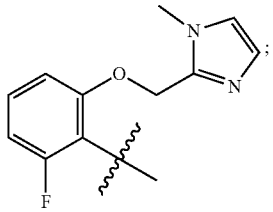
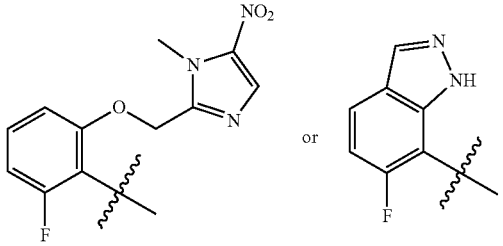
In some other embodiments, $R^1$ has one of the following structures:
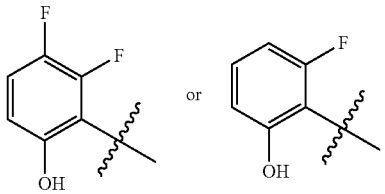
In still different embodiments, $R^1$ has one of the following structures:
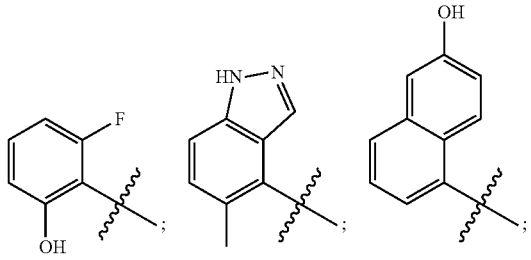
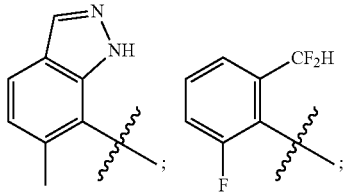

-continued

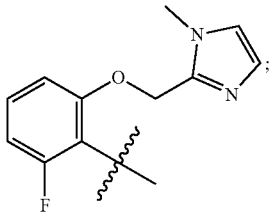

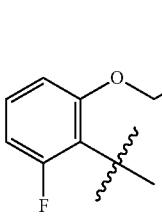

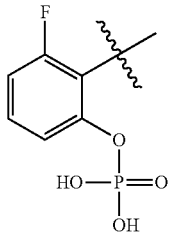

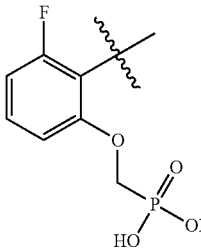

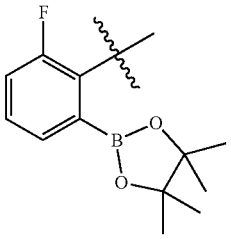

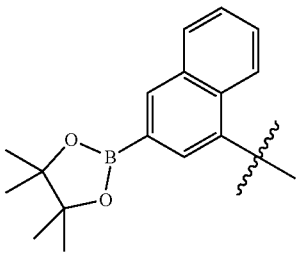

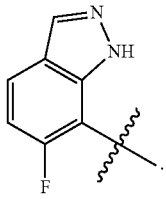

In some different embodiments of the foregoing compounds, $R^1$ is heteroaryl, for example a heteroaryl comprising nitrogen. In other embodiments, $R^1$ is indazolyl or quinolinyl. In more embodiments, $R^1$ is heteroaryl which is substituted with one or more substituents. For example, in certain embodiments, $R^1$ is substituted with hydroxyl, halo or $C_1$-$C_6$ alkyl, or both, for example hydroxyl or $C_1$-$C_6$ alkyl, or both.

In some embodiments, $R^{2a}$, $R^{2b}$ and/or $R^{2c}$ are $CF_3$. In some of the foregoing embodiments $R^{2c}$ is H. In other of any of the foregoing embodiments, $R^{2a}$ and $R^{2b}$ are each halo. For example, in some embodiments $R^{2a}$ is fluoro, and in other embodiments, $R^{2b}$ is chloro. In different embodiments $R^{2a}$ is fluoro, and $R^{2b}$ is chloro.

In some more specific embodiments, the compounds have the following structure (II'f):

(II'f)

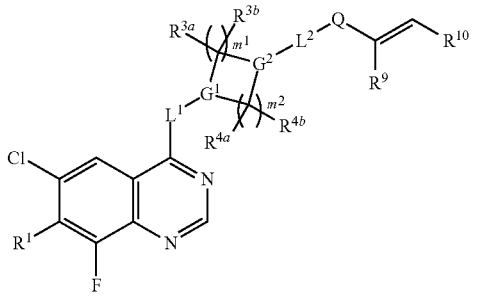

For example, in even further different embodiments, the compounds have one of the following structures (II'g) or (II'h):

(II'g)

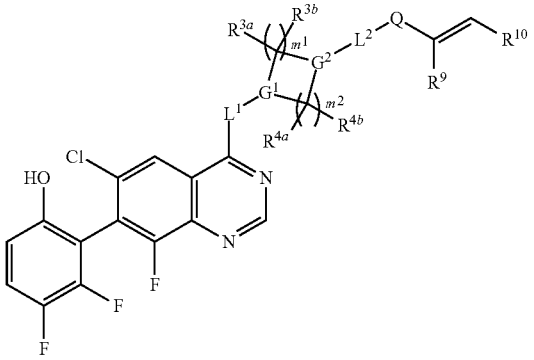

or (II'h)

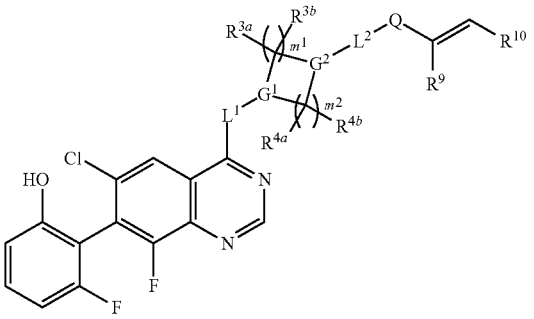

In some further embodiments, A is mono-cyclic heterocycle (e.g., a 7-membered mon-cyclic heterocycle), fused-bicyclic heterocycle, a spiro-bicyclic heterocycle, heteroaryl or aryl. For example, in some embodiments A is phenyl, pyridinyl, thiazolyl, oxazolyl, imidazolyl, pyrrolyl, pyrazolyl, diazapanyl, 2,6-diazaspiro[3.3]heptanyl, 2,6-diazaspiro[3.4]octanyl, piperazinyl or octahydropyrrolo[3,4-c]pyrrole. In more specific embodiments, A has one of the following structures:

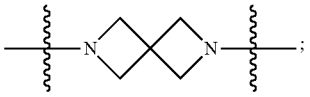

-continued

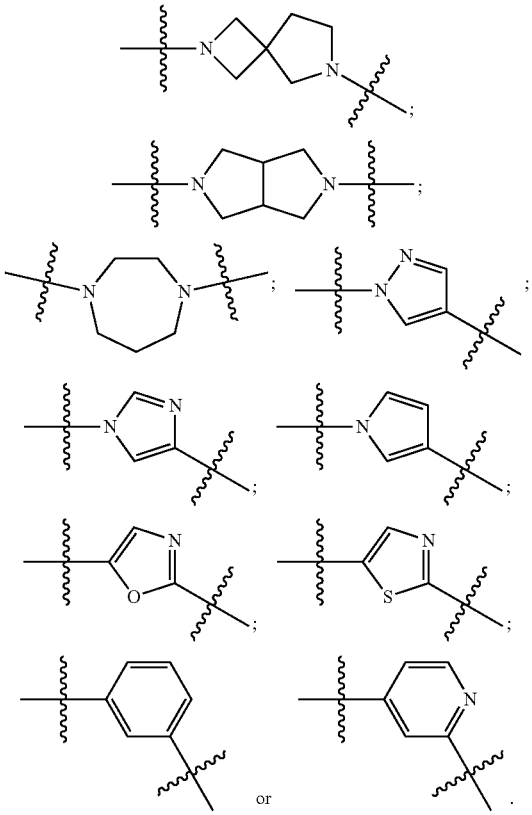

In some specific embodiments, A has the following structure:

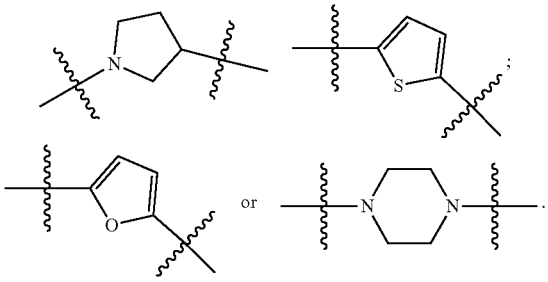

In some specific embodiments, A has the following structure:

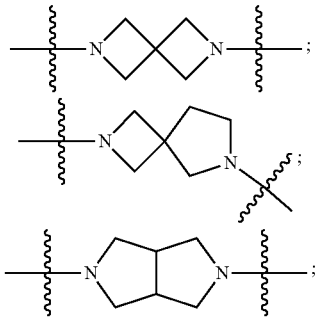

-continued

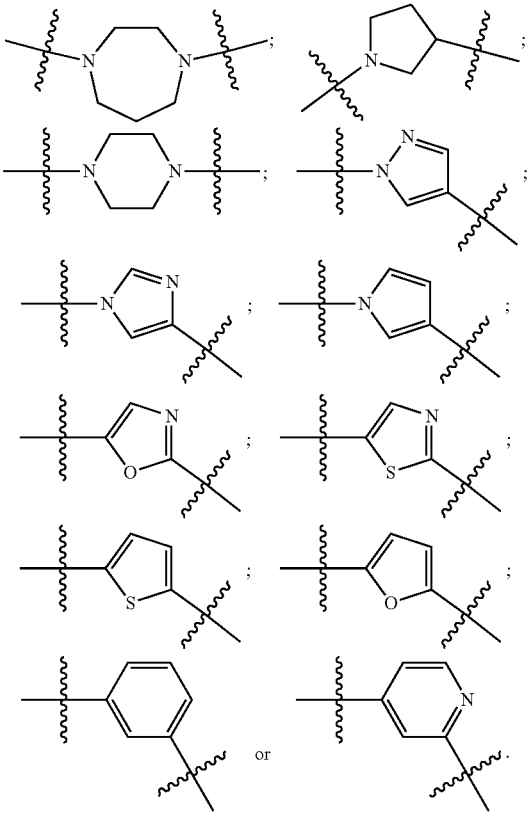

In yet more of any of the foregoing embodiments, E has the following structure:

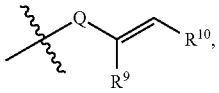

wherein:

Q is —C(═O)—, —C(═NR$^{8'}$)—, —NR$^{8}$C(═O)—, —S(═O)$_2$— or —NR S(═O)$_2$—;

R$^{8}$ is H, C$_1$-C$_6$alkyl or hydroxylalkyl;

R$^{8'}$ is H, —OH, —CN or C$_1$-C$_6$alkyl; and

R$^{9}$ and R$^{10}$ are each independently H, halo, cyano, carboxyl, C$_1$-C$_6$ alkyl, alkoxycarbonyl, aminylalkyl, alkylaminylalkyl, aryl, heterocyclyl, heterocyclylalkyl, heteroaryl or hydroxylalkyl, or R$^{9}$ and R$^{10}$ join to form a carbocyclic, heterocyclic or heteroaryl ring.

In still other of any of the foregoing embodiments, E has the following structure:

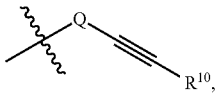

wherein:

Q is —C(═O)—, —NR$^{8}$C(═O)—, —S(═O)$_2$— or —NR$^{8}$S(═O)$_2$—;

R$^{8}$ is H, C$_1$-C$_6$alkyl or hydroxylalkyl; and

R$^{10}$ is H, C$_1$-C$_6$alkyl, aminylalkyl, alkylaminylalkyl or hydroxylalkyl.

The Q moiety is typically selected to optimize the reactivity (i.e., electrophilicity) of E. In some of the foregoing embodiments Q is —C(=O)—, —$NR^8$C(=O)—, —S(=O)$_2$— or —$NR^8$S(=O)$_2$—. In certain of the foregoing embodiments, Q is —C(=O)—. In other embodiments, Q is —S(=O)$_2$—. In still more embodiments, Q is —$NR^8$C(=O)—. In still more different embodiments, Q is —$NR^8$S(=O)$_2$—.

In some other of the foregoing embodiments, Q is —C(=$NR^{8'}$)—, wherein $R^{8'}$ is H, —OH, —CN or $C_1$-$C_6$alkyl. For example, in some embodiments $R^{8'}$ is H. In other embodiments, $R^{8'}$ is —CN. In other embodiments, $R^{8'}$ is —OH.

In some of the foregoing embodiments, $R^8$ is H. In other of these embodiments, $R^8$ is hydroxylalkyl, for example in some embodiments the hydroxylalkyl is 2-hydroxylalkyl.

In some of any one of the foregoing embodiments, at least one of $R^9$ or $R^{10}$ is H. For example, in some embodiments each of $R^9$ and $R^{10}$ are H.

In other of the foregoing embodiments, $R^{10}$ is alkylaminylalkyl. In some of these embodiments, $R^{10}$ has the following structure:

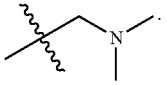

In other embodiments, $R^{10}$ is hydroxylalkyl, such as 2-hydroxylalkyl.

In some other different embodiments of the foregoing embodiments, $R^9$ and $R^{10}$ join to form a carbocyclic ring. For example, in some of these embodiments the carbocyclic ring is a cyclopentene, cyclohexene or phenyl ring. In other embodiments, the carbocyclic ring is a cyclopentene or cyclohexene ring. In other embodiments, the carbocyclic ring is a phenyl ring, for example a phenyl ring having the following structure:

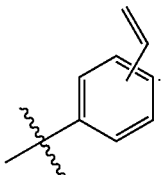

In some of any of the foregoing embodiments E is an electrophile capable of bonding with a KRAS, HRAS or NRAS protein comprising G12C mutation. In some embodiments, the electrophile E is capable of forming an irreversible covalent bond with a G12C mutant KRAS, HRAS or NRAS protein. In some cases, the electrophile E may bind with the cysteine residue at the position 12 of a G12C mutant KRAS, HRAS or NRAS protein. In various embodiments of any of the foregoing, E has one of the following structures:

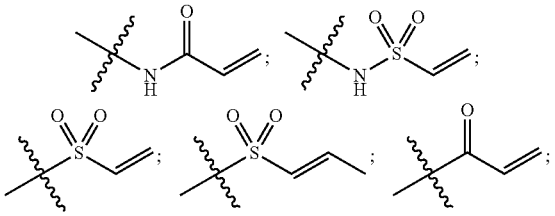

-continued

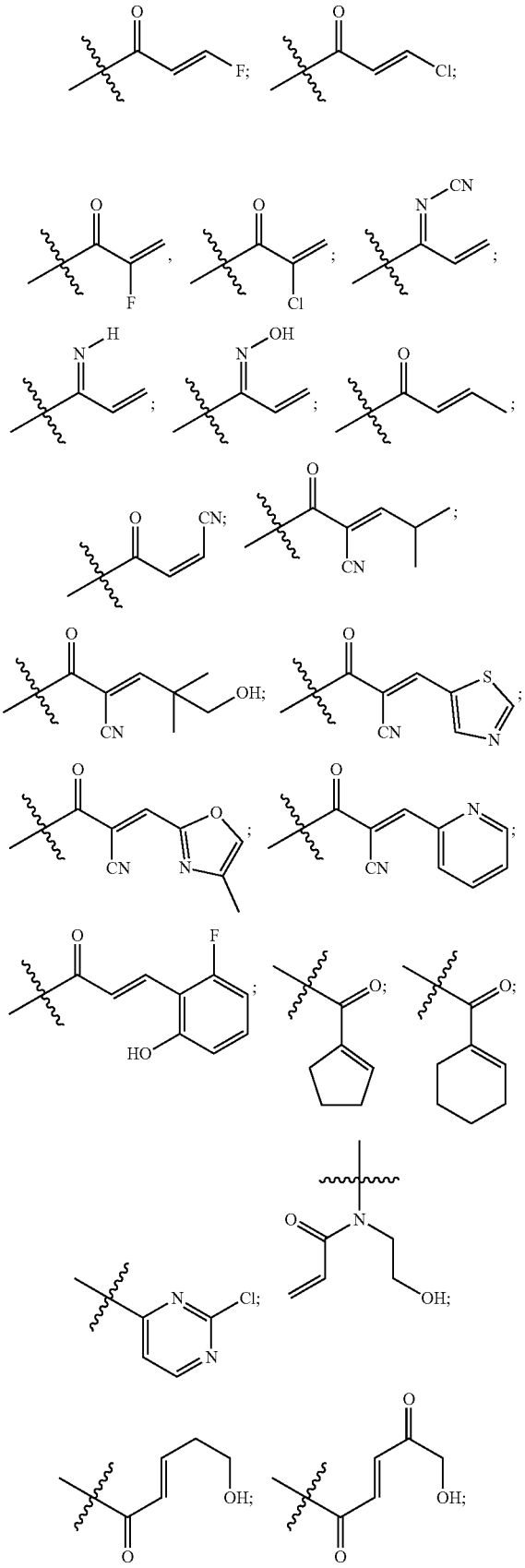

-continued
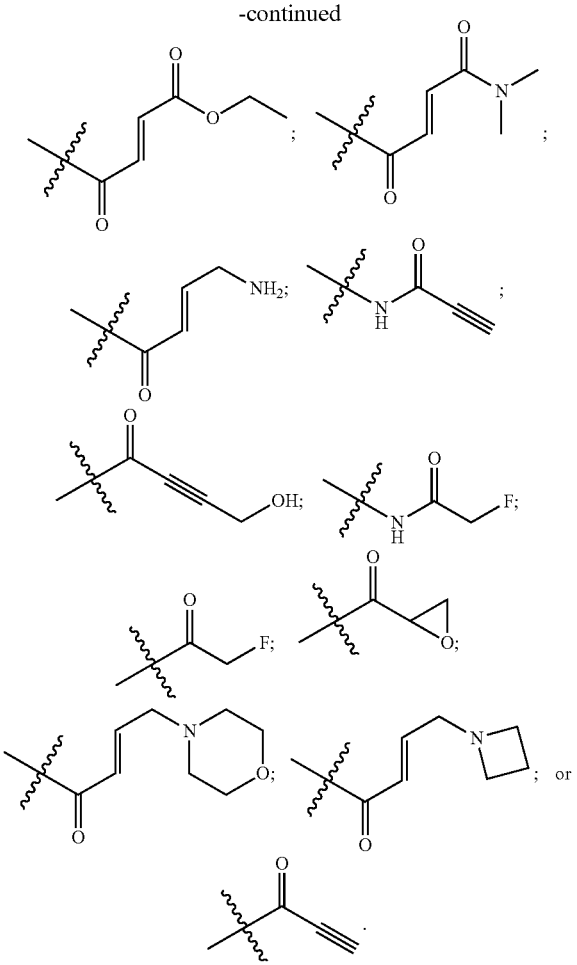
In some embodiments, E has one of the following structures:
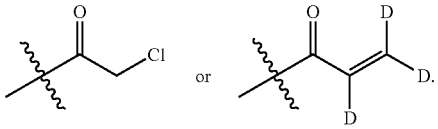
In other embodiments of any of the foregoing, E has one of the following structures:
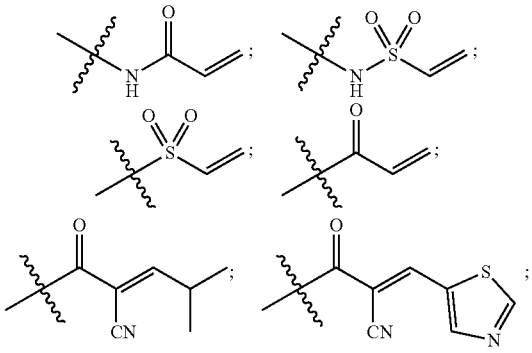
-continued
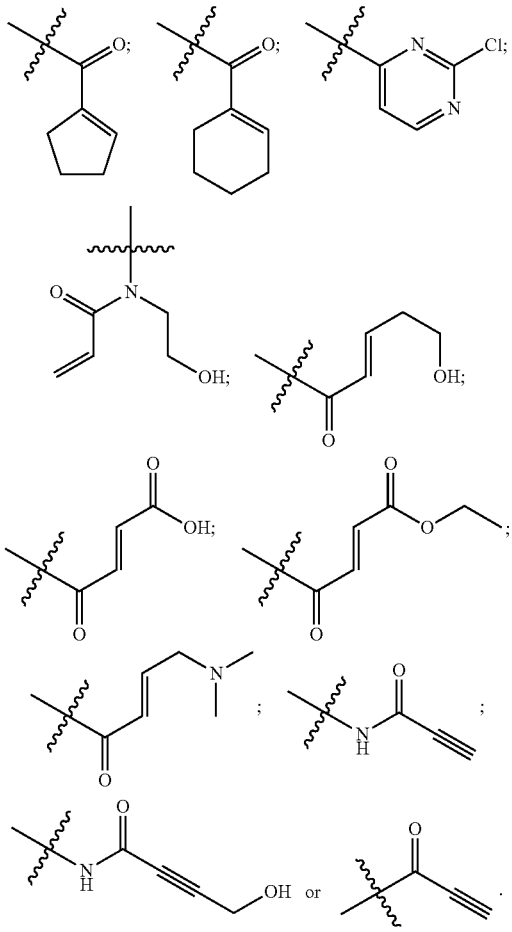
In different embodiments, E has one of the following structures:
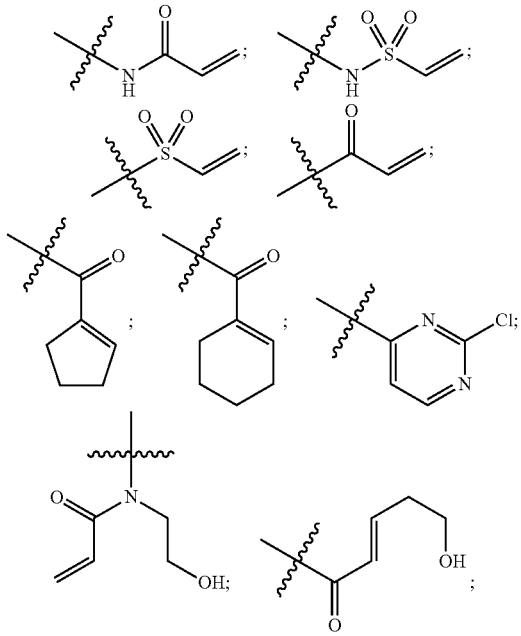

-continued

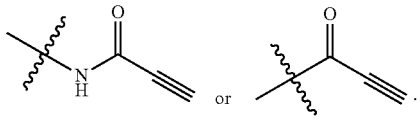

In some embodiments, E has the following structure:

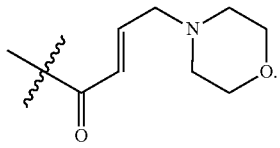

In other embodiments, E has the following structure:

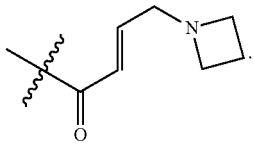

In some cases E has one of the following structures:

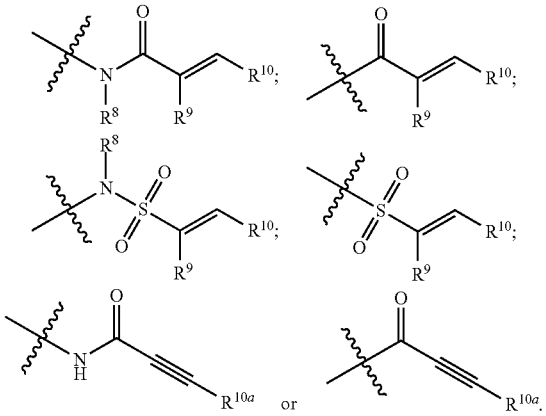

wherein:

$R^8$ is H or $C_1$-$C_6$alkyl;

$R^9$ is H, cyano or $C_1$-$C_6$alkyl, or $R^9$ joins with $R^{10}$ to form a carbocycle;

$R^{10}$ is H or $C_1$-$C_6$alkyl or $R^{10}$ joins with $R^9$ to form a carbocycle and $R^{10a}$ is H or $C_1$-$C_6$alkyl.

In some embodiments E is

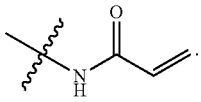

In some embodiments E is

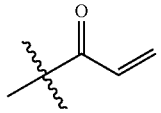

In some embodiments E is

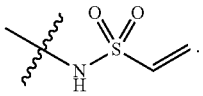

In some of any of the foregoing embodiments, $L^1$ is a bond. In other embodiments, $L^1$ is $NR^5$. For example, in some of these embodiments, $R^5$ is $C_1$-$C_6$alkyl. In other embodiments, $L^1$ is NH.

$L^2$ can be selected to provide proper spacing and/or orientation for the E group to form a bond with the KRAS, HRAS or NRAS protein. In some of the foregoing embodiments, $L^2$ is a bond. In other of the foregoing embodiments, $L^2$ is alkylene. In some embodiments, the alkylene is substituted. In other embodiments the alkylene is unsubstituted. For example, in some embodiments $L^2$ is $CH_2$ or $CH_2CH_2$.

In certain embodiments, $R^{3a}$ and $R^{3b}$ are, at each occurrence, independently H, —OH, —$NH_2$, —$CO_2H$, halo, cyano, hydroxylalkly, aminylalkyl, cyanoalkyl, carboxyalkyl or aminylcarbonyl, and $R^{4a}$ and $R^{4b}$ are, at each occurrence, independently H, —OH, —$NH_2$, —$CO_2H$, halo, cyano, hydroxylalkly, aminylalkyl, cyanoalkyl, carboxyalkyl or aminylcarbonyl.

In other of the foregoing embodiments, $R^{3a}$ and $R^{4a}$ are, at each occurrence, independently H, —OH, hydroxylalkly, cyano, or aminylcarbonyl and $R^{3b}$ and $R^{4b}$ are H.

In other of the foregoing embodiments, $R^{3a}$ and $R^{4a}$ are, at each occurrence, independently H or $C_1$-$C_6$ alkyl. In some embodiments, at least one of $R^{3a}$, $R^{4a}$, $R^{3b}$ and $R^{4b}$ is independently $C_1$-$C_6$ alkyl, such as methyl. In some embodiments, one occurrence of $R^{3a}$ is $C_1$-$C_6$ alkyl, such as methyl, and the remaining $R^{3a}$ and each $R^{4a}$ is H. In some other embodiments, two occurrences of $R^{3a}$ are $C_1$-$C_6$ alkyl, such as methyl, and the remaining $R^{3a}$ and each $R^{4a}$ is H. In some other embodiments, one occurrence of $R^{3a}$ and one occurrence of $R^{4a}$ is independently $C_1$-$C_6$ alkyl, such as methyl, and the remaining $R^{3a}$ and $R^{4a}$ are each H.

In certain other embodiments, $R^{3a}$ and $R^{4a}$ are H and $R^{3b}$ and $R^{4b}$ are, at each occurrence, independently H, —OH, —$NH_2$, —$CO_2H$, halo, cyano, hydroxylalkly, aminylalkyl, cyanoalkyl, carboxyalkyl or aminylcarbonyl.

In any of the foregoing embodiments, at least one of $R^{3a}$, $R^{3b}$, $R^{4a}$ or $R^{4b}$ is H. In some embodiments, each of $R^{3a}$, $R^{3b}$, $R^{4a}$ and $R^{4b}$ are H.

In some embodiments, $R^{3a}$ is —OH, —$NH_2$, —$CO_2H$, halo, cyano, hydroxylalkly, aminylalkyl, cyanoalkyl, carboxyalkyl or aminylcarbonyl, and $R^{3b}$, $R^{4a}$ and $R^{4b}$ are H.

In other embodiments, $R^{4a}$ is —OH, —$NH_2$, —$CO_2H$, halo, cyano, hydroxylalkly, aminylalkyl, cyanoalkyl, carboxyalkyl or aminylcarbonyl, and $R^{3a}$, $R^{3b}$ and $R^{4b}$ are H.

In other embodiments, $R^{3a}$ is H, —OH, —$NH_2$, —$CO_2H$, halo, cyano, hydroxylalkly, aminylalkyl, cyanoalkyl, carboxyalkyl or aminylcarbonyl, and $R^{3b}$ joins with $R^{4b}$ to form a carbocyclic or heterocyclic ring;

In still more embodiments, $R^{4a}$ is H, —OH, —$NH_2$, —$CO_2H$, halo, cyano, hydroxylalkly, aminylalkyl, cyanoalkyl, carboxyalkyl or aminylcarbonyl, and $R^{4b}$ joins with $R^{3b}$ to form a carbocyclic or heterocyclic ring.

In other embodiments, $R^{3a}$ and $R^{3b}$ join to form a carbocyclic or heterocyclic ring. In other embodiments, $R^{4a}$ and $R^{4b}$ join to form a carbocyclic or heterocyclic ring.

In still other embodiments, $R^{3a}$ or $R^{4a}$ is aminylcarbonyl. For example, in certain embodiments, the aminylcarbonyl is

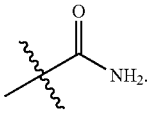

In other embodiments, $R^{3a}$ or $R^{4a}$ is cyano. In other embodiments, $R^{3a}$ or $R^{4a}$ is —OH. In other embodiments, $R^{3a}$ or $R^{4a}$ is hydroxylalkyl, for example hydroxylmethyl.

In some embodiments of any of the foregoing compounds (e.g., the compounds of structures (II), (II'a), (II'b), (II'c), (II'd) or (II'e)), $R^1$ is aryl or heteroaryl and $R^{2a}$, $R^{2b}$ and $R^{2c}$ are independently selected from H and halo, for example in some further embodiments $R^1$ is aryl or heteroaryl and $R^{2a}$ and $R^{2b}$ are independently selected from halo, such as chloro and fluoro, and $R^{2c}$ is H. In some embodiments, $R^1$ is aryl or heteroaryl, $R^{2a}$ is chloro, $R^{2b}$ is fluoro and $R^{2c}$ is H. In other embodiments $R^1$ is aryl or heteroaryl, one of $R^{2a}$ or $R^{2b}$ is halo, such as chloro or fluoro, and the other one of $R^{2a}$ or $R^{2b}$ is H.

In some embodiments of any of the compounds described herein, $C_1$-$C_6$ haloalkyl is $CF_3$ (e.g., when one or more of $R^{2a}$, $R^{2b}$ or $R^{2c}$ is $C_1$-$C_6$ haloalkyl).

In some embodiments $m^1$ is 1. In other embodiments $m^1$ is 2. In still more embodiments, $m^1$ is 3. In different embodiments, $m^2$ is 1. In some other embodiments, $m^2$ is 2. In yet still more embodiments, $m^2$ is 3.

In some other particular embodiments of any of the foregoing compounds, $m^1$ is 1, and $m^2$ is 1. In other embodiments, $m^1$ is 1 and, $m^2$ is 2. In still other embodiments $m^1$ is 2, and $m^2$ is 2. In more embodiments, $m^1$ is 1, and $m^2$ is 3.

In any of the foregoing embodiments, $G^1$ and $G^2$ are each independently selected from N and CH. In some embodiments, at least one of $G^1$ or $G^2$ is N. In some embodiments, each of $G^1$ and $G^2$ are N. In some embodiments, each of $G^1$ and $G^2$ are N and $m^1$ and $m^2$ are each 2. In some other embodiments, at least one of $G^1$ or $G^2$ is CH. In other embodiments, each of $G^1$ and $G^2$ are CH.

For example, in other embodiments the compounds have one of the following structures (II'i) or (II'j):

(II'i)

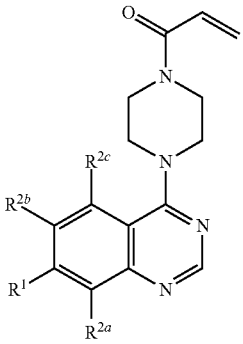

or (II'j)

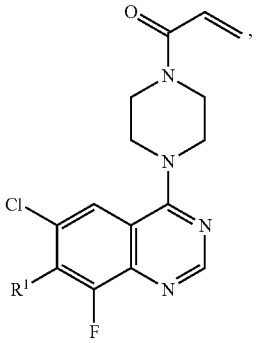

wherein $R^1$, $R^{2a}$, $R^{2b}$ and $R^{2c}$ are as defined according to any of the foregoing embodiments.

In any of the foregoing embodiments, A is N. In other of the foregoing embodiments, A is C—CN.

Some embodiments of the compounds include more than one stereoisomer. Other embodiments are directed to a single stereoisomer. In some embodiments the compounds are racemic (e.g., mixture of atropisomers), while in other embodiments the compounds are substantially a single isomer, for example a substantially purified atropisomer.

In various different embodiments, the compound of structure (II) has one of the structures set forth in Table 3 below. The compounds in Table 3 were each prepared and analyzed by mass spectrometry and/or $^1H$ NMR. Experimental mass spectrometry data is included in Table 3. Exemplary synthetic procedures are described in more detail below and in the Examples. General methods by which the compounds may be prepared are provided below and indicated in Table 3.

TABLE 3

Representative Compounds of Structure (II)

| No. | Structure | Name | Method | [M + H]+ |
|---|---|---|---|---|
| II-1 | 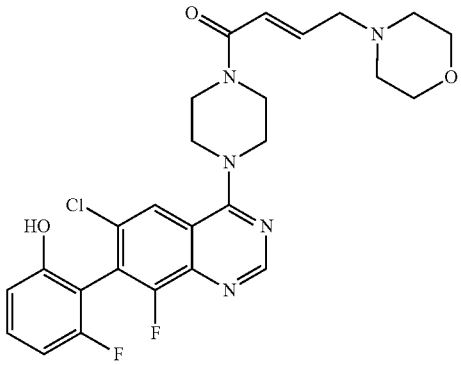 | (E)-1-(4-(6-chloro-8-fluoro-7-(2-fluoro-6-hydroxyphenyl) quinazolin-4-yl)piperazin-1-yl)-4-morpholinobut-2-en-1-one | R | 530.2 |
| II-2 | 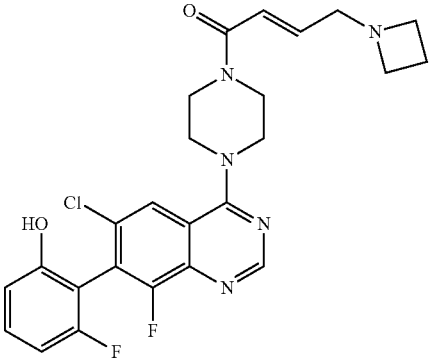 | (E)-4-(azetidin-1-yl)-1-(4-(6-chloro-8-fluoro-7-(2-fluoro-6-hydroxyphenyl) quinazolin-4-yl)piperazin-1-yl)but-2-en-1-one | R | 500.2 |
| II-3 | 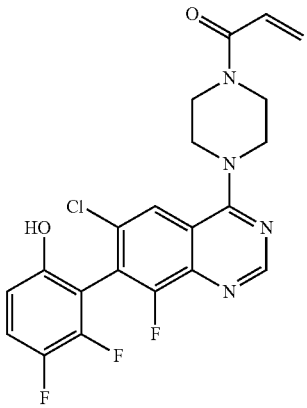 | 1-(4-(6-chloro-7-(2,3-difluoro-6-hydroxyphenyl)-8-fluoroquinazolin-4-yl)piperazin-1-yl)prop-2-en-1-one | R | 449.1 |
| II-4 | 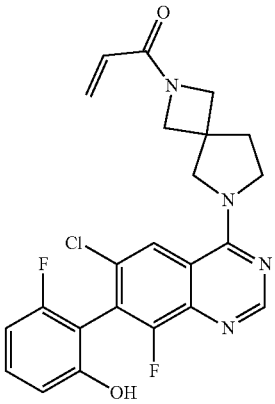 | 1-(6-(6-chloro-8-fluoro-7-(2-fluoro-6-hydroxyphenyl) quinazolin-4-yl)-2,6-diazaspiro[3.4]octan-2-yl)prop-2-en-1-one | S | 457.15 |

TABLE 3-continued
Representative Compounds of Structure (II)
| No. | Structure | Name | Method | $[M + H]^+$ |
|---|---|---|---|---|
| II-5 | 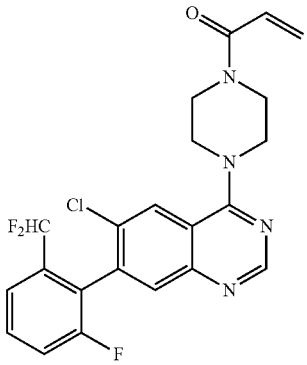 | 1-(4-(6-chloro-7-(2-(difluoromethyl)-6-fluorophenyl) quinazolin-4-yl) piperazin-1-yl)prop-2-en-1-one | R | 447.10 |
| II-6 | 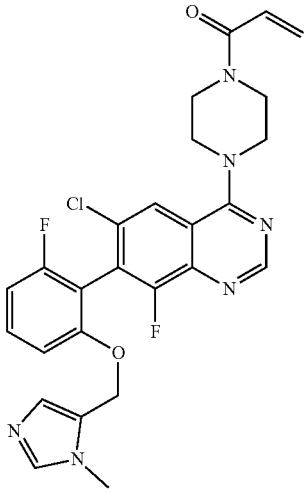 | 1-(4-(6-chloro-8-fluoro-7-(2-fluoro-6-((1-methyl-1H-imidazol-5-yl)methoxy)phenyl) quinazolin-4-yl)piperazin-1-yl)prop-2-en-1-one | R | 525.30 |
| II-7 | 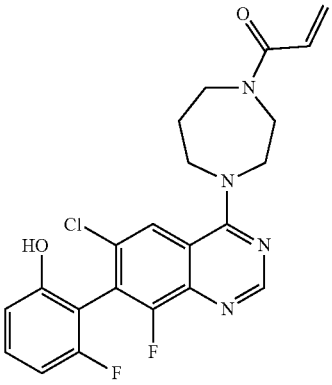 | 1-(4-(6-chloro-8-fluoro-7-(2-fluoro-6-hydroxyphenyl) quinazolin-4-yl)-1,4-diazepan-1-yl)prop-2-en-1-one | S | 445.15 |

TABLE 3-continued

Representative Compounds of Structure (II)

| No. | Structure | Name | Method | $[M + H]^+$ |
|---|---|---|---|---|
| II-8 | 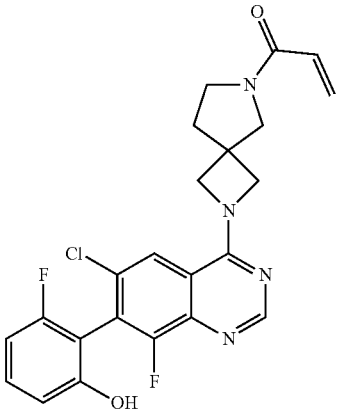 | 1-(2-(6-chloro-8-fluoro-7-(2-fluoro-6-hydroxyphenyl) quinazolin-4-yl)-2,6-diazaspiro[3.4]octan-6-yl)prop-2-en-1-one | S | 457.10 |
| II-9 | 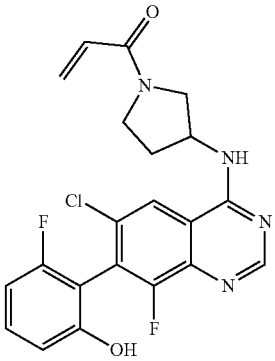 | 1-(3-((6-chloro-8-fluoro-7-(2-fluoro-6-hydroxyphenyl) quinazolin-4-yl)amino)pyrrolidin-1-yl)prop-2-en-1-one | S | 431.10 |
| II-10 | 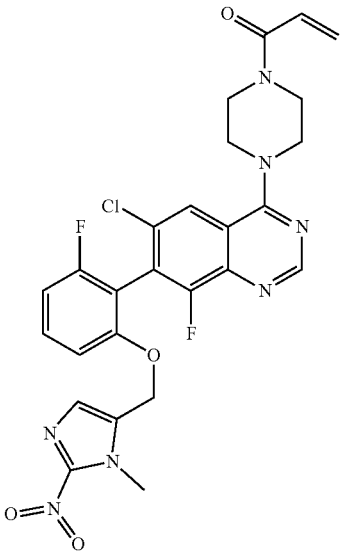 | 1-(4-(6-chloro-8-fluoro-7-(2-fluoro-6-((1-methyl-2-nitro-1H-imidazol-5-yl)methoxy)phenyl) quinazolin-4-yl)piperazin-1-yl)prop-2-en-1-one | S | 570.15 |

TABLE 3-continued

Representative Compounds of Structure (II)

| No. | Structure | Name | Method | [M + H]+ |
|---|---|---|---|---|
| II-11 | 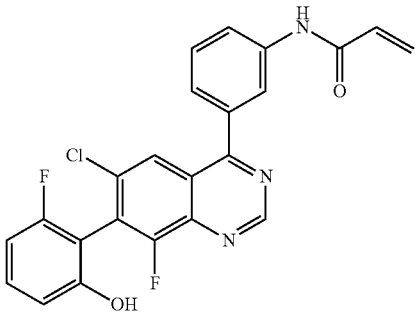 | N-(3-(6-chloro-8-fluoro-7-(2-fluoro-6-hydroxyphenyl) quinazolin-4-yl)phenyl)acrylamide | T | 438.15 |
| II-12 | 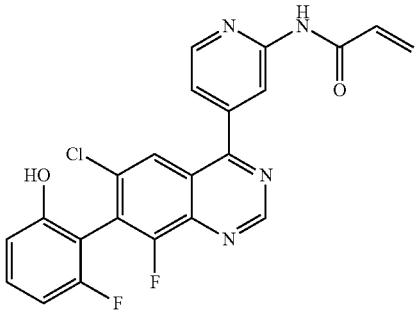 | N-(4-(6-chloro-8-fluoro-7-(2-fluoro-6-hydroxyphenyl) quinazolin-4-yl)pyridin-2-yl)acrylamide | T | 439.10 |
| II-13 | 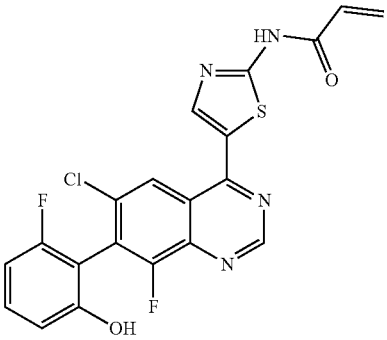 | N-(5-(6-chloro-8-fluoro-7-(2-fluoro-6-hydroxyphenyl)-quinazolin-4-yl)thiazol-2-yl)acrylamide | T | 445.00 |
| II-14 | 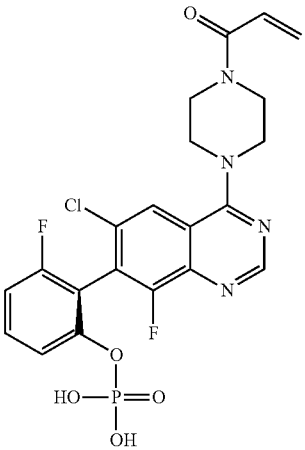 | (S)-2-(4-(4-acryloylpiperazin-1-yl)-6-chloro-8-fluoroquinazolin-7-yl)-3-fluorophenyl dihydrogen phosphate | R | 511.0 |

TABLE 3-continued

| Representative Compounds of Structure (II) | | | | |
|---|---|---|---|---|
| No. | Structure | Name | Method | $[M + H]^+$ |
| II-15 | 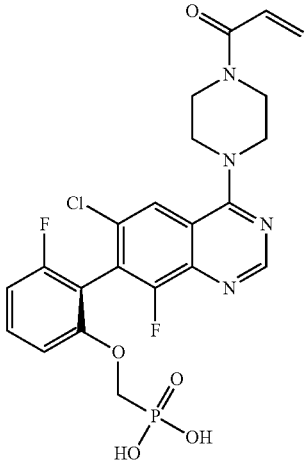 | (S)-(2-(4-(4-acryloylpiperazin-1-yl)-6-chloro-8-fluoroquinazolin-7-yl)-3-fluoro-phenoxy)methyl-phosphonic acid | R | 541.1* |

*$M + Na^+$

In various different embodiments of any of the embodiments of the compounds of structure (II), the compounds illustrated in Table 4 are excluded from the invention.

TABLE 4

| Compounds Excluded From Certain Embodiments | | |
|---|---|---|
| No. | Structure | Name |
| 2-1 | 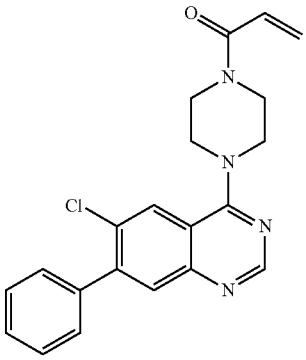 | 1-(4-(6-chloro-7-phenyl-quinazolin-4-yl)piperazin-1-yl)prop-2-en-1-one |
| 2-2 | 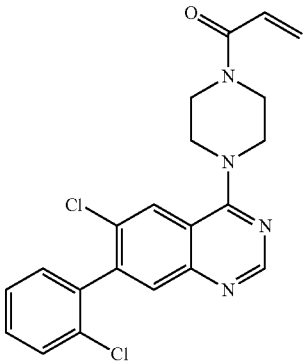 | 1-(4-(6-chloro-7-(2-chlorophenyl) quinazolin-4-yl)piperazin-1-yl)prop-2-en-1-one |

TABLE 4-continued

| Compounds Excluded From Certain Embodiments | | |
|---|---|---|
| No. | Structure | Name |
| 2-3 | 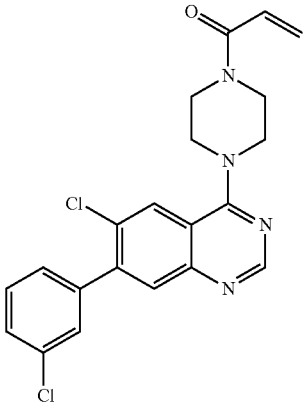 | 1-(4-(6-chloro-7-(3-chlorophenyl) quinazolin-4-yl)piperazin-1-yl)prop-2-en-1-one |
| 2-4 | 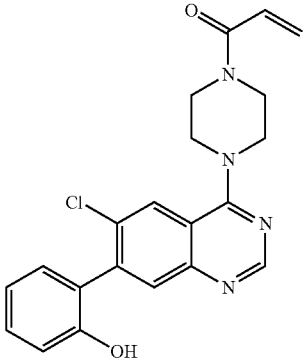 | 1-(4-(6-chloro-7-(2-hydroxy-phenyl) quinazolin-4-yl)piperazin-1-yl)prop-2-en-1-one |

TABLE 4-continued

Compounds Excluded From Certain Embodiments

| No. | Structure | Name |
|---|---|---|
| 2-5 | 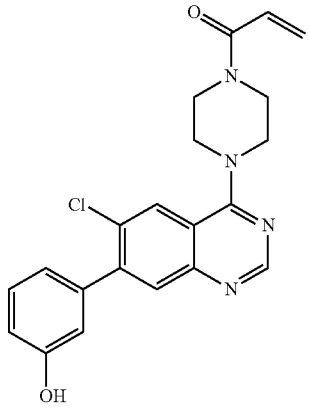 | 1-(4-(6-chloro-7-(3-hydroxy-phenyl) quinazolin-4-yl)piperazin-1-yl)prop-2-en-1-one |
| 2-6 | 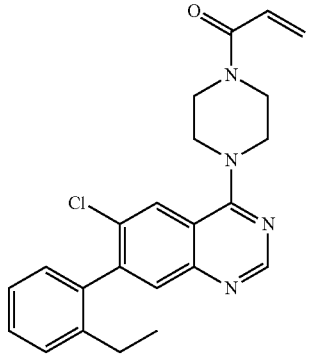 | 1-(4-(6-chloro-7-(2-ethylphenyl) quinazolin-4-yl)piperazin-1-yl)prop-2-en-1-one |
| 2-7 | 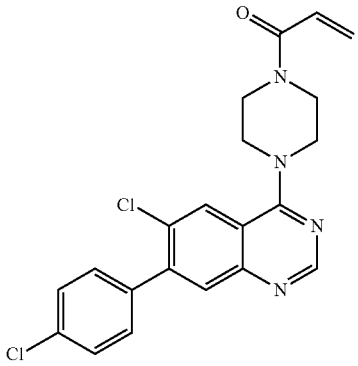 | 1-(4-(6-chloro-7-(4-chlorophenyl) quinazolin-4-yl)piperazin-1-yl)prop-2-en-1-one |
| 2-8 | 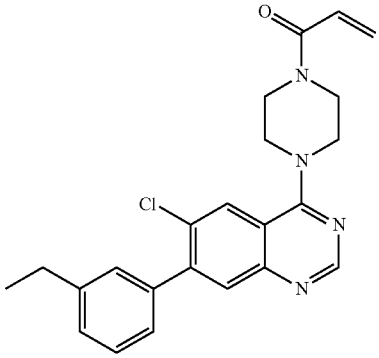 | 1-(4-(6-chloro-7-(3-ethylphenyl) quinazolin-4-yl)piperazin-1-yl)prop-2-en-1-one |

TABLE 4-continued

Compounds Excluded From Certain Embodiments

| No. | Structure | Name |
|---|---|---|
| 2-9 | 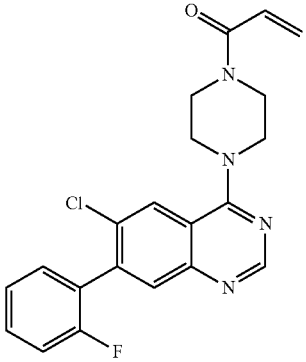 | 1-(4-(6-chloro-7-(2-fluorophenyl) quinazolin-4-yl)piperazin-1-yl)prop-2-en-1-one |
| 2-10 | 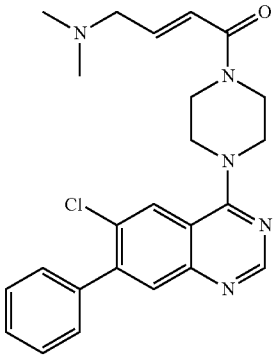 | (E)-1-(4-(6-chloro-7-phenyl-quinazolin-4-yl)piperazin-1-yl)-4-(dimethyl-amino)but-2-en-1-one |
| 2-11 | 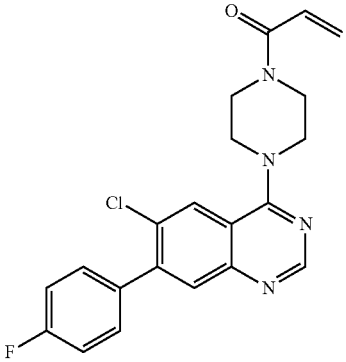 | 1-(4-(6-chloro-7-(4-fluorophenyl) quinazolin-4-yl)piperazin-1-yl)prop-2-en-1-one |
| 2-12 | 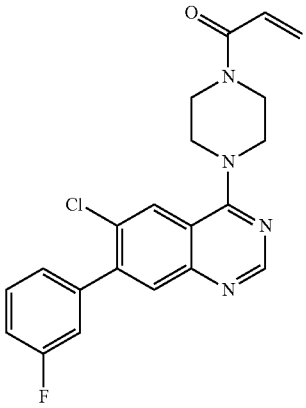 | 1-(4-(6-chloro-7-(3-fluorophenyl) quinazolin-4-yl)piperazin-1-yl)prop-2-en-1-one |

TABLE 4-continued

Compounds Excluded From Certain Embodiments

| No. | Structure | Name |
|---|---|---|
| 2-13 | 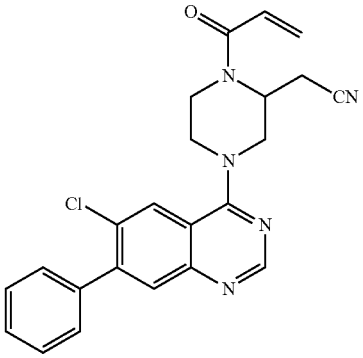 | 2-(1-acryloyl-4-(6-chloro-7-phenyl-quinazolin-4-yl)piperazin-2-yl)acetonitrile |
| 2-14 | 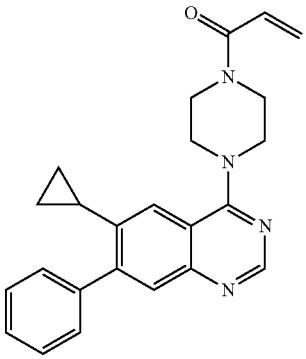 | 1-(4-(6-cyclopropyl-7-phenyl-quinazolin-4-yl)piperazin-1-yl)prop-2-en-1-one |
| 2-15 | 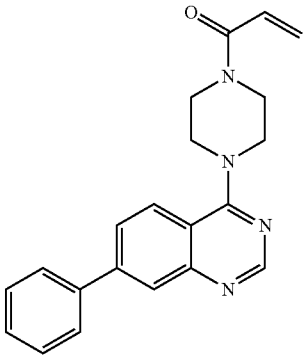 | 1-(4-(7-phenyl-quinazolin-4-yl)piperazin-1-yl)prop-2-en-1-one |
| 2-16 | 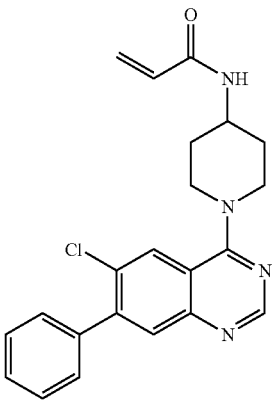 | N-(1-(6-chloro-7-phenyl-quinazolin-4-yl)piperidin-4-yl)acrylamide |

TABLE 4-continued

Compounds Excluded From Certain Embodiments

| No. | Structure | Name |
|---|---|---|
| 2-17 | 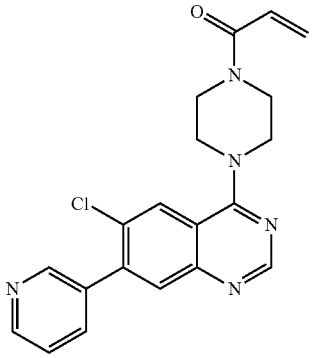 | 1-(4-(6-chloro-7-(pyridin-3-yl) quinazolin-4-yl)piperazin-1-yl)prop-2-en-1-one |
| 2-18 | 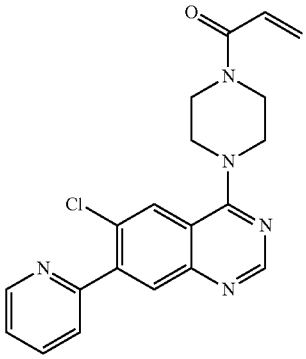 | 1-(4-(6-chloro-7-(pyridin-2-yl) quinazolin-4-yl)piperazin-1-yl)prop-2-en-1-one |
| 2-19 | 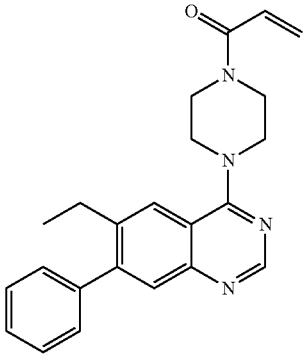 | 1-(4-(6-ethyl-7-phenyl-quinazolin-4-yl)piperazin-1-yl)prop-2-en-1-one |
| 2-20 | 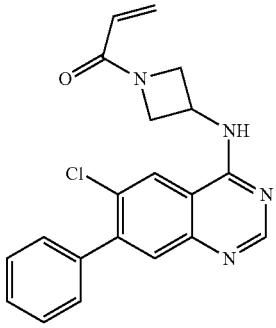 | 1-(3-(6-chloro-7-phenyl-quinazolin-4-ylamino) azetidin-1-yl)prop-2-en-1-one |

TABLE 4-continued

Compounds Excluded From Certain Embodiments

| No. | Structure | Name |
|---|---|---|
| 2-21 | 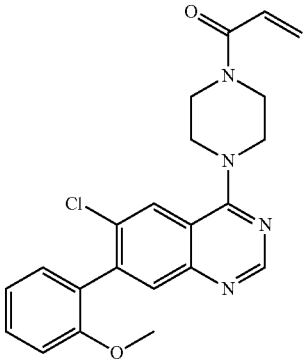 | 1-(4-(6-chloro-7-(2-methoxy-phenyl) quinazolin-4-yl)piperazin-1-yl)prop-2-en-1-one |
| 2-22 | 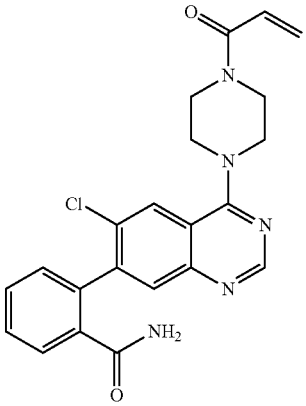 | 2-(4-(4-acryloyl-piperazin-1-yl)-6-chloro-quinazolin-7-yl) benzamide |
| 2-23 | 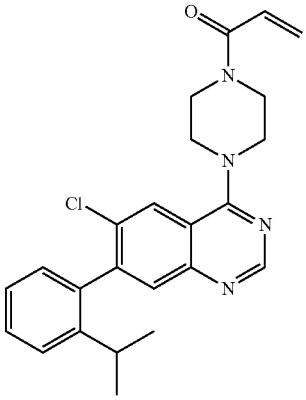 | 1-(4-(6-chloro-7-(2-isopropyl-phenyl) quinazolin-4-yl)piperazin-1-yl)prop-2-en-1-one |
| 2-24 | 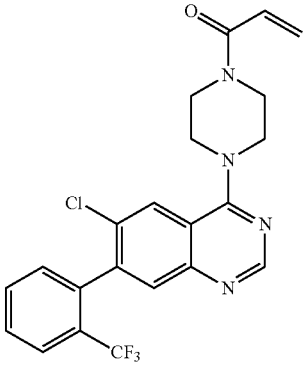 | 1-(4-(6-chloro-7-(2-(trifluoro-methyl) phenyl) quinazolin-4-yl) piperazin-1-yl)prop-2-en-1-one |

TABLE 4-continued

Compounds Excluded From Certain Embodiments

| No. | Structure | Name |
|---|---|---|
| 2-25 | 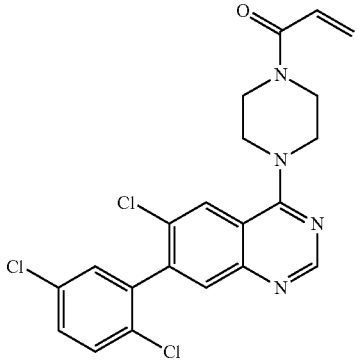 | 1-(4-(6-chloro-7-(2,5-dichloro-phenyl) quinazolin-4-yl)piperazin-1-yl)prop-2-en-1-one |
| 2-26 | 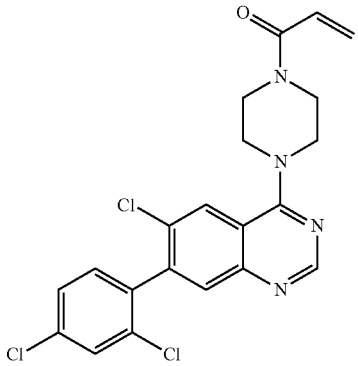 | 1-(4-(6-chloro-7-(2,4-dichloro-phenyl) quinazolin-4-yl)piperazin-1-yl)prop-2-en-1-one |
| 2-27 | 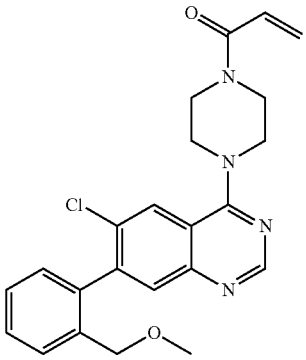 | 1-(4-(6-chloro-7-(2-(methoxy-methyl) phenyl) quinazolin-4-yl)piperazin-1-yl)prop-2-en-1-one |
| 2-28 | 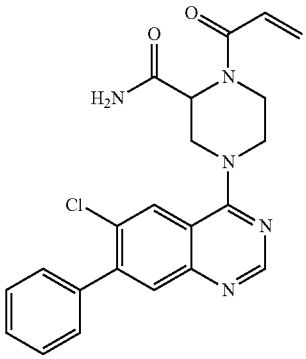 | 1-acryloyl-4-(6-chloro-7-phenyl-quinazolin-4-yl)piperazine-2-carboxamide |

TABLE 4-continued

Compounds Excluded From Certain Embodiments

| No. | Structure | Name |
|---|---|---|
| 2-29 | 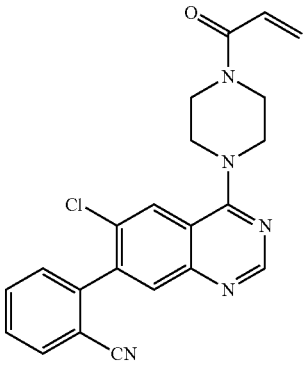 | 2-(4-(4-acryloyl-piperazin-1-yl)-6-chloro-quinazolin-7-yl) benzonitrile |
| 2-30 | 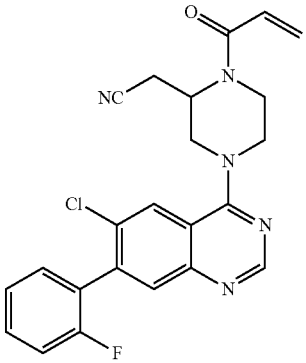 | 2-(1-acryloyl-4-(6-chloro-7-(2-fluorophenyl) quinazolin-4-yl)piperazin-2-yl) acetonitrile |
| 2-31 | 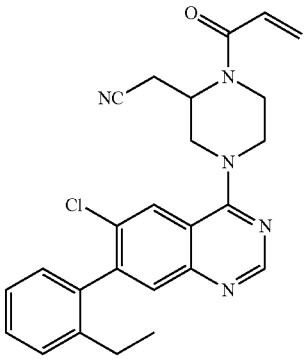 | 2-(1-acryloyl-4-(6-chloro-7-(2-ethylphenyl) quinazolin-4-yl)piperazin-2-yl) acetonitrile |
| 2-32 | 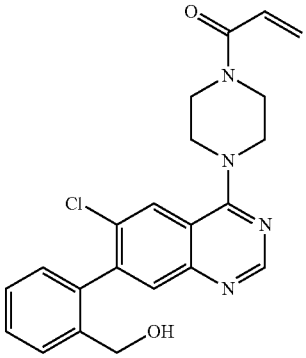 | 1-(4-(6-chloro-7-(2-(hydroxy-methyl) phenyl) quinazolin-4-yl)piperazin-1-yl)prop-2-en-1-one |

TABLE 4-continued

Compounds Excluded From Certain Embodiments

| No. | Structure | Name |
|---|---|---|
| 2-33 | 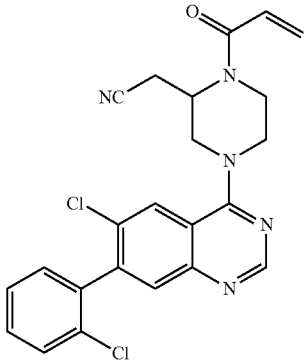 | 2-(1-acryloyl-4-(6-chloro-7-(2-chlorophenyl) quinazolin-4-yl)piperazin-2-yl) acetonitrile |
| 2-34 | 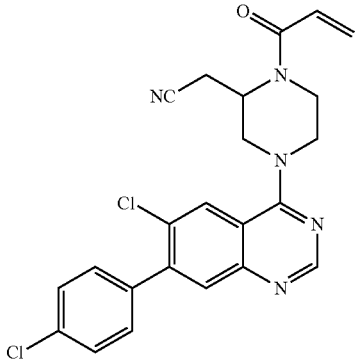 | 2-(1-acryloyl-4-(6-chloro-7-(4-chlorophenyl) quinazolin-4-yl)piperazin-2-yl) acetonitrile |
| 2-35 | 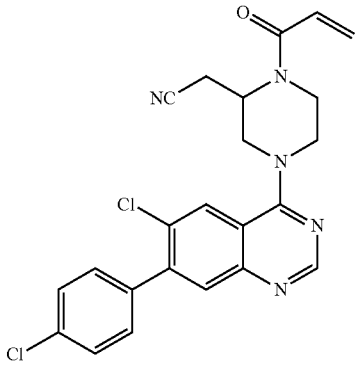 | 2-(1-acryloyl-4-(6-chloro-7-(4-chlorophenyl) quinazolin-4-yl)piperazin-2-yl) acetonitrile |
| 2-36 | 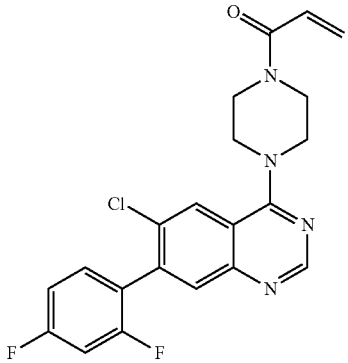 | 1-(4-(6-chloro-7-(2,4-difluoro-phenyl) quinazolin-4-yl)piperazin-1-yl)prop-2-en-1-one |

TABLE 4-continued

Compounds Excluded From Certain Embodiments

| No. | Structure | Name |
|---|---|---|
| 2-37 | 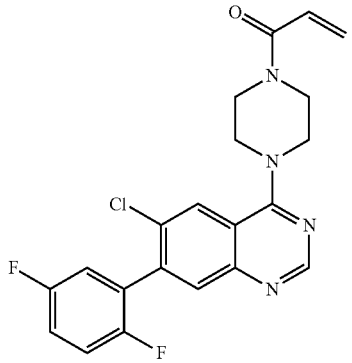 | 1-(4-(6-chloro-7-(2,5-difluoro-phenyl) quinazolin-4-yl)piperazin-1-yl)prop-2-en-1-one |
| 2-38 | 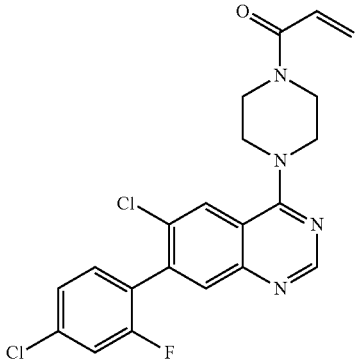 | 1-(4-(6-chloro-7-(4-chloro-2-fluorophenyl) quinazolin-4-yl)piperazin-1-yl)prop-2-en-1-one |
| 2-39 | 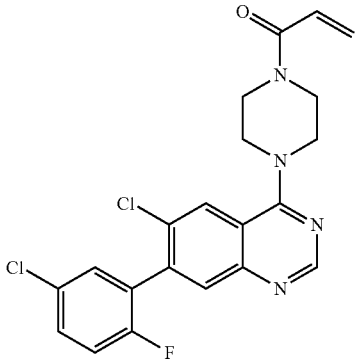 | 1-(4-(6-chloro-7-(5-chloro-2-fluorophenyl) quinazolin-4-yl)piperazin-1-yl)prop-2-en-1-one |
| 2-40 | 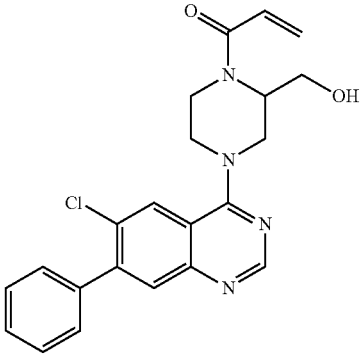 | 1-(4-(6-chloro-7-phenyl-quinazolin-4-yl)-2-(hydroxy-methyl) piperazin-1-yl)prop-2-en-1-one |

TABLE 4-continued

Compounds Excluded From Certain Embodiments

| No. | Structure | Name |
|---|---|---|
| 2-41 | 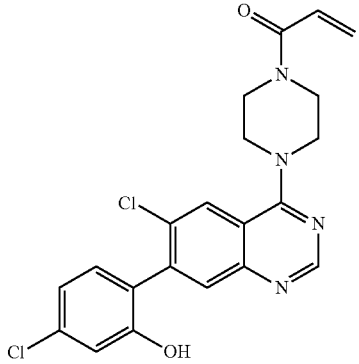 | 1-(4-(6-chloro-7-(4-chloro-2-hydroxy-phenyl) quinazolin-4-yl)piperazin-1-yl)prop-2-en-1-one |
| 2-42 | 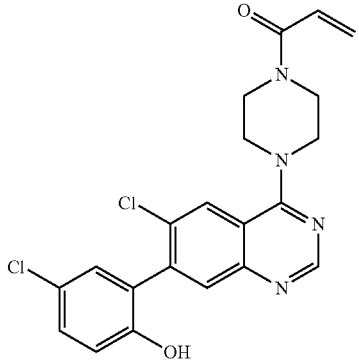 | 1-(4-(6-chloro-7-(5-chloro-2-hydroxy-phenyl) quinazolin-4-yl)piperazin-1-yl)prop-2-en-1-one |
| 2-43 | 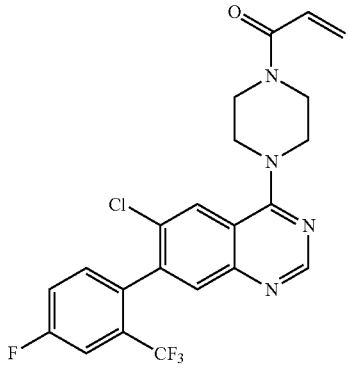 | 1-(4-(6-chloro-7-(4-fluoro-2-(trifluoro-methyl) phenyl) quinazolin-4-yl)piperazin-1-yl)prop-2-en-1-one |
| 2-44 | 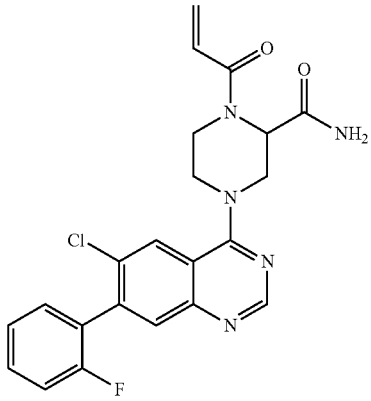 | 1-acryloyl-4-(6-chloro-7-(2-fluorophenyl) quinazolin-4-yl)piperazine-2-carboxamide |

TABLE 4-continued

Compounds Excluded From Certain Embodiments

| No. | Structure | Name |
|---|---|---|
| 2-45 | 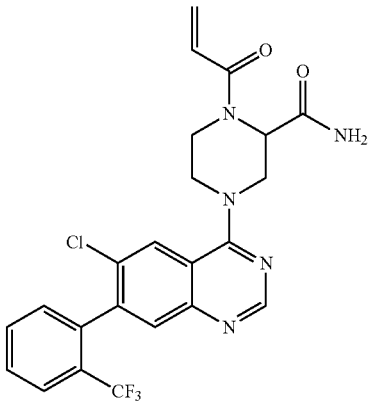 | l-acryloyl-4-(6-chloro-7-(2-(trifluoro-methyl) phenyl) quinazolin-4-yl)piperazine-2-carboxamide |
| 2-46 | 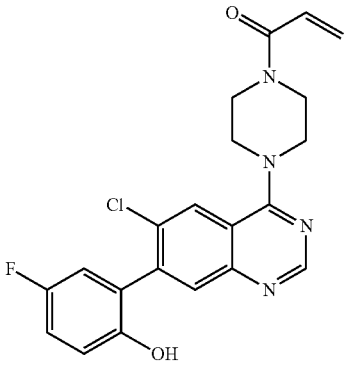 | 1-(4-(6-chloro-7-(5-fluoro-2-hydroxy-phenyl) quinazolin-4-yl)piperazin-1-yl)prop-2-en-1-one |
| 2-47 | 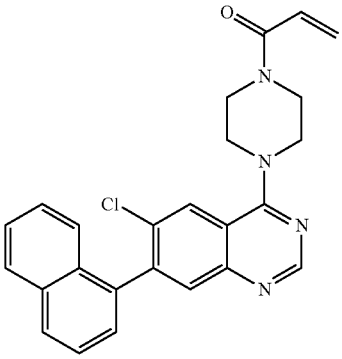 | 1-(4-(6-chloro-7-(naphthalen-1-yl) quinazolin-4-yl)piperazin-1-yl)prop-2-en-1-one |
| 2-48 | 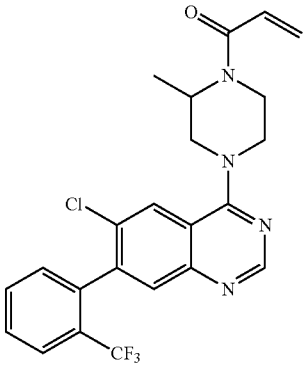 | 1-(4-(6-chloro-7-(2-(trifluoro-methyl) phenyl) quinazolin-4-yl)-2-methyl-piperazin-1-yl)prop-2-en-1-one |

TABLE 4-continued

Compounds Excluded From Certain Embodiments

| No. | Structure | Name |
|---|---|---|
| 2-49 | 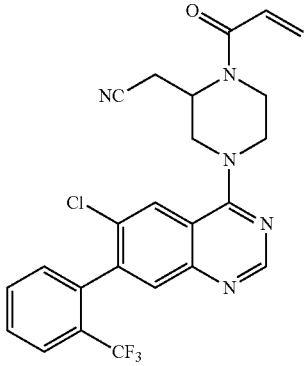 | 2-(1-acryloyl-4-(6-chloro-7-(2-(trifluoro-methyl) phenyl) quinazolin-4-yl)piperazin-2-yl) acetonitrile |
| 2-50 | 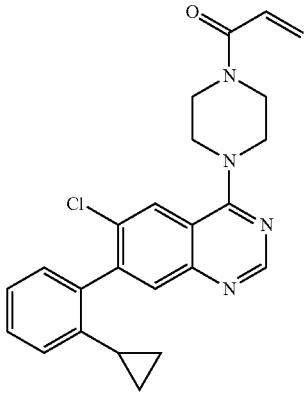 | 1-(4-(6-chloro-7-(2-cyclopropyl-phenyl) quinazolin-4-yl)piperazin-1-yl)prop-2-en-1-one |
| 2-51 | 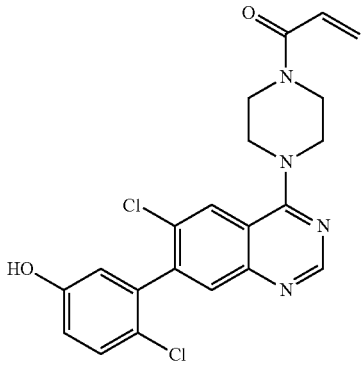 | 1-(4-(6-chloro-7-(2-chloro-5-hydroxy-phenyl) quinazolin-4-yl)piperazin-1-yl)prop-2-en-1-one |
| 2-52 | 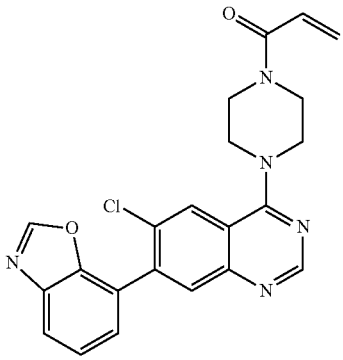 | 1-(4-(7-(benzo[d] oxazol-7-yl)-6-chloro-quinazolin-4-yl)piperazin-1-yl)prop-2-en-1-one |

TABLE 4-continued

Compounds Excluded From Certain Embodiments

| No. | Structure | Name |
|---|---|---|
| 2-53 | 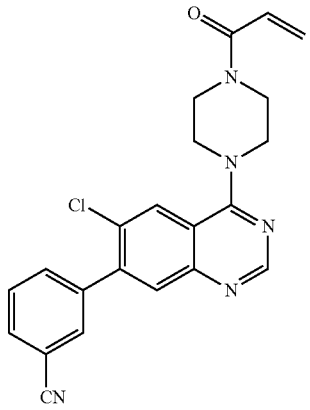 | 3-(4-(4-acryloyl-piperazin-1-yl)-6-chloro-quinazolin-7-yl) benzonitrile |
| 2-54 | 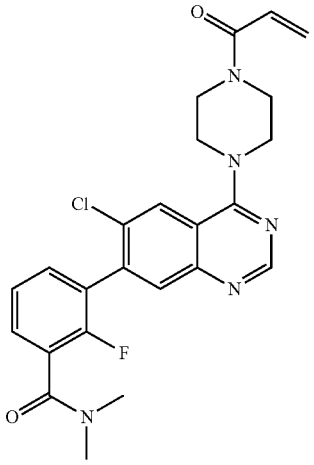 | 3-(4-(4-acryloyl-piperazin-1-yl)-6-chloro-quinazolin-7-yl)-2-fluoro-N,N-dimethyl-benzamide |
| 2-55 | 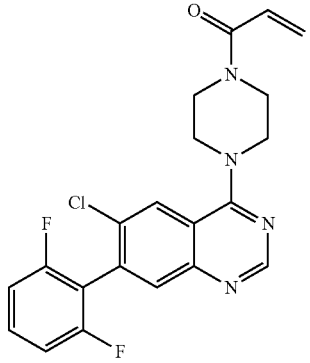 | 1-(4-(6-chloro-7-(2,6-difluoro-phenyl) quinazolin-4-yl)piperazin-1-yl)prop-2-en-1-one |

TABLE 4-continued

Compounds Excluded From Certain Embodiments

| No. | Structure | Name |
|---|---|---|
| 2-56 | 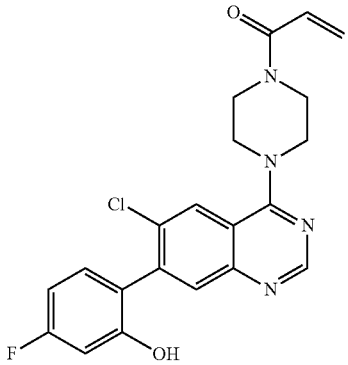 | 1-(4-(6-chloro-7-(4-fluoro-2-hydroxy-phenyl) quinazolin-4-yl)piperazin-1-yl)prop-2-en-1-one |
| 2-57 | 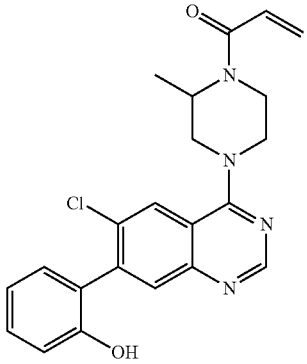 | 1-(4-(6-chloro-7-(2-hydroxy-phenyl) quinazolin-4-yl)-2-methyl-piperazin-1-yl)prop-2-en-1-one |
| 2-58 | 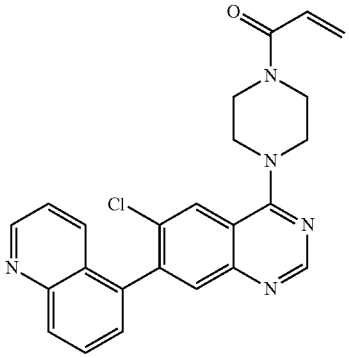 | 1-(4-(6-chloro-7-(quinolin-5-yl) quinazolin-4-yl)piperazin-1-yl)prop-2-en-1-one |
| 2-59 | 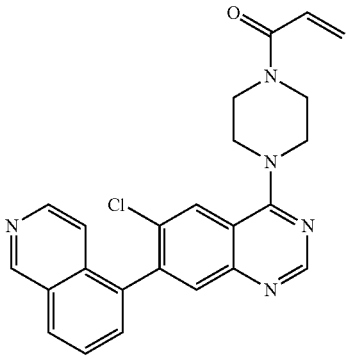 | 1-(4-(6-chloro-7-(isoquinolin-5-yl) quinazolin-4-yl)piperazin-1-yl)prop-2-en-1-one |

TABLE 4-continued

Compounds Excluded From Certain Embodiments

| No. | Structure | Name |
|---|---|---|
| 2-60 | 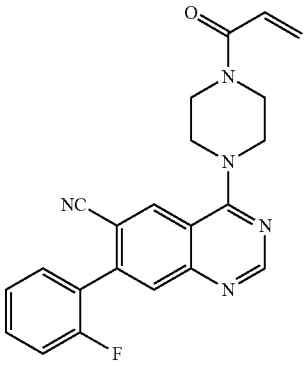 | 4-(4-acryloyl-piperazin-1-yl)-7-(2-fluorophenyl) quinazoline-6-carbonitrile |
| 2-61 | 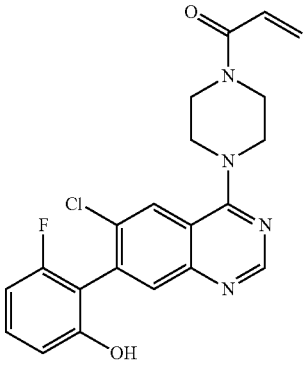 | 1-(4-(6-chloro-7-(2-fluoro-6-hydroxy-phenyl) quinazolin-4-yl)piperazin-1-yl)prop-2-en-1-one |
| 2-62 | 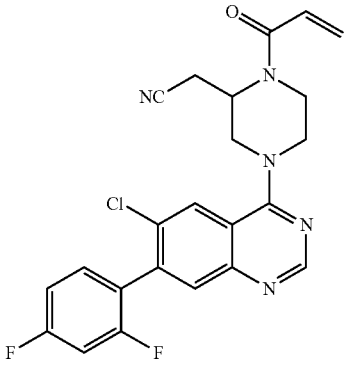 | 2-(1-acryloyl-4-(6-chloro-7-(2,4-difluoro-phenyl) quinazolin-4-yl)piperazin-2-yl) acetonitrile |
| 2-63 | 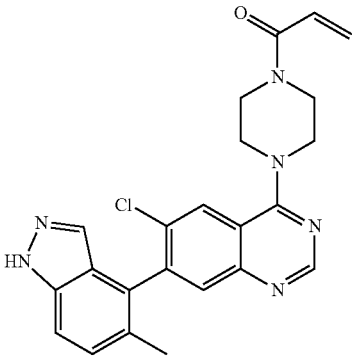 | 1-(4-(6-chloro-7-(5-methyl-1H-indazol-4-yl) quinazolin-4-yl)piperazin-1-yl)prop-2-en-1-one |

TABLE 4-continued

Compounds Excluded From Certain Embodiments

| No. | Structure | Name |
|---|---|---|
| 2-64 | 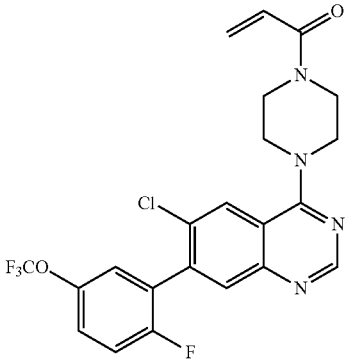 | 1-(4-(6-chloro-7-(2-fluoro-5-(trifluoro-methoxy) phenyl) quinazolin-4-yl)piperazin-1-yl)prop-2-en-1-one |
| 2-65 | 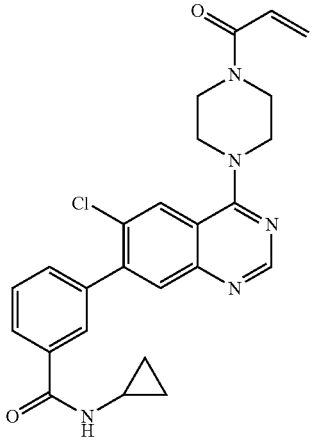 | 3-(4-(4-acryloyl-piperazin-1-yl)-6-chloro-quinazolin-7-yl)-N-cyclopropyl-benzamide |
| 2-66 | 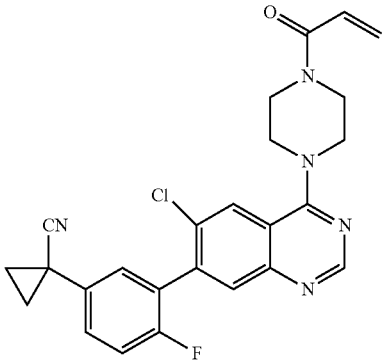 | 1-(3-(4-(4-acryloyl-piperazin-1-yl)-6-chloro-quinazolin-7-yl)-4-fluorophenyl) cyclopropane-carbonitrile |
| 2-67 | 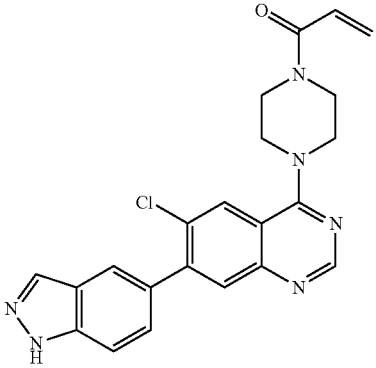 | 1-(4-(6-chloro-7-(1H-indazol-5-yl) quinazolin-4-yl)piperazin-1-yl)prop-2-en-1-one |

TABLE 4-continued

Compounds Excluded From Certain Embodiments

| No. | Structure | Name |
|---|---|---|
| 2-68 | 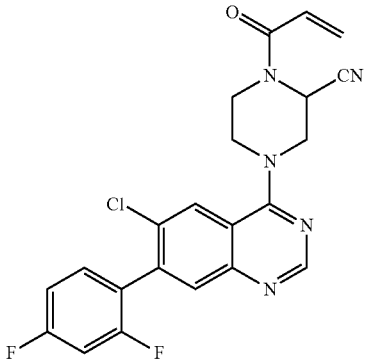 | 1-acryloyl-4-(6-chloro-7-(2,4-difluoro-phenyl) quinazolin-4-yl)piperazine-2-carbonitrile |
| 2-69 | 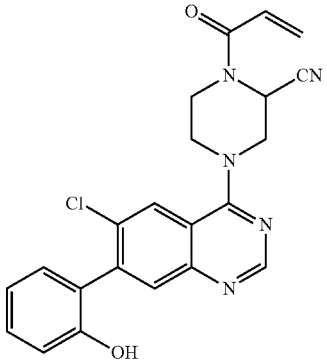 | 1-acryloyl-4-(6-chloro-7-(2-hydroxy-phenyl) quinazolin-4-yl)piperazine-2-carbonitrile |
| 2-70 | 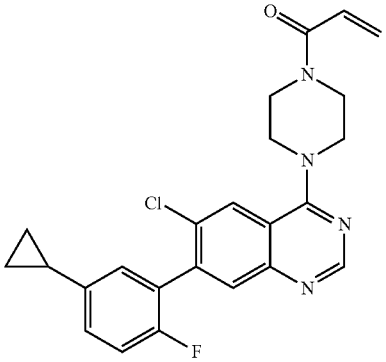 | 1-(4-(6-chloro-7-(5-cyclopropyl-2-fluoro-phenyl) quinazolin-4-yl)piperazin-1-yl)prop-2-en-1-one |
| 2-71 | 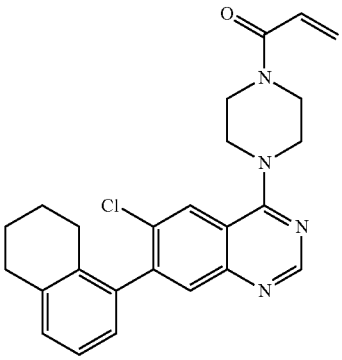 | 1-(4-(6-chloro-7-(5,6,7,8-tetrahydro-naphthalen-1-yl) quinazolin-4-yl)piperazin-1-yl)prop-2-en-1-one |

TABLE 4-continued

Compounds Excluded From Certain Embodiments

| No. | Structure | Name |
|---|---|---|
| 2-72 | 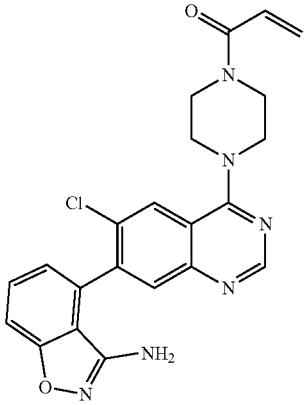 | 1-(4-(7-(3-amino-benzo[d] isoxazol-4-yl)-6-chloro-quinazolin-4-yl)piperazin-1-yl)prop-2-en-1-one |
| 2-73 | 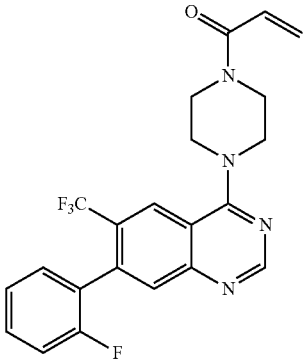 | 1-(4-(7-(2-fluorophenyl)-6-(trifluoro-methyl) quinazolin-4-yl)piperazin-1-yl)prop-2-en-1-one |
| 2-74 | 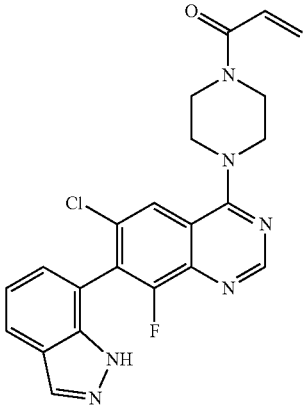 | 1-(4-(6-chloro-7-(1H-indazol-7-yl) quinazolin-4-yl)piperazin-1-yl)prop-2-en-1-one |
| 2-75 | 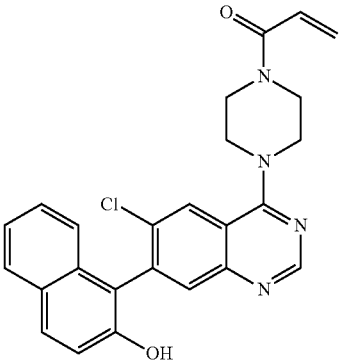 | 1-(4-(6-chloro-7-(2-hydroxy-naphthalen-1-yl) quinazolin-4-yl)piperazin-1-yl)prop-2-en-1-one |

TABLE 4-continued

Compounds Excluded From Certain Embodiments

| No. | Structure | Name |
|---|---|---|
| 2-76 | 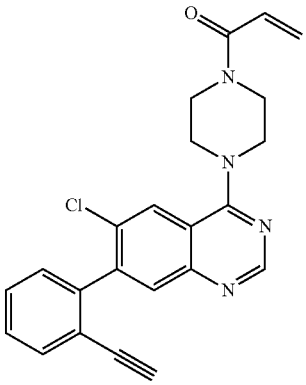 | 1-(4-(6-chloro-7-(2-ethynyl-phenyl) quinazolin-4-yl)piperazin-1-yl)prop-2-en-1-one |
| 2-77 | 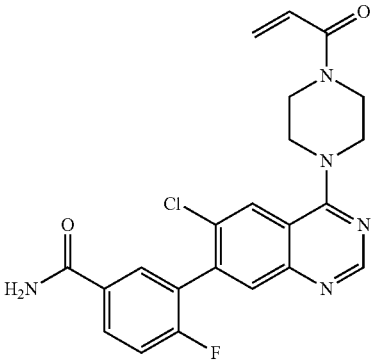 | 3-(4-(4-acryloyl-piperazin-1-yl)-6-chloro-quinazolin-7-yl)-4-fluoro-benzamide |
| 2-78 | 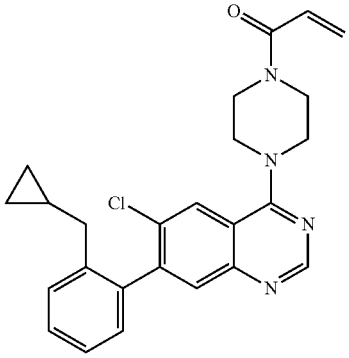 | 1-(4-(6-chloro-7-(2-(cyclopropyl-methyl) phenyl) quinazolin-4-yl)piperazin-1-yl)prop-2-en-1-one |
| 2-79 | 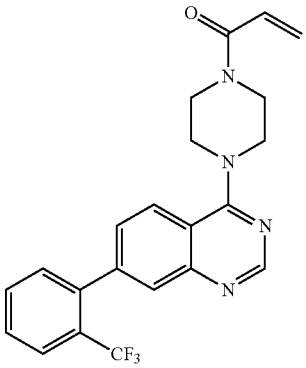 | 1-(4-(7-(2-(trifluoro-methyl) phenyl) quinazolin-4-yl)piperazin-1-yl)prop-2-en-1-one |

TABLE 4-continued

Compounds Excluded From Certain Embodiments

| No. | Structure | Name |
|---|---|---|
| 2-80 | 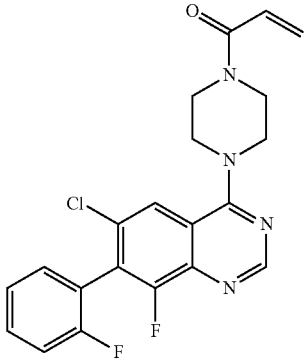 | 1-(4-(6-chloro-8-fluoro-7-(2-fluorophenyl) quinazolin-4-yl)piperazin-1-yl)prop-2-en-1-one |
| 2-81 | 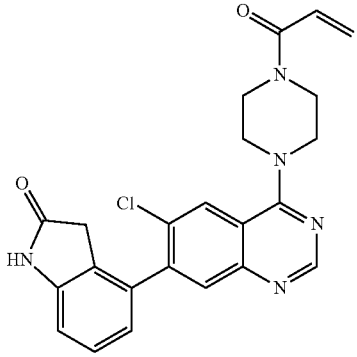 | 4-(4-(4-acryloyl-piperazin-1-yl)-6-chloro-quinazolin-7-yl)indolin-2-one |
| 2-82 | 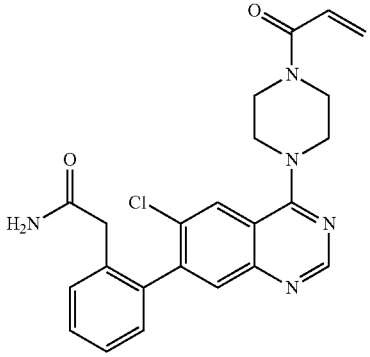 | 2-(2-(4-(4-acryloyl-piperazin-1-yl)-6-chloro-quinazolin-7-yl)phenyl) acetamide |
| 2-83 | 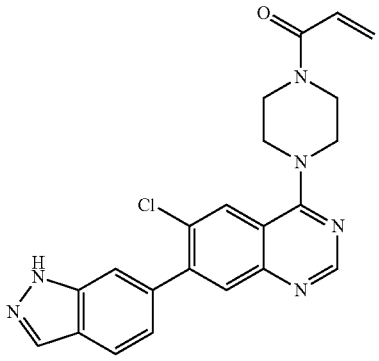 | 1-(4-(6-chloro-7-(1H-indazol-6-yl)quinazolin-4-yl)piperazin-1-yl)prop-2-en-1-one |

TABLE 4-continued

Compounds Excluded From Certain Embodiments

| No. | Structure | Name |
|---|---|---|
| 2-84 | 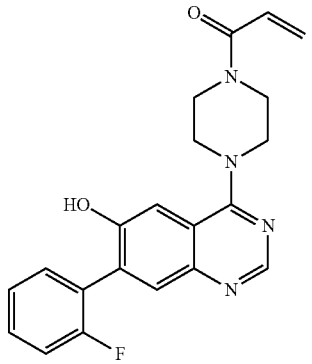 | 1-(4-(7-(2-fluorophenyl)-6-hydroxy-quinazolin-4-yl)piperazin-1-yl)prop-2-en-1-one |
| 2-85 | 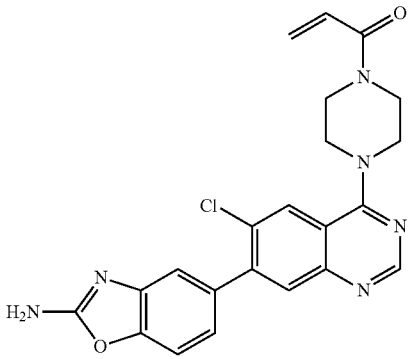 | 1-(4-(7-(2-aminobenzo[d]oxazol-5-yl)-6-chloro-quinazolin-4-yl)piperazin-1-yl)prop-2-en-1-one |
| 2-86 | 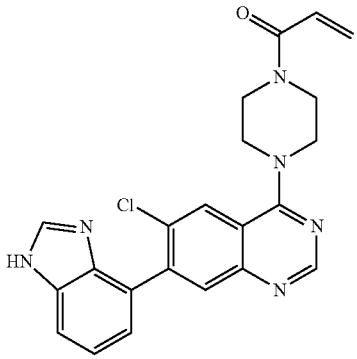 | 1-(4-(7-(1H-benzo[d]imidazol-4-yl)-6-chloro-quinazolin-4-yl)piperazin-1-yl)prop-2-en-1-one |
| 2-87 | 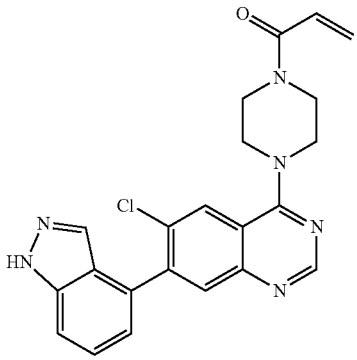 | 1-(4-(6-chloro-7-(1H-indazol-4-yl) quinazolin-4-yl)piperazin-1-yl)prop-2-en-1-one |

TABLE 4-continued

Compounds Excluded From Certain Embodiments

| No. | Structure | Name |
|---|---|---|
| 2-88 | 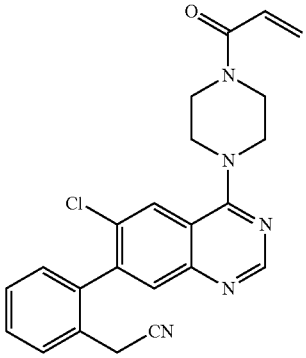 | 2-(2-(4-(4-acryloyl-piperazin-1-yl)-6-chloro-quinazolin-7-yl)phenyl) acetonitrile |
| 2-89 | 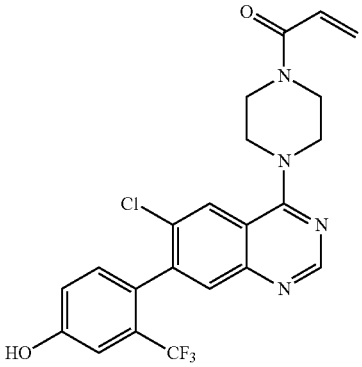 | 1-(4-(6-chloro-7-(4-hydroxy-2-(trifluoro-methyl) phenyl) quinazolin-4-yl)piperazin-1-yl)prop-2-en-1-one |
| 2-90 | 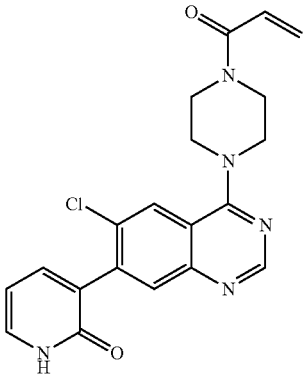 | 3-(4-(4-acryloyl-piperazin-1-yl)-6-chloro-quinazolin-7-yl)pyridin-2(1H)-one |
| 2-91 | 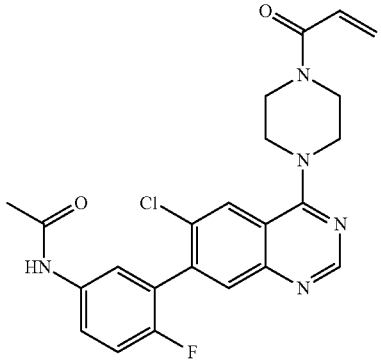 | N-(3-(4-(4-acryloyl-piperazin-1-yl)-6-chloro-quinazolin-7-yl)-4-fluorophenyl) acetamide |

TABLE 4-continued

Compounds Excluded From Certain Embodiments

| No. | Structure | Name |
|---|---|---|
| 2-92 | 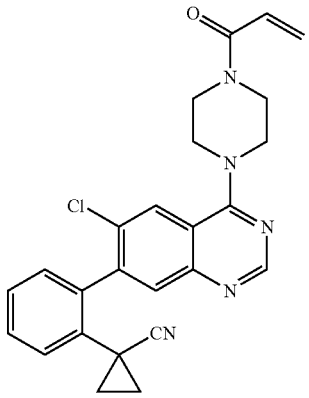 | 1-(2-(4-(4-acryloyl-piperazin-1-yl)-6-chloro-quinazolin-7-yl)phenyl) cyclopropane-carbonitrile |
| 2-93 | 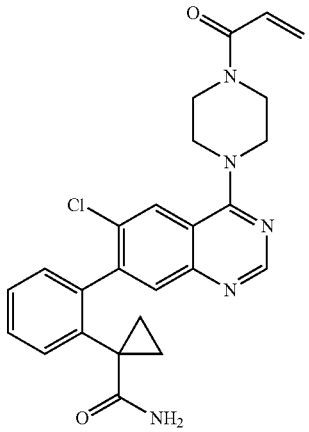 | 1-(2-(4-(4-acryloyl-piperazin-1-yl)-6-chloro-quinazolin-7-yl)phenyl) cyclopropane-carboxamide |
| 2-94 | 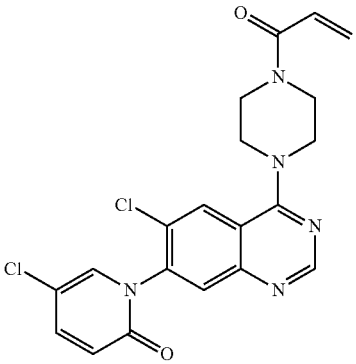 | 1-(4-(4-acryloyl-piperazin-1-yl)-6-chloro-quinazolin-7-yl)-5-chloro-pyridin-2(1H)-one |

TABLE 4-continued

Compounds Excluded From Certain Embodiments

| No. | Structure | Name |
|---|---|---|
| 2-95 | 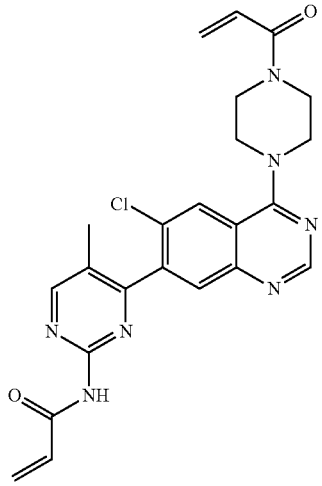 | N-(4-(4-(4-acryloyl-piperazin-1-yl)-6-chloro-quinazolin-7-yl)-5-methyl-pyrimidin-2-yl)acrylamide |
| 2-96 | 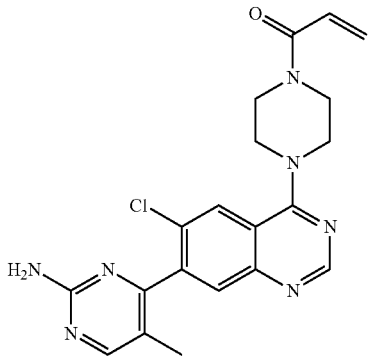 | 1-(4-(7-(2-amino-5-methyl-pyrimidin-4-yl)-6-chloro-quinazolin-4-yl)piperazin-1-yl)prop-2-en-1-one |
| 2-97 | 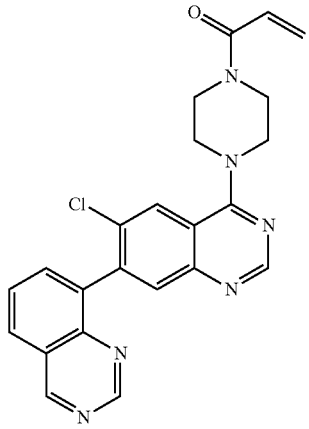 | 1-(4-(6-chloro-7,8'-biquinazolin-4-yl) piperazin-1-yl)prop-2-en-1-one |

TABLE 4-continued

Compounds Excluded From Certain Embodiments

| No. | Structure | Name |
|---|---|---|
| 2-98 | 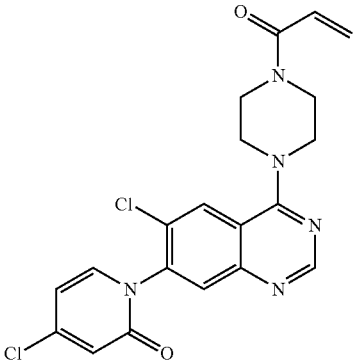 | 1-(4-(4-acryloyl-piperazin-1-yl)-6-chloro-quinazolin-7-yl)-4-chloro-pyridin-2(1H)-one |
| 2-99 | 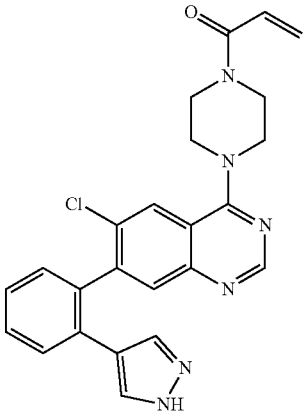 | 1-(4-(7-(2-(1H-pyrazol-4-yl)phenyl)-6-chloro-quinazolin-4-yl)piperazin-1-yl)prop-2-en-1-one |
| 2-100 | 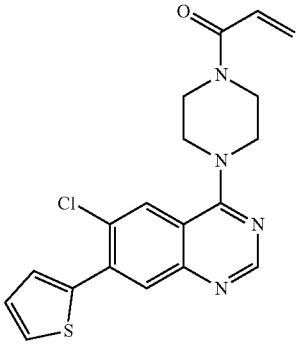 | 1-(4-(6-chloro-7-(thiophen-2-yl) quinazolin-4-yl)piperazin-1-yl)prop-2-en-1-one |
| 2-101 | 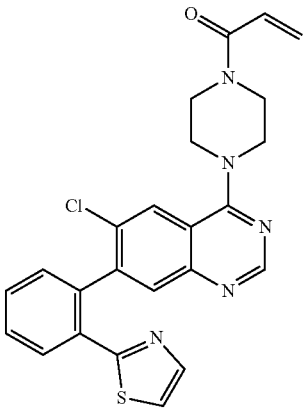 | 1-(4-(6-chloro-7-(2-(thiazol-2-yl)phenyl) quinazolin-4-yl)piperazin-1-yl)prop-2-en-1-one |

TABLE 4-continued

Compounds Excluded From Certain Embodiments

| No. | Structure | Name |
|---|---|---|
| 2-102 | 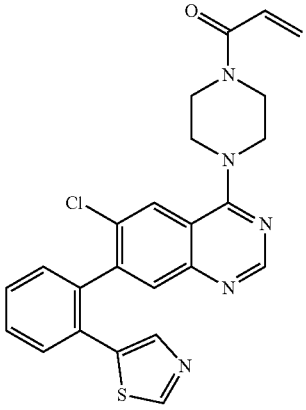 | 1-(4-(6-chloro-7-(2-(thiazol-5-yl)phenyl) quinazolin-4-yl)piperazin-1-yl)prop-2-en-1-one |
| 2-103 | 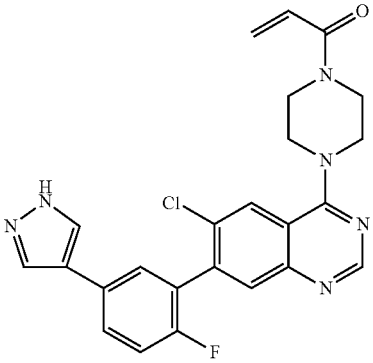 | 1-(4-(6-chloro-7-(2-fluoro-5-(1H-pyrazol-4-yl)phenyl) quinazolin-4-yl)piperazin-1-yl)prop-2-en-1-one |
| 2-104 | 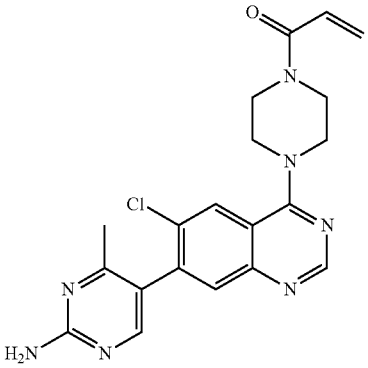 | 1-(4-(7-(2-amino-4-methyl-pyrimidin-5-yl)-6-chloro-quinazolin-4-yl)piperazin-1-yl)prop-2-en-1-one |
| 2-105 | 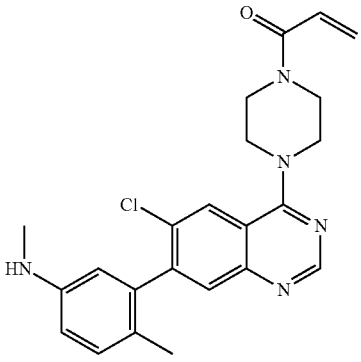 | 1-(4-(6-chloro-7-(2-methyl-5-(methyl-amino) phenyl) quinazolin-4-yl)piperazin-1-yl)prop-2-en-1-one |

TABLE 4-continued

Compounds Excluded From Certain Embodiments

| No. | Structure | Name |
|---|---|---|
| 2-106 | 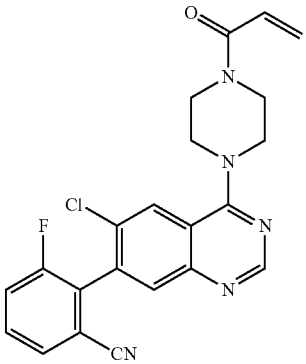 | 2-(4-(4-acryloyl-piperazin-1-yl)-6-chloro-quinazolin-7-yl)-3-fluoro-benzonitrile |
| 2-107 | 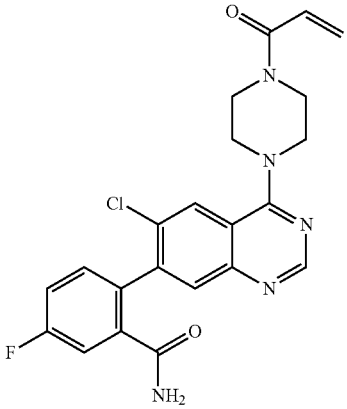 | 2-(4-(4-acryloyl-piperazin-1-yl)-6-chloro-quinazolin-7-yl)-5-fluoro-benzamide |
| 2-108 | 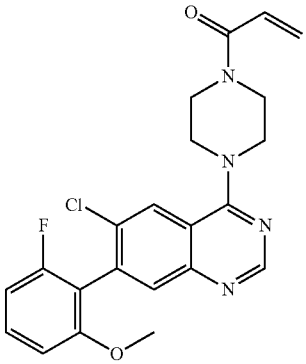 | 1-(4-(6-chloro-7-(2-fluoro-6-methoxy-phenyl) quinazolin-4-yl)piperazin-1-yl)prop-2-en-1-one |
| 2-109 | 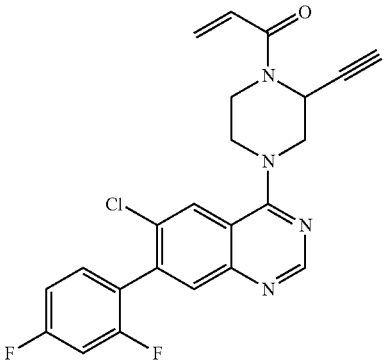 | 1-(4-(6-chloro-7-(2,4-difluoro-phenyl) quinazolin-4-yl)-2-ethynyl-piperazin-1-yl)prop-2-en-1-one |

TABLE 4-continued

Compounds Excluded From Certain Embodiments

| No. | Structure | Name |
|---|---|---|
| 2-110 | 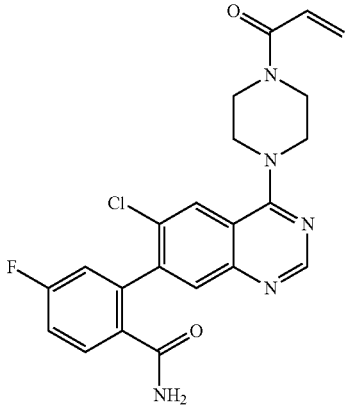 | 2-(4-(4-acryloyl-piperazin-1-yl)-6-chloro-quinazolin-7-yl)-4-fluoro-benzamide |
| 2-111 | 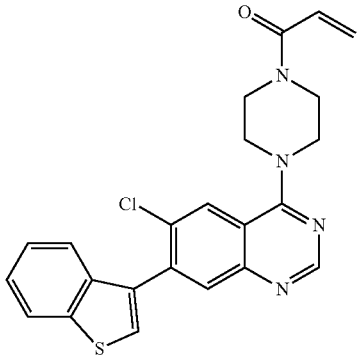 | 1-(4-(7-(benzo[b] thiophen-3-yl)-6-chloro-quinazolin-4-yl)piperazin-1-yl)prop-2-en-1-one |
| 2-112 | 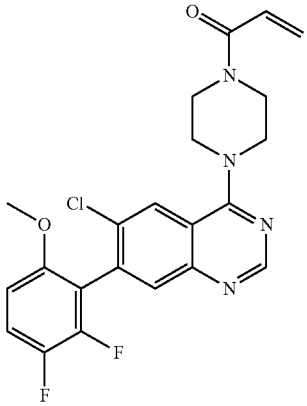 | 1-(4-(6-chloro-7-(2,3-difluoro-6-methoxy-phenyl) quinazolin-4-yl)piperazin-1-yl)prop-2-en-1-one |
| 2-113 | 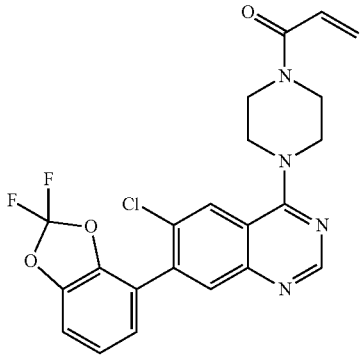 | 1-(4-(6-chloro-7-(2,2-difluoro-benzo[d] [1,3]dioxol-4-yl) quinazolin-4-yl)piperazin-1-yl)prop-2-en-1-one |

TABLE 4-continued

Compounds Excluded From Certain Embodiments

| No. | Structure | Name |
|---|---|---|
| 2-114 | 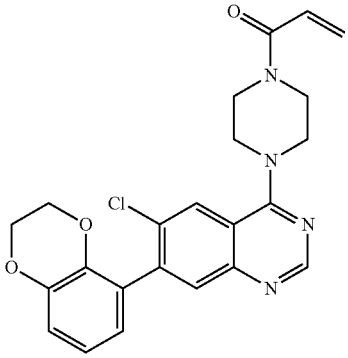 | 1-(4-(6-chloro-7-(2,3-dihydro-benzo[b][1,4]dioxin-5-yl) quinazolin-4-yl)piperazin-1-yl)prop-2-en-1-one |
| 2-115 | 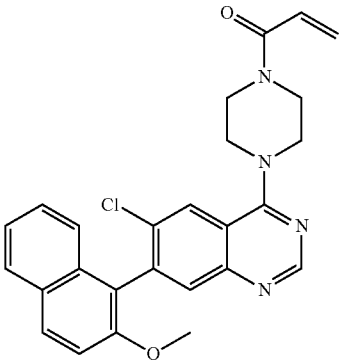 | 1-(4-(6-chloro-7-(2-methoxy-naphthalen-1-yl) quinazolin-4-yl)piperazin-1-yl)prop-2-en-1-one |
| 2-116 | 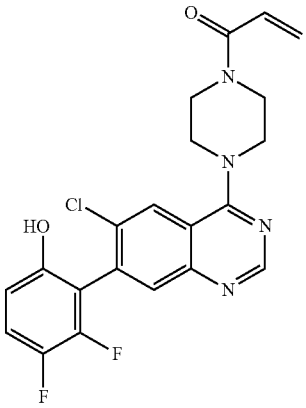 | 1-(4-(6-chloro-7-(2,3-difluoro-6-hydroxy-phenyl) quinazolin-4-yl)piperazin-1-yl)prop-2-en-1-one |
| 2-117 | 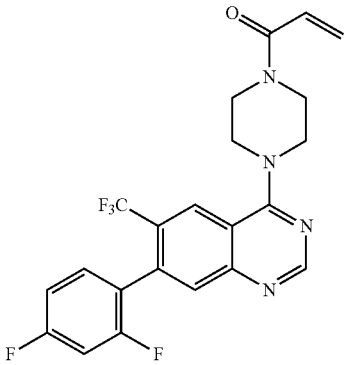 | 1-(4-(7-(2,4-difluoro-phenyl)-6-(trifluoro-methyl) quinazolin-4-yl)piperazin-1-yl)prop-2-en-1-one |

TABLE 4-continued

Compounds Excluded From Certain Embodiments

| No. | Structure | Name |
|---|---|---|
| 2-118 | 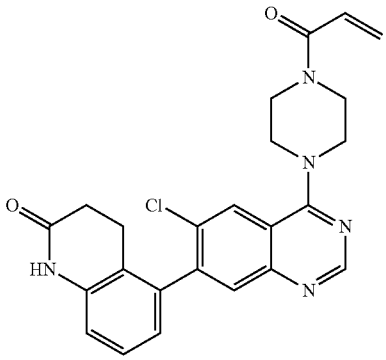 | 5-(4-(4-acryloyl-piperazin-1-yl)-6-chloro-quinazolin-7-yl)-3,4-dihydro-quinolin-2(1H)-one |
| 2-119 | 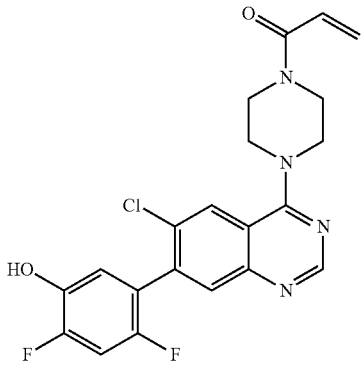 | 1-(4-(6-chloro-7-(2,4-difluoro-5-hydroxy-phenyl) quinazolin-4-yl)piperazin-1-yl)prop-2-en-1-one |
| 2-120 | 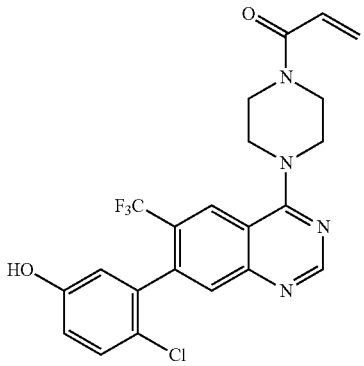 | 1-(4-(7-(2-chloro-5-hydroxy-phenyl)-6-(trifluoro-methyl) quinazolin-4-yl)piperazin-1-yl)prop-2-en-1-one |
| 2-121 | 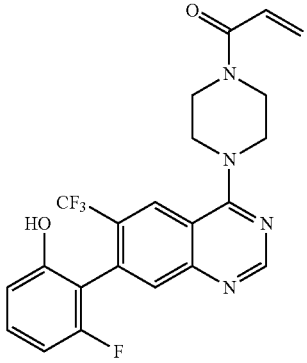 | 1-(4-(7-(2-fluoro-6-hydroxy-phenyl)-6-(trifluoro-methyl) quinazolin-4-yl)piperazin-1-yl)prop-2-en-1-one |

TABLE 4-continued

Compounds Excluded From Certain Embodiments

| No. | Structure | Name |
|---|---|---|
| 2-122 | 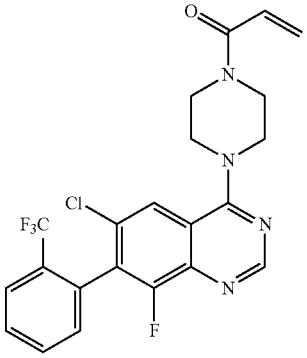 | 1-(4-(6-chloro-8-fluoro-7-(2-(trifluoromethyl)phenyl)quinazolin-4-yl)piperazin-1-yl)prop-2-en-1-one |
| 2-123 | 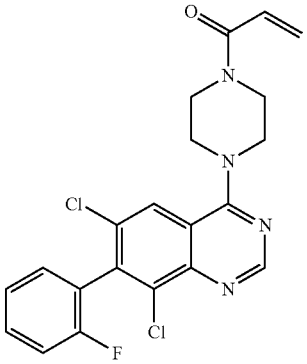 | 1-(4-(6,8-dichloro-7-(2-fluorophenyl)quinazolin-4-yl)piperazin-1-yl)prop-2-en-1-one |
| 2-124 | 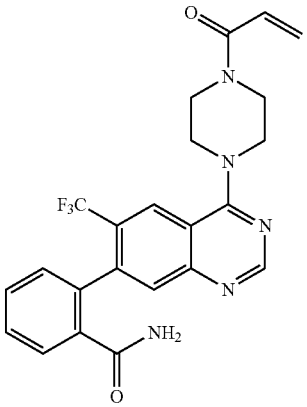 | 2-(4-(4-acryloylpiperazin-1-yl)-6-(trifluoromethyl)quinazolin-7-yl)benzamide |
| 2-125 | 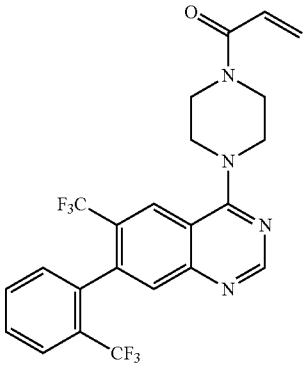 | 1-(4-(6-(trifluoromethyl)-7-(2-(trifluoromethyl)phenyl)quinazolin-4-yl)piperazin-1-yl)prop-2-en-1-one |

TABLE 4-continued

Compounds Excluded From Certain Embodiments

| No. | Structure | Name |
|---|---|---|
| 2-126 | 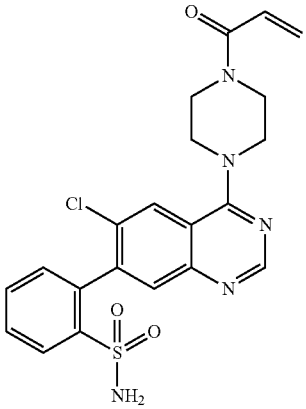 | 2-(4-(4-acryloylpiperazin-1-yl)-6-chloroquinazolin-7-yl)benzenesulfonamide |
| 2-127 | 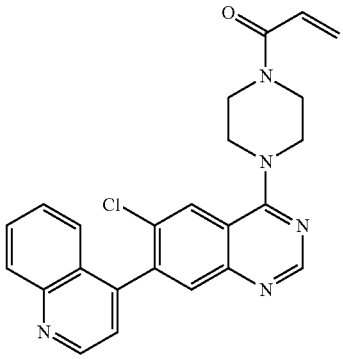 | 1-(4-(6-chloro-7-(quinolin-4-yl)quinazolin-4-yl)piperazin-1-yl)prop-2-en-1-one |
| 2-128 | 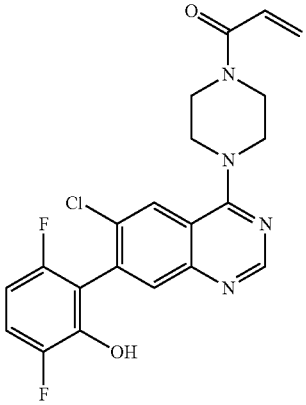 | 1-(4-(6-chloro-7-(3,6-difluoro-2-hydroxyphenyl)quinazolin-4-yl)piperazin-1-yl)prop-2-en-1-one |
| 2-129 | 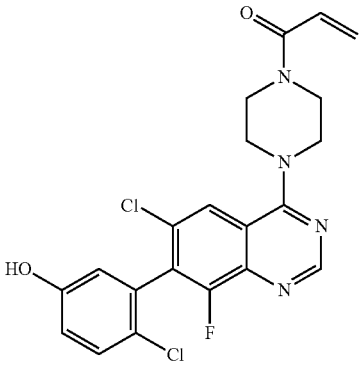 | 1-(4-(6-chloro-7-(2-chloro-5-hydroxyphenyl)-8-fluoroquinazolin-4-yl)piperazin-1-yl)prop-2-en-1-one |

TABLE 4-continued

Compounds Excluded From Certain Embodiments

| No. | Structure | Name |
|---|---|---|
| 2-130 | 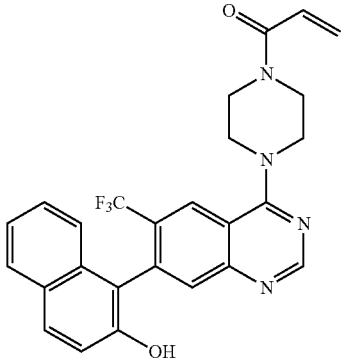 | 1-(4-(7-(2-hydroxy-naphthalen-1-yl)-6-(trifluoro-methyl) quinazolin-4-yl)piperazin-1-yl)prop-2-en-1-one |
| 2-131 | 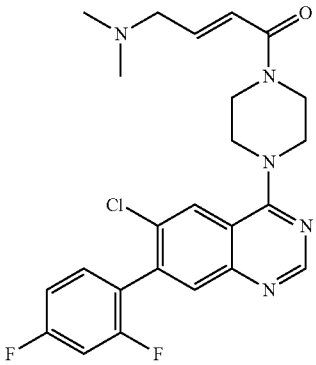 | (E)-1-(4-(6-chloro-7-(2,4-difluoro-phenyl) quinazolin-4-yl)piperazin-1-yl)-4-(dimethyl-amino)but-2-en-1-one |
| 2-132 | 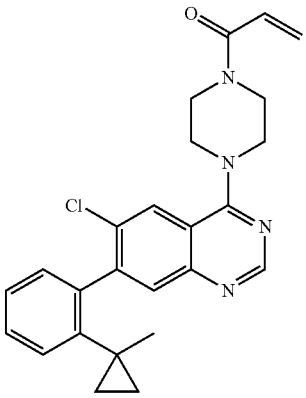 | 1-(4-(6-chloro-7-(2-(1-methyl-cyclopropyl) phenyl) quinazolin-4-yl)piperazin-1-yl)prop-2-en-1-one |
| 2-133 | 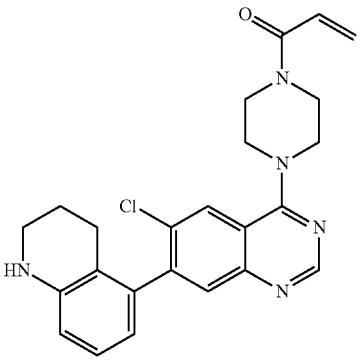 | 1-(4-(6-chloro-7-(1,2,3,4-tetrahydro-quinolin-5-yl) quinazolin-4-yl)piperazin-1-yl)prop-2-en-1-one |

TABLE 4-continued

Compounds Excluded From Certain Embodiments

| No. | Structure | Name |
|---|---|---|
| 2-134 | 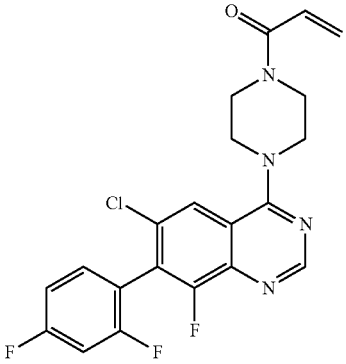 | 1-(4-(6-chloro-7-(2,4-difluoro-phenyl)-8-fluoro-quinazolin-4-yl)piperazin-1-yl)prop-2-en-1-one |
| 2-135 | 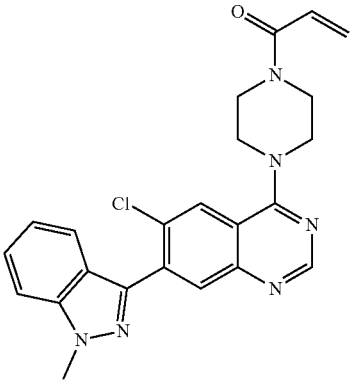 | 1-(4-(6-chloro-7-(1-methyl-1H-indazol-3-yl) quinazolin-4-yl)piperazin-1-yl)prop-2-en-1-one |
| 2-136 | 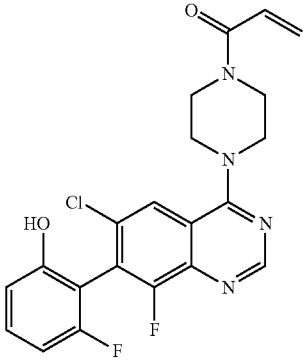 | 1-(4-(6-chloro-8-fluoro-7-(2-fluoro-6-hydroxy-phenyl) quinazolin-4-yl)piperazin-1-yl)prop-2-en-1-one |
| 2-137 | 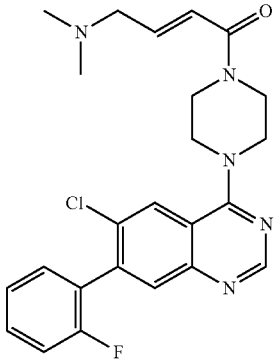 | (E)-1-(4-(6-chloro-7-(2-fluorophenyl) quinazolin-4-yl)piperazin-1-yl)-4-(dimethyl-amino)but-2-en-1-one |

TABLE 4-continued

Compounds Excluded From Certain Embodiments

| No. | Structure | Name |
|---|---|---|
| 2-138 | 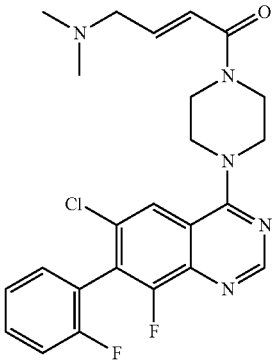 | (E)-1-(4-(6-chloro-8-fluoro-7-(2-fluorophenyl) quinazolin-4-yl)piperazin-1-yl)-4-(dimethyl-amino)but-2-en-1-one |
| 2-139 | 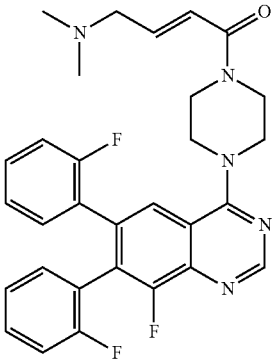 | (E)-4-(dimethyl-amino)-1-(4-(8-fluoro-6,7-bis(2-fluorophenyl) quinazolin-4-yl)piperazin-1-yl)but-2-en-1-one |
| 2-140 | 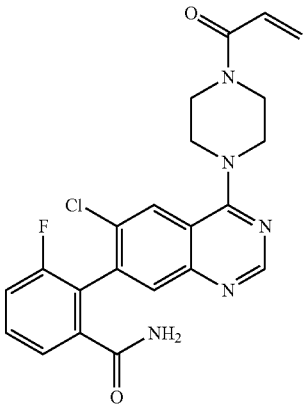 | 2-(4-(4-acryloyl-piperazin-1-yl)-6-chloro-quinazolin-7-yl)-3-fluoro-benzamide |
| 2-141 | 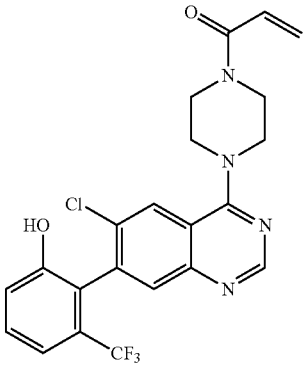 | 1-(4-(6-chloro-7-(2-hydroxy-6-(trifluoro-methyl) phenyl) quinazolin-4-yl)piperazin-1-yl)prop-2-en-1-one |

TABLE 4-continued

Compounds Excluded From Certain Embodiments

| No. | Structure | Name |
|---|---|---|
| 2-142 | 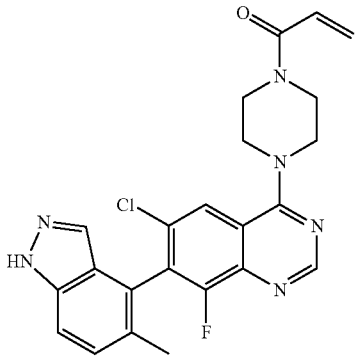 | 1-(4-(6-chloro-8-fluoro-7-(5-methyl-1H-indazol-4-yl) quinazolin-4-yl)piperazin-1-yl)prop-2-en-1-one |
| 2-143 | 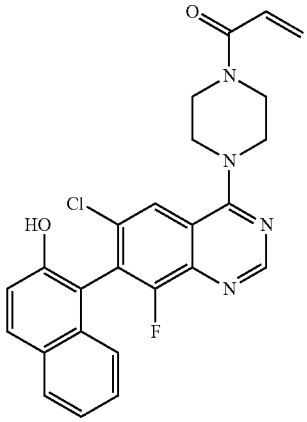 | 1-(4-(6-chloro-8-fluoro-7-(2-hydroxy-naphthalen-1-yl) quinazolin-4-yl)piperazin-1-yl)prop-2-en-1-one |
| 2-144 | 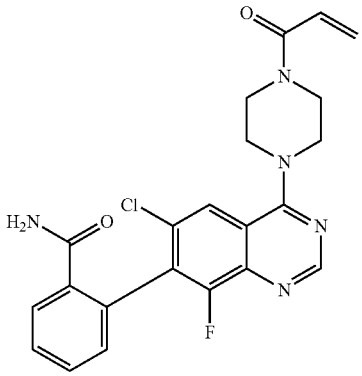 | 2-(4-(4-acryloyl-piperazin-1-yl)-6-chloro-8-fluoro-quinazolin-7-yl)benzamide |
| 2-145 | 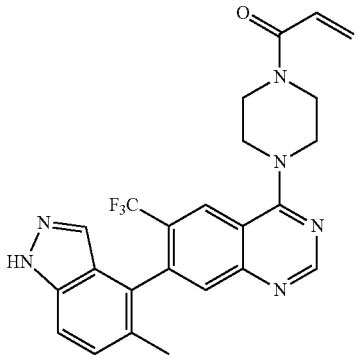 | 1-(4-(7-(5-methyl-1H-indazol-4-yl)-6-(trifluoro-methyl) quinazolin-4-yl)piperazin-1-yl)prop-2-en-1-one |

TABLE 4-continued

Compounds Excluded From Certain Embodiments

| No. | Structure | Name |
|---|---|---|
| 2-146 | 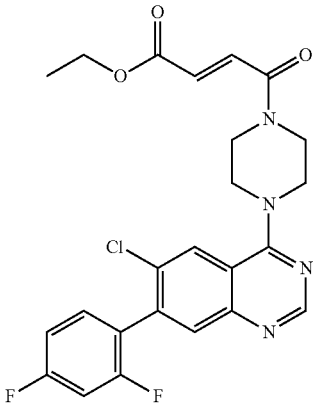 | (E)-ethyl 4-(4-(6-chloro-7-(2,4-difluoro-phenyl) quinazolin-4-yl)piperazin-1-yl)-4-oxobut-2-enoate |
| 2-147 | 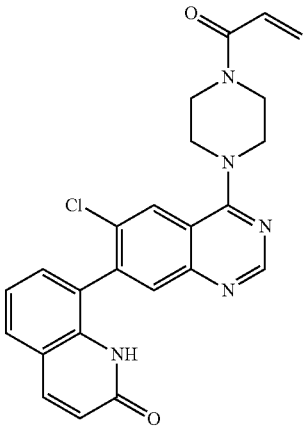 | 8-(4-(4-acryloyl-piperazin-1-yl)-6-chloro-quinazolin-7-yl)quinolin-2(1H)-one |
| 2-148 | 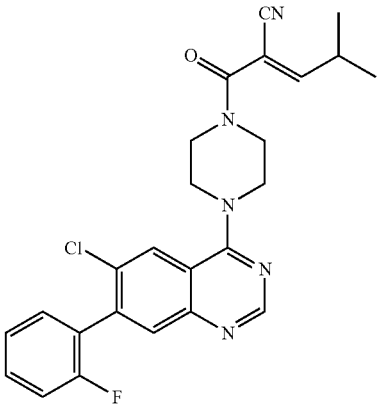 | (E)-2-(4-(6-chloro-7-(2-fluorophenyl) quinazolin-4-yl)piperazine-1-carbonyl)-4-methyl-pent-2-enenitrile |

TABLE 4-continued

Compounds Excluded From Certain Embodiments

| No. | Structure | Name |
|---|---|---|
| 2-149 | 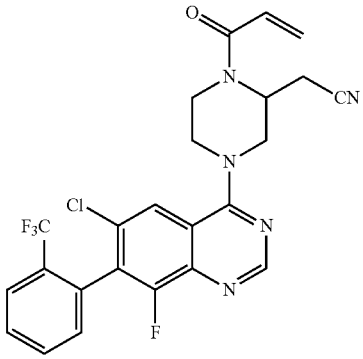 | 2-(1-acryloyl-4-(6-chloro-8-fluoro-7-(2-(trifluoro-methyl) phenyl) quinazolin-4-yl)piperazin-2-yl) acetonitrile |
| 2-150 | 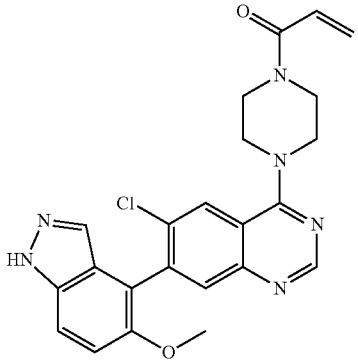 | 1-(4-(6-chloro-7-(5-methoxy-1H-indazol-4-yl) quinazolin-4-yl)piperazin-1-yl)prop-2-en-1-one |
| 2-151 | 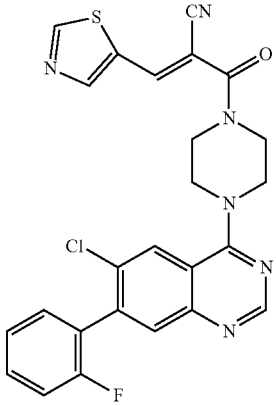 | (E)-2-(4-(6-chloro-7-(2-fluorophenyl) quinazolin-4-yl)piperazine-1-carbonyl)-3-(thiazol-5-yl) acrylonitrile |
| 2-152 | 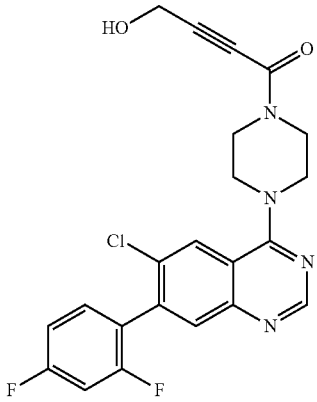 | 1-(4-(6-chloro-7-(2,4-difluoro-phenyl) quinazolin-4-yl)piperazin-1-yl)-4-hydroxybut-2-yn-1-one |

TABLE 4-continued

Compounds Excluded From Certain Embodiments

| No. | Structure | Name |
|---|---|---|
| 2-153 | 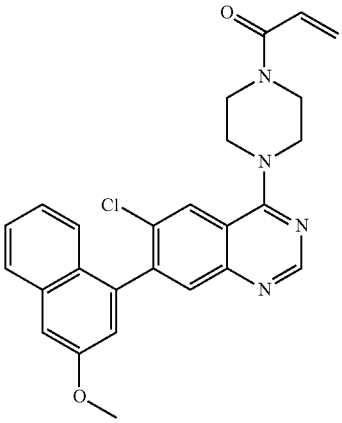 | 1-(4-(6-chloro-7-(3-methoxy-naphthalen-1-yl) quinazolin-4-yl)piperazin-1-yl)prop-2-en-1-one |
| 2-154 | 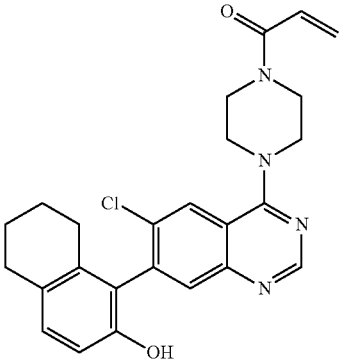 | 1-(4-(6-chloro-7-(2-hydroxy-5,6,7,8-tetrahydro-naphthalen-1-yl) quinazolin-4-yl)piperazin-1-yl)prop-2-en-1-one |
| 2-155 | 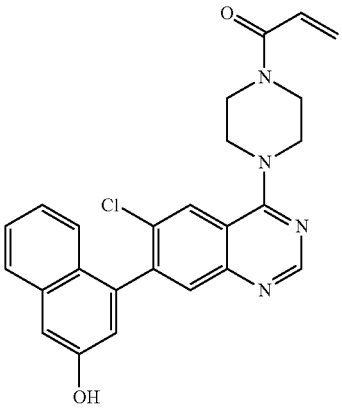 | 1-(4-(6-chloro-7-(3-hydroxy-naphthalen-1-yl) quinazolin-4-yl)piperazin-1-yl)prop-2-en-1-one |
| 2-156 | 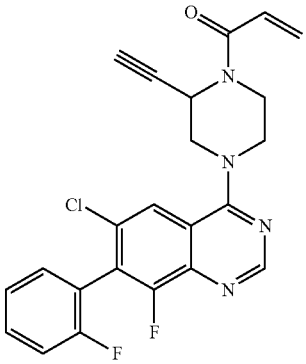 | 1-(4-(6-chloro-8-fluoro-7-(2-fluorophenyl) quinazolin-4-yl)-2-ethynyl-piperazin-1-yl)prop-2-en-1-one |

TABLE 4-continued

Compounds Excluded From Certain Embodiments

| No. | Structure | Name |
|---|---|---|
| 2-157 | 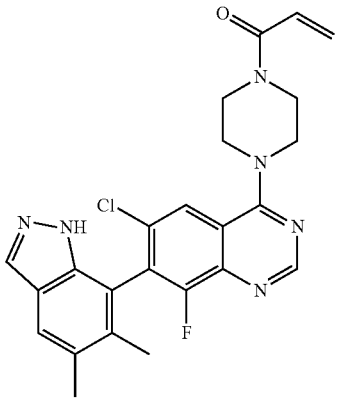 | 1-(4-(6-chloro-7-(5,6-dimethyl-1H-indazol-7-yl)-8-fluoro-quinazolin-4-yl)piperazin-1-yl)prop-2-en-1-one |
| 2-158 | 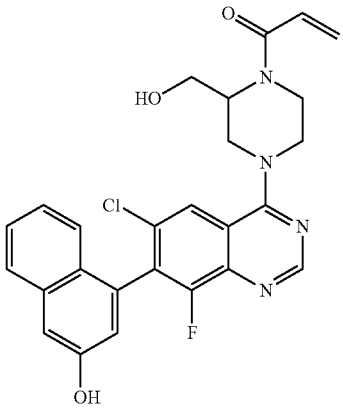 | 1-(4-(6-chloro-8-fluoro-7-(3-hydroxy-naphthalen-1-yl) quinazolin-4-yl)-2-(hydroxy-methyl) piperazin-1-yl)prop-2-en-1-one |
| 2-159 | 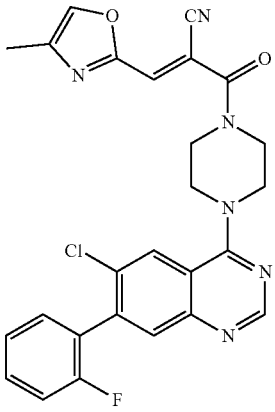 | (E)-2-(4-(6-chloro-7-(2-fluorophenyl) quinazolin-4-yl)piperazine-1-carbonyl)-3-(4-methyl-oxazo1-2-yl) acrylonitrile |

TABLE 4-continued

Compounds Excluded From Certain Embodiments

| No. | Structure | Name |
|---|---|---|
| 2-160 | 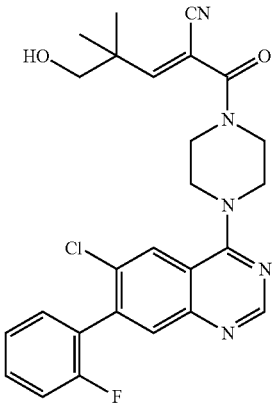 | (E)-2-(4-(6-chloro-7-(2-fluorophenyl) quinazolin-4-yl)piperazine-1-carbonyl)-5-hydroxy-4,4-dimethyl-pent-2-enenitrile |
| 2-161 | 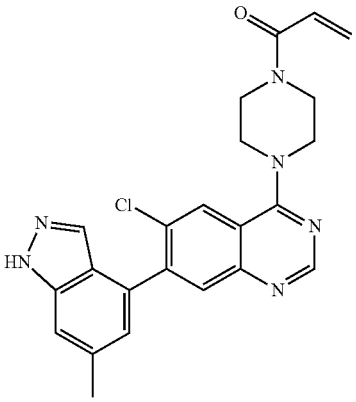 | 1-(4-(6-chloro-7-(6-methyl-1H-indazol-4-yl)quinazolin-4-yl) piperazin-1-yl)prop-2-en-1-one |
| 2-162 | 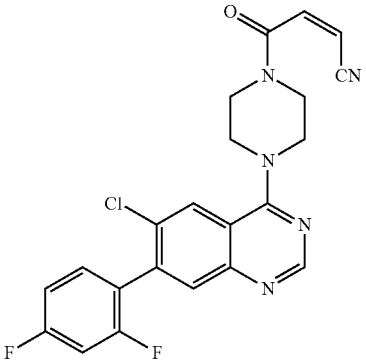 | (Z)-4-(4-(6-chloro-7-(2,4-difluoro-phenyl) quinazolin-4-yl)piperazin-1-yl)-4-oxobut-2-enenitrile |

TABLE 4-continued

Compounds Excluded From Certain Embodiments

| No. | Structure | Name |
|---|---|---|
| 2-163 | 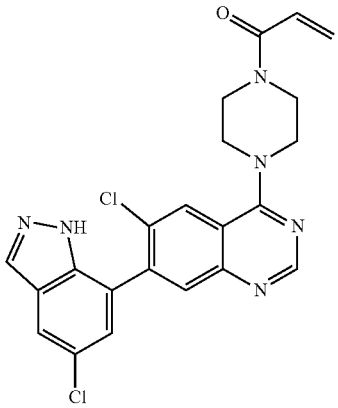 | 1-(4-(6-chloro-7-(5-chloro-1H-indazol-7-yl)quinazolin-4-yl) piperazin-1-yl)prop-2-en-1-one |
| 2-164 | 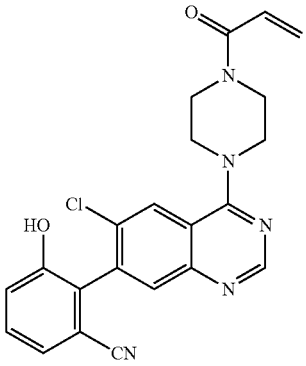 | 2-(4-(4-acryloyl-piperazin-1-yl)-6-chloro-quinazolin-7-yl)-3-hydroxy-benzonitrile |
| 2-165 | 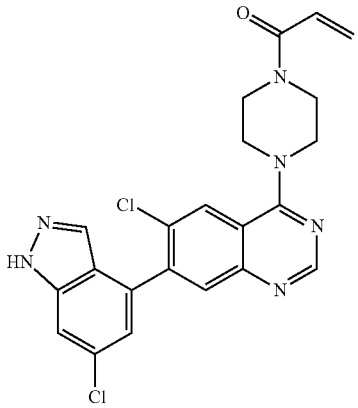 | 1-(4-(6-chloro-7-(6-chloro-1H-indazol-4-yl)quinazolin-4-yl) piperazin-1-yl)prop-2-en-1-one |
| 2-166 | 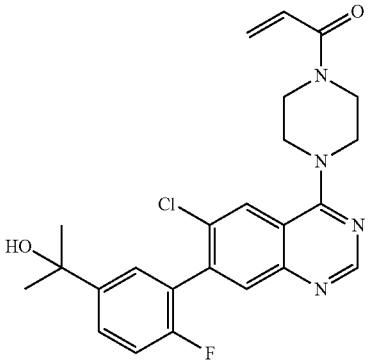 | 1-(4-(6-chloro-7-(2-fluoro-5-(2-hydroxy-propan-2-yl)phenyl) quinazolin-4-yl)piperazin-1-yl)prop-2-en-1-one |

TABLE 4-continued

Compounds Excluded From Certain Embodiments

| No. | Structure | Name |
|---|---|---|
| 2-167 | 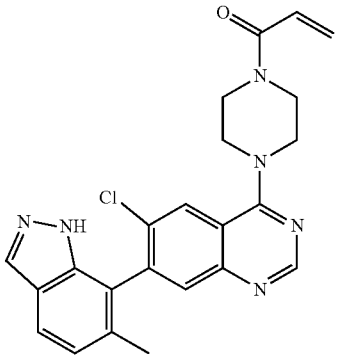 | 1-(4-(6-chloro-7-(6-methyl-1H-indazol-7-yl)quinazolin-4-yl)piperazin-1-yl)prop-2-en-1-one |
| 2-168 | 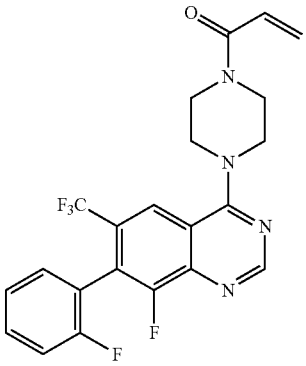 | 1-(4-(8-fluoro-7-(2-fluorophenyl)-6-(trifluoromethyl)quinazolin-4-yl)piperazin-1-yl)prop-2-en-1-one |
| 2-169 | 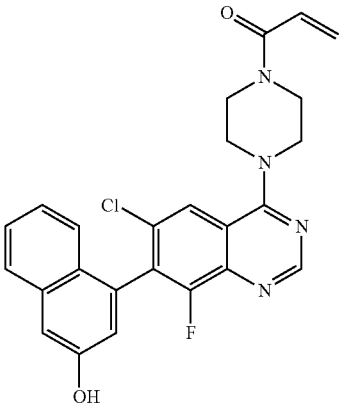 | 1-(4-(6-chloro-8-fluoro-7-(3-hydroxynaphthalen-1-yl)quinazolin-4-yl)piperazin-1-yl)prop-2-en-1-one |
| 2-170 | 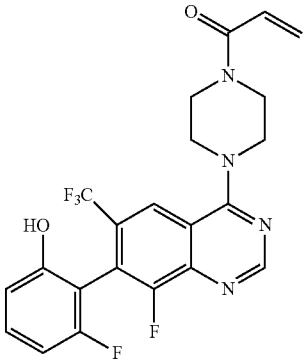 | 1-(4-(8-fluoro-7-(2-fluoro-6-hydroxyphenyl)-6-(trifluoromethyl)quinazolin-4-yl)piperazin-1-yl)prop-2-en-1-one |

TABLE 4-continued

Compounds Excluded From Certain Embodiments

| No. | Structure | Name |
|---|---|---|
| 2-171 | 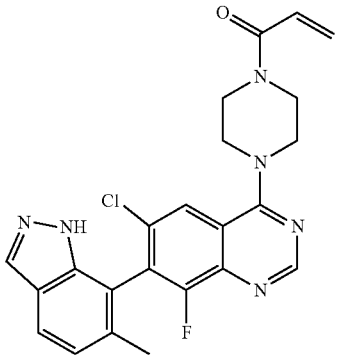 | 1-(4-(6-chloro-8-fluoro-7-(6-methyl-1H-indazol-7-yl)quinazolin-4-yl)piperazin-1-yl)prop-2-en-1-one |
| 2-172 | 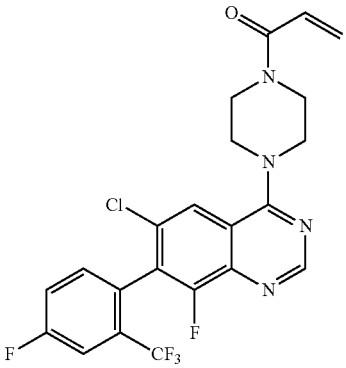 | 1-(4-(6-chloro-8-fluoro-7-(4-fluoro-2-(trifluoromethyl)phenyl)quinazolin-4-yl)piperazin-1-yl)prop-2-en-1-one |
| 2-173 | 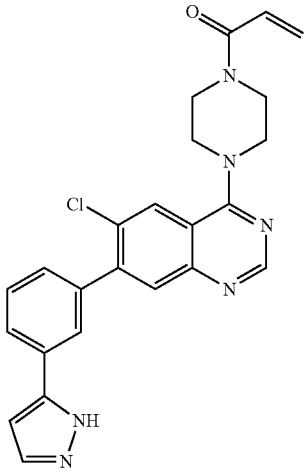 | 1-(4-(7-(3-(1H-pyrazol-5-yl)phenyl)-6-chloroquinazolin-4-yl)piperazin-1-yl)prop-2-en-1-one |

TABLE 4-continued

Compounds Excluded From Certain Embodiments

| No. | Structure | Name |
|---|---|---|
| 2-174 | 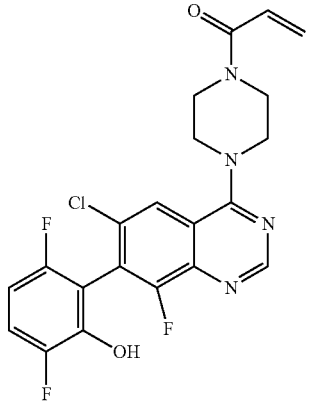 | 1-(4-(6-chloro-7-(3,6-difluoro-2-hydroxy-phenyl)-8-fluoro-quinazolin-4-yl)piperazin-1-yl)prop-2-en-1-one |
| 2-175 | 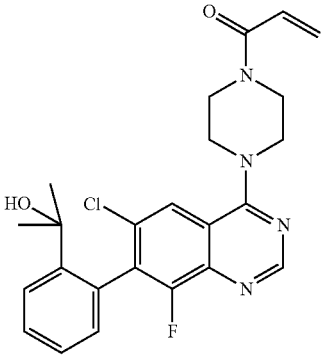 | 1-(4-(6-chloro-8-fluoro-7-(2-(2-hydroxy-propan-2-yl)phenyl) quinazolin-4-yl)piperazin-1-yl)prop-2-en-1-one |
| 2-176 | 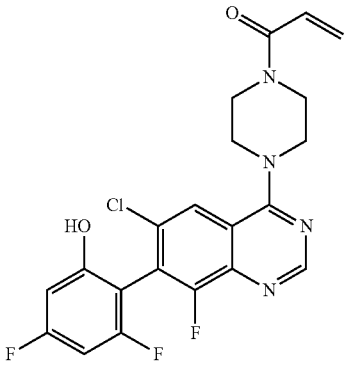 | 1-(4-(6-chloro-7-(2,4-difluoro-6-hydroxy-phenyl)-8-fluoro-quinazolin-4-yl)piperazin-1-yl)prop-2-en-1-one |
| 2-177 | 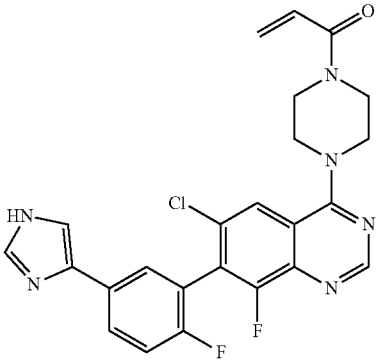 | 1-(4-(6-chloro-8-fluoro-7-(2-fluoro-5-(1H-imidazol-4-yl)phenyl) quinazolin-4-yl)piperazin-1-yl)prop-2-en-1-one |

TABLE 4-continued

Compounds Excluded From Certain Embodiments

| No. | Structure | Name |
|---|---|---|
| 2-178 | 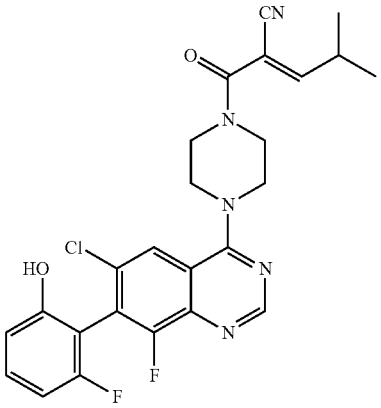 | (E)-2-(4-(6-chloro-8-fluoro-7-(2-fluoro-6-hydroxy-phenyl) quinazolin-4-yl)piperazine-1-carbonyl)-4-methylpent-2-enenitrile |
| 2-179 | 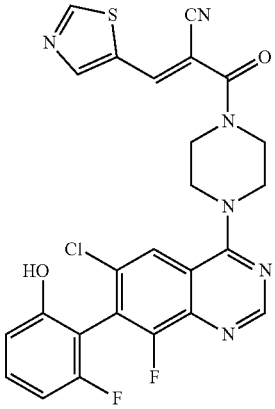 | (E)-2-(4-(6-chloro-8-fluoro-7-(2-fluoro-6-hydroxy-phenyl) quinazolin-4-yl)piperazine-1-carbonyl)-3-(thiazol-5-yl) acrylonitrile |
| 2-180 | 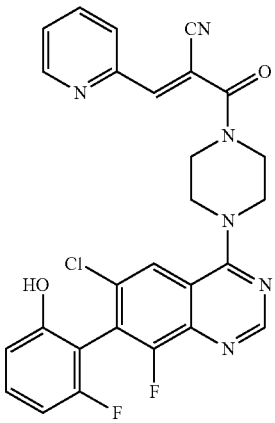 | (E)-2-(4-(6-chloro-8-fluoro-7-(2-fluoro-6-hydroxy-phenyl) quinazolin-4-yl)piperazine-1-carbonyl)-3-(pyridin-2-yl) acrylonitrile |

TABLE 4-continued

Compounds Excluded From Certain Embodiments

| No. | Structure | Name |
|---|---|---|
| 2-181 | 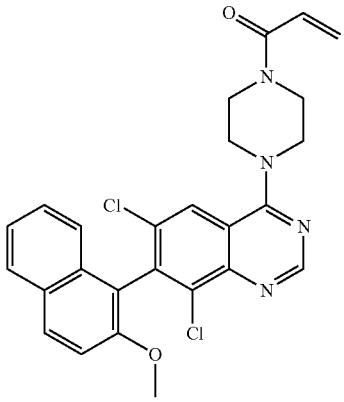 | 1-(4-(6,8-dichloro-7-(2-methoxy-naphthalen-1-yl) quinazolin-4-yl)piperazin-1-yl)prop-2-en-1-one |
| 2-182 | 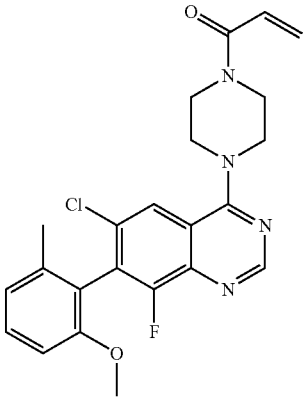 | 1-(4-(6-chloro-8-fluoro-7-(2-methoxy-6-methylphenyl) quinazolin-4-yl) piperazin-1-yl)prop-2-en-1-one |
| 2-183 | 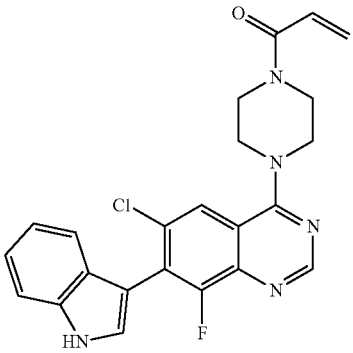 | 1-(4-(6-chloro-8-fluoro-7-(1H-indol-3-yl)quinazolin-4-yl) piperazin-1-yl)prop-2-en-1-one |
| 2-184 | 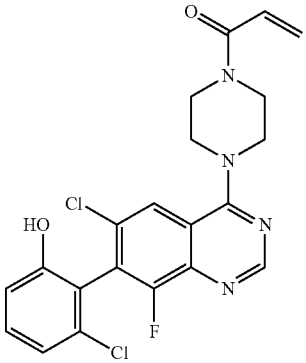 | 1-(4-(6-chloro-7-(2-chloro-6-hydroxy-phenyl)-8-fluoro-quinazolin-4-yl)piperazin-1-yl)prop-2-en-1-one |

TABLE 4-continued

Compounds Excluded From Certain Embodiments

| No. | Structure | Name |
|---|---|---|
| 2-185 | 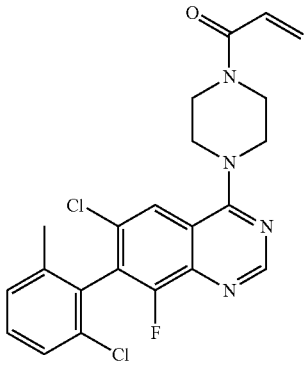 | 1-(4-(6-chloro-7-(2-chloro-6-methyl-phenyl)-8-fluoro-quinazolin-4-yl)piperazin-1-yl)prop-2-en-1-one |
| 2-186 | 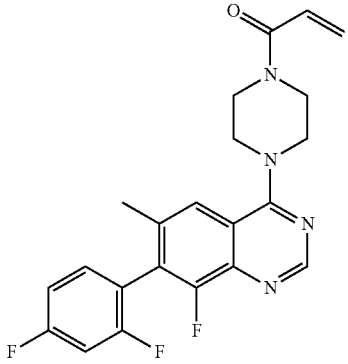 | 1-(4-(7-(2,4-difluoro-phenyl)-8-fluoro-6-methyl-quinazolin-4-yl)piperazin-1-yl)prop-2-en-1-one |
| 2-187 | 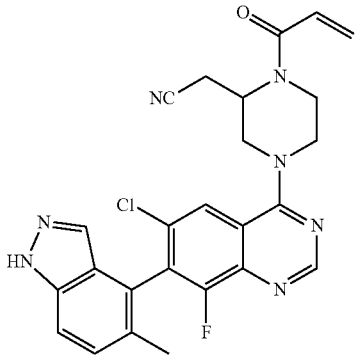 | 2-(1-acryloyl-4-(6-chloro-8-fluoro-7-(5-methyl-1H-indazol-4-yl) quinazolin-4-yl)piperazin-2-yl) acetonitrile |
| 2-188 | 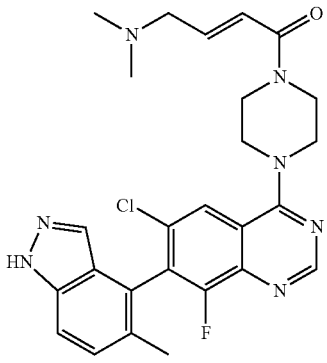 | (E)-1-(4-(6-chloro-8-fluoro-7-(5-methyl-1H-indazol-4-yl)quinazolin-4-yl) piperazin-1-yl)-4-(dimethyl-amino)but-2-en-1-one |

TABLE 4-continued

Compounds Excluded From Certain Embodiments

| No. | Structure | Name |
|---|---|---|
| 2-189 | 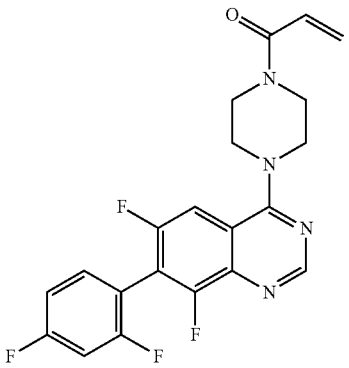 | 1-(4-(7-(2,4-difluoro-phenyl)-6,8-difluoro-quinazolin-4-yl)piperazin-1-yl)prop-2-en-1-one |
| 2-190 | 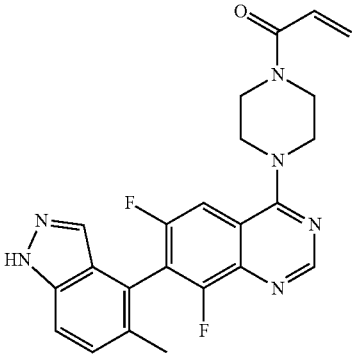 | 1-(4-(6,8-difluoro-7-(5-methyl-1H-indazol-4-yl) quinazolin-4-yl)piperazin-1-yl)prop-2-en-1-one |
| 2-191 | 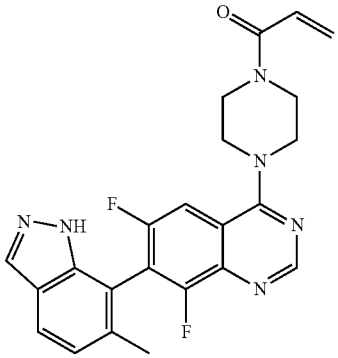 | 1-(4-(6,8-difluoro-7-(6-methyl-1H-indazol-7-yl) quinazolin-4-yl)piperazin-1-yl)prop-2-en-1-one |
| 2-192 | 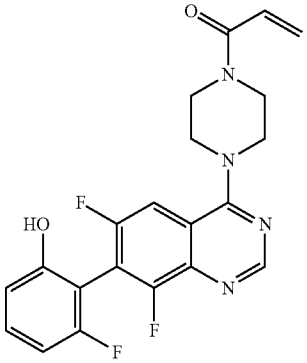 | 1-(4-(6,8-difluoro-7-(2-fluoro-6-hydroxy-phenyl) quinazolin-4-yl)piperazin-1-yl)prop-2-en-1-one |

TABLE 4-continued

Compounds Excluded From Certain Embodiments

| No. | Structure | Name |
|---|---|---|
| 2-193 | 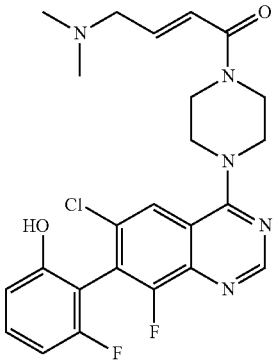 | (E)-1-(4-(6-chloro-8-fluoro-7-(2-fluoro-6-hydroxy-phenyl) quinazolin-4-yl)piperazin-1-yl)-4-(dimethyl-amino)but-2-en-1-one |
| 2-194 | 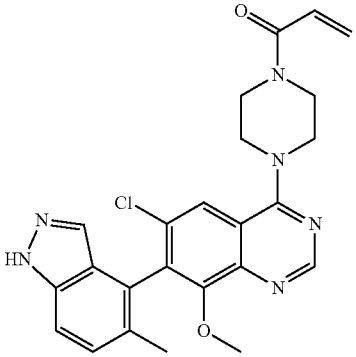 | 1-(4-(6-chloro-8-methoxy-7-(5-methyl-1H-indazol-4-yl) quinazolin-4-yl)piperazin-1-yl)prop-2-en-1-one |
| 2-195 | 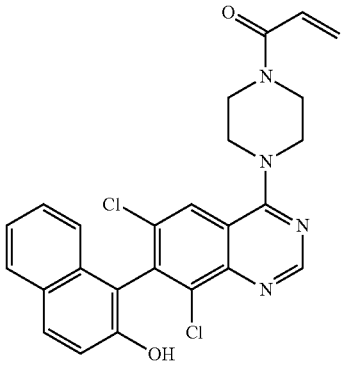 | 1-(4-(6,8-dichloro-7-(2-hydroxy-naphthalen-1-yl) quinazolin-4-yl)piperazin-1-yl)prop-2-en-1-one |
| 2-196 | 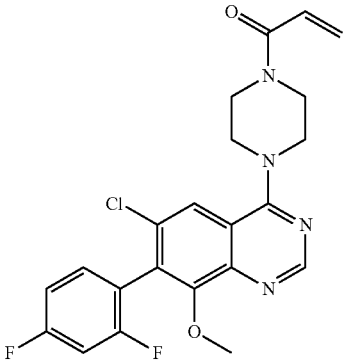 | 1-(4-(6-chloro-7-(2,4-difluoro-phenyl)-8-methoxy-quinazolin-4-yl)piperazin-1-yl)prop-2-en-1-one |

TABLE 4-continued

Compounds Excluded From Certain Embodiments

| No. | Structure | Name |
|---|---|---|
| 2-197 | 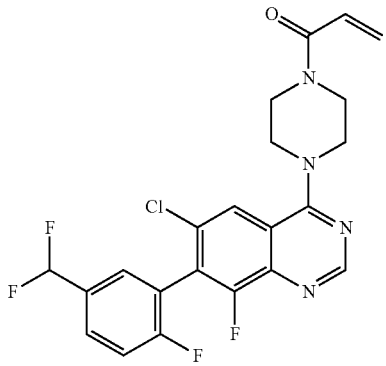 | 1-(4-(6-chloro-7-(5-(difluoro-methyl)-2-fluorophenyl)-8-fluoro-quinazolin-4-yl)piperazin-1-yl)prop-2-en-1-one |
| 2-198 | 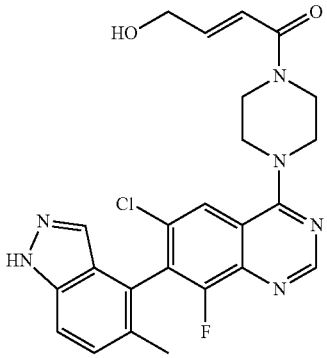 | (E)-4-amino-1-(4-(6-chloro-8-fluoro-7-(5-methyl-1H-indazol-4-yl) quinazolin-4-yl)piperazin-1-yl)but-2-en-1-one |
| 2-199 | 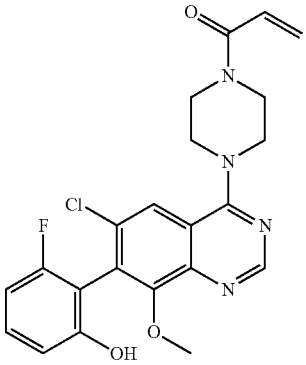 | 1-(4-(6-chloro-7-(2-fluoro-6-hydroxy-phenyl)-8-methoxy-quinazolin-4-yl)piperazin-1-yl)prop-2-en-1-one |
| 2-200 | 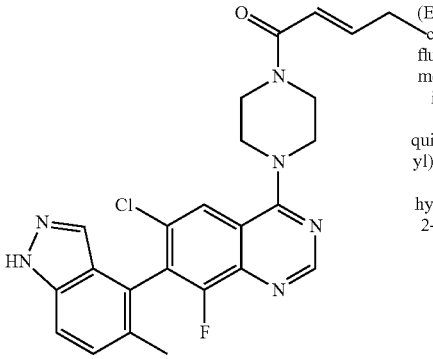 | (E)-1-(4-(6-chloro-8-fluoro-7-(5-methyl-1H-indazol-4-yl) quinazolin-4-yl)piperazin-1-yl)-4-hydroxybut-2-en-1-one |

TABLE 4-continued

Compounds Excluded From Certain Embodiments

| No. | Structure | Name |
|---|---|---|
| 2-201 | 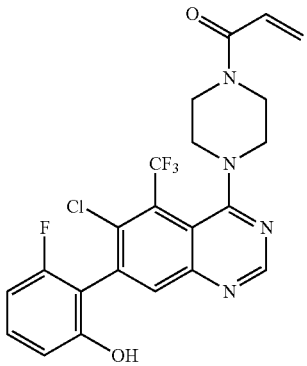 | 1-(4-(6-chloro-7-(2-fluoro-6-hydroxy-phenyl)-5-(trifluoro-methyl) quinazolin-4-yl)piperazin-1-yl)prop-2-en-1-one |
| 2-202 | 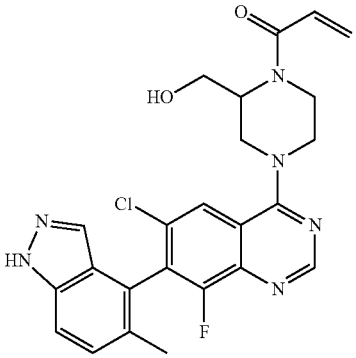 | 1-(4-(6-chloro-8-fluoro-7-(5-methyl-1H-indazol-4-yl)quinazo-lin-4-yl)-2-(hydroxy-methyl) piperazin-2-yl)prop-2-en-1-one |
| 2-203 | 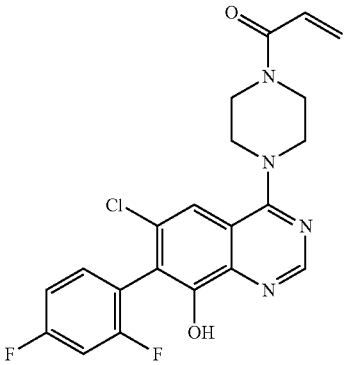 | 1-(4-(6-chloro-7-(2,4-difluoro-phenyl)-8-hydroxy-quinazolin-4-yl)piperazin-1-yl)prop-2-en-1-one |
| 2-204 | 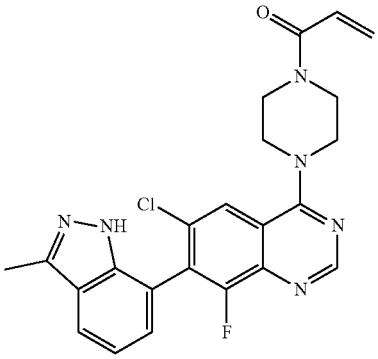 | 1-(4-(6-chloro-8-fluoro-7-(3-methyl-1H-indazol-7-yl) quinazolin-4-yl)piperazin-1-yl)prop-2-en-1-one |

TABLE 4-continued

Compounds Excluded From Certain Embodiments

| No. | Structure | Name |
|---|---|---|
| 2-205 | 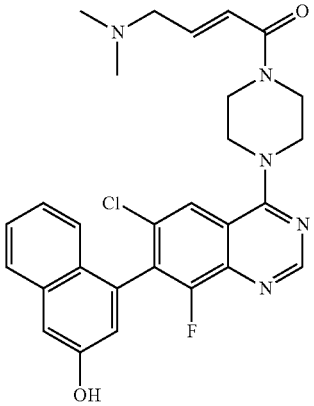 | (E)-1-(4-(6-chloro-8-fluoro-7-(3-hydroxy-naphthalen-1-yl) quinazolin-4-yl)piperazin-1-yl)-4-(dimethyl-amino)but-2-en-1-one |
| 2-206 | 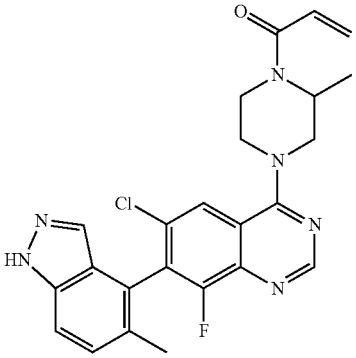 | 1-(4-(6-chloro-8-fluoro-7-(5-methyl-1H-indazol-4-yl) quinazolin-4-yl)-2-methyl-piperazin-1-yl)prop-2-en-1-one |
| 2-207 | 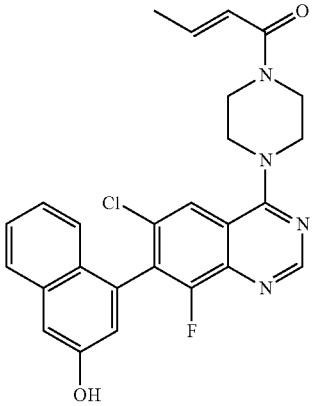 | (E)-1-(4-(6-chloro-8-fluoro-7-(3-hydroxy-naphthalen-1-yl) quinazolin-4-yl)piperazin-1-yl)but-2-en-1-one |
| 2-208 | 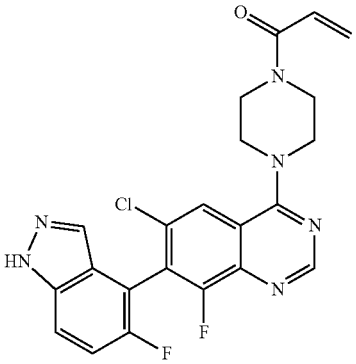 | 1-(4-(6-chloro-8-fluoro-7-(5-fluoro-1H-indazol-4-yl) quinazolin-4-yl)piperazin-1-yl)prop-2-en-1-one |

TABLE 4-continued

Compounds Excluded From Certain Embodiments

| No. | Structure | Name |
|---|---|---|
| 2-209 | 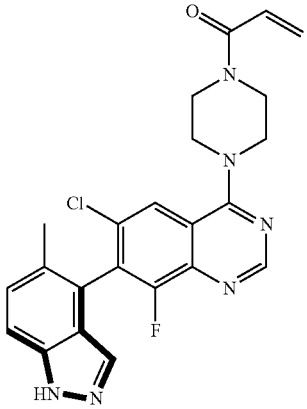 | (R)-1-(4-(6-chloro-8-fluoro-7-(5-methyl-1H-indazol-4-yl) quinazolin-4-yl)piperazin-1-yl)prop-2-en-1-one |
| 2-210 | 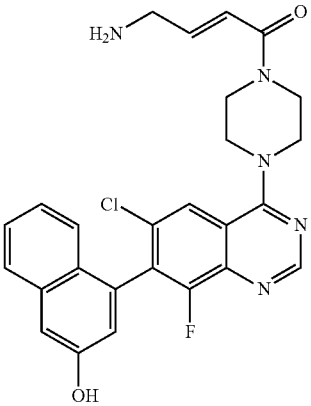 | (E)-4-amino-1-(4-(6-chloro-8-fluoro-7-(3-hydroxy-naphthalen-1-yl) quinazolin-4-yl)piperazin-1-yl)but-2-en-1-one |
| 2-211 | 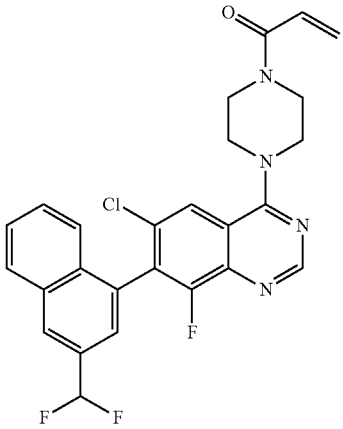 | 1-(4-(6-chloro-7-(3-(difluoro-methyl) naphthalen-1-yl)-8-fluoro-quinazolin-4-yl)piperazin-1-yl)prop-2-en-1-one |

TABLE 4-continued

Compounds Excluded From Certain Embodiments

| No. | Structure | Name |
|---|---|---|
| 2-212 | 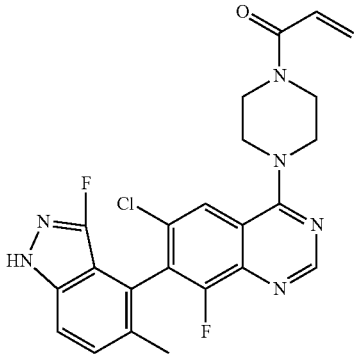 | 1-(4-(6-chloro-8-fluoro-7-(3-fluoro-5-methyl-1H-indazol-4-yl) quinazolin-4-yl)piperazin-1-yl)prop-2-en-1-one |
| 2-213 | 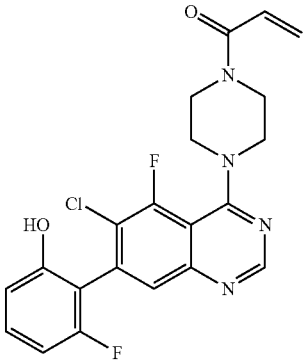 | 1-(4-(6-chloro-5-fluoro-7-(2-fluoro-6-hydroxy-phenyl) quinazolin-4-yl)piperazin-1-yl)prop-2-en-1-one |
| 2-214 | 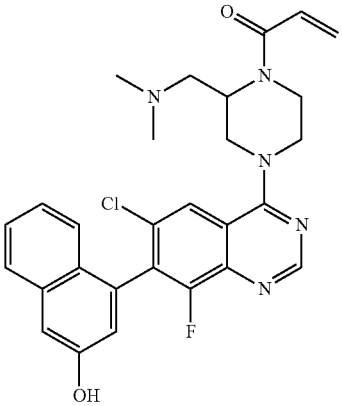 | 1-(4-(6-chloro-8-fluoro-7-(3-hydroxy-naphthalen-1-yl) quinazolin-4-yl)-2-((dimethyl-amino) methyl) piperazin-1-yl)prop-2-en-1-one |
| 2-215 | 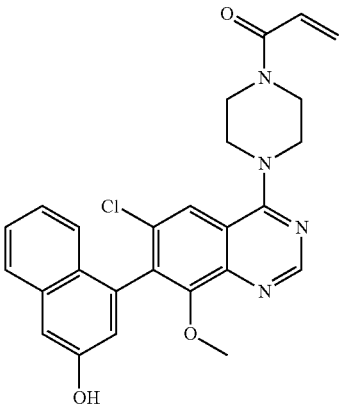 | 1-(4-(6-chloro-7-(3-hydroxy-naphthalen-1-yl)-8-methoxy-quinazolin-4-yl)piperazin-1-yl)prop-2-en-1-one |

TABLE 4-continued

Compounds Excluded From Certain Embodiments

| No. | Structure | Name |
|---|---|---|
| 2-216 | 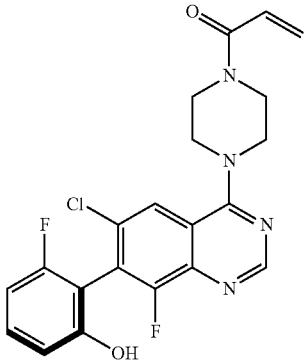 | (S)-1-(4-(6-chloro-8-fluoro-7-(2-fluoro-6-hydroxy-phenyl) quinazolin-4-yl)piperazin-1-yl)prop-2-en-1-one |
| 2-217 | 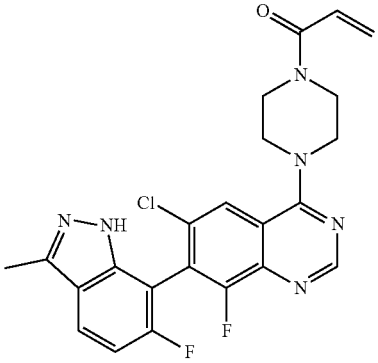 | 1-(4-(6-chloro-8-fluoro-7-(6-fluoro-3-methyl-1H-indazol-7-yl) quinazolin-4-yl)piperazin-1-yl)prop-2-en-1-one |
| 2-218 | 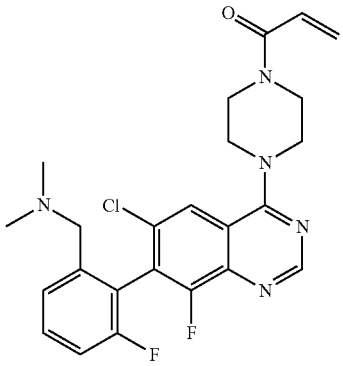 | 1-(4-(6-chloro-7-(2-((dimethyl-amino) methyl)-6-fluorophenyl)-8-fluoro-quinazolin-4-yl)piperazin-1-yl)prop-2-en-1-one |
| 2-219 | 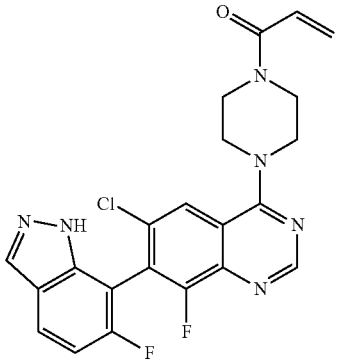 | 1-(4-(6-chloro-8-fluoro-7-(6-fluoro-1H-indazol-7-yl) quinazolin-4-yl)piperazin-1-yl)prop-2-en-1-one |

TABLE 4-continued

| Compounds Excluded From Certain Embodiments | | |
|---|---|---|
| No. | Structure | Name |
| 2-220 | 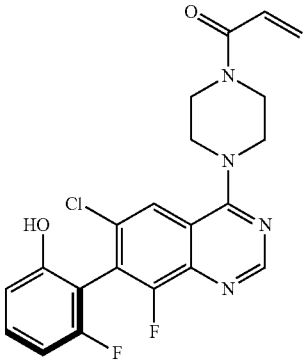 | (R)-1-(4-(6-chloro-8-fluoro-7-(2-fluoro-6-hydroxy-phenyl) quinazolin-4-yl)piperazin-1-yl)prop-2-en-1-one |

The following General Reaction Schemes illustrate exemplary methods of making compounds of compounds of structure (II):

(II)

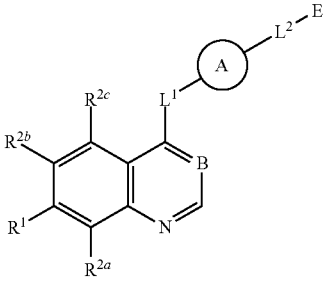

or a pharmaceutically acceptable salt, stereoisomer or prodrug thereof, wherein $R^1$, $R^{2a}$, $R^{2b}$, $R^{2c}$, $L^1$, $L^2$, A, B and E are as defined herein. It is understood that one skilled in the art may be able to make these compounds by similar methods or by combining other methods known to one skilled in the art. It is also understood that one skilled in the art would be able to make, in a similar manner as described below, other compounds of structure (II) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

General Reaction Scheme 18

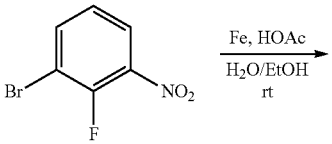

R-1

-continued

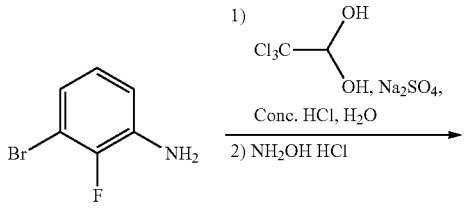

R-2

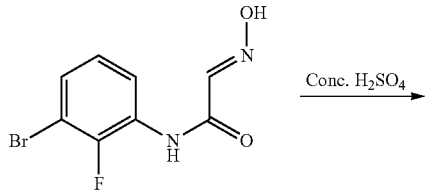

R-3

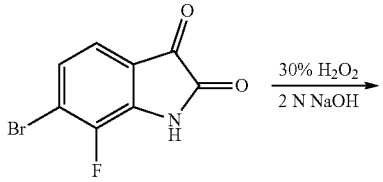

R-4

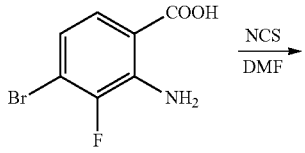

R-5

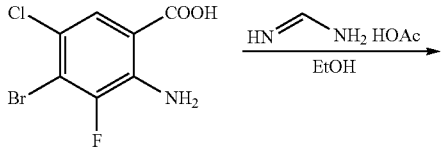

R-6

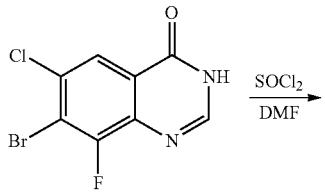

R-7

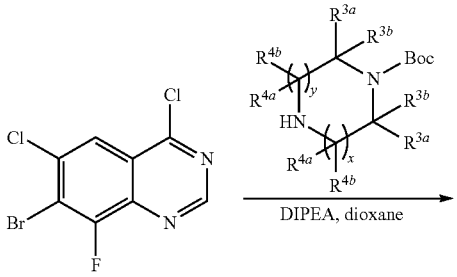

R-8

-continued

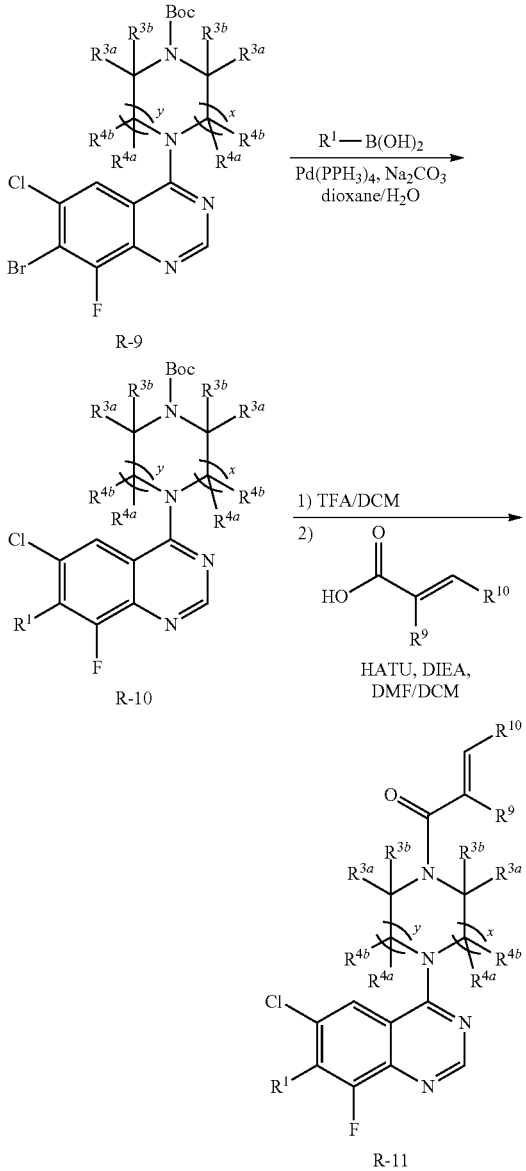

Embodiments of the compound of structure (II) (e.g., compound R-11) can be prepared according to General Reaction Scheme 18 ("Method R"), wherein $R^1$, $R^9$ and $R^{10}$ are as defined herein above. Referring to General Reaction Scheme 18, compounds of structure R-1 are purchased from commercial sources and reduced under appropriate conditions to form aniline R-2. R-2 is then treated with 2,2,2-trichloroethane-1,1-diol and sodium sulfate to yield R-3, which is subsequently cyclized by treatment with concentrated sulfuric acid. Ring-opening oxidation of R-4 then yields R-5, which can be optionally chlorinated to yield R-6 when a chloro substituent in the $R^{2b}$ position is desired. Cyclization of R-6 provides R-7, which is then treated with thionyl chloride to provide R-8. Compound R-8 is then reacted with mono-boc piperazine to provide R-9. The desired $R^1$ moiety is installed via Suzuki chemistry to provide R-10. Deprotection of R-10, followed by reaction with an appropriate acrylic acid under amide coupling conditions then yields R-11.

General Reaction Scheme 19

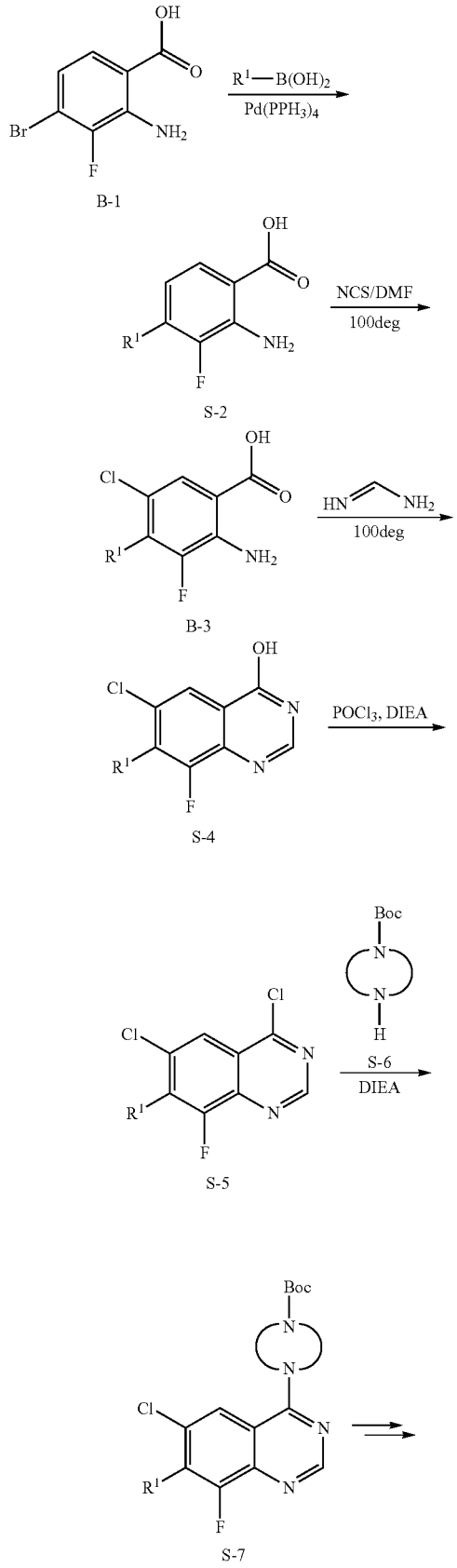

-continued

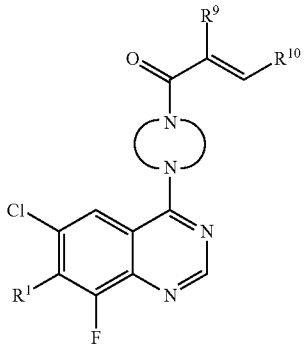

S-8

Embodiments of the compound of structure (I) (e.g., compound S-8) can be prepared according to General Reaction Scheme 19 ("Method S"), wherein $R^1$, $R^9$ and $R^{10}$ are as defined herein above. Referring to General Reaction Scheme 19, compounds of structure S-1 are purchased from commercial sources and treated under Suzuki conditions to yield S-2. Chlorination of S-2 with N-chlorosuccinimide yields S-3, which is cyclized to quinazolinol S-4. Chlorination of S-4 and reaction with an appropriate heterocycle (e.g., monocyclic or spirocyclic as represented by S-6) or substituted amine (not illustrated) yields S-7. Treatment of S-7 according to the general procedures described above yields S-8.

General Reaction Scheme 20

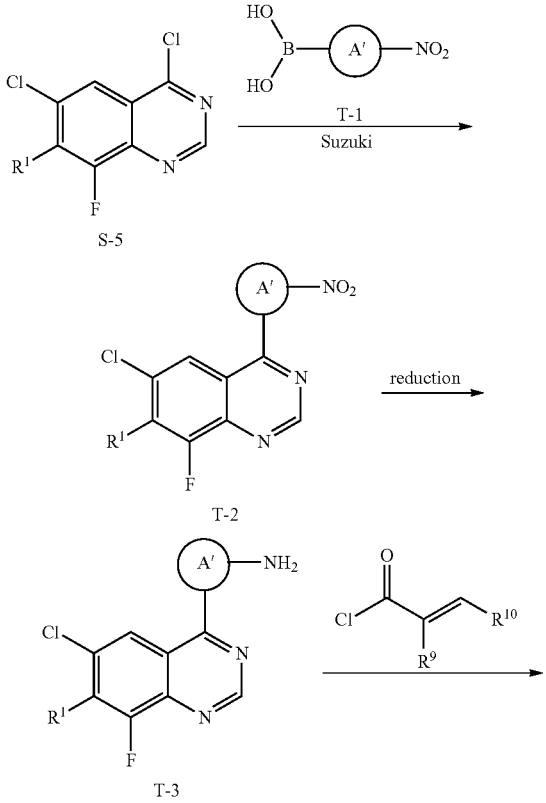

-continued

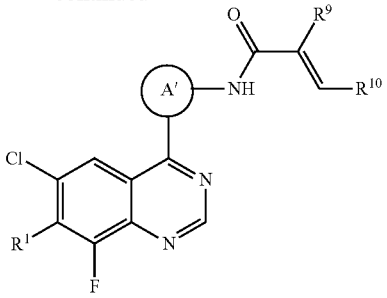

T-4

Embodiments of the compound of structure (I) (e.g., compound T-4) can be prepared according to General Reaction Scheme 20 ("Method T"), wherein A', $R^1$, $R^9$ and $R^{10}$ are as defined herein above. Referring to General Reaction Scheme 20, compounds of structure S-5 are prepared according to General Reaction Scheme 2. Suzuki coupling of B-5 with T-1 yields T-2, which can be reduced to amine T-3. Acylation of T-3 under appropriate conditions yields T-4.

Compounds of Structure (III)

In yet other embodiments, the compounds have the following structure (III):

(III)

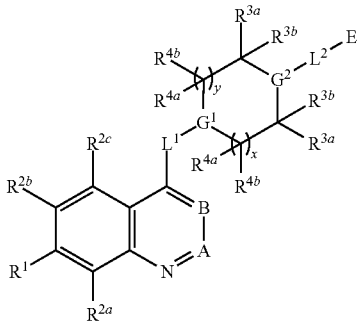

or a pharmaceutically acceptable salt, stereoisomer or prodrug thereof, wherein:

A is N or CH:

B is N or CR';

$G^1$ and $G^2$ are each independently N or CH;

$L^1$ is a bond or $NR^5$;

$L^2$ is a bond or alkylene;

R' is H, cyano, alkyl, cycloalkyl, amino, aminylalkyl, alkoxy, alkoxyalkyl, alkoxycarbonyl, aminylalkoxy, alkylaminylalkoxy, alkylaminyl, alkylaminylalkyl, aminylalkylaminyl, carboxyalkyl, alkylcarbonylaminyl, aminylcarbonyl, alkylaminylcarbonyl or aminylcarbonylalkyl;

$R^1$ is aryl or heteroaryl;

$R^{2a}$ and $R^{2b}$ are each independently amino, halo, hydroxyl, cyano, $C_1$-$C_6$ alkyl, $C_1$-$C_6$ alkyl amino, $C_1$-$C_6$ haloalkyl, $C_1$-$C_6$ alkoxy, $C_1$-$C_6$ haloalkoxy, $C_3$-$C_8$ cycloalkyl, heterocycyclylalkyl, $C_1$-$C_6$ alkynyl, $C_1$-$C_6$ alkenyl, aminylalkyl, alkylaminylalkyl, cyanoalkyl, carboxyalkyl, aminylcarbonylalkyl, aminylcarbonyl, heteroaryl or aryl;

$R^{2c}$ is H, amino, halo, hydroxyl, cyano, $C_1$-$C_6$ alkyl, $C_1$-$C_6$ alkyl amino, $C_1$-$C_6$ haloalkyl, $C_1$-$C_6$ alkoxy, $C_1$-$C_6$ haloalkoxy, $C_3$-$C_8$ cycloalkyl, heterocycyclylalkyl, $C_1$-$C_6$ alkynyl, $C_1$-$C_6$ alkenyl, aminylalkyl, alkylaminylalkyl, cyanoalkyl, carboxyalkyl, aminylcarbonylalkyl, aminylcarbonyl, heteroaryl or aryl;

$R^{3a}$ and $R^{3b}$ are, at each occurrence, independently H, —OH, —$NH_2$, —$CO_2H$, halo, cyano, unsubstituted $C_1$-$C_6$ alkyl, $C_1$-$C_6$ haloalkyl, $C_3$-$C_8$ cycloalkyl, heterocyclylalkyl, $C_1$-$C_6$ haloalkyl, $C_1$-$C_6$ haloalkoxy, hydroxylalkly, alkoxyalkyl, aminylalkyl, carboxyalkyl, aminylcarbonylalkyl or aminylcarbonyl; or $R^{3a}$ and $R^{3b}$ join to form oxo, a carbocyclic or heterocyclic ring; or $R^{3a}$ is H, —OH, —$NH_2$, —$CO_2H$, halo, cyano, $C_1$-$C_6$ alkyl, $C_1$-$C_6$ haloalkyl, $C_1$-$C_6$ haloalkoxy, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl, and $R^{3b}$ joins with $R^{4b}$ to form a carbocyclic or heterocyclic ring;

$R^{4a}$ and $R^{4b}$ are, at each occurrence, independently H, —OH, —$NH_2$, —$CO_2H$, halo, cyano, unsubstituted $C_1$-$C_6$ alkyl, $C_1$-$C_6$ haloalkyl, $C_3$-$C_8$ cycloalkyl, heterocyclylalkyl, $C_1$-$C_6$ haloalkyl, $C_1$-$C_6$ haloalkoxy, hydroxylalkly, alkoxyalkyl, aminylalkyl, carboxyalkyl, aminylcarbonylalkyl or aminylcarbonyl; or $R^{4a}$ and $R^{4b}$ join to form oxo, a carbocyclic or heterocyclic ring; or $R^{4a}$ is H, —OH, —$NH_2$, —$CO_2H$, halo, cyano, $C_1$-$C_6$ alkyl, $C_1$-$C_6$ haloalkyl, $C_1$-$C_6$ haloalkoxy, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl, and $R^{4b}$ joins with $R^{3b}$ to form a carbocyclic or heterocyclic ring;

$R^5$ is, at each occurrence, independently H, $C_1$-$C_6$ alkyl, $C_3$-$C_8$ cycloalkyl or heterocyclylalkyl;

x and y are independently integers ranging from 0 to 2; and

E is an electrophilic moiety capable of forming a covalent bond with the cysteine residue at position 12 of a KRAS, HRAS or NRAS G12C mutant protein, wherein each occurrence of alkylene, aryl, heteroaryl, cycloalkyl, heterocyclyl, alkylaminyl, haloalkyl, alkoxy, alkoxyalkyl, haloalkoxy, cycloalkyl, hereocyclylalkyl, aminylalkyl, carboxyalkyl, aminylcarbonylalkyl, and carbocyclic and heterocyclic rings is optionally substituted with one or more substituents unless otherwise specified; and provided that at least one occurrence of $R^{3a}$, $R^{3b}$, $R^{4a}$ or $R^{4b}$ is not H, and provided that when $R^1$ is indazolyl or naphthyl and one of $R^{3a}$ or $R^{3b}$ is methyl, dimethylaminomethyl or hydroxylmethyl, then at least one additional occurrence of $R^{3a}$ or $R^{3b}$ or at least one occurrence of $R^{4a}$ or $R^{4b}$ is not H.

In different embodiments of compounds of structure (III):

A is N or CH:

B is N, CH or C—CN;

$G^1$ and $G^2$ are each independently N or CH;

$L^1$ is a bond or $NR^5$;

$L^2$ is a bond or alkylene;

$R^1$ is aryl or heteroaryl;

$R^{2a}$ and $R^{2b}$ are each independently amino, halo, hydroxyl, cyano, $C_1$-$C_6$ alkyl, $C_1$-$C_6$ alkyl amino, $C_1$-$C_6$ haloalkyl, $C_1$-$C_6$ alkoxy, $C_1$-$C_6$ haloalkoxy, $C_3$-$C_8$ cycloalkyl, heterocycyclylalkyl, heteroaryl or aryl;

$R^{2c}$ is H, amino, halo, hydroxyl, cyano, $C_1$-$C_6$ alkyl, $C_1$-$C_6$ alkyl amino, $C_1$-$C_6$ haloalkyl, $C_1$-$C_6$ alkoxy, $C_1$-$C_6$ haloalkoxy, $C_3$-$C_8$ cycloalkyl, heterocycyclylalkyl, heteroaryl or aryl;

$R^{3a}$ and $R^{3b}$ are, at each occurrence, independently H, —OH, —$NH_2$, —$CO_2H$, halo, cyano, unsubstituted $C_1$-$C_6$ alkyl, $C_1$-$C_6$ haloalkyl, $C_1$-$C_6$ haloalkoxy, hydroxylalkly, alkoxyalkyl, aminylalkyl, carboxyalkyl, aminylcarbonylalkyl or aminylcarbonyl; or $R^{3a}$ and $R^{3b}$ join to form oxo, a carbocyclic or heterocyclic ring; or $R^{3a}$ is H, —OH, —$NH_2$, —$CO_2H$, halo, cyano, $C_1$-$C_6$ alkyl, $C_1$-$C_6$ haloalkyl, $C_1$-$C_6$ haloalkoxy, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl, and $R^{3b}$ joins with $R^{4b}$ to form a carbocyclic or heterocyclic ring;

$R^{4a}$ and $R^{4b}$ are, at each occurrence, independently H, —OH, —$NH_2$, —$CO_2H$, halo, cyano, unsubstituted $C_1$-$C_6$ alkyl, $C_1$-$C_6$ haloalkyl, $C_1$-$C_6$ haloalkoxy, hydroxylalkly, alkoxyalkyl, aminylalkyl, carboxyalkyl, aminylcarbonylalkyl or aminylcarbonyl; or $R^{4a}$ and $R^{4b}$ join to form oxo, a carbocyclic or heterocyclic ring; or $R^{4a}$ is H, —OH, —$NH_2$, —$CO_2H$, halo, cyano, $C_1$-$C_6$ alkyl, $C_1$-$C_6$ haloalkyl, $C_1$-$C_6$ haloalkoxy, $C_1$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl, and $R^{4b}$ joins with $R^{3b}$ to form a carbocyclic or heterocyclic ring;

$R^5$ is, at each occurrence, independently H, $C_1$-$C_6$ alkyl, $C_3$-$C_8$ cycloalkyl or heterocyclylalkyl;

x and y are independently integers ranging from 0 to 2; and

E is an electrophilic moiety capable of forming a covalent bond with the cysteine residue at position 12 of a KRAS, HRAS or NRAS G12C mutant protein, wherein each occurrence of alkylene, aryl, heteroaryl, cycloalkyl, heterocyclyl, alkylaminyl, haloalkyl, alkoxy, alkoxyalkyl, haloalkoxy, cycloalkyl, hereocyclylalkyl, aminylalkyl, carboxyalkyl, aminylcarbonylalkyl, and carbocyclic and heterocyclic rings is optionally substituted with one or more substituents unless otherwise specified; and provided that at least one occurrence of $R^{3a}$, $R^{3b}$, $R^{4a}$ or $R^{4b}$ is not H, and provided that when $R^1$ is indazolyl or naphthyl and one of $R^{3a}$ or $R^{3b}$ is methyl or hydroxyl methyl, then at least one additional occurrence of $R^{3a}$ or $R^{3b}$ or at least one occurrence of $R^{4a}$ or $R^{4b}$ is not H.

In some other embodiments, the compound has the following structure (IIIa):

(IIIa)

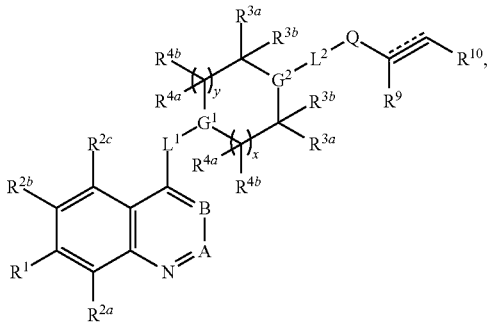

wherein:

≡ represents a double or triple bond;

Q is —C(=O)—, —C(=$NR^{8'}$)—, —$NR^8$C(=O)—, —S(=O)$_2$— or —$NR^8$S(=O)$_2$—; $R^8$ is H, $C_1$-$C_6$ alkyl, hydroxylalkyl, aminoalkyl, alkoxyalkyl, aminylalkyl, alkylaminylalkyl, cyanoalkyl, carboxyalkyl, aminylcarbonylalkyl, $C_3$—C cycloalkyl or heterocycloalkyl;

$R^{8'}$ is H, —OH, —CN or $C_1$-$C_6$ alkyl;

when ≡ is a double bond then $R^9$ and $R^{10}$ are each independently H, halo, cyano, carboxyl, $C_1$-$C_6$ alkyl, alkoxycarbonyl, aminylalkyl, alkylaminylalkyl, aryl, heterocyclyl, heterocyclylalkyl, heteroaryl or hydroxylalkyl, or $R^9$ and $R^{10}$ join to form a carbocyclic, heterocyclic or heteroaryl ring; and when ≡ is a triple bond then $R^9$ is absent and $R^{10}$ is H, $C_1$-$C_6$ alkyl, aminylalkyl, alkylaminylalkyl or hydroxylalkyl.

In some different embodiments, B is N. In other embodiments, B is C—CN. In other embodiments, B is CH.

In still different embodiments, A is N. In more embodiments, A is CH.

The structure of E in the compounds of structure (III) is not particularly limited provided it is capable of forming a covalent bond with a nucleophile, such as the cysteine residue at position 12 of a KRAS, HRAS or NRAS G12C mutant protein. Accordingly, moieties which are capable of reaction with (e.g., by covalent bond formation) a nucleophile are preferred. In certain embodiments, E is capable of reacting in a conjugate addition manner (e.g., 1.4-conjugate addition) with an appropriately reactive nucleophile. In some embodiments, E comprises conjugated pi bonds such that delocalization of electrons results in at least one atom (e.g., a carbon atom) having a positive charge, partial positive charge or a polarized bond. In other embodiments, E comprises one or more bonds wherein the electronegativity of the two atoms forming the bonds is sufficiently different such that a partial positive charge (e.g., by polarization of the bond) resides on one of the atoms, for example on a carbon atom. E moieties comprising carbon-halogen bonds, carbon-oxygen bonds or carbon bonds to various leaving groups known in the art are examples of such E moieties.

In certain embodiments of the foregoing, E has the following structure:

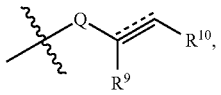

wherein:

≡ represents a double or triple bond;

Q is —C(=O)—, —C(=NR$^{8'}$)—, —NR$^8$C(=O)—, —S(=O)$_2$— or —NR S(=O)$_2$—;

R$^8$ is H, C$_1$-C$_6$ alkyl, hydroxylalkyl, aminoalkyl, alkoxyalkyl, aminylalkyl, alkylaminylalkyl, cyanoalkyl, carboxyalkyl, aminylcarbonylalkyl, C$_3$-C$_8$ cycloalkyl or heterocycloalkyl;

R$^8$ is H, —OH, —CN or C$_1$-C$_6$ alkyl; and when ≡ is a double bond then R$^9$ and R$^{10}$ are each independently H, halo, cyano, carboxyl, C$_1$-C$_6$ alkyl, alkoxycarbonyl, aminylalkyl, alkylaminylalkyl, aryl, heterocyclyl, heterocyclylalkyl, heteroaryl or hydroxylalkyl, or R$^9$ and R$^{10}$ join to form a carbocyclic, heterocyclic or heteroaryl ring;

when ≡ is a triple bond; then R$^9$ is absent and R$^{10}$ is H, C$_1$-C$_6$alkyl, aminylalkyl, alkylaminylalkyl or hydroxylalkyl.

In certain embodiments when ≡ is a double bond then R$^9$ and R$^{10}$ are each independently H, cyano, C$_1$-C$_6$alkyl, aminylalkyl, alkylaminylalkyl, or hydroxylalkyl or R$^9$ and R$^{10}$ join to form a carbocyclic or heterocyclic ring.

In some of the foregoing embodiments, Q is —C(=O)—, —NR$^8$C(=O)—, —S(=O)$_2$— or —NR$^8$S(=O)$_2$—.

In some other of the foregoing embodiments, Q is —C(=NR$^{8'}$)—, wherein R$^8$ is H, —OH, —CN or C$_1$-C$_6$alkyl. For example, in some embodiments R$^{8'}$ is H. In other embodiments, R$^{8'}$ is —CN. In other embodiments, R$^{8'}$ is —OH.

Accordingly, in some embodiments, the compound has one of the following structures (IIIb), (IIIc), (IIId), (IIIe), (IIIf) or (IIIg):

(IIIb)

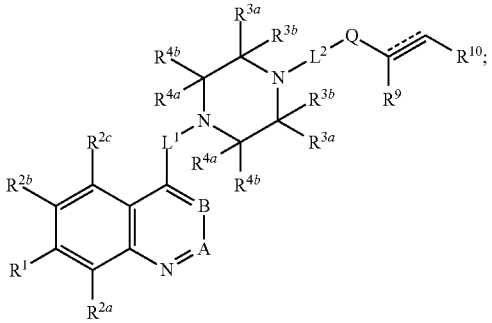

(IIIc)

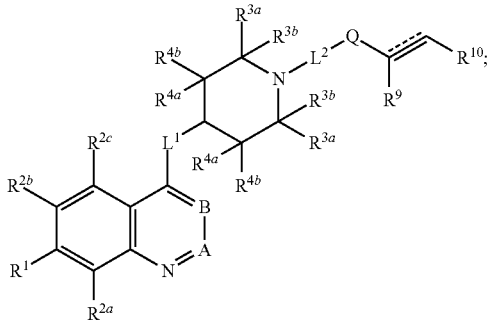

(IIId)

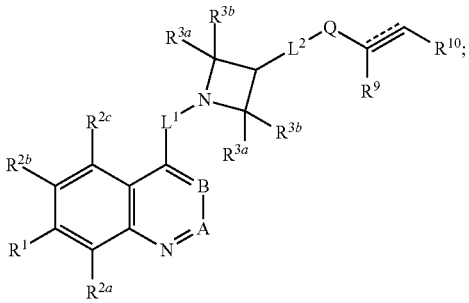

(IIIe)

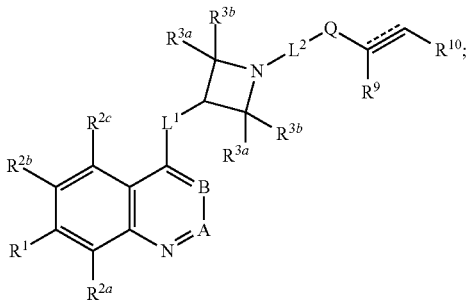

(IIIf)

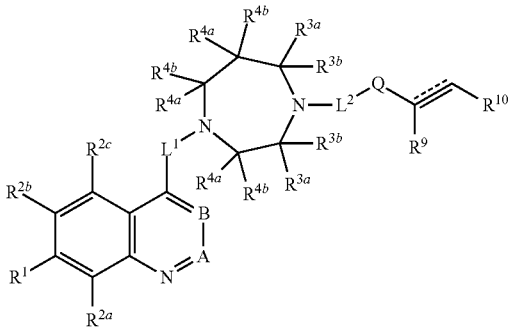

or

-continued (IIIg)

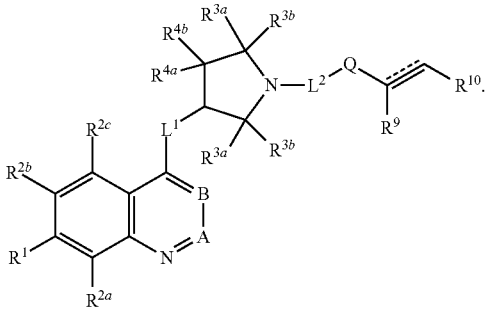

In some embodiments, the compound has one of structures (IIIa), (IIIb), (IIIc), (IIId), (IIIe), (IIIf) or (IIIg).

In any of the foregoing embodiments of the compounds of structure (III), (IIIa), (IIIb), (IIIc), (IIId), (IIIe), (IIIf) or (IIIg) B is N. In some other of the foregoing embodiments of the compounds of structure (III), (IIIa), (IIIb), (IIIc), (IIId), (IIIe), (IIIf) or (IIIg), B is C—CN. In any of the foregoing embodiments of the compounds of structure (III), (IIIa), (IIIb), (IIIc), (IIId), (IIIe), (IIIf) or (IIIg) B is CH. In any of the foregoing embodiments of the compounds of structure (III), (IIIa), (IIIb), (IIIc), (IIId), (IIIe), (IIIf) or (IIIg) A is N. In any of the foregoing embodiments of the compounds of structure (III), (IIIa), (IIIb), (IIIc), (IIId), (IIIe), (IIIf) or (IIIg) A is CH.

Without wishing to be bound by theory, Applicants believe correct selection of the $R^1$ substituent may play a part in the compounds' inhibitory activity (e.g., against KRAS, HRAS or NRAS G12C). In some embodiments, $R^1$ is aryl or heterocyclyl (e.g., heteroaryl or aliphatic heterocyclyl), each of which is optionally substituted with one or more substituents. In some embodiments, $R^1$ is capable of reversible interaction with KRAS, HRAS or NRAS G12C mutant protein. In some embodiments $R^1$ has high affinity towards KRAS, HRAS or NRAS and is highly specific towards G12C KRAS, HRAS or NRAS. In some embodiments $R^1$ is capable of hydrophobic interaction with KRAS, HRAS or NRAS G12C. In some embodiments $R^1$ is able to form hydrogen bonds with various residues of G12C KRAS, HRAS or NRAS protein.

In any of the foregoing embodiments, $R^1$ is aryl. For example in some embodiments at least one occurrence of $R^{3a}$, $R^{3b}$, $R^{4a}$ or $R^{4b}$ is not H, and $R^1$ is phenyl. In other embodiments $R^1$ is naphthyl. $R^1$ is substituted or unsubstituted. In some specific embodiments, $R^1$ is substituted with one or more substituents. For example, in some embodiments $R^1$ is substituted with halo, cyano, amino, hydroxyl, $C_1$-$C_6$ alkyl, $C_1$-$C_6$ haloalkyl, $C_1$-$C_6$ alkoxy, heteroarylalkyloxy or $C_1$-$C_6$ alkylcarbonyloxy, or combinations thereof. In some other embodiments $R^1$ is substituted with halo, hydroxyl, $C_1$-$C_6$ alkyl, $C_1$-$C_6$ haloalkyl, $C_1$-$C_6$ alkoxy or $C_1$-$C_6$ alkylcarbonyloxy, or combinations thereof. In some even more embodiments, $R^1$ is substituted with fluoro or hydroxyl, or combinations thereof.

In some more specific embodiments, $R^1$ has one of the following structures:

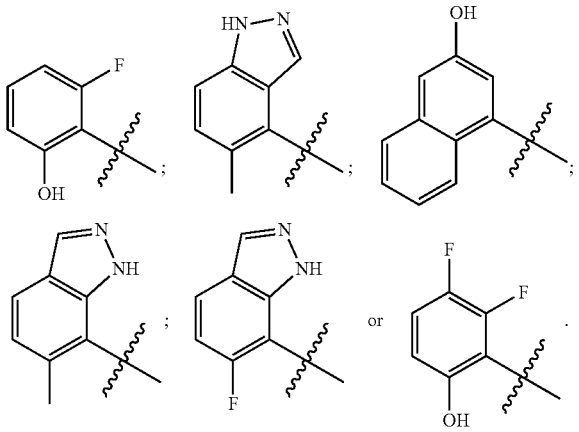

In some more specific embodiments, $R^1$ has one of the following structures:

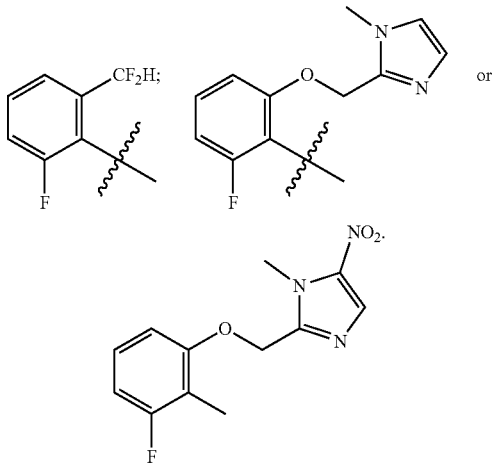

In some more specific embodiments, $R^1$ has one of the following structures:

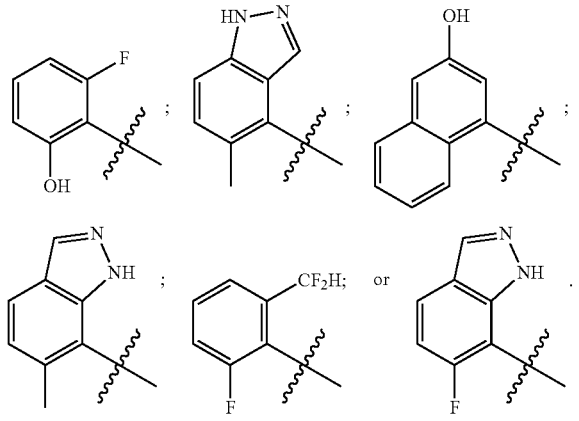

In some other embodiments, $R^1$ has one of the following structures:

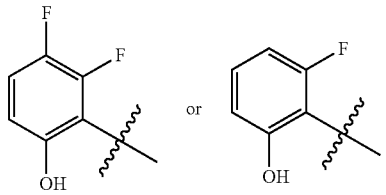

In some different embodiments of the foregoing compounds, $R^1$ is heteroaryl, for example a heteroaryl comprising nitrogen. In other embodiments, $R^1$ is indazolyl or quinolinyl. In more embodiments, $R^1$ is heteroaryl which is substituted with one or more substituents. For example, in certain embodiments, $R^1$ is substituted with hydroxyl, halo or $C_1$-$C_6$ alkyl, or both, for example hydroxyl or $C_1$-$C_6$ alkyl, or both.

In some other embodiments of structure (III), $R^{2a}$ and $R^{2b}$ are each independently amino, halo, hydroxyl, cyano, $C_1$-$C_6$ alkyl, $C_1$-$C_6$ alkyl amino, $C_1$-$C_6$ haloalkyl, $C_1$-$C_6$ alkoxy, $C_1$-$C_6$ haloalkoxy, $C_3$-$C_8$ cycloalkyl, heterocycyclylalkyl, heteroaryl or aryl; and $R^{2c}$ is H, amino, halo, hydroxyl, cyano, $C_1$-$C_6$ alkyl, $C_1$-$C_6$ alkyl amino, $C_1$-$C_6$ haloalkyl, $C_1$-$C_6$ alkoxy, $C_1$-$C_6$ haloalkoxy, $C_3$-$C_8$ cycloalkyl, heterocycyclylalkyl, heteroaryl or aryl. In some embodiments, $R^{2a}$, $R^{2b}$ and/or $R^{2c}$ are $CF_3$. In some of the foregoing embodiments $R^{2c}$ is H. In other of any of the foregoing embodiments, $R^{2a}$ and $R^{2b}$ are each halo. For example, in some embodiments $R^{2a}$ is fluoro, and in other embodiments, $R^{2b}$ is chloro. In different embodiments $R^{2a}$ is fluoro, and $R^{2b}$ is chloro.

In some more specific embodiments, the compounds have the following structure (IIIh):

(IIIh)

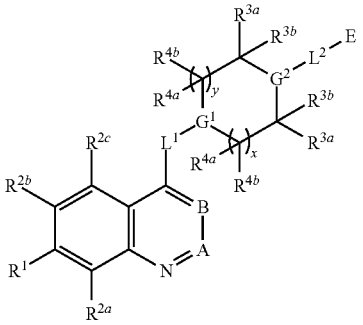

For example, in even further different embodiments, the compounds have one of the following structures (IIIi) or (IIIj):

(IIIi)

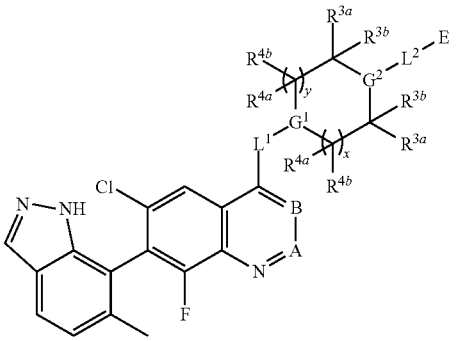

or (IIIj)

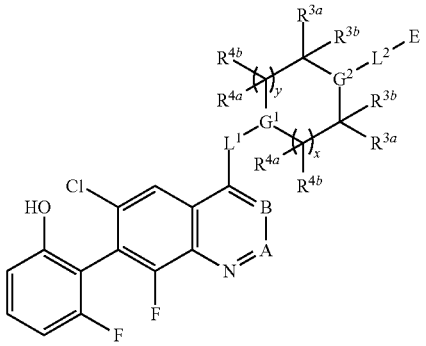

In other embodiments, the compound has one of the following structures:

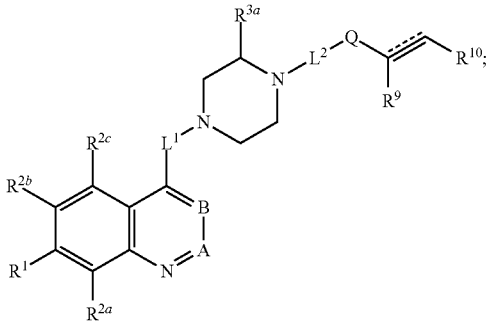

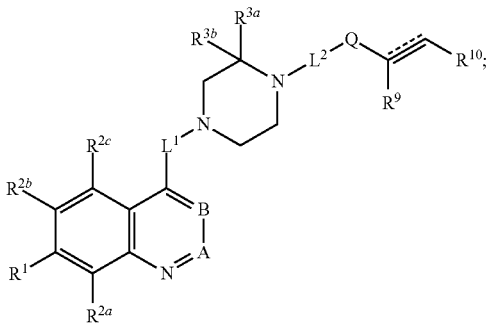

-continued
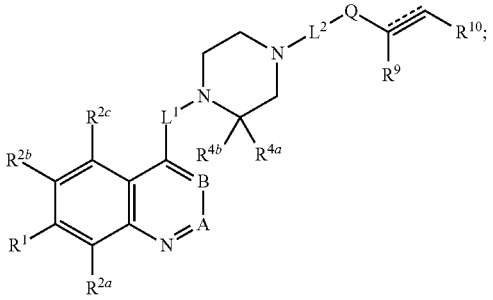
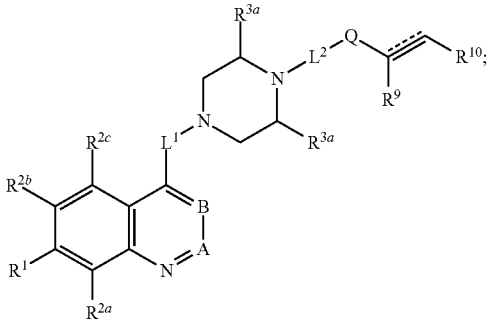
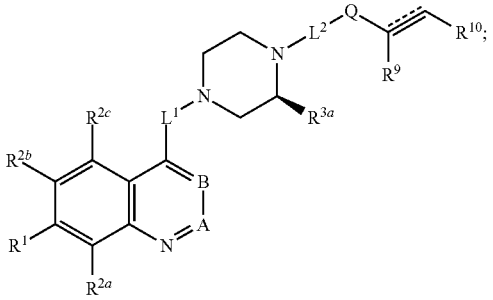
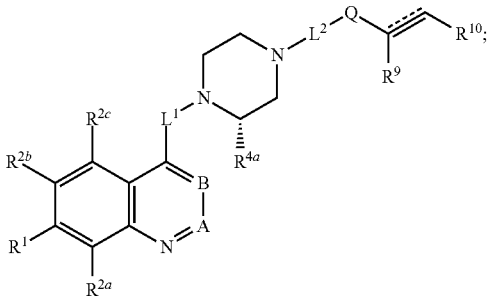
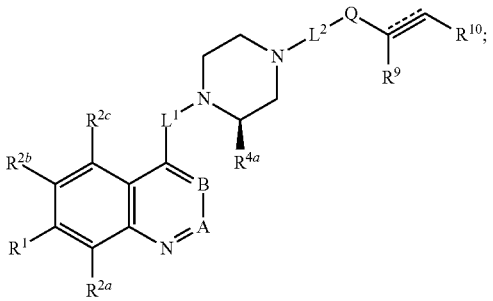
-continued
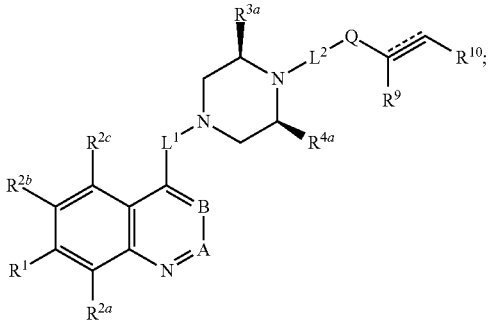
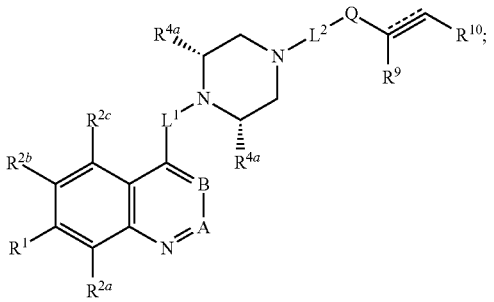
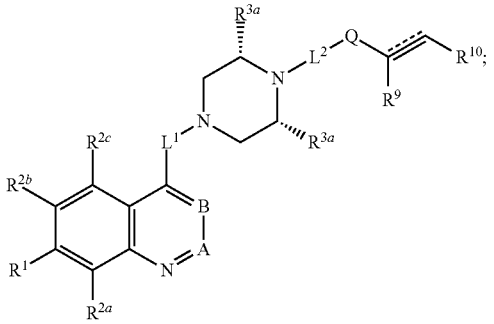
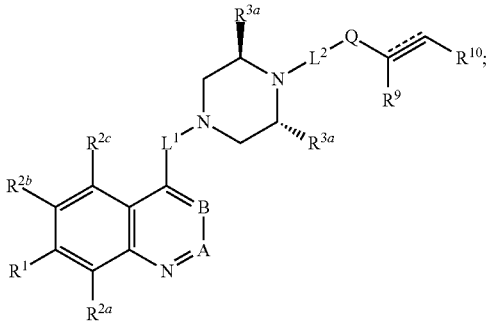
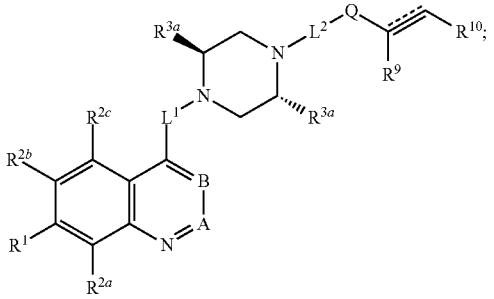

-continued

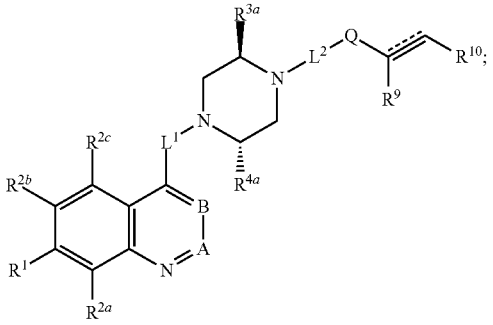

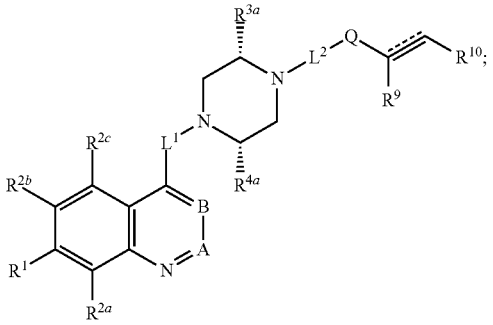

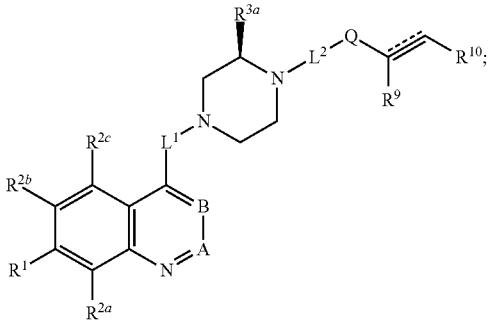

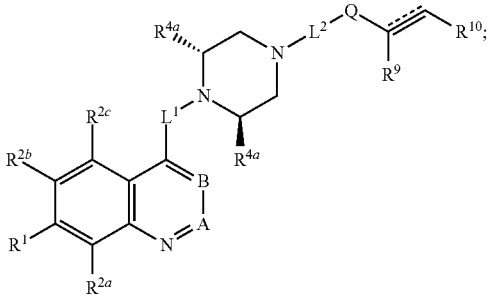

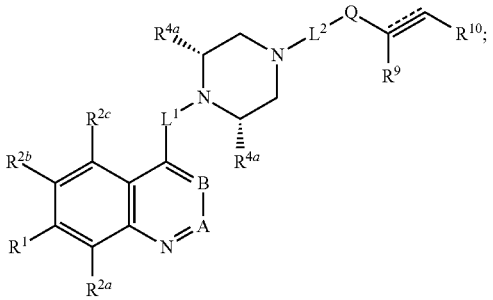

-continued

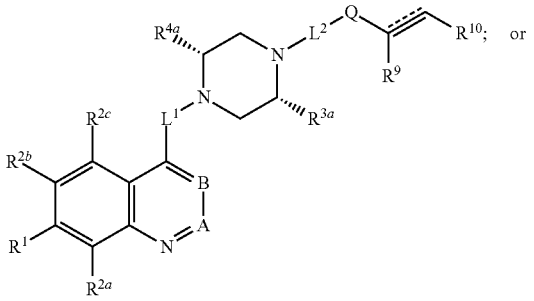

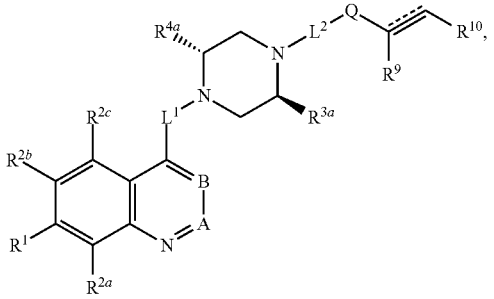

wherein $R^{3a}$, $R^{3b}$, $R^{4a}$ and $R^{4b}$ are independently —OH, —$NH_2$, —$CO_2H$, halo, cyano, unsubstituted $C_1$-$C_6$ alkyl, $C_1$-$C_6$ haloalkyl, $C_1$-$C_6$ haloalkoxy, $C_1$-$C_6$ alkynyl, hydroxylalkly, alkoxyalkyl, aminylalkyl, carboxyalkyl, aminylcarbonylalkyl or aminylcarbonyl; or wherein $R^{3a}$, $R^{3b}$, $R^{4a}$ and $R^{4b}$ are independently —OH, —$NH_2$, —$CO_2H$, halo, cyano, unsubstituted $C_1$-$C_6$ alkyl, $C_1$-$C_6$ haloalkyl, $C_1$-$C_6$ haloalkoxy, $C_1$-$C_6$ alkynyl, hydroxylalkly, alkoxyalkyl, carboxyalkyl, aminylcarbonylalkyl or aminylcarbonyl. For example, in some of the foregoing embodiments $R^{3a}$, $R^{3b}$, $R^{4a}$ and $R^{4b}$ are independently unsubstituted $C_1$-$C_6$ alkyl, $C_1$-$C_6$ haloalkyl or hydroxylalkly. In some of these embodiments, $C_1$-$C_6$ alkyl is methyl, ethyl or isopropyl.

In other embodiments, $R^{3a}$ and $R^{3b}$ join to form oxo or a carbocyclic ring; or wherein $R^{4a}$ and $R^{4b}$ join to form oxo, or a carbocyclic ring, for example cyclopropyl.

In yet more of any of the foregoing embodiments, E has the following structure:

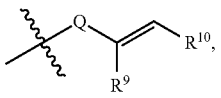

wherein:

Q is —C(═O)—, —C(═$NR^{8'}$)—, —$NR^8$C(═O)—, —S(═O)$_2$— or —$NR^8$S(═O)$_2$—;

$R^8$ is H, $C_1$-$C_6$alkyl or hydroxylalkyl;

$R^{8'}$ is H, —OH, —CN or $C_1$-$C_6$alkyl; and $R^9$ and $R^{10}$ are each independently H, halo, cyano, carboxyl, $C_1$-$C_6$ alkyl, alkoxycarbonyl, aminylalkyl, alkylaminylalkyl, aryl, heterocyclyl, heterocyclylalkyl, heteroaryl or hydroxylalkyl, or $R^9$ and $R^{10}$ join to form a carbocyclic, heterocyclic or heteroaryl ring.

In still other of any of the foregoing embodiments, E has the following structure:

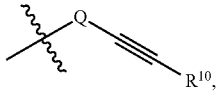

wherein:

Q is —C(═O)—, —NR$^8$C(═O)—, —S(═O)$_2$— or —NR$^8$S(═O)$_2$—;

R$^8$ is H, C$_1$-C$_6$alkyl or hydroxylalkyl; and

R$^{10}$ is H, C$_1$-C$_6$alkyl, aminylalkyl, alkylaminylalkyl or hydroxylalkyl.

The Q moiety is typically selected to optimize the reactivity (i.e., electrophilicity) of E. In some of the foregoing embodiments Q is —C(═O)—, NR$^8$C(═O)—, —S(═O)$_2$— or —NR$^8$S(═O)$_2$—. In certain of the foregoing embodiments, Q is —C(═O)—. In other embodiments, Q is —S(═O)$_2$—. In still more embodiments, Q is —NR$^8$C(═O)—. In still more different embodiments, Q is —NR$^8$S(═O)$_2$—.

In some other of the foregoing embodiments, Q is —C(═NR$^{8'}$)—, wherein R$^{8'}$ is H, —OH, —CN or C$_1$-C$_6$alkyl. For example, in some embodiments R$^{8'}$ is H. In other embodiments, R$^{8'}$ is —CN. In other embodiments, R$^{8'}$ is —OH.

In some of the foregoing embodiments, R$^8$ is H. In other of these embodiments, R$^8$ is hydroxylalkyl, for example in some embodiments the hydroxylalkyl is 2-hydroxylalkyl.

In some of any one of the foregoing embodiments, at least one of R$^9$ or R$^{10}$ is H. For example, in some embodiments each of R$^9$ and R$^{10}$ are H.

In other of the foregoing embodiments, R$^{10}$ is alkylaminylalkyl. In some of these embodiments, R$^{10}$ has the following structure:

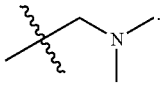

In other embodiments, R$^{10}$ is hydroxylalkyl, such as 2-hydroxylalkyl.

In some other different embodiments of the foregoing embodiments, R$^9$ and R$^{10}$ join to form a carbocyclic ring. For example, in some of these embodiments the carbocyclic ring is a cyclopentene, cyclohexene or phenyl ring. In other embodiments, the carbocyclic ring is a cyclopentene or cyclohexene ring. In other embodiments, the carbocyclic ring is a phenyl ring, for example a phenyl ring having the following structure:

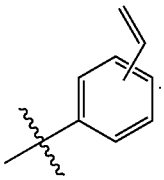

In some of any of the foregoing embodiments E is an electrophile capable of bonding with a KRAS, HRAS or NRAS protein comprising G12C mutation. In some embodiments, the electrophile E is capable of forming an irreversible covalent bond with a G12C mutant KRAS, HRAS or NRAS protein. In some cases, the electrophile E may bind with the cysteine residue at the position 12 of a G12C mutant KRAS, HRAS or NRAS protein. In various embodiments of any of the foregoing, E has one of the following structures:

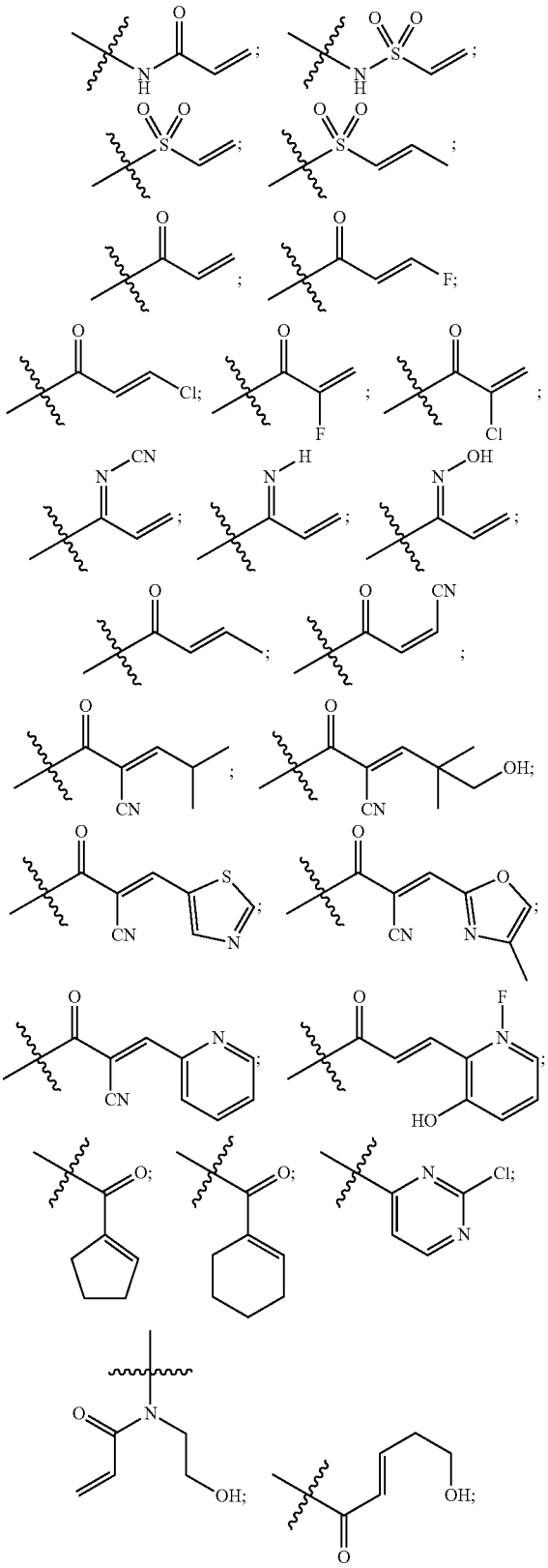

-continued
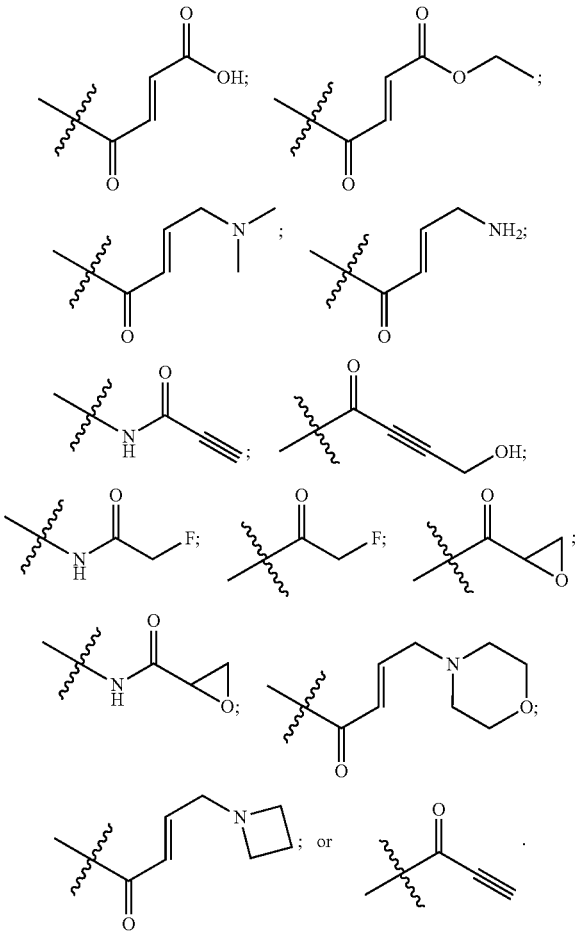
In some embodiments, E has one of the following structures:
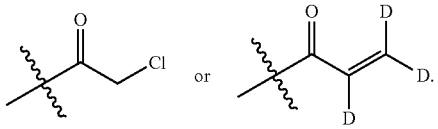
In other embodiments of any of the foregoing, E has one of the following structures:
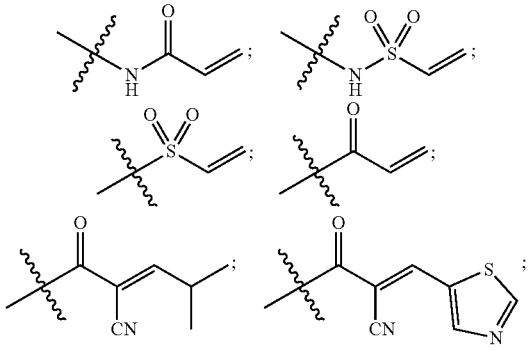
-continued
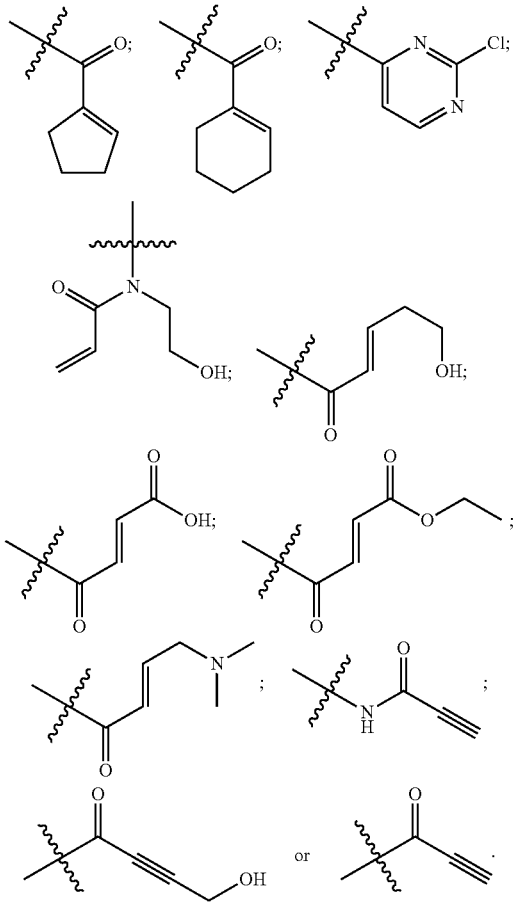
In different embodiments, E has one of the following structures:
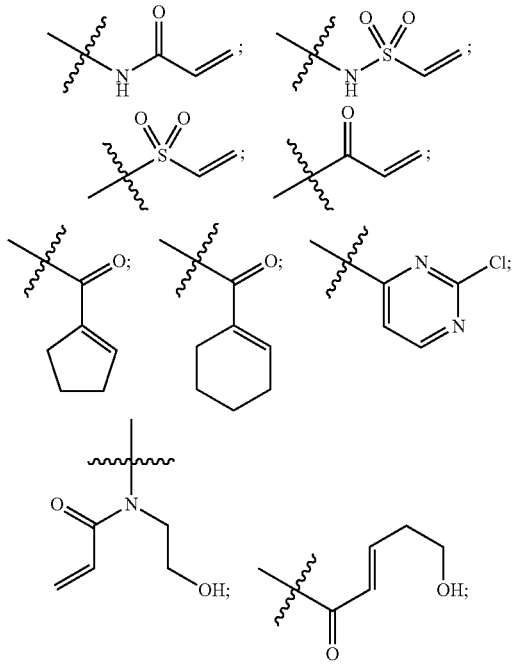

-continued

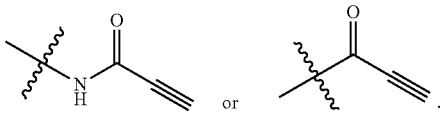

In some embodiments, E has the following structure:

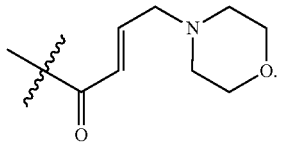

In other embodiments, E has the following structure:

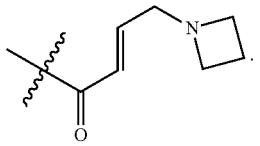

In some cases E has one of the following structures:

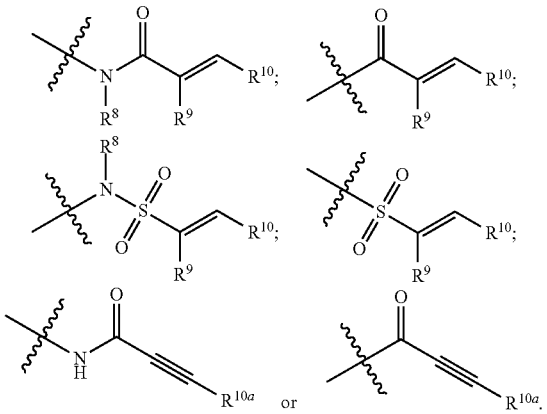

wherein:

$R^8$ is H or $C_1$-$C_6$alkyl;

$R^9$ is H, cyano or $C_1$-$C_6$alkyl, or $R^9$ joins with $R^{10}$ to form a carbocycle;

$R^{10}$ is H or $C_1$-$C_6$alkyl or $R^{10}$ joins with $R^9$ to form a carbocycle and $R^{10a}$ is H or $C_1$-$C_6$alkyl.

In some embodiments E is

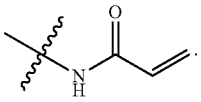

In some embodiments E is

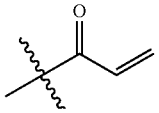

In some embodiments E is H

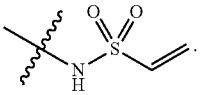

In some of any of the foregoing embodiments, $L^1$ is a bond. In other embodiments, $L^1$ is $NR^5$. For example, in some of these embodiments, $R^5$ is $C_1$-$C_6$alkyl. In other embodiments, $L^1$ is NH.

$L^2$ can be selected to provide proper spacing and/or orientation for the E group to form a bond with the KRAS, HRAS or NRAS protein. In some of the foregoing embodiments, $L^2$ is a bond. In other of the foregoing embodiments, $L^2$ is alkylene. In some embodiments, the alkylene is substituted. In other embodiments the alkylene is unsubstituted. For example, in some embodiments $L^2$ is $CH_2$ or $CH_2CH_2$.

In certain embodiments, $R^{3a}$ and $R^{3b}$ are, at each occurrence, independently H, —OH, —$NH_2$, —$CO_2H$, halo, cyano, hydroxylalkly, aminylalkyl, carboxyalkyl or aminylcarbonyl, and $R^{4a}$ and $R^{4b}$ are, at each occurrence, independently H, —OH, —$NH_2$, —$CO_2H$, halo, cyano, hydroxylalkly, aminylalkyl, cyanoalkyl, carboxyalkyl or aminylcarbonyl, provided at least one of $R^{3a}$, $R^{3b}$, $R^{4a}$ or $R^{4b}$ is not H.

In other of the foregoing embodiments, $R^{3a}$ and $R^{4a}$ are, at each occurrence, independently H, —OH, hydroxylalkly, cyano, or aminylcarbonyl and $R^{3b}$ and $R^{4b}$ are H, provided at least one of $R^{3a}$ or $R^{4a}$ is not H.

In other of the foregoing embodiments, $R^{3a}$ and $R^{4a}$ are, at each occurrence, independently H or $C_1$-$C_6$ alkyl, provided at least one of $R^{3a}$, $R^{3b}$, $R^{4a}$ or $R^{4b}$ is H. In some embodiments, at least one of $R^{3a}$, $R^{4a}$, $R^{3b}$ and $R^{4b}$ is independently $C_1$-$C_6$ alkyl, such as methyl. In some embodiments, one occurrence of $R^{3a}$ is $C_1$-$C_6$ alkyl, such as methyl, and the remaining $R^{3a}$ and each $R^{4a}$ is H. In some other embodiments, two occurrences of $R^{3a}$ are $C_1$-$C_6$ alkyl, such as methyl, and the remaining $R^{3a}$ and each $R^{4a}$ is H. In some other embodiments, one occurrence of $R^{3a}$ and one occurrence of $R^{4a}$ is independently $C_1$-$C_6$ alkyl, such as methyl, and the remaining $R^{3a}$ and $R^{4a}$ are each H.

In certain other embodiments, $R^{3a}$ and $R^{4a}$ are H and $R^{3b}$ and $R^{4b}$ are, at each occurrence, independently H, —OH, —$NH_2$, —$CO_2H$, halo, cyano, hydroxylalkly, aminylalkyl, carboxyalkyl or aminylcarbonyl, provided at least one of $R^{3a}$, $R^{3b}$, $R^{4a}$ or $R^{4b}$ is not H.

In any of the foregoing embodiments, at least one of $R^{3a}$, $R^{3b}$, $R^{4a}$ or $R^{4b}$ is H, provided at least one of $R^{3a}$, $R^{3b}$, $R^{4a}$ or $R^{4b}$ is not H.

In some embodiments, $R^{3a}$ is —OH, —$NH_2$, —$CO_2H$, halo, cyano, hydroxylalkly, aminylalkyl, carboxyalkyl or aminylcarbonyl, and $R^{3b}$, $R^{4a}$ and $R^{4b}$ are H.

In other embodiments, $R^{4a}$ is —OH, —$NH_2$, —$CO_2H$, halo, cyano, hydroxylalkly, aminylalkyl, carboxyalkyl or aminylcarbonyl, and $R^{3a}$, $R^{3b}$ and $R^{4b}$ are H.

In other embodiments, $R^{3a}$ is H, —OH, —$NH_2$, —$CO_2H$, halo, cyano, hydroxylalkly, aminylalkyl, carboxyalkyl or aminylcarbonyl, and $R^{3b}$ joins with $R^{4b}$ to form a carbocyclic or heterocyclic ring;

In still more embodiments, $R^{4a}$ is H, —OH, —$NH_2$, —$CO_2H$, halo, cyano, hydroxylalkly, aminylalkyl, carboxyalkyl or aminylcarbonyl, and $R^{4b}$ joins with $R^{3b}$ to form a carbocyclic or heterocyclic ring.

In other embodiments, $R^{3a}$ and $R^{3b}$ join to form a carbocyclic or heterocyclic ring. In other embodiments, $R^{4a}$ and $R^{4b}$ join to form a carbocyclic or heterocyclic ring.

In still other embodiments, $R^{3a}$ or $R^{4a}$ is aminylcarbonyl. For example, in certain embodiments, the aminylcarbonyl is

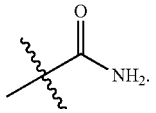

In other embodiments, $R^{3a}$ or $R^{4a}$ is cyano. In other embodiments, $R^{3a}$ or $R^{4a}$ is —OH. In other embodiments, $R^{3a}$ or $R^{4a}$ is hydroxylalkyl, for example hydroxylmethyl.

In some embodiments of any of the foregoing compounds (e.g., the compounds of structures (III), (IIIa), (IIIb), (IIIc), (IIId), (IIIe), (IIIf), (IIIg), (IIIh), (IIIi) or (IIIj)), $R^1$ is aryl or heteroaryl and $R^{2a}$, $R^{2b}$ and $R^{2c}$ are independently selected from H and halo, for example in some further embodiments $R^1$ is aryl or heteroaryl and $R^{2a}$ and $R^{2b}$ are independently selected from halo, such as chloro and fluoro, and $R^{2c}$ is H. In some embodiments, $R^1$ is aryl or heteroaryl, $R^{2a}$ is chloro, $R^{2b}$ is fluoro and $R^{2c}$ is H. In other embodiments $R^1$ is aryl or heteroaryl, one of $R^{2a}$ or $R^{2b}$ is halo, such as chloro or fluoro, and the other one of $R^{2a}$ or $R^{2b}$ is H.

In some embodiments of any of the compounds described herein, $C_1$-$C_6$ haloalkyl is $CF_3$ (e.g., when one or more of $R^{2a}$, $R^{2b}$ or $R^{2c}$ is $C_1$-$C_6$ haloalkyl).

In some embodiments x is 0. In other embodiments x is 1. In still more embodiments, x is 2. In different embodiments, y is 0. In some other embodiments, y is 1. In yet still more embodiments, y is 2.

In some other particular embodiments of any of the foregoing compounds, x is 1, and y is 1. In other embodiments, x is 1 and, y is 2. In still other embodiments x is 0, and y is 2. In more embodiments, x is 0, and y is 2.

In any of the foregoing embodiments, $G^1$ and $G^2$ are each independently selected from N and CH. In some embodiments, at least one of $G^1$ or $G^2$ is N. In some embodiments, each of $G^1$ and $G^2$ are N. In some embodiments, each of $G^1$ and $G^2$ are N and $m^1$ and $m^2$ are each 2. In some other embodiments, at least one of $G^1$ or $G^2$ is CH. In other embodiments, each of $G^1$ and $G^2$ are CH.

In any of the foregoing embodiments, B is N. In other of the foregoing embodiments, B is C—CN. In other of the foregoing embodiments, B is CH.

In other of the foregoing embodiments, A is N. In other of the foregoing embodiments, A is CH.

Some embodiments of the compounds include more than one stereoisomer. Other embodiments are directed to a single stereoisomer. In some embodiments the compounds are racemic (e.g., mixture of atropisomers), while in other embodiments the compounds are substantially a single isomer, for example a substantially purified atropisomer.

In various different embodiments, the compound of structure (III) has one of the structures set forth in Table 5 below. The compounds in Table 5 were each prepared and analyzed by mass spectrometry and/or $^1H$ NMR. Experimental mass spectrometry data is included in Table 5. Exemplary synthetic procedures are described in more detail below and in the Examples. General methods by which the compounds may be prepared are provided below and indicated in Table 5.

TABLE 5

Representative Compounds of Structure (III)

| No. | Structure | Name | Method | $[M + H]^+$ |
|---|---|---|---|---|
| III-1 | 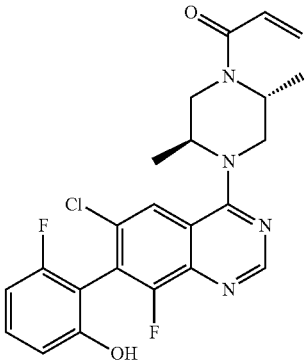 | 1-((2R,5S)-4-(6-chloro-8-fluoro-7-(2-fluoro-6-hydroxy-phenyl) quinazolin-4-yl)-2,5-dimethyl-piperazin-1-yl)prop-2-en-1-one | U | 459.10 |

TABLE 5-continued

| Representative Compounds of Structure (III) | | | | |
|---|---|---|---|---|
| No. | Structure | Name | Method | $[M + H]^+$ |
| III-2 | 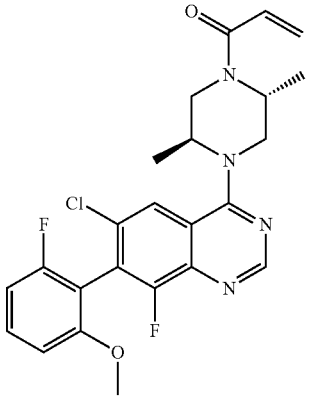 | 1-((2R,5S)-4-(6-chloro-8-fluoro-7-(2-fluoro-6-methoxy-phenyl) quinazolin-4-yl)-2,5-dimethyl-piperazin-1-yl)prop-2-en-1-one | U | 473.20 |
| III-3 | 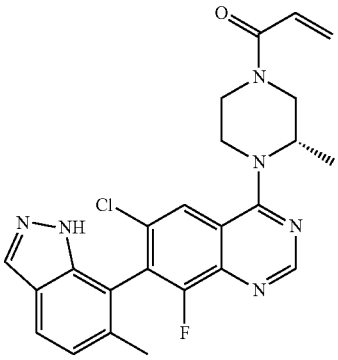 | 1-((3S)-4-(6-chloro-8-fluoro-7-(6-methyl-1H-indazol-7-yl) quinazolin-4-yl)-3-methyl-piperazin-1-yl)prop-2-en-1-one | R | 465.35 |
| III-4 | 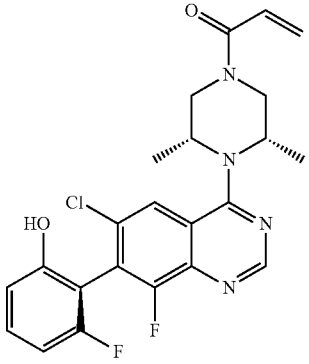 | 1-((3S,5R)-4-((R)-6-chloro-8-fluoro-7-(2-fluoro-6-hydroxy-phenyl) quinazolin-4-yl)-3,5-dimethyl-piperazin-1-yl)prop-2-en-1-one | U | 459.25 |
| III-5 | 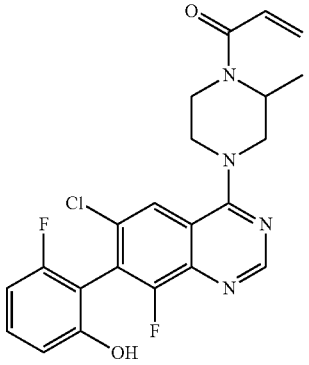 | 1-(4-(6-chloro-8-fluoro-7-(2-fluoro-6-hydroxy-phenyl) quinazolin-4-yl)-2-methyl-piperazin-1-yl)prop-2-en-1-one | U | 445.20 |

TABLE 5-continued

| Representative Compounds of Structure (III) | | | | |
|---|---|---|---|---|
| No. | Structure | Name | Method | $[M + H]^+$ |
| III-6 | 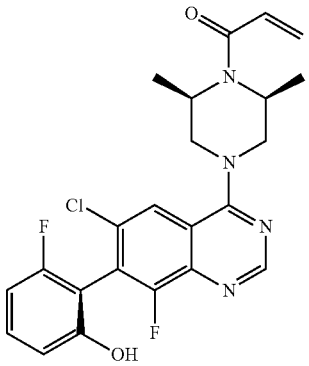 | 1-((2S,6R)-4-((S)-(6-chloro-8-fluoro-7-(2-fluoro-6-hydroxy-phenyl) quinazolin-4-yl)-2,6-dimethyl-piperazin-1-yl)prop-2-en-1-one | U | 459.25 |
| III-7 | 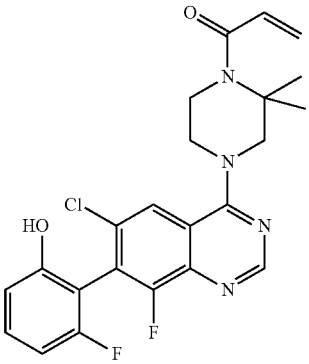 | 1-(4-(6-chloro-8-fluoro-7-(2-fluoro-6-hydroxy-phenyl) quinazolin-4-yl)-2,2-dimethyl-piperazin-1-yl)prop-2-en-1-one | U | 459.60 |
| III-8 | 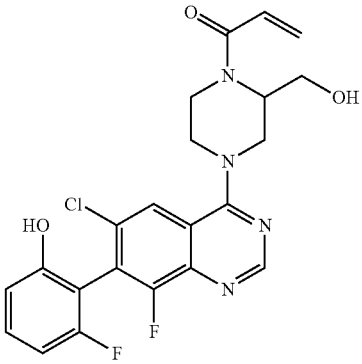 | 1-(4-(6-chloro-8-fluoro-7-(2-fluoro-6-hydroxy-phenyl) quinazolin-4-yl)-2-(hydroxy-methyl) piperazin-1-yl)prop-2-en-1-one | R | 461.15 |
| III-9 | 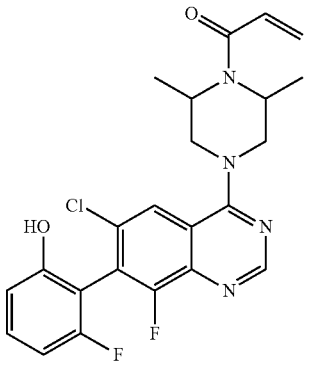 | 1-(4-(6-chloro-8-fluoro-7-(2-fluoro-6-hydroxy-phenyl) quinazolin-4-yl)-2,6-dimethyl-piperazin-1-yl)prop-2-en-1-one | U | 459.55 |

TABLE 5-continued

| Representative Compounds of Structure (III) | | | | |
|---|---|---|---|---|
| No. | Structure | Name | Method | $[M + H]^+$ |
| III-10 | 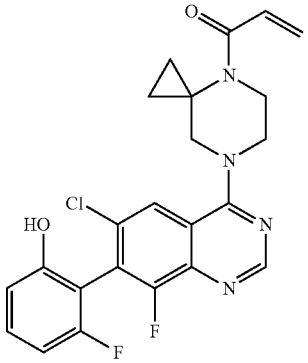 | 1-(7-(6-chloro-8-fluoro-7-(2-fluoro-6-hydroxy-phenyl) quinazolin-4-yl)-4,7-diazaspiro [2.5]octan-4-yl)prop-2-en-1-one | U | 457.45 |
| III-11 | 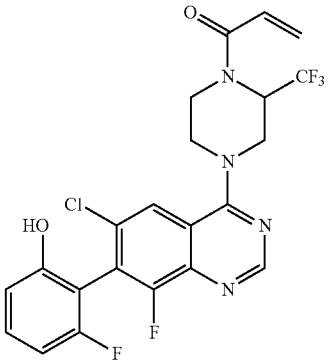 | 1-(4-(6-chloro-8-fluoro-7-(2-fluoro-6-hydroxy-phenyl) quinazolin-4-yl)-2-(trifluoro-methyl) piperazin-1-yl)prop-2-en-1-one | U | 499.55 |
| III-12 | 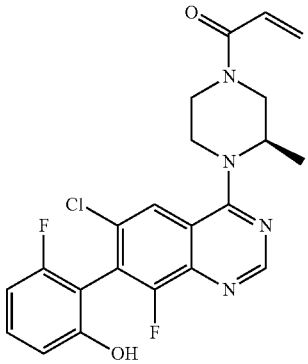 | 1-((3R)-4-(6-chloro-8-fluoro-7-(2-fluoro-6-hydroxy-phenyl) quinazolin-4-yl)-3-methyl-piperazin-1-yl)prop-2-en-1-one | V | 445.10 |
| III-13 | 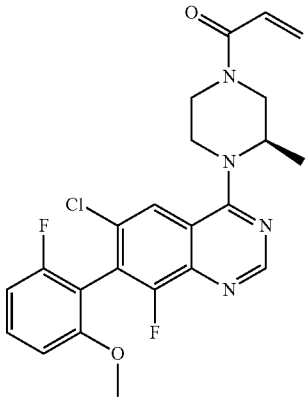 | 1-((3R)-4-(6-chloro-8-fluoro-7-(2-fluoro-6-methoxy-phenyl) quinazolin-4-yl)-3-methyl-piperazin-1-yl)prop-2-en-1-one | V | 459.1 |

TABLE 5-continued

| Representative Compounds of Structure (III) | | | | |
|---|---|---|---|---|
| No. | Structure | Name | Method | $[M + H]^+$ |
| III-14 | 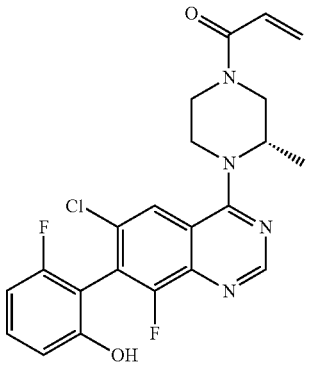 | 1-((3S)-4-(6-chloro-8-fluoro-7-(2-fluoro-6-hydroxy-phenyl) quinazolin-4-yl)-3-methyl-piperazin-1-yl)prop-2-en-1-one | V | 445.10 |
| III-15 | 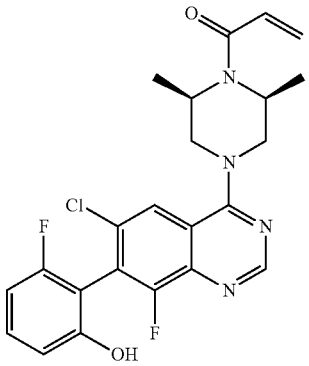 | 1-((2S,6R)-4-(6-chloro-8-fluoro-7-(2-fluoro-6-hydroxy-phenyl) quinazolin-4-yl)-2,6-dimethyl-piperazin-1-yl)prop-2-en-1-one | U | 459.15 |
| III-16 | 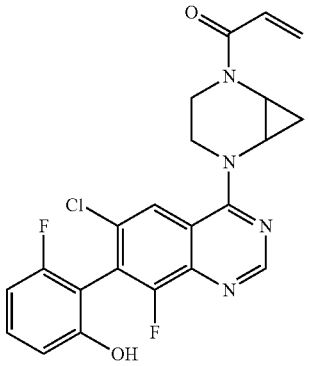 | 1-(5-(6-chloro-8-fluoro-7-(2-fluoro-6-hydroxy-phenyl) quinazolin-4-yl)-2,5-diazabicyclo[4.1.0.]heptan-2-yl)prop-2-en-1-one | U | 443.05 |
| III-17 | 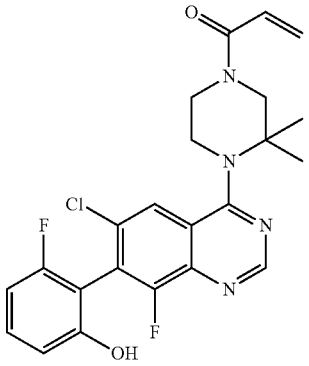 | 1-(4-(6-chloro-8-fluoro-7-(2-fluoro-6-hydroxy-phenyl) quinazolin-4-yl)-3,3-dimethyl-piperazin-1-yl)prop-2-en-1-one | V | 459.15 |

TABLE 5-continued

| Representative Compounds of Structure (III) | | | | |
|---|---|---|---|---|
| No. | Structure | Name | Method | $[M + H]^+$ |
| III-18 | 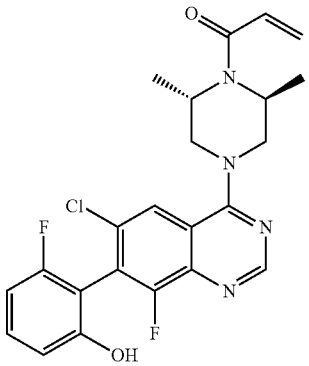 | 1-((2S,6S)-4-(6-chloro-8-fluoro-7-(2-fluoro-6-hydroxy-phenyl) quinazolin-4-yl)-2,6-dimethyl-piperazin-1-yl)prop-2-en-1-one | U | 459.15 |
| III-19 | 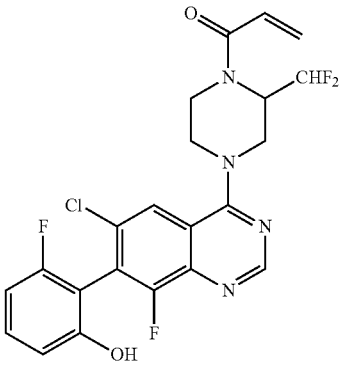 | 1-(4-(6-chloro-8-fluoro-7-(2-fluoro-6-hydroxy-phenyl) quinazolin-4-yl)-2-(difluoro-methyl) piperazin-1-yl)prop-2-en-1-one | U | 481.15 |
| III-20 | 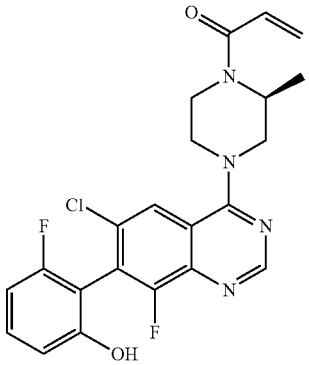 | 1-((2S)-4-(6-chloro-8-fluoro-7-(2-fluoro-6-hydroxy-phenyl) quinazolin-4-yl)-2-methyl-piperazin-1-yl)prop-2-en-1-one | U | 445.15 |
| III-21 | 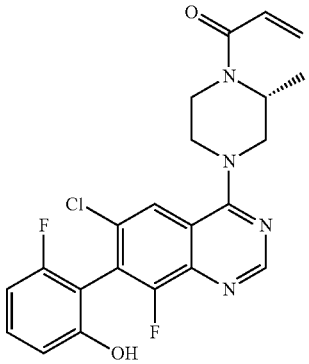 | 1-((2R)-4-(6-chloro-8-fluoro-7-(2-fluoro-6-hydroxy-phenyl) quinazolin-4-yl)-2-methyl-piperazin-1-yl)prop-2-en-1-one | U | 445.05 |

TABLE 5-continued

| Representative Compounds of Structure (III) | | | | |
|---|---|---|---|---|
| No. | Structure | Name | Method | $[M + H]^+$ |
| III-22 | 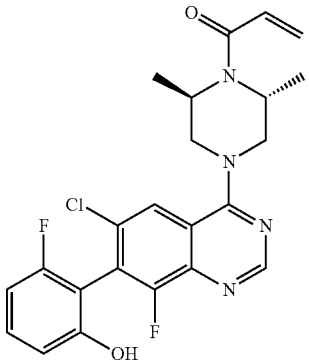 | 1-((2R,6R)-4-(6-chloro-8-fluoro-7-(2-fluoro-6-hydroxy-phenyl) quinazolin-4-yl)-2,6-dimethyl-piperazin-1-yl)prop-2-en-1-one | U | 459.20 |
| III-23 | 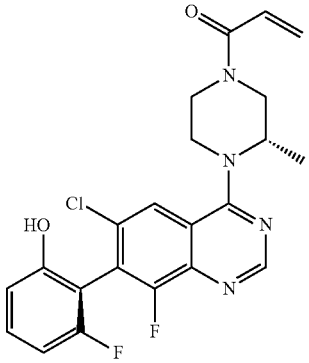 | 1-((S)-4-((R)-6-chloro-8-fluoro-7-(2-fluoro-6-hydroxy-phenyl) quinazolin-4-yl)-3-methyl-piperazin-1-yl)prop-2-en-1-one | U | 445.15 |
| III-24 | 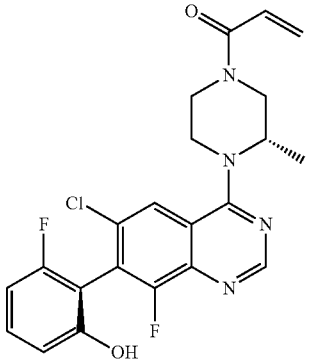 | 1-((S)-4-((S)-6-chloro-8-fluoro-7-(2-fluoro-6-hydroxy-phenyl) quinazolin-4-yl)-3-methyl-piperazin-1-yl)prop-2-en-1-one | U | 445.15 |
| III-25 | 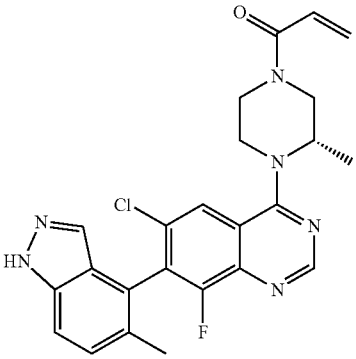 | 1-((3S)-4-(6-chloro-8-fluoro-7-(5-methyl-1H-indazol-4-yl) quinazolin-4-yl)-3-methyl-piperazin-1-yl)prop-2-en-1-one | R | 465.25 |

TABLE 5-continued

Representative Compounds of Structure (III)

| No. | Structure | Name | Method | $[M + H]^+$ |
|---|---|---|---|---|
| III-26 | 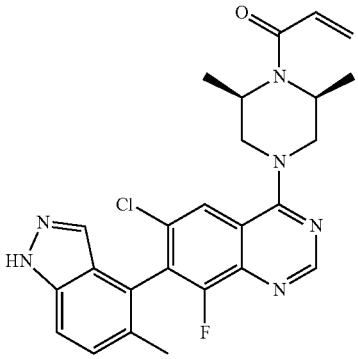 | 1-((2S,6R)-4-(6-chloro-8-fluoro-7-(5-methyl-1H-indazol-4-yl) quinazolin-4-yl)-2,6-dimethyl-piperazin-1-yl)prop-2-en-1-one | R | 479.20 |
| III-27 | 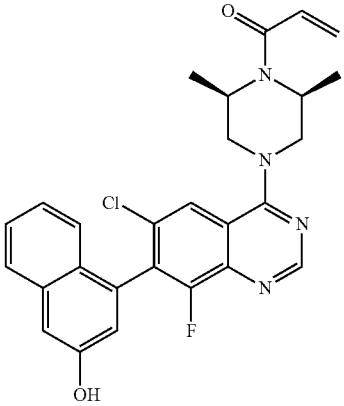 | 1-((2S,6R)-4-(6-chloro-8-fluoro-7-(3-hydroxy-naphthalen-1-yl)quinazolin-4-yl)-2,6-dimethyl-piperazin-1-yl)prop-2-en-1-one | R | 491.20 |
| III-28 | 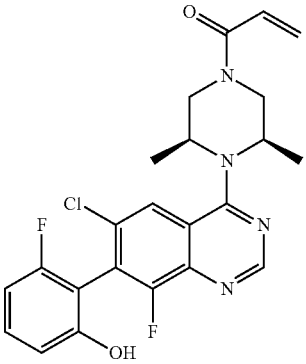 | 1-((3R,5S)-4-(6-chloro-8-fluoro-7-(2-fluoro-6-hydroxy-phenyl) quinazolin-4-yl)-3,5-dimethyl-piperazin-1-yl)prop-2-en-1-one | U | 459.1 |
| III-29 | 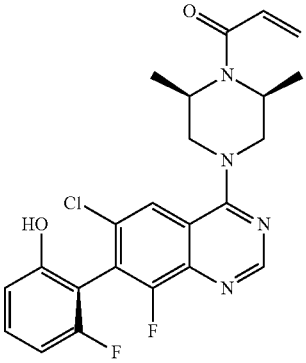 | 1-((2S,6R)-4-((R)-6-chloro-8-fluoro-7-(2-fluoro-6-hydroxy-phenyl) quinazolin-4-yl)-2,6-dimethyl-piperazin-1-yl)prop-2-en-1-one | U | 459.25 |

TABLE 5-continued

Representative Compounds of Structure (III)

| No. | Structure | Name | Method | $[M + H]^+$ |
|---|---|---|---|---|
| III-30 | 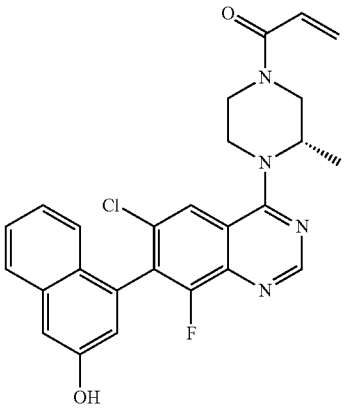 | 1-((3S)-4-(6-chloro-8-fluoro-7-(3-hydroxy-naphthalen-1-yl)quinazolin-4-yl)-3-methyl-piperazin-1-yl)prop-2-en-1-one | R | 477.30 |
| III-31 | 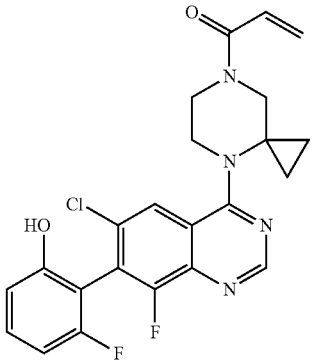 | 1-(4-(6-chloro-8-fluoro-7-(2-fluoro-6-hydroxy-phenyl) quinazolin-4-yl)-4,7-diazaspiro [2.5]octan-7-yl)prop-2-en-1-one | U | 457.1 |
| III-32 | 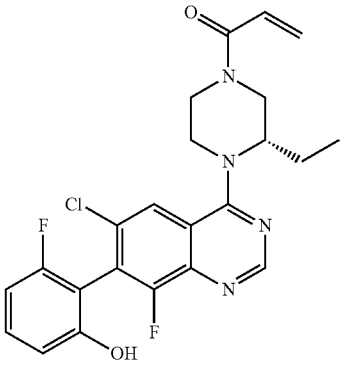 | 1-((3S)-4-(6-chloro-8-fluoro-7-(2-fluoro-6-hydroxy-phenyl) quinazolin-4-yl)-3-ethyl-piperazin-1-yl)prop-2-en-1-one | U | 459.30 |
| III-33 | 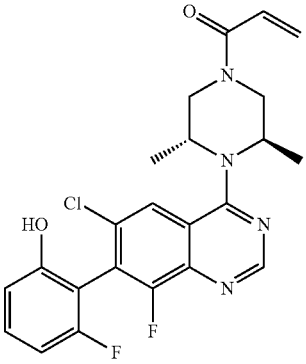 | 1-((3R,5R)-4-(6-chloro-8-fluoro-7-(2-fluoro-6-hydroxy-phenyl) quinazolin-4-yl)-3,5-dimethyl-piperazin-1-yl)prop-2-en-1-one | U | 459.25 |

TABLE 5-continued

Representative Compounds of Structure (III)

| No. | Structure | Name | Method | $[M + H]^+$ |
|---|---|---|---|---|
| III-34 | 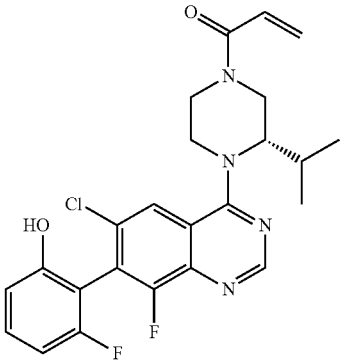 | 1-((3S)-4-(6-chloro-8-fluoro-7-(2-fluoro-6-hydroxy-phenyl) quinazolin-4-yl)-3-isopropyl-piperazin-1-yl)prop-2-en-1-one | U | 473.30 |
| III-35 | 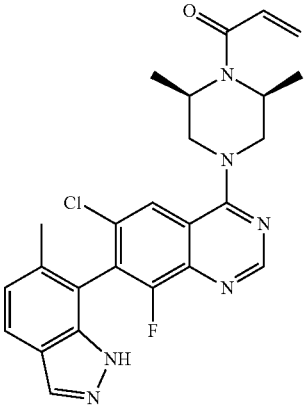 | 1-((2S,6R)-4-(6-chloro-8-fluoro-7-(6-methyl-1H-indazol-7-yl) quinazolin-4-yl)-2,6-dimethyl-piperazin-1-yl)prop-2-en-1-one | R | 479.30 |
| III-36 | 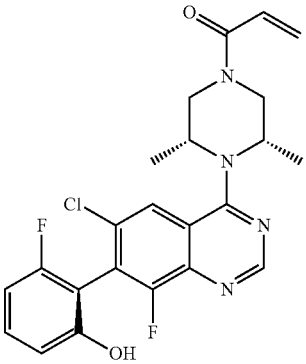 | 1-((3S,5R)-4-((S)-(6-chloro-8-fluoro-7-(2-fluoro-6-hydroxy-phenyl) quinazolin-4-yl)-3,5-dimethyl-piperazin-1-yl)prop-2-en-1-one | U | 459.25 |
| III-37 | 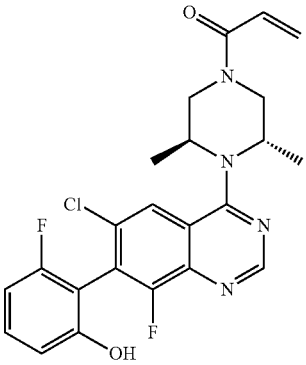 | 1-((3S,5S)-4-(6-chloro-8-fluoro-7-(2-fluoro-6-hydroxy-phenyl) quinazolin-4-yl)-3,5-dimethyl-piperazin-1-yl)prop-2-en-1-one | U | 459.30 |

TABLE 5-continued

Representative Compounds of Structure (III)

| No. | Structure | Name | Method | $[M + H]^+$ |
|---|---|---|---|---|
| III-38 | 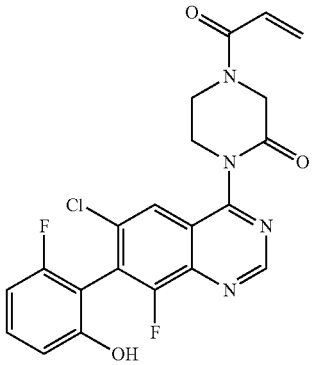 | 4-acryloyl-1-(6-chloro-8-fluoro-7-(2-fluoro-6-hydroxy-phenyl) quinazolin-4-yl) piperazin-2-one | U | 445.10 |
| III-39 | 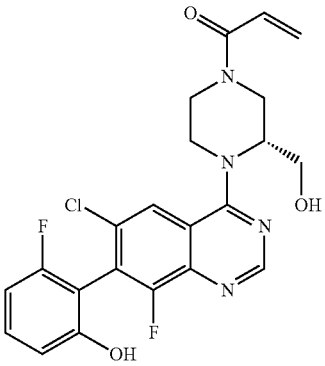 | 1-((3R)-4-(6-chloro-8-fluoro-7-(2-fluoro-6-hydroxy-phenyl) quinazolin-4-yl)-3-(hydroxy-methyl) piperazin-1-yl)prop-2-en-1-one | U | 461.15 |
| III-40 | 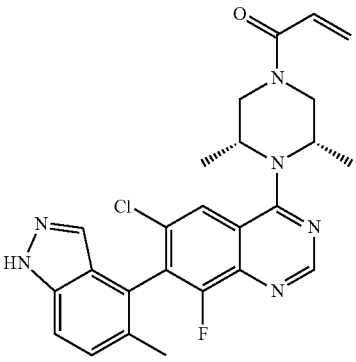 | 1-((3S,5R)-4-(6-chloro-8-fluoro-7-(5-methyl-1H-indazol-4-yl) quinazolin-4-yl)-3,5-dimethyl-piperazin-1-yl)prop-2-en-1-one | R | 479.30 |
| III-41 | 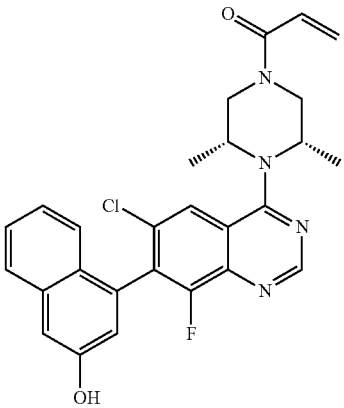 | 1-((3S,5R)-4-(6-chloro-8-fluoro-7-(3-hydroxy-naphthalen-1-yl)quinazolin-4-yl)-3,5-dimethyl-piperazin-1-yl)prop-2-en-1-one | R | 491.3 |

TABLE 5-continued

Representative Compounds of Structure (III)

| No. | Structure | Name | Method | $[M + H]^+$ |
|---|---|---|---|---|
| III-42 | 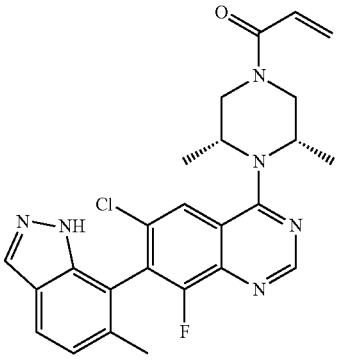 | 1-((3S,5R)-4-(6-chloro-8-fluoro-7-(6-methyl-1H-indazol-7-yl) quinazolin-4-yl)-3,5-dimethyl-piperazin-1-yl)prop-2-en-1-one | R | 479.30 |
| III-43 | 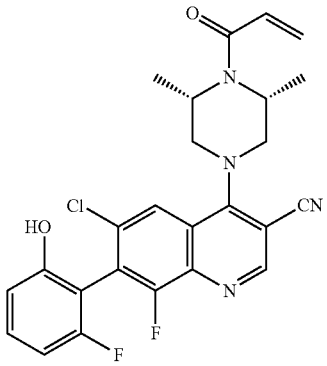 | 4-((3R,5S)-4-acryloyl-3,5-dimethyl-piperazin-1-yl)(6-chloro-8-fluoro-7-(2-fluoro-6-hydroxy-phenyl) quinoline-3-carbonitrile | W | 483.15 |

It is understood that in the present description, combinations of substituents and/or variables of the depicted formulae are permissible only if such contributions result in stable compounds.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

The following General Reaction Schemes illustrate exemplary methods of making compounds of compounds of structure (III):

(III)

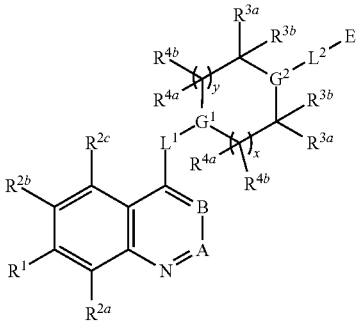

or a pharmaceutically acceptable salt, stereoisomer or prodrug thereof, wherein x, y, $R^1$, $R^{2a}$, $R^{2b}$, $R^{2c}$, $R^{3a}$, $R^{3b}$, $R^{4a}$, $R^{4b}$, $G^1$, $G^2$, $L^1$, $L^2$, A, B and E are as defined herein. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

Certain embodiments of the compounds of structure (III) are prepared according to General reaction Scheme 11 above. Other general methods for preparation of compounds of structure (III) are provided below.

General Reaction Scheme 21

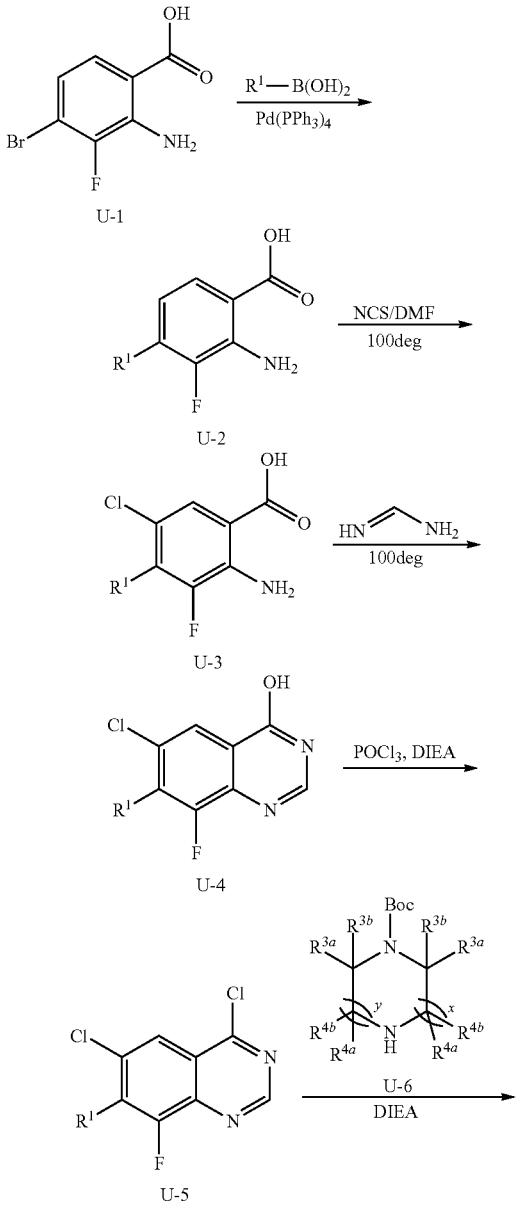

-continued

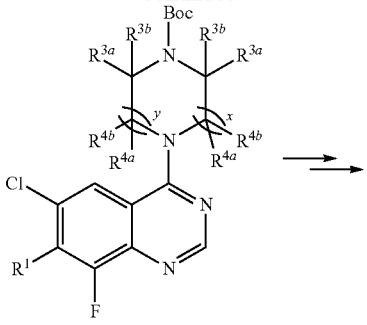

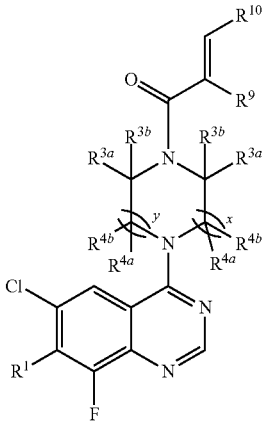

Embodiments of the compound of structure (III) (e.g., compound U-8) can be prepared according to General Reaction Scheme 21 ("Method U"), wherein $R^1$, $R^9$ and $R^{10}$ are as defined herein above. Referring to General Reaction Scheme 21, compounds of structure U-1 are purchased from commercial sources and treated under Suzuki conditions to yield U-2. Chlorination of U-2 with N-chlorosuccinimide yields U-3, which is cyclized to quinazolinol U-4. Chlorination of U-4 and reaction with an appropriate heterocycle (e.g., U-6) yields U-7. Treatment of U-7 according to the general procedures described above yields U-8.

General Reaction Scheme 22

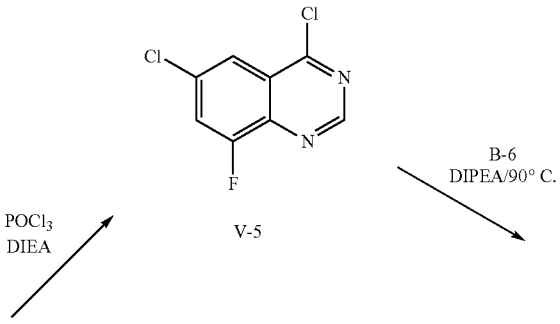

-continued

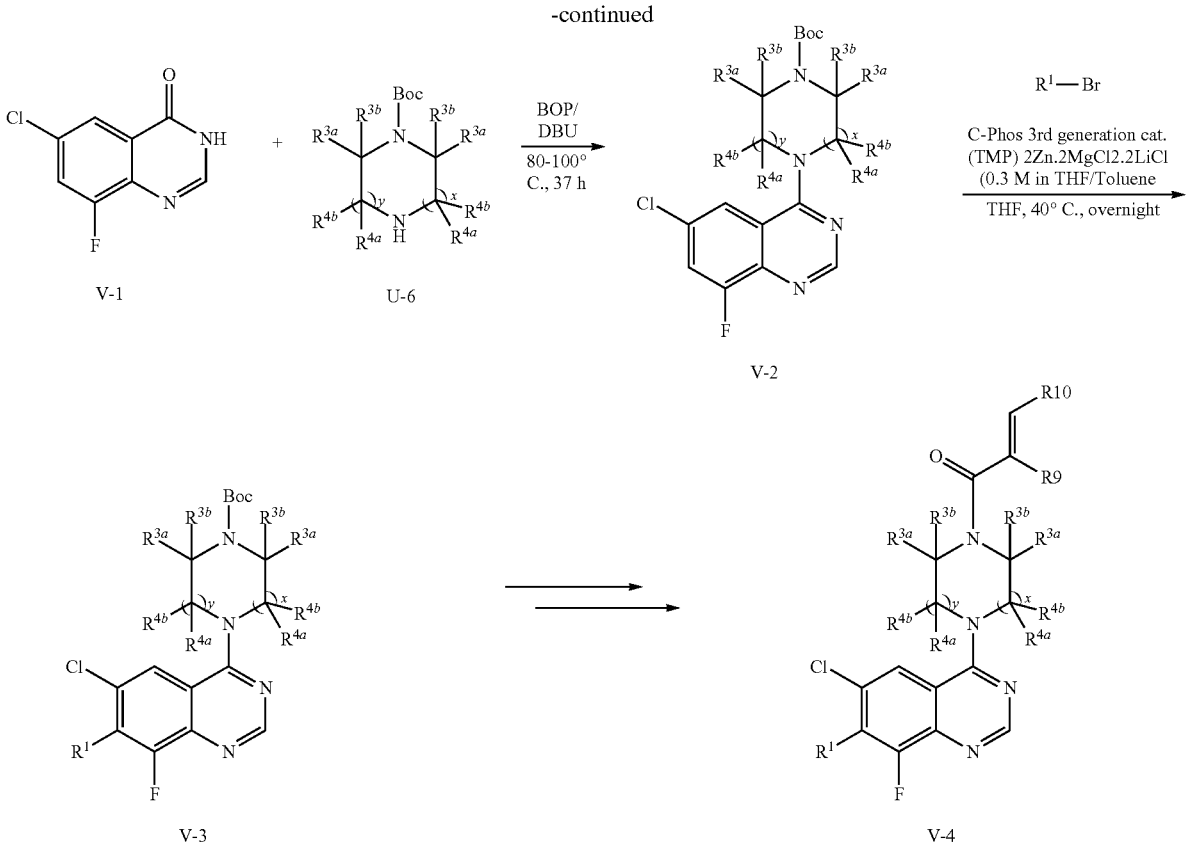

Embodiments of the compound of structure (I) (e.g., compound V-4) can be prepared according to General Reaction Scheme 22 ("Method V"), wherein x, y $R^1$, $R^{3a}$, $R^{3b}$, $R^{4a}$, $R^{4b}$, $R^9$ and $R^{10}$ are as defined herein above. Referring to General Reaction Scheme 22, compounds of structure V-1 are purchased from commercial sources or prepared according to methods. Reaction of V-1 with an appropriate heterocycle (U-6) yields V-2. Alternatively, V-2 can be prepared from V-1 via a two-step procedure through V-5 intermediate. The desired $R^1$ moiety is then installed using mixed metal catalyzed chemistry and an appropriate aryl or heteroaryl bromide ($R^1$—Br) to yield V-3. Treatment of V-3 according to the general procedures described above yields V-4.

General Reaction Scheme 23

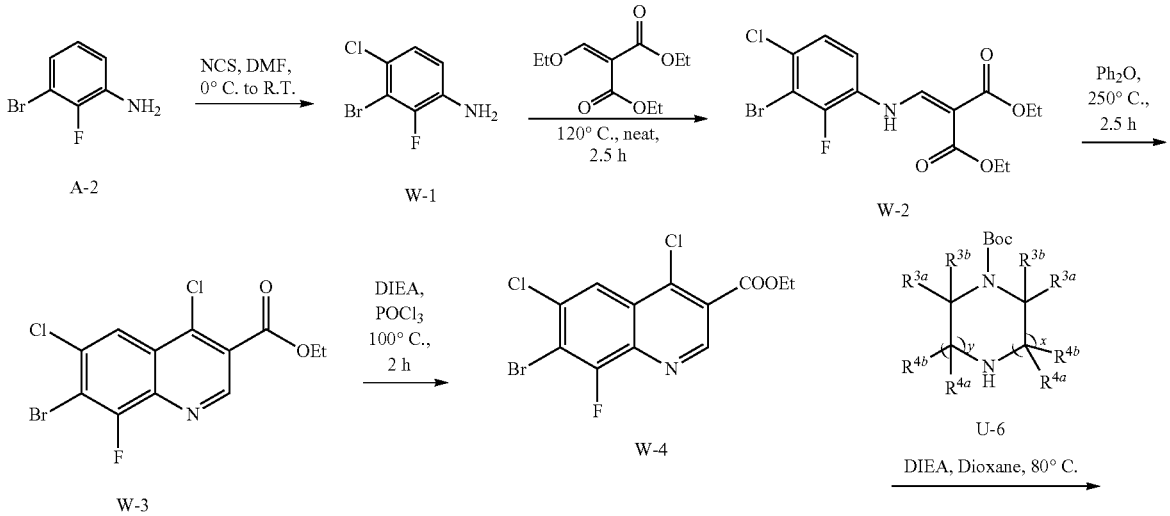

-continued

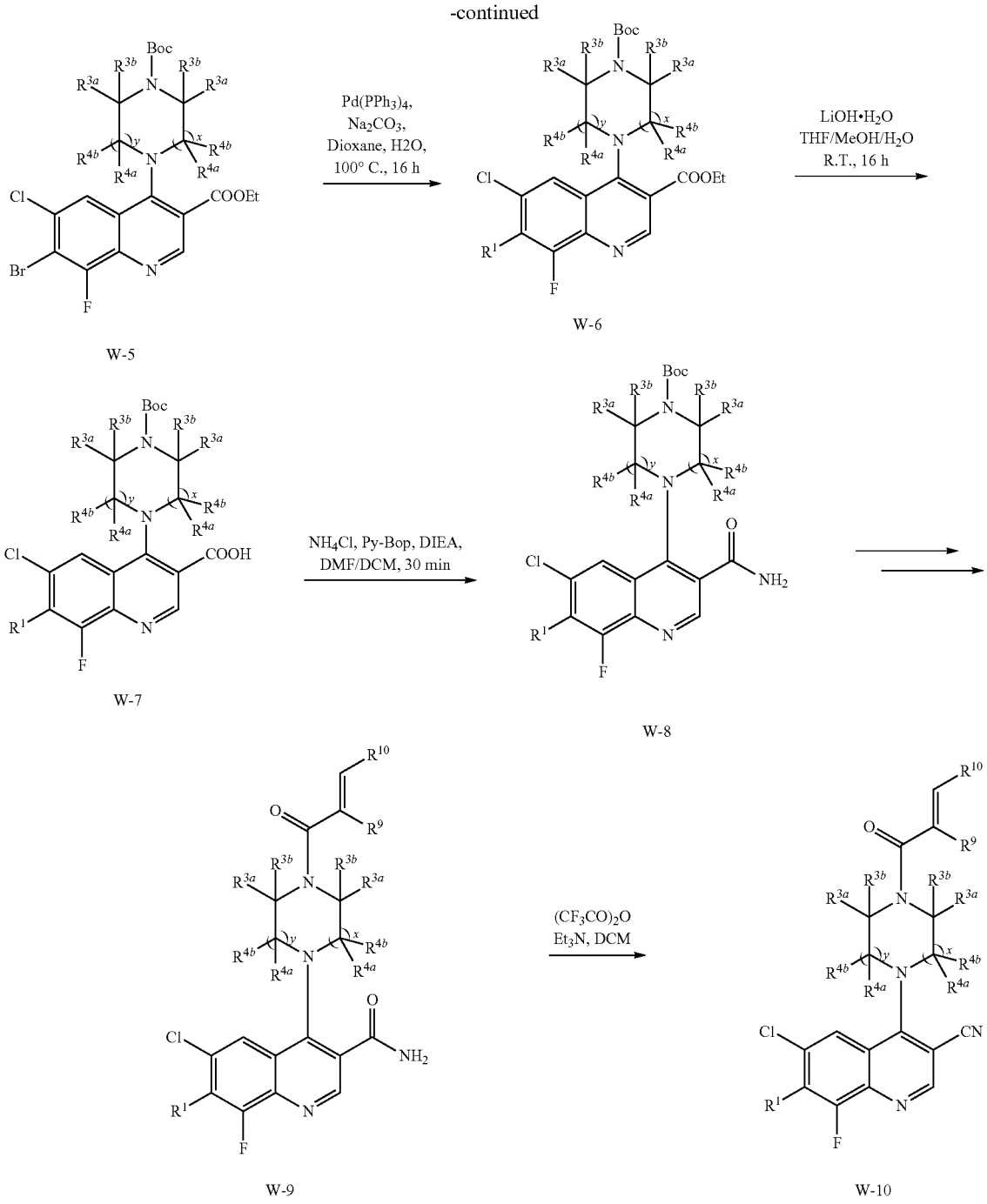

Embodiments of the compound of structure (I) (e.g., compound W-10) can be prepared according to General Reaction Scheme 23 ("Method W"), wherein x, y $R^1$, $R^{3a}$, $R^{3b}$, $R^{4a}$, $R^{4b}$, $R^9$ and $R^{10}$ are as defined herein above. Referring to General Reaction Scheme 23, compounds of structure A-2 are prepared as described above. Chlorination of A-2 with N-chlorosuccinimide yields W-1, which is cyclized to N-3 via a two-step procedure. Chlorination of W-3 and reaction with an appropriate heterocycle (e.g., U-6) yields W-5. Treatment of W-5 under Suzuki conditions yields W-6. Saponification followed by amination then yields amide W-8. Treatment of W-8 according to the general procedures described above yields W-9. Finally, W-10 can be obtained by treatment of W-9 with an appropriate dehydrating reagent, such as trifluoroacetic anhydride.

Additional general synthetic methods are provided in the Examples. It will be apparent to one of ordinary skill in the art that all compounds of structure (I), (II) and (III) can be prepared according to one or more of the methods described herein or otherwise known in the art. It will also be apparent that in some instances it will be necessary to use a differently substituted starting material and/or protecting groups to arrive at the desired compound when following the general procedures described herein. Various substituents may also be added at various points in the synthetic scheme to prepare the desired compound.

Further, one skilled in the art will recognize that certain modifications to the above schemes and those provided in the examples are possible to prepare different embodiments of compounds of structure (I), (II) and (III). For example, for ease of illustration the General Reaction Schemes above depict preparation of compounds of structure (I), (II) and (III) wherein $R^{2a}$, $R^{2b}$ and $R^{2c}$ are fluoro, chloro and H, respectively. However, it will be apparent to one of ordinary skill in the art that differently substituted compounds of structure (I), (II) and (III) can be prepared according the general methods provided herein by using differently substituted starting materials and/or adding the desired substituent using methods known in the art.

Further, the General Reaction Schemes depict compounds comprising a piperazine ring, but other compounds can be prepared according to the provided methods by using alternative reagents, for example a reagent having the following structure:

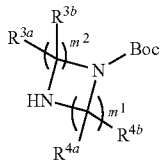

can be used in place of the piperazine illustrated in the above schemes. One of ordinary skill in the art will also readily recognize that compounds wherein $L^1$ is $NR^5$ can be prepared by substituting the piperazine illustrated in the above schemes with a heterocycle having the following structure:

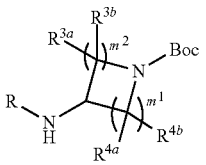

where R is H, a protecting group or $C_1$-$C_6$alkyl.

It will also be appreciated by those skilled in the art that in the processes for preparing the compounds described herein the functional groups of intermediate compounds may need to be protected by suitable protecting groups. Such functional groups include, but are not limited to, hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups are optionally added or removed in accordance with standard techniques, which are known to one skilled in the art and as described herein. The use of protecting groups is described in detail in Green, T. W. and P. G. M. Wutz, Protective Groups in Organic Synthesis (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Pharmaceutical Compositions

Other embodiments are directed to pharmaceutical compositions. The pharmaceutical composition comprises any one (or more) of the foregoing compounds and a pharmaceutically acceptable carrier. In some embodiments, the pharmaceutical composition is formulated for oral administration. In other embodiments, the pharmaceutical composition is formulated for injection. In still more embodiments, the pharmaceutical compositions comprise a compound as disclosed herein and an additional therapeutic agent (e.g., anticancer agent). Non-limiting examples of such therapeutic agents are described herein below.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that are used in some embodiments. An exemplary dosage is 10 to 30 mg per day. The exact dosage will depend upon the route of administration, the form in which the compound is administered, the subject to be treated, the body weight of the subject to be treated, and the preference and experience of the attending physician.

In some embodiments, a compound of the invention is administered in a single dose. Typically, such administration will be by injection, e.g., intravenous injection, in order to introduce the agent quickly. However, other routes are used as appropriate. A single dose of a compound of the invention may also be used for treatment of an acute condition.

In some embodiments, a compound of the invention is administered in multiple doses. In some embodiments, dosing is about once, twice, three times, four times, five times, six times, or more than six times per day. In other embodiments, dosing is about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

In some embodiments, the compounds of the invention are administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Provided herein are pharmaceutical compositions comprising a compound of structure (I), (II) or (III) and a pharmaceutically acceptable diluent(s), excipient(s), or carrier(s). In certain embodiments, the compounds described are administered as pharmaceutical compositions in which compounds of structure (I), (II) or (III) are mixed with other active ingredients, as in combination therapy. Encompassed herein are all combinations of actives set forth in the combination therapies section below and throughout this disclosure. In specific embodiments, the pharmaceutical compositions include one or more compounds of structure (I), (II) or (III).

A pharmaceutical composition, as used herein, refers to a mixture of a compound of structure (I), (II) or (III) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds of structure (I), (II) or (III) provided herein are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, one or more compounds of structure (I), (II) or (III) is formulated in an aqueous solutions. In specific embodiments, the aqueous solution is selected from, by way of example only, a physiologically compatible buffer, such as Hank's solution, Ringer's solution, or physiological saline buffer. In other embodiments, one or more compound of structure (I), (II) or (III) is/are formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or nonaqueous solutions. In specific embodiments, such solutions include physiologically compatible buffers and/or excipients.

In another embodiment, compounds described herein are formulated for oral administration. Compounds described herein are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds (e.g., compounds of structure (I), (II) or (III)) are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In still other embodiments, the compounds of structure (I), (II) or (III) are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds of structure (I), (II) or (III) are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the compounds of structure (I), (II) or (III) is accomplished by means of iontophoretic patches and the like. In certain embodiments, transdermal patches provide controlled delivery of the compounds of structure (I), (II) or (III). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the compounds of structure (I), (II) or (III) are formulated for administration by inhalation. Various forms suitable for administration by inhalation include, but are not limited to, aerosols, mists or powders. Pharmaceutical compositions of any of compound of structure (I), (II) or (III) are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator are formulated containing a powder mix of the compound and a suitable powder base such as lactose or starch.

In still other embodiments, the compounds of structure (I), (II) or (III) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are optionally used as suitable. Pharmaceutical compositions comprising a compound of structure (I), (II) or (III) are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound of structure (I), (II) or (III), described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least one compound of structure (I), (II) or (III) illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspensions contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a compound of structure (I), (II) or (III). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the concentration of one or more compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more compounds of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more compounds of the invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds of the invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more compounds of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more compounds of the invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

Kits/Articles of Manufacture

For use in the therapeutic applications described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical compositions is presented in a pack or dispenser device which contains one or more unit dosage forms containing a compound provided herein. The pack for example contains metal or plastic foil, such as a blister pack.

Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

Methods

Embodiments of the present invention provide a method of inhibiting RAS-mediated cell signaling comprising contacting a cell with an effective amount of one or more compounds disclosed herein. Inhibition of RAS-mediated signal transduction can be assessed and demonstrated by a wide variety of ways known in the art. Non-limiting examples include a showing of (a) a decrease in GTPase activity of RAS; (b) a decrease in GTP binding affinity or an increase in GDP binding affinity; (c) an increase in K off of GTP or a decrease in K off of GDP; (d) a decrease in the levels of signaling transduction molecules downstream in the RAS pathway, such as a decrease in pMEK level; and/or (e) a decrease in binding of RAS complex to downstream signaling molecules including but not limited to Raf. Kits and commercially available assays can be utilized for determining one or more of the above.

Embodiments also provide methods of using the compounds or pharmaceutical compositions of the present invention to treat disease conditions, including but not limited to conditions implicated by G12C KRAS, HRAS or NRAS mutation, G12C HRAS mutation and/or G12C NRAS mutation (e.g., cancer).

In some embodiments, a method for treatment of cancer is provided, the method comprising administering an effective amount of any of the foregoing pharmaceutical compositions comprising a compound of structure (I), (II) or (III) to a subject in need thereof. In some embodiments, the pharmaceutical composition comprises a compound of structure (I). In some embodiments, the pharmaceutical composition comprises a compound of structure (II). In some embodiments, the pharmaceutical composition comprises a compound of structure (III). In some embodiments, the cancer is mediated by a KRAS, HRAS or NRAS G12C mutation. In other embodiments, the cancer is pancreatic cancer, colon cancer, MYH associated polyposis, colorectal cancer or lung cancer.

In some embodiments the invention provides method of treating a disorder in a subject in need thereof, wherein the said method comprises determining if the subject has a KRAS, HRAS or NRAS G12C mutation and if the subject is determined to have the KRAS, HRAS or NRAS G12C mutation, then administering to the subject a therapeutically effective dose of at least one compound of structure (I), (II) or (III) or a pharmaceutically acceptable salt, ester, prodrug, tautomer, solvate, hydrate or derivative thereof.

The disclosed compounds strongly inhibit anchorage-independent cell growth and therefore have the potential to inhibit tumor metastasis. Accordingly, in another embodiment the disclosure provides a method for inhibiting tumor metastasis, the method comprising administering an effective amount a pharmaceutical composition of comprising any of the compounds disclosed herein and a pharmaceutically acceptable carrier to a subject in need thereof.

KRAS, HRAS or NRAS G12C mutations have also been identified in hematological malignancies (e.g., cancers that affect blood, bone marrow and/or lymph nodes). Accordingly, certain embodiments are directed to administration of a disclosed compounds (e.g., in the form of a pharmaceutical composition) to a patient in need of treatment of a hematological malignancy. Such malignancies include, but are not limited to leukemias and lymphomas. For example, the presently disclosed compounds can be used for treatment of diseases such as Acute lymphoblastic leukemia (ALL), Acute myelogenous leukemia (AML), Chronic lymphocytic leukemia (CLL), small lymphocytic lymphoma (SLL), Chronic myelogenous leukemia (CML), Acute monocytic leukemia (AMoL) and/or other leukemias. In other embodiments, the compounds are useful for treatment of lymphomas such as all subtypes of Hodgkin's lymphoma or non-Hodgkin's lymphoma.

Determining whether a tumor or cancer comprises a G12C KRAS, HRAS or NRAS mutation can be undertaken by assessing the nucleotide sequence encoding the KRAS, HRAS or NRAS protein, by assessing the amino acid sequence of the KRAS, HRAS or NRAS protein, or by assessing the characteristics of a putative KRAS, HRAS or NRAS mutant protein. The sequence of wild-type human KRAS, HRAS or NRAS is known in the art, (e.g. Accession No. NP203524).

Methods for detecting a mutation in a KRAS, HRAS or NRAS nucleotide sequence are known by those of skill in the art. These methods include, but are not limited to, polymeRASe chain reaction-restriction fragment length polymorphism (PCR-RFLP) assays, polymeRASe chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for G12C KRAS, HRAS or NRAS mutations by real-time PCR. In real-time PCR, fluorescent probes specific for the KRAS, HRAS or NRAS G12C mutation are used. When a mutation is present, the probe binds and fluorescence is detected. In some embodiments, the KRAS, HRAS or NRAS G12C mutation is identified using a direct sequencing method of specific regions (e.g., exon 2 and/or exon 3) in the KRAS, HRAS or NRAS gene. This technique will identify all possible mutations in the region sequenced.

Methods for detecting a mutation in a KRAS, HRAS or NRAS protein are known by those of skill in the art. These methods include, but are not limited to, detection of a KRAS, HRAS or NRAS mutant using a binding agent (e.g., an antibody) specific for the mutant protein, protein electrophoresis and Western blotting, and direct peptide sequencing.

Methods for determining whether a tumor or cancer comprises a G12C KRAS, HRAS or NRAS mutation can use a variety of samples. In some embodiments, the sample is taken from a subject having a tumor or cancer. In some embodiments, the sample is taken from a subject having a cancer or tumor. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA.

Embodiments also relate to a method of treating a hyperproliferative disorder in a mammal that comprises administering to said mammal a therapeutically effective amount of a compound of the present invention, or a pharmaceutically acceptable salt, ester, prodrug, solvate, hydrate or derivative thereof. In some embodiments, said method relates to the treatment of cancer such as acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin's lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-Hodgkin's lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments, said method relates to the treatment of a non-cancerous hyperproliferative disorder such as benign hyperplasia of the skin (e. g., psoriasis), restenosis, or prostate (e. g., benign prostatic hypertrophy (BPH)).

In certain particular embodiments, the invention relates to methods for treatment of lung cancers, the methods comprise administering an effective amount of any of the above described compound (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In other embodiments, the lung cancer is a small cell lung carcinoma. Other lung cancers treatable with the disclosed compounds include, but are not limited to, glandular tumors, carcinoid tumors and undifferentiated carcinomas.

Subjects that can be treated with compounds of the invention, or pharmaceutically acceptable salt, ester, prodrug, solvate, tautomer, hydrate or derivative of said compounds, according to the methods of this invention include, for example, subjects that have been diagnosed as having acute myeloid leukemia, acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin's lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-Hodgkin's lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments subjects that are treated with the compounds of the invention include subjects that have been diagnosed as having a non-cancerous hyperproliferative disorder such as benign hyperplasia of the skin (e. g., psoriasis), restenosis, or prostate (e. g., benign prostatic hypertrophy (BPH)).

Embodiments further provide methods of modulating a G12C Mutant KRAS, HRAS or NRAS protein activity by contacting the protein with an effective amount of a compound of the invention. Modulation can be inhibiting or activating protein activity. In some embodiments, the invention provides methods of inhibiting protein activity by contacting the G12C Mutant KRAS, HRAS or NRAS protein with an effective amount of a compound of the invention in solution. In some embodiments, the invention provides methods of inhibiting the G12C Mutant KRAS, HRAS or NRAS protein activity by contacting a cell, tissue, organ that express the protein of interest. In some embodiments, the invention provides methods of inhibiting protein activity in subject including but not limited to rodents and mammal (e.g., human) by administering into the subject an effective amount of a compound of the invention. In some embodiments, the percentage modulation exceeds 25%, 30%, 40%, 50%, 60%, 70%, 80%, or 90%. In some embodiments, the percentage of inhibiting exceeds 25%, 30%, 40%, 50%, 60%, 70%, 80%, or 90%.

In some embodiments, the invention provides methods of inhibiting KRAS, HRAS or NRAS G12C activity in a cell by contacting said cell with an amount of a compound of the invention sufficient to inhibit the activity of KRAS, HRAS or NRAS G12C in said cell. In some embodiments, the invention provides methods of inhibiting KRAS, HRAS or NRAS G12C activity in a tissue by contacting said tissue with an amount of a compound of the invention sufficient to inhibit the activity of KRAS, HRAS or NRAS G12C in said tissue. In some embodiments, the invention provides methods of inhibiting KRAS, HRAS or NRAS G12C activity in an organism by contacting said organism with an amount of a compound of the invention sufficient to inhibit the activity of KRAS, HRAS or NRAS G12C in said organism. In some embodiments, the invention provides methods of inhibiting KRAS, HRAS or NRAS G12C activity in an animal by contacting said animal with an amount of a compound of the invention sufficient to inhibit the activity of KRAS, HRAS or NRAS G12C in said animal. In some embodiments, the invention provides methods of inhibiting KRAS, HRAS or NRAS G12C activity in a mammal by contacting said mammal with an amount of a compound of the invention sufficient to inhibit the activity of KRAS, HRAS or NRAS G12C in said mammal. In some embodiments, the invention provides methods of inhibiting KRAS, HRAS or NRAS G12C activity in a human by contacting said human with an amount of a compound of the invention sufficient to inhibit the activity of KRAS, HRAS or NRAS G12C in said human. In other embodiments, the present invention provides methods of treating a disease mediated by KRAS, HRAS or NRAS G12C activity in a subject in need of such treatment.

Other embodiments provide methods for combination therapies in which an agent known to modulate other pathways, or other components of the same pathway, or even overlapping sets of target enzymes are used in combination with a compound of the present invention, or a pharmaceutically acceptable salt, ester, prodrug, solvate, tautomer, hydrate or derivative thereof. In one aspect, such therapy includes but is not limited to the combination of one or more compounds of the invention with chemotherapeutic agents, therapeutic antibodies, and radiation treatment, to provide a synergistic or additive therapeutic effect.

Many chemotherapeutics are presently known in the art and can be used in combination with the compounds of the invention. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomeRASe inhibitors, biological response modifiers, anti-hormones, angiogenesis inhibitors, and anti-androgens.

Non-limiting examples are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomeRASe inhibitor RFS 2000; difluoromethylornithine (DMFO). Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

Embodiments further relate to a method for using the compounds or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt, ester, prodrug, solvate, hydrate or derivative thereof, which amount is effective is sensitizing abnormal cells to treatment with radiation. The amount of the compound, salt, or solvate in this method can be determined according to the means for ascertaining effective amounts of such compounds described herein.

The compounds or pharmaceutical compositions of the invention can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloprotienase 9) inhibitors, and COX-11 (cyclooxygenase 11) inhibitors, can be used in conjunction with a compound of the invention and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i. e., MAP-1, MMP-3, MMP-4, MMP-5, MMP-6, MMP-7, MMP-8, MMP-10, MMP-11, MMP-12, and MMP-13). Some specific examples of MMP inhibitors useful in the invention are AG-3340, RO 32-3555, and RS 13-0830.

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

Different embodiments also relate to a method of and to a pharmaceutical composition for treating a cardiovascular disease in a mammal which comprises an amount of a compound of the invention, or a pharmaceutically acceptable salt, ester, prodrug, solvate, tautomer, hydrate or derivative thereof, or an isotopically-labeled derivative thereof, and an amount of one or more therapeutic agents use for the treatment of cardiovascular diseases.

Exemplary agents for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to effect therapeutic delivery focally within the vessel wall. By incorporation of the active agent in a swellable polymer, the active agent will be released upon swelling of the polymer.

In some embodiments, the compounds described herein are formulated or administered in conjunction with liquid or solid tissue barriers also known as lubricants. Examples of tissue barriers include, but are not limited to, polysaccharides, polyglycans, seprafilm, interceed and hyaluronic acid.

In some embodiments, medicaments which are administered in conjunction with the compounds described herein include any suitable drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments are used in the form of salts (e.g. as alkali metal or amine salts or as acid addition salts) or as esters (e.g. lower alkyl esters) or as solvates (e.g. hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesteRASe agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-lactam antibiotics, an agent comprising an aminoglycoside, protein synthesis inhibitors, drugs used in the chemotherapy of tuberculosis, Mycobacterium avium complex disease, and leprosy, antifungal agents, antiviral agents including nonretroviral agents and antiretroviral agents.

Examples of therapeutic antibodies that can be combined with a compound of the invention include but are not limited to anti-receptor tyrosine kinase antibodies (cetuximab, panitumumab, tRAStuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

For treating renal carcinoma, one may combine a compound of the present invention with sorafenib and/or avastin. For treating an endometrial disorder, one may combine a compound of the present invention with doxorubincin, taxotere (taxol), and/or cisplatin (carboplatin). For treating ovarian cancer, one may combine a compound of the present invention with cisplatin (carboplatin), taxotere, doxorubincin, topotecan, and/or tamoxifen. For treating breast cancer, one may combine a compound of the present invention with taxotere (taxol), gemcitabine (capecitabine), tamoxifen, letrozole, tarceva, lapatinib, PD0325901, avastin, herceptin, OSI-906, and/or OSI-930. For treating lung cancer, one may combine a compound of the present invention with taxotere (taxol), gemcitabine, cisplatin, pemetrexed, Tarceva, PD0325901, and/or avastin.

In other embodiments, agents useful in methods for combination therapy with one or more compounds of structure (I), (II) or (III) include, but are not limited to: Erlotinib, Afatinib, Iressa, GDC0941, MLN1117, BYL719 (Alpelisib), BKM120 (Buparlisib), CYT387, GLPG0634, Baricitinib, Lestaurtinib, momelotinib, Pacritinib, Ruxolitinib, TG101348, Crizotinib, tivantinib, AMG337, cabozantinib, foretinib, onartuzumab, NVP-AEW541, Dasatinib, Ponatinib, saracatinib, bosutinib, trametinib, selumetinib, cobimetinib, PD0325901, RO5126766, Axitinib, Bevacizumab, Bostutinib, Cetuximab, Crizotinib, Fostamatinib, Gefitinib, Imatinib, Lapatinib, Lenvatinib, Ibrutinib, Nilotinib, Panitumumab, Pazopanib, Pegaptanib, Ranibizumab, Ruxolitinib, Sorafenib, Sunitinib, SU6656, Trastuzumab, Tofacitinib, Vandetanib, Vemurafenib, Irinotecan, Taxol, Docetaxel, Rapamycin or MLN0128.

Further therapeutic agents that can be combined with a compound of the invention are found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the one or more compounds of the invention will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the invention and any of the agents described above can be simultaneously administered, wherein both the agents are present in separate formulations. In another alternative, a compound of the present invention can be administered just followed by and any of the agents described above, or vice versa. In some embodiments of the separate administration protocol, a compound of the invention and any of the agents described above are administered a few minutes apart, or a few hours apart, or a few days apart.

The examples and preparations provided below further illustrate and exemplify the compounds of the present invention and methods of preparing such compounds. It is to be understood that the scope of the present invention is not limited in any way by the scope of the following examples and preparations. In the following examples, and throughout the specification and claims, molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

The following examples are provided for exemplary purposes. Other compounds of structure (I), (II) or (III) were prepared according to the following general procedures as indicated in Tables 1, 3 and 5.

Example 1

1-(4-(6-chloro-8-fluoro-7-(2-fluoro-6-hydroxyphenyl)-2-(2-morpholinoethoxy)quinazolin-4-yl)piperazin-1-yl)prop-2-en-1-one

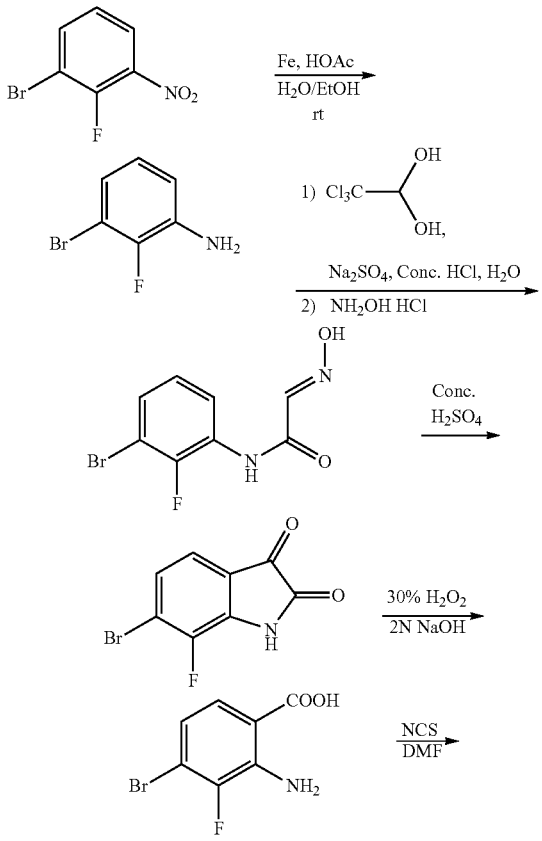

-continued

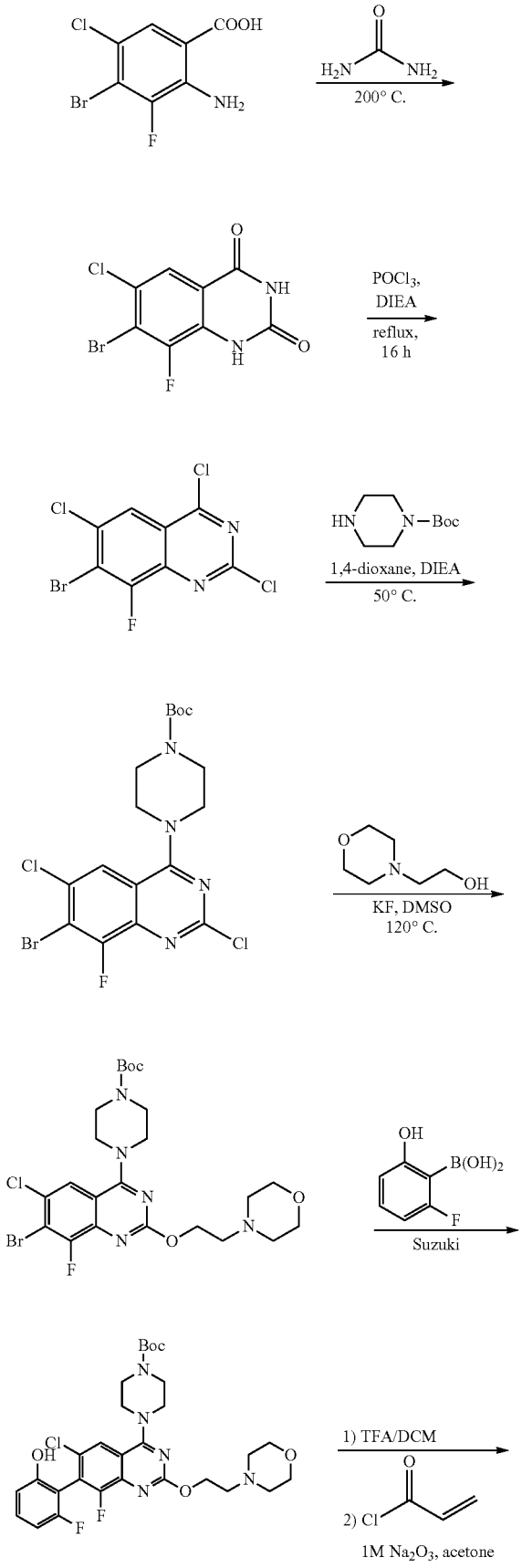

-continued

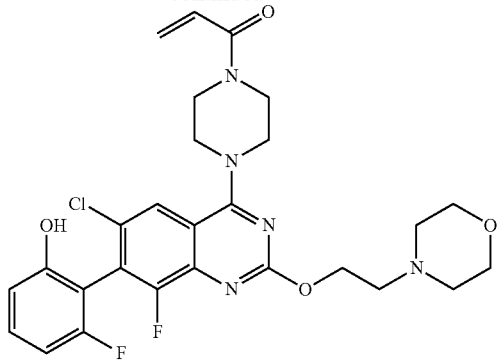

Example 1 provides an exemplary preparation according to General Synthetic Method A.

3-Bromo-2-fluorobenzenamine

To a mixture of 1-bromo-2-fluoro-3-nitrobenzene (50 g, 228.4 mmol), HOAc (41.1 g, 685.2 mmol), EtOH (420 mL) and $H_2O$ (140 mL) at room temperature, iron powder (38.4 g, 685.2 mmol) was added portion-wise. The resulting mixture was stirred at room temperature for 16 h and then was neutralized with NaOH (5 N) solution. The mixture was extracted with ethyl acetate. The organic layer was washed with brine, dried over $Na_2SO_4$, filtered and concentrated in vacuo. The residue was purified by flash column chromatography on silica gel (petroleum ether) to afford the crude product (48 g) as a brown oil.

N-(3-Bromo-2-fluorophenyl)-2-(hydroxyimino)acetamide

A mixture of 2,2,2-Trichloroethane-1,1-diol (37.7 g, 228.6 mmol) and $Na_2SO_4$ (243.5 g, 1714.5 mmol) were dissolved in water (600 mL) at 60° C. (form a clear solution). 3-Bromo-2-fluorobenzenamine (36 g, 190.5 mmol) was added to the mixture. The mixture was stirred at 60° C. for 1 h, and then 35% aqueous HCl (31.7 mL, 381 mmol) was added. The resulting mixture was stirred at 60° C. for 1 h. To this mixture, hydroxylamine hydrochloride (65.7 g, 952.5 mmol) was added. The resulting mixture was stirred at 60° C. for 4 h and then stirred at 100° C. for 16 h. The yellow precipitate was formed. The mixture was allowed to cool to room temperature. The solid was collected by filtration, rinsed with water, and dried to afford the desired product (38.9 g, 78% yield).

6-Bromo-7-fluoroindoline-2,3-dione

To the concentrated sulfuric acid (270 mL) at 60° C., N-(3-bromo-2-fluorophenyl)-2-(hydroxyimino)acetamide (29.4 g, 113.1 mmol) was added. The resulting mixture was stirred at 90° C. for 1 h. The TLC showed complete consumption of the starting material. The reaction mixture was allowed to cool to room temperature and poured into ice to get yellow precipitate. The mixture was extracted with ethyl acetate. The organic layer was washed with water, saturated $NaHCO_3$ and brine, dried over $Na_2SO_4$ and concentrated in vacuo. The residue was purified by column chromatography on silica gel (dichloromethane/ethyl acetate=200:1 to 20:1) to afford the desired product as a yellow solid (18.9 g, 68% yield). ESI-MS m/z: 278.9

[M+H]$^+$; $^1$H NMR (400 MHz, DMSO-d6) δ: 11.75 (s, 1H), 7.39 (dd, J=5.7, 7.9 Hz, 1H), 7.31 (d, J=8.2 Hz, 1H).

2-Amino-4-bromo-3-fluorobenzoic Acid

To a mixture of 6-bromo-7-fluoroindoline-2,3-dione (18.9 g, 77.5 mmol) in 2 N NaOH (350 mL) at 0° C., $H_2O_2$(30%, 40 mL) was added. The mixture was stirred at room temperature for 16 h. The mixture was quenched with $Na_2SO_3$, and the mixture was acidified with conc. HCl to adjust pH to 2. The precipitate was collected by filtration and dried to afford the desired product as a white solid (17 g, 94% yield).

2-Amino-4-bromo-5-chloro-3-fluorobenzoic Acid

To a solution of 2-amino-4-bromo-3-fluorobenzoic acid (17 g, 72.6 mmol) in DMF (200 mL) at room temperature, NCS (10.2 g, 76.2 mmol) was added and the resulting mixture was stirred at 70° C. for 16 h. The mixture was allowed to cool to room temperature and poured into cold brine. The precipitate was collected by filtration, rinsed with water and dried to afford the desired product as a white solid (14.6 g, 75% yield). ESI-MS m/z: 269.8 [M+H]$^+$.

7-Bromo-6-chloro-8-fluoroquinazoline-2,4(1H,3H)-dione

A mixture of 2-amino-4-bromo-5-chloro-3-fluorobenzoic acid (23.3 g, 110 mmol) and urea (68 g, 1100 mmol) was stirred at 200° C. for 4 h. The mixture was allowed to cool to room temperature. The solid was rinsed with boiling water 3 times, collected by filtration and dried to afford the desired product (24 g, 74% yield) as a gray solid.

7-Bromo-2,4,6-trichloro-8-fluoroquinazoline

The mixture of 7-bromo-6-chloro-8-fluoroquinazoline-2,4(1H,3H)-dione (14 g, 48 mmol) in $POCl_3$ (200 mL) and DIPEA (20 mL) was stirred at reflux for 16 h. The mixture was allowed to cool to room temperature and then concentrated in vacuo to remove $POCl_3$. The residue was purified by flash chromatography on silica gel (2% ethyl acetate/petroleum ether) and then washed with HCl (1M) to afford the product (9 g, 57% yield) as a yellow solid.

tert-Butyl 4-(7-bromo-2,6-dichloro-8-fluoroquinazolin-4-yl)piperazine-1-carboxylate To a solution of 7-bromo-2,4,6-trichloro-8-fluoroquinazoline (9 g, 27.3 mmol) and $Et_3N$ (11.4 mL, 82 mmol) in 1,4-dioxane (60 mL) at room temperature, the tert-butyl piperazine-1-carboxylate (5.07 g, 27.3 mmol) was added and the resulting mixture was stirred at 50° C. for 20 min. The mixture was allowed to cool to room temperature and partitioned between water and dichloromethane. The organic layer was washed with 1N HCl, water, saturated $NaHCO_3$ and brine, dried over $Na_2SO_4$ and concentrated in vacuo. The residue was triturated with a mixture of petroleum ether/ethyl acetate=5:1 to afford the desired product (12 g, 91.5% yield) as a light yellow solid. ESI-MS m/z: 447.2 [M+H]$^+$. $^1$H-NMR (400 MHz, $CDCl_3$) δ: 7.76 (d, J=1.8 Hz, 1H), 3.90-3.87 (m, 4H), 3.67-3.64 (m, 4H), 1.49 (s, 9H).

tert-butyl 4-(7-bromo-6-chloro-8-fluoro-2-(2-morpholinoethoxy)quinazolin-4-yl)piperazine-1-carboxylate The mixture of compound tert-butyl 4-(7-bromo-2,6-dichloro-8-fluoroquinazolin-4-yl)piperazine-1-carboxylate (1 g, 2.1 mmol), 2-morpholinoethan-1-ol (1.4 g, 10.5 mmol) and KF (0.25 g, 4.2 mmol) in dry DMSO (6 mL) was stirred at 120° C. for 3 h. The mixture was allowed to cool to RT, diluted with water and extracted with DCM. The organic layer was dried over $Na_2CO_3$, filtered and concentrated in vacuo. The residue was purified via Isolera One (EtOAc/Hexane=0-100%) to afford the desired product (675 mg, 56% yield).

tert-Butyl 4-(6-chloro-8-fluoro-7-(2-fluoro-6-hydroxyphenyl)-2-(2-morpholinoethoxy)quinazolin-4-yl)piperazine-1-carboxylate To a solution of tert-butyl 4-(7-bromo-6-chloro-8-fluoro-2-(2-morpholinoethoxy)quinazolin-4-yl)piperazine-1-carboxylate (835 mg, 1.0 eq.) in 1,4-dioxane (10 mL) in the sealed tube, (2-fluoro-6-hydroxyphenyl) boronic acid (1.16 g, 5.0 eq., 98%), tetrakis (842 mg, 0.5 eq.) and 5 mL of aqueous $Na_2CO_3$ (1 M) were added and the resulting mixture was stirred at 120° C. in the Microwave Reactor for 1 h. Above procedure was repeated with another batch of 4-(7-bromo-6-chloro-8-fluoro-2-(2-morpholinoethoxy)quinazolin-4-yl)piperazine-1-carboxylate (647 mg, 1.0 eq.), (2-fluoro-6-hydroxyphenyl) boronic acid (899 mg, 5.0 eq., 98%), tetrakis (653 mg, 0.5 eq.) in 5 mL of aqueous $Na_2CO_3$ (1 M) and 10 mL of dioxane in the sealed tube. These two batches of reaction mixture were combined, filtered and partitioned between EtOAc and water. The organic layer was dried with $Na_2SO_4$, filtered and concentrated in vacuo. The residue was purified by flash column chromatography on silica gel (DCM/MeOH=10:1) to afford the desired product (811 mg, 52% yield) as a solid. ESI-MS m/z: 606.2 [M+H]$^+$.

1-(4-(6-Chloro-8-fluoro-7-(2-fluoro-6-hydroxyphenyl)-2-(2-morpholinoethoxy)quinazolin-4-yl)piperazin-1-yl)prop-2-en-1-one 2.5 mL of TFA was added into tert-butyl 4-(6-chloro-8-fluoro-7-(2-fluoro-6-hydroxyphenyl)-2-(2-morpholinoethoxy)quinazolin-4-yl)piperazine-1-carboxylate (811 mg, 1.0 eq.) in DCM (12 mL). The reaction mixture was stirred at RT for 1 h. and was concentrated in vacuo.

The above obtained residue was suspended in aqueous $Na_2CO_3$ (1 M, 20 mL) and acetone (8 mL). Acryloyl chloride (268 μl, 2.1 eq.) was added. After stirring at RT for 2 h, the reaction mixture was concentrated in vacuo to remove acetone. The residue was taken in water, extracted with ethyl acetate, dried over $Na_2SO_4$ and concentrated in vacuo. The residue was purified by flash column chromatography on silica gel (DCM/MeOH=10:1) to afford the desired product (135 mg, 18% yield over two steps). $^1$H NMR (500 MHz, DMSO-d6) δ: 10.23 (s, 1H), 7.95 (s, 1H), 7.34 (dd, J=15, 8.5 Hz, 1H), 6.85 (d, J=8.5 Hz, 1H), 6.80 (m, 2H), 6.17 (dd, J=17, 2.5 Hz, 1H), 5.74 (dd, J=10.5, 2.5 Hz, 1H), 4.46 (t, J=5.5 Hz, 2H), 3.90-3.76 (m, 8H), 3.55 (t, J=5 Hz, 4H), 2.70 (t, J=5.5 Hz, 2H), 2.47 (m, 4H); ESI-MS m/z: 560.2 [M+H]$^+$.

Example 2

1-(4-(6-chloro-2-((1-cyclopropylpiperidin-4-yl)amino)-8-fluoro-7-(5-methyl-1H-indazol-4-yl)quinazolin-4-yl)piperazin-1-yl)prop-2-en-1-one

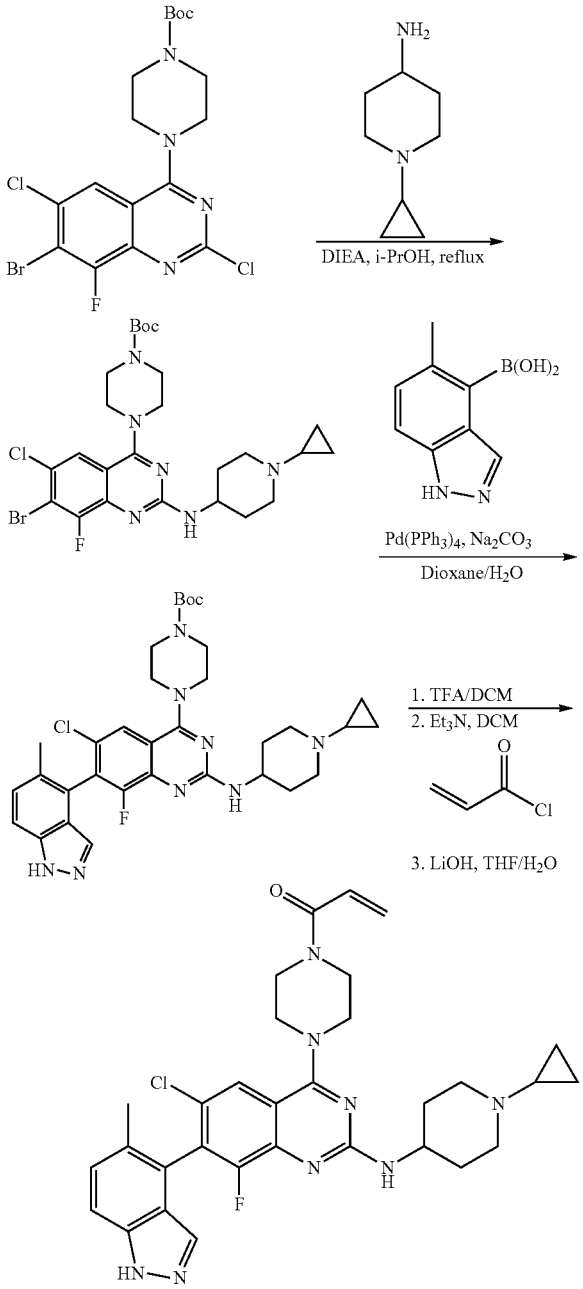

Example 2 provides an exemplary preparation according to General Synthetic Method B.

4-(7-bromo-6-chloro-2-((1-cyclopropylpiperidin-4-yl)amino)-8-fluoroquinazolin-4-yl)piperazine-1-carboxylate To a stirred mixture of tert-butyl 4-(7-Bromo-2,6-dichloro-8-fluoroquinazolin-4-yl)piperazine-1-carboxylate (5 g, 10.43 mmol) and 1-cyclopropylpiperidin-4-amine (4.4 g, 31.24 mmol) in i-PrOH (80 mL), DIPEA (3.4 g, 26.03 mmol) was added in one portion. The resulting mixture was stirred at reflux for 18 h. The mixture was allowed to cool to room temperature, poured into water and extracted with ethyl acetate (100 mL×2). The combined organic layer was washed with water and brine, dried over $Na_2SO_4$, filtered and concentrated in vacuo. The residue was purified by column chromatography on silica gel (dichloromethane: MeOH=150:1 to 20:1) to afford the desired product (6 g, 98% yield).

tert-Butyl 4-(6-chloro-2-((1-cyclopropylpiperidin-4-yl)amino)-8-fluoro-7-(5-methyl-1H-indazol-4-yl)quinazolin-4-yl)piperazine-1-carboxylate tert-Butyl 4-(7-bromo-6-chloro-2-((1-cyclopropylpiperidin-4-yl)amino)-8-fluoroquinazolin-4-yl)piperazine-1-carboxylate (6 g, 10.28 mmol), (5-methyl-1H-indazol-4-yl)boronic acid (5.4 g, 30.83 mmol), $Na_2CO_3$ (3.3 g, 30.83 mmol), $Pd(PPh_3)_4$(1.2 g, 1.03 mmol) were suspended in a mixture of dioxane (160 mL) and water (40 mL). The resulting mixture was stirred at reflux for 16 h. The mixture was allowed to cool to room temperature, poured into water, and then extracted with ethyl acetate (150 mL×2). The combined organic layer was dried over $Na_2SO_4$, filtered and concentrated in vacuo. The residue was purified by column chromatography on silica gel (DCM:MeOH=100:1 to 20:1) to afford the desired product (3.8 g, 54% yield).

1-(4-(6-Chloro-2-((1-cyclopropylpiperidin-4-yl)amino)-8-fluoro-7-(5-methyl-1H-indazol-4-yl)quinazolin-4-yl)piperazin-1-yl)prop-2-en-1-one To a stirred solution of tert-butyl 4-(6-chloro-2-((1-cyclopropylpiperidin-4-yl)amino)-8-fluoro-7-(5-methyl-1H-indazol-4-yl)quinazolin-4-yl)piperazine-1-carboxylate (2.7 g, 4.26 mmol) in dichloromethane (40 mL), TFA (10 mL) was added and the resulting mixture was stirred at room temperature for 1 h. The mixture was concentrated in vauco. The residue was dissolved in dichloromethane (60 mL), treated with $NaHCO_3$, washed with water and brine, dried over $Na_2SO_4$ and concentrated in vacuo to afford crude product (2.0 g). The crude product was dissolved in dichloromethane (60 mL) and cooled to −78° C. under a nitrogen atmosphere. To this mixture, TEA (1.1 g, 11.24 mmol) was added, followed by slow additional of acryloyl chloride (481 mg, 5.34 mmol) in dichloromethane (30 mL) (over 10 min). The resulting mixture was stirred at −78° C. for 15 min. The mixture was allowed to warm to room temperature, washed with $NaHCO_3$, dried over $Na_2SO_4$ and concentrated in vacuo. The residue was dissolved in the mixture of THF and $H_2O$ (4/1, 20 mL). Then $LiOH.H_2O$ (1.0 g, 25 mmol) was added and the mixture was stirred for 30 min. TLC showed complete conversion. The mixture was acidified with HCl (1N) to adjust pH=6-7 and then extracted with dichloromethane (50 mL×3). The combined organic layer was concentrated in vacuo. The residue was purified by column chromatography on silica gel (DCM/MeOH=100:1, 50:1, 20:1) to afford the pure product (800 mg, 36.4%) (Note: The temperature of rotary evaporator water bath was controlled below 30° C.). 1H NMR (400 MHz, DMSO-d6) δ:13.15 (s, 1H), 7.80 (s, 1H), 7.57-7.55 (M, 2H), 7.38-7.36 (m, 2H), 6.86 (dd, J=10.4, 16.4 Hz, 1H), 6.18 (dd, J=2, 16.4 Hz, 1H), 5.77-5.73 (m, 1H), 3.84-3.70 (m, 9H), 2.92 (s, 2H), 2.26-

2.20 (m, 2H), 2.17 (s, 3H), 1.85-1.83 (m, 2H), 1.61-1.56 (m, 1H), 1.50-1.40 (m, 2H), 0.40-0.28 (m, 4H). ESI-MS m/z: 589.3[M+H]$^+$.

Example 3

1-(4-(6-chloro-8-fluoro-7-(2-fluoro-6-hydroxyphenyl)-2-((1-methylpiperidin-4-yl)amino)quinazolin-4-yl)piperazin-1-yl)prop-2-en-1-one

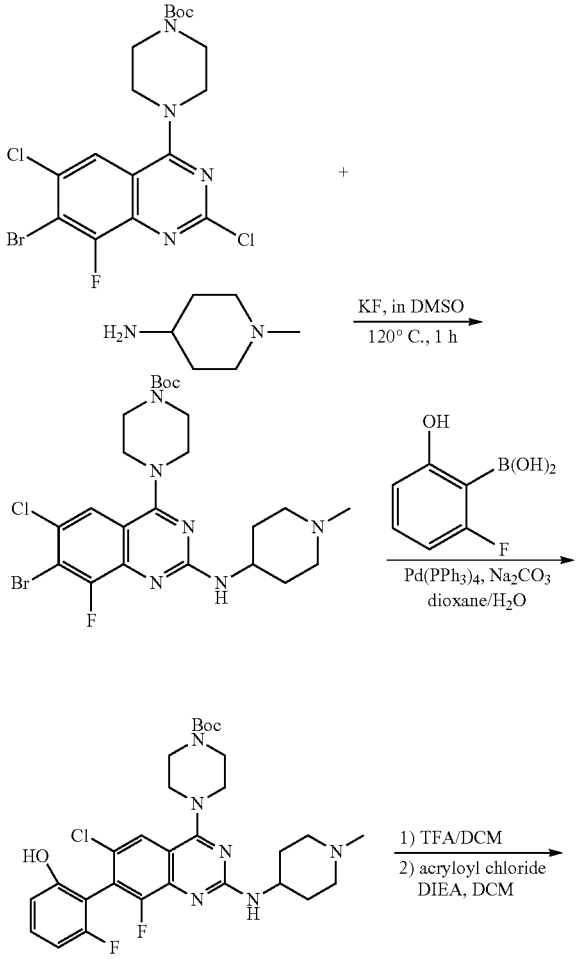

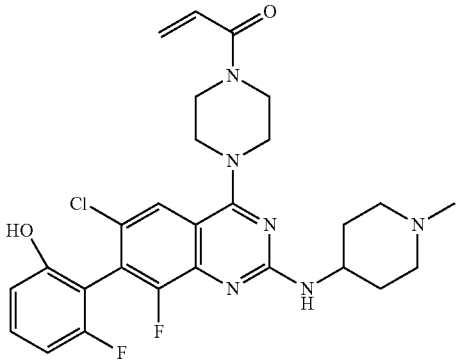

Example 3 provides another exemplary preparation according to General Synthetic Method B.

tert-Butyl 4-(7-bromo-6-chloro-8-fluoro-2-((1-methylpiperidin-4-yl)amino)quinazolin-4-yl)piperazine-1-carboxylate To a solution of tert-butyl 4-(7-bromo-2,6-dichloro-8-fluoroquinazolin-4-yl)piperazine-1-carboxylate (504 mg, 1.0 eq.) in DMSO (20 mL), KF (308 mg, 5.0 eq.) and 1-methylpiperidin-4-amine (192 μl, 1.4 eq.) were added and the resulting mixture was stirred at 120° C. for 1 h. The mixture was allowed to cool to RT, diluted with water and extracted with 20% isopropanol in dichloromethane. The combined organic layer was dried with $Na_2SO_4$, filtered and concentrated in vacuo. The residue was purified by flash column chromatography on silica gel (DCM/MeOH=10:1) to afford the desired product (614 mg, 100% yield) as a solid. ESI-MS m/z: 557.1 [M+H]$^+$.

tert-Butyl 4-(6-chloro-8-fluoro-7-(2-fluoro-6-hydroxyphenyl)-2-((1-methylpiperidin-4-yl)amino)quinazolin-4-yl)piperazine-1-carboxylate To a solution of tert-butyl 4-(7-bromo-6-chloro-8-fluoro-2-((1-methylpiperidin-4-yl)amino)quinazolin-4-yl)piperazine-1-carboxylate (362 mg, 1.0 eq.) in 1,4-dioxane (10 mL) in the sealed tube, (2-fluoro-6-hydroxyphenyl) boronic acid (476 mg, 5.0 eq., 98%), tetrakis (346 mg, 0.5 eq.) and aqueous $Na_2CO_3$ (1M, 5 mL) were added. The reaction mixture was stirred at 120° C. in the Microwave Reactor for 1 h. After cooling down, it was filtered and partitioned between EtOAc and water. The organic layer was dried with $Na_2SO_4$, filtered and concentrated in vacuo. The residue was purified by flash column chromatography on silica gel (DCM/MeOH=10:1) to afford the desired product (352 mg, 100% yield) as a solid. ESI-MS m/z: 589.3 [M+H]$^+$.

1-(4-(6-Chloro-8-fluoro-7-(2-fluoro-6-hydroxyphenyl)-2-((1-methylpiperidin-4-yl)amino)quinazolin-4-yl)piperazin-1-yl)prop-2-en-1-one To a stirred solution of above obtained tert-butyl 4-(6-chloro-8-fluoro-7-(2-fluoro-6-hydroxyphenyl)-2-((1-methylpiperidin-4-yl)amino)quinazolin-4-yl)piperazine-1-carboxylate (352 mg, 1.0 eq.) in dichloromethane (10 mL), TFA (2 mL) was added and the resulting mixture was stirred at RT for 1 h. The mixture was concentrated in vacuo. The residue was dissolved in EtOAc, concentrated and dried in vacuo. The crude product was dissolved in DCM (10 mL) and cooled to −78° C. To this mixture, DIEA (1.04 mL, 10.0 eq.) and acryloyl chloride (53 μL, 1.1 eq.) were added at −78° C. The reaction mixture was stirred at −78° C. for 3 h. The mixture was warmed to RT, washed with $NaHCO_3$, dried over $Na_2SO_4$ and concentrated in vacuo. The residue was purified by column chromatography on silica gel (DCM/MeOH=10:1) to afford the desired product (40 mg, 12% yield). 1H NMR (500 MHz, DMSO-d6) δ: 10.20 (s, 1H), 7.74 (s, 1H), 7.32 (dd, J=15, 8 Hz, 1H), 6.803 (m, 3H), 6.166 (dd, J=16.5, 2 Hz, 1H), 5.74 (dd, J=10.5, 2 Hz, 1H), 4.03 (s, 1H), 3.80-3.75 (m, 8H), 3.04 (s, 2H), 2.70 (s, 3H), 2.08 (m, 2H), 1.75 (s, 2H); ESI-MS m/z: 543.2 [M+H]$^+$.

Example 4

1-(4-(6-chloro-8-fluoro-7-(2-fluoro-6-hydroxyphenyl)-2-(2-(pyridin-2-yl)ethoxy)quinazolin-4-yl)piperazin-1-yl)prop-2-en-1-one

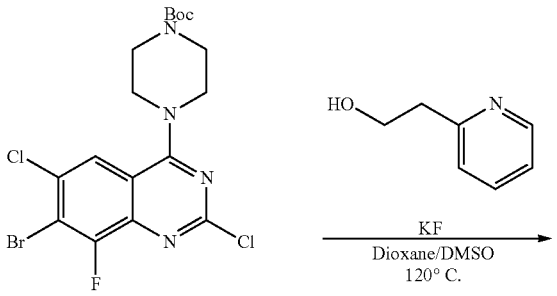

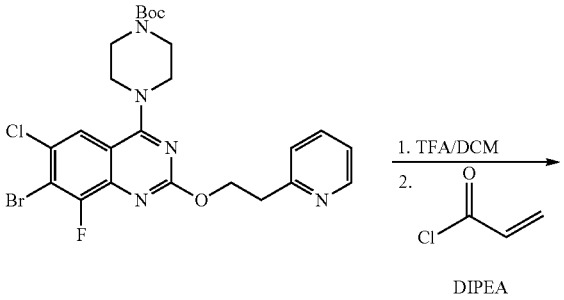

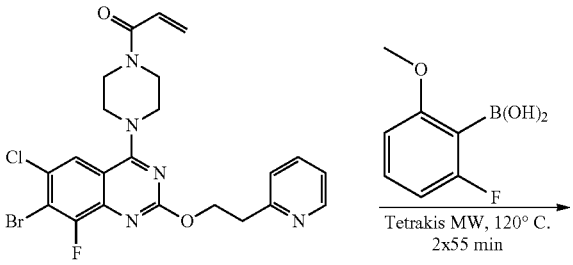

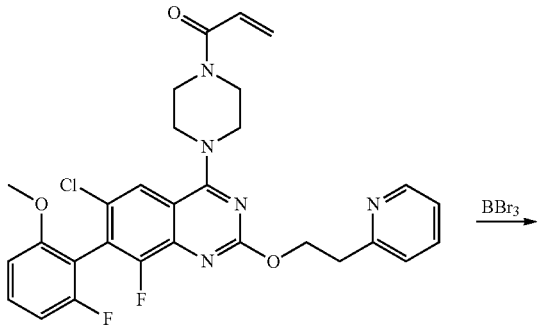

-continued

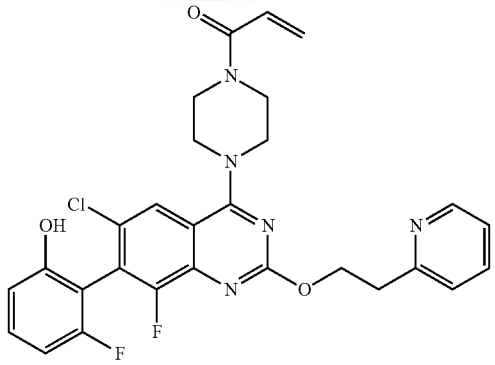

Example 4 provides an exemplary preparation according to General Synthetic Method C.

tert-butyl 4-(7-Bromo-6-chloro-8-fluoro-2-(2-(pyridin-2-yl)ethoxy)quinazolin-4-yl)piperazine-1-carboxylate The mixture of tert-butyl 4-(7-bromo-2,6-dichloro-8-fluoroquinazolin-4-yl)piperazine-1-carboxylate (1 g, 1.04 mmol), 2-(pyridin-2-yl)ethan-1-ol (1.28 g, 10.5 mmol) and KF (0.61 g, 10.5 mmol) in dry dioxane/DMSO (1:1, 10 mL) was stirred at 120° C. overnight. The mixture was allowed to cool to RT, diluted with EtOAc and washed with water. The organic layer was concentrated in vacuo. The residue was purified by column chromatography on silica gel (Isolera One Biotage, EtOAc/Hexane=0-100%) to afford the desired product. The material was used directly in the next step.

1-(4-(7-Bromo-6-chloro-8-fluoro-2-(2-(pyridin-2-yl)ethoxy)quinazolin-4-yl)piperazin-1-yl)prop-2-en-1-one The mixture of above obtained 4-(7-bromo-6-chloro-8-fluoro-2-(2-(pyridin-2-yl)ethoxy)quinazolin-4-yl)piperazine-1-carboxylate in 50% of TFA in DCM (10 mL) was stirred at RT for 30 min. The mixture was concentrated in vacuo. The residue was re-dissolved in DCM and washed with sat. $NaHCO_3$. The organic layer was dried over $Na_2SO_4$ and filtered. The mixture was concentrated in vacuo to reduce the solvent volume to 10 mL. To this mixture at 0° C., 0.3 mL of NEt3 was added followed by acrylic chloride (190 mg, 2.1 mmol), and the resulting mixture was stirred at 0° C. for 1 h. The mixture was partitioned between water and DCM. The organic layer was dried over $Na_2SO_4$ and concentrated in vacuo to give crude product (0.6 g), which was used in the next step without purification.

1-(4-(6-Chloro-8-fluoro-7-(2-fluoro-6-methoxyphenyl)-2-(2-(pyridin-2-yl)ethoxy)quinazolin-4-yl)piperazin-1-yl)prop-2-en-1-one A mixture of above obtained 1-(4-(7-bromo-6-chloro-8-fluoro-2-(2-(pyridin-2-yl)ethoxy)quinazolin-4-yl)piperazin-1-yl)prop-2-en-1-one (135 mg, 0.26 mmol), (2-fluoro-6-methoxyphenyl)boronic acid (78.5 mg, 0.39 mmol) and tetrakis (45 mg, 0.039 mmol) in co-solvent of dioxane (3 mL) and 0.5 M $Na_2CO_3$ (1 mL) was stirred in a sealed tube in microwave reactor at 120° C. for 55 min. Additional amount of (2-fluoro-6-methoxyphenyl)boronic acid (78.5 mg, 0.39 mmol) and tetrakis (45 mg, 0.039 mmol) were added and the resulting mixture was stirred in microwave reactor at 120° C. for 55 min. The mixture was diluted with DCM and washed with water. The organic layer was dried over $Na_2SO_4$ and concentrated in vacuo. The above reaction at the same scale was repeated. The combined two batches were purified via Isolera One (MeOH/DCM=0-5%) to afford the desired product (120 mg, 82% yield).

1-(4-(6-Chloro-8-fluoro-7-(2-fluoro-6-hydroxyphenyl)-2-(2-(pyridin-2-yl)ethoxy)quinazolin-4-yl)piperazin-1-yl)prop-2-en-1-one To a solution of 1-(4-(6-chloro-8-fluoro-7-(2-fluoro-6-methoxyphenyl)-2-(2-(pyridin-2-yl)ethoxy)quinazolin-4-yl)piperazin-1-yl)prop-2-en-1-one (120 mg, 0.21 mmol) in DCM (5 mL) at −78° C., $BBr_3$ (1.0 M, 2 mL) in DCM was added and the resulting mixture was stirred from −78° C. to RT for 3 h. To this mixture, i-PrOH (1 mL) was added and stirring was continued for 1 h. The mixture was partitioned between DCM and water. The organic layer was dried over $Na_2SO_4$ and concentrated in vacuo. The residue was purified via Isolera One (MeOH/DCM=0-5%) to afford the desired product (59 mg, 50% yield) as a solid. $^1$H NMR (500 MHz, $CDCl_3$) δ: 8.51 (d, J=4.0 Hz, 1H), 7.94 (s, 1H), 7.73 (m, 1H), 7.31-7.39 (m, 2H), 7.24 (m, 1H), 6.76-6.87 (m, 3H), 6.16 (d, J=16.5 Hz, 1H), 5.73 (d, J=10.5 Hz, 1H), 4.74 (dd, J=6.5, 7.0 Hz, 2H), 3.7-3.9 (m, 8H), 3.23 (t, J=7.0 Hz, 2H); ESI-MS m/z: 553.2 $[M+H]^+$.

Example 5

1-(4-(6-chloro-8-fluoro-2-((2-(2-methyl-1H-imidazol-1-yl)ethyl)amino)-7-(5-methyl-1H-indazol-4-yl)quinazolin-4-yl)piperazin-1-yl)prop-2-en-1-one

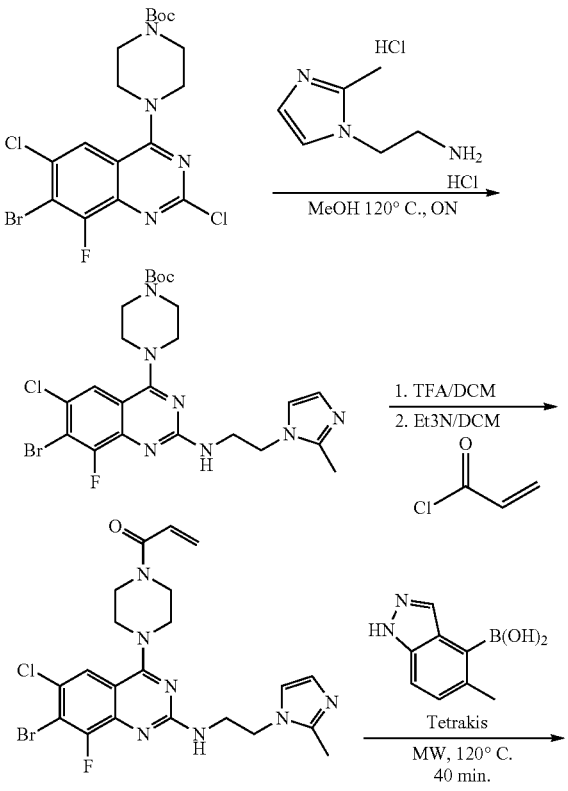

-continued

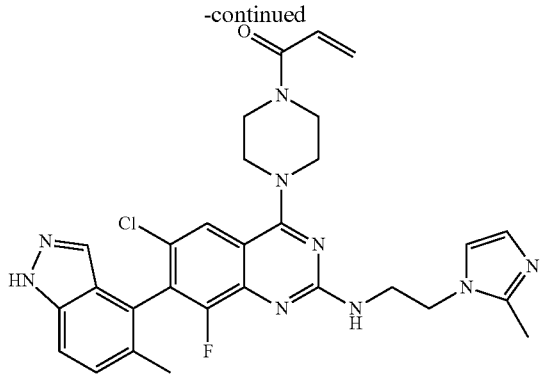

Example 5 provides an exemplary preparation according to General Synthetic Method D.

tert-Butyl 4-(7-bromo-6-chloro-8-fluoro-2-((2-(2-methyl-1H-imidazol-1-yl)ethyl)amino)quinazolin-4-yl)piperazine-1-carboxylate The mixture of tert-butyl 4-(7-bromo-2,6-dichloro-8-fluoroquinazolin-4-yl)piperazine-1-carboxylate (240 mg, 0.5 mmol), 2-(2-methyl-1H-imidazol-1-yl)ethan-1-amine dihydrochloride (119 mg, 0.6 mmol) and DIEA (195 mg, 1.5 mmol) in MeOH (10 mL) in pressure vessel was stirred at 120° C. overnight. The mixture was allowed to cool to RT and partitioned between DCM and water. The organic layer was dried over $Na_2SO_4$ and concentrated in vacuo. The crude product was used directly in the next step without further purification.

1-(4-(6-Chloro-8-fluoro-2-((2-(2-methyl-1H-imidazol-1-yl)ethyl)amino)-7-(5-methyl-1H-indazol-4-yl)quinazolin-4-yl)piperazin-1-yl)prop-2-en-1-one The title compound was prepared from tert-butyl 4-(7-bromo-6-chloro-8-fluoro-2-((2-(2-methyl-1H-imidazol-1-yl)ethyl)amino)quinazolin-4-yl)piperazine-1-carboxylate using (5-methyl-1H-indazol-4-yl)boronic acid instead of (2-fluoro-6-methoxyphenyl)boronic acid in the Suzuki coupling step according to the procedure described in Example 4. $^1$H NMR (500 MHz, $CDCl_3$) δ: 13.14 (s, 1H), 7.82 (s, 1H), 7.55-7.58 (m, 2H), 7.37 (d, J=9.0 Hz, 1H), 7.02 (s, 1H), 6.85 (dd, J=10.5, 16.5 Hz, 1H), 6.67 (s, 1H), 6.18 (d, J=16.5 Hz, 1H), 5.74 (d, J=10.5 Hz, 1H), 4.08 (br s, 2H), 3.53-3.87 (m, 10H), 2.26 (s, 3H), 2.17 (s, 3H); ESI-MS m/z: 575.2 $[M+H]^+$.

Example 6

1-(4-(6-chloro-2-(2-(dimethylamino)ethyl)-8-fluoro-7-(5-methyl-1H-indazol-4-yl)quinazolin-4-yl)piperazin-1-yl)prop-2-en-1-one

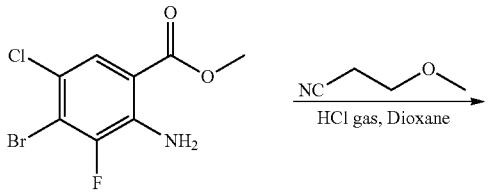

-continued

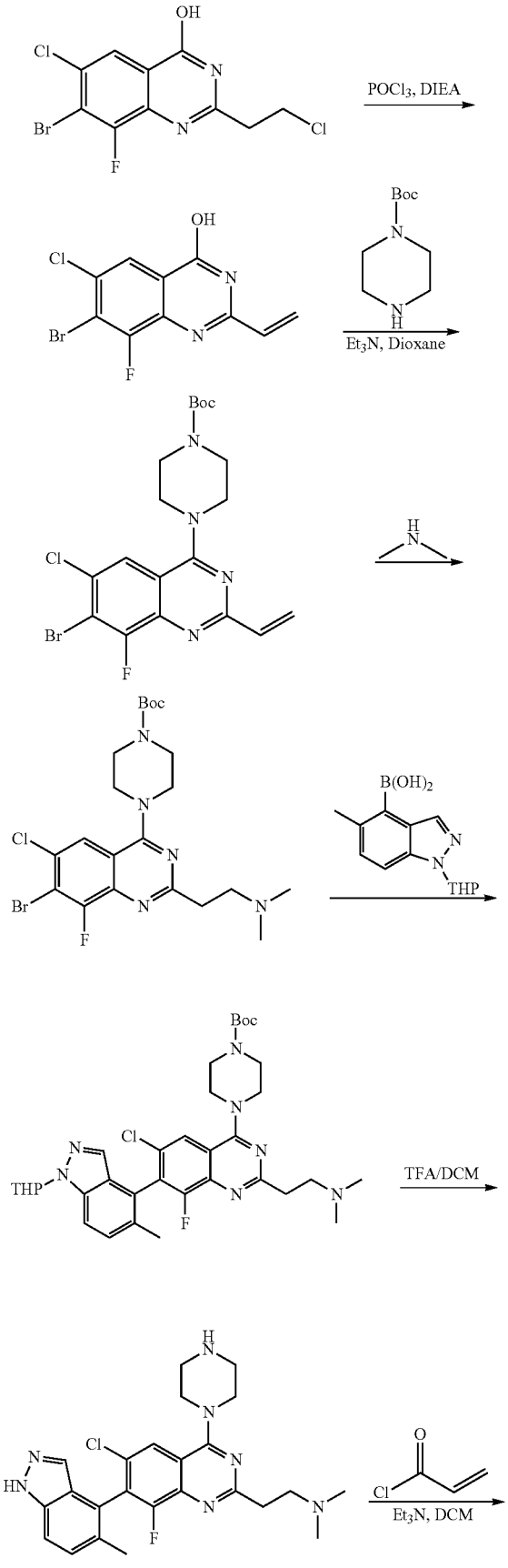

-continued

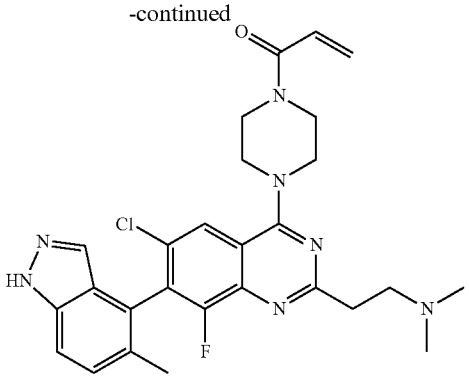

Example 6 provides an exemplary preparation according to General Synthetic Method E.

7-Bromo-6-chloro-2-(2-chloroethyl)-8-fluoroquinazolin-4-ol

A mixture of methyl 2-amino-4-bromo-5-chloro-3-fluorobenzoate (500 mg, 1.77 mmol) and 3-methoxypropanenitrile (1.1 g, 12.94 mmol) in dioxane (30 mL) was blown with HCl gas for 50 min at R.T. The mixture was stirred at 80° C. for 16 h. The mixture was allowed to cool to RT, poured into water (200 mL), and extracted with ethyl acetate (50 mL×3). The combined organic layer was washed with brine, dried over $Na_2SO_4$ and concentrated in vacuo. The residue was purified by column chromatography (DCM/MeOH=20:1) to afford the product as a faint yellow solid (58 mg, 10% yield). ESI-MS m/z: 339.9 $[M+H]^+$.

7-Bromo-4,6-dichloro-8-fluoro-2-vinylquinazoline

The mixture of 7-bromo-6-chloro-2-(2-chloroethyl)-8-fluoroquinazolin-4-ol (350 mg, 1.03 mmol) and DIEA (3 mL) in $POCl_3$ (30 mL) was stirred at 130° C. for 2 h. The mixture was evaporated under reduced pressure. The residue was added to a dichloromethane-$Et_3N$ solution. The resulting mixture was poured into 1M HCl (150 mL) solution. The aqueous phase was extracted with DCM (30 mL×2). The organic layer was dried over $Na_2SO_4$ and concentrated in vacuo. The residue was purified by column chromatography on silica gel (ethyl acetate/Petroleum ether=1:10) to afford the product (120 mg, 36% yield) as a yellow solid. ESI-MS m/z: 322.9 $[M+H]^+$.

tert-Butyl-4-(7-bromo-6-chloro-8-fluoro-2-vinylquinazolin-4-yl)piperazine-1-carboxylate A mixture of 7-bromo-4,6-dichloro-8-fluoro-2-vinylquinazoline (120 mg, 0.373 mmol), tert-butyl piperazine-1-carboxylate (84 mg, 0.447 mmol) and $Et_3N$ (38 mg, 0.373 mmol) in dioxane (20 mL) was stirred at 50° C. for 1.5 h. The mixture was extracted with ethyl acetate. The organic layer was washed with Sat. $NaHCO_3$ and brine, dried over $Na_2SO_4$ and concentrated in vacuo. The residue was purified by column chromatography on silica gel (ethyl acetate/Petroleum ether=1:5) to afford the product (110 mg, 63% yield) as an orange oil. ESI-MS m/z: 473.1$[M+H]^+$.

tert-Butyl-4-(7-bromo-6-chloro-2-(2-(dimethylamino)ethyl)-8-fluoroquinazolin-4-yl)piperazine-1-carboxylate To a mixture of tert-butyl-4-(7-bromo-6-chloro-8-fluoro-2-vinylquinazolin-4-yl)piperazine-1-carboxylate (110 mg, 0.23 mmol) in dimethylamine (2.0 M in THF) AcOH (5 drops) was added and the resulting mixture was stirred at 60° C. for 3 h. The mixture was evaporated under reduced pressure. The residue was purified by column chromatography on silica gel (MeOH/DCM=1:10) to afford the desired product (82 mg, 69% yield) as a brown solid. ESI-MS m/z: 516.2 $[M+H]^+$.

tert-butyl-4-(6-chloro-2-(2-(dimethylamino)ethyl)-8-fluoro-7-(5-methyl-1-(tetrahydro-2H-pyran-2-yl)-1H-indazol-4-yl)quinazolin-4-yl)piperazine-1-carboxylate A mixture of tert-butyl 4-(7-bromo-6-chloro-2-(2-(dimethylamino)ethyl)-8-fluoroquinazolin-4-yl)piperazine-1-carboxylate (82 mg, 0.16 mmol), (5-methyl-1-(tetrahydro-2H-pyran-2-yl)-1H-indazol-4-yl)boronic acid (165 mg, 0.64 mmol), $Pd(PPh_3)_4$ (28 mg, 0.024 mmol) and $Na_2CO_3$ (51 mg, 0.48 mmol) in 1,4-dioxane/$H_2O$ (15 mL/5 mL) was stirred at 110° C. under argon for 16 h. The mixture was allowed to cool to RT and extracted with ethyl acetate (50 mL). The organic layer was washed with 2 M NaOH solution, dried over $Na_2SO_4$, filtered and concentrated in vacuo. The residue was purified by flash column chromatography on silica gel (DCM/MeOH=20:1 to 10:1) to afford the desired product (37 mg, 36% yield) as an orange color oil. ESI-MS m/z: 652.4 $[M+H]^+$.

1-(4-(6-Chloro-2-(2-(dimethylamino)ethyl)-8-fluoro-7-(5-methyl-1H-indazol-4-yl)quinazolin-4-yl)piperazin-1-yl)prop-2-en-1-one A mixture of tert-butyl-4-(6-chloro-2-(2-(dimethylamino)ethyl)-8-fluoro-7-(5-methyl-1-(tetrahydro-2H-pyran-2-yl)-1H-indazol-4-yl)quinazolin-4-yl)piperazine-1-carboxylate (37 mg, 0.057 mmol) in 10 mL of 20% TFA-DCM solution was stirred for 16 h. The mixture was concentrated in vacuo.

To a solution of above obtained residue in DCM (20 mL) and $Et_3N$ (58 mg, 0.57 mmol) at −40° C., acryloyl chloride (5 mg, 0.057 mmol) in DCM (1 mL) was added dropwise and the resulting mixture was stirred for 10 min. The mixture was quenched with 20 mL of saturated $NaHCO_3$ solution. The organic layer was separated, dried over $Na_2SO_4$, filtered and concentrated in vacuo. The residue was purified through $Al_2O_3$ chromatography followed by Pre-HPLC purification to afford the desired product. ESI-MS m/z: 523.3 $[M+H]^+$.

Example 7

1-(4-(6-chloro-8-fluoro-7-(2-fluoro-6-hydroxyphenyl)-2-(morpholine-4-carbonyl)quinazolin-4-yl)piperazin-1-yl)prop-2-en-1-one

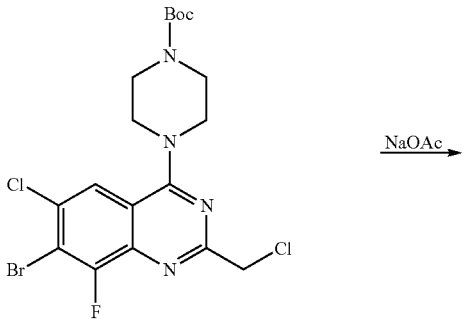

-continued

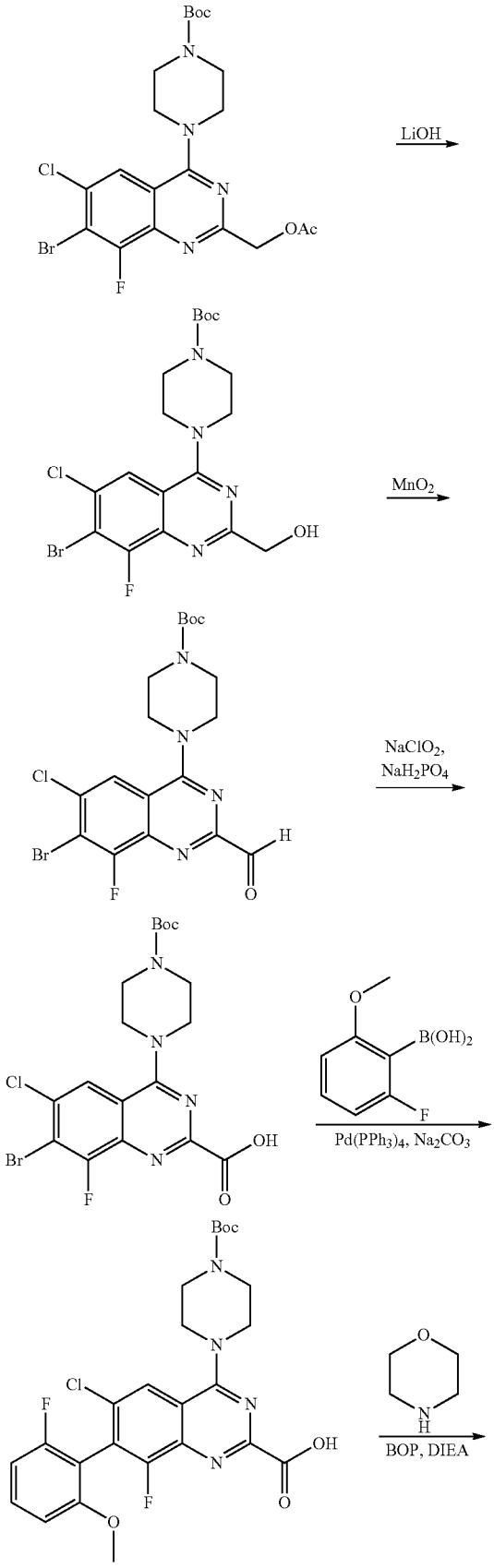

-continued

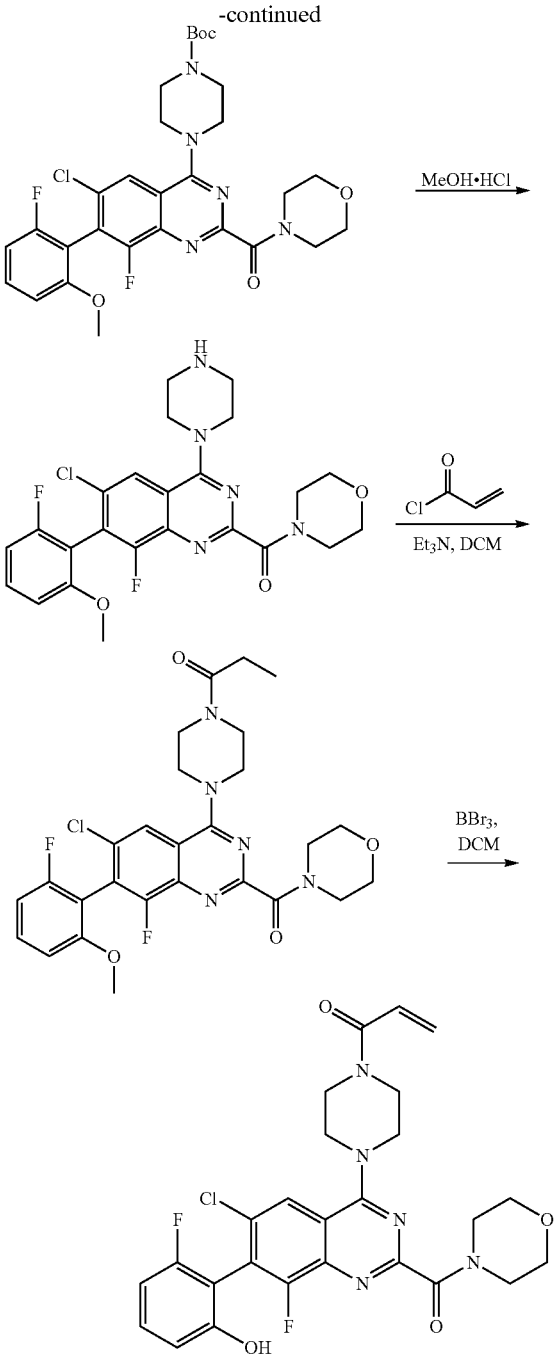

Example 7 provides an exemplary preparation according to General Synthetic Method F.

tert-Butyl-4-(2-(acetoxymethyl)-7-bromo-6-chloro-8-fluoroquinazolin-4-yl)piperazine-1-carboxylate A mixture of tert-butyl-4-(7-bromo-6-chloro-2-(chloromethyl)-8-fluoroquinazolin-4-yl)piperazine-1-carboxylate (2.25 g, 4.56 mmol) and NaOAc (1.12 g, 13.69 mmol) in DMSO (70 mL) was stirred at 80° C. for 16 h. The mixture was allowed to cool to RT, poured into water (150 mL) and extracted with ethyl acetate (30 mL×4). The organic layer was washed with Sat. $NaHCO_3$ and brine, dried over $Na_2SO_4$ and concentrated in vacuo. The residue was purified by column chromatography on silica gel (ethyl acetate/petroleum ether=1:5 to 1:3) to afford the desired product (1.27 g, 53% yield) as a yellow solid. ESI-MS m/z: 519.2 $[M+H]^+$.

tert-Butyl-4-(7-bromo-6-chloro-8-fluoro-2-(hydroxymethyl)quinazolin-4-yl)piperazine-1-carboxylate To a mixture of tert-butyl-4-(2-(acetoxymethyl)-7-bromo-6-chloro-8-fluoroquinazolin-4-yl)piperazine-1-carboxylate (1.27 g, 2.45 mmol) in THF (50 mL), $LiOH.H_2O$ (412 mg, 9.81 mmol) in water (40 mL) was added and the resulting mixture was stirred at RT for 2 h. The mixture was diluted with brine (100 mL) and extracted with ethyl acetate (50 mL×3). The organic layer was washed with brine, dried over $Na_2SO_4$ and concentrated in vacuo. The residue was purified by column chromatography on silica gel (ethyl acetate/petroleum ether=1:5 to 1:2) to afford the desired product (969 mg, 83% yield) as a yellow solid. ESI-MS m/z: 477.1 $[M+H]^+$.

tert-Butyl-4-(7-bromo-6-chloro-8-fluoro-2-formylquinazolin-4-yl)piperazine-1-carboxylate A mixture of tert-butyl-4-(7-bromo-6-chloro-8-fluoro-2-(hydroxymethyl)quinazolin-4-yl)piperazine-1-carboxylate (969 mg, 2.04 mmol) in dichloromethane (110 mL) $MnO_2$ (1.77 g, 20.38 mmol) was added and the resulting mixture was stirred at 80° C. for 16 h. The mixture allowed to cool to RT and filtered through silica chromatography and concentrated in vacuo to afford the desired product (892 mg, 92% yield) as a yellow solid.

7-Bromo-4-(4-(tert-butoxycarbonyl)piperazin-1-yl)-6-chloro-8-fluoroquinazoline-2-carboxylic Acid A mixture of tert-butyl-4-(7-bromo-6-chloro-8-fluoro-2-formylquinazolin-4-yl) piperazine-1-carboxylate (892 mg, 1.88 mmol) in a mixture of THF (30 mL), dichloromethane (10 mL), t-BuOH (30 mL) and $H_2O$ (30 mL) at 0° C., $NaClO_2$ (682 mg, 7.54 mmol), $NaH_2PO_4$ (904 mg, 7.54 mmol), and 2-methylbut-2-ene (923 mg, 13.19 mmol) were added and the resulting mixture was stirred for 2 h. The mixture was evaporated under reduced pressure. The residue was diluted with 50 mL of water and 100 mL of ethyl acetate, and then adjusted pH to 3 with 1M HCl. The mixture was extracted with ethyl acetate (30 mL×3). The organic layer was washed with brine, dried over $Na_2SO_4$ and concentrated in vacuo to afford the crude product (1.35 g) as a yellow solid. ESI-MS m/z: 489.3 $[M+H]^+$. The crude product was used directly in the next step.

4-(4-(tert-Butoxycarbonyl)piperazin-1-yl)-6-chloro-8-fluoro-7-(2-fluoro-6-methoxyphenyl)quinazoline-2-carboxylic Acid A mixture of 7-bromo-4-(4-(tert-butoxycarbonyl)piperazin-1-yl)-6-chloro-8-fluoroquinazoline-2-carboxylic acid (800 mg, 1.63 mmol) and (2-fluoro-6-methoxyphenyl)boronic acid (832 mg, 4.90 mmol), $Na_2CO_3$ (692 mg, 6.54 mmol) in dioxane (40 mL) and $H_2O$ (10 mL) was stirred at 100° C. under argon for 5 h. The mixture was diluted with ethyl acetate (60 mL), added 50 mL 0.5 M HCl, and then extracted with ethyl acetate (30 mL×2). The organic layer was washed with brine, dried over $Na_2SO_4$ and concentrated in vacuo to afford the product (725 mg, 83% yield) as a yellow solid. ESI-MS m/z: 535.3 $[M+H]^+$.

tert-Butyl-4-(6-chloro-8-fluoro-7-(2-fluoro-6-methoxyphenyl)-2-(morpholine-4-carbonyl)quinazolin-4-yl)piperazine-1-carboxylate A mixture of 4-(4-(tert-butoxycarbonyl)piperazin-1-yl)-6-chloro-8-fluoro-7-(2-fluoro-6-methoxyphenyl)quinazoline-2-carboxylic acid (200 mg, 0.37 mmol), morpholine (81 mg, 0.94 mmol) and BOP (248 mg, 0.56 mmol) in DMF (20 mL), DIEA (193 mg, 1.496 mmol) was added and the resulting mixture was stirred at RT for 2 h. The mixture was quenched with water and extracted with ethyl acetate (30 mL×3). The organic layer was washed with brine, dried over $Na_2SO_4$ and concentrated in vacuo. The residue was purified by column chromatography on silica gel (ethyl acetate/petroleum ether=1:2 to 1:1 and dichloromethane/MeOH=40:1) to afford the desired product (213 mg, 94% yield) as a white solid. ESI-MS m/z: 604.4 $[M+H]^+$.

1-(4-(6-Chloro-8-fluoro-7-(2-fluoro-6-methoxyphenyl)-2-(morpholine-4-carbonyl)quinazolin-4-yl)piperazin-1-yl)prop-2-en-1-one A mixture of tert-butyl 4-(6-chloro-8-fluoro-7-(2-fluoro-6-methoxyphenyl)-2-(morpholine-4-carbonyl)quinazolin-4-yl)piperazine-1-carboxylate (213 mg, 0.33 mmol) in MeOH.HCl (20 mL, 2.8 M) solution was stirred for 2 h. The mixture was concentrated in vacuo. The residue was dissolved in DCM (30 mL) and $Et_3N$ (178 mg, 1.76 mmol). The mixture was cooled to 0° C. and acryloyl chloride (48 mg, 0.33 mmol) in DCM (1 mL) was added dropwise. The resulting mixture was stirred for 10 min, and quenched by 20 mL saturated $NaHCO_3$ solution. The organic layer was separated, dried over $Na_2SO_4$, filtered and concentrated in vacuo. The residue was purified by column chromatography on silica gel (DCM/MeOH=30:1) to afford the desired product (169 mg, 85% yield) as a yellow solid. ESI-MS m/z: 558.3 $[M+H]^+$.

1-(4-(6-Chloro-8-fluoro-7-(2-fluoro-6-hydroxyphenyl)-2-(morpholine-4-carbonyl)quinazolin-4-yl)piperazin-1-yl)prop-2-en-1-one To a solution of 1-(4-(6-chloro-8-fluoro-7-(2-fluoro-6-methoxyphenyl)-2-(morpholine-4-carbonyl)quinazolin-4-yl)piperazin-1-yl)prop-2-en-1-one (169 mg, 0.30 mmol) in DCM (30 mL) at −78° C. under nitrogen, $BBr_3$ (265 mg, 1.06 mmol) was added and the resulting mixture was stirred at RT for 1 h and at 30° C. for 1 h. The mixture was quenched with $NaHCO_3$ solution at −30° C., and then extracted with 10% MeOH-DCM co-solvent. The organic layer was dried over $Na_2SO_4$, filtered and concentrated in vacuo. The residue was purified by column chromatography on silica gel (DCM/MeOH=30:1) followed by pre-TLC plate purification to afford the desired product (25 mg, 18% yield) as a white solid. 1H NMR (400 MHz, DMSO-d6) δ: 10.35 (s, 1H), 8.08 (s, 1H), 7.41 (dd, J=8.4, 15.6 Hz, 1H), 6.88 (m, 3H), 6.20 (dd, J=2.4, 16.8 Hz, 1H), 5.76 (dd, J=2.4, 10.0 Hz, 1H), 3.98 (m, 16H); ESI-MS m/z: 454.3 $[M+H]^+$.

Example 8

4-(4-acryloylpiperazin-1-yl)-6-chloro-8-fluoro-7-(2-fluoro-6-hydroxyphenyl)quinazoline-2-carbonitrile

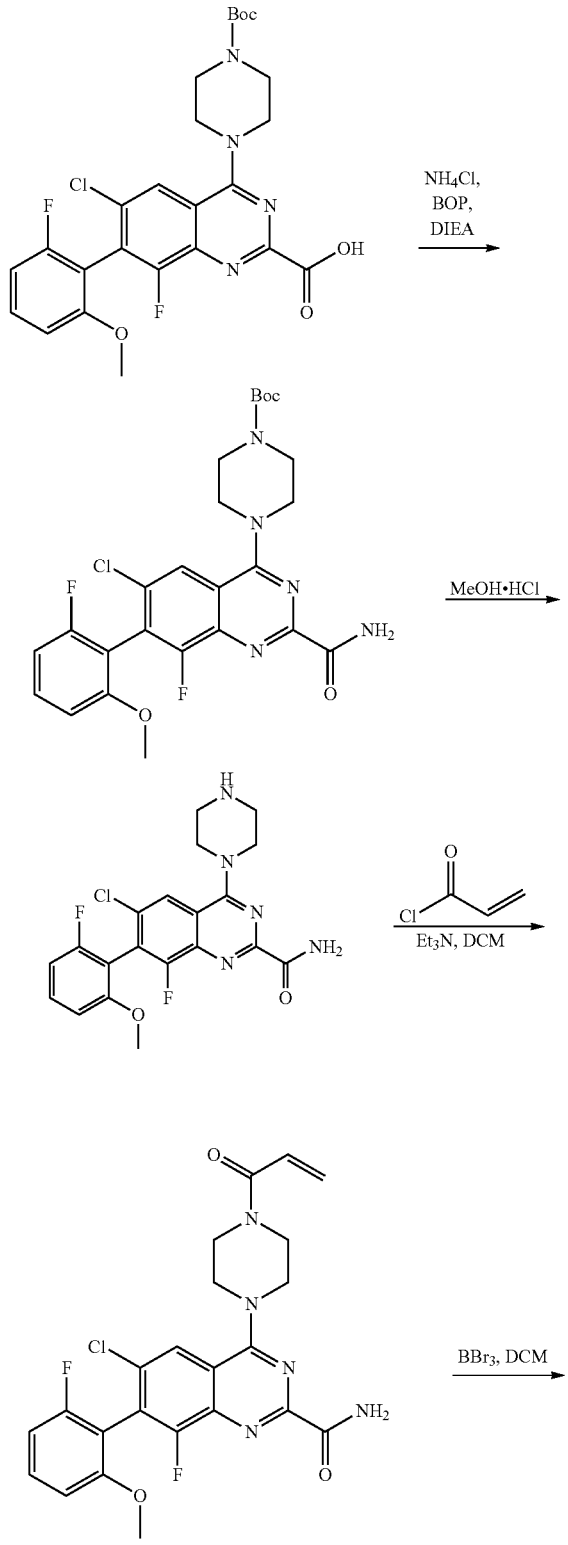

-continued

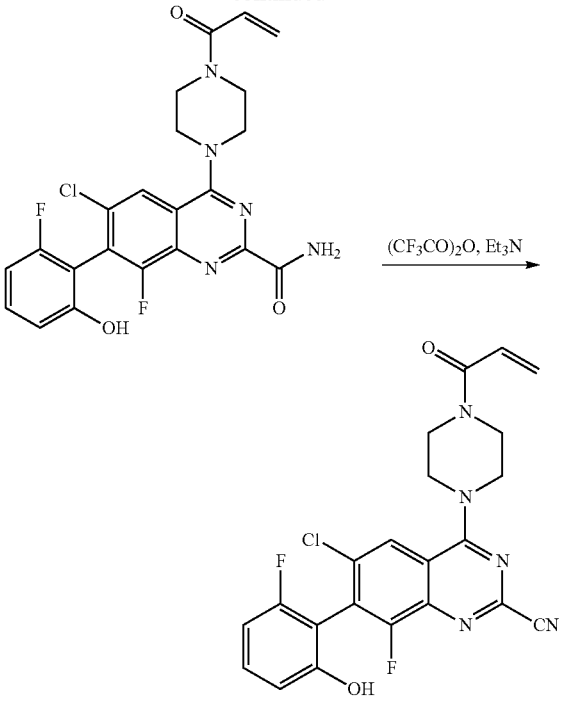

Example 8 provides an exemplary preparation according to General Synthetic Method G.

tert-Butyl-4-(2-carbamoyl-6-chloro-8-fluoro-7-(2-fluoro-6-methoxyphenyl)quinazolin-4-yl)piperazine-1-carboxylate To a mixture of 4-(4-(tert-butoxycarbonyl)piperazin-1-yl)-6-chloro-8-fluoro-7-(2-fluoro-6-methoxyphenyl)quinazoline-2-carboxylic acid (525 mg, 0.98 mmol) and $NH_4Cl$ (131 mg, 2.45 mmol), BOP (651 mg, 1.47 mmol) in DMF (20 mL), DIEA (633 mg, 4.91 mmol) was added and the resulting mixture was stirred at RT for 2 h. The mixture was quenched with water and extracted with ethyl acetate (30 mL×3). The organic layer was washed with brine, dried over $Na_2SO_4$, filtered and concentrated in vacuo. The residue was purified by column chromatography (DCM/MeOH=40:1 to 30:1) to afford the desired product (288 mg, 55% yield) as a white solid. ESI-MS m/z: 604.4 $[M+H]^+$.

4-(4-Acryloylpiperazin-1-yl)-6-chloro-8-fluoro-7-(2-fluoro-6-hydroxyphenyl)quinazoline-2-carboxamide The title compound was prepared from tert-butyl 4-(2-carbamoyl-6-chloro-8-fluoro-7-(2-fluoro-6-methoxyphenyl)quinazolin-4-yl)piperazine-1-carboxylate according to the procedure described in Example 7.1H NMR (400 MHz, DMSO-d6) δ: 10.34 (s, 1H), 8.13 (m, 2H), 7.79 (s, 1H), 7.39 (t, $J_1$=8.4 Hz, $J_2$=15.6 Hz, 1H), 6.89-6.81 (m, 3H), 6.20 (dd, $J_1$=2.0 Hz, $J_2$=16.4 Hz, 1H), 5.77 (dd, $J_1$=2.4 Hz, $J_2$=10.8 Hz, 1H), 4.04 (m, 4H), 3.84 (m, 4H); ESI-MS m/z: 474.3 $[M+H]^+$.

4-(4-Acryloylpiperazin-1-yl)-6-chloro-8-fluoro-7-(2-fluoro-6-hydroxyphenyl)quinazoline-2-carbonitrile To a mixture of 4-(4-acryloylpiperazin-1-yl)-6-chloro-8-fluoro-7-(2-fluoro-6-hydroxyphenyl)quinazoline-2-carboxamide (70 mg, 0.15 mmol) in DCM (30 mL) and $Et_3N$ (2 mL), $(CF_3CO)_2O$ (0.5 mL) was added and the resulting mixture was stirred at RT for 20 min. The mixture was quenched with saturated $NaHCO_3$ aqueous solution (70 mL) and extracted with DCM (30 mL×2). The organic layer was dried over $Na_2SO_4$ and concentrated in vacuo. The residue was purified by column chromatography (dichloromethane/ethyl acetate=1:1) to afford the product as a white solid (24 mg, 36% yield). 1H NMR (400 MHz, DMSO-d6) δ: 10.43 (s, 1H), 8.15 (s, 1H), 7.42 (m, 1H), 6.89 (m, 3H), 6.21 (m, 1H), 5.76 (m, 1H), 4.06 (m, 8H); ESI-MS m/z: 456.3 $[M+H]^+$.

Example 9

1-(4-(6-chloro-8-fluoro-7-(2-fluoro-6-hydroxyphenyl)-2-(2-(pyrimidin-2-ylamino)ethyl)quinazolin-4-yl)piperazin-1-yl)prop-2-en-1-one

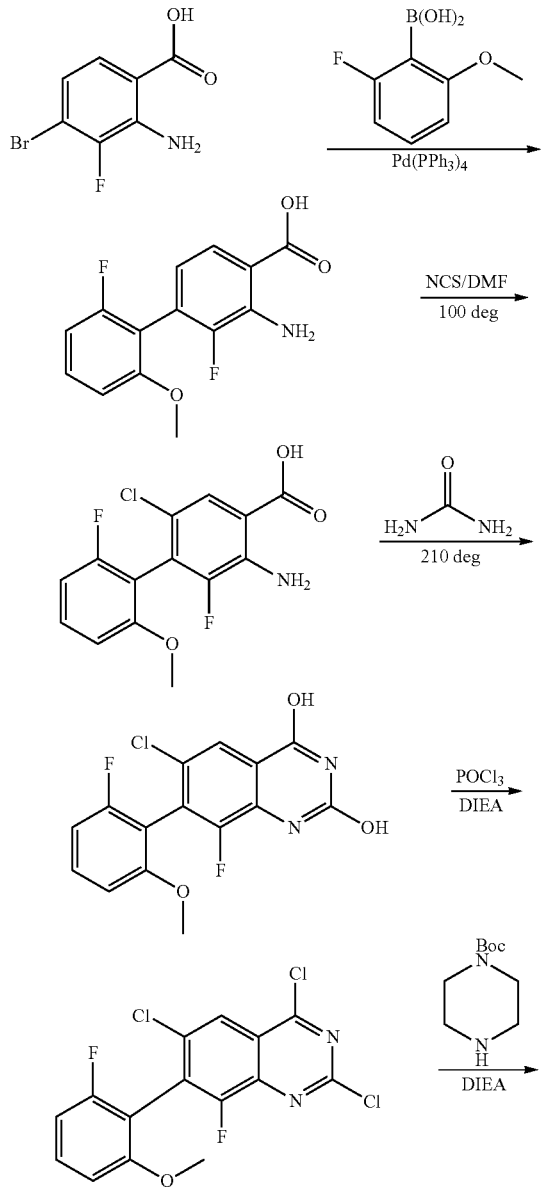

-continued

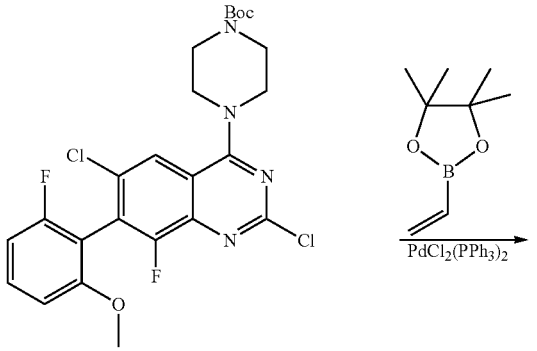

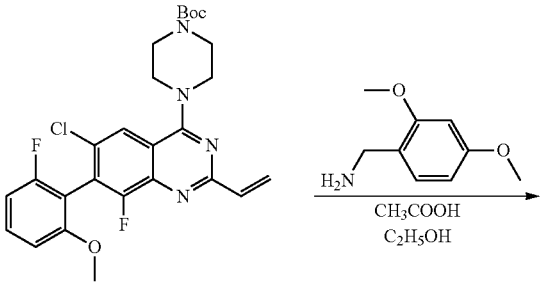

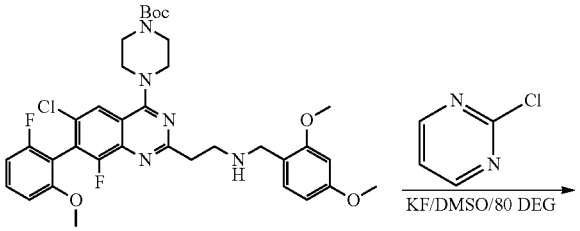

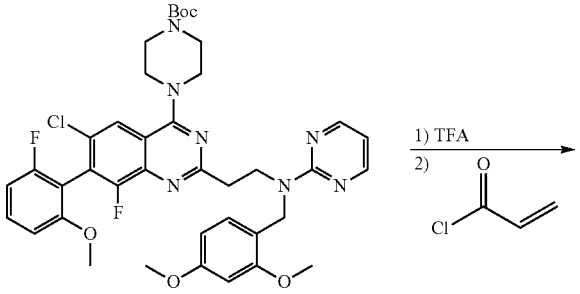

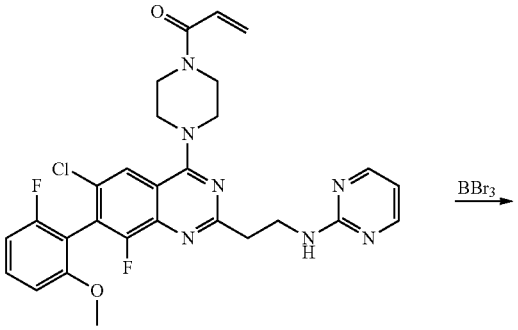

-continued

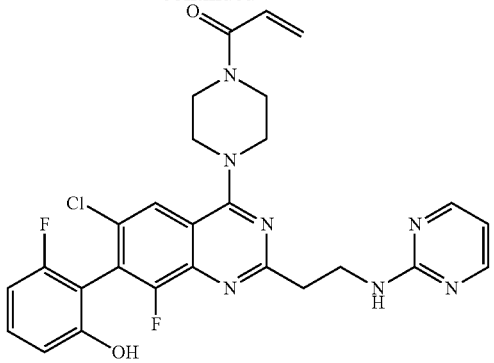

Example 9 provides an exemplary preparation according to General Synthetic Method H.

3-Amino-2,2'-difluoro-6'-methoxy-[1,1'-biphenyl]-4-carboxylic Acid

To a stirred solution of 2-amino-4-bromo-3-fluorobenzoic acid (10 g, 43 mmol) in 1,4-dioxane (400 mL) and water (100 mL), 2-fluoro-6-methoxyphenylboronic acid (36 g, 213 mmol), tetrakis(triphenylphosphine)palladium (2.5 g, 2.15 mmol) and $Na_2CO_3$ (27 g, 258 mmol) were added. The mixture was degassed and back-filled with nitrogen several times, and then stirred at 100° C. overnight. The mixture was allowed to cool to RT and partitioned between water ethyl acetate. The organic layer was discarded, and 1M HCl solution was added to aqueous phase to adjust pH <3. The aqueous phase was extracted with ethyl acetate (200 mL×2), washed with brine, dried over $Na_2SO_4$ and concentrated in vacuo to afford the desired product (11 g, 92% yield) as a white solid. ESI-MS m/z: 280.1 $[M+H]^+$.

3-Amino-6-chloro-2,2'-difluoro-6'-methoxy-[1,1'-biphenyl]-4-carboxylic Acid

To a solution of 3-amino-2,2'-difluoro-6'-methoxy-[1,1'-biphenyl]-4-carboxylic acid (11 g, 39.6 mmol) in N,N-dimethylformamide (100 mL) at RT, N-chlorosuccinimide (5.27 g, 39.6 mmol) was added and the resulting mixture was stirred at 100° C. for 1 h. The mixture was allowed to cool to RT, and then slowly added to $H_2O$ (300 mL). The mixture was filtered and the cake was dried to afford the desired product (11.5 g, 93.1% yield) as a brown solid.

6-Chloro-8-fluoro-7-(2-fluoro-6-methoxyphenyl) quinazoline-2,4-diol

A mixture of methyl 3-amino-6-chloro-2,2'-difluoro-6'-methoxy-[1,1'-biphenyl]-4-carboxylic acid (11.5 g, 37 mmol) and urea (22.5 g, 370 mmol) was stirred at 210° C. for 3 h. The mixture was allowed to cool to RT and diluted with water (300 mL). The mixture was filtered and the cake was dried to afford the desired product (10 g, 80% yield) as a brown solid.

2,4,6-Trichloro-8-fluoro-7-(2-fluoro-6-methoxyphenyl)quinazoline

The mixture of 6-chloro-8-fluoro-7-(2-fluoro-6-methoxyphenyl)quinazoline-2,4-diol (10 g, 29.7 mmol) in $POCl_3$ (200 mL) and DIPEA (20 mL) was stirred at reflux for 16 h. The mixture was allowed to cool to RT and concentrated in vacuo to remove $POCl_3$. The residue was purified by flash chromatography on silica gel (30% ethyl acetate/petroleum ether) to afford the product (6.8 g, 61.5% yield) as a brown solid.

tert-Butyl 4-(2,6-dichloro-8-fluoro-7-(2-fluoro-6-methoxyphenyl)quinazolin-4-yl) piperazine-1-carboxylate To a solution of 2,4,6-trichloro-8-fluoro-7-(2-fluoro-6-methoxyphenyl)quinazoline (6.8 g, 18.2 mmol) and DIEA (2.82 g, 21.8 mmol) in 1,4-dioxane (100 mL) at RT, tert-butyl piperazine-1-carboxylate (3.39 g, 18.2 mmol) was added and the resulting mixture was stirred at RT for 2 h. The mixture was partitioned between water and ethyl acetate. The organic layer was washed with brine, dried over $Na_2SO_4$ and concentrated in vacuo. The residue was purified by flash column chromatography on silica gel (ethyl acetate/petroleum ether=0-50%) to afford the desired product (9 g, 94% yield) as a yellow solid. ESI-MS m/z: 524.1 $[M+H]^+$.

tert-Butyl 4-(6-chloro-8-fluoro-7-(2-fluoro-6-methoxyphenyl)-2-vinylquinazolin-4-yl)piperazine-1-carboxylate To a stirred solution of tert-butyl 4-(2,6-dichloro-8-fluoro-7-(2-fluoro-6-meth oxyphenyl)quinazolin-4-yl) piperazine-1-carboxylate (3.14 g, 6 mmol) in THF (100 mL), 4,4,5,5-tetramethyl-2-vinyl-1,3,2-dioxaborolane (1.85 g, 12 mmol), palladium(II)bis(triphenylphosphine)dichloride (420 mg, 0.598 mmol) and $K_3PO_4.3H_2O$ (27 g, 258 mmol) were added. The mixture was flushed with nitrogen several times, and then stirred at 80° C. overnight. The mixture was allowed to cool to RT, diluted with water (50 mL), and extracted with ethyl acetate (20 mL×3). The combined organic layer was washed with brine, dried over $Na_2SO_4$ and concentrated in vacuo. The residue was purified by flash column chromatography on silica gel (ethyl acetate/petroleum ether=0-50%) afford the desired product (2.5 g, 81% yield) as a yellow solid. ESI-MS m/z: 517.1 $[M+H]^+$.

tert-Butyl 4-(6-chloro-2-(2-((2,4-dimethoxybenzyl) amino)ethyl)-8-fluoro-7-(2-fluoro-6-methoxyphenyl) quinazolin-4-yl)piperazine-1-carboxylate The mixture of tert-butyl 4-(6-chloro-8-fluoro-7-(2-fluoro-6-methoxyphenyl)-2-vinylquinazolin-4-yl)piperazine-1-carboxylate (2.5 g, 4.84 mmol) and (2,4-dimethoxyphenyl)methanamine (1.62 g, 9.68 mmol) in ethanol (20 mL) and acetic acid (2 mL) was stirred at reflux for 48 h. The mixture was allowed to cool to RT and concentrated in vacuo to remove ethanol. $NaHCO_3$ solution was added to adjust pH >7, and then extracted with ethyl acetate (30 mL×3). After evaporation of the combined organic layer, the residue was purified by flash chromatography on silica gel (7M $NH_3$ in $CH_3OH$/DCM=0-10%) to afford the desired product (800 mg, 24% yield) as a white solid. ESI-MS m/z: 684 $[M+H]^+$.

tert-Butyl 4-(6-chloro-2-(2-((2,4-dimethoxybenzyl) (pyrimidin-2-yl)amino)ethyl)-8-fluoro-7-(2-fluoro-6-methoxyphenyl)quinazolin-4-yl)piperazine-1-carboxylate To a stirred solution of 4-(6-chloro-2-(2-((2,4-dimethoxybenzyl)amino)ethyl)-8-fluoro-7-(2-fluoro-6-methoxyphenyl)quinazolin-4-yl)piperazine-1-carboxylate (300 mg, 0.44 mmol) in DMSO (15 mL), KF (76 mg, 1.32 mmol) and 2-chloropyrimidine (100 mg, 0.88 mmol) were added and the resulting mixture was stirred at 80° C. overnight. The mixture was allowed to cool to RT, diluted with water (50 mL) and extracted with ethyl acetate (30 mL×2). The combined organic layer was washed with brine, dried over $Na_2SO_4$ and concentrated in vacuo. The residue was purified by flash column chromatography on silica gel (MeOH/DCM=0-5%) to afford the desired product (310 mg, 92.6% yield) as a yellow solid. ESI-MS m/z: 762.1 $[M+H]^+$.

N-(2-(6-Chloro-8-fluoro-7-(2-fluoro-6-methoxyphenyl)-4-(piperazin-1-yl)quinazolin-2-yl)ethyl)pyrimidin-2-amine The mixture of tert-butyl 4-(6-chloro-2-(2-((2,4-dimethoxybenzyl)(pyrimidin-2-yl)amino)ethyl)-8-fluoro-7-(2-fluoro-6-methoxyphenyl)quinazolin-4-yl)piperazine-1-carboxylate (310 mg, 0.41 mmol) in 2,2,2-trifluoroacetic acid (10 mL) was stirred at RT for 2 h and then concentrated in vacuo. The residue was basified with $NaHCO_3$ solution to adjust pH >7, and then extracted with ethyl acetate (30 mL×3). After evaporation of the combined organic layer, the desired product was obtained (200 mg, 74% yield) as a yellow solid. ESI-MS m/z: 662.1 $[M+H]^+$.

1-(4-(6-Chloro-8-fluoro-7-(2-fluoro-6-hydroxyphenyl)-2-(2-(pyrimidin-2-ylamino)ethyl)quinazolin-4-yl)piperazin-1-yl)prop-2-en-1-one The title compound was prepared from N-(2-(6-chloro-8-fluoro-7-(2-fluoro-6-methoxyphenyl)-4-(piperazin-1-yl) quinazolin-2-yl)ethyl)pyrimidin-2-amine according to the procedure described in Example 7. $^1H$ NMR (400 MHz, DMSO-d6) δ: 10.28 (s, 1H), 8.25-8.24 (d, 2H), 7.99 (s, 1H), 7.38-7.36 (m, 1H), 7.20-7.17 (m, 1H), 6.88-6.80 (m, 3H), 6.55-6.53 (m, 1H), 6.20-6.16 (dd, J=1.6, 18.4 Hz, 1H), 5.16-5.13 (dd, J=1.2, 12.0 Hz, 1H), 3.88-3.76 (m, 10H), 3.10-3.06 (m, 2H). ESI-MS m/z: 552.1 $[M+H]^+$.

Example 10

1-(4-(6-chloro-7-(2-fluoro-6-hydroxyphenyl)-2,8-dimethoxyquinazolin-4-yl)piperazin-1-yl)prop-2-en-1-one

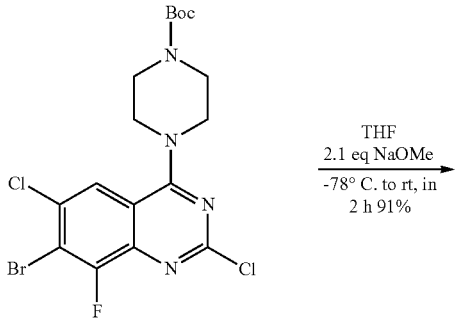

-continued

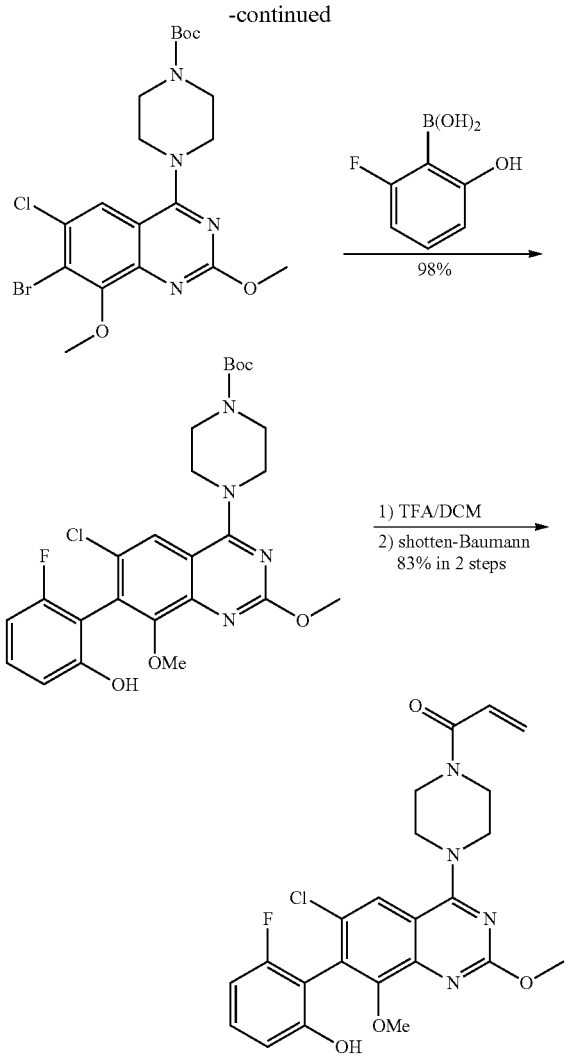

Example 10 provides an exemplary preparation according to General Synthetic Method J.

tert-Butyl 4-(7-bromo-6-chloro-2,8-dimethoxyquinazolin-4-yl)piperazine-1-carboxylate tert-Butyl 4-(7-bromo-2,6-dichloro-8-fluoroquinazolin-4-yl)piperazine-1-carboxylate (240 mg, 0.5 mmol) in a flask was dried under high vacuum overnight. NaH was added and the mixture was cooled down to −78° C., then THF (2 mL, cooled to −78° C.) was added. The reaction mixture was slowly warmed up to RT in 2 h, and then was frozen at −78° C. overnight. The reaction was quenched with THF/water and further diluted with EtOAc (100 mL). The organic layer was separated, washed with water and brine, dried with $Na_2SO_4$, filtered and concentrated in vacuo. The residue was purified by column chromatography on silica gel (1-4% MeOH in DCM) to afford the desired product (221 mg, 91% yield). ESI-MS m/z: 487.1 $[M+H]^+$.

2-(6-Chloro-2,8-dimethoxy-4-(piperazin-1-yl)quinazolin-7-yl)-3-fluorophenol

A solution of tert-butyl 4-(6-chloro-7-(2-fluoro-6-hydroxyphenyl)-2,8-dimethoxyquinazolin-4-yl)piperazine-1-carboxylate (117 mg, 0.27 mmol) in DCM (2 mL) and TFA (2 mL) was stirred for 10 min at RT. The mixture was concentrated in vacuo and the residue obtained 2-(6-chloro-2,8-dimethoxy-4-(piperazin-1-yl)quinazolin-7-yl)-3-fluorophenol was used directly in the next step.

1-(4-(6-Chloro-7-(2-fluoro-6-hydroxyphenyl)-2,8-dimethoxyquinazolin-4-yl)piperazin-1-yl)prop-2-en-1-one To a solution of 2-(6-chloro-2,8-dimethoxy-4-(piperazin-1-yl)quinazolin-7-yl)-3-fluorophenol (supposedly 0.226 mmol) in 4 mL of methyl-THF and 2 mL of water, $NaHCO_3$ solid (190 mg, 2.26 mmol, 10 eq.) was slowly added and the resulting mixture was stirred for 5 min. Then acryloyl chloride was added and the reaction was stirred at RT for 0.5 h. The mixture was treated with NaOH aq (1N, 2 mL) for 5 min. The organic layer was separated from water layer and the water layer was further extracted with EtOAc (10 mL×3). The combined organic layer was dried over $Na_2SO_4$, filtered and concentrated in vacuo. The residue was purified by column chromatography on silica gel (0-7% MeOH in DCM) to afford the desired product (88.4 mg, 83%). $^1H$ NMR (500 MHz, $CDCl_3$) δ: 7.72 (s, 1H), 7.31 (m, 1H), 6.86 (d, J=8.0 Hz, 1H), 6.80 (t, J=9.0 Hz, 1H), 6.60 (dd, J=17, 10.5 Hz, 1H), 6.37 (dd, J=17, 1.5 Hz, 1H), 5.78 (m, 2H), 4.08 (s, 3H), 4.03 (s, 3H); ESI-MS m/z: 473.1 $[M+H]^+$.

Example 11

1-(4-(6-chloro-2-(3-(4-cyclopropylpiperazin-1-yl)azetidin-1-yl)-8-fluoro-7-(2-fluoro-6-hydroxyphenyl)quinazolin-4-yl)piperazin-1-yl)prop-2-en-1-one

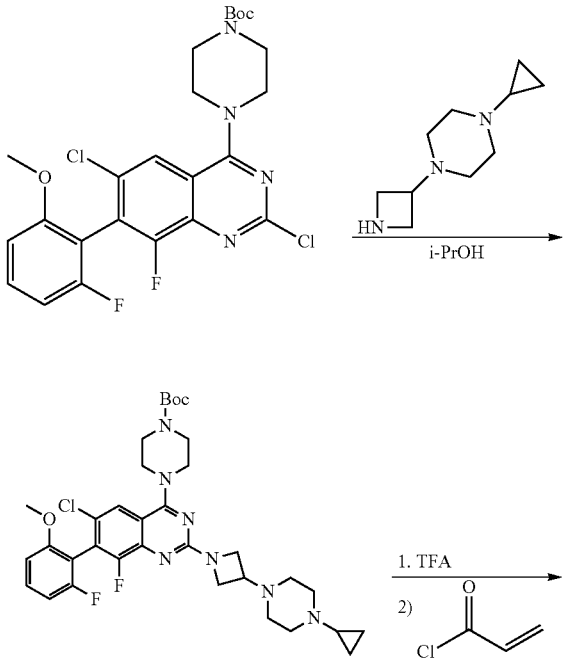

-continued

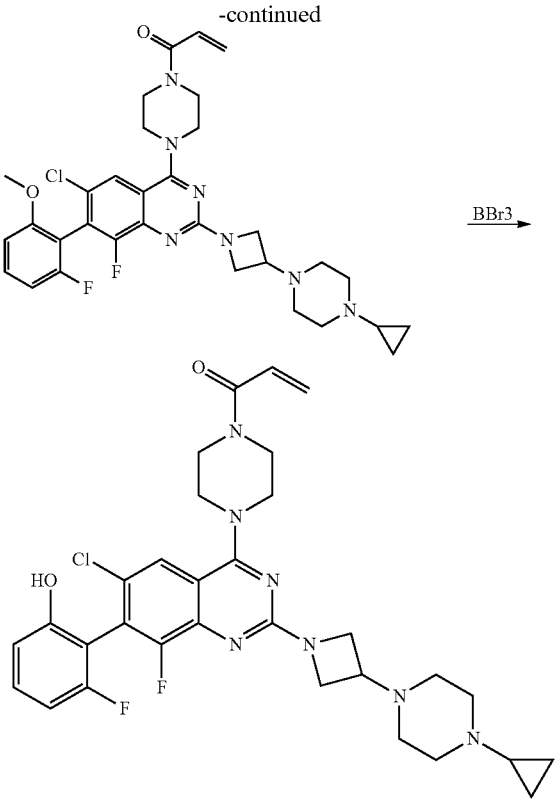

Example 11 provides an exemplary preparation according to General Synthetic Method K.

tert-Butyl 4-(6-chloro-2-(3-(4-cyclopropylpiperazin-1-yl)azetidin-1-yl)-8-fluoro-7-(2-fluoro-6-methoxyphenyl)quinazolin-4-yl)piperazine-1-carboxylate tert-Butyl 4-(2,6-dichloro-8-fluoro-7-(2-fluoro-6-methoxyphenyl)quinazolin-4-yl)piperazine-1-carboxylate (400 mg, 0.76 mmol), 1-(azetidin-3-yl)-4-cyclopropylpiperazine (207 mg, 1.14 mmol) and DIEA (186 mg, 1.53 mmol) were dissolved in i-PrOH (20 mL). The solution was stirred at 100° C. for 16 h. It was allowed to cool to RT and partitioned between water and ethyl acetate. The organic layer was washed with brine, dried over $Na_2SO_4$ and concentrated in vacuo. The residue was purified by flash column chromatography on silica gel (MeOH/dichloromethane=0-5%) to afford the desired product (300 mg, 58.7% yield) as a yellow solid. ESI-MS m/z: 670.5 $[M+H]^+$.

1-(4-(6-Chloro-2-(3-(4-cyclopropylpiperazin-1-yl)azetidin-1-yl)-8-fluoro-7-(2-fluoro-6-methoxyphenyl)quinazolin-4-yl)piperazin-1-yl)prop-2-en-1-one The mixture of tert-butyl 4-(6-chloro-2-(3-(4-cyclopropylpiperazin-1-yl)azetidin-1-yl)-8-fluoro-7-(2-fluoro-6-methoxyphenyl)quinazolin-4-yl)piperazine-1-carboxylate (300 mg, 0.45 mmol) in 2,2,2-trifluoroacetic acid (10 mL) was stirred at RT for 2 h. The mixture was concentrated in vacuo to remove 2,2,2-trifluoroacetic acid. $NaHCO_3$ solution was added to adjust pH >7, and then extracted with ethyl acetate. The organic layer was washed with saturated $NaHCO_3$ aqueous solution and brine, dried over $Na_2SO_4$ and concentrated in vacuo. The residue was dissolved in DCM (10 mL), $Et_3N$ (68 mg, 0.38 mmol) was added and the resulting solution was cooled to 0° C. Acryloyl chloride (50 mg, 0.54 mmol) was added to the mixture. The resulting mixture was stirred at RT for 0.5 h, poured into water and then extracted with dichloromethane. The organic layer was washed with brine, dried over $Na_2SO_4$ and concentrated in vacuo. The residue was purified by flash column chromatography on silica gel (1-2% methanol/dichloromethane) to afford the desired product (220 mg, 78.7% yield) as a yellow solid. ESI-MS m/z: 624.3 $[M+H]^+$.

1-(4-(6-Chloro-2-(3-(4-cyclopropylpiperazin-1-yl)azetidin-1-yl)-8-fluoro-7-(2-fluoro-6-hydroxyphenyl)quinazolin-4-yl)piperazin-1-yl)prop-2-en-1-one To a solution of 1-(4-(6-chloro-2-(3-(4-cyclopropylpiperazin-1-yl)azetidin-1-yl)-8-fluoro-7-(2-fluoro-6-methoxyphenyl)quinazolin-4-yl)piperazin-1-yl)prop-2-en-1-one (220 mg, 0.35 mmol) in dichloromethane (40 mL) at −78° C., $BBr_3$ (883 mg, 3.53 mmol) was added. The resulting solution was allowed to warm to RT and stirred at RT for 4 h. The mixture was cooled to −40° C., quenched with $NaHCO_3$, and extracted with DCM (30 mL×3). The combined organic layer was washed with brine, dried over $Na_2SO_4$ and concentrated in vacuo. The residue was purified by flash column chromatography on silica gel (MeOH/dichloromethane=0-5%) to afford the desired product (55 mg, 25.6% yield) as a yellow solid. ESI-MS m/z: 610.3 $[M+H]^+$; $^1H$ NMR (400 MHz, DMSO-d6) δ: 10.20 (s, 1H), 7.77 (s, 1H), 7.36-7.30 (m, 1H), 6.87-6.77 (m, 3H), 6.20-6.15 (dd, J=2, 16.8 Hz, 1H), 5.75-5.72 (dd, J=2.4, 10.8 Hz, 1H), 4.13-4.09 (m, 2H), 3.92-3.75 (m, 8H), 3.36-3.34 (m, 2H), 3.19-3.16 (m, 1H), 2.55-2.31 (m, 8H), 1.60-1.57 (m, 1H), 0.40-0.38 (m, 2H), 0.28-0.27 (m, 2H).

Example 12

1-(4-(6-chloro-2-((1-cyclopropylpiperidin-4-yl)methoxy)-8-fluoro-7-(2-fluoro-6-hydroxyphenyl)quinazolin-4-yl)piperazin-1-yl)prop-2-en-1-one

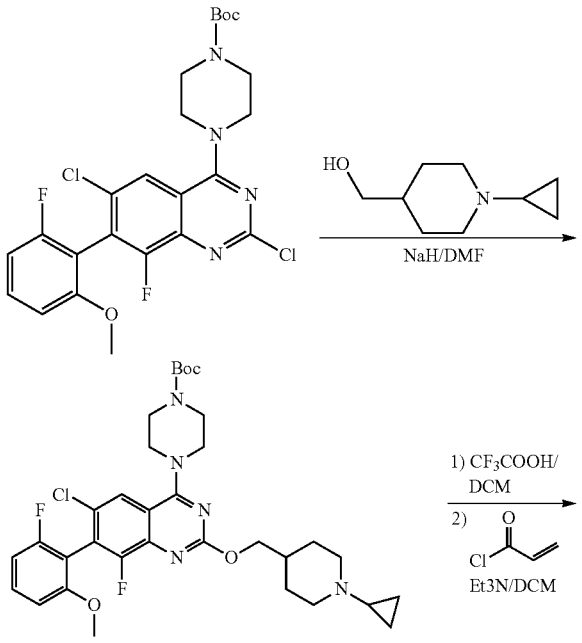

-continued

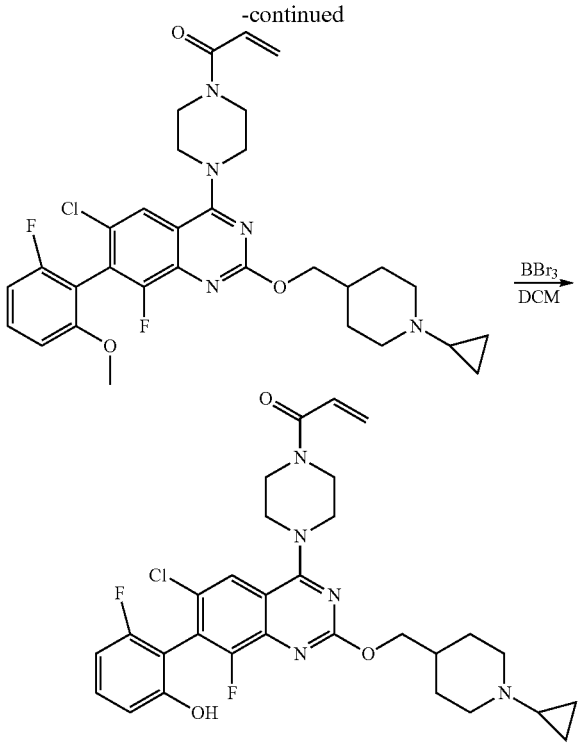

Example 12 provides an exemplary procedure according to Method L tert-butyl 4-(2-((1-cyclopropylpiperidin-4-yl) methoxy)-6-chloro-8-fluoro-7-(2-fluoro-6-methoxyphenyl)quinazolin-4-yl)piperazine-1-carboxylate To a solution of (1-cyclopropylpiperidin-4-yl)methanol (258 mg, 1.67 mmol) in DMF (20 mL) at 0° C., NaH (67 mg, 1.67 mmol, 60% in oil) was added. The mixture was stirred at 0° C. for 30 min, tert-butyl 4-(2,6-dichloro-8-fluoro-7-(2-fluoro-6-methoxyphenyl)quinazolin-4-yl)piperazine-1-carboxylate (400 mg, 0.83 mmol) was added and the resulting mixture was stirred at RT for 16 h. This mixture was quenched with saturated $NH_4Cl$ solution and extracted with ethyl acetate. The organic layer was washed with brine, dried over $Na_2SO_4$ and concentrated in vacuo. The residue was purified by flash column chromatography on silica gel (5-10% methanol/dichloroethane) to afford the desired product (150 mg, 28% yield).

1-(4-(2-((1-Cyclopropylpiperidin-4-yl)methoxy)-6-chloro-8-fluoro-7-(2-fluoro-6-methoxyphenyl)quinazolin-4-yl)piperazin-1-yl)prop-2-en-1-one To a solution of tert-butyl 4-(2-((1-cyclopropylpiperidin-4-yl)methoxy)-6-chloro-8-fluoro-7-(2-fluoro-6-methoxyphenyl)quinazolin-4-yl)piperazine-1-carboxylat (150 mg, 0.28 mmol) in dichloromethane (5 mL), TFA (2.5 mL) was added and the resulting mixture was stirred at RT for 2 h. The mixture was concentrated in vacuo. The residue was added to the mixture of $Et_3N$ (83.6 mg, 0.83 mmol) in dichloromethane (10 mL). The mixture was stirred for 5 min and then acryloyl chloride (25 mg, 0.28 mmol) was added. The resulting mixture was stirred at RT for 0.5 h, poured into water and then extracted with dichloromethane. The organic layer was washed with brine, dried over $Na_2SO_4$ and concentrated in vacuo. The residue was purified by flash column chromatography on silica gel (1-2% methanol/dichloromethane) to afford the desired product (100 mg, 61% yield).

1-(4-(2-((1-Cyclopropylpiperidin-4-yl)methoxy)-6-chloro-8-fluoro-7-(2-fluoro-6-hydroxyphenyl)quinazolin-4-yl)piperazin-1-yl)prop-2-en-1-one To a solution of 1-(4-(2-((1-cyclopropylpiperidin-4-yl) methoxy)-6-chloro-8-fluoro-7-(2-fluoro-6-methoxyphenyl) quinazolin-4-yl)piperazin-1-yl)prop-2-en-1-one (100 mg, 0.167 mmol) in dichloromethane (10 mL) at −78° C., $BBr_3$ (418 mg, 1.67 mmol) was added and the resulting mixture was stirred at RT for 1 h. This mixture was quenched with saturated $NaHCO_3$ and extracted with dichloromethane. The organic layer was washed with saturated $NaHCO_3$ aqueous solution and brine, dried over $Na_2SO_4$ and concentrated in vacuo. The residue was purified by flash column chromatography on silica gel (5-10% methanol/dichloroethane) to afford the desired product (28 mg, 29% yield) as a solid. ESI-MS m/z: 584.3 $[M+H]^+$; $^1$H-NMR (400 MHz, DMSO-d6) δ: 10.28 (s, 1H), 7.95 (s, 1H), 7.36 (m, 1H), 6.87-6.79 (m, 3H), 6.20-6.16 (dd, J=2.4, 16.8 Hz, 1H), 5.77-5.73 (dd, J=2.1, 10.0 Hz, 1H), 4.20 (m, 2H), 3.89-3.76 (m, 8H), 2.97 (m, 2H), 2.19 (m, 1H), 1.70 (m, 2H), 1.60 (m, 1H), 1.24-1.16 (m, 4H), 0.41 (m, 2H), 0.28 (m, 2H).

Example 13

1-(4-(6-chloro-8-fluoro-7-(2-fluoro-6-hydroxyphenyl)-2-((pyridin-2-ylamino)methyl)quinazolin-4-yl) piperazin-1-yl)prop-2-en-1-one

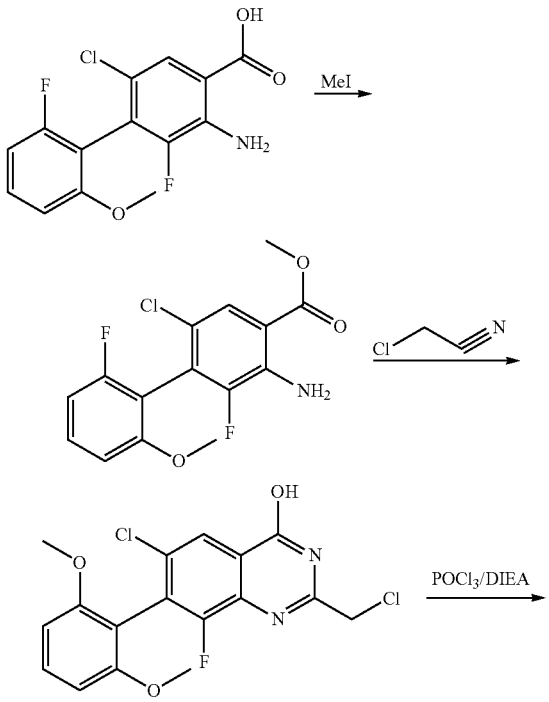

-continued

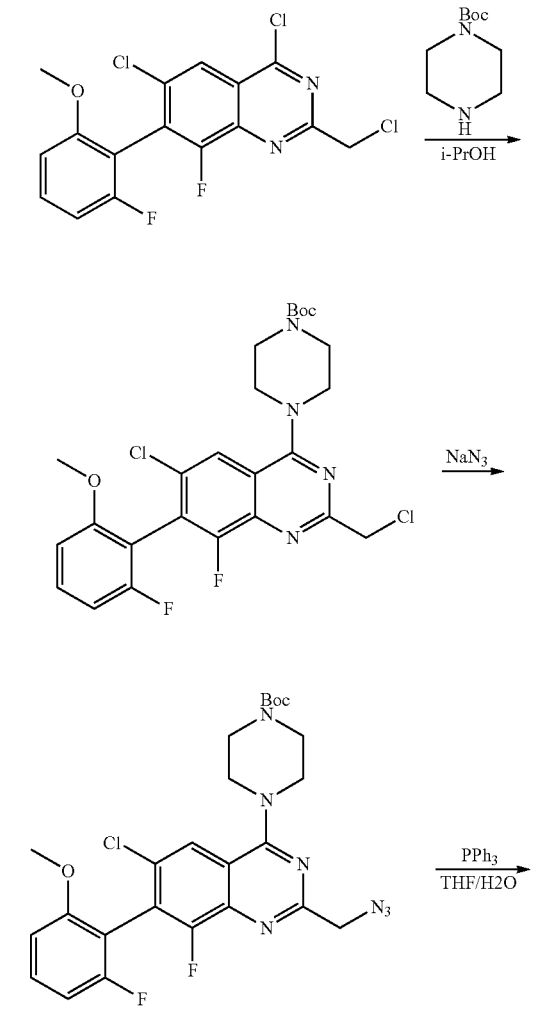

-continued

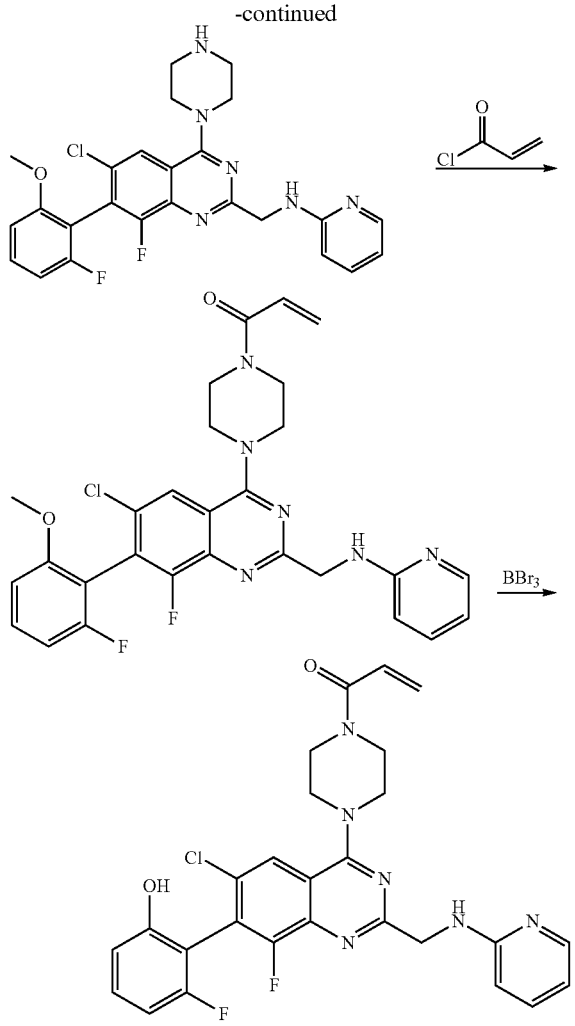

Example 13 provides an exemplary procedure according to Method M

Methyl 3-amino-6-chloro-2,2'-difluoro-6'-methoxy-[1,1'-biphenyl]-4-carboxylate

3-Amino-6-chloro-2,2'-difluoro-6'-methoxy-[1,1'-biphenyl]-4-carboxylic acid (2 g, 6.41 mmol) and $K_2CO_3$ (1.33 g, 9.62 mmol) were dissolved in DMF (20 mL), $CH_3I$ (0.994 g, 7.05 mmol) was added and the resulting mixture was stirred at RT for 2 h. The mixture was partitioned between water and ethyl acetate. The organic layer was washed with brine, dried over $Na_2SO_4$ and concentrated in vacuo. The residue was purified by flash column chromatography on silica gel (petroleum ether/ethyl acetate=3:1) to afford the desire product (1.9 g, 90.3% yield) as an off-white solid. ESI-MS m/z: 328.0 $[M+H]^+$.

6-Chloro-2-(chloromethyl)-8-fluoro-7-(2-fluoro-6-methoxyphenyl)quinazolin-4-ol

Methyl 3-amino-6-chloro-2,2'-difluoro-6'-methoxy-[1,1'-biphenyl]-4-carboxylate (1.85 g, 5.67 mmol) and 2-chloroacetonitrile (2.2 g, 28.37 mmol) were dissolved in 1,4-dioxane (80 mL), HCl gas was vapored into the solution for 30 min. The resulting mixture was stirred at 100° C. for 16 h. The mixture was partitioned between water and ethyl acetate. The organic layer was washed with brine, dried over $Na_2SO_4$ and concentrated in vacuo. The residue was purified by flash column chromatography on silica gel (petroleum ether/ethyl acetate=3:1) to afford the desire product (1.85 g, 88.5% yield) as an off-white solid. ESI-MS m/z: 371.1 $[M+H]^+$.

4,6-Dichloro-2-(chloromethyl)-8-fluoro-7-(2-fluoro-6-methoxyphenyl)quinazoline

6-Chloro-2-(chloromethyl)-8-fluoro-7-(2-fluoro-6-methoxyphenyl)quinazolin-4-ol (1.9 g, 5.14 mmol) was dissolved in $POCl_3$ (40 mL), DIPEA (4 mL) was added and the resulting mixture was stirred at 110° C. for 16 h. The mixture was concentrated in vacuo and the residue was partitioned between water and ethyl acetate. The organic layer was washed with brine, dried over $Na_2SO_4$ and concentrated in vacuo. The residue was purified by flash column chromatography on silica gel (petroleum ether/ethyl acetate=4:1) to afford the desire product (1.1 g, 55.3% yield) as an off-white solid.

tert-Butyl 4-(6-chloro-2-(chloromethyl)-8-fluoro-7-(2-fluoro-6-methoxyphenyl)quinazolin-4-yl)piperazine-1-carboxylate A solution of 4,6-dichloro-2-(chloromethyl)-8-fluoro-7-(2-fluoro-6-methoxyphenyl)quinazoline (1.1 g, 2.84 mmol) and tert-butyl piperazine-1-carboxylate (791 mg, 4.25 mmol) in isopropanol (100 mL) was stirred at 80° C. for 2 h. The mixture was partitioned between water and ethyl acetate. The organic layer was washed with brine, dried over $Na_2SO_4$ and concentrated in vacuo. The residue was purified by flash column chromatography on silica gel (ethyl acetate/petroleum ether=0-50%) to afford the desired product (650 mg, 42.6% yield) as a yellow solid.

tert-Butyl 4-(2-(azidomethyl)-6-chloro-8-fluoro-7-(2-fluoro-6-methoxyphenyl)quinazolin-4-yl)piperazine-1-carboxylate To a stirred solution of tert-butyl 4-(6-chloro-2-(chloromethyl)-8-fluoro-7-(2-fluoro-6-methoxyphenyl)quinazolin-4-yl)piperazine-1-carboxylate (650 mg, 1.21 mmol) in DMSO (10 mL), $NaN_3$ (118 mg, 1.81 mmol) was added and the resulting mixture was stirred at 60° C. for 1 h. The mixture was partitioned between water and ethyl acetate. The organic layer was washed with brine, dried over $Na_2SO_4$ and concentrated in vacuo. The residue was purified by flash column chromatography on silica gel (petroleum ether/ethyl acetate=3:1) to afford the desire product (600 mg, 90.1% yield) as an off-white solid.

tert-Butyl 4-(2-(aminomethyl)-6-chloro-8-fluoro-7-(2-fluoro-6-methoxyphenyl)quinazolin-4-yl)piperazine-1-carboxylate 4-(2-(Azidomethyl)-6-chloro-8-fluoro-7-(2-fluoro-6-methoxyphenyl)quinazolin-4-yl)piperazine-1-carboxylate (600 mg, 1.09 mmol) and $PPh_3$ (574 mg, 2.18 mmol) were dissolved in THF (10 mL) and $H_2O$ (10 mL), and the resulting mixture was stirred at RT for 16 h. The mixture was concentrated in vacuo and the residue was purified by flash column chromatography on silica gel (petroleum ether/ethyl acetate=3:1) to give a crude desired product (600 mg). ESI-MS m/z: 520.7 $[M+H]^+$.

tert-Butyl 4-(6-chloro-8-fluoro-7-(2-fluoro-6-methoxyphenyl)-2-((pyridin-2-ylamino)methyl)quinazolin-4-yl)piperazine-1-carboxylate To a stirred solution of tert-butyl 4-(2-(aminomethyl)-6-chloro-8-fluoro-7-(2-fluoro-6-methoxyphenyl)quinazolin-4-yl)piperazine-1-carboxylate (600 mg, 1.15 mmol), pyridine N-oxide (120 mg, 1.26 mmol) and Py-BrOP (804 mg, 1.73 mmol), DIEA (445 mg, 3.45 mmol) was added and the resulting mixture was stirred at RT for 2 h. The mixture was partitioned between water and ethyl acetate. The organic layer was washed with brine, dried over $Na_2SO_4$ and concentrated in vacuo. The residue was purified by flash column chromatography on silica gel (petroleum ether/ethyl acetate=3:1) to afford the desire product (450 mg, 66.1% yield) as an off-white solid. ESI-MS m/z: 597.3 $[M+H]^+$.

N-((6-Chloro-8-fluoro-7-(2-fluoro-6-methoxyphenyl)-4-(piperazin-1-yl)quinazolin-2-yl)methyl)pyridin-2-amine 4-(6-Chloro-8-fluoro-7-(2-fluoro-6-methoxyphenyl)-2-((pyridin-2-ylamino)methyl)quinazolin-4-yl)piperazine-1-carboxylate (450 mg, 0.76 mmol) was dissolved in 2,2,2-trifluoroacetic acid (10 mL). The resulting mixture was stirred at RT for 2 h. The mixture was concentrated in vacuo to remove TFA. $NaHCO_3$ solution was added to adjust pH >7, and then extracted with ethyl acetate. The organic layer was concentrated in vacuo to afford the desired product (330 mg, 87.8% yield) as a yellow solid.

1-(4-(6-Chloro-8-fluoro-7-(2-fluoro-6-methoxyphenyl)-2-((pyridin-2-ylamino)methyl)quinazolin-4-yl)piperazin-1-yl)prop-2-en-1-one N-((6-Chloro-8-fluoro-7-(2-fluoro-6-methoxyphenyl)-4-(piperazin-1-yl)quinazolin-2-yl)methyl)pyridin-2-amine (330 mg, 0.667 mmol) and $Et_3N$ (80.8 mg, 0.801 mmol) were dissolved in dichloromethane (20 mL) and cooled to −78° C., acryloyl chloride (61 mg, 0.337 mmol) was added into the solution. The resulting mixture was stirred at RT for 10 min, $NaHCO_3$ solution was added to adjust pH >7, and extracted with ethyl acetate. The organic layer was washed with brine, dried over $Na_2SO_4$ and concentrated in vacuo. The residue was purified by flash column chromatography on silica gel (dichloromethane/MeOH=30:1) to afford the desired product (220 mg, 60% yield) as an off-white solid. ESI-MS m/z: 551.6 $[M+H]^+$.

1-(4-(6-Chloro-8-fluoro-7-(2-fluoro-6-hydroxyphenyl)-2-((pyridin-2-ylamino)methyl)quinazolin-4-yl)piperazin-1-yl)prop-2-en-1-one 1-(4-(6-Chloro-8-fluoro-7-(2-fluoro-6-methoxyphenyl)-2-((pyridin-2-ylamino)methyl)quinazolin-4-yl)piperazin-1-yl)prop-2-en-1-one (220 mg, 0.4 mmol) was dissolved in dichloromethane (20 mL) and the mixture was cooled to −78° C., $BBr_3$ (1.0 g, 4 mmol) was added drop wise into the solution. The resulting mixture was allowed to warm to RT and stirred at RT for 4 h. The mixture was cooled to −30° C. and $NaHCO_3$ solution was added to adjust pH >7, and then extracted with dichloromethane. The organic layer was washed with brine, dried over $Na_2SO_4$ and concentrated. The residue was purified by flash column chromatography on silica gel (dichloromethane/MeOH=30:1) followed by Pre-HPLC to afford the desire product (40 mg, 18.7% yield) as an off-white solid. ESI-MS m/z: 537.7 $[M+H]^+$. $^1$H-NMR (400 MHz, DMSO-d6) δ: 10.30 (s, 1H), 8.00 (s, 1H), 7.93-7.92 (m, 1H), 7.40-7.35 (m, 2H), 6.90-6.80 (m, 4H), 6.66-6.64 (m, 1H), 6.50-6.47 (m, 1H), 6.20-6.15 (m, 1H), 5.76-5.73 (m, 1H), 4.61-4.59 (m, 2H), 3.87-3.68 (m, 8H).

Example 14

1-(4-(6-chloro-8-fluoro-7-(2-fluoro-6-hydroxyphenyl)-2-(trifluoromethyl)quinazolin-4-yl)piperazin-1-yl)prop-2-en-1-one

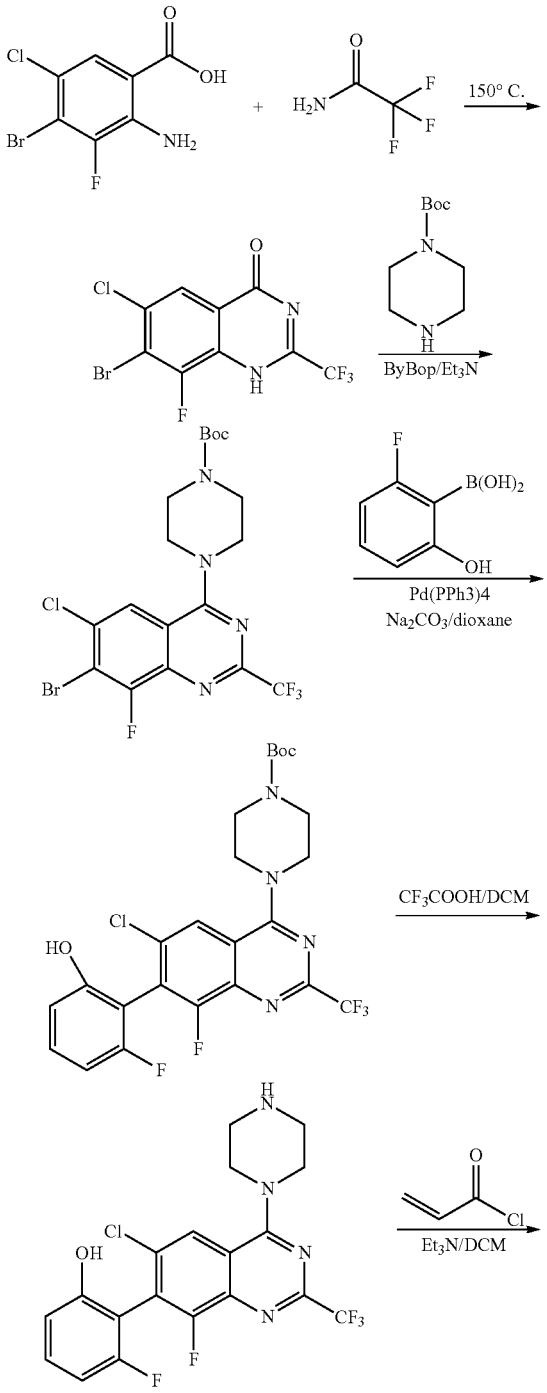

-continued

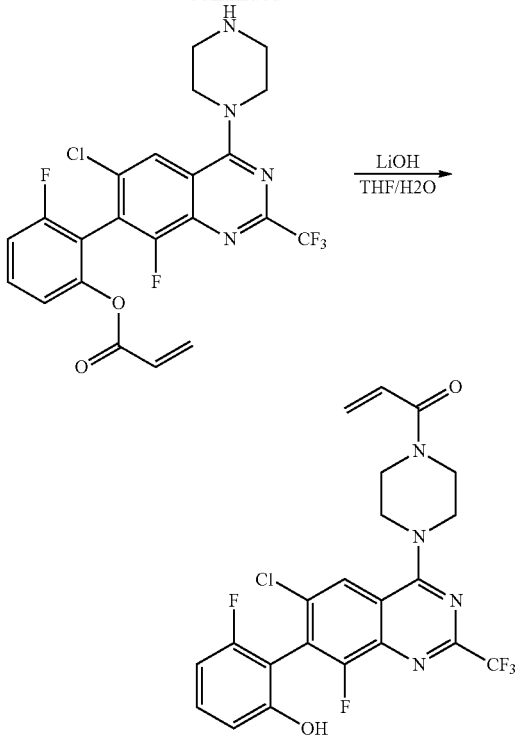

Example 14 provides an exemplary procedure according to Method O.

7-Bromo-6-chloro-8-fluoro-2-(trifluoromethyl)quinazolin-4(1H)-one

The mixture of 2-amino-4-bromo-5-chloro-3-fluorobenzoic acid (2.0 g, 7.49 mmol) and 2,2,2-trifluoroacetamide (2.54 g, 22.5 mmol) was stirred at 150° C. for 48 h. The mixture was extracted with EtOAc (150 mL). The organic layer was washed with brine, dried over $Na_2SO_4$ and concentrated in vacuo. The residue was purified by flash column chromatography on silica gel (50% ethyl acetate/petroleum ether) to afford the desired product (500 mg, 19% yield).

tert-Butyl 4-(7-bromo-6-chloro-8-fluoro-2-(trifluoromethyl)quinazolin-4-yl)piperazine-1-carboxylate The mixture of 7-bromo-6-chloro-8-fluoro-2-(trifluoromethyl)quinazolin-4(1H)-one (500 mg, 1.45 mmol), tert-butylpiperazine-1-carboxylate (537 mg, 2.89 mmol), triethylamine (439 mg, 4.35 mmol) and benzotriazol-1-yl-oxytripyrrolidinophosphonium hexafluorophosphate (1.5 g, 2.89 mmol) in THF (15 mL) was stirred at 50° C. for 16 h. The mixture was extracted with EtOAc (150 mL). The organic layer was washed with brine, dried over $Na_2SO_4$ and concentrated in vacuo. The residue was purified by flash column chromatography on silica gel (50% ethyl acetate/petroleum ether) to afford the desired product (600 mg, 81% yield). ESI-MS m/z: 513.3$[M+H]^+$.

tert-Butyl 4-(6-chloro-8-fluoro-7-(2-fluoro-6-hydroxyphenyl)-2-(trifluoromethyl)quinazolin-4-yl)piperazine-1-carboxylate A mixture of tert-butyl 4-(7-bromo-6-chloro-8-fluoro-2-(trifluoromethyl)quinazolin-4-yl)piperazine-1-carboxylate (250 mg, 0.48 mmol), 2-fluoro-6-hydroxyphenylboronic acid (449 mg, 2.91 mmol), $Pd(PPh_3)_4$(56 mg, 0.048 mmol) and $Na_2CO_3$ (257 mg, 2.43 mmol) in 1,4-dioxane/$H_2O$ (10 mL/2 mL) was stirred at 100° C. for 16 h under argon. The mixture was allowed to cool to RT and concentrated in vacuo. The residue was purified by flash column chromatography on silica gel (dichloromethane/methanol=100:1) to yield the desired product (130 mg, 49% yield) as an off-white solid. ESI-MS m/z: 545.2 $[M+H]^+$.

2-(6-Chloro-8-fluoro-2-(trifluoromethyl)-4-(piperazin-1-yl)quinazolin-7-yl)-3-fluorophenol To a solution of tert-butyl 4-(6-chloro-8-fluoro-7-(2-fluoro-6-hydroxyphenyl)-2-(trifluoromethyl)quinazolin-4-yl)piperazine-1-carboxylate (130 mg, 0.24 mmol) in dichloromethane (5 mL) at RT, TFA (1 mL) was added and the resulting mixture was stirred at RT for 1 h. The mixture was concentrated in vacuo. The residue was partitioned between $NaHCO_3$ solution and ethyl acetate. The organic layer was washed with brine, dried over $Na_2SO_4$ and concentrated in vacuo to afford the desired product (100 mg, 100% yield).

2-(4-(4-Acryloylpiperazin-1-yl)-6-chloro-8-fluoro-2-(trifluoromethyl)quinazolin-7-yl)-3-fluorophenyl Acrylate To a solution of above obtained crude 2-(6-chloro-8-fluoro-2-(trifluoromethyl)-4-(piperazin-1-yl)quinazolin-7-yl)-3-fluorophenol (100 mg, 0.238 mmol) in $Et_3N$ (72 mg, 0.71 mmol) and dichloromethane (10 mL) at 0° C., acryloyl chloride (32 mg, 0.35 mmol) was added and the resulting mixture was stirred at 0° C. for 2 h. The reaction mixture was quenched with saturated $NaHCO_3$ aqueous solution, and extracted with ethyl acetate. The organic layer was washed with saturated $NaHCO_3$ solution and brine, dried over $Na_2SO_4$ and concentrated in vacuo to afford crude product (50 mg) which was used in the next step directly.

1-(4-(6-Chloro-8-fluoro-7-(2-fluoro-6-hydroxyphenyl)-2-(trifluoromethyl)quinazolin-4-yl)piperazin-1-yl)prop-2-en-1-one 2-(4-(4-Acryloylpiperazin-1-yl)-6-chloro-8-fluoro-2-(trifluoromethyl)quinazolin-7-yl)-3-fluorophenyl acrylate (50 mg, 0.09 mmol) was dissolved in a mixture of THF (5 mL) and $H_2O$ (2.5 mL). $LiOH.H_2O$ (37 mg, 0.92 mmol) was added and the mixture was stirred at RT for 2 h. The mixture was poured into water and extracted with EtOAc. The organic layer was washed with water and brine, dried over $Na_2SO_4$, concentrated in vacuo. The residue was purified by flash column chromatography on silica gel (1-5% MeOH/dichoromethane) to afford the desired product (30 mg, 65% yield) as a white solid. ESI-MS m/z: 499.1 $[M+H]^+$; $^1$HNMR (400 MHz, DMSO-d6) δ: 10.38 (s, 1H), 8.17 (s, 1H), 7.43-7.37 (m, 1H), 6.89-6.79 (m, 3H), 6.21-6.17 (dd, J=2.4, 16.8 Hz, 1H), 5.76-5.74 (dd, J=2.1, 10.0 Hz, 1H), 4.10 (m, 4H), 3.88-3.79 (m, 8H).

Example 15

1-(4-(6-chloro-2-(dimethylphosphoryl)-8-fluoro-7-(2-fluoro-6-hydroxyphenyl)quinazolin-4-yl)piperazin-1-yl)prop-2-en-1-one

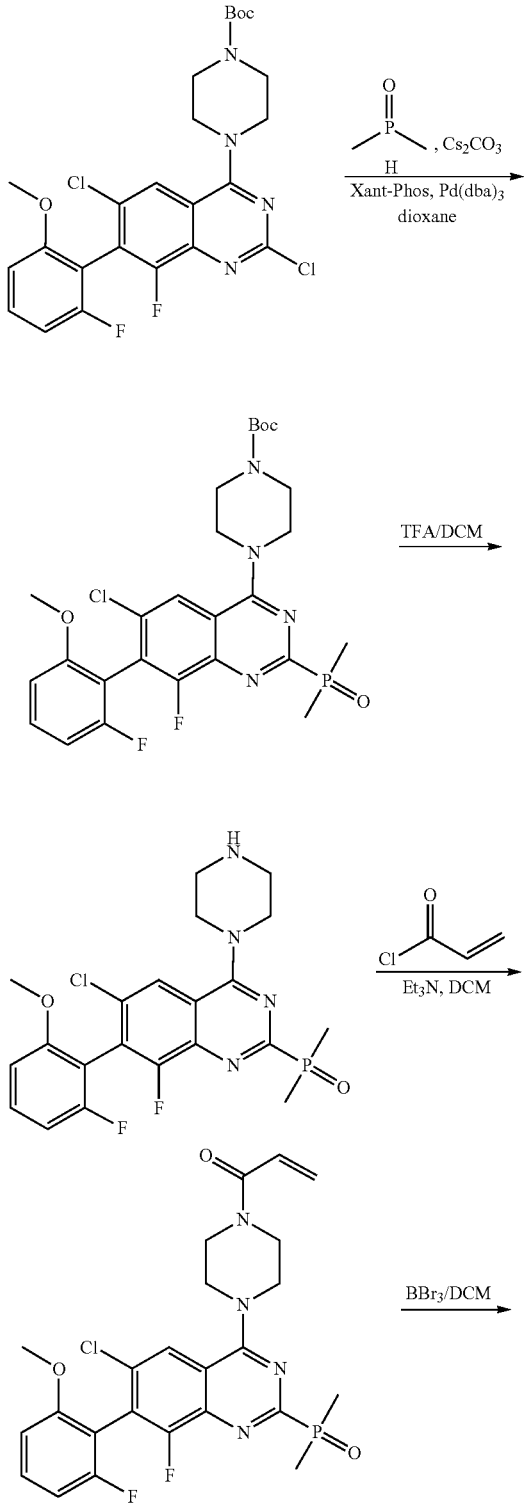

-continued

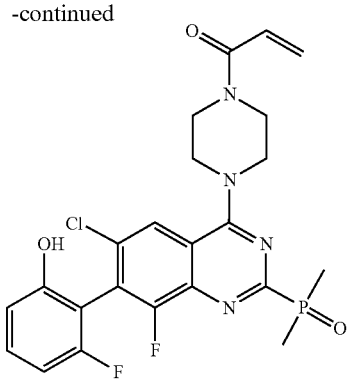

Example 15 provides an exemplary procedure according to Method Q.

tert-Butyl4-(6-chloro-2-(dimethylphosphoryl)-8-fluoro-7-(2-fluoro-6-methoxyphenyl)quinazolin-4-yl)piperazine-1-carboxylate A mixture of tert-butyl4-(2,6-dichloro-8-fluoro-7-(2-fluoro-6-methoxyphenyl)quinazolin-4-yl)piperazine-1-carboxylate (200 mg, 0.38 mmol), $Pd_2(dba)_3$ (35 mg, 0.038 mmol), $Cs_2CO_3$ (372 mg, 1.14 mmol), Xantphos (22 mg, 0.038 mmol) and dimethylphosphine oxide (118 mg, 1.52 mmol) in dioxane (25 mL) was stirred at reflux under $N_2$ for 5 h. The mixture was allowed to cool to RT, and partitioned between ethyl acetate and water. The organic layer was washed with brine, dried over $Na_2SO_4$ and concentrated in vacuo. The residue was purified by flash column chromatography on silica gel (1-2% methanol/dichloromethane) to afford the desired product (129 mg, 60% yield) as a solid.

(6-Chloro-8-fluoro-7-(2-fluoro-6-methoxyphenyl)-4-(piperazin-1-yl)quinazolin-2-yl)dimethylphosphine Oxide A mixture of tert-butyl4-(6-chloro-2-(dimethylphosphoryl)-8-fluoro-7-(2-fluoro-6-methoxyphenyl)quinazolin-4-yl)piperazine-1-carboxylate (129 mg, 0.23 mmol) in dichloromethane (20 mL), TFA (5 mL) was added and the resulting mixture was stirred at RT for 2 h. The mixture was concentrated in vacuo to afford the crude product (106 mg) which was used directly in the next step without further purification.

1-(4-(6-Chloro-2-(dimethylphosphoryl)-8-fluoro-7-(2-fluoro-6-methoxyphenyl)quinazolin-4-yl)piperazin-1-yl)prop-2-en-1-one (6-Chloro-8-fluoro-7-(2-fluoro-6-methoxyphenyl)-4-(piperazin-1-yl)quinazolin-2-yl)dimethylphosphine oxide (106 mg, 0.23 mmol) was added to the mixture of $Et_3N$ (70 mg, 0.69 mmol) in dichloromethane (10 mL). The mixture was stirred for 5 min and then acryloyl chloride (25 mg, 0.27 mmol) was added. The resulting mixture was stirred at RT for 0.5 h, poured into water and then extracted with dichloromethane. The organic layer was washed with brine, dried over $Na_2SO_4$ and concentrated in vacuo. The residue was purified by flash column chromatography on silica gel (1-2% methanol/dichloromethane) to afford the desired product (60 mg, 51% yield) as a solid.

1-(4-(6-Chloro-2-(dimethylphosphoryl)-8-fluoro-7-(2-fluoro-6-hydroxyphenyl)quinazolin-4-yl)piperazin-1-yl)prop-2-en-1-one To a solution of 1-(4-(6-Chloro-2-(dimethylphosphoryl)-8-fluoro-7-(2-fluoro-6-methoxyphenyl)quinazolin-4-yl)piperazin-1-yl)prop-2-en-1-one (60 mg, 0.12 mmol) in dichloromethane (30 mL) at −78° C., $BBr_3$ (0.5 mL, 5.3 mmol) was added. The reaction mixture was stirred at RT for 1 h. This mixture was quenched with saturated $NaHCO_3$ and extracted with dichloromethane. The organic layer was washed with saturated $NaHCO_3$ aqueous solution and brine, dried over $Na_2SO_4$ and concentrated in vacuo. The residue was purified by flash column chromatography on silica gel (5-10% methanol/dichloromethane) to afford the desired product (30 mg, 52% yield) as a solid. ESI-MS m/z: 507.2 $[M+H]^+$; $^1$H-NMR (400 MHz, DMSO-d6) δ:10.35 (d, J=2.0 Hz, 1H), 8.09 (d, J=0.8 Hz, 1H), 7.41-7.35 (m, 1H), 6.88-6.80 (m, 3H), 6.18 (dd, J=2.4, 16.8 Hz, 1H), 5.75 (dd, J=2.4, 10.0 Hz, 1H), 4.03-4.01 (m, 4H), 3.85-3.77 (m, 4H), 1.78 (s, 3H), 1.75 (s, 3H).

Example 16

1-(4-(6-chloro-2-((dimethylphosphoryl)methyl)-8-fluoro-7-(2-fluoro-6-hydroxyphenyl)quinazolin-4-yl)piperazin-1-yl)prop-2-en-1-one

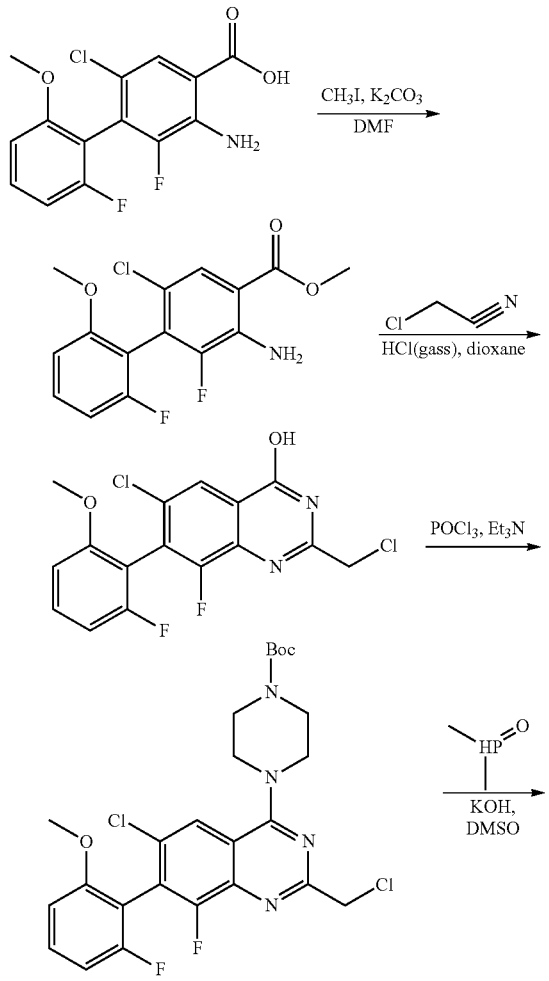

-continued

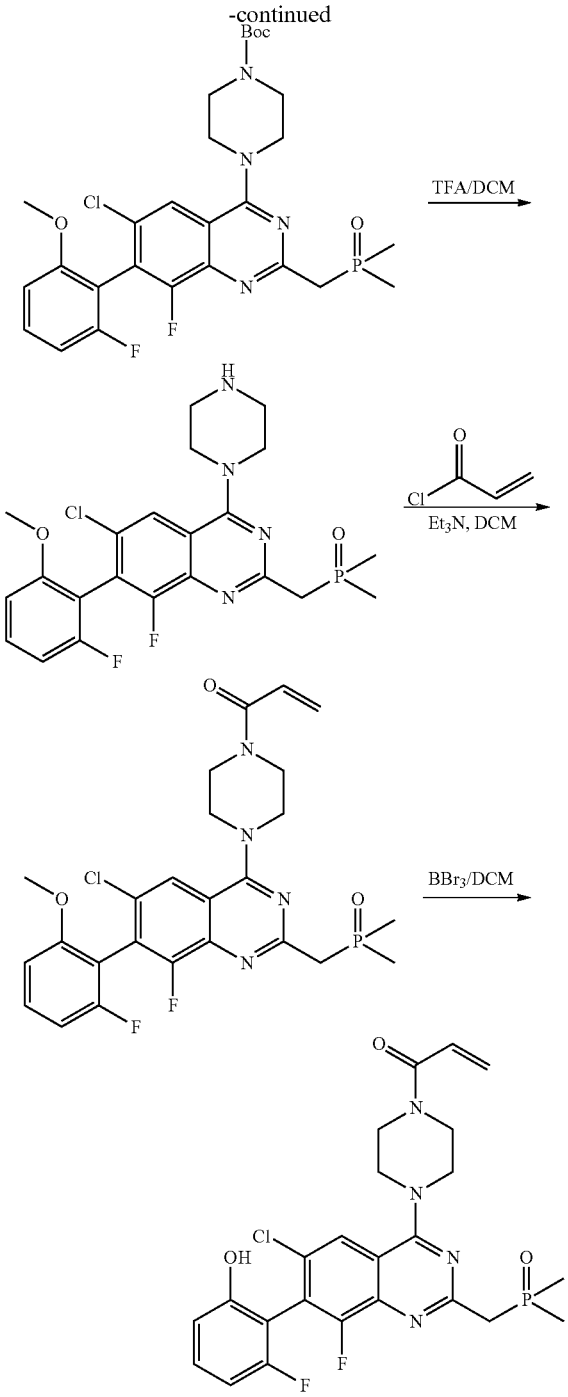

Example 16 provides and exemplary procedure according to Method R.

Methyl 3-amino-6-chloro-2,2'-difluoro-6'-methoxy-[1,1'-biphenyl]-4-carboxylate

To a mixture of 3-amino-6-chloro-2,2'-difluoro-6'-methoxy-[1,1'-biphenyl]-4-carboxylic acid (2.0 g, 6.4 mmol) in DMF (15 mL) at RT, $K_2CO_3$ (1.8 g, 12.8 mmol) and $CH_3I$ (1.1 g, 7.7 mmol) were added and the resulting mixture was stirred at RT for 1 h. The mixture was poured into water, extracted with ethyl acetate and washed with brine. The organic layer was dried over anhydrous $Na_2SO_4$, filtered and concentrated in vacuo to afford the desired product (2.0 g, 95% yield) as a solid.

6-Chloro-2-(chloromethyl)-8-fluoro-7-(2-fluoro-6-methoxyphenyl)quinazolin-4-ol

To a mixture of methyl 3-amino-6-chloro-2,2'-difluoro-6'-methoxy-[1,1'-biphenyl]-4-carboxylate (2.0 g, 6.12 mmol), 2-chloroacetonitrile (2.3 g, 30.6 mmol) in dioxane (30 mL), HCl (gas) was bubbled for 1 h and the resulting mixture was stirred at 100° C. for 15 h. The mixture was allowed to cool to RT, and partitioned between ethyl acetate and water. The organic layer was washed with brine, dried over $Na_2SO_4$ and concentrated in vacuo. The residue was purified by flash column chromatography on silica gel (10-20% ethyl acetate/petroleum ether) to afford the desired product (2.1 g, 93% yield) as a solid.

4,6-Dichloro-2-(chloromethyl)-8-fluoro-7-(2-fluoro-6-methoxyphenyl)quinazoline

A mixture of 6-chloro-2-(chloromethyl)-8-fluoro-7-(2-fluoro-6-methoxyphenyl)quinazolin-4-ol (2.1 g, 5.66 mmol), $Et_3N$ (4 mL) in $POCl_3$ (40 mL) was stirred at 100° C. for 15 h. The mixture was concentrated in vacuo and partitioned between ethyl acetate and water. The organic layer was washed with brine, dried over $Na_2SO_4$ and concentrated in vacuo to afford the crude product (2.0 g) which was used directly in the next step without further purification.

tert-Butyl4-(6-chloro-2-(chloromethyl)-8-fluoro-7-(2-fluoro-6-methoxyphenyl)quinazolin-4-yl)piperazine-1-carboxylate To a mixture of 4,6-dichloro-2-(chloromethyl)-8-fluoro-7-(2-fluoro-6-methoxyphenyl)quinazoline (2.6 g, 5.13 mmol), $Et_3N$ (1.6 g, 15.39 mmol) in THF (40 mL), tert-butyl piperazine-1-carboxylate (1.43 g, 7.69 mmol) was added. The resulting mixture was stirred at room temperature for 1 h, poured into water and then extracted with MeOH/DCM. The organic layer was washed with brine, dried over $Na_2SO_4$ and concentrated in vacuo. The residue was purified by flash column chromatography on silica gel (20-50% ethyl acetate/petroleum ether) to afford the desired product (2.0 g, 72% yield) as a solid.

tert-Butyl4-(6-chloro-2-((dimethylphosphoryl)methyl)-8-fluoro-7-(2-fluoro-6-methoxyphenyl)quinazolin-4-yl)piperazine-1-carboxylate A mixture of tert-butyl4-(6-chloro-2-(chloromethyl)-8-fluoro-7-(2-fluoro-6-methoxyphenyl)quinazolin-4-yl)piperazine-1-carboxylate (1.0 g, 1.86 mmol), KOH (312 mg, 1.14 mmol), and dimethylphosphine oxide (435 mg, 1.52 mmol) in DMSO (30 mL) was stirred at 100° C. for 15 h. The mixture was allowed to cool to RT, and then partitioned between ethyl acetate and water. The organic layer was washed with brine, dried over $Na_2SO_4$ and concentrated in vacuo. The residue was purified by flash column chromatography on silica gel (1-5% methanol/dichloromethane) to afford the desired product (400 mg, 36% yield) as a solid.

((6-Chloro-8-fluoro-7-(2-fluoro-6-methoxyphenyl)-4-(piperazin-1-yl)quinazolin-2-yl)methyl)dimethylphosphine Oxide To a mixture of tert-butyl4-(6-chloro-2-((dimethylphosphoryl)methyl)-8-fluoro-7-(2-fluoro-6-methoxyphenyl)quinazolin-4-yl)piperazine-1-carboxylate (400 mg, 0.69 mmol) in DCM (20 mL), TFA (5 mL) was added and the resulting mixture was stirred at RT for 1 h. The mixture was concentrated in vacuo to afford the crude product (200 mg) which was used directly in the next step without further purification.

1-(4-(6-Chloro-2-((dimethylphosphoryl)methyl)-8-fluoro-7-(2-fluoro-6-methoxyphenyl)quinazolin-4-yl)piperazin-1-yl)prop-2-en-1-one ((6-Chloro-8-fluoro-7-(2-fluoro-6-methoxyphenyl)-4-(piperazin-1-yl)quinazolin-2-yl)methyl)dimethylphosphine oxide (200 mg, 0.42 mmol) was added to the mixture of $Et_3N$ (127 mg, 1.26 mmol) in DCM (15 mL). The mixture was stirred for 5 min and then acryloyl chloride (76 mg, 0.84 mmol) was added. The resulting mixture was stirred at RT for 0.5 h, poured into water and then extracted with MeOH/DCM. The organic layer was washed with brine, dried over $Na_2SO_4$ and concentrated in vacuo. The residue was purified by flash column chromatography on silica gel (1-2% methanol/dichloroethane) to afford the desired product (150 mg, 68% yield) as a solid.

1-(4-(6-Chloro-2-((dimethylphosphoryl)methyl)-8-fluoro-7-(2-fluoro-6-hydroxyphenyl)quinazolin-4-yl)piperazin-1-yl)prop-2-en-1-one To a solution of 1-(4-(6-chloro-2-((dimethylphosphoryl)methyl)-8-fluoro-7-(2-fluoro-6-methoxyphenyl)quinazolin-4-yl)piperazin-1-yl)prop-2-en-1-one (150 mg, 0.28 mmol) in DCM (20 mL) at −78° C., $BBr_3$ (0.5 mL, 5.3 mmol) was added and the resulting mixture was stirred at RT for 1 h. The mixture was poured into ice water, $NaHCO_3$ (50 mL) was added and the mixture was extracted with ethyl acetate. The organic layer was washed with brine, dried over $Na_2SO_4$ and concentrated in vacuo. The residue was purified by flash column chromatography on silica gel (5-10% methanol/dichloroethane) to afford the desired product (90 mg, 62% yield) as a solid. ESI-MS m/z: 521.2 $[M+H]^+$; $^1H$ NMR (400 MHz, DMSO-d6) δ: 10.31 (d, J=1.6 Hz, 1H), 8.02 (s, 1H), 7.40-7.34 (m, 1H), 6.88-6.80 (m, 3H), 6.18 (dd, J=2.4, 16.8 Hz, 1H), 5.75 (dd, J=2.4, 10.0 Hz, 1H), 3.92-3.77 (m, 8H), 3.45 (d, J=15.6 Hz, 2H), 1.57 (s, 3H), 1.54 (s, 3H).

Example 17

4-(4-acryloylpiperazin-1-yl)-6-chloro-2-(3-(dimethylamino)azetidin-1-yl)-8-fluoro-7-(2-fluoro-6-hydroxyphenyl)quinoline-3-carbonitrile

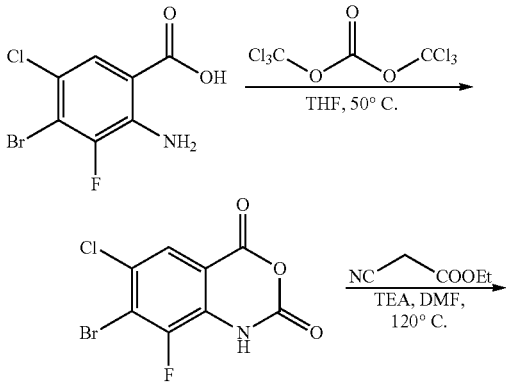

-continued

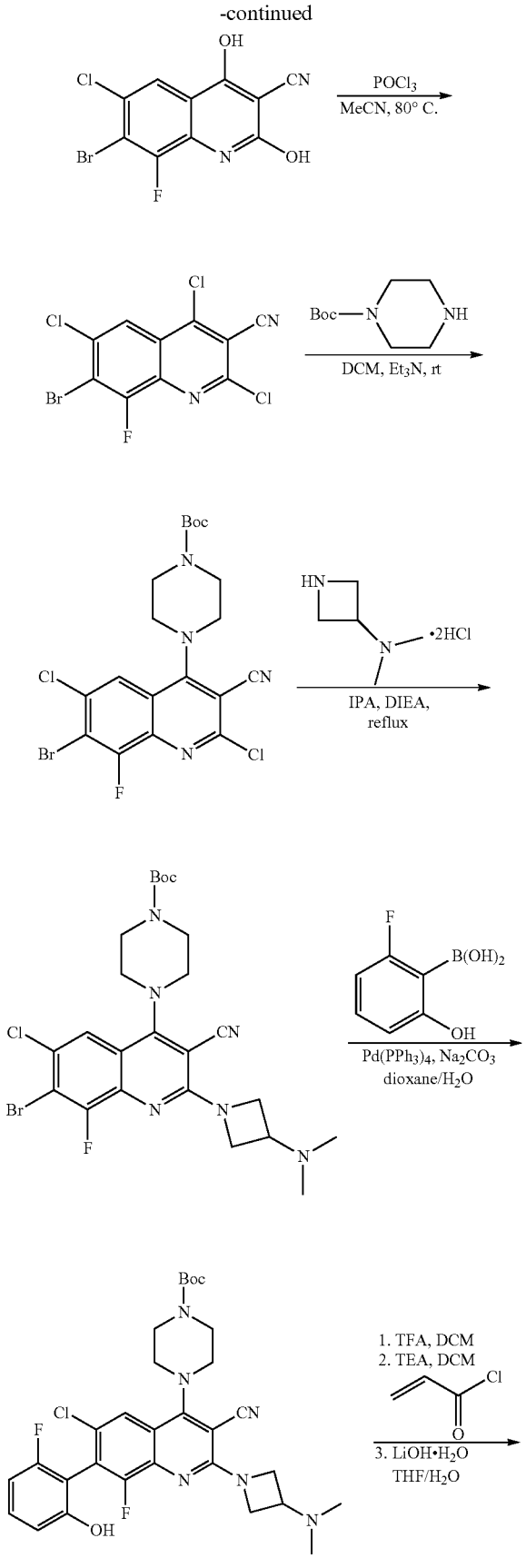

-continued

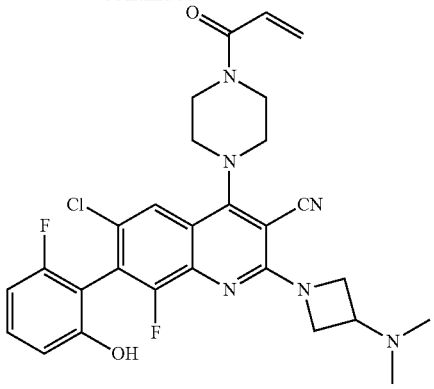

Example 17 provides an exemplary method according to Method U.

7-Bromo-6-chloro-8-fluoro-1H-benzo[d][1,3] oxazine-2,4-dione

2-Amino-4-bromo-5-chloro-3-fluorobenzoic acid (5 g, 18.6 mmol) was dissolved in THF (60 mL) in a 250 mL single neck flask, then cooled to 0° C., bis(trichloromethyl) carbonate (5.52 g, 18.6 mmol) was added dropwise. The mixture was warmed to 50° C. and stirred at 50° C. for 16 h. The solvent was removed in vacuo. The residue was dissolved with ethyl acetate. The mixture was washed with brine and saturated $NaHCO_3$ solution. The organic layer was dried over anhydrous $Na_2SO_4$, filtered and concentrated in vacuo. The residue was purified by flash column chromatography on silica gel (ethyl acetate/petroleum ether=1:1) to give the desired compound as yellow solid (2.3 g, 42% yield).

7-Bromo-6-chloro-8-fluoro-2,4-dihydroxyquinoline-3-carbonitrile

A mixture of 7-bromo-6-chloro-8-fluoro-1H-benzo[d][1,3]oxazine-2,4-dione (1.4 g, 4.75 mmol), ethyl 2-cyanoacetate (806 mg, 7.13 mmol) and $Et_3N$ (1.92 g, 19.01 mmol) in DMF (30 mL) was stirred at 120° C. under argon for 16 h. The mixture was allowed to cool to RT, and then washed with 1M HCl. The solid was collected by filtration, dried and give the target compound as brown solid (2.1 g, crude) without further purification used in next step.

7-Bromo-2,4,6-trichloro-8-fluoroquinoline-3-carbonitrile

7-Bromo-6-chloro-8-fluoro-2,4-dihydroxyquinoline-3-carbonitrile (1.8 g, 5.67 mmol) in MeCN (5 mL) and $POCl_3$ (30 mL) was stirred at 90° C. for 16 h. The mixture was evaporated under reduced pressure. The residue was poured into dichloromethane/$Et_3N$ (200/10 mL) solution and washed with ice water. The mixture was extracted with ethyl acetate. The organic layer was dried over $Na_2SO_4$ and concentrated in vacuo to give the desired product as brown solid (947 mg, crude) without further purification used in next step.

tert-Butyl 4-(7-bromo-2,6-dichloro-3-cyano-8-fluoroquinolin-4-yl)piperazine-1-carboxylate A mixture of 7-bromo-2,4,6-trichloro-8-fluoroquinoline-3-carbonitrile (200 mg, 0.56 mmol), tert-butyl piperazine-1-carboxylate (210 mg, 1.13 mmol) and $Et_3N$ (228 mg, 2.25 mmol) in dichloromethane (30 mL) was stirred at RT for 1 h. The mixture was quenched with saturated $NaHCO_3$ solution and partitioned between water and ethyl acetate. The organic layer was dried over anhydrous $Na_2SO_4$, filtered and concentrated in vacuo. The residue was purified by flash column chromatography on silica gel (ethyl acetate/petroleum ether=1:4) to afford the desired product (268 mg, 95% yield) as a yellow solid. ESI-MS m/z: 505.2 $[M+H]^+$.

tert-Butyl 4-(7-bromo-6-chloro-3-cyano-2-(3-(dimethylamino)azetidin-1-yl)-8-fluoroquinolin-4-yl) piperazine-1-carboxylate A mixture of tert-butyl 4-(7-bromo-2,6-dichloro-3-cyano-8-fluoroquinolin-4-yl)piperazine-1-carboxylate (268 mg, 0.53 mmol), N,N-dimethylazetidin-3-amine dihydrochloride (368 mg, 2.12 mmol) and DIEA (549 mg, 4.25 mmol) in i-PrOH (20 mL) was stirred at 120° C. for 1 h and then was allowed to cool to RT. The mixture was quenched with saturated $NaHCO_3$ solution and partitioned between water and ethyl acetate. The organic layer was dried over anhydrous $Na_2SO_4$, filtered and concentrated in vacuo. The residue was purified by flash column chromatography on silica gel (MeOH/dichloromethane=1:40) to afford the desired product (189 mg, 62% yield) as a yellow solid. ESI-MS m/z: 569.3 $[M+H]^+$.

tert-Butyl 4-(3-cyano-2-(3-(dimethylamino)azetidin-1-yl)-8-fluoro-7-(2-fluoro-6-hydroxyphenyl)-6-methylquinolin-4-yl)piperazine-1-carboxylate A mixture of tert-butyl 4-(7-bromo-6-chloro-3-cyano-2-(3-(dimethylamino)azetidin-1-yl)-8-fluoroquinolin-4-yl) piperazine-1-carboxylate (189 mg, 0.33 mmol), (2-fluoro-6-hydroxyphenyl)boronic acid (208 mg, 1.33 mmol), 1.5 M $Na_2CO_3$ solution (0.56 mL, 0.84 mmol) and $Pd(PPh_3)_4$(38 mg, 0.033 mmol) in dioxane (30 mL) and $H_2O$ (2 mL) was stirred at 80° C. under argon for 16 h. The mixture was evaporated. The residue was purified by flash column chromatography on silica gel (MeOH/dichloromethane=1:40) to afford the desired product (85 mg, 19% yield) as a yellow solid. ESI-MS m/z: 599.35$[M+H]^+$.

4-(4-Acryloylpiperazin-1-yl)-2-(3-(dimethylamino) azetidin-1-yl)-8-fluoro-7-(2-fluoro-6-hydroxyphenyl)-6-methylquinoline-3-carbonitrile To a mixture of tert-butyl 4-(6-chloro-3-cyano-2-(3-(dimethylamino)azetidin-1-yl)-8-fluoro-7-(2-fluoro-6-hydroxyphenyl)quinolin-4-yl)piperazine-1-carboxylate (85 mg, 0.14 mmol) in dichloromethane (8 mL), TFA (2 mL) was added. The mixture was stirred at RT for 2 h and then concentrated in vacuo. The residue was dissolved in dichloromethane (20 ml), triethylamine (86 mg, 0.85 mmol) and acryloyl chloride (26 mg, 0.28 mmol) were added at 0° C. The resulting mixture was stirred at RT for 10 min, and then quenched with sat. $NaHCO_3$ solution. The mixture was extracted with ethyl acetate. The organic layer was dried over anhydrous $Na_2SO_4$, filtered and concentrated in vacuo. The residue was dissolved in THF (20 mL) and water (10 mL), $LiOH.H_2O$ (30 mg, 0.71 mmol) was added. The mixture was stirred at RT for 1.5 h, adjusted pH=8 with 1M HCl, and extracted with ethyl acetate. The organic layer was dried over $Na_2SO_4$, filtered and concentrated in vacuo. The residue was purified by flash column chromatography on silica gel (MeOH/dichloromethane=1:40) and followed by Pre-TLC to afford the desired product (35 mg, 45% yield) as a yellow solid. ESI-MS m/z: 553.3[M+H]$^+$; $^1$H-NMR (400 MHz, DMSO-d6) δ: 10.25 (s, 1H), 7.82 (s, 1H), 7.37-7.31 (m, 1H), 6.93-6.7 (m, 3H), 6.19 (dd, J=2.4, 16.6 Hz, 1H), 5.75 (dd, J=2.3, 10.3 Hz, 1H), 4.31 (t, J=8.2 Hz, 2H), 4.07-4.04 (m, 2H), 3.86-3.83 (m, 4H), 3.62 (brs, 4H), 3.19-3.17 (m, 1H), 2.12 (s, 6H).

Example 18

1-(4-(6-chloro-8-fluoro-7-(2-fluoro-6-hydroxyphenyl)-2-(((3-fluoropyridin-2-yl)methoxy)methyl)quinazolin-4-yl)piperazin-1-yl)prop-2-en-1-one

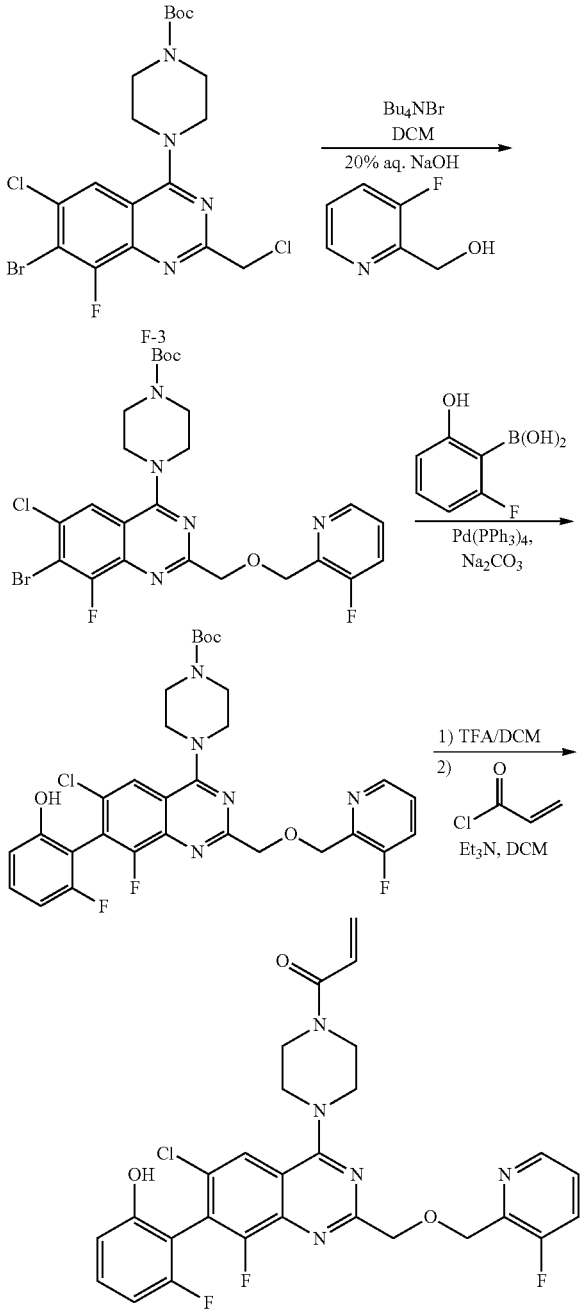

Example 18 provides an exemplary preparation according to General Synthetic Method Q.

tert-Butyl 4-(7-bromo-6-chloro-8-fluoro-2-(((3-fluoropyridin-2-yl)methoxy)methyl)quinazolin-4-yl)piperazine-1-carboxylate To a solution of tert-butyl 4-(7-bromo-6-chloro-2-(chloromethyl)-8-fluoroquinazolin-4-yl)piperazine-1-carboxylate (494 mg, 1 mmol), (3-fluoropyridin-2-yl)methanol (381 mg, 3 mmol) and $Bu_4NBr$ (322 mg, 1 mmol) in 5 mL of DCM, 5 mL of 20% NaOH aqueous solution was added. The resulting mixture was stirred at 50° C. in a sealed vial for 48 h. The mixture was allowed to cool to RT and partitioned between DCM and water. The organic layer was dried over $Na_2SO_4$, filtered and concentrated in vacuo. The residue was purified via Isolera One (MeOH/DCM=0-10%) to afford the desired product (450 mg. 77% yield).

1-(4-(6-Chloro-8-fluoro-7-(2-fluoro-6-hydroxyphenyl)-2-(((3-fluoropyridin-2-yl)methoxy)methyl)quinazolin-4-yl)piperazin-1-yl)prop-2-en-1-one The title compound was prepared from tert-butyl 4-(7-bromo-6-chloro-8-fluoro-2-(((3-fluoropyridin-2-yl)methoxy)methyl)quinazolin-4-yl)piperazine-1-carboxylate in two steps in analogous fashion to the synthesis of 1-(4-(6-chloro-8-fluoro-7-(2-fluoro-6-hydroxyphenyl)-2-((1-methylpiperidin-4-yl)amino)quinazolin-4-yl)piperazin-1-yl)prop-2-en-1-one in Example 3. $^1$H NMR (500 MHz, DMSO-d6) δ: 10.28 (s, 1H), 8.38 (d, J=6.0 Hz, 1H), 8.02 (s, 1H), 7.71 (m, 1H), 7.45 (m, 1H), 7.36 (m, 1H), 6.77-6.88 (m, 3H), 6.16 (d, J=2.5, 14.5 Hz, 1H), 5.73 (d, J=2.0, 8.5 Hz, 1H), 4.85 (s, 2H), 4.68 (s, 2H), 3.70-3.98 (m, 8H); ESI-MS m/z: 569.6 [M+H]$^+$.

Example 19

1-(4-(6-chloro-7-(2,3-difluoro-6-hydroxyphenyl)-8-fluoroquinazolin-4-yl)piperazin-1-yl)prop-2-en-1-one

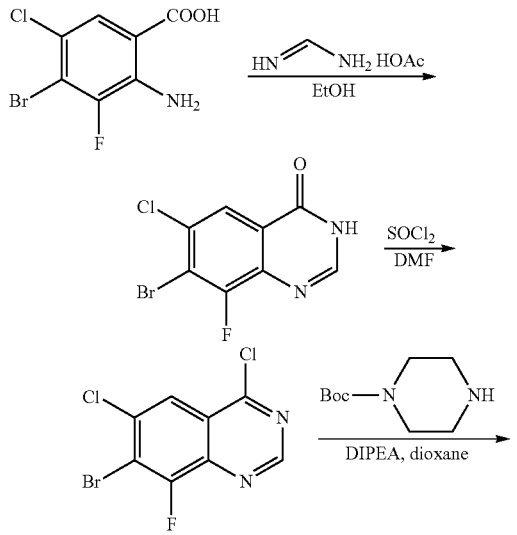

-continued

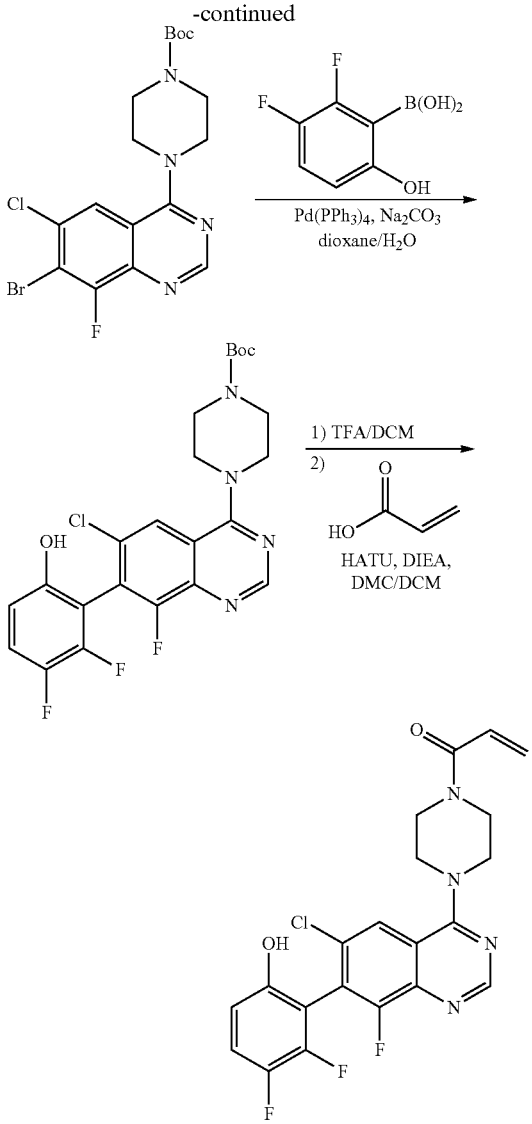

Example 19 provides an exemplary preparation according to General Synthetic Method R.

7-Bromo-6-chloro-8-fluoroquinazolin-4(3H)-one

To a solution of 2-amino-4-bromo-5-chloro-3-fluorobenzoic acid (21.2 g, 79.1 mmol) in EtOH (200 mL) at room temperature, formamidine acetate (82 g, 791 mmol) was added and the resulting mixture was stirred at reflux for 16 h. The mixture was concentrated in vacuo. The residue was rinsed with $H_2O$ and dried to afford the desired product as a gray solid (17.6 g, 80% yield). ESI-MS m/z: 278.9 $[M+H]^+$.

7-Bromo-4,6-dichloro-8-fluoroquinazoline

A mixture of 7-bromo-6-chloro-8-fluoroquinazolin-4(3H)-one (17.6 g, 63.43 mmol), $SOCl_2$ (300 mL) and DMF (12 drops) was stirred at reflux for 16 h. The mixture was allowed to cool to room temperature and then concentrated in vacuo to afford the crude product (19.6 g). The crude product was used in the next step without further purification.

tert-Butyl 4-(7-bromo-6-chloro-8-fluoroquinazolin-4-yl)piperazine-1-carboxylate

To a solution of 7-bromo-4,6-dichloro-8-fluoroquinazoline (19.6 g, 65.6 mmol) in dichloromethane (150 mL) at room temperature, tert-butyl piperazine-1-carboxylate (24.6 g, 197 mmol) and $Et_3N$ (27.5 mL, 197 mmol) were added. The resulting mixture was stirred at room temperature for 40 min. The mixture was extracted with dichloromethane. The organic layer was washed with 1N HCl, water, saturated $NaHCO_3$ solution and brine. The organic layer was dried over $Na_2SO_4$ and concentrated in vacuo. The residue was triturated with mixture of petroleum ether/ethyl acetate=5:1 to afford the desired product as a white solid (26 g, 89% yield). $^1$HNMR (400 MHz, $CDCl_3$) δ: 8.78 (S, 1H), 7.81 (d, J=2 Hz, 1H), 3.83-3.80 (m, 4H), 3.68-3.66 (m, 4H), 1.52 (s, 9H); ESI-MS m/z: 446.1 $[M+H]^+$.

tert-Butyl 4-(6-chloro-7-(2,3-difluoro-6-hydroxyphenyl)-8-fluoroquinazolin-4-yl)piperazine-1-carboxylate To a solution of tert-butyl 4-(7-bromo-6-chloro-8-fluoroquinazolin-4-yl)piperazine-1-carboxylate (405 mg, 1.0 eq.) in dioxane (10 mL) in the sealed tube, (2,3-difluoro-6-hydroxyphenyl)boronic acid (317 mg, 2.0 eq.), tetrakis (211 mg, 0.2 eq.) and aqueous $Na_2CO_3$ (1M, 3 mL) were added and the resulting mixture was stirred at 120° C. in the Microwave Reactor for 1 h. After cooling down, it was filtered and partitioned between EtOAc and water. The organic layer was dried with $Na_2SO_4$, filtered and concentrated in vacuo. The residue was purified by flash column chromatography on silica gel (DCM/MeOH=10:1) to afford the desired product (87 mg, 19% yield) as a solid. ESI-MS m/z: 495.1 $[M+H]^+$.

1-(4-(6-Chloro-7-(2,3-difluoro-6-hydroxyphenyl)-8-fluoroquinazolin-4-yl)piperazin-1-yl)prop-2-en-1-one To a solution of tert-butyl 4-(6-chloro-7-(2,3-difluoro-6-hydroxyphenyl)-8-fluoroquinazolin-4-yl)piperazine-1-carboxylate (87 mg, 1.0 eq.) in DCM (10 mL), TFA (1.3 mL) was added and the resulting mixture was stirred at RT for 1.5 h. The mixture was concentrated in vacuo. The residue was taken in ethyl acetate, neutralized with sat. $NaHCO_3$ aqueous solution, washed with brine, dried over $Na_2SO_4$ and concentrated in vacuo. The crude product was used in the next step directly.

At −78° C., DIEA (86 ul, 3.4 eq.) was added into the mixture of acrylic acid (12 μL, 1.12 eq.) and HATU (67 mg, 1.12 eq.) in DCM/DMF (2 mL/2 mL) and the resulting mixture was stirred for 10 min. Then cooling bath was removed and stirring was continued for 20 min at RT. At −78° C., it was added into the above obtained residue in DCM (10 mL). The reaction mixture was gradually warmed to RT and stirred for 2 h. The mixture was diluted with 20% isopropanol in DCM, washed with water and brine, dried over $Na_2SO_4$, filtered and concentrated in vacuo. The residue was purified by column purification (DCM/MeOH=10:1) to afford the desired product (23 mg, 29% yield over two steps). $^1$H NMR (500 MHz, DMSO-d6) δ: 10.29 (s, 1H), 8.70 (s, 1H), 8.06 (s, 1H), 7.44 (dd, J=20, 9.5 Hz, 1H), 6.82 (m, 2H), 6.17 (dd, J=16.5, 2 Hz, 1H), 5.74 (dd, J=10, 2.0 Hz, 1H), 3.93-3.76 (m, 8H); ESI-MS m/z: 449.1 $[M+H]^+$.

Example 20

1-(2-(6-chloro-8-fluoro-7-(2-fluoro-6-hydroxyphenyl)quinazolin-4-yl)-2,6-diazaspiro[3.4]octan-6-yl) prop-2-en-1-one

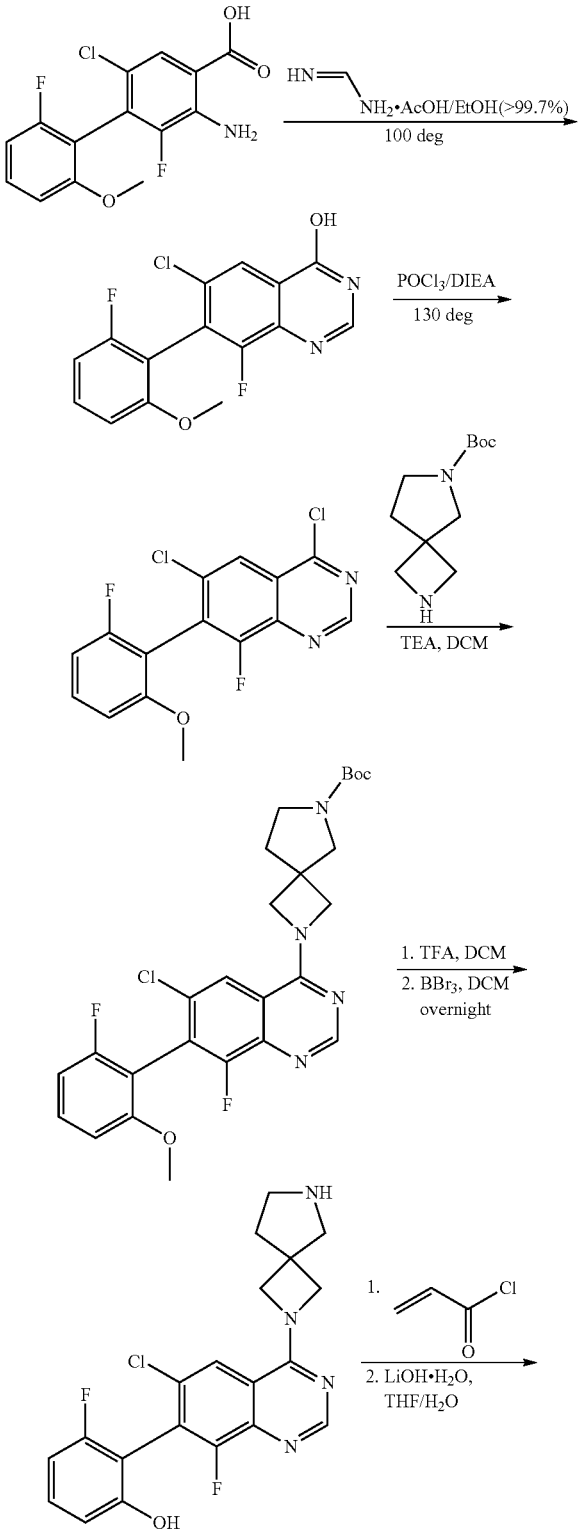

-continued

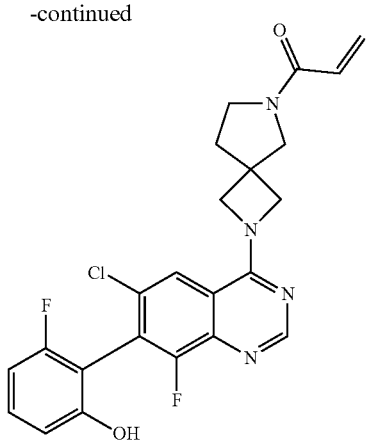

Example 20 provides and exemplary procedure according to Method S.

6-Chloro-8-fluoro-7-(2-fluoro-6-methoxyphenyl) quinazolin-4-ol

To a solution of 3-amino-6-chloro-2,2'-difluoro-6'-methoxy-[1,1'-biphenyl]-4-carboxylic acid (8.1 g, 25.88 mmol) in EtOH (100 mL, >99.7%) at RT, formimidamide acetate (35 g, 336.4 mmol) was added and the resulting mixture was stirred at reflux for 16 h. The reaction mixture was concentrated in vacuo to remove EtOH, and slowly added to $H_2O$, the mixture was filtered and the cake was dried to afford the desired product (7.5 g, 90.4%) as a white solid.

4,6-Dichloro-8-fluoro-7-(2-fluoro-6-methoxyphenyl) quinazoline

A mixture of 6-chloro-8-fluoro-7-(2-fluoro-6-methoxyphenyl)quinazolin-4-ol (10 g, 31.1 mmol), $POCl_3$ (100 mL) and DIPEA (10 mL) was stirred at reflux for 16 h. The mixture was allowed to cool to RT and concentrated in vacuo to remove $POCl_3$. The residue was dissolved with ethyl acetate. The organic layer was wash with brine, dried over $Na_2SO_4$, filtered and concentrated in vacuo. The residue was purified by flash chromatography on silica gel (ethyl acetate/petroleum ether=2.5-10%) to afford the product (9.3 g, 87.7% yield) as a brown solid.

tert-Butyl 2-(6-chloro-8-fluoro-7-(2-fluoro-6-methoxyphenyl)quinazolin-4-yl)-2,6-diazaspiro[3.4] octane-6-carboxylate A mixture of 4,6-dichloro-8-fluoro-7-(2-fluoro-6-methoxyphenyl)quinazoline (100 mg, 0.29 mmol), tert-butyl 2,6-diazaspiro[3.4]octane-6-carboxylate (80 mg, 0.37 mmol), TEA (60 mg, 0.58 mmol) and dichloromethane (5 mL) was stirred at RT for 0.5 h. The mixture was quenched with saturated $NaHCO_3$ solution and partitioned between water and ethyl acetate. The organic layer was dried over anhydrous $Na_2SO_4$, filtered and concentrated in vacuo. The residue was purified by flash column chromatography on silica gel (ethyl acetate/petroleum ether=1:5) to afford the desired product (120 mg, 80% yield) as white solid.

2-(6-Chloro-8-fluoro-4-(2,6-diazaspiro[3.4]octan-2-yl)quinazolin-7-yl)-3-fluorophenol A mixture of 2-(6-chloro-8-fluoro-7-(2-fluoro-6-methoxyphenyl)quinazolin-4-yl)-2,6-diazaspiro[3.4]octane- 6-carboxylate (120 mg, 0.23 mmol), TFA (2 mL) and DCM (5 mL) was stirred at RT for 1 h. The mixture was concentrated in vacuo. The residue was dissolved in DCM (5 mL) and cooled to −78° C., $BBr_3$ (1 mL, 10.79 mmol) was added to the mixture at −78° C. The reaction mixture was stirred at RT for 1 h. This mixture was quenched with saturated $NaHCO_3$ and extracted with dichloromethane. The organic layer was washed with saturated $NaHCO_3$ aqueous solution and brine, dried over $Na_2SO_4$ and concentrated in vacuo. The residue was purified by flash column chromatography on silica gel (5-10% methanol/dichloroethane) to afford the desired product (20 mg, 21% yield) as a solid.

1-(2-(6-Chloro-8-fluoro-7-(2-fluoro-6-hydroxyphenyl)quinazolin-4-yl)-2,6-diazaspiro[3.4]octan-6-yl) prop-2-en-1-one To a mixture of 2-(6-chloro-8-fluoro-4-(2,6-diazaspiro[3.4]octan-2-yl)quinazolin-7-yl)-3-fluoropheno (20 mg, 0.05 mmol) and TEA (20 mg, 0.2 mmol) in dichloromethane (3 mL) at RT, acryloyl chloride (6 mg, 1.2 mmol) was added and the resulting mixture was stirred at RT for 1 h. The mixture was quenched with saturated $NaHCO_3$ solution. The mixture was extracted with ethyl acetate. The organic layer was dried over $Na_2SO_4$, and concentrated in vacuo. The residue was dissolved in THF/$H_2O$ (3 mL/1.5 mL), LiOH.$H_2O$ (21 mg, 0.5 mmol) was added. The mixture was stirred at RT for 1 h and then 1M HCl solution was added to adjust the pH to 6. The mixture was extracted with ethyl acetate. The organic layer was dried over $Na_2SO_4$ and concentrated in vacuo. The residue was purified by silica chromatography on silica gel (DCM:MeOH=50:1 to 20:1) to give the crude compound, which was further purified by Pre-TLC to give the target compound (4 mg, 18% yield) as white solid. ESI-MS m/z: 457.1 $[M+H]^+$; $^1$H-NMR (400 MHz, $CDCl_3$) δ: 8.40-8.38 (m, 1H), 7.57 (s, 1H), 7.37-7.31 (m, 1H), 6.92-6.90 (m, 1H), 6.79-6.74 (m, 1H), 6.46-6.38 (m, 2H), 5.79-5.72 (m, 1H), 4.50-4.43 (m, 4H), 3.88-3.78 (m, 2H), 3.75-3.62 (m, 2H), 2.35-2.31 (m, 1H), 2.29-2.22 (m, 1H).

Example 21

N-(3-(6-chloro-8-fluoro-7-(2-fluoro-6-hydroxyphenyl)quinazolin-4-yl)phenyl)acrylamide

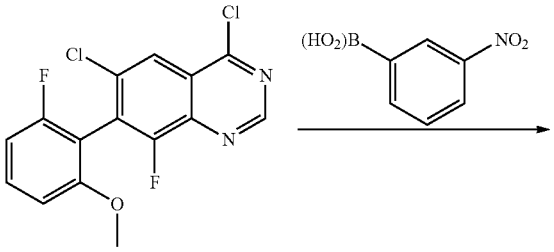

-continued

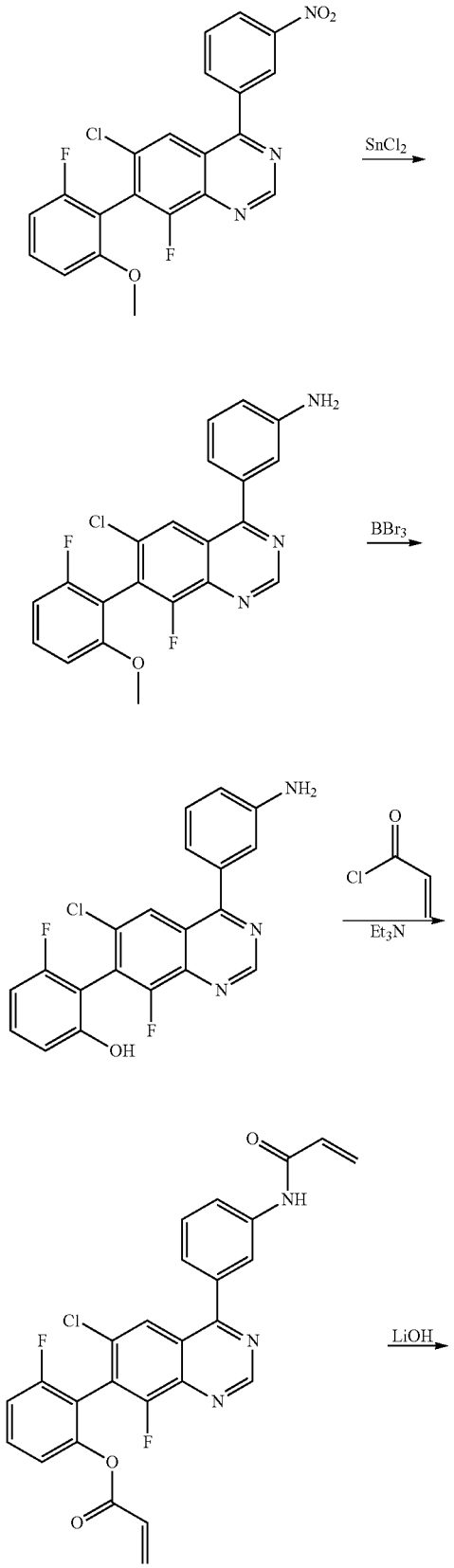

-continued

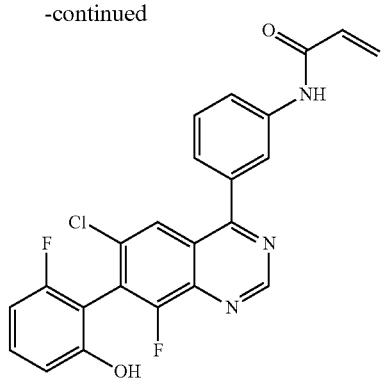

Example 21 provides an exemplary procedure according to Method T.

6-Chloro-8-fluoro-7-(2-fluoro-6-methoxyphenyl)-4-(3-nitrophenyl)quinazoline

To a stirred solution of 4,6-dichloro-8-fluoro-7-(2-fluoro-6-methoxyphenyl)quinazoline (380 mg, 1.12 mmol) in THF (30 mL), 3-nitrophenylboronic acid (560 mg, 3.36 mmol), $PdCl_2(PPh_3)_2$(84 mg, 0.12 mmol) and $K_3PO_4$ (1.2 g, 5.6 mmol) were added and the resulting mixture was stirred at 80° C. under nitrogen overnight. The mixture was allowed to cool to RT and partitioned between water and ethyl acetate. The organic layer was washed with brine, dried over $Na_2SO_4$ and concentrated to afford the desired product (180 mg, 42.2% yield) as an off white solid.

3-(6-Chloro-8-fluoro-7-(2-fluoro-6-methoxyphenyl) quinazolin-4-yl)benzenamine

To a solution of 6-chloro-8-fluoro-7-(2-fluoro-6-methoxyphenyl)-4-(3-nitrophenyl)quinazoline (360 mg, 0.42 mmol) in $CH_3CH_2OH$ (30 mL) was added $SnCl_2$ (396 mg, 2.10 mmol) and the resulting mixture was stirred at 70° C. for 5 h. The mixture cooled to RT and partitioned between saturated $NaHCO_3$ solution (40 mL) and ethyl acetate. The organic layer was washed with brine, dried over $Na_2SO_4$ and concentrated in vacuo. The residue was purified by flash column chromatography on silica gel (petroleum ether/ethyl acetate=10:1) to afford the desire product (140 mg, 83.3% yield) as an off-white solid.

2-(4-(3-Aminophenyl)-6-chloro-8-fluoroquinazolin-7-yl)-3-fluorophenol

To a solution of 3-(6-chloro-8-fluoro-7-(2-fluoro-6-methoxyphenyl)quinazolin-4-yl)benzenamine (140 mg, 0.35 mmol) in dichloromethane (20 mL) at −78° C., $BBr_3$ (880 mg, 3.5 mmol) was added drop wise and the resulting mixture was stirred at RT for 8 h. The mixture was cooled to −10° C., $NaHCO_3$ solution was added to adjust pH >7, and then extracted with dichloromethane. The organic layer was washed with brine, dried over $Na_2SO_4$ and concentrated in vacuo. The residue was purified by flash column chromatography on silica gel (petroleum ether/ethyl acetate=1:1) followed by Pre-HPLC to afford the desire product (60 mg, 44.6% yield) as an off-white solid.

2-(4-(3-(Acrylamido)phenyl)-6-chloro-8-fluoroquinazolin-7-yl)-3-fluorophenyl Acrylate To a solution of 2-(4-(3-aminophenyl)-6-chloro-8-fluoroquinazolin-7-yl)-3-fluorophenol (60 mg, 0.156 mmol) in dichloromethane (20 mL) at 0° C., acryloyl chloride (72 mg, 0.78 mmol) and $Et_3N$ (158 mg, 1.56 mmol) were added and the resulting mixture was allowed to warm to RT and stirred at RT for 3 h. The mixture was quenched with $H_2O$ and extracted with dichloromethane. The organic layer was washed with brine, dried over $Na_2SO_4$ and concentrated in vacuo to afford a crude desired product (75 mg, 91.7% yield) as an off-white solid.

N-(3-(6-Chloro-8-fluoro-7-(2-fluoro-6-hydroxyphenyl)quinazolin-4-yl)phenyl)acrylamide To a solution of 2-(4-(3-(acrylamido)phenyl)-6-chloro-8-fluoroquinazolin-7-yl)-3-fluorophenyl acrylate (75 mg, 0.143 mmol) in THF (10 mL) and $H_2O$ (10 mL), $LiOH.H_2O$ (18 mg, 0.428 mmol) was added and the resulting mixture was stirred at RT for 2 h. The mixture was partitioned between water and ethyl acetate. The organic layer was washed with brine, dried over $Na_2SO_4$ and concentrated in vacuo. The residue was purified by flash column chromatography on silica gel (petroleum ether/ethyl acetate=1:1) to afford the desired product (30 mg, 48% yield) as an off-white solid. ESI-MS m/z: 438.1 $[M+H]^+$; $^1H$ NMR (400 MHz, DMSO-d6) δ: 10.47-10.42 (m, 1H), 9.49 (s, 1H), 8.21 (s, 1H), 8.14-8.13 (m, 1H), 7.96-7.94 (m, 1H), 7.66-7.58 (m, 2H), 7.45-7.39 (m, 1H), 6.91-6.84 (m, 2H), 6.51-6.45 (m, 1H), 6.34-6.29 (dd, J=2.0, 16.8 Hz, 1H), 5.83-5.80 (dd, J=2.0, 10.4 Hz, 1H).

Example 22

2-(4-(4-acryloylpiperazin-1-yl)-6-chloro-8-fluoroquinazolin-7-yl)-3-fluorophenyl Dihydrogen Phosphate

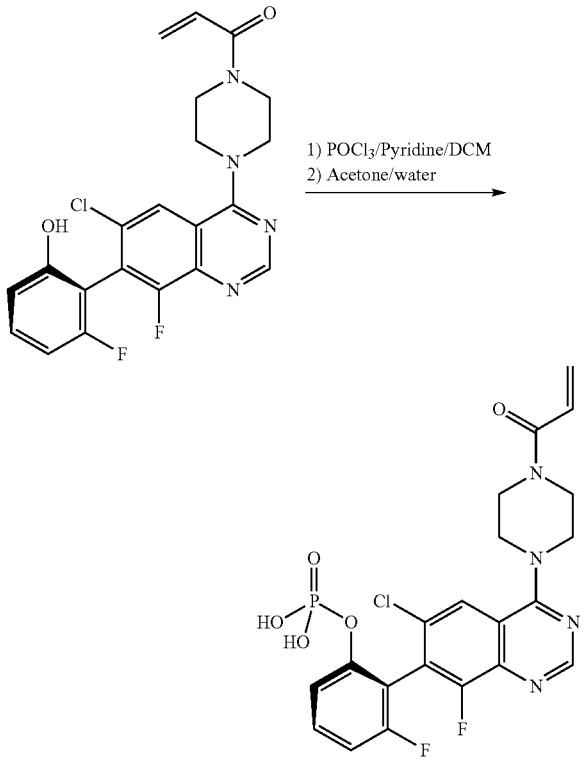

To a stirred solution of (S)-1-(4-(6-chloro-8-fluoro-7-(2-fluoro-6-hydroxyphenyl)quinazolin-4-yl)piperazin-1-yl) prop-2-en-1-one (400 mg, 0.93 mmol) in anhydrous DCM (5 mL) at 0° C. under nitrogen (prepared according to the above general procedures), pyridine (1.54 g, 19.5 mmol) was added followed by slow addition of $POCl_3$ solution (1.42 g, 9.3 mmol) in 5 mL of dry DCM (over 10 min). After addition of $POCl_3$, the reaction mixture was stirred at 0° C. for 2 h. The reaction was then quenched by dropwise addition of 1:1 mixture of acetone/water (6 mL) and the resulting mixture was stirred at RT overnight. The mixture was concentrated in vacuo, and the residue purified by pre-HPLC to afford the desired product (274 mg, 58% yield). ESI-MS m/z: 511.0 $[M+H]^+$; $^1$H-NMR (500 MHz, DMSO-d6) δ: 8.91 (s, 1H), 8.13 (s, 1H), 7.57 (dd, J=8.5, 15.5 Hz, 1H), 7.41 (d, J=8.5 Hz, 1H), 7.20 (t, J=8.5, 8.5 Hz, 1H), 6.83 (dd, J=10.5, 17.0 Hz, 1H), 6.17 (dd, J=2.5, 17.0 Hz, 1H), 5.74 (dd, J=2.5, 11.5 Hz, 1H), 3.75-3.95 (m, 8H).

Example 23

(S)-(2-(4-(4-acryloylpiperazin-1-yl)-6-chloro-8-fluoroquinazolin-7-yl)-3-fluorophenoxy)methyl Dihydrogen Phosphate

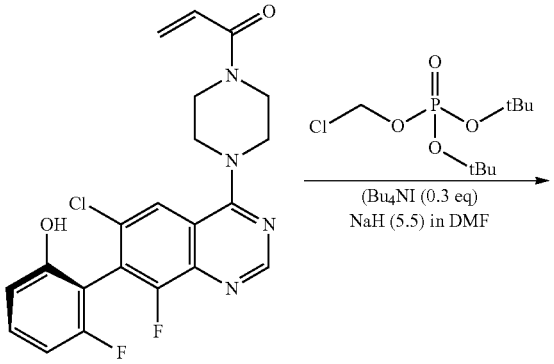

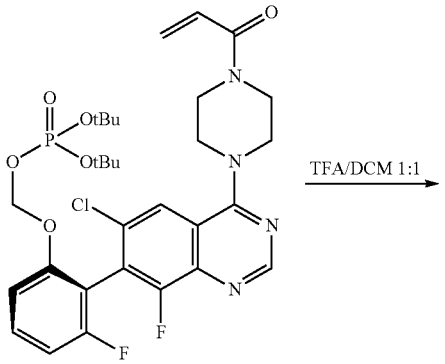

-continued

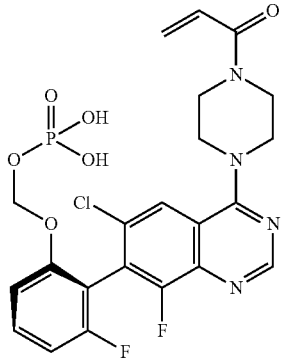

(S)-(2-(4-(4-Acryloylpiperazin-1-yl)-6-chloro-8-fluoroquinazolin-7-yl)-3-fluorophenoxy)methyl di-tert-butyl Phosphate (S)-1-(4-(6-chloro-8-fluoro-7-(2-fluoro-6-hydroxyphenyl)quinazolin-4-yl)piperazin-1-yl)prop-2-en-1-one (722 mg, 1.68 mmol), sodium hydride (60%, 370 mg, 9.2 mmol), tetrabutylammonium iodide (208 mg, 0.56 mmol,) were charged to a flask and cooled down to −78° C. Di-tert-butyl (chloromethyl) phosphate (2.7 g, 10.4 mmol) was dissolved in cold DMF (4 mL) and was added in portions. THF (2 mL) was added to solubilize the mixture at −78° C. The Reaction was vigorously stirred and slowly warmed up to 0° C. in 4 h, and the resulting mixture was stirred at RT for another 4 hours. Reaction was diluted with DCM (100 mL), filtered, cooled down to −78° C., and treated with ice. Reaction was then warmed up to RT, washed with brine and water, dried over $Na_2SO_4$, and concentrated in vacuo. The residue obtained was purified on silica gel (0-6% methanol in DCM) to afford the desired product. The product was directly used in the next step. ESI-MS m/z: 653.2 $[M+H]^+$.

(S)-(2-(4-(4-acryloylpiperazin-1-yl)-6-chloro-8-fluoroquinazolin-7-yl)-3-fluorophenoxy)methyl Dihydrogen Phosphate (S)-(2-(4-(4-acryloylpiperazin-1-yl)-6-chloro-8-fluoroquinazolin-7-yl)-3-fluorophenoxy)methyl di-tert-butyl phosphate (about 1.1 g, 1.68 mmol,) was dissolved in 1:1 mixture of DCM/TFA (2 mL). The mixture was vigorously stirred at RT for 20 min, stripped off solvents, and then purified by prep-HPLC (5-60% MeCN in water) to give the desired product (138 mg, 15% yield). ESI-MS m/z: 541.0 $[M+H]^+$; $^1$H-NMR (500 MHz, DMSO-d6) δ: 8.69 (s, 1H), 8.05 (s, 1H), 7.60 (q, J1=6.4 Hz, J2=12.0 Hz, 1H), 7.26 (d, J=6.8 Hz, 1H), 7.13 (t, J=6.8 Hz, 1H), 6.82 (dd, J1=8.4 Hz, J2=13.6 Hz), 6.17 (dd, J1=2 Hz, J2=13.6 Hz, 1H), 5.74 (dd, J1=2 Hz, J2=8.4 Hz), 5.48 (m, 2H), 3.90-6.70 (br m, 12).

Example 24

Synthesis of 1-((3 S)-4-(6-chloro-8-fluoro-7-(2-fluoro-6-hydroxyphenyl)quinazolin-4-yl)-3-methylpiperazin-1-yl)prop-2-en-1-one

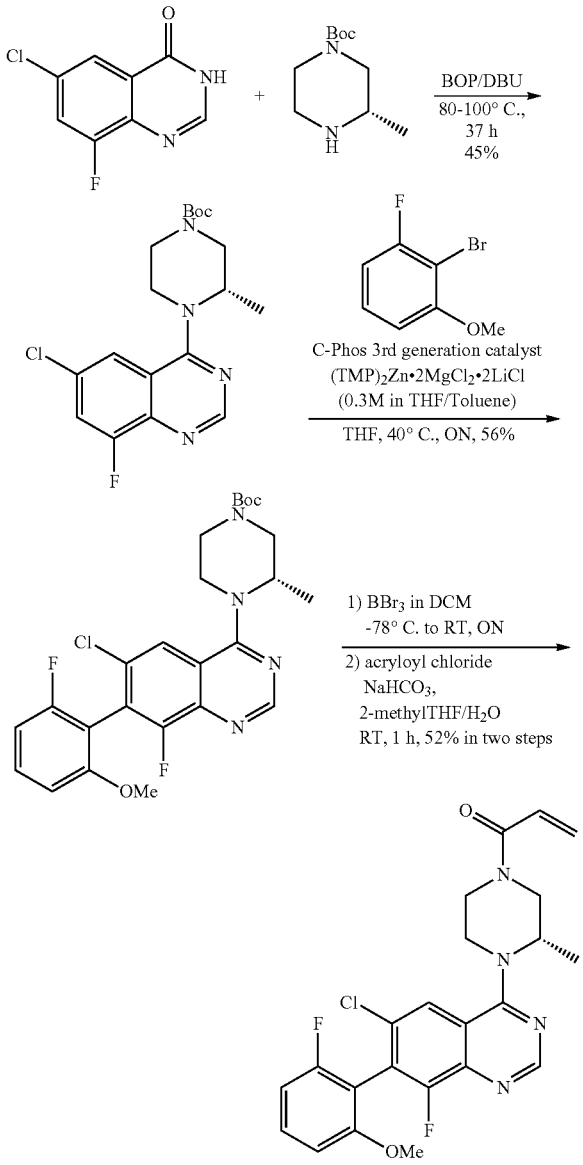

Example 24 provides an exemplary preparation according to General Synthetic Method V.

tert-Butyl (S)-4-(6-chloro-8-fluoroquinazolin-4-yl)-3-methylpiperazine-1-carboxylate To a mixture of 800 mg (4.04 mmol, 1.0 eq.) of 6-chloro-8-fluoroquinazolin-4(3H)-one and BOP (1.1 eq.) in acetonitrile, DBU (1.3 eq.) and tert-butyl (S)-3-methylpiperazine-1-carboxylate (1.1 eq.) were added sequentially. The resulting mixture was stirred at 80-100° C. for 37 h. The mixture was cooled down, concentrated in vacuo and then partitioned between water and ethyl acetate. The combined organic layer was washed with brine, dried over anhydrous sodium sulfate, filtered and concentrated in vacuo. The residue was purified by flash column chromatography (stepwise gradient of 0-10% MeOH in dichloromethane) to afford the desired product (685 mg, 45% yield).

tert-Butyl (3S)-4-(6-chloro-8-fluoro-7-(2-fluoro-6-methoxyphenyl)quinazolin-4-yl)-3-methylpiperazine-1-carboxylate A flame dried round bottle (evacuated under vacuum and filled with $N_2$) was fitted with mechanical stirring, and charged with tert-butyl (S)-4-(6-chloro-8-fluoroquinazolin-4-yl)-3-methylpiperazine-1-carboxylate (685 mg, 1.80 mmol, 1.0 eq.) solution in dry THF. Bis(2,2,6,6-tetramethylpiperidinyl)zinc, lithium chloride, magnesium chloride complex ($(TMP)_2Zn.2\ MgCl_2.2\ LiCl$) (0.35 M solution in THF/toluene, 1.0 eq.) was dropwise added. The reaction was allowed to stir for 45 min at RT and then degassed by bubbling nitrogen through the solution for 15 min. Solid 2-bromo-1-fluoro-3-methoxybenzene (1.0 eq.) and CPhos 3rd generation precatalyst (0.1 eq.) were added, and the resulting mixture was stirred at 40° C. for 16 h. The reaction mixture was concentrated in vacuo, dissolved in ethyl acetate, cooled in an ice bath, and quenched with a 1:1 solution of saturated ammonium chloride and $H_2O$. The layers were separated, and the aqueous layer was extracted with ethyl acetate. The combined organic layer was dried ($Na_2SO_4$), filtered and concentrated in vacuo. The residue was purified by flash column chromatography (stepwise gradient of 20%-30% EtOAc in hexanes) to afford the desired product (504 mg, 56% yield).

1-((3S)-4-(6-Chloro-8-fluoro-7-(2-fluoro-6-hydroxyphenyl)quinazolin-4-yl)-3-methylpiperazin-1-yl)prop-2-en-1-one At −78° C., $BBr_3$ in dichloromethane (1M, 6.0 eq.) was dropwise added into tert-butyl (3 S)-4-(6-chloro-8-fluoro-7-(2-fluoro-6-methoxyphenyl)quinazolin-4-yl)-3-methylpiperazine-1-carboxylate (228 mg, 0.45 mmol, 1.0 eq.) solution in dichloromethane. After addition was complete, the reaction was warmed to RT, and the suspension was stirred for 19 h. The reaction was cooled to 0° C. and quenched with an ice/water. Additional water was added and the layers were separated. The water layer was collected. The organic layer was extracted with water. The combined water layer was concentrated, added 2-MeTHF and solid $NaHCO_3$ (20.0 eq.). The reaction mixture was allowed to stir for 5 min. The acryloyl chloride (2.5 eq.) was added at RT and the resulting mixture was stirred at RT for 1 h. Then 5 N NaOH (0.5 mL) was added to quench the reaction, followed by adding 1 mL of 1 N HCl for neutralization. The organic layer was separated and the aqueous layer was extracted with ethyl acetate. The combined organic layer was washed with brine, dried over anhydrous $Na_2SO_4$, and concentrated in vacuo. The residue was purified by flash column chromatography (stepwise gradient of 0-10% MeOH in dichloromethane) to afford the desired product (104 mg, 52% yield). ESI-MS m/z: 445.1 $[M+H]^+$; $^1H$ NMR (500 MHz, DMSO-d6) δ 10.27 (s, 1H), 8.70 (s, 1H), 7.94 (s, 1H), 7.39-7.34 (q, J=8.5 Hz, 1H), 6.87-6.80 (m, 3H), 6.21-6.16 (m, 1H), 5.43 (dd, J=10, 2.5 Hz, 1H), 4.78 (broad s, 1H), 4.40-3.96 (m, 4H), 3.70-3.61 (m, 2H), 1.30 (s, 3H).

Example 25
Synthesis of 4-((3R,5 S)-4-acryloyl-3,5-dimethylpiperazin-1-yl)-6-chloro-8-fluoro-7-(2-fluoro-6-hydroxyphenyl)quinoline-3-carbonitrile
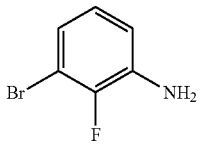
NCS, DMF
0° C. to R.T.
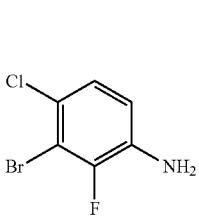
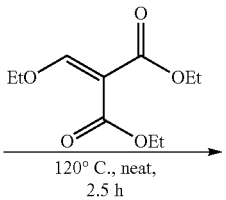
120° C., neat,
2.5 h
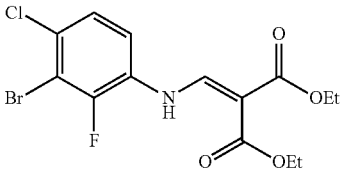
$Ph_2O$,
250° C., 2.5 h
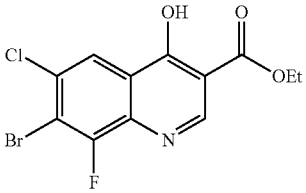
DIEA, $POCl_3$
100° C., 2 h
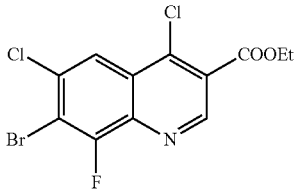
DIEA, Dioxane, 80° C.
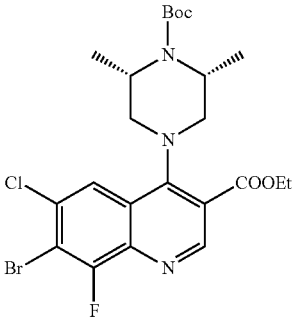
$Pd(PPh_3)_4$, $Na_2CO_3$,
Dioxane, $H_2O$, 100° C., 16 h
-continued
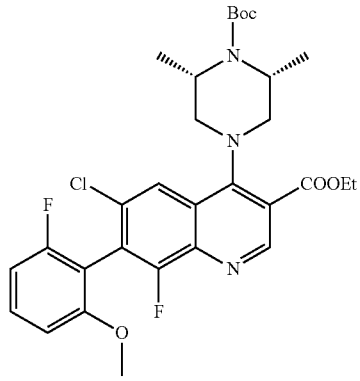
$LiOH{\bullet}H_2O$
THF/MeOH/$H_2O$
R.T., 16 h
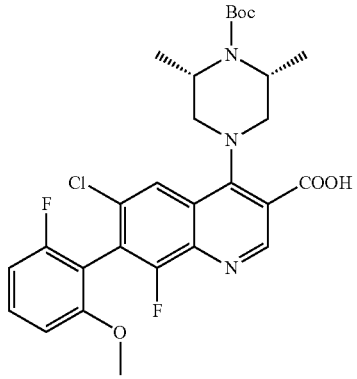
$NH_4Cl$, Py-BOP,
DIEA, DMF/DCM,
30 min
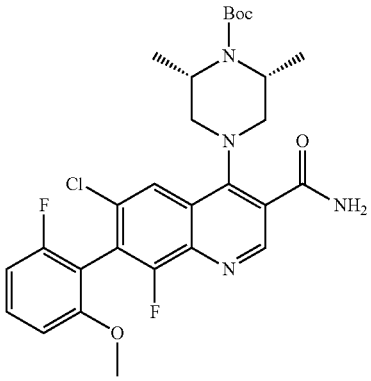
1) $CF_3COOH$, DCM
2) $Et_3N$, DCM
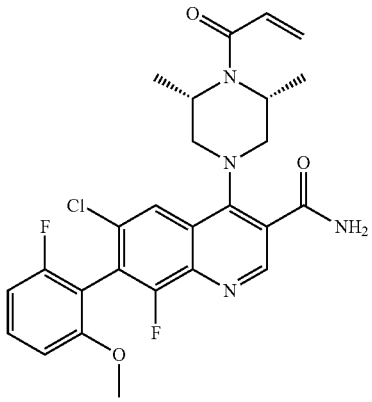
$BBr_3$, DCM -continued

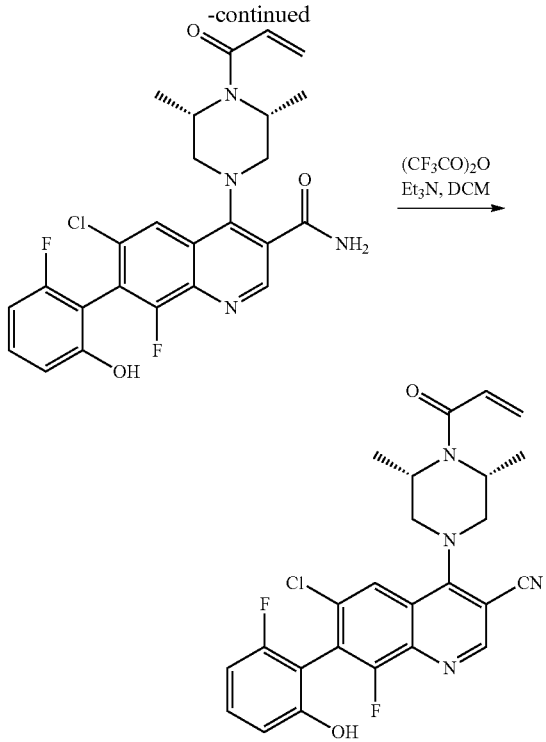

Example 25 provides an exemplary preparation according to General Synthetic Method W.

3-Bromo-4-chloro-2-fluorobenzenamine

To a solution of 3-bromo-2-fluorobenzenamine (1.9 g, 10 mmol) in DMF (10 mL) at RT, NCS (1.4 g, 10.5 mmol) was added and the resulting mixture was stirred at RT for 16 h. The mixture was poured into ice water and extracted with ethyl acetate. The organic layer was washed with brine, dried over $Na_2SO_4$ and concentrated in vacuo. The residue was purified by column chromatography on silica gel (petroleum ether/ethyl acetate=30:1) to afford the desired product (1.15 g, 51% yield). ESI-MS m/z: 225.9 $[M+H]^+$.

Diethyl 2-((3-bromo-4-chloro-2-fluorophenylamino) methylene)malonate

A mixture of 3-bromo-4-chloro-2-fluorobenzenamine (2.3 g, 10.2 mmol) and diethyl2-(ethoxymethylene) malonate (2.42 g, 11.22 mmol) was stirred at 120° C. for 3 h. The mixture was allowed to cool to RT, petroleum was added and the resulting mixture was stirred at RT for 1 h. The precipitate was collected by filtration and dried to afford the desired product (2.76 g, 68.7% yield). ESI-MS m/z: 395.9$[M+H]^+$.

Ethyl 7-bromo-6-chloro-8-fluoro-4-hydroxyquinoline-3-carboxylate

Diethyl 2-((3-bromo-4-chloro-2-fluorophenylamino) methylene)malonate (2.76 g, 6.99 mmol) was suspended in $Ph_2O$ (20 mL). The mixture was stirred at 250° C. for 2 h. The mixture was allowed to cool to RT and then 100 mL of petroleum ether was added. The white solid was collected by filtration and rinsed with petroleum ether (100 mL) to afford the desired product (1.85 g, 76% yield). ESI-MS m/z: 349.9 $[M+H]^+$.

Ethyl 7-bromo-4,6-dichloro-8-fluoroquinoline-3-carboxylate

A mixture of ethyl 7-bromo-6-chloro-8-fluoro-4-hydroxyquinoline-3-carboxylate (1.85 g, 5.31 mmol) and $POCl_3$ (10 mL) was stirred at reflux for 4 h. The mixture was allowed to cool to RT and concentrated in vacuo to afford the crude product (1.41 g).

Ethyl 7-bromo-4-((3R,5S)-4-(tert-butoxycarbonyl)-3,5-dimethylpiperazin-1-yl)-6-chloro-8-fluoroquinoline-3-carboxylate A mixture of ethyl 7-bromo-4,6-dichloro-8-fluoroquinoline-3-carboxylate (552 mg, 1.50 mmol), (2R,6S)-tert-butyl 2,6-dimethylpiperazine-1-carboxylate (644 mg, 3.0 mmol), DIPEA (774 mg, 6.0 mmol) in dioxane (40 mL) was stirred at 90° C. under argon for 2 h. The mixture was cooled to RT and then concentrated in vacuo. The residue was purified by column chromatography on silica gel (petroleum ether/ethyl acetate=3:1) to afford the desired product as a yellow solid (794 mg, 94.7% yield). ESI-MS m/z: 546.3 $[M+H]^+$.

Ethyl 4-((3R,5S)-4-(tert-butoxycarbonyl)-3,5-dimethylpiperazin-1-yl)-6-chloro-8-fluoro-7-(2-fluoro-6-methoxyphenyl)quinoline-3-carboxylate A mixture of ethyl 7-bromo-4-((3R,5 S)-4-(tert-butoxycarbonyl)-3,5-dimethylpiperazin-1-yl)-6-chloro-8-fluoroquinoline-3-carboxylate (794 mg, 1.46 mmol) and (2-fluoro-6-methoxyphenyl)boronic acid (1.24 g, 7.29 mmol) and $Na_2CO_3$ (464 mg, 4.37 mmol) in $H_2O$ (20 mL) and dioxane (80 mL) under argon, $Pd(PPh_3)_4$(201 mg, 0.17 mmol) was added and the resulting mixture was stirred at 90° C. for 16 h. The mixture was concentrated in vacuo and the residue was purified by column chromatography on silica gel (petroleum ether/ethyl acetate=4:1) to afford the desired product (178 mg, 20.7% yield).

4-((3R,5S)-4-(tert-Butoxycarbonyl)-3,5-dimethylpiperazin-1-yl)-6-chloro-8-fluoro-7-(2-fluoro-6-methoxyphenyl)quinoline-3-carboxylic acid A mixture of ethyl 4-((3R,5 S)-4-(tert-butoxycarbonyl)-3,5-dimethylpiperazin-1-yl)-6-chloro-8-fluoro-7-(2-fluoro-6-methoxyphenyl)quinoline-3-carboxylate (178 mg, 0.30 mmol) in THF (10 mL) and water (10 mL), lithium hydroxide (51 mg, 1.21 mmol) was added and the resulting mixture was stirred at RT for 16 h. The mixture was diluted with 2M NaOH (30 mL), and extracted with 50% ethyl acetate/petroleum ether. The water phase was acidified by 1M HCl and extracted with ethyl acetate. The organic layer was concentrated in vacuo to afford the crude product (189 mg) which was used in the next step directly.

(2R,6S)-tert-Butyl 4-(3-carbamoyl-6-chloro-8-fluoro-7-(2-fluoro-6-methoxyphenyl)quinolin-4-yl)-2,6-dimethylpiperazine-1-carboxylate A mixture of 4-((3R,5S)-4-(tert-butoxycarbonyl)-3,5-dimethylpiperazin-1-yl)-6-chloro-8-fluoro-7-(2-fluoro-6-methoxyphenyl)quinoline-3-carboxylic acid (189 mg, 0.34 mmol) and $NH_4Cl$ (54 mg, 1.01 mmol) and Py-BOP (350 mg, 0.67 mmol) in DMF (20 mL), DIPEA (174 mg, 1.34 mmol) was added and the resulting mixture was stirred at RT for 30 min. The mixture was partitioned between water and ethyl acetate. The organic layer was concentrated in vacuo and the residue was purified by column chromatography on silica gel (dichloromethane/MeOH=30:1) to afford a crude product (310 mg). ESI-MS m/z: 561.4 $[M+H]^+$.

4-((3R,5S)-4-Acryloyl-3,5-dimethylpiperazin-1-yl)-6-chloro-8-fluoro-7-(2-fluoro-6-methoxyphenyl) quinoline-3-carboxamide A mixture of (2R,6S)-tert-butyl 4-(3-carbamoyl-6-chloro-8-fluoro-7-(2-fluoro-6-methoxyphenyl)quinolin-4-yl)-2,6-dimethylpiperazine-1-carboxylate (310 mg) in dichloromethane (10 mL), TFA (3 mL) was added and the resulting mixture was stirred at RT for 30 min. The mixture was added drop wise to a stirred mixture of 2M NaOH (40 mL) and ethyl acetate (40 mL). Then acryloyl chloride (1.5 mL) was added drop wise to the reaction. The mixture was extracted with ethyl acetate. The residue was purified by column chromatography on silica gel (DCM/MeOH=30:1) to afford the desired product (84 mg). ESI-MS m/z: 515.30 $[M+H]^+$.

4-((3R,5S)-4-Acryloyl-3,5-dimethylpiperazin-1-yl)-6-chloro-8-fluoro-7-(2-fluoro-6-hydroxyphenyl)quinoline-3-carboxamide A mixture of 4-((3R,5S)-4-acryloyl-3,5-dimethylpiperazin-1-yl)-6-chloro-8-fluoro-7-(2-fluoro-6-methoxyphenyl) quinoline-3-carboxamide (84 mg, 0.16 mmol) in dichloromethane (10 mL) at −78° C., $BBr_3$ (409 mg, 1.63 mmol) was added and the resulting mixture was stirred at RT for 2 h. The mixture was poured to ice water, partitioned between ethyl acetate and $NaHCO_3$ solution. The organic layer was dried over $Na_2SO_4$ and concentrated in vacuo to afford the desired product (57 mg). ESI-MS m/z: 501.2 $[M+H]^+$.

4-((3R,5S)-4-Acryloyl-3,5-dimethylpiperazin-1-yl)-6-chloro-8-fluoro-7-(2-fluoro-6-hydroxyphenyl)quinoline-3-carbonitrile To a solution of 4-((3R,5S)-4-acryloyl-3,5-dimethylpiperazin-1-yl)-6-chloro-8-fluoro-7-(2-fluoro-6-hydroxyphenyl)quinoline-3-carboxamide (57 mg) and $Et_3N$ (10 mL), $(CF_3CO)_2O$ (1.5 mL) was added. The mixture was stirred at RT for 10 min, and quenched with water (50 mL). The mixture was extracted by DCM (10 mL×2). The organic layer was washed with brine, dried over $Na_2SO_4$ and concentrated in vacuo. The residue was purified by column chromatography on silica gel (dichloromethane/MeOH=50:1) followed by Pre-TLC to afford the desire product (30 mg, 35% yield). ESI-MS m/z: 483.2 $[M+H]^+$; $^1H$ NMR (400 MHz, DMSO-d6) δ: 10.45 (s, 1H), 8.96 (s, 1H), 8.39 (s, 1H), 7.42 (t, J=8.4 Hz, $J_2$=15.6 Hz, 1H), 6.90 (m, 3H), 6.23 (dd, $J_1$=1.6 Hz, $J_2$=16.4 Hz, 1H), 5.78 (dd, $J_1$=2.0 Hz, $J_2$=10.4 Hz, 1H), 4.63 (m, 2H), 3.76 (m, 4H), 1.53 (m, 6H).

Example 26

Synthesis of 1-(4-(6-chloro-8-fluoro-7-(2-fluoro-6-hydroxyphenyl)quinazolin-4-yl)-2-methylpiperazin-1-yl)prop-2-en-1-one

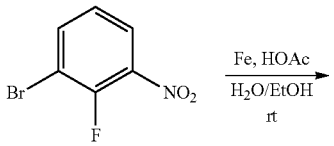

-continued

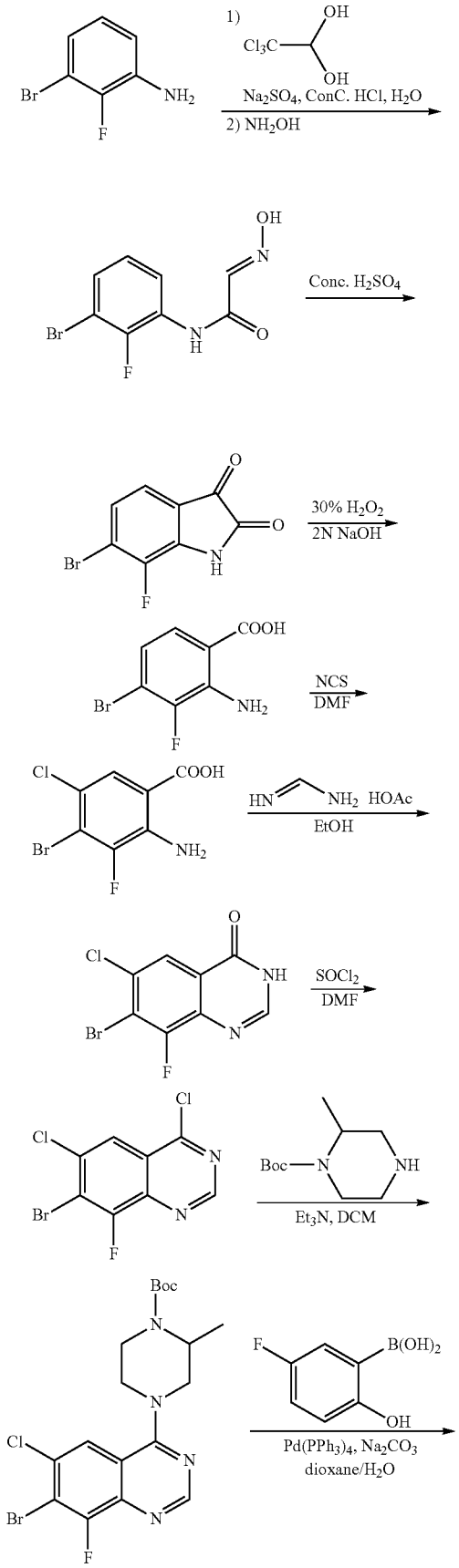

-continued

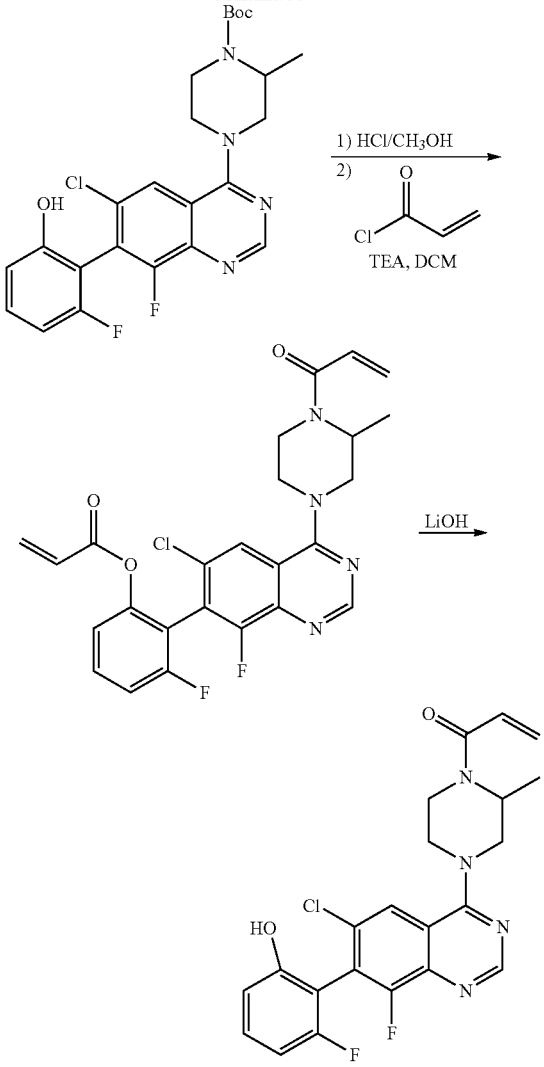

Example 26 provides an exemplary preparation according to General Synthetic Method U.

3-bromo-2-fluorobenzenamine

To a mixture of 1-bromo-2-fluoro-3-nitrobenzene (50 g, 228.4 mmol), HOAc (41.1 g, 685.2 mmol), EtOH (420 mL) and $H_2O$ (140 mL) at room temperature, iron powder (38.4 g, 685.2 mmol) was added portion-wise. The resulting mixture was stirred at room temperature for 16 h and then was neutralized with NaOH (5 N) solution. Then the mixture was extracted with ethyl acetate. The organic layer was washed with brine, dried over $Na_2SO_4$ and concentrated in vacuo. The residue was purified by flash column chromatography on silica gel (petroleum ether) to afford the crude product (48 g, 111% yield) as a brown oil.

N-(3-bromo-2-fluorophenyl)-2-(hydroxyimino)acetamide

A mixture of 2,2,2-Trichloroethane-1,1-diol (37.7 g, 228.6 mmol) and $Na_2SO_4$ (243.5 g, 1714.5 mmol) were dissolved in water (600 mL) at 60° C. to be a clear solution. 3-bromo-2-fluorobenzenamine (36 g, 190.5 mmol) was added. Then the mixture was stirred at 60° C. for 1 h, followed by 35% aqueous HCl (31.7 mL, 381 mmol). Then this mixture was stirred at 60° C. for 1 h. Then hydroxylamine hydrochloride (65.7 g, 952.5 mmol) was added. The resulting mixture was stirred at 60° C. for 4 h and 100° C. for 16 h. Then the yellow precipitate was formed. The mixture was cooled to room temperature, the solid was filtered, washed with water, and dried in the air to afford the desired product (38.9 g, 78% yield).

6-bromo-7-fluoroindoline-2,3-dione

To the concentrated sulfuric acid (270 mL) at 60° C. was added N-(3-bromo-2-fluorophenyl)-2-(hydroxyimino)acetamide (29.4 g, 113.1 mmol). The temperature was raised to 90° C. and maintained for 1 h. Then the TLC show complete consumption of the starting material. The reaction mixture was cooled to room temperature and poured into ice to get yellow precipitate. Then the mixture was extracted with ethyl acetate. The organic layer was washed with water, Sa. $NaHCO_3$ and brine, dried over $Na_2SO_4$ and concentrated in vacuo. The residue was purified by column chromatography on silica gel (dichloromethane/ethyl acetate=200:1 to 20:1) to afford the crude desired product as a yellow solid (18.9 g, 68% yield). ESI-MS m/z: 278.9 $[M+H]^+$. $^1H$ NMR (400 MHz, DMSO-d6) δ: 11.75 (s, 1H), 7.39 (dd, J=5.7, 7.9 Hz, 1H), 7.31 (d, J=8.2 Hz, 1H).

2-amino-4-bromo-3-fluorobenzoic Acid

To a mixture of 6-bromo-7-fluoroindoline-2,3-dione (18.9 g, 77.5 mmol) in 2 N NaOH (350 mL) was added $H_2O_2$ (30%, 40 mL) at 0° C. Then the mixture was warmed to RT and stirred at RT for 16 h. The mixture was quenched with $Na_2SO_3$, and solution was acidified with Conc. HCl to adjust pH=2. The precipitate was formed, filtered and dried in the air to afford the desired product as a white solid (17 g, 94% yield).

2-amino-4-bromo-5-chloro-3-fluorobenzoic Acid

To a solution of 2-amino-4-bromo-3-fluorobenzoic acid (17 g, 72.6 mmol) in DMF (200 mL) was added NCS (10.2 g, 76.2 mmol) at rt, the mixture was stirred at 70° C. for 16 h. The mixture was cooled to rt and poured into cold brine, the precipitate was filtered, washed with water and dried to afford the desired product as a white solid (14.6 g, 75% yield). ESI-MS m/z: 269.8 $[M+H]^+$.

7-bromo-6-chloro-8-fluoroquinazolin-4(3H)-one

To a solution of 2-amino-4-bromo-5-chloro-3-fluorobenzoic acid (21.2 g, 79.1 mmol) in EtOH (200 mL) was added formamidine acetate (82 g, 791 mmol) at room temperature. The mixture was stirred at reflux for 16 h. Then mixture was evaporated, the solid was washed with $H_2O$, dried over air to afford the desired product as a gray solid (17.6 g, 80% yield). ESI-MS m/z: 278.9 $[M+H]^+$.

7-Bromo-4,6-dichloro-8-fluoroquinazoline

A mixture of 7-bromo-6-chloro-8-fluoroquinazolin-4(3H)-one (2 g, 7.21 mmol), $SOCl_2$ (30 mL) and DMF (2 drops) was stirred at reflux for 16 h. The mixture was cooled to RT and concentrated in vacuo to afford the crude product (2.4 g) using in the next step without further purification.

tert-Butyl 4-(7-bromo-6-chloro-8-fluoroquinazolin-4-yl)-2-methylpiperazine-1-carboxylate To a solution of 7-bromo-4,6-dichloro-8-fluoroquinazoline (2.4 g, 8.25 mmol) in dichloromethane (25 mL) at RT, tert-butyl 2-methylpiperazine-1-carboxylate (3.3 g, 16.5 mmol) and $Et_3N$ (5.3 g, 41.25 mmol) was added. The resulting mixture was stirred at RT for 40 min. The mixture was extracted with dichloromethane. The organic layer was washed with 1N HCl, water, saturated $NaHCO_3$ solution and brine. The organic dried over $Na_2SO_4$ and concentrated. The residue was washed with mixture of petroleum ether/ethyl acetate=5:1 to afford the desired product as a white solid (2.8 g, 74% yield).

tert-Butyl4-(6-chloro-8-fluoro-7-(2-fluoro-6-hydroxyphenyl)quinazolin-4-yl)-2-methylpiperazine-1-carboxylate A mixture of tert-butyl 4-(7-bromo-6-chloro-8-fluoroquinazolin-4-yl)-2-methylpiperazine-1-carboxylate (1 g, 2.18 mmol), 2-fluoro-6-hydroxyphenylboronic acid (1.7 g, 10.9 mmol), $Pd(PPh_3)_4$(252 mg, 0.218 mmol) and $Na_2CO_3$ (693 mg, 6.54 mmol) in 1,4-dioxane/$H_2O$ (40 mL/10 mL) was stirred at 90° C. for 16 h under argon. The mixture was allowed to cool to RT and concentrated in vacuo. The residue was purified by column chromatography on silica gel (dichloromethane/methanol=100:1) to afford the desired product (700 mg, 65% yield). ESI-MS m/z: 491.2 $[M+H]^+$.

1-(4-(6-Chloro-8-fluoro-7-(2-fluoro-6-hydroxyphenyl)quinazolin-4-yl)-2-methylpiperazin-1-yl)prop-2-en-1-one A mixture of tert-butyl 4-(6-chloro-8-fluoro-7-(2-fluoro-6-hydroxyphenyl)quinazolin-4-yl)-2-methylpiperazine-1-carboxylate (150 mg, 0.30 mmol) and HCl in MeOH (10 mL, 4 N) was stirred at RT for 1 h. The mixture was concentrated in vacuo to yield the crude product which was used directly in next step without further purification. The above obtained crude was dissolved in $Et_3N$ (157 mg, 1.55 mmol) and dichloromethane (15 mL) and cooled to −20° C. To this mixture, acryloyl chloride (69 mg, 0.76 mmol) was added. The resulting mixture was stirred at 0° C. for 2 h. The reaction mixture was quenched with saturated $NaHCO_3$ solution, and then extracted with ethyl acetate. The organic layer was washed with saturated $NaHCO_3$ solution and brine, dried over $Na_2SO_4$ and concentrated in vacuo. The residue was dissolved in THF/$H_2O$ (10 mL/2 mL), LiOH.$H_2O$ (52 mg, 1.24 mmol) was added and the resulting mixture was stirred for 1 h. The mixture was adjusted pH to 8 by 1N HCl aqueous solution and $NaHCO_3$ aqueous solution and then extracted with ethyl acetate. The organic layer was dried over $Na_2SO_4$, filtered and concentrated in vacuo. The residue was purified by flash chromatography on silica gel (dichloromethane/methanol=20:1) to afford the product (32 mg, 23% yield in 3 steps). ESI-MS m/z: 445.1 $[M+H]^+$; $^1H$ NMR (400 MHz, DMSO-d6) δ: 10.34 (s, 1H), 8.69 (s, 1H), 8.07 (s, 1H), 7.41-7.35 (m, 1H), 6.89-6.77 (m, 3H), 6.17 (d, J=16.4 Hz, 1H), 5.73 (d, J=10.4 Hz, 1H), 4.70-4.52 (m, 1H), 4.34-4.32 (m, 1H), 4.18-4.14 (m, 1H), 3.79-3.75 (m, 1H), 3.53-3.52 (m, 2H), 3.68 (m, 1H), 1.13 (m, 3H).

Example 27

Synthesis of 1-((2S,6R)-4-(6-chloro-8-fluoro-7-(2-fluoro-6-hydroxyphenyl)quinazolin-4-yl)-2,6-dimethylpiperazin-1-yl)prop-2-en-1-one

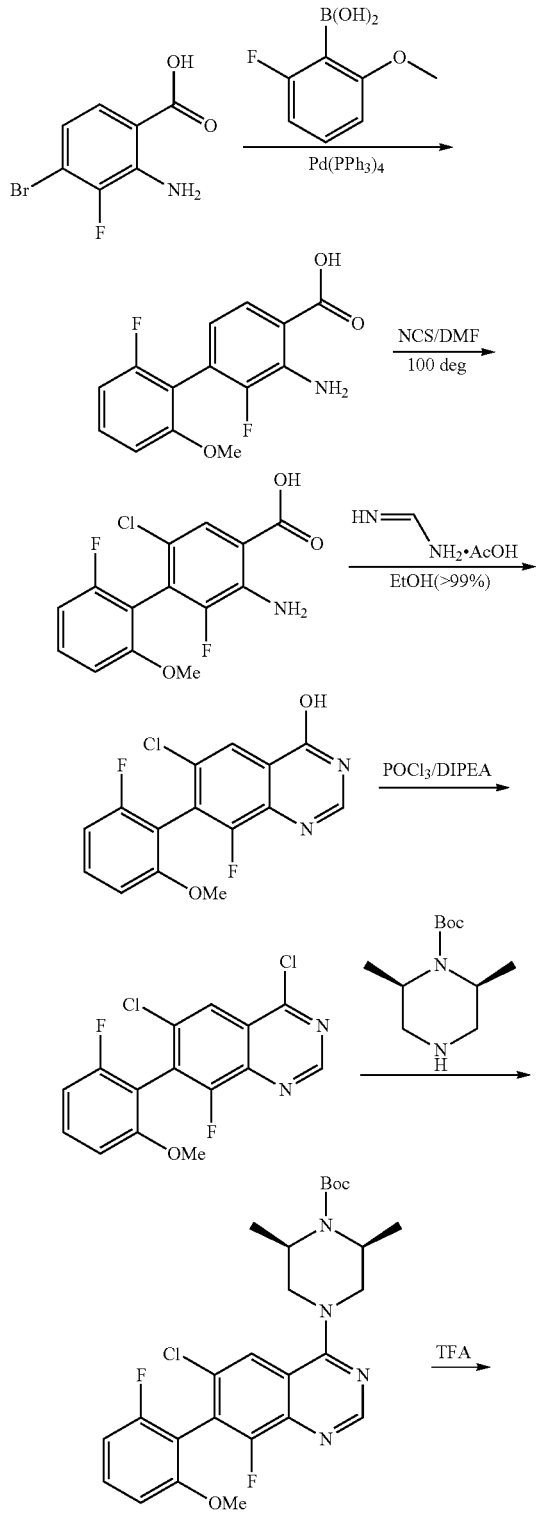

-continued

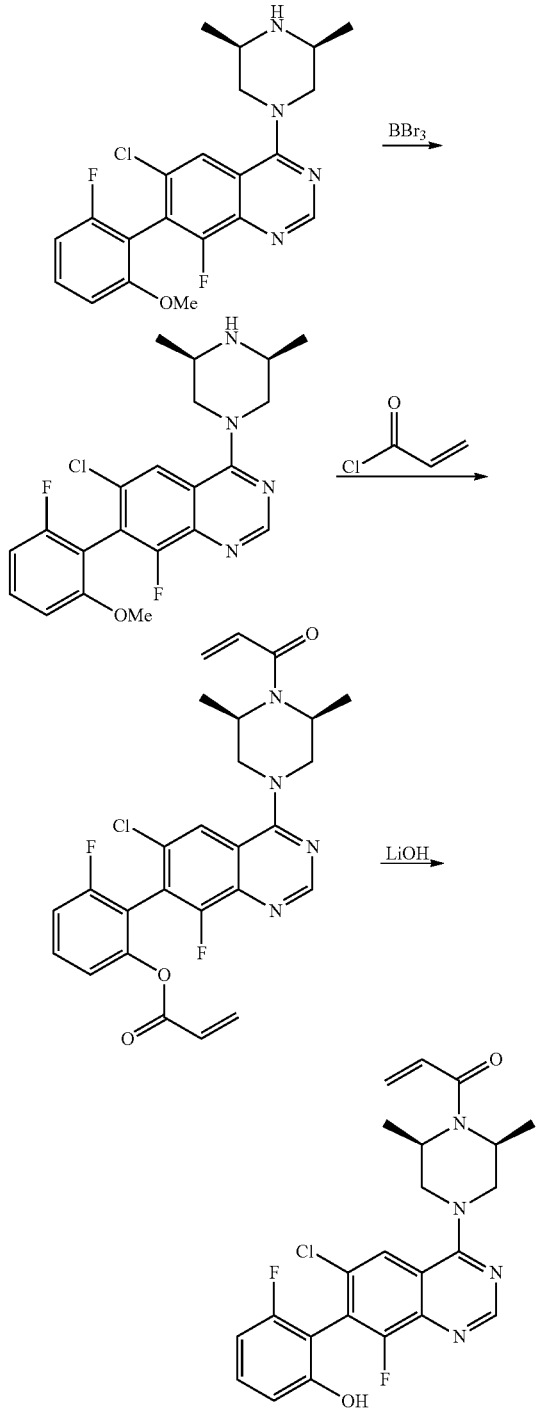

Example 27 provides an exemplary preparation according to General Synthetic Method U.

a3-Amino-2,2'-difluoro-6'-methoxy-[1,1'-biphenyl]-4-carboxylic Acid

To a stirred solution of 2-amino-4-bromo-3-fluorobenzoic acid (10 g, 43 mmol) in 1,4-dioxane (400 mL) and $H_2O$ (100 mL), 2-fluoro-6-methoxyphenylboronic acid (36 g, 213 mmol), tetrakis(triphenylphosphine)palladium (2.5 g, 2.15 mmol) and $Na_2CO_3$ (27 g, 258 mmol) were added. The mixture was degassed and back-filled with $N_2$ several times, and then heated to 100° C. and was stirred overnight. The mixture was allowed to cool to RT, water (500 mL) was added, and then extracted with ethyl acetate (200 mL×2). The organic layer was discarded, and 1M HCl solution was added to aqueous phase to adjust pH <3. The aqueous phase was extracted with ethyl acetate (200 mL×2), washed with brine, dried over $Na_2SO_4$ and concentrated in vacuo to afford the desired product (11 g, 92% yield) as a white solid. ESI-MS m/z: 280.1 $[M+H]^+$.

3-Amino-6-chloro-2,2'-difluoro-6'-methoxy-[1,1'-biphenyl]-4-carboxylic Acid

To a solution of 3-amino-2,2'-difluoro-6'-methoxy-[1,1'-biphenyl]-4-carboxylic acid (1 μg, 39.6 mmol) in N,N-dimethylformamide (100 mL) at RT, N-chlorosuccinimde (5.27 g, 39.6 mmol) was added. The resulting mixture was stirred at 100° C. for 1 h. The mixture was allowed to cool to RT, and the reaction mixture was slowly added to water (300 mL). The mixture was filtered and the cake was dried to afford the desired product (11.5 g, 93.1% yield) as a brown solid.

6-Chloro-8-fluoro-7-(2-fluoro-6-methoxyphenyl) quinazolin-4-ol

A mixture of 3-amino-6-chloro-2,2'-difluoro-6'-methoxy-[1,1-biphenyl]-4-carboxylic acid (8.1 g, 25.8 mmol) in EtOH (>99%) (150 mL), formimidamide acetate (35 g, 336.4 mmol) was added. The mixture was stirred at 100° C. overnight. The reaction mixture was concentrated in vacuo and water was added. The mixture was filter and the cake was dried to afford the desired product (7.5 g, 90.3%) as a light yellow solid.

4,6-Dichloro-8-fluoro-7-(2-fluoro-6-methoxyphenyl) quinazoline

The mixture of 6-chloro-8-fluoro-7-(2-fluoro-6-methoxyphenyl)quinazolin-4-ol (10 g, 31.1 mmol) in $POCl_3$ (100 mL) and DIPEA (10 mL) were stirred at reflux for 16 h. The mixture was allowed to cool to RT and concentrated in vacuo to remove $POCl_3$. The residue was dissolved in ethyl acetate, washed with brine, dried over $Na_2SO_4$, filtered and concentrated in vacuo. The residue was purified by flash chromatography on silica gel (ethyl acetate/petroleum ether=2.5-10%) to afford the product (9.3 g, 88% yield) as a brown solid.

(2S,6R)-tert-Butyl 4-(6-chloro-8-fluoro-7-(2-fluoro-6-methoxyphenyl)quinazolin-4-yl)-2,6-dimethylpiperazine-1-carboxylate To a solution of 4,6-dichloro-8-fluoro-7-(2-fluoro-6-methoxyphenyl)quinazoline (250 mg, 0.733 mmol) in dioxane (30 mL) at RT, DIEA (303 mg, 2.35 mmol) and (2S,6R)-tert-butyl 2,6-dimethylpiperazine-1-carboxylate (251 mg, 1.17 mmol) were added. The resulting mixture was stirred at 90° C. for 30 min. The mixture was concentrated in vacuo and the residue was purified by column chromatography on silica gel (ethyl acetate/petroleum ether=1:3) to afford the desired product (346 mg, 91% yield). ESI-MS m/z: 519.3 $[M+H]^+$ 6-Chloro-4-((3S,5R)-3,5-dimethylpiperazin-1-yl)-8-fluoro-7-(2-fluoro-6-methoxyphenyl)quinazoline To a solution of (2S,6R)-tert-butyl 4-(6-chloro-8-fluoro-7-(2-fluoro-6-methoxyphenyl)quinazolin-4-yl)-2,6-dimethylpiperazine-1-carboxylate (346 mg, 0.67 mmol) in DCM (8 mL), TFA (2 mL) was added and the resulting mixture was stirred at RT for 2 h. The mixture was concentrated in vacuo. The residue was extracted with ethyl acetate and washed with $NaHCO_3$ aqueous solution. The organic layer was dried over $Na_2SO_4$, filtered and concentrated in vacuo to afford the desired product (263 mg, 94% yield) as a solid. ESI-MS m/z: 419.1 $[M+H]^+$.

2-(6-Chloro-4-((3S,5R)-3,5-dimethylpiperazin-1-yl)-8-fluoroquinazolin-7-yl)-3-fluorophenol To a solution of 6-chloro-4-((3 S,5R)-3,5-dimethylpiperazin-1-yl)-8-fluoro-7-(2-fluoro-6-methoxyphenyl)quinazoline (263 mg, 0.63 mmol) in DCM (15 mL) at −78° C., $BBr_3$ (784 mg, 3.14 mmol) was added and the resulting mixture was stirred at RT for 2 h. The mixture was poured to ice water and extracted with ethyl acetate. The organic layer was washed with $NaHCO_3$ aqueous solution, dried over $Na_2SO_4$, filtered and concentrated in vacuo. The residue was purified by column chromatography on silica gel (dichloromethane/methanol=20:1) to afford the desired product (160 mg, 63% yield). ESI-MS m/z: 405.1 $[M+H]^+$.

2-(4-((3S,5R)-4-Acryloyl-3,5-dimethylpiperazin-1-yl)-6-chloro-8-fluoroquinazolin-7-yl)-3-fluorophenyl Acrylate To a solution of 2-(6-chloro-4-((3 S,5R)-3,5-dimethylpiperazin-1-yl)-8-fluoroquinazolin-7-yl)-3-fluorophenol (80 mg, 0.19 mmol) and $Et_3N$ (120 mg, 1.19 mmol) in DCM (20 mL) at 0° C., acryloyl chloride (143 mg, 1.58 mmol) was added and the resulting mixture was stirred for 30 min. The mixture was extracted with dichloromethane and washed with $NaHCO_3$ aqueous solution. The organic layer was dried over $Na_2SO_4$, filtered and concentrated in vacuo to afford the crude product (130 mg).

1-((2S,6R)-4-(6-Chloro-8-fluoro-7-(2-fluoro-6-hydroxyphenyl)quinazolin-4-yl)-2,6-dimethylpiperazin-1-yl)prop-2-en-1-one To a solution of 2-(4-((3 S,5R)-4-acryloyl-3,5-dimethylpiperazin-1-yl)-6-chloro-8-fluoroquinazolin-7-yl)-3-fluorophenyl acrylate (130 mg, crude) in THF (5 mL) and water (5 mL), lithium hydroxide (83 mg, 1.98 mmol) was added and the resulting mixture was stirred at RT for 1 h. The mixture was acidified with 1N HCl to adjust pH to 8, and then extracted with ethyl acetate. The organic layer was dried over $Na_2SO_4$, filtered and concentrated in vacuo. The residue was purified by flash chromatography on silica gel (dichloromethane/methanol=20:1) to afford the product (51 mg, 56% yield in 2 steps). ESI-MS m/z: 459.1 $[M+H]^+$. $^1H$ NMR (400 MHz, DMSO-d6) δ: 10.36 (s, 1H), 8.75 (s, 1H), 8.09 (s, 1H), 7.40 (t, $J_1$=7.2 Hz, $J_2$=14.4 Hz, 1H), 6.89 (m, 3H), 6.21 (d, J=16.4 Hz, 1H), 5.75 (m, 1H), 4.59 (m, 2H), 4.26 (m, 2H), 3.48 (m, 2H), 1.40 (m, 6H).

Example 28

Biochemical Assay of the Compounds

Test compounds were prepared as 10 mM stock solutions in DMSO (Fisher cat #BP-231-100). KRAS G12C 1-169, his-tagged protein, GDP-loaded was diluted to 2 μm in buffer (20 mM Hepes, 150 mM NaCl, 1 mM $MgCl_2$). Compounds were tested for activity as follows:

Compounds were diluted to 50× final test concentration in DMSO in 96-well storage plates. Compound stock solutions were vortexed before use and observed carefully for any sign of precipitation. Dilutions were as follow:

For 100 μM final compound concentration, compounds were diluted to 5000 μM (5 μl 10 mM compound stock+5 μl DMSO and mixed well by pipetting.

For 30 μM final compound concentration, compounds were diluted to 1500 μM (3 μl 10 mM compound stock+17p DMSO) and mixed well by pipetting.

For 10 μM final compound concentration, compounds were diluted to 500 μM (2 μl 10 mM compound stock+38p DMSO) and mixed well by pipetting. 49p of the stock protein solution was added to each well of a 96-well PCR plate (Fisher cat #1423027). 1 μl of the diluted 50× compounds were added to appropriate wells in the PCR plate using 12-channel pipettor. Reactions were mixed carefully and thoroughly by pipetting up/down with a 200·1 multi-channel pipettor. The plate was sealed well with aluminum plate seal, and stored in drawer at room temperature for 30 min, 2 hour or 24 hrs. 5·1 of 2% formic acid (Fisher cat #A117) in DI $H_2O$ was then added to each well followed by mixing with a pipette. The plate was then resealed with aluminum seal and stored on dry ice until analyzed as described below.

The above described assays were analyzed by mass spectrometry according to one of the following two procedures:

RapidFire/TOF Assay:

The MS instrument is set to positive polarity, 2 GHz resolution, and low mass (1700) mode and allowed to equilibrate for 30 minutes. The instrument is then calibrated, switched to acquisition mode and the appropriate method loaded.

After another 30 minute equilibration time, a blank batch (i.e., buffer) is run to ensure equipment is operating properly. The samples are thawed at 37° C. for 10 minutes, briefly centrifuged, and transfer to the bench top. Wells A1 and H12 are spiked with 1 uL 500 uM internal standard peptide, and the plates centrifuged at 2000×g for 5 minutes. The method is then run and masses of each individual well recorded.

The masses (for which integration data is desired) for each well are pasted into the platemap and exported from the analysis. Masses for the internal standards are exported as well. The data at 50 ppm is extracted for the +19 charge state, and identity of well A1 is assigned using the internal standard spike and integrated. Peak data is exported as a TOF list and the above steps are repeated individually, for the +20, 21, 22, 23, 24, and 25 charge states.

Q-Exactive Assay:

The masses and peak intensities of KRAS G12C protein species were measured using a Dionex RSLCnano system (Thermo Scientific) connected to a Q Exactive Plus mass spectrometer (Thermo Scientific).

20 mL of sample was each loaded onto a Aeris™ 3.6 μm WIDEPORE C4 200 Å, LC Column 50×2.1 mm column maintained at 40° C. at a flow rate of 600 μl $min^{-1}$ with 20% Solvent A (0.1% formic acid in $H_2O$) and 80% Solvent B (0.1% formic acid in acetonitrile). The liquid chromatography conditions were 20% solvent B for 1 min, 20% to 60% solvent B for 1.5 min, 60% to 90% solvent for 0.5 min, 90% solvent B for 0.2 min, 90% to 20% solvent B for 0.2 min, and then equilibrated for 1.6 min before the following sample injection. The flow rate was maintained at 600 μl $min^{-1}$ throughout the sample analysis.

The mass spectrometer was operated in profile mode at a resolution of 17500, 5 microscans, using 50 msec max injection time and an AGC target of 1e6, and a full mass range from 800-1850 m/z was recorded. The HCD trapping gas was optimized for maximum sensitivity for intact proteins. The ionization method was electrospray ionization, which used a spray voltage of 4 kV, sheath gas flow set to 50 au, auxiliary gas flow set to 10 au and sweep gas flow set to 1 au. The capillary ion transfer temperature was 320° C. and the S-lens RF level was set to 50 voltage. Protein Deconvolution software (Thermo Scientific) was used to deconvolute the charge envelopes of protein species in samples.

Data was analyzed using the Thermo protein deconvolution package. Briefly the charge envelope for each observed species was quantitatively deconvoluted to determine the mass and intensity of each parent species (modified or unmodified protein). % modification was calculated based on the deconvoluted peak intensities.

Other in vitro analyses are as follows:

Inhibition of Cell Growth:

The ability of the subject compounds to inhibit RAS-mediated cell growth is assessed and demonstrated as follows. Cells expressing a wildtype or a mutant RAS are plated in white, clear bottom 96 well plates at a density of 5,000 cells per well. Cells are allowed to attach for about 2 hours after plating before a compound disclosed herein is added. After certain hours (e.g., 24 hours, 48 hours, or 72 hours of cell growth), cell proliferation is determined by measuring total ATP content using the Cell Titer Glo reagent (Promega) according to manufacturer's instructions. Proliferation EC50s is determined by analyzing 8 point compound dose responses at half-log intervals decreasing from 100 M.

Inhibition of RAS-Mediated Signaling Transduction:

The ability of the compounds disclosed herein in inhibiting RAS-mediated signaling is assessed and demonstrated as follows. Cells expressing wild type or a mutant RAS (such as G12C, G12V, or G12A) are treated with or without (control cells) a subject compound. Inhibition of RAS signaling by one or more subject compounds is demonstrated by a decrease in the steady-state level of phosphorylated MEK, phosphorylated ERK, phosphorylated RSK, and/or Raf binding in cells treated with the one or more of the subject compounds as compared to the control cells.

Each of the compounds in Table 1 were tested according to the above methods and found to covalently bind to KRAS G12C to the extent of at least about 10% (i.e., at least about 10% of the protein present in the well was found to be covalently bound to test compound).

TABLE 6

Activity of Representative Compounds of Structure (I)*

| No. | Binding % | No. | Binding % | No. | Binding % | No. | Binding % |
|---|---|---|---|---|---|---|---|
| I-1 | +++ | I-2 | + | I-3 | +++ | I-4 | ++ |
| I-5 | + | I-6 | +++ | I-7 | ++ | I-8 | +++ |
| I-9 | ++ | I-10 | +++ | I-11 | +++ | I-12 | ++ |
| I-13 | +++ | I-14 | +++ | I-15 | +++ | I-16 | +++ |
| I-17 | ++ | I-18 | +++ | I-19 | ++ | I-20 | +++ |
| I-21 | + | I-22 | ++ | I-23 | ++ | I-24 | +++ |
| I-25 | +++ | I-26 | +++ | I-27 | +++ | I-28 | + |
| I-29 | +++ | I-30 | +++ | I-31 | +++ | I-32 | + |
| I-33 | +++ | I-34 | +++ | I-35 | ++ | I-36 | +++ |
| I-37 | +++ | I-38 | +++ | I-39 | +++ | I-40 | +++ |
| I-41 | +++ | I-42 | +++ | I-43 | +++ | I-44 | +++ |
| I-45 | +++ | I-46 | +++ | I-47 | +++ | I-48 | +++ |

TABLE 6-continued

Activity of Representative Compounds of Structure (I)*

| No. | Binding % | No. | Binding % | No. | Binding % | No. | Binding % |
|---|---|---|---|---|---|---|---|
| I-49 | +++ | I-50 | ++ | I-51 | +++ | I-52 | + |
| I-53 | +++ | I-54 | + | I-55 | +++ | I-56 | +++ |
| I-57 | +++ | I-58 | +++ | I-59 | +++ | I-60 | ++ |
| I-61 | +++ | I-62 | +++ | I-63 | +++ | I-64 | +++ |
| I-65 | +++ | I-66 | +++ | I-67 | +++ | I-68 | +++ |
| I-69 | +++ | I-70 | +++ | I-71 | +++ | I-72 | +++ |
| I-73 | +++ | I-74 | +++ | I-75 | +++ | I-76 | +++ |
| I-77 | +++ | I-78 | +++ | I-79 | + | I-80 | +++ |
| I-81 | + | I-82 | +++ | I-83 | +++ | I-84 | +++ |
| I-85 | +++ | I-86 | +++ | I-87 | +++ | I-88 | + |
| I-89 | +++ | I-90 | +++ | I-91 | +++ | I-92 | +++ |
| I-93 | +++ | I-94 | +++ | I-95 | +++ | I-96 | + |
| I-97 | +++ | I-98 | + | I-99 | +++ | I-100 | +++ |
| I-101 | +++ | I-102 | + | I-103 | +++ | I-104 | + |
| I-105 | +++ | I-106 | +++ | I-107 | +++ | I-108 | +++ |
| I-109 | +++ | I-110 | +++ | I-111 | + | I-112 | +++ |
| I-113 | +++ | I-114 | +++ | I-115 | +++ | I-116 | +++ |
| I-117 | + | I-118 | +++ | I-119 | + | I-120 | ++ |
| I-121 | +++ | I-122 | +++ | I-123 | +++ | I-124 | +++ |
| I-125 | +++ | I-126 | + | I-127 | +++ | I-128 | +++ |
| I-129 | +++ | I-130 | +++ | I-131 | +++ | I-132 | +++ |
| I-133 | ++ | I-134 | +++ | I-135 | +++ | I-136 | +++ |
| I-137 | +++ | I-138 | +++ | I-139 | +++ | I-140 | +++ |
| I-141 | +++ | I-142 | +++ | I-143 | +++ | I-144 | +++ |
| I-145 | +++ | I-146 | +++ | I-147 | ++ | I-148 | +++ |
| I-149 | +++ | I-150 | +++ | I-151 | +++ | I-152 | +++ |
| I-153 | +++ | I-154 | +++ | I-155 | +++ | I-156 | +++ |
| I-157 | +++ | I-158 | +++ | I-159 | +++ | I-160 | +++ |
| I-161 | +++ | I-162 | + | I-163 | +++ | I-164 | ++ |
| I-165 | ++ | I-166 | ++ | I-167 | ++ | I-168 | +++ |
| I-169 | ++ | I-170 | ++ | I-171 | ++ | I-172 | +++ |
| I-173 | + | I-174 | + | I-175 | ++ | I-176 | ++ |
| I-177 | +++ | I-178 | ++ | I-179 | + | I-180 | +++ |
| I-181 | + | I-182 | + | I-183 | +++ | I-184 | + |
| I-185 | + | I-186 | ++ | I-187 | + | I-188 | ++ |
| I-189 | ++ | I-190 | + | I-191 | +++ | I-192 | +++ |
| I-193 | +++ | I-194 | + | I-195 | ++ | I-196 | ++ |
| I-197 | ++ | I-198 | ++ | I-199 | +++ | I-200 | ++ |
| I-201 | ++ | I-202 | ++ | I-203 | ++ | I-204 | ++ |
| I-205 | ++ | I-206 | +++ | I-207 | ++ | I-208 | ++ |
| I-209 | ++ | I-210 | +++ | --- | --- | --- | --- |

+ indicates binding activity up to 50%

++ indicates binding activity from 50 to 90%

+++ indicates binding activity greater than 90%

TABLE 7

| Activity of Representative Compounds of Structure (II) | | | | | | | |
|---|---|---|---|---|---|---|---|
| No. | Binding % | No. | Binding % | No. | Binding % | No. | Binding % |
| II-1 | + | II-2 | +++ | II-3 | +++ | II-4 | + |
| II-5 | + | II-6 | ++ | II-7 | + | II-8 | + |
| II-9 | + | II-10 | +++ | II-11 | + | II-12 | + |
| II-13 | ++ | II-14 | ---- | II-15 | ----- | ----- | ----- |

+ indicates binding activity up to to 50%
++ indicates binding activity greater than 50% and less than 75%
+++ indicates binding activity of 75% or greater
+++ indicates binding activity of 90% or greater

TABLE 8

| Activity of Representative Compounds of Structure (III) | | | | | | | |
|---|---|---|---|---|---|---|---|
| No. | Binding % | No. | Binding % | No. | Binding % | No. | Binding % |
| III-1 | ++ | III-2 | + | III-3 | ++ | III-4 | + |
| III-5 | ++ | III-6 | +++ | III-7 | + | III-8 | ++ |
| III-9 | ++ | III-10 | + | III-11 | +++ | III-12 | + |
| III-13 | + | III-14 | ++ | III-15 | ++ | III-16 | + |
| III-17 | ++ | III-18 | + | III-19 | +++ | III-20 | ++ |
| III-21 | ++ | III-22 | + | III-23 | + | III-24 | +++ |
| III-25 | +++ | III-26 | ++ | III-27 | +++ | III-28 | +++ |
| III-29 | + | III-30 | +++ | III-31 | + | III-32 | ++ |
| III-33 | + | III-34 | + | III-35 | +++ | III-36 | +++ |
| III-37 | ++ | III-38 | ++ | III-39 | + | III-40 | ++ |
| III-41 | ++ | III-42 | ++ | III-43 | ++ | III-44 | +++ |

+ indicates binding activity up to 50%
++ indicates activity from 50% to 90%
+++ indicates binding activity greater than 90%

Example 29

Whole Blood Stability of Compounds of Structure (III)

Representative compounds of structure (III) were tested for their whole blood stability as follows:

Test compounds were prepared as a 500 μM stock solution in DMSO (Adding 10 μl of 10 mM DMSO stock solution to 190 μl of 100% DMSO). Whole blood was thawed on ice. A whole blood plate was prepared by adding 460 μl of the whole blood (different species as needed) to a 96-well in ml deep well plate. The whole blood plate was preincubated at 37° C. for 10 min. 4 μl of compound solution and 396 μl of whole blood was added to the plate and mixed thoroughly. Each sample was aliquoted (30 μl) to the incubation plate (cluster tubes) and quenched at time zero with ice-cold 100% ACN, and the incubation plates were added to the 37° C. incubator (200 μl).

The time zero sample was maintained at 4° C. until centrifuged. All other samples were quench at different time points (1, 2, 4 hr), vortexed for 30 seconds and centrifuged at 3500 rpm for 15 min at 4° C. 30 μl of supernatant was added to 170 μl 0.1% FA aqueous solution and the sample was analyzes by LC/MS/MS.

For comparative purposes, the following compound (A) was also tested:

(A)

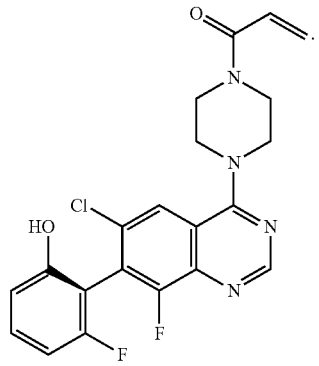

Table 3 provides whole blood stability for the representative compounds and the comparative compound. The data show that compounds of structure III, wherein at least one of $R^{3a}$, $R^{3b}$, $R^{4a}$ and $R^{4b}$ is not H, have a better whole blood stability than compound A, wherein each of $R^{3a}$, $R^{3b}$, $R^{4a}$ and $R^{4b}$ are H.

TABLE 9

| Whole Blood Stability of Representative Compounds and a Comparative Compound | |
|---|---|
| Compound | Whole Blood Stability ($T_{1/2}$) hr. Mouse |
| A | 3.99 |
| III-14 | 6.2 |
| III-15 | 11.1 |
| III-17 | 12.5 |
| III-18 | 8.8 |
| III-20 | 10.6 |
| III-21 | >12.0 |
| III-22 | >12.0 |
| III-23 | >12.0 |
| III-24 | 10.4 |
| III-29 | 10.9 |
| III-37 | 9.9 |

All of the U.S. patents, U.S. patent application publications, U.S. patent applications, foreign patents, foreign patent applications and non-patent publications referred to in this specification or the attached Application Data Sheet are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A compound having the following structure (I):

(I)

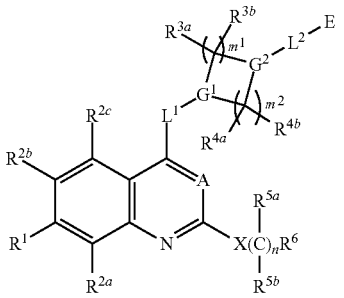

or a pharmaceutically acceptable salt, stereoisomer or prodrug thereof, wherein:

A is N;

$G^1$ and $G^2$ are each independently N or CH;

$L^1$ is a bond or $NR^7$;

$L^2$ is a bond or alkylene;

$R^1$ is *aryl or* heteroaryl;

$R^{2a}$, $R^{2b}$ and $R^{2c}$ are each independently H, amino, halo, hydroxyl, $C_1$-$C_6$ alkyl, $C_1$-$C_6$ alkylaminyl, $C_1$-$C_6$ haloalkyl, $C_1$-$C_6$ alkoxy, $C_3$-$C_8$ cycloalkyl, heteroaryl or aryl;

$R^{3a}$, $R^{3b}$, $R^{4a}$ and $R^{4b}$ are, at each occurrence, independently H, —OH, —$NH_2$, —$CO_2H$, halo, cyano, $C_1$-$C_6$ alkyl, $C_2$-$C_6$ alkynyl, hydroxylalkly, alkoxyalkyl, aminylalkyl, alkylaminylalkyl, cyanoalkyl, carboxyalkyl, aminylcarbonylalkyl or aminylcarbonyl;

$R^{5a}$ and $R^{5b}$ are, at each occurrence, independently H, hydroxyl, halo or $C_1$-$C_6$ alkyl, or $R^{5a}$ and $R^{5b}$ join to form oxo;

$R^6$ is heterocyclyl;

$R^7$ is H, $C_1$-$C_6$ alkyl, $C_3$-$C_8$ cycloalkyl or heterocyclylalkyl;

$m^1$ and $m^2$ are each independently 1, 2 or 3;

n is 0;

X is a bond; and

E is an electrophilic moiety capable of forming a covalent bond with the cysteine residue at position 12 of a KRAS, HRAS or NRAS G12C mutant protein, wherein each occurrence of alkyl, alkylene, aryl, heteroaryl, heterocyclyl, alkynyl, hydroxylalkly, alkoxyalkyl, aminylalkyl, alkylaminylalkyl, cyanoalkyl, carboxyalkyl, aminylcarbonylalkyl, aminylcarbonyl, alkylaminyl, haloalkyl, alkoxy, cycloalkyl and heterocyclylalkyl is optionally substituted with one or more substituents unless otherwise specified, the optional substituents being selected from the group consisting of aminyl, cyano, hydroxyl, imino, nitro, oxo, thioxo, halo, aminylsulfonyl, aminylcarbonyl, $C_1$-$C_{12}$ alkyl, $C_1$-$C_6$ alkylaminylcarbonyl, aminylcarbonyl$C_1$-$C_6$ alkyl, $C_1$-$C_{12}$ haloalkyl, $C_1$-$C_6$ alkoxy, $C_1$-$C_6$ haloalkoxy, $C_1$-$C_6$ alkoxyalkyl, $C_1$-$C_6$ haloalkoxyalkyl, cyano$C_1$-$C_6$ alkyl, $C_1$-$C_6$ alkylcycloalkyl, $C_1$-$C_6$ alkylheterocycloalkyl, $C_2$-$C_6$ alkynyl, $C_1$-$C_6$ alkylaminyl, $C_1$-$C_6$ alkylcarbonylaminyl, $C_1$-$C_6$ hydroxyalkyl, $C_2$-$C_6$ alkenylcarbonylaminyl, $C_1$-$C_6$ thioalkyl, aryl, aralkyl, $C_3$-$C_8$ cycloalkyl, $C_3$-$C_8$ cycloalkylalkyl, aminylcarbonyl$C_3$-$C_8$ cycloalkyl, $C_3$-$C_8$ cycloalkylaminylcarbonyl, $C_3$-$C_8$ fused cycloalkyl, heterocyclyl, N-heterocyclyl, heterocyclylalkyl, heteroaryl, N-heteroaryl and heteroarylalkyl, and wherein: i) each aryl comprises a 6- to 18-membered carbocyclic aromatic ring radical; ii) each heterocyclyl comprises a 3- to 18-membered non-aromatic ring radical having one to twelve ring carbon atoms and from one to six ring heteroatoms selected from the group consisting of nitrogen, oxygen and sulfur; and iii) each heteroaryl comprises a 5- to 14-membered ring radical comprising hydrogen atoms, one to thirteen ring carbon atoms, one to six ring heteroatoms selected from the group consisting of nitrogen, oxygen and sulfur, and at least one aromatic ring.

2. The compound of claim 1, wherein the compound has the following structure (I'a):

(I'a)

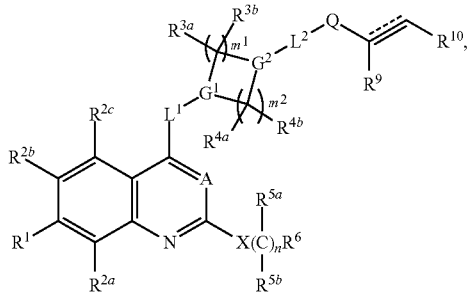

wherein:

≡ represents a double or triple bond;

Q is C(=O)—, —C(=$NR^{8'}$)—, $NR^8C$(=O)—, —S(=O)$_2$— or —$NR^8S$(=O)$_2$—;

$R^8$ is H, $C_1$-$C_6$ alkyl, hydroxylalkyl, aminoalkyl, alkoxyalkyl, aminylalkyl, alkylaminylalkyl, cyanoalkyl, carboxyalkyl, aminylcarbonylalkyl, $C_3$-$C_8$ cycloalkyl or heterocycloalkyl;

$R^{8'}$ is H, —OH, —CN or $C_1$-$C_6$ alkyl;

when ≡ is a double bond then $R^9$ and $R^{10}$ are each independently H, halo, cyano, carboxyl, $C_1$-$C_6$ alkyl, alkoxycarbonyl, aminylalkyl, alkylaminylalkyl, aryl, heterocyclyl, heterocyclylalkyl, heteroaryl or hydroxylalkyl, or $R^9$ and $R^{10}$ join to form a carbocyclic, heterocyclic or heteroaryl ring; and when ≡ is a triple bond then $R^9$ is absent and $R^{10}$ is H, $C_1$-$C_6$ alkyl, aminylalkyl, alkylaminylalkyl or hydroxylalkyl.

3. The compound of claim 2, wherein the compound has one of the following structures (I'b), (I'c), (I'd) or (I'e):

(I'b)

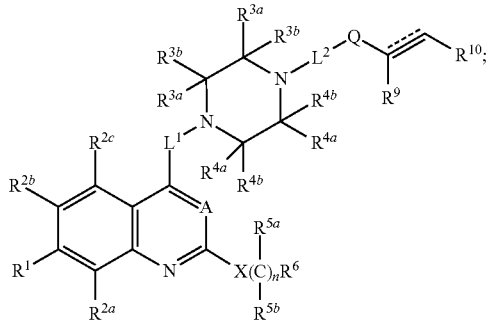

-continued (I'c)

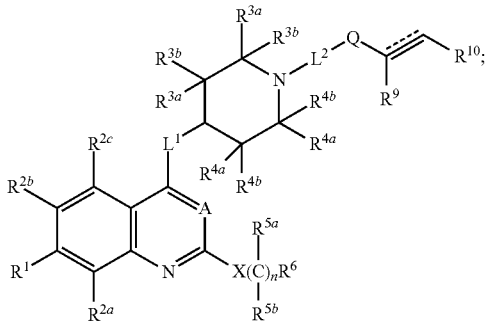

(I'd)

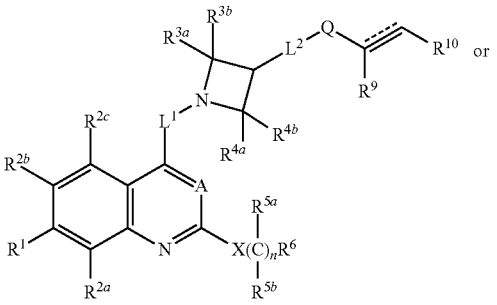

(I'e)

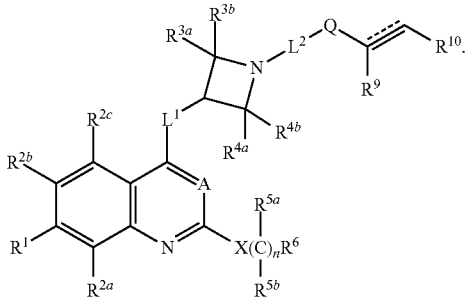

4. The compound of claim 1, wherein $R^1$ comprises nitrogen.

5. The compound of claim 4, wherein $R^1$ is indazolyl or quinolinyl.

6. The compound of claim 1, wherein $R^1$ is substituted with one or more substituents.

7. The compound of claim 6, wherein $R^1$ is substituted with halo, amino, hydroxyl, $C_1$-$C_6$ alkyl, cyano, $C_1$-$C_6$ haloalkyl, $C_1$-$C_6$ alkoxy, alkylaminyl, cycloalkyl, heterocyclylalkyl, aryl, heteroaryl, boronic acid, —OC(=O)R, phosphate, phosphoalkoxy or $C_1$-$C_6$ alkylcarbonyloxy, or combinations thereof, wherein R is $C_1$-$C_6$ alkyl.

8. The compound of claim 6, wherein $R^1$ is substituted with hydroxyl or $C_1$-$C_6$ alkyl, or both.

9. The compound of claim 1, wherein $R^1$ has one of the following structures:

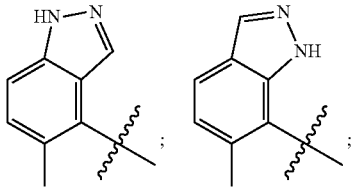

-continued

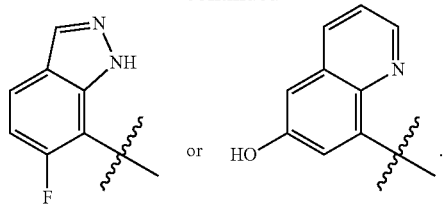

10. The compound of claim 1, wherein $R^{2c}$ is H.

11. The compound of claim 1, wherein $R^{2a}$ and $R^{2b}$ are each halo.

12. The compound of claim 1, wherein $R^{2a}$ is fluoro.

13. The compound of claim 1, wherein $R^{2b}$ is chloro.

14. The compound of claim 1, wherein $R^6$ is azetidinyl, pyrrolidinyl, piperidinyl or morpholinyl.

15. The compound of claim 14, wherein $R^6$ is substituted.

16. The compound of claim 15, wherein $R^6$ is substituted with $C_1$-$C_6$ alkyl, $C_1$-$C_6$ alkylaminyl, heterocyclyl or spiroheterocyclyl, or combinations thereof.

17. The compound of claim 1, wherein $R^6$ has one of the following structures:

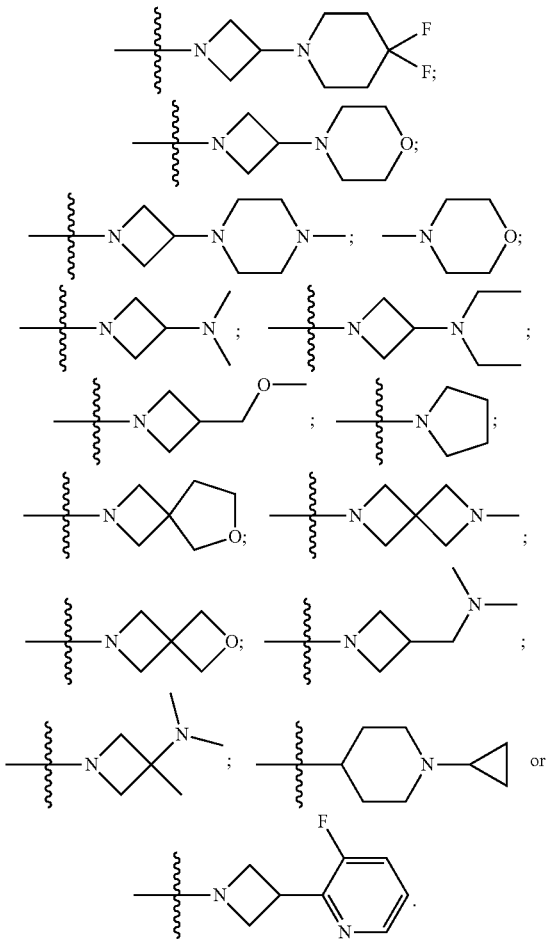

18. The compound of claim 2, wherein Q is —C(=O)—.

19. The compound of claim 2, wherein each of $R^9$ and $R^{10}$ are H.

20. The compound of claim 1, wherein E has one of the following structures:

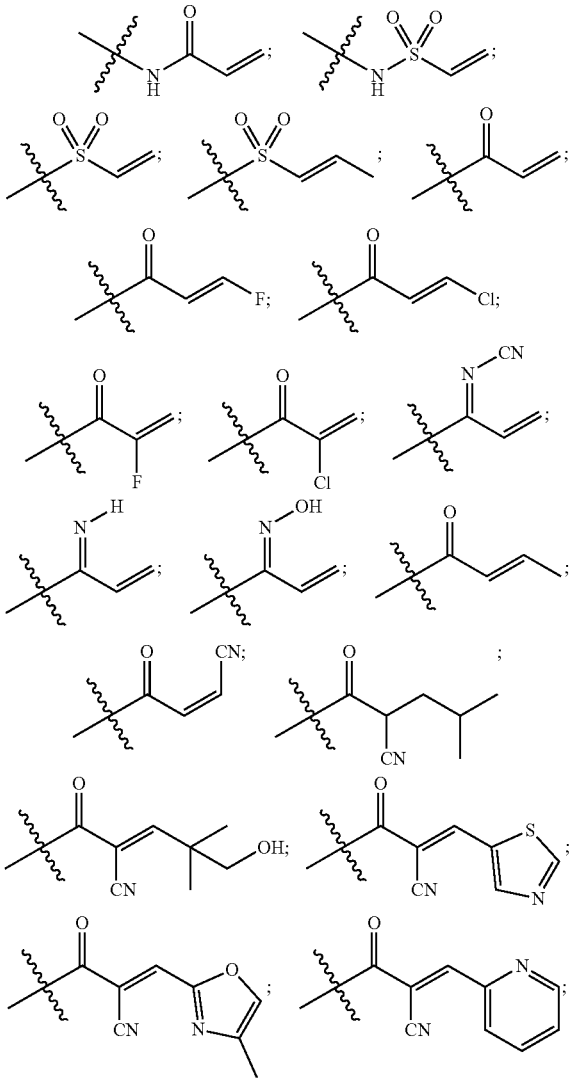
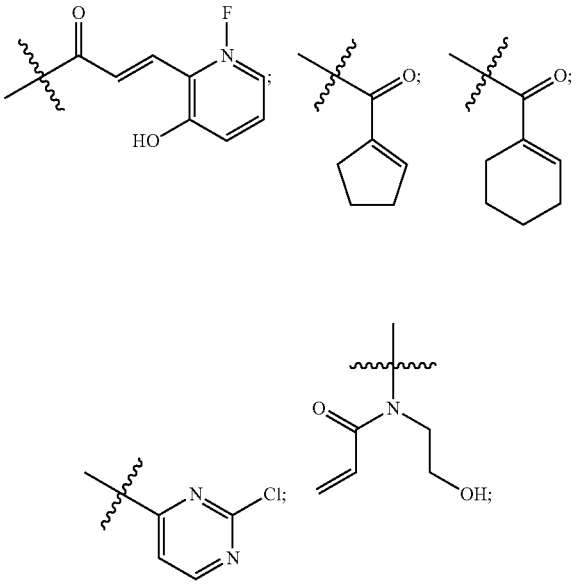
-continued
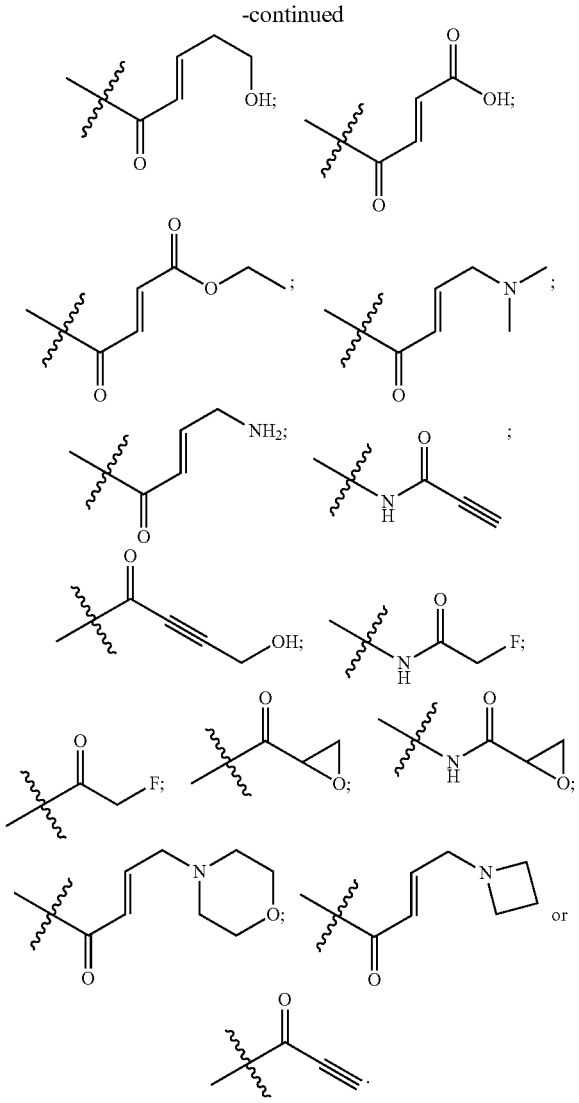
21. The compound of claim 1, wherein $L^1$ is a bond.
22. The compound of claim 1, wherein $L^2$ is a bond.
23. The compound of claim 1, wherein $R^{3a}$, $R^{3b}$, $R^{4a}$ and $R^{4b}$ are, at each occurrence, independently H or $C_1$-$C_6$ alkyl.
24. The compound of claim 1, wherein the compound has one of the following structures:
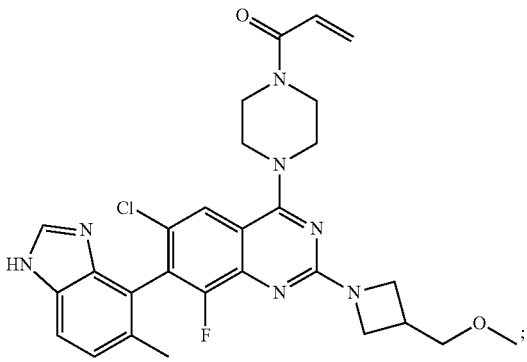

-continued

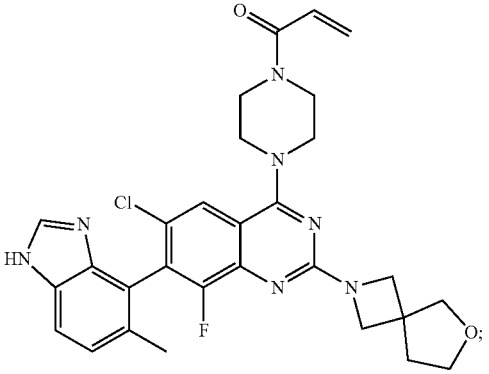

-continued

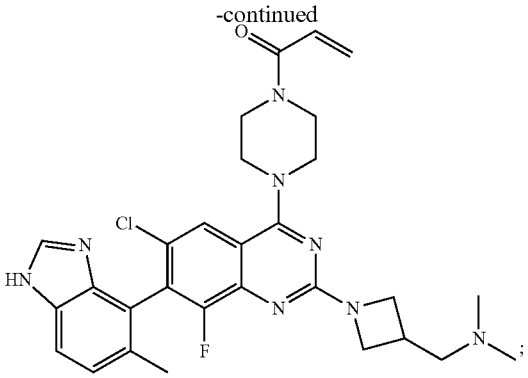

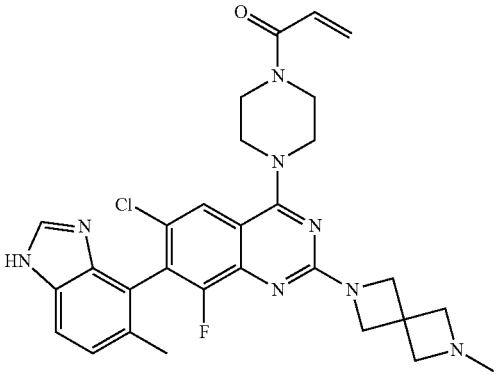

or

25. A substantially purified atropisomer of the compound of claim 1.

26. A pharmaceutical composition comprising a compound of claim 1 and a pharmaceutically acceptable carrier.

27. A method for treatment of cancer, the method comprising administering an effective amount of the pharmaceutical composition of claim 26 to a subject in need thereof.

28. The method of claim 27, wherein the cancer is mediated by a KRAS G12C, HRAS G12C or NRAS G12C mutation.

29. The method of claim 27, wherein the cancer is a hematological cancer, pancreatic cancer, MYH associated polyposis, colorectal cancer or lung cancer.

* * * * *